US012018002B2

(12) United States Patent
Qian et al.

(10) Patent No.: US 12,018,002 B2
(45) Date of Patent: *Jun. 25, 2024

(54) CERTAIN CHEMICAL ENTITIES, COMPOSITIONS, AND METHODS

(71) Applicant: NEUPHARMA, INC, Foster City, CA (US)

(72) Inventors: Xiangping Qian, Foster City, CA (US); Yong-Liang Zhu, Fremont, CA (US)

(73) Assignee: NEUPHARMA, INC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/506,367

(22) Filed: Oct. 20, 2021

(65) Prior Publication Data

US 2023/0043970 A1    Feb. 9, 2023

Related U.S. Application Data

(60) Division of application No. 16/702,936, filed on Dec. 4, 2019, now Pat. No. 11,208,388, which is a continuation of application No. 15/676,852, filed on Aug. 14, 2017, now Pat. No. 10,544,106.

(60) Provisional application No. 62/375,382, filed on Aug. 15, 2016.

(51) Int. Cl.

| C07D 239/74 | (2006.01) |
| A61K 45/06  | (2006.01) |
| C07D 239/84 | (2006.01) |
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 403/14 | (2006.01) |
| C07D 471/04 | (2006.01) |
| C07D 473/32 | (2006.01) |
| C07D 487/04 | (2006.01) |

(52) U.S. Cl.
CPC ............ *C07D 239/74* (2013.01); *A61K 45/06* (2013.01); *C07D 239/84* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 471/04* (2013.01); *C07D 473/32* (2013.01); *C07D 487/04* (2013.01)

(58) Field of Classification Search
CPC .......................... C07D 239/74; C07D 239/84
See application file for complete search history.

(56) References Cited

U.S. PATENT DOCUMENTS

| 5,033,252 A | 7/1991 | Carter |
| 5,052,558 A | 10/1991 | Carter |
| 5,323,907 A | 6/1994 | Kalvelage |
| 5,846,514 A | 12/1998 | Foster et al. |
| 6,334,997 B1 | 1/2002 | Foster et al. |
| 6,399,603 B1 | 6/2002 | Jacobs et al. |
| 6,579,868 B1 | 6/2003 | Asano et al. |
| 7,932,262 B2 | 4/2011 | Ramurthy et al. |
| 8,946,235 B2 | 2/2015 | Butterworth et al. |
| 9,550,770 B2 | 1/2017 | Qian et al. |
| 9,849,139 B2 | 12/2017 | Qian et al. |
| 10,172,868 B2 | 1/2019 | Qian et al. |
| 10,544,106 B2 | 1/2020 | Qian et al. |
| 10,653,701 B2 | 5/2020 | Qian et al. |
| 10,947,201 B2 | 3/2021 | Qian et al. |
| 11,208,388 B2 | 12/2021 | Qian et al. |
| 11,304,957 B2 | 4/2022 | Qian et al. |
| 2010/0048561 A1 | 2/2010 | Ramurthy et al. |
| 2010/0099658 A1 | 4/2010 | Kondoh et al. |
| 2010/0144707 A1 | 6/2010 | Bartolozzi et al. |
| 2013/0059847 A1 | 3/2013 | Bearss et al. |
| 2013/0109693 A1 | 5/2013 | Routier et al. |
| 2014/0080848 A1 | 3/2014 | Shiau et al. |
| 2014/0088100 A1 | 3/2014 | Bifulco, Jr. et al. |
| 2014/0255428 A1 | 9/2014 | Li et al. |
| 2015/0175601 A1 | 6/2015 | Qian et al. |
| 2017/0050936 A1 | 2/2017 | Qian et al. |
| 2017/0313683 A1 | 11/2017 | Wang et al. |
| 2021/0163423 A1 | 6/2021 | Qian et al. |
| 2022/0354864 A1 | 11/2022 | Qian et al. |

FOREIGN PATENT DOCUMENTS

| CA | 2917364 A1 | 1/2015 |
| CN | 101454294 A | 6/2009 |
| CN | 102260263 A | 11/2011 |
| CN | 103554038 A | 2/2014 |
| CN | 103864792 A | 6/2014 |
| CN | 103889962 A | 6/2014 |
| CN | 103936742 A | 7/2014 |
| CN | 104053442 A | 9/2014 |
| CN | 105315283 A | 2/2016 |

(Continued)

OTHER PUBLICATIONS

Guo, et al. European Journal of Medicinal Chemistry 178 (2019) 767-781.*
Bajji, et al. Document No. 148:11252, retrieved from STN; Nov. 22, 2007.
Basu, et al., Structure-based design and synthesis of covalent-reversible inhibitors to overcome drug resistance in EGFR. Bioorganic & Medicinal chemistry. 2015; 23(12):2767-2780.
Bundgaard. Design of Prodrugs. Elsevier, 1985.

(Continued)

*Primary Examiner* — Shawquia Jackson
(74) *Attorney, Agent, or Firm* — Wilson Sonsini Goodrich & Rosati

(57) ABSTRACT

Chemical entities that are kinase inhibitors, pharmaceutical compositions and methods of treatment of cancer are described.

15 Claims, No Drawings

(56) References Cited

FOREIGN PATENT DOCUMENTS

| | | | |
|---|---|---|---|
| CN | 105777759 A | 7/2016 | |
| EP | 2269993 A1 | 1/2011 | |
| EP | 2578584 A1 | 4/2013 | |
| GB | 587936 A | 5/1947 | |
| JP | S62487 A | 1/1987 | |
| JP | H11263789 A | 9/1999 | |
| JP | 2006502165 A | 1/2006 | |
| JP | 2013507381 A | 3/2013 | |
| JP | 2014530194 A | 11/2014 | |
| JP | 2015533822 A | 11/2015 | |
| WO | WO-9722596 A1 | 6/1997 | |
| WO | WO-9729106 A1 | 8/1997 | |
| WO | WO-9730035 A1 | 8/1997 | |
| WO | WO-9732856 A1 | 9/1997 | |
| WO | WO-9813354 A1 | 4/1998 | |
| WO | WO-9902166 A1 | 1/1999 | |
| WO | WO-0040529 A1 | 7/2000 | |
| WO | WO-0041669 A2 | 7/2000 | |
| WO | WO-0047212 A1 | 8/2000 | |
| WO | WO-0102400 A1 | 1/2001 | |
| WO | WO-0121598 A1 | 3/2001 | |
| WO | WO-0192224 A1 | 12/2001 | |
| WO | WO-0204434 A1 | 1/2002 | |
| WO | WO-0208213 A1 | 1/2002 | |
| WO | WO-2004082606 A2 | 9/2004 | |
| WO | WO-2005032481 A2 | 4/2005 | |
| WO | WO-2006045828 A1 | 5/2006 | |
| WO | WO-2007071393 A2 | 6/2007 | |
| WO | WO-2007117607 A2 | 10/2007 | |
| WO | WO-2009131173 A1 | 10/2009 | |
| WO | WO-2010019762 A1 | 2/2010 | |
| WO | WO-2010056758 A1 | 5/2010 | |
| WO | WO-2010129053 A2 | 11/2010 | |
| WO | WO-2011046964 A2 | 4/2011 | |
| WO | WO-2011079231 A1 | 6/2011 | |
| WO | WO-2011106168 A1 | 9/2011 | |
| WO | WO-2011135259 A1 | 11/2011 | |
| WO | WO-2013005157 A1 | 1/2013 | |
| WO | WO-2013013031 A1 | 1/2013 | |
| WO | WO-2013106792 A1 | 7/2013 | |
| WO | WO-2013118817 A1 | 8/2013 | |
| WO | WO-2013130660 A1 | 9/2013 | |
| WO | WO-2014011900 A2 | 1/2014 | |
| WO | WO-2014037750 A1 | 3/2014 | |
| WO | WO-2014130693 A1 | 8/2014 | |
| WO | WO-2014135245 A1 | 9/2014 | |
| WO | WO-2014180524 A1 | 11/2014 | |
| WO | WO-2015022926 A1 | 2/2015 | |
| WO | WO-2015027222 A2 | 2/2015 | |
| WO | WO-2015069441 A1 | 5/2015 | |
| WO | WO-2015140566 A1 | 9/2015 | |
| WO | WO-2015175813 A1 | 11/2015 | |
| WO | WO-2015184661 A1 | 12/2015 | |
| WO | WO-2015193740 A2 | 12/2015 | |
| WO | WO-2016019233 A1 | 2/2016 | |
| WO | WO-2016110821 A1 | 7/2016 | |
| WO | WO-2016112637 A1 | 7/2016 | |
| WO | WO-2016133935 A1 | 8/2016 | |
| WO | WO-2018035061 A1 | 2/2018 | |

OTHER PUBLICATIONS

Bursavich, et al. Novel Mps1 kinase inhibitors: from purine to pyrrolopyrimidine and quinazoline leads. Bioorg Med Chem Lett. Dec. 15, 2013;23(24):6829-33. doi: 10.1016/j.bmcl.2013.10.008. Epub Oct. 11, 2013.
CAS Registry No. 1026642-77-2; STN entry date: Jun. 8, 2008.
CAS Registry No. 1082700-91-1; STN entry date: Dec. 10, 2008.
Chen et al., Targeting the epidermal growth factor receptor in non-small cell lung cancer cells: the effect of combining RNA interference with tyrosine kinase inhibitors or cetuximab. BMC Medicine. 10(28):1-15 (2012).
Cho, et al. Synthesis and antitumor activity of 3-arylisoquinoline derivatives. Arch Pharm Res. Jun. 1997;20(3):264-8.
Dille, et al. CAPLUS Abstract of: Journal of Organic Chemistry (1955), 20, 171-7.
EVANS. Synthesis of radiolabeled compounds, J. Radioanal. Chem. 1981; 64(1-2):9-32.
Galtea et al.: Single-Step Formation of Pyrimido[4,5-d]pyridazines by a Pyrimidine-Tetrazine Tandem Reaction. Org Lett. 18(15):3594-3597 doi:10.1021/acs.orglett.6b01601 (2016).
Georgescu et al., New Pyrrolo[1,2-c]Pyrimidine Derivatives. Revue Roumaine de Chimie 42(1): 11-15 (1997).
Georgescu et al., Preparation of some new pyrrolo [1,2-c]pyrimidine derivatives. Revista de Chimie 34(12): 1130-1131 (1983). [English Abstract included].
Golub et al., Molecular classification of cancer: class discovery and class prediction by gene expression monitoring. Science. 286(5439):531-537 (1999).
Han, et al., Balancing potency, metabolic stability and permeability in pyrrolopyrimidine-based EGFR inhibitors. European Journal of medicinal chemistry. 2016; 124: 583-607.
He, et al. Synthesis and SAR of novel quinazolines as potent and brain-penetrant c-jun N-terminal kinase (JNK) inhibitors. Bioorg Med Chem Lett. Mar. 15, 2011;21(6):1719-23. doi: 10.1016/j.bmcl. 2011.01.079. Epub Jan. 22, 2011.
Higuchi, et al. Pro-drugs as novel drug delivery systems. American Chemical Society. ACS symposium series 14. 1975.
Janssen, et al. Document No. 144:450727, retrieved from STN; May 4, 2006.
Johnson et al.: A comparison of the ability of rilpivirine (TMC278) and selected analogues to inhibit clinically relevant HIV-1 reverse transcriptase mutants. Retrovirology. 9:99:1-11 doi:10.1186/1742-4690-9-99 (2012).
Kalbalka, et al. The Synthesis of Radiolabeled Compounds via Organometallic Intermediates, Tetrahedron. 1989; 45(21):6601-21.
Kashima et al., Preparation of 2-aminoquinazoline derivatives as Tie-2 kinase inhibitors. Document No. 151. STNext (2020).
Kim et al.: Discovery of (2S)-1-[4-(2-{6-amino-8-[(6-bromo-1,3-benzodioxol-5-yl)sulfanyl]-9H-purin-9-yl}ethyl)piperidin-1-yl]-2-hydroxypropan-1-one (MPC-3100), a purine-based Hsp90 inhibitor. J Med Chem. 55(17):7480-7501 doi:10.1021/jm3004619 (2012).
Kubinyi, et al., 3D QSAR in Drug Design:Ligand-Protein Interactions and Molecular Similarity. 1998; vol. 2-3: 243-244.
Lala, et al., Role of Nitric and Oxide in Tumor Progression: Lessons from Experimental Tumors. Cancer Metastasis Reviews. 17(1):91-106 (1998).
Lombardo et al., Discovery of N-(2-Chloro-6-methyl-phenyl)-2-(6-(4-(2-hydroxyethyl)-piperazin-1-yl)-2-methylpyrimidin-4-ylamino)thiazole-5-carboxamide (BMS-354825), a Dual Src/Abl kinase inhibitor with potent antitumor activity in preclinical assays. J. Med. Chem., 47: 6658-6661, 2004.
McMahon. VEGF receptor signaling in tumor angiogenesis. The Oncologist. 2000; 5(suppl 1):3-10.
MedlinePlus. Cancer. https://medlineplus.gov/cancer.html# . 1-12 (2019).
Osol, et al. eds. Remington's Pharmaceutical Sciences. Easton, PA USA. Mack Publishing Company. 1980. 16th edition. (Table of Contents).
PCT/US2014/52409 International Search Report and Written Opinion dated Feb. 10, 2015.
PCT/US2016/018129 International Search Report and Written Opinion dated Jul. 25, 2016.
PCT/US2017/046819 International Search Report and Written Opinion dated Nov. 30, 2017.
Pinedo, et al. Translational research: The role of VEGF in tumor angiogenesis. The Oncologist. 2000; 5(suppl 1):1-2.
PubChem. Compound Summary for CID 68388374. Create date: Nov. 30, 2012.
Remington's Pharmaceutical Sciences. 18th Edition, Mack Publishing Company (1990).
Remington: The Science and Practice of Pharmacy. 21st Edition, Lippincott Williams & Wilkins (2005).
Roche. Bioreversible Carriers in Drug Design, American Pharmaceutical Association and Pergamon Press, 1987.
Saravanan et al.: Nucleoside transport inhibitors: structure-activity relationships for pyrimido[5,4-d]pyrimidine derivatives that poten-

(56) References Cited

OTHER PUBLICATIONS tiate pemetrexed cytotoxicity in the presence of α1-acid glycoprotein. J Med Chem. 54(6):1847-1859 doi:10.1021/jm101493z (2011).

Shi et al.: Synthesis and antimicrobial activity of polyhalobenzonitrile quinazolin-4(3H)-one derivatives. Bioorg Med Chem Lett. 23(21):5958-5963 doi:10.1016/j.bmcl.2013.08.068 (2013).

Stem, et al. Overview of monoclonal antibodies in cancer therapy: present and promise. Crit Rev Oncol Hematol. Apr. 2005;54(1):11-29.

STN Search Report. American Chemical Society. https://www.stn.org/ (Feb. 28, 2022).

Tanji et al.: Purines. VI. Reactions of 2-Chloro-and 2-(Methylsulfonyl)-9-phenyl-9H-purines with Nucleophiles. Chemical & Pharmaceutical Bulletin. 35(12): 4972-4976 doi:10.1248/cpb.35.4972 (1987).

The United States Department of Health and Human Services, Food and Drug Administration, "Guidance for Industry, Q1A(R2) Stability testing of New Drug Substances and Drug Products" Nov. 2003, Revision 2, pp. 1-25.

Troger, et al. (CAPLUS Abstract of: Journal fuer Praktische Chemie (Leipzig) (1927), 117, p. 117-41).

Warmuth, C. The Practice of Medicinal Chemistry. 2nd edition. 2003.Elsevier. chs. 9-10.

U.S. Appl. No. 15/044,966 Final Office Action dated Aug. 21, 2017.
U.S. Appl. No. 15/044,966 Final Office Action dated Sep. 12, 2019.
U.S. Appl. No. 15/044,966 Final Office Action dated Sep. 25, 2018.
U.S. Appl. No. 15/044,966 Non-Final Office Action dated Apr. 2, 2019.
U.S. Appl. No. 15/044,966 Non-Final Office Action dated Jan. 13, 2017.
U.S. Appl. No. 15/044,966 Non-Final Office Action dated Jan. 27, 2020.
U.S. Appl. No. 15/044,966 Non-Final Office Action dated Jan. 29, 2018.
U.S. Appl. No. 15/676,852 Non-Final Office Action dated Sep. 21, 2018.
U.S. Appl. No. 16/702,936 Final Office Action dated Apr. 26, 2021.
U.S. Appl. No. 16/702,936 Non-Final Office Action dated Oct. 26, 2020.
U.S. Appl. No. 17/172,435 Non-Final Office Action dated Aug. 23, 2023.

\* cited by examiner

CERTAIN CHEMICAL ENTITIES, COMPOSITIONS, AND METHODS

CROSS-REFERENCE

This application is a divisional of U.S. application Ser. No. 16/702,936, filed on Dec. 4, 2019, now U.S. Pat. No. 11,208,388, issued Dec. 28, 2021, which is a continuation of U.S. application Ser. No. 15/676,852, filed Aug. 14, 2017, now U.S. Pat. No. 10,544,106, issued Jan. 28, 2020, which claims priority from U.S. Provisional Application No. 62/375,382, filed Aug. 15, 2016, all of which are incorporated herein by reference in their entirety.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

The identification of effective small compounds which specifically inhibit signal transduction and cellular proliferation by modulating the activity of tyrosine and serine/threonine kinases to regulate and modulate abnormal or inappropriate cell proliferation, differentiation, or metabolism is therefore desirable. In particular, the identification of compounds that specifically inhibit the function of a kinase which is essential for processes leading to cancer would be beneficial.

SUMMARY OF THE INVENTION

In one aspect, the present disclosure provides a compound of Formula I:

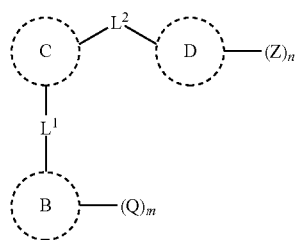

Formula I or a pharmaceutically acceptable salt thereof, wherein

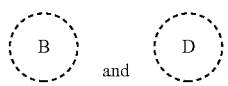

are each independently selected from the group consisting of aryl, heteroaryl and heterocycloalkyl;

is selected from the group consisting of:

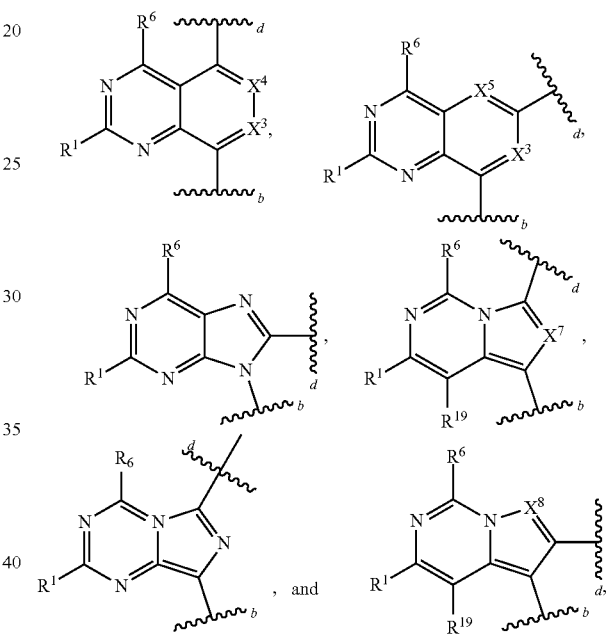

wherein ⁓b is a point of attachment for $L^1$ and ⁓d is a point of attachment for $L^2$;

$X^3$ is C—$R^3$ or N;
$X^4$ is C—$R^4$ or N;
$X^5$ is C—$R^5$ or N;
$X^7$ is C—$R^{20}$ or N;
$X^8$ is C—$R^{21}$ or N;
$L^1$ and $L^2$ are each independently selected from the group consisting of bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—, optionally substituted $C_{1-6}$ alkylene, optionally substituted $C_{2-6}$ alkenylene, optionally substituted $C_{2-6}$ alkynylene, optionally substituted 1-to 6-membered heteroalkylene, optionally substituted 2-to 6-membered heteroalkenylene, and optionally substituted 2-to 6-membered heteroalkynylene;

$R^1$, $R^3$, $R^4$, $R^5$, $R^6$, $R^{19}$, $R^{20}$ and $R^{21}$ are each independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl and optionally substituted carbamimidoyl;

$R^{51}$ is independently selected at each occurrence from hydrogen, sulfonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted acyl, optionally substituted alkoxycarbonyl, optionally substituted aminocarbonyl, optionally substituted aminosulfonyl and optionally substituted carbamimidoyl;

Q and Z are each independently selected at each occurrence from hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl and E; wherein E is an electrophilic group capable of forming a covalent bond with a nucleophile; and m and n are each independently 0, 1, 2, 3, 4 or 5;
wherein at least one of

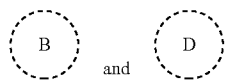
and is substituted with E.

In some embodiments,

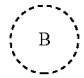

is selected from 5-to 7-membered aryl, 5-to 7-membered heteroaryl and 5- to 7-membered heterocycloalkyl.

In some embodiments,

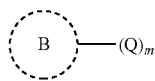

is selected from the group consisting of:

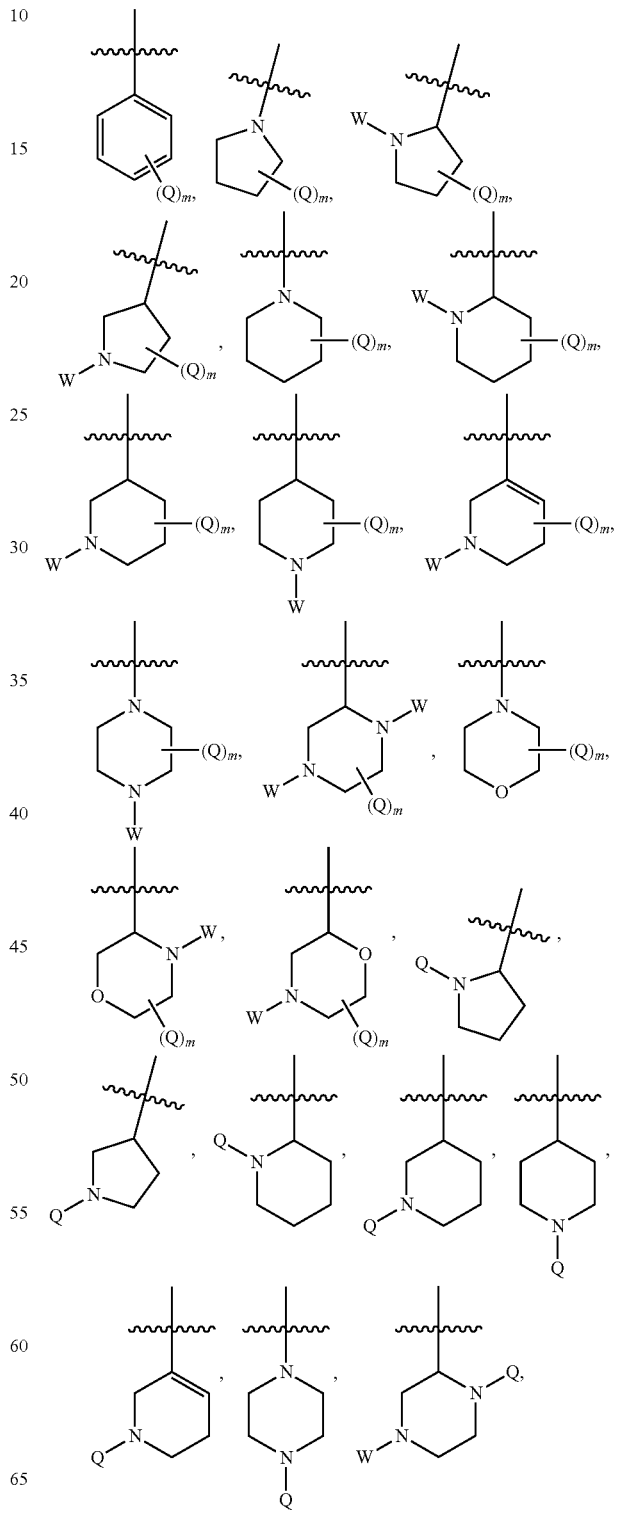

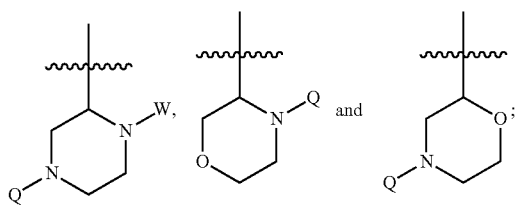 

wherein each W is independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or E; wherein each E is independently an electrophilic group capable of forming a covalent bond with a nucleophile.

In some embodiments,

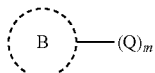

is selected from the group consisting of

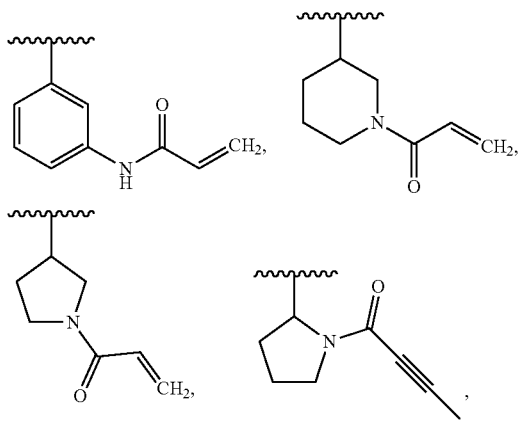

In some embodiments,

m is selected from the group consisting of

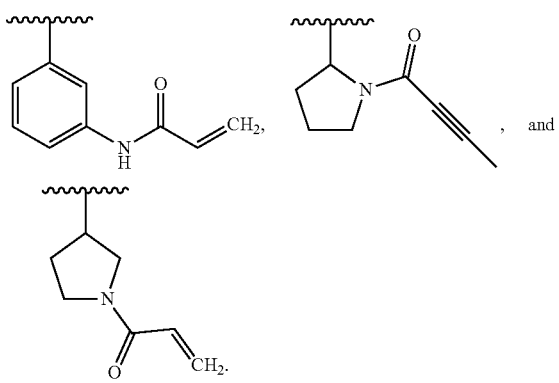

In some embodiments,

is selected from phenyl, pyridinyl, pyrimidinyl, pyrazinyl, thiazolyl, oxazolyl, imidazolyl, pyrazolyl, isoxazolyl, thienyl, piperazinyl, morpholinyl, piperidinyl, thiomorpholinyl, pyrrolidinyl, tetrahydrofuranyl and diazepanyl. In some embodiments,

is selected from phenyl, piperidinyl and pyrazolyl.

In some embodiments,

is selected from the group consisting of:

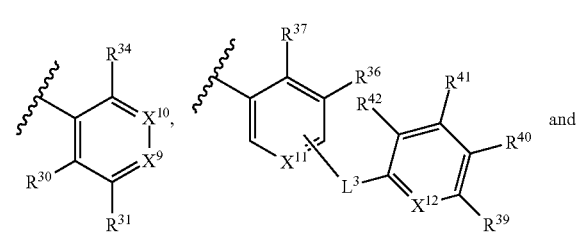

-continued

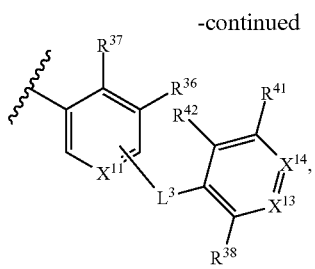

wherein:
X$^9$ is C—R$^{32}$ or N;
X$^{10}$ is C—R$^{33}$ or N;
X$^{11}$ is C—R$^{35}$ or N;
X$^{12}$ is C—R$^{38}$ or N;
X$^{13}$ is C—R$^{39}$ or N;
X$^{14}$ is C—R$^{40}$ or N;
L$^3$ is selected from the group consisting of bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—, optionally substituted C$_{1-6}$ alkylene, optionally substituted C$_{2-6}$ alkenylene, optionally substituted C$_{2-6}$ alkynylene, optionally substituted 1- to 6-membered heteroalkylene, optionally substituted 2- to 6-membered heteroalkenylene, and optionally substituted 2- to 6-membered heteroalkynylene; and
R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$ and R$^{42}$ are each independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl and optionally substituted carbamimidoyl.

In some embodiments, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$ and R$^{42}$ are each independently selected from the group consisting of hydrogen, cyano, halo, C$_1$-C$_3$ alkyl, C$_1$-C$_3$ haloalkyl, C$_1$-C$_3$ alkoxy, 3- to 6-membered cycloalkyl, aminocarbonyl and amino. In some embodiments, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$ and R$^{42}$ are each independently selected from the group consisting of hydrogen, halo, cyclopropyl, —CN, —CH$_3$, —CF$_3$, —CONH$_2$, —NH$_2$, and —OCH$_3$. In some embodiments, R$^{30}$, R$^{31}$, R$^{32}$ and R$^{41}$ are each independently selected from the group consisting of hydrogen, halo, cyclopropyl, —CN, —CH$_3$, —CF$_3$, —CONH$_2$, —NH$_2$, and —OCH$_3$; and R$^{33}$, R$^{34}$, R$^{35}$, R$^{36}$, R$^{37}$, R$^{38}$, R$^{39}$, R$^{40}$ and R$^{42}$ are each hydrogen.

In some embodiments, R$^{30}$, R$^{31}$, R$^{32}$, R$^{33}$ and R$^{34}$ are each independently selected from the group consisting of hydrogen, halo, cyano, optionally substituted alkyl, optionally substituted alkoxy, and optionally substituted cycloalkyl. In some embodiments, R$^{30}$, R$^{31}$, R$^{32}$, R$^{33}$ and R$^{34}$ are each independently selected from the group consisting of hydrogen, chloro, fluoro, cyano, —CH$_3$, —CF$_3$, —OCH$_3$ and —OPh.

In some embodiments, R$^{35}$, R$^{36}$, R$^{37}$, R$^{38}$, R$^{39}$, R$^{40}$, R$^{41}$, and R$^{42}$ are each independently selected from the group consisting of hydrogen, halo, cyano, optionally substituted alkyl, optionally substituted alkoxy, and optionally substituted cycloalkyl. In some embodiments, R$^{35}$, R$^{36}$, R$^{37}$, R$^{38}$, R$^{39}$, R$^{40}$, R$^{41}$, and R$^{42}$ are each independently selected from the group consisting of hydrogen, chloro, fluoro, cyano, cyclopropyl, —CH$_3$, —CF$_3$, —OCH$_3$ and —OPh.

In some embodiments, wherein X$^{12}$ is N.

In some embodiments, L$^3$ is selected from —O—, —N(R$^{51}$)—, —C(O)N(R$^{51}$)— and —N(R$^{51}$)C(O)—. In some embodiments, L$^3$ is selected from —O—, —NH— and —C(O)NH—.

In some embodiments,

is selected from 5- to 7-membered aryl and 5- to 7-membered heteroaryl. In some embodiments,

is selected from phenyl, pyridinyl, pyrimidinyl, pyrazinyl, thiazolyl, oxazolyl, imidazolyl, pyrazolyl, isoxazolyl and thienyl. In some embodiments,

is selected form phenyl and pyridinyl.

In some embodiments, L$^1$ is a bond.
In some embodiments, L$^2$ is a bond.
In some embodiments, m is 1, 2, 3, 4 or 5.
In some embodiments, each Q is independently selected at each occurrence from cyano, halo, hydroxy, azido, nitro, carboxy, oxo, sulfinyl, sulfanyl, sulfonyl, alkoxy, alkyl, haloalkyl, alkenyl, alkynyl, amino, acyl, alkoxycarbonyl, aminocarbonyl, aminosulfonyl, carbamimidoyl and E. In some embodiments, at least one Q is E. In some embodiments, m is 1 and Q is E.

In some embodiments, n is 0. In some embodiments, n is 1, 2, 3, 4 or 5. In some embodiments, n is 1 or 2.

In some embodiments, Z is independently selected at each occurrence from cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted alkyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, and E. In some embodiments, Z is independently selected at each occurrence from cyano, halo, optionally substituted aryloxy, optionally substituted amino, and optionally substituted aminocarbonyl.

In some embodiments, each E is independently an electrophilic group capable of forming a covalent bond with a cysteine residue of a protein. In some embodiments, E comprises a substituted or unsubstituted vinyl sulfone moiety, substituted or unsubstituted vinyl sulfonamide moiety, substituted or unsubstituted fluoro($C_1$-$C_4$)alkylketone moiety, substituted or unsubstituted chloro($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

In some embodiments, E is selected from a group consisting of

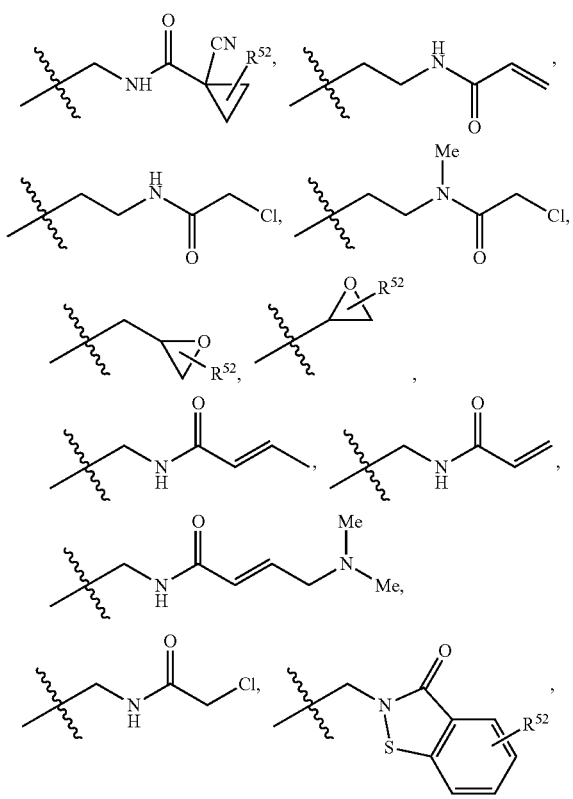

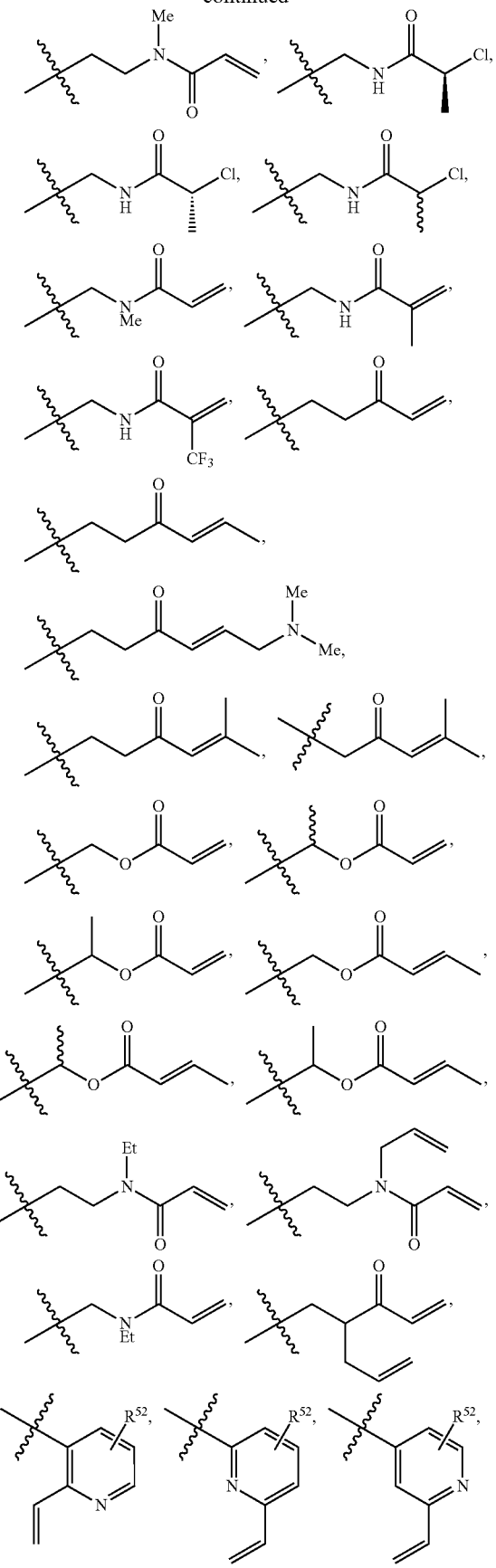

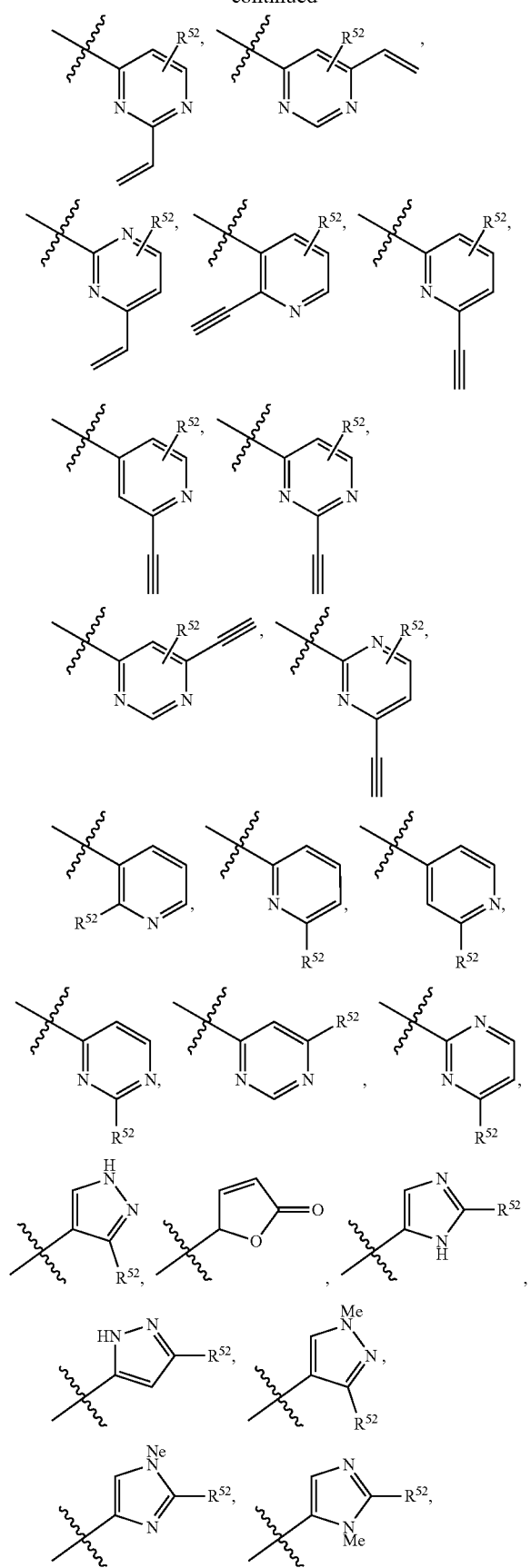
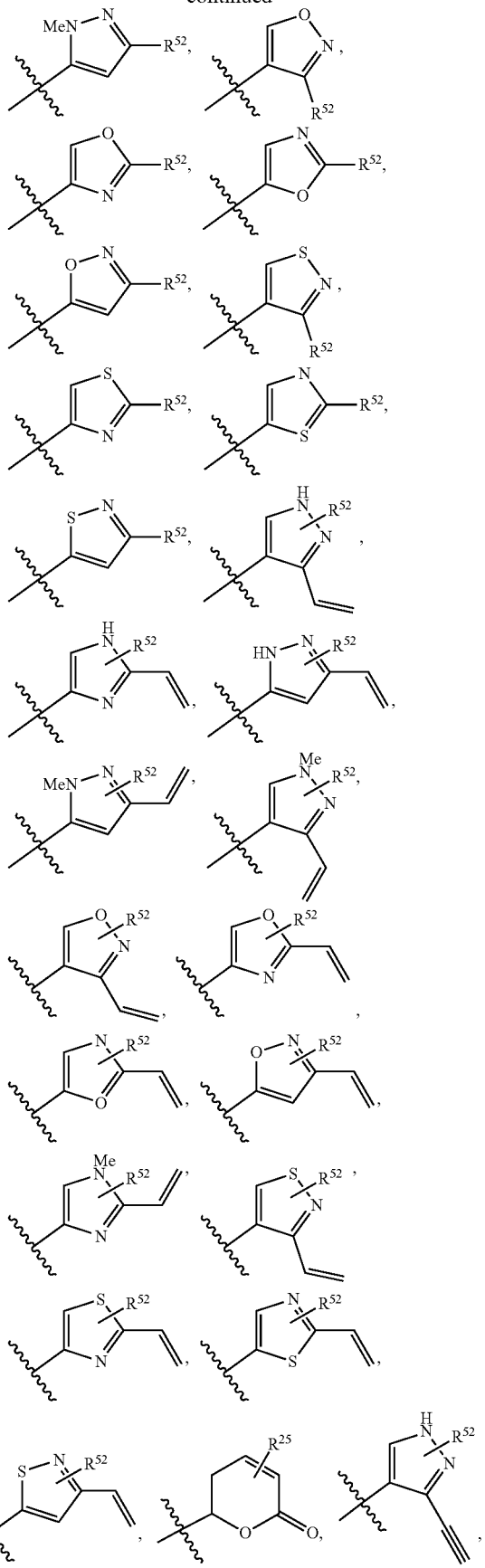

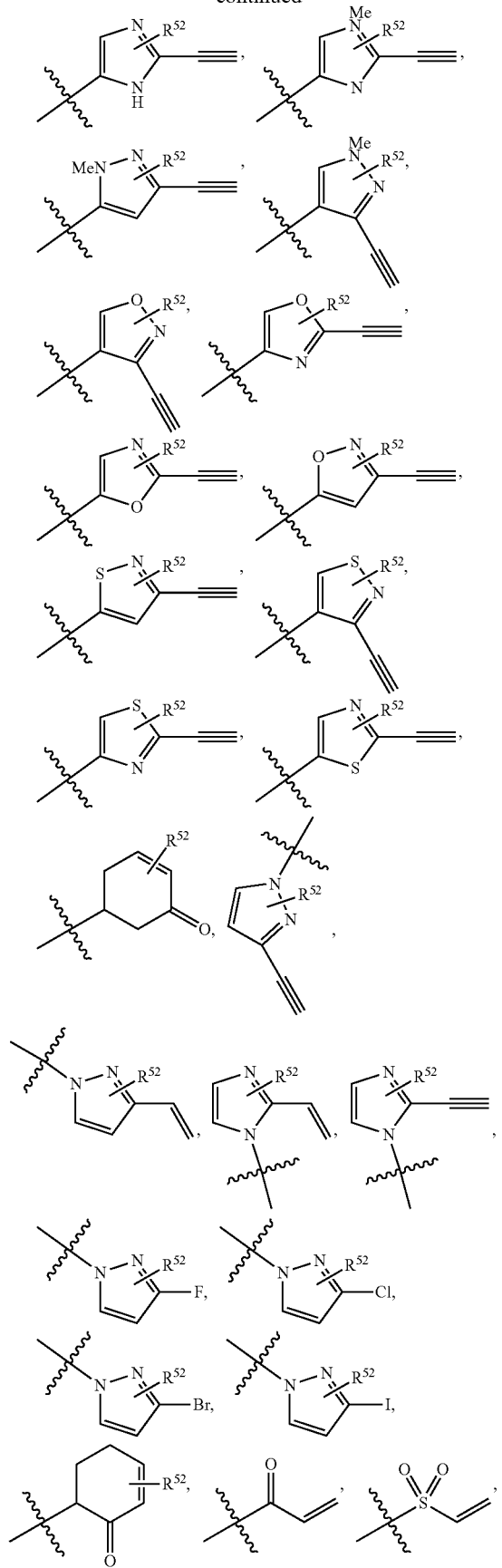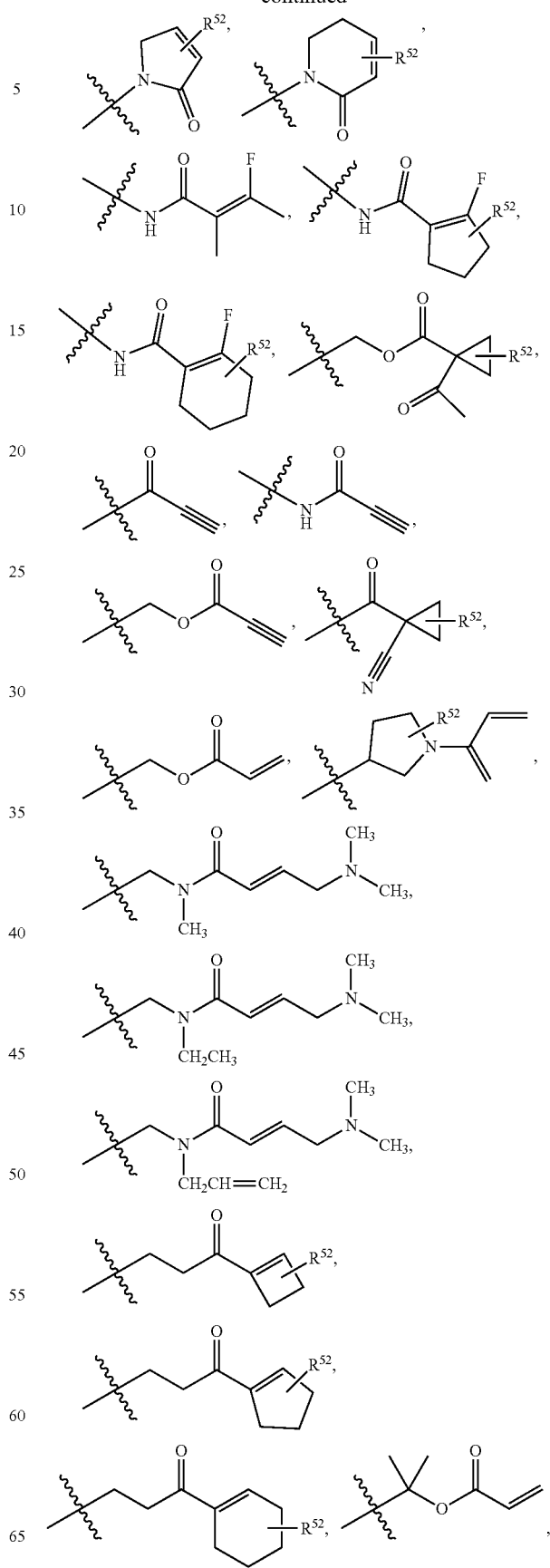

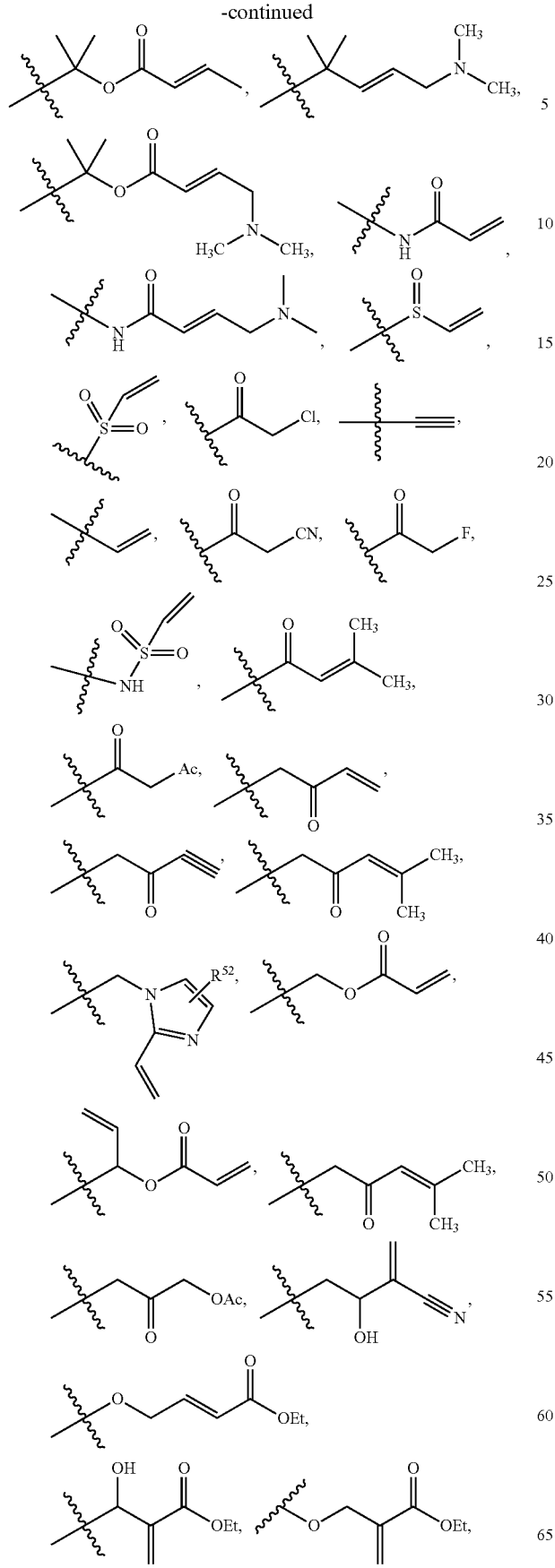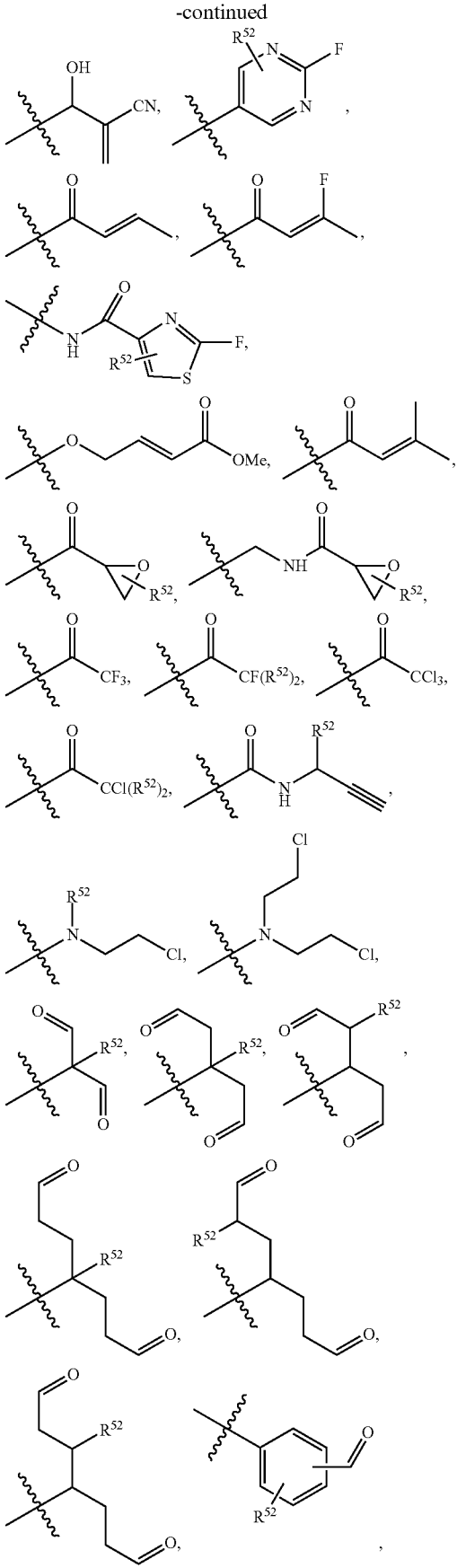

joined to form a substituted or unsubstituted cycloalkyl or substituted or unsubstituted heterocycloalkyl. In some embodiments, $R^{52}$ is hydrogen. In some embodiments, $R^{52}$ is methyl. In some embodiments, $R^{52}$ is ethyl. In some embodiments, $R^{52}$ is —CN. In some embodiments, $R^{52}$ is —$NO_2$.

$R^{53}$, $R^{54}$, $R^{55}$, and $R^{56}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{53}$ and $R^{54}$ substituents bonded to the same nitrogen atom may optionally be joined to form a substituted or unsubstituted heterocycloalkyl or substituted or unsubstituted heteroaryl. In some embodiments, $R^{53}$, $R^{54}$, $R^{55}$, and $R^{56}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol p is independently 1 or 2. In some embodiments, p is 1. In some embodiments, p is 2. The symbol q is independently an integer from 1 to 2. In some embodiments, q is 1. In some embodiments, q is 2. The symbol r is independently an integer from 0 to 4. In some embodiments, r is 0. In some embodiments, r is 1. In some embodiments, r is 2. In some embodiments, r is 3. In some embodiments, r is 4. $X^a$ is independently —Cl, —Br, —I, or —F. In some embodiments, $X^a$ is —Cl. In some embodiments, $X^a$ is —Br. In some embodiments, $X^a$ is —I. In some embodiments, $X^a$ is —F.

In some embodiments, each E is independently selected from the group consisting of:

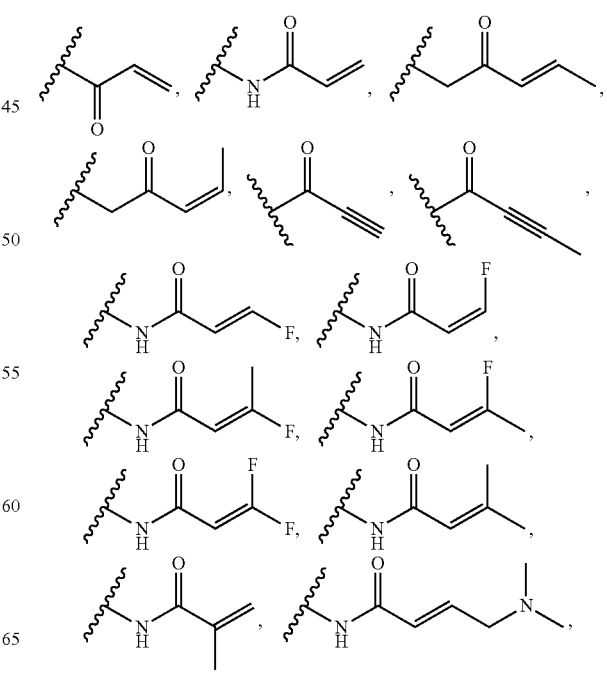

-continued

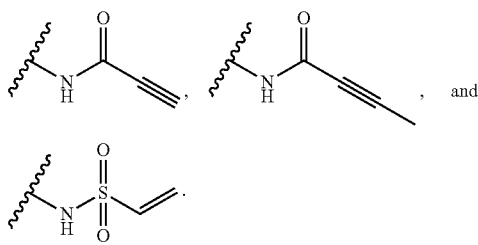, and

In some embodiments, each E is independently selected from the group consisting of

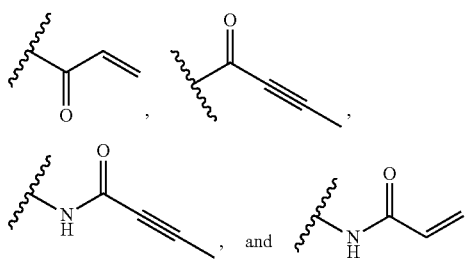, and

In some embodiments,

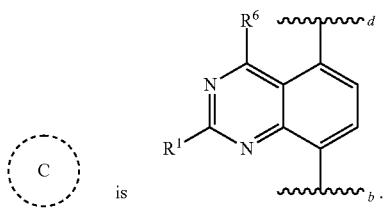 is 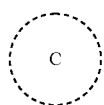

In some embodiments,

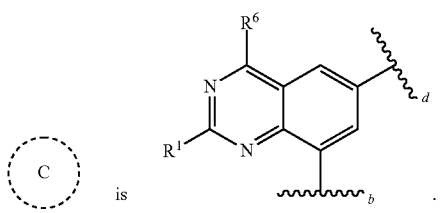 is

In some embodiments,

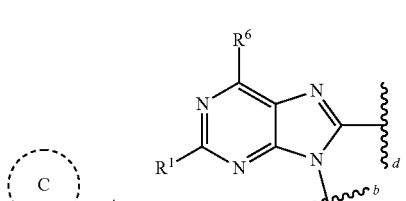 is

In some embodiments, wherein

 is 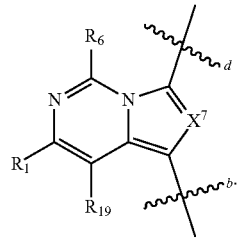

In some embodiments,

 is 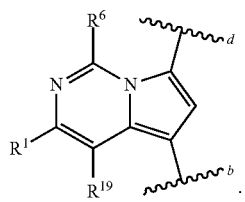

In some embodiments,

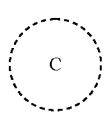 is 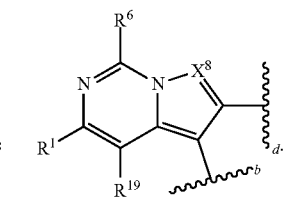

In some embodiments,

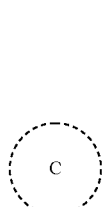 is 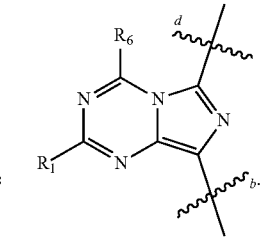

In some embodiments, $R^1$, $R^3$, $R^4$, $R^5$, $R^6$, $R^{20}$ and $R^{21}$ are independently selected from the group consisting of hydrogen, cyano, halo, hydroxy, optionally substituted alkyl, optionally substituted aryl, optionally substituted heteroaryl, and optionally substituted amino. In some embodiments, $R^1$, $R^3$, $R^4$, $R^5$, $R^6$, $R^{20}$ and $R^{21}$ are independently selected from the group consisting of hydrogen, optionally substituted aryl and optionally substituted amino. In some embodiments, $R^1$, $R^3$, $R^4$, $R^5$, $R^6$, $R^{20}$ and $R^{21}$ are independently selected from the group consisting of hydrogen and optionally substituted amino.

In some embodiments, $R^1$ is selected from the group consisting of hydrogen, cyano, halo, hydroxy, optionally substituted alkyl, optionally substituted aryl, optionally substituted heteroaryl, and optionally substituted amino. In some embodiments, $R^1$ is selected from the group consisting of hydrogen, optionally substituted aryl and optionally substituted amino. In some embodiments, $R^1$ is selected from hydrogen and —NH$_2$. In some embodiments, R$^1$ is hydrogen. In some embodiments, R$^1$ is optionally substituted aryl. In some embodiments, R$^1$ is optionally substituted amino.

In some embodiments, R$^6$ is selected from the group consisting of hydrogen, cyano, halo, hydroxy, optionally substituted alkyl, optionally substituted aryl, optionally substituted heteroaryl, and optionally substituted amino. In some embodiments, R$^6$ is selected from the group consisting of hydrogen, optionally substituted aryl and optionally substituted amino. In some embodiments, R$^6$ is selected from hydrogen and —NH$_2$. In some embodiments, R$^6$ is hydrogen. In some embodiments, R$^6$ is optionally substituted aryl. In some embodiments, R$^6$ is optionally substituted amino In some embodiments, R$^{19}$ is hydrogen.
In some embodiments, X$^3$ is CH.
In some embodiments, X$^4$ is CH.
In some embodiments, X$^5$ is CH.
In some embodiments, X$^7$ is CH.
In some embodiments, X$^8$ is CH.
In some embodiments,

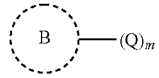

is selected from the group consisting of

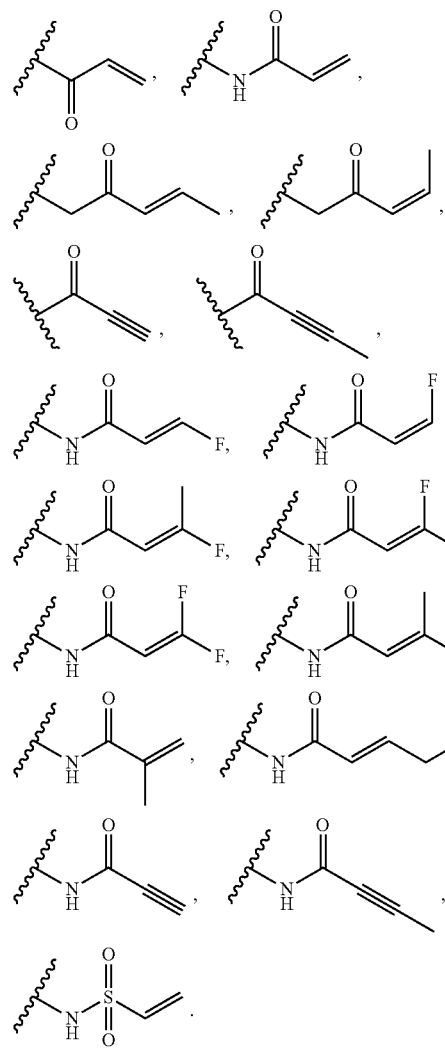

L$^1$ and L$^2$ are each a bond; Z is independently selected at each occurrence from cyano, halo, optionally substituted aryloxy, optionally substituted amino, and optionally substituted aminocarbonyl; R$^1$ is selected from the group consisting of hydrogen, cyano, halo, hydroxy, optionally substituted alkyl, optionally substituted aryl, optionally substituted heteroaryl, and optionally substituted amino; and R$^6$ is selected from hydrogen and —NH$_2$.

In some embodiments, L$^1$ and L$^2$ are each a bond;

is selected from the group consisting of phenyl and 5- to 8-membered heterocycloalkyl; m is 1, 2, 3 or 4; Q is independently selected at each occurrence from cyano, halo, hydroxy, azido, nitro, carboxy, oxo, sulfinyl, sulfanyl, sulfonyl, alkoxy, alkyl, haloalkyl, alkenyl, alkynyl, amino, acyl, alkoxycarbonyl, aminocarbonyl, aminosulfonyl, carbamimidoyl and E; and E is selected from the group consisting of:

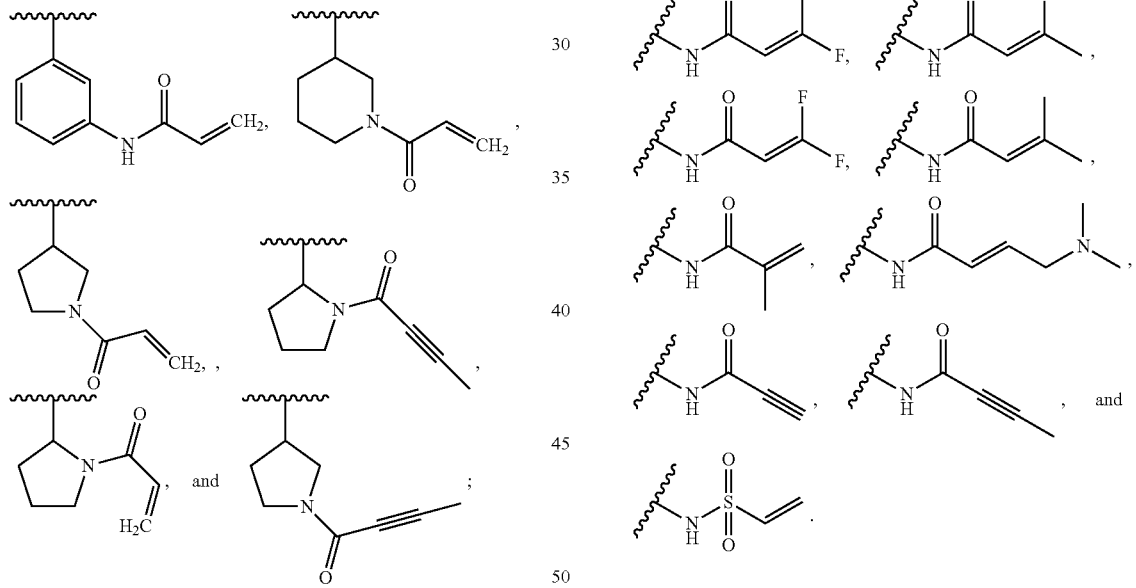

In some embodiments, the compounds have the Formula Ia:

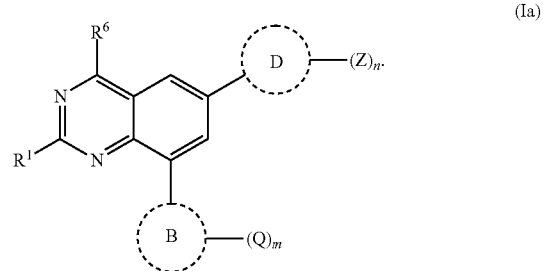

(Ia)

In some embodiments, the compounds have the Formula Ib:

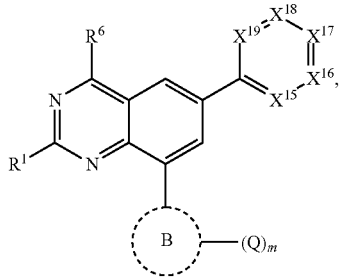

(Ib)

wherein
X$^{15}$ is N or CR$^{43}$;
X$^{16}$ is N or CR$^{44}$;
X$^{17}$ is N or CR$^{45}$;
X$^{18}$ is N or CR$^{46}$;
X$^{19}$ is N or CR$^{47}$; and
R$^{43}$, R$^{44}$, R$^{45}$, R$^{46}$ and R$^{47}$ are independently selected from hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl and E; wherein E is an electrophilic group capable of forming a covalent bond with a nucleophile.

In some embodiments, E comprises a substituted or unsubstituted vinyl sulfone moiety, substituted or unsubstituted vinyl sulfonamide moiety, substituted or unsubstituted fluoro(C$_1$-C$_4$)alkylketone moiety, substituted or unsubstituted chloro(C$_1$-C$_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

In some embodiments, E is selected from a group consisting of

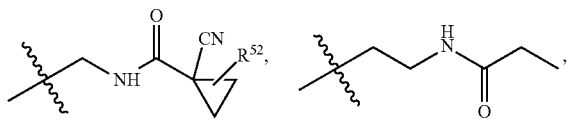

-continued

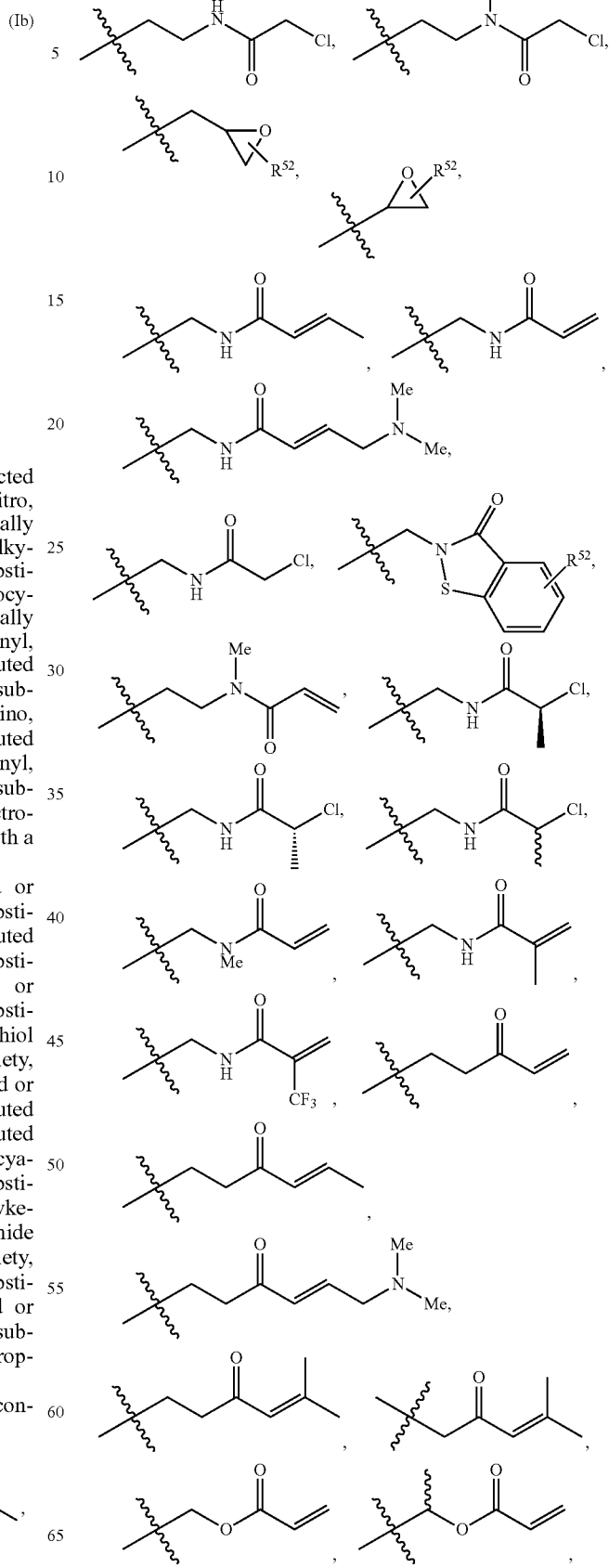

-continued
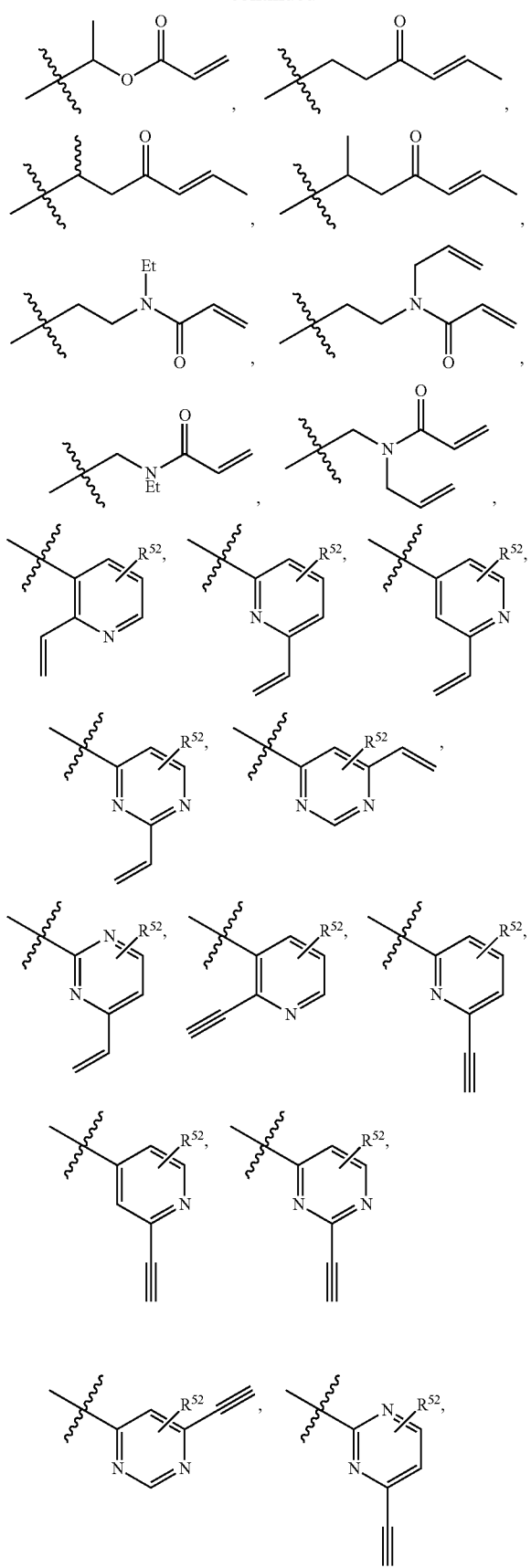
-continued
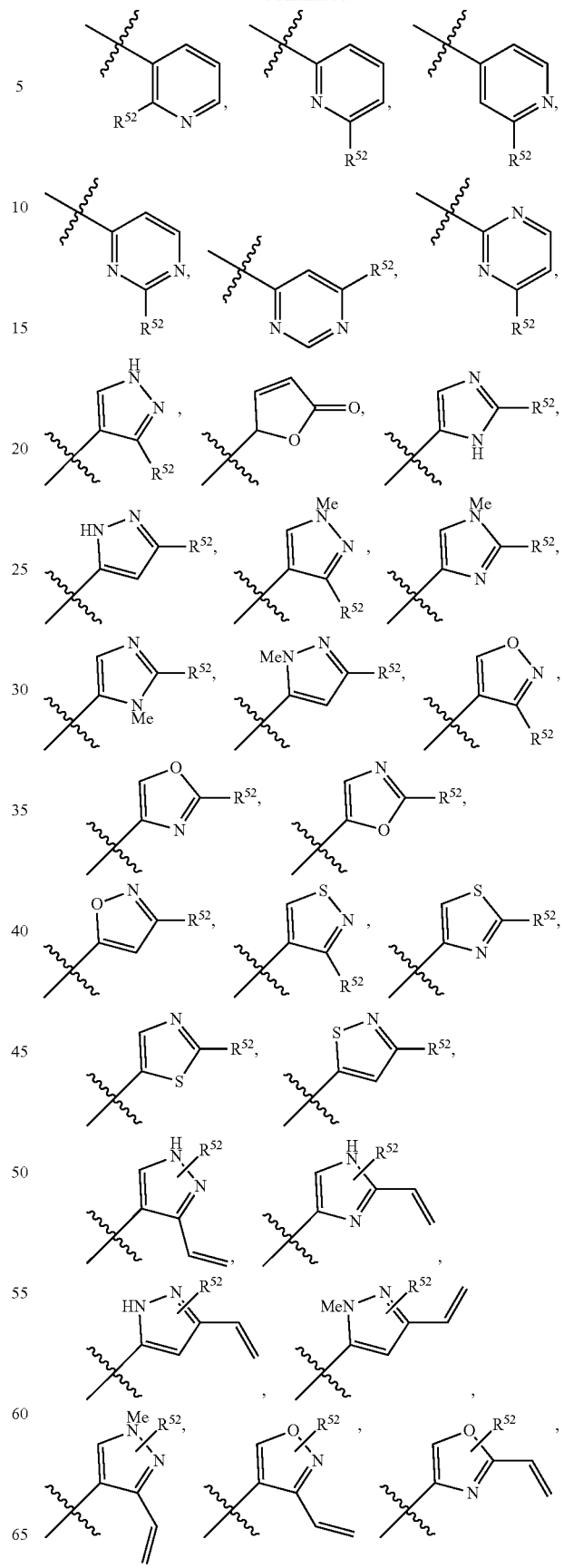

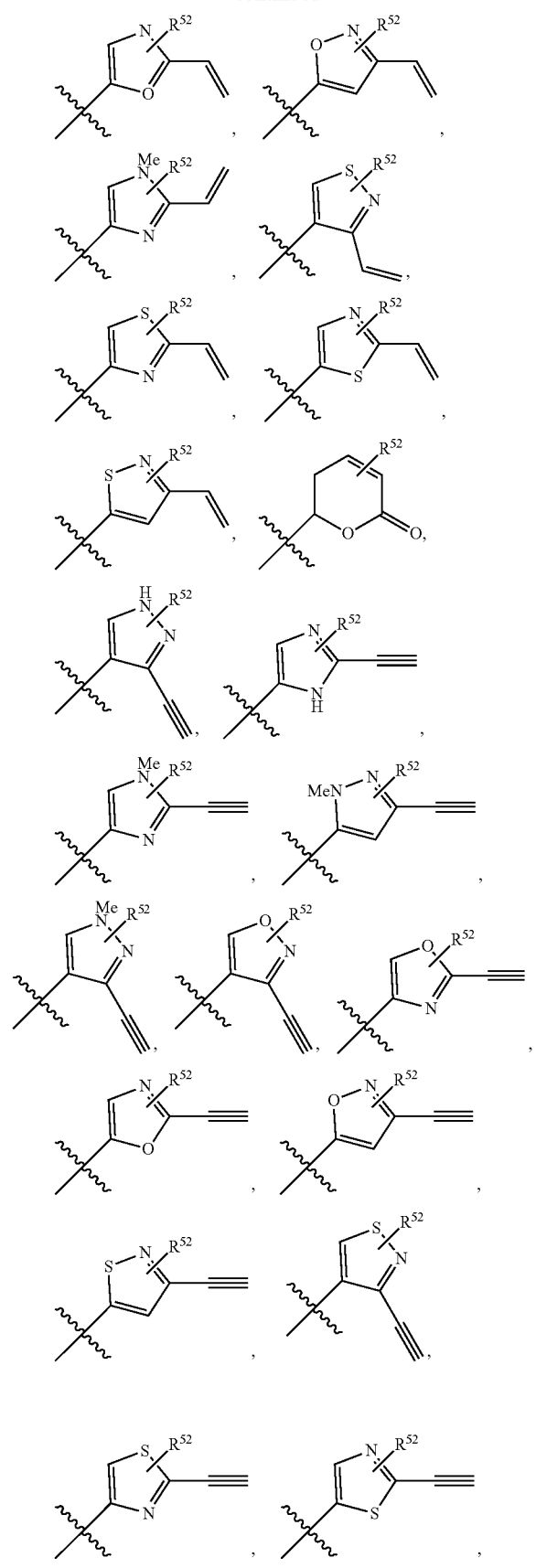
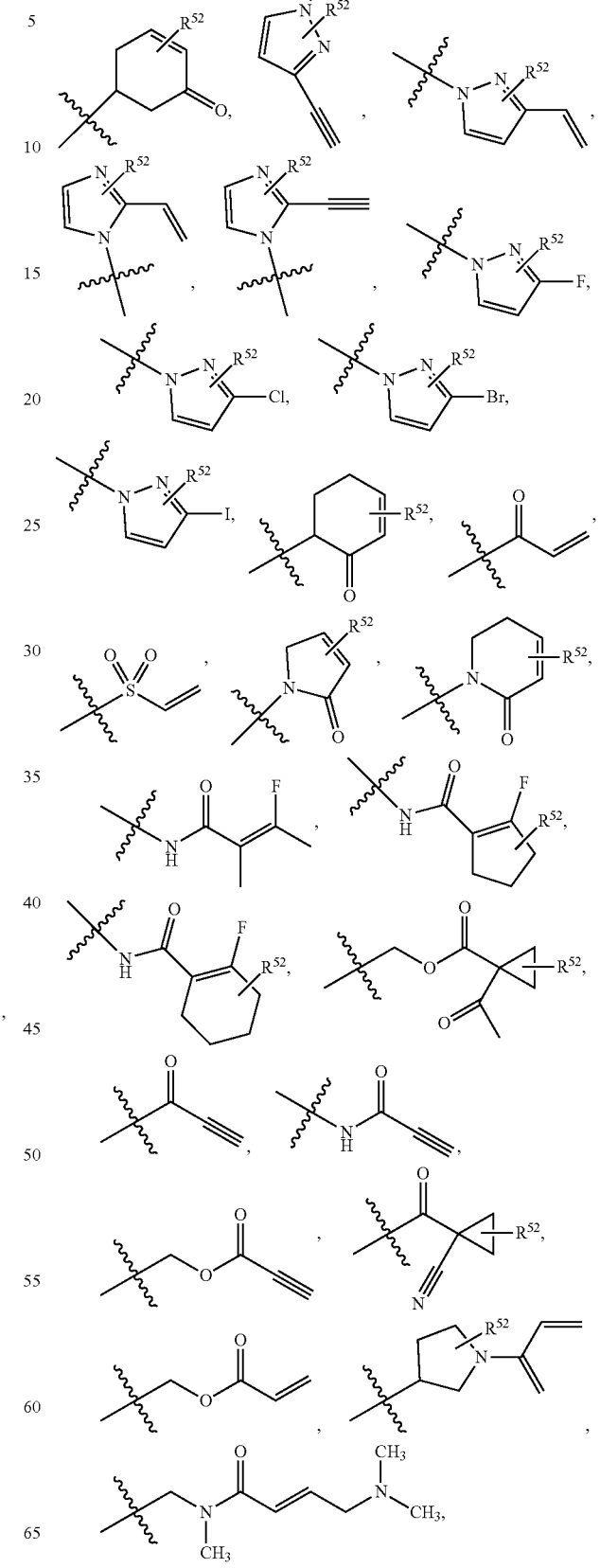

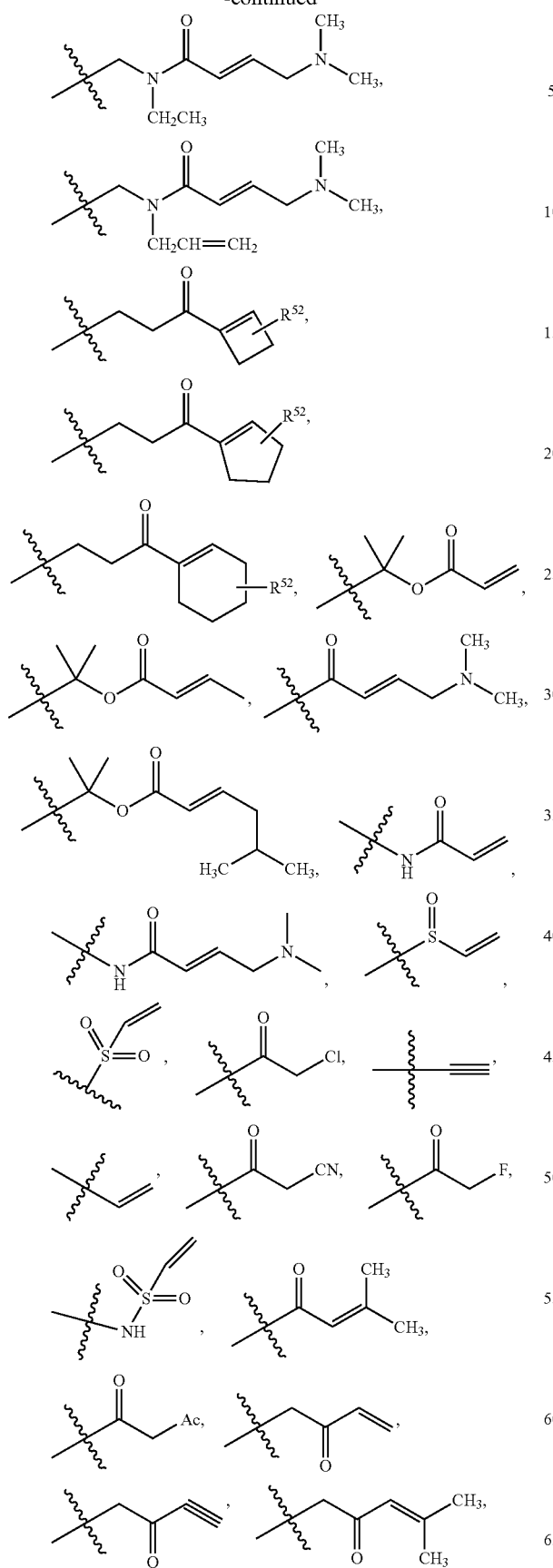
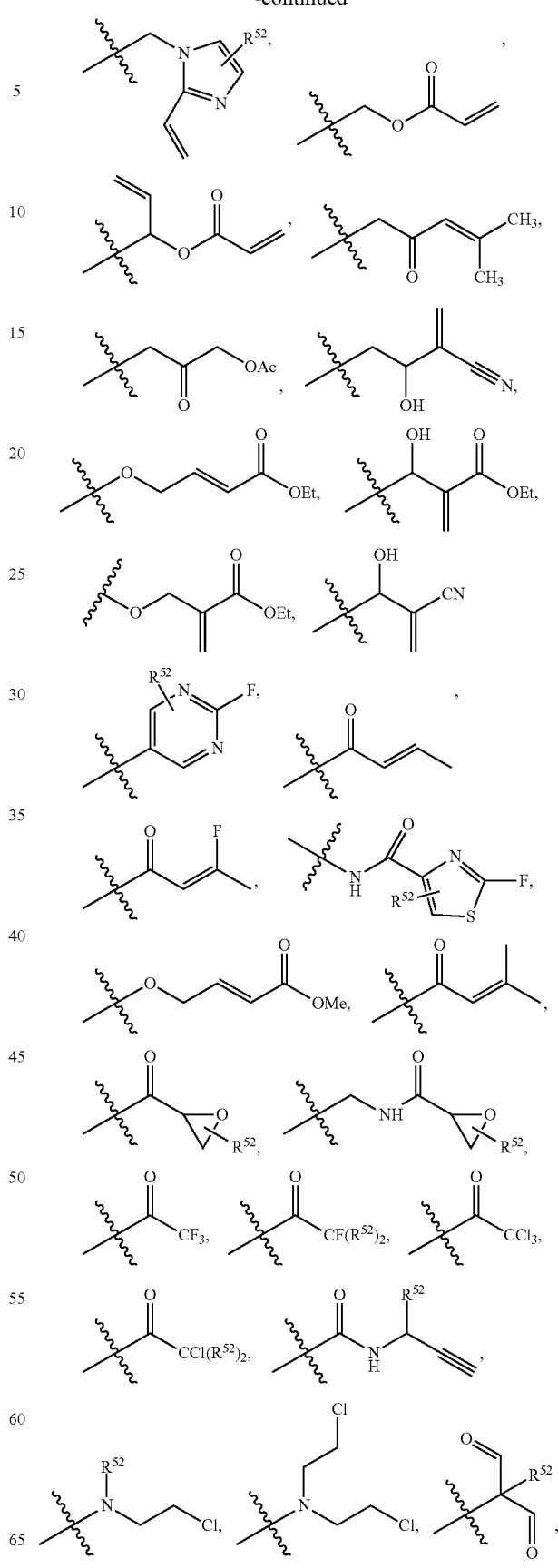

-continued

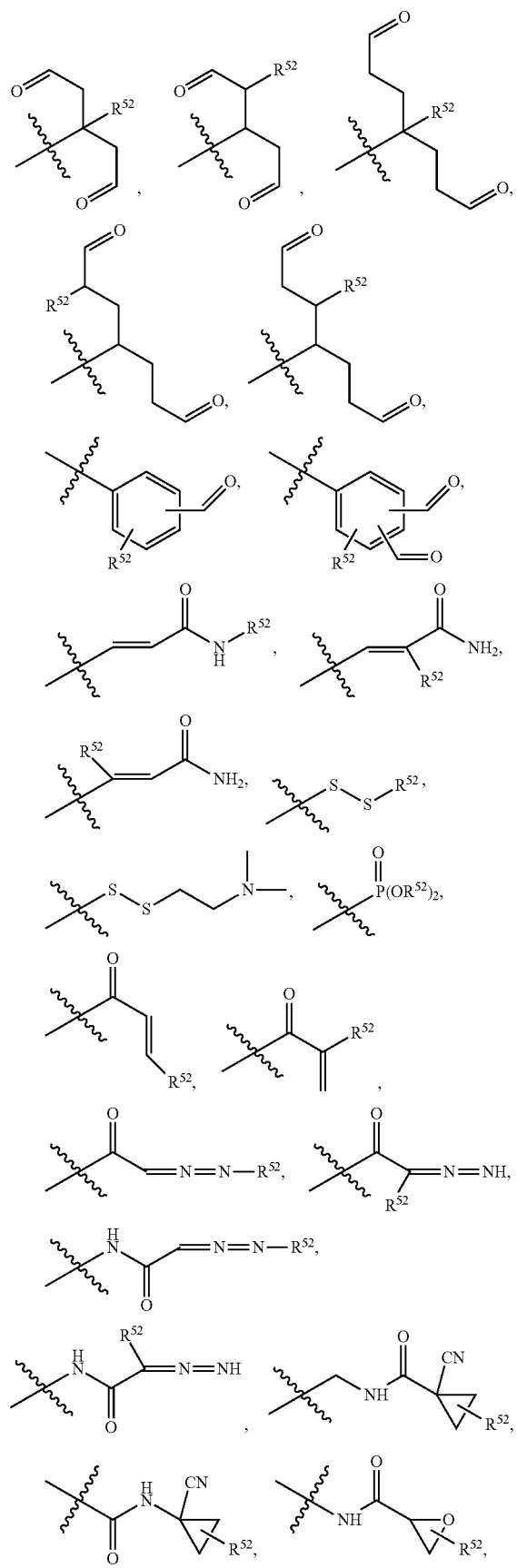

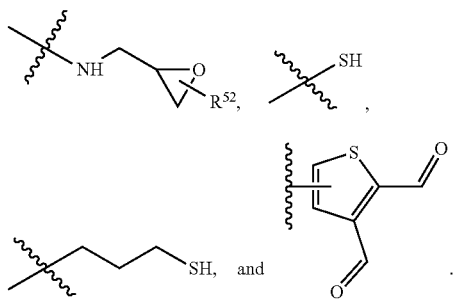

$R^{52}$ is independently hydrogen, oxo, halogen, —$CX^b_3$, —CN, —$SO_2Cl$, —$SO_rR^{56}$, —$SO_pNR^{53}R^{54}$, —$NHNH_2$, —$ONR^{53}R^{54}$, —$NHC=(O)NHNH_2$, —$NHC=(O)NR^{53}R^{54}$, —$N(O)_q$, —$NR^{53}R^{54}$, —$C(O)R^{55}$, —$C(O)OR^{55}$, —$C(O)NR^{53}R^{54}$, —$OR^{56}$, —$NR^{53}SO_2R^{56}$, —$NR^{53}C=(O)R^{55}$, —$NR^{53}C(O)$—$OR^{55}$, —$NR^{53}OR^{55}$, —$OCX^b_3$, —$OCHX^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^{52}$ substituents may optionally be joined to form a substituted or unsubstituted cycloalkyl, substituted or unsubstituted heterocycloalkyl, substituted or unsubstituted aryl, or substituted or unsubstituted heteroaryl. Two $R^{52}$ substituents bonded to the same atom may optionally be joined to form a substituted or unsubstituted cycloalkyl or substituted or unsubstituted heterocycloalkyl. In some embodiments, $R^{52}$ is hydrogen. In some embodiments, $R^{52}$ is methyl. In some embodiments, $R^{52}$ is ethyl. In some embodiments, $R^{52}$ is —CN. In some embodiments, $R^{52}$ is —$NO_2$.

$R^{53}$, $R^{54}$, $R^{55}$, and $R^{56}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{53}$ and $R^{54}$ substituents bonded to the same nitrogen atom may optionally be joined to form a substituted or unsubstituted heterocycloalkyl or substituted or unsubstituted heteroaryl. In some embodiments, $R^{53}$, $R^{54}$, $R^{55}$, and $R^{56}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol p is independently 1 or 2. In some embodiments, p is 1. In some embodiments, p is 2. The symbol q is independently an integer from 1 to 2. In some embodiments, q is 1. In some embodiments, q is 2. The symbol r is independently an integer from 0 to 4. In some embodiments, r is 0. In some embodiments, r is 1. In some embodiments, r is 2. In some embodiments, r is 3. In some embodiments, r is 4. $X^a$ is independently —Cl, —Br, —I, or —F. In some embodiments, $X^a$ is —Cl. In some embodiments, $X^a$ is —Br. In some embodiments, $X^a$ is —I. In some embodiments, $X^a$ is —F.

In some embodiments,
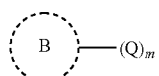
is selected from the group consisting of
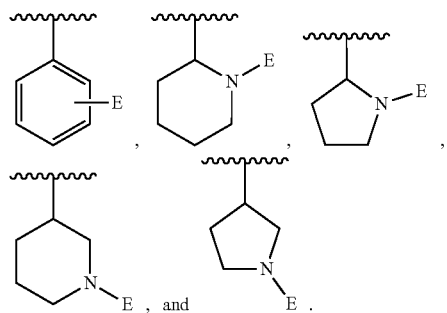
In some embodiments,
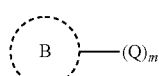
is selected from the group consisting of
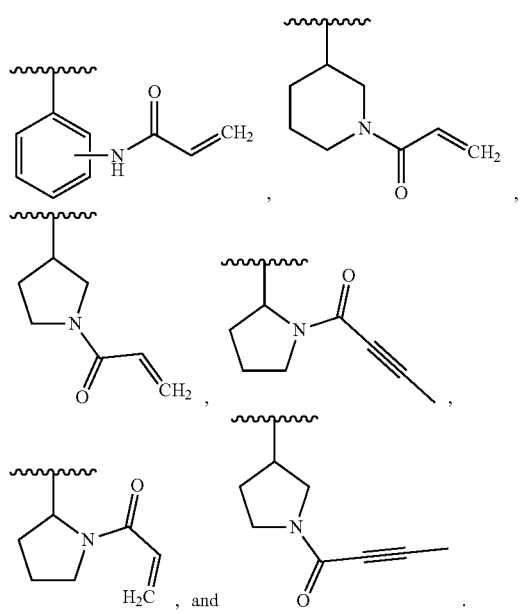
In some embodiments,
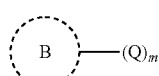
is selected from the group consisting of
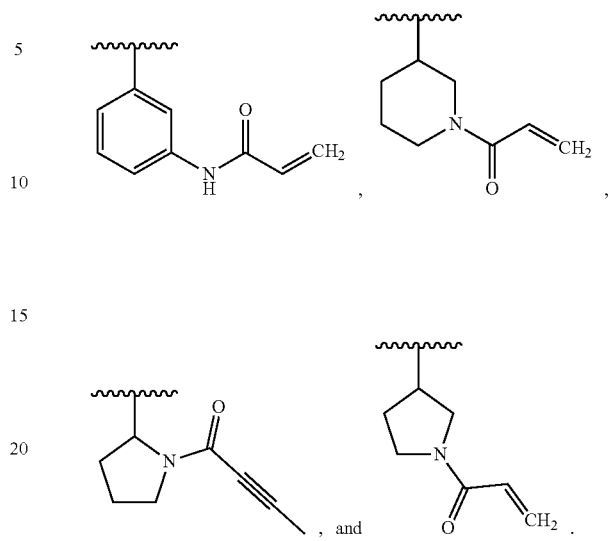
In some embodiments,
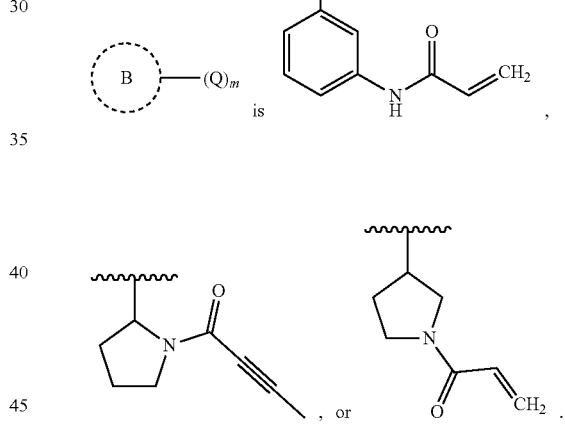
In some embodiments, the compounds have the Formula Ic:
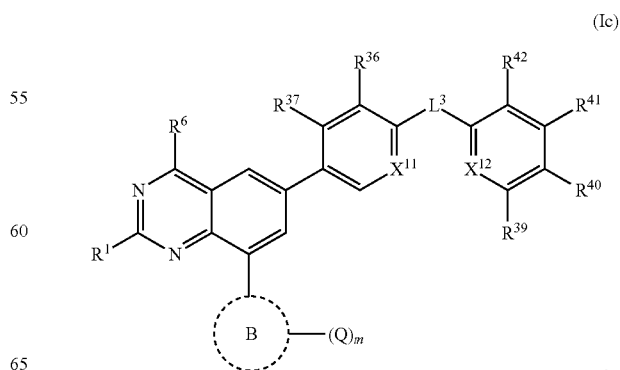

In some embodiments, the compounds have the Formula Id:

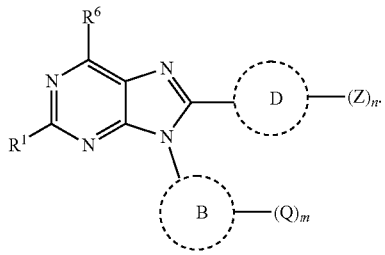
(Id)

In some embodiments, the compounds have the Formula Ie:

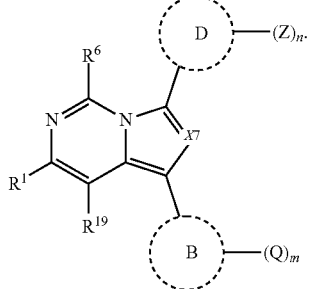
(Ie)

In some embodiments, the compounds have the Formula If:

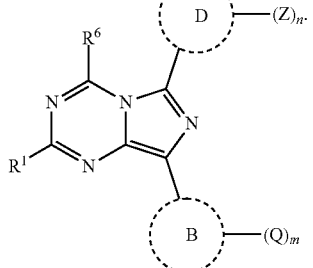
(If)

In some embodiments, the compounds have the Formula Ig:

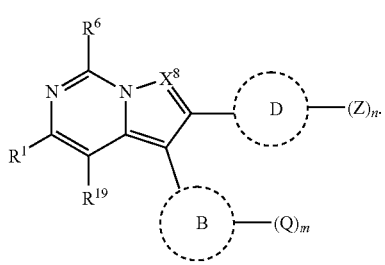
(Ig)

In some embodiments, for the compounds of Formula Ic, Id, Ie, If, and Ig,

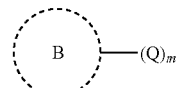

is selected from the group consisting of

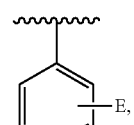

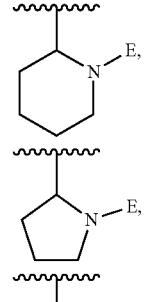

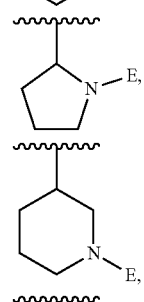

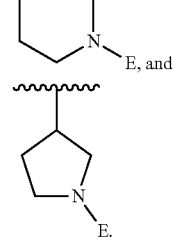

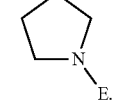

In some embodiments,

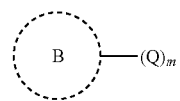

is selected from the group consisting of

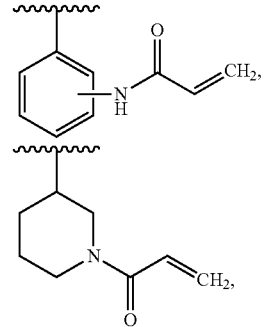

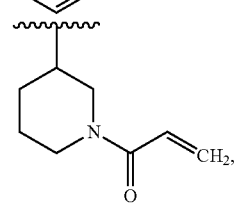

-continued

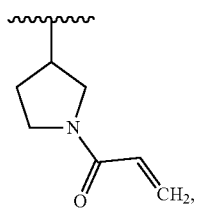

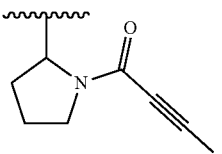

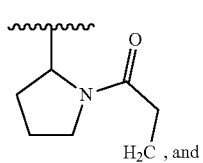

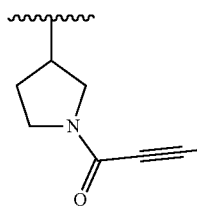

In some embodiments,

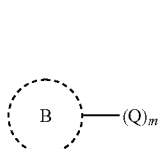 is 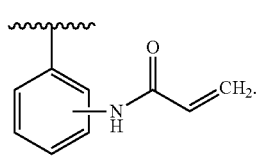

In some embodiments,

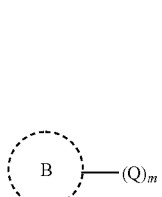 is 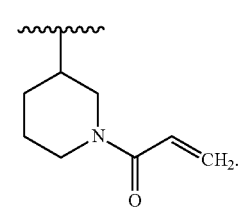

In some embodiments,

 is 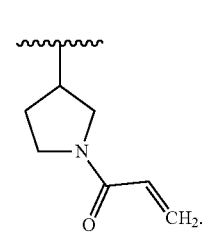

In some embodiments,

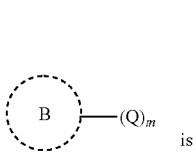 is 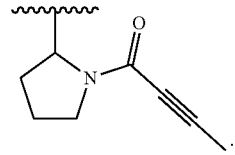

In some embodiments,

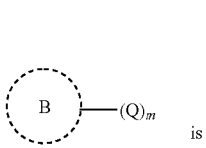 is 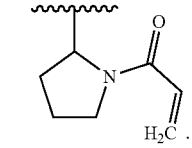

In some embodiments,

 is 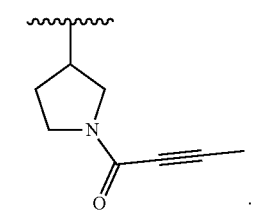

In some embodiments, for the compounds of Formula Ic, Id, Ie, If, and Ig,

 is: 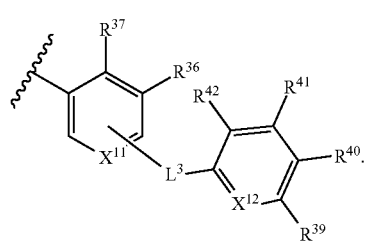

In some embodiments, $L^3$ is selected from —O— and —C(O)NH—. In some embodiments, $L^3$ is —C(O)NH—. In some embodiments, $L^3$ is —O—. In some embodiments, $X^{11}$ is C—$R^{35}$. In some embodiments, $X^{12}$ is N. In some embodiments, $R^{35}$, $R^{36}$, $R^{37}$, $R^{38}$, $R^{39}$, $R^{40}$, $R^{41}$, and $R^{42}$ are each independently selected from the group consisting of hydrogen, chloro, fluoro, cyano, cyclopropyl, —CH$_3$, —CF$_3$, —OCH$_3$ and —OPh. In some embodiments, $R^{35}$, $R^{36}$, $R^{37}$, $R^{38}$, $R^{39}$, $R^{40}$, $R^{41}$, and $R^{42}$ are each independently selected from the group consisting of hydrogen, cyclopropyl, —CF$_3$, and —OCH$_3$.

In another aspect, the present disclosure provides a compound of Formula (II):

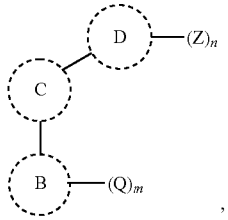

or a pharmaceutically acceptable salt thereof, wherein:

is selected from the group consisting of aryl, heteroaryl and heterocycloalkyl, each of which is substituted with E;

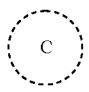

is optionally substituted heteroaryl;

is selected from the group consisting of aryl, heteroaryl and heterocycloalkyl;

Q and Z are each independently selected at each occurrence from hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl and E;

E is an electrophilic group capable of forming a covalent bond with a nucleophile; and m and n are each independently 0, 1, 2, 3, 4 or 5.

In some embodiments, E comprises a substituted or unsubstituted vinyl sulfone moiety, substituted or unsubstituted vinyl sulfonamide moiety, substituted or unsubstituted fluoro($C_1$-$C_4$)alkylketone moiety, substituted or unsubstituted chloro($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

In some embodiments, E is selected from a group consisting of

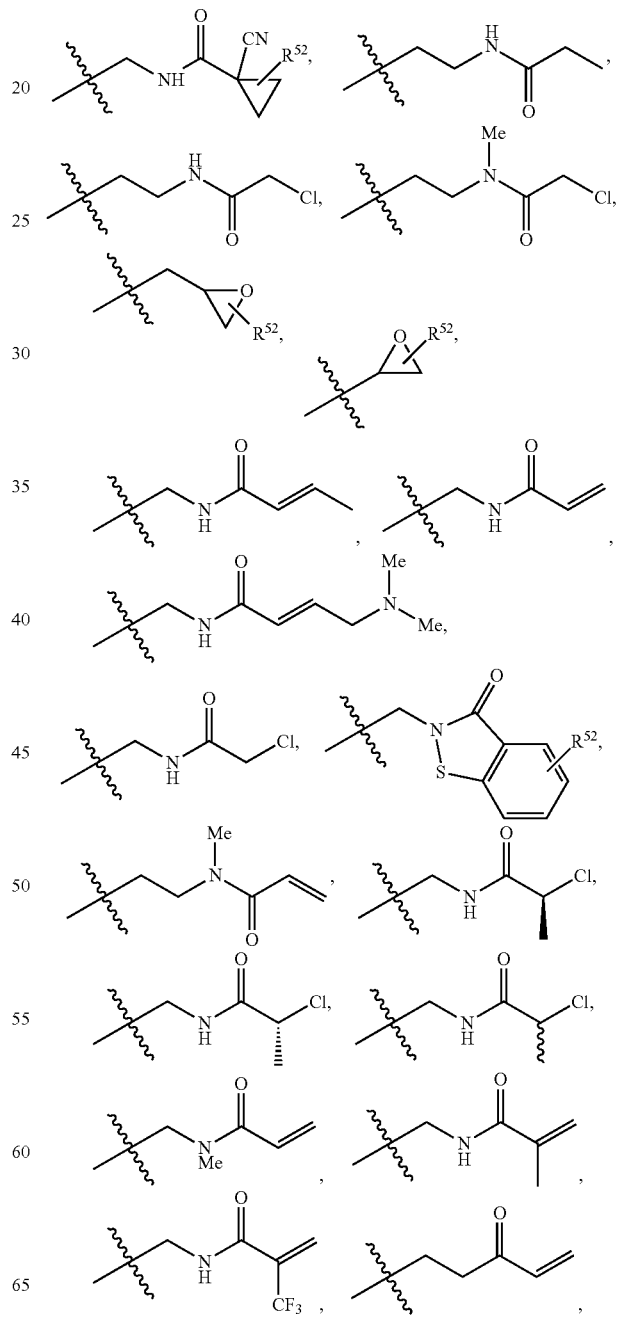

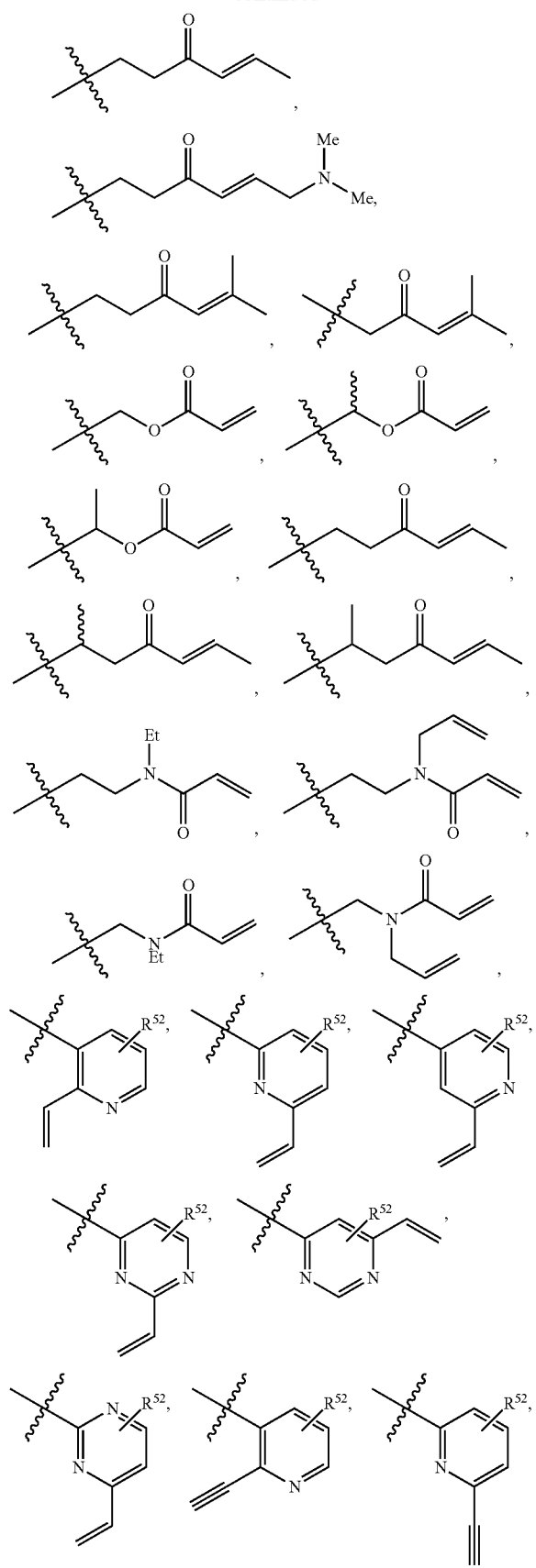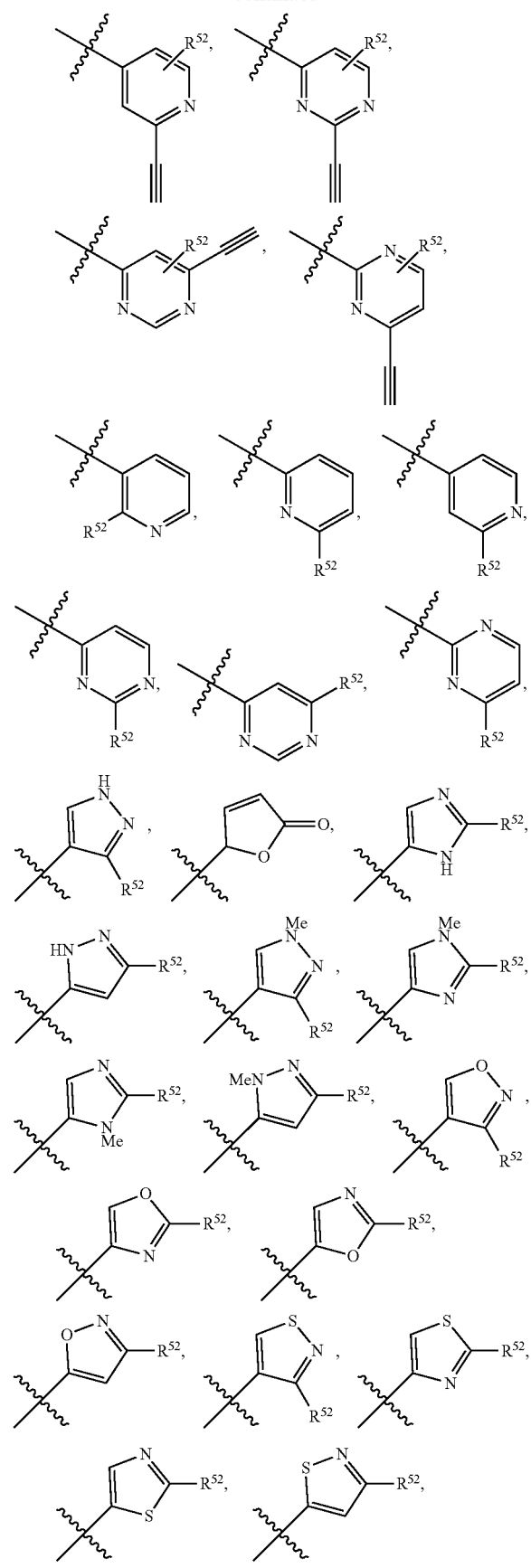

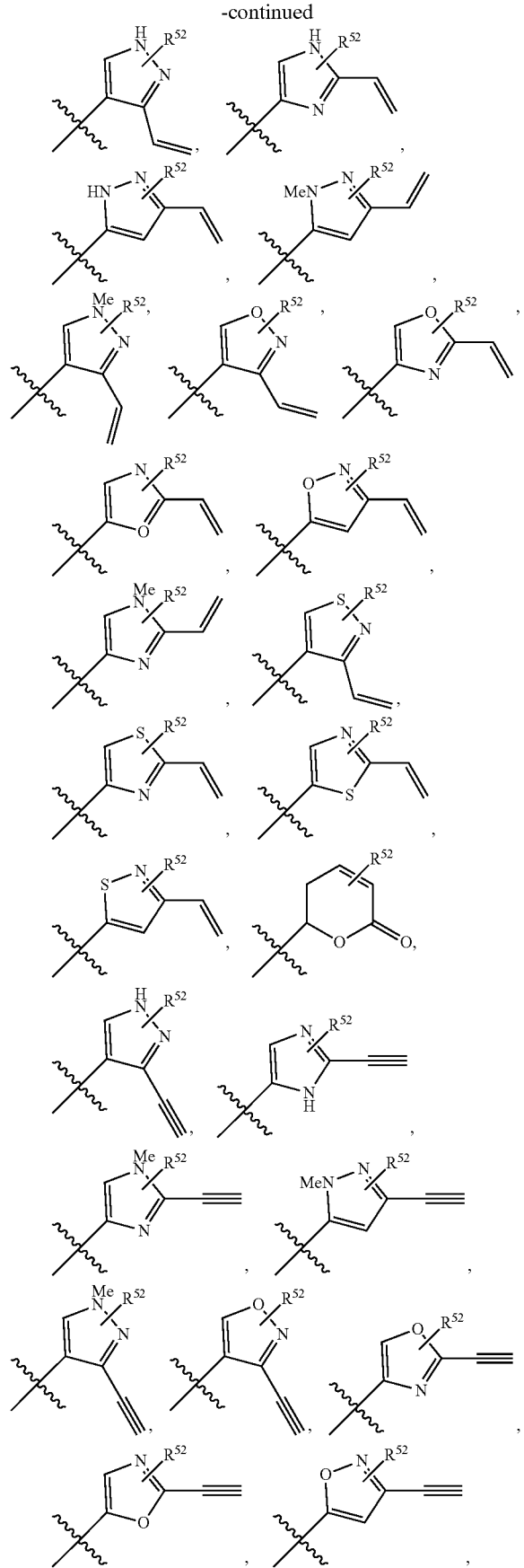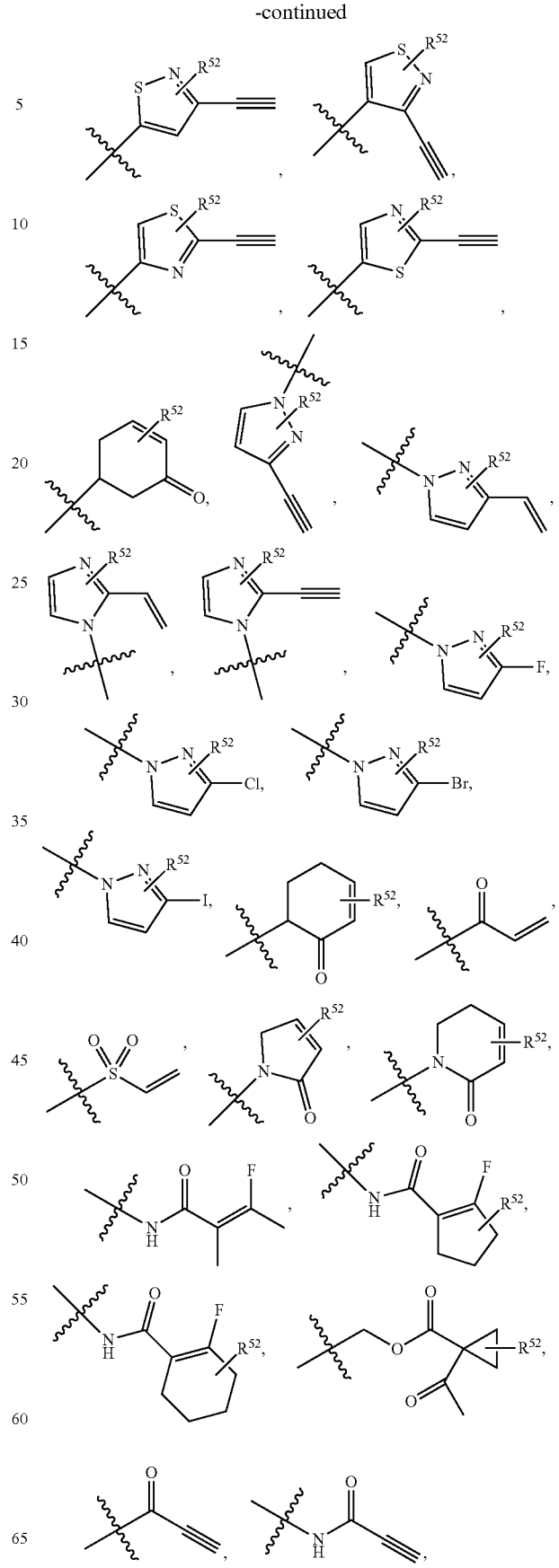

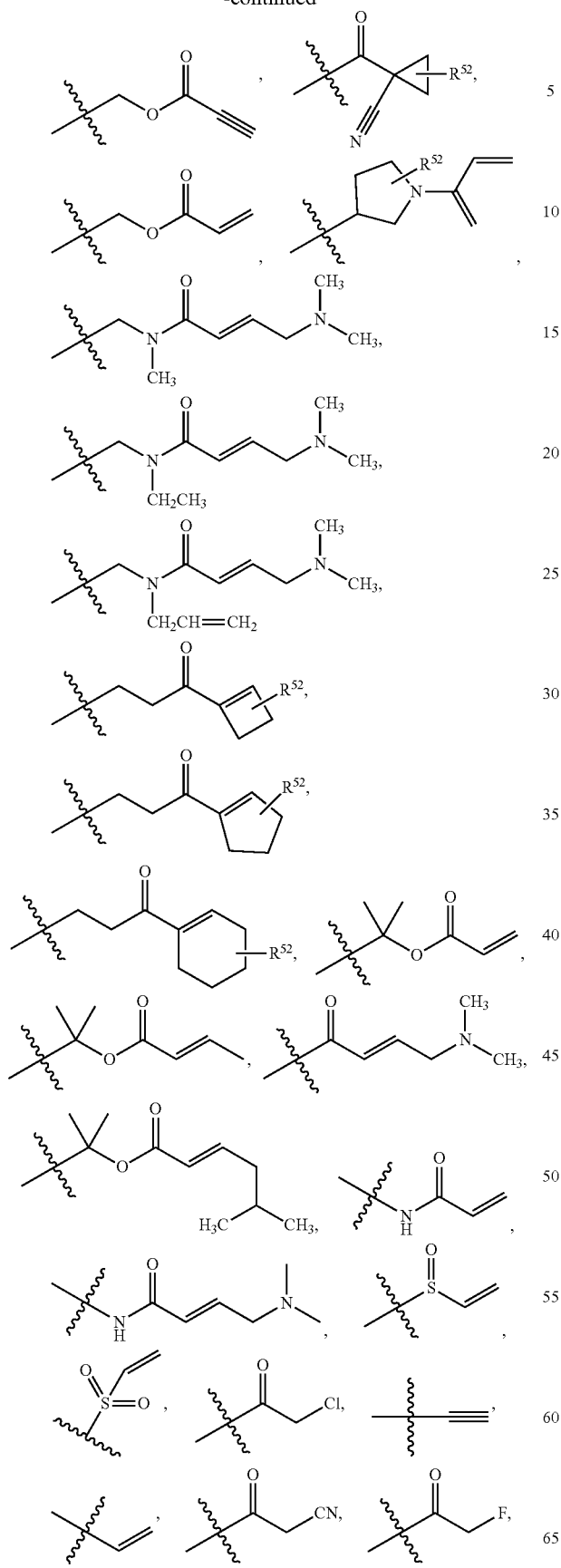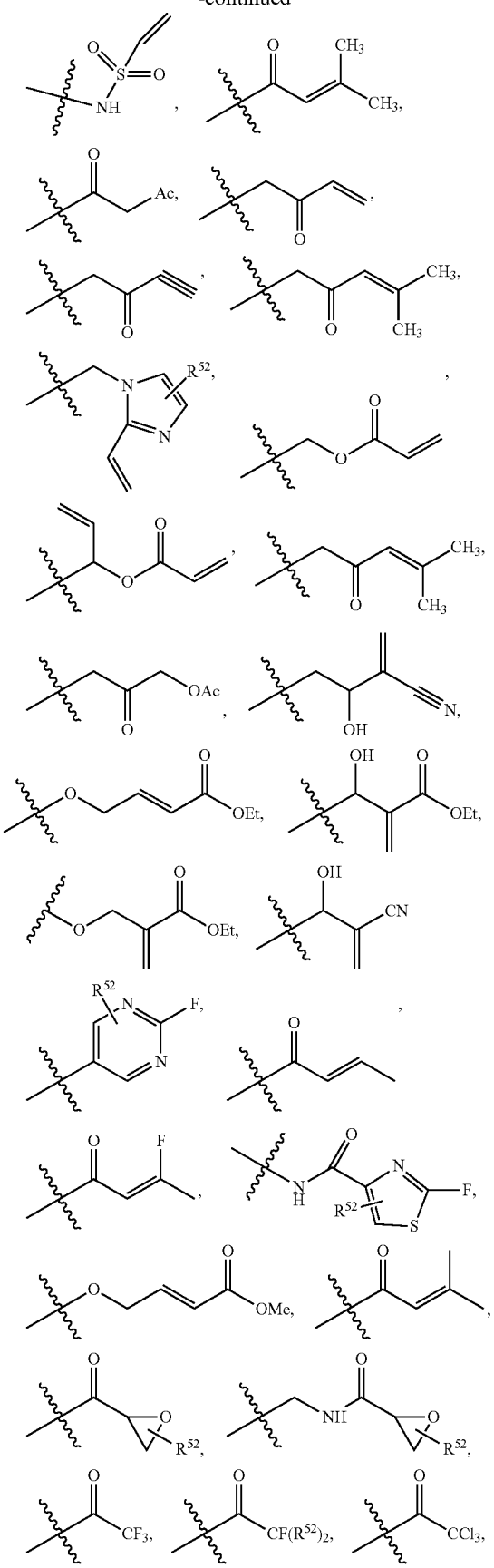

-continued

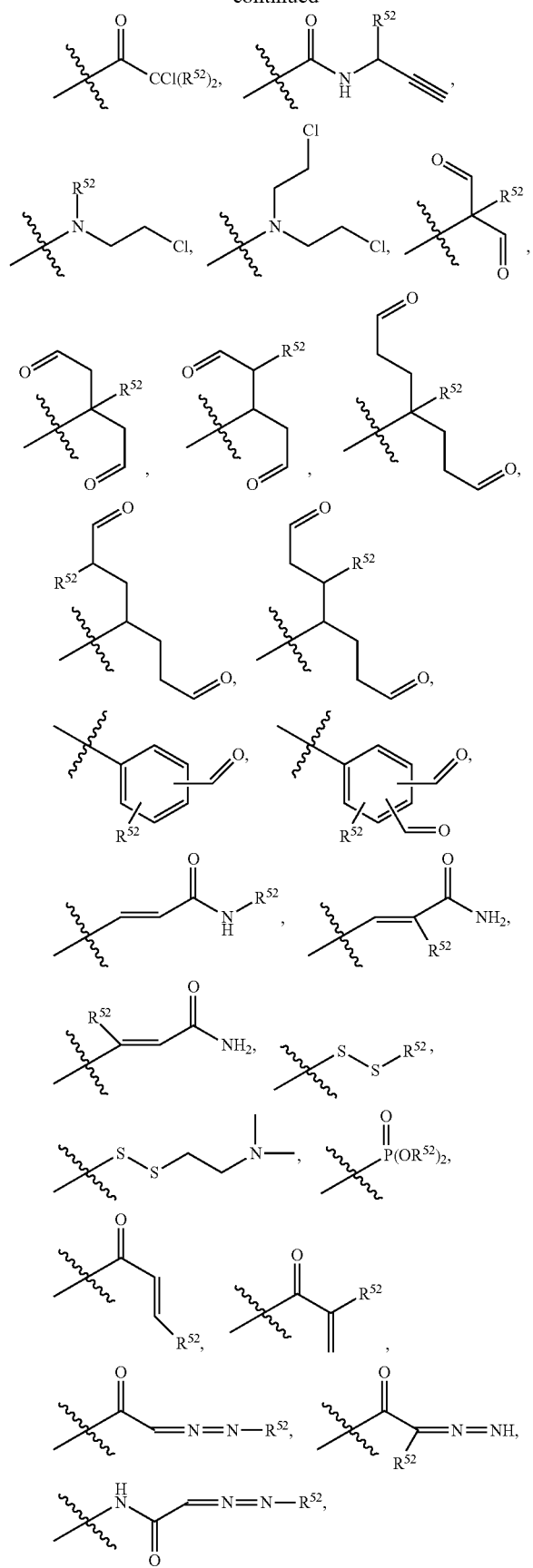

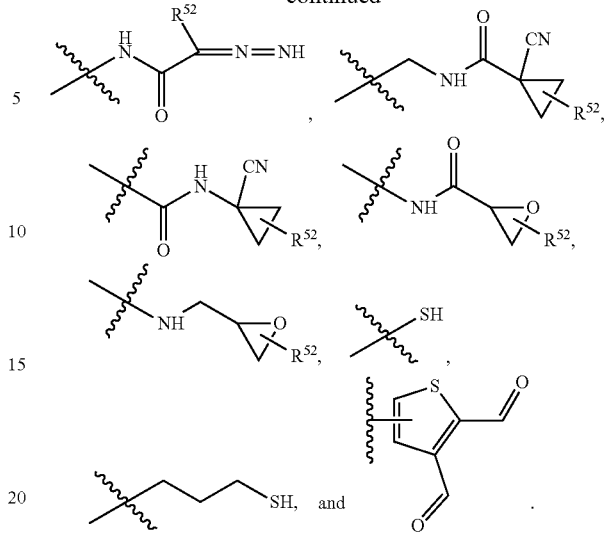

$R^{52}$ is independently hydrogen, oxo, halogen, $-CX^b_3$, $-CN$, $-SO_2Cl$, $-SO_rR^{56}$, $-SO_pNR^{53}R^{54}$, $-NHNH_2$, $-ONR^{53}R^{54}$, $-NHC=(O)NHNH_2$, $-NHC=(O)NR^{53}R^{54}$, $-N(O)_q$, $-NR^{53}R^{54}$, $-C(O)R^{55}$, $-C(O)-OR^{55}$, $-C(O)NR^{53}R^{54}$, $-OR^{56}$, $-NR^{53}SO_2R^{56}$, $-NR^{53}C=(O)R^{55}$, $-NR^{53}C(O)-OR^{55}$, $-NR^{53}OR^{55}$, $-OCX^b_3$, $-OCHX^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^{52}$ substituents may optionally be joined to form a substituted or unsubstituted cycloalkyl, substituted or unsubstituted heterocycloalkyl, substituted or unsubstituted aryl, or substituted or unsubstituted heteroaryl. Two $R^{52}$ substituents bonded to the same atom may optionally be joined to form a substituted or unsubstituted cycloalkyl or substituted or unsubstituted heterocycloalkyl. In some embodiments, $R^{52}$ is hydrogen. In some embodiments, $R^{52}$ is methyl. In some embodiments, $R^{52}$ is ethyl. In some embodiments, $R^{52}$ is $-CN$. In some embodiments, $R^{52}$ is $-NO_2$.

$R^{53}$, $R^{54}$, $R^{55}$, and $R^{56}$ are independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{53}$ and $R^{54}$ substituents bonded to the same nitrogen atom may optionally be joined to form a substituted or unsubstituted heterocycloalkyl or substituted or unsubstituted heteroaryl. In some embodiments, $R^{53}$, $R^{54}$, $R^{55}$, and $R^{56}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol p is independently 1 or 2. In some embodiments, p is 1. In some embodiments, p is 2. The symbol q is independently an integer from 1 to 2. In some embodiments, q is 1. In some embodiments, q is 2. The symbol r is independently an integer from 0 to 4. In some embodiments, r is 0. In some embodiments, r is 1. In some embodiments, r is 2. In some embodiments, r is 3. In some embodiments, r is 4. $X^a$ is independently —Cl, —Br, —I, or —F. In some embodiments, $X^a$ is —Cl. In some embodiments, $X^a$ is —Br. In some embodiments, $X^a$ is —I. In some embodiments, $X^a$ is —F.

In some embodiments, each E is selected from the group consisting of:

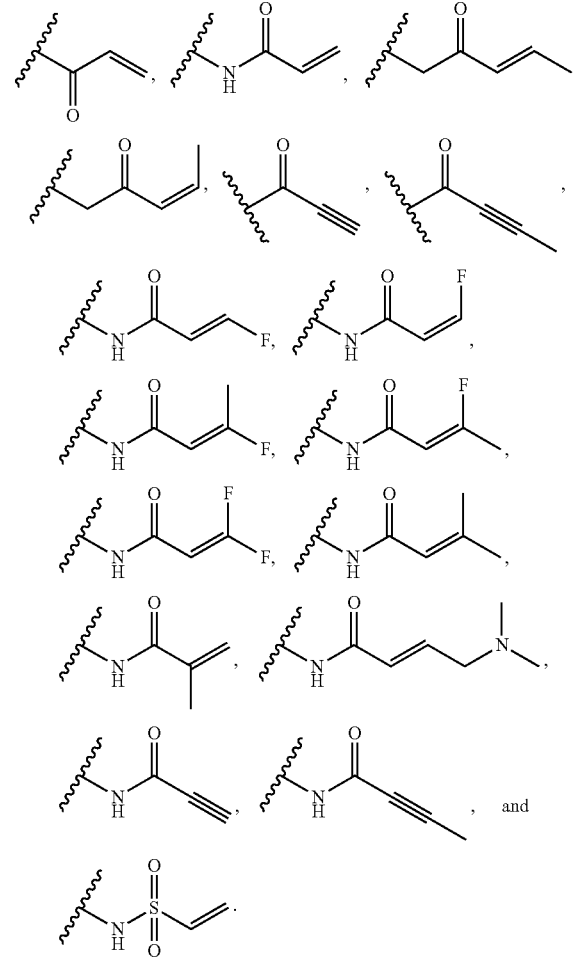

In some embodiments, each E is selected from the group consisting of:

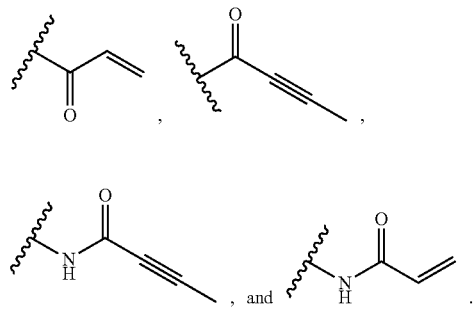

In some embodiments,

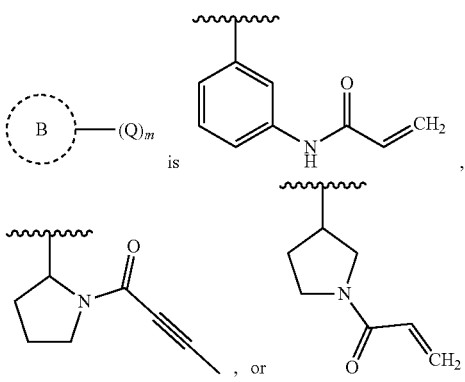

In some embodiments,

is optionally substituted quinazolinylene or optionally substituted purinylene. In some embodiments,

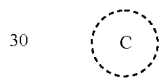

is optionally substituted quinazolinylene.

In some embodiments,

is aryl or heteroaryl.

In some embodiments, Z is independently selected at each occurrence from cyano, halo, optionally substituted aryloxy, optionally substituted amino, and optionally substituted aminocarbonyl.

In another aspect, the disclosure provides pharmaceutically acceptable salt of the compound disclosed herein. In some embodiments, the pharmaceutically acceptable salt is a chloride, carbonate, gluconate, benzoate, acetate, lactate, citrate, propionate, hydrogenphosphate, fumarate, succinate, TRIS (hydroxymethyl-aminomethane), maleate, malonate, tartrate, oxalate, pamoate, or stearate salt. In some embodiments, the pharmaceutically acceptable salt is a chloride, fumarate, malonate, maleate, acetate, lactate, citrate, succinate, or tartrate salt. salt is a chloride, fumarate, malonate, maleate, or tartrate salt.

In another aspect, the disclosure provides pharmaceutical composition comprising a pharmaceutically acceptable carrier and the compound or pharmaceutically acceptable salt disclosed herein. In some embodiments, the pharmaceutical composition is formulated in a form selected from the group consisting of tablets, capsules, powders, liquids, suspensions, suppositories, and aerosols.

In another aspect, the disclosure provides packaged pharmaceutical composition comprising the pharmaceutical composition described herein and instructions for using the composition to treat a subject suffering from cancer.

In another aspect, the disclosure provides a method of treating cancer in a subject, the method comprising administering to a subject in need thereof a therapeutically effective amount of the compound or salt disclosed herein. In some embodiments, the cancer is colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, thyroid cancer, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In some embodiments, the cancer is non-small cell lung cancer, breast cancer, colon cancer, thyroid cancer, or ovarian cancer.

In another aspect, the disclosure provides a method of treating a disorder mediated by EGFR in a subject in need thereof, the method comprising administering to the subject a therapeutically effective amount of the compound or salt described herein.

In another aspect, the disclosure provides a method of treating a disorder in a subject in need thereof, the method comprising: (a) determining the presence or absence of an EGFR mutation in a biological sample isolated from the subject; and (b) if the EGFR mutation or double mutation is determined to be present in the subject, administering to the subject a therapeutically effective amount of the compound or salt described herein. In some embodiments, the EGFR mutation is in codon 790. In some embodiments, the EGFR mutation is del E746-A750, del E747-E749/A750P, del E747-S752/P753S, del E747-T751/Sins/A750P, del S752-I759, G719S, G719C, L861Q, L858R, T790M, or L858R/T790M. In some embodiments, the determining the presence or absence of the EGFR mutation comprises amplifying EGFR nucleic acid from the biological sample and sequencing the amplified nucleic acid. In some embodiments, the determining the presence or absence of the EGFR mutation comprises detecting a mutant EGFR polypeptide in the biological sample using a binding agent to a mutant EGFR polypeptide. In some embodiments, the binding agent is an antibody. In some embodiments, the biological sample is isolated from a tumor of the subject.

In another aspect, the disclosure provides a method of treating a disorder mediated by BTK in a subject in need thereof, the method comprising administering to the subject a therapeutically effective amount of the compound or salt described herein. In some embodiments, the disorder is cancer. In some embodiments, the cancer is colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease. In some embodiments, the cancer is non-small cell lung cancer, colon cancer, thyroid cancer, or ovarian cancer.

In some embodiments, the methods disclosed herein further comprise administering an additional anti-cancer and/or cytotoxic agent.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DETAILED DESCRIPTION OF THE INVENTION

As used herein, the following words and phrases are generally intended to have the meanings as set forth below, except to the extent that the context in which they are used indicates otherwise.

The following abbreviations and terms have the indicated meanings throughout:

AcOH=acetic acid
Boc=tert-butoxycarbonyl
c-=cyclo
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr hour
HBTU=O-(benzotriazol-1-yl)-N,N,N',N'-tetramethyluronium hexafluorophosphate
HOBt=hydroxybenzotriazole
HPLC=high pressure liquid chromatography
i-=iso kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
n-=normal
NaOAc=sodium acetate
PE=petroleum ether
Ph=phenyl
Prep=preparative
quant.=quantitative
RP-HPLC=reverse phase-high pressure liquid chromatography
rt, r.t., or RT=room temperature
s-=sec-=secondary
satd.=saturated
t-=tert-=tertiary
THF=tetrahydrofuran
TLC=thin layer chromatography
UV=ultraviolet As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —CONH$_2$ is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

As used herein, "formyl" refers to the group —C(O)H.

As used herein, "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

As used herein, "azido" refers to the group —$N_3$.

As used herein, "amino" refers to the group —$NH_2$.

As used herein, "mono- and di-(alkyl)amino" refers to secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, "aminocarbonyl" refers to the group —CONR$^b$R$^c$, where
- R$^b$ is H, optionally substituted $C_1$-$C_6$ alkyl, optionally substituted cycloalkyl, optionally substituted heterocycloalkyl, optionally substituted aryl, optionally substituted heteroaryl, or optionally substituted alkoxy; and
- R$^c$ is hydrogen or optionally substituted $C_1$-$C_4$ alkyl; or
- R$^b$ and R$^c$ taken together with the nitrogen to which they are bound, form an optionally substituted 4- to 8-membered nitrogen-containing heterocycloalkyl which optionally includes 1 or 2 additional heteroatoms chosen from O, N, and S in the heterocycloalkyl ring;
- where each substituted group is independently substituted with one or more substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), or —NHSO$_2$($C_1$-$C_4$ haloalkyl).

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 4- to 8-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "aryloxy" refers to the group —O-aryl.
As used herein, "arylalkyl" refers to the group -alkyl-aryl.
As used herein, "carbamimidoyl" refers to the group —C(=NH)—NH2.

As used herein, "substituted carbamimidoyl" refers to the group —C(=NR$^e$)—NR$^f$R$^g$ where
- R$^e$ is hydrogen, cyano, optionally substituted alkyl, optionally substituted cycloalkyl, optionally substituted heterocycloalkyl, optionally substituted aryl, optionally substituted heteroaryl, or optionally substituted heterocycloalkyl; and
- R$^f$ and R$^g$ are independently hydrogen optionally substituted alkyl, optionally substituted cycloalkyl, optionally substituted aryl, optionally substituted heteroaryl, or optionally substituted heterocycloalkyl,
- provided that at least one of R$^e$, R$^f$, and R$^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently —R$^a$, —OR$^b$, optionally substituted amino (including —NR$^c$COR$^b$, —NR$^c$CO$_2$R$^a$, —NR$^c$-CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), or sulfonyl (such as —SO$_2$R$^a$ and —SO$_2$NR$^b$R$^c$),
- where R$^a$ is optionally substituted C1-C6 alkyl, optionally substituted aryl, or optionally substituted heteroaryl;
- R$^b$ is H, optionally substituted C1-C6 alkyl, optionally substituted aryl, or optionally substituted heteroaryl; and
- R$^c$ is hydrogen or optionally substituted $C_1$-$C_4$ alkyl; or
- R$^b$ and R$^c$, and the nitrogen to which they are attached, form an optionally substituted heterocycloalkyl group; and
- where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), or —NHSO$_2$($C_1$-$C_4$ haloalkyl).

As used herein, E refers to the electrophilic group capable of forming a covalent bond with a nucleophile. In some embodiments, compounds comprising E can undergo a spontaneous reaction with a protein. In some embodiments, compounds comprising E can undergo a spontaneous reaction with a protein to form a new covalent bond under moderate reaction conditions. In some embodiments, compounds comprising E can undergo a spontaneous reaction with a protein to form a new covalent bond wherein the new covalent bond forms between the compound and the nitrogen or sulfur of an amino acid residue sidechain. Some non-limiting examples of the amino acid can be lysine or cysteine, for example. In some embodiments, moderate reaction conditions can be at a temperature below about 50° C., 45° C., 40° C., 39° C., 38° C., 37° C., 36° C., 35° C., 34° C., 33° C., 30° C., 27° C., 25° C., 20° C., or 5° C. in an aqueous solution at a concentration of protein and compound below about 1M for example. In some embodiments, E is an electrophilic group capable of forming a covalent bond with a cysteine residue of a protein. In some embodiments, compounds comprising E are capable of forming a covalent bond with a cysteine residue of a protein. In some embodiments, E comprises a substituted or unsubstituted vinyl sulfone moiety, substituted or unsubstituted vinyl sulfonamide moiety, substituted or unsubstituted fluoro($C_1$-$C_4$)alkylketone moiety, substituted or unsubstituted chloro ($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

In some embodiments, E is selected from a group consisting of

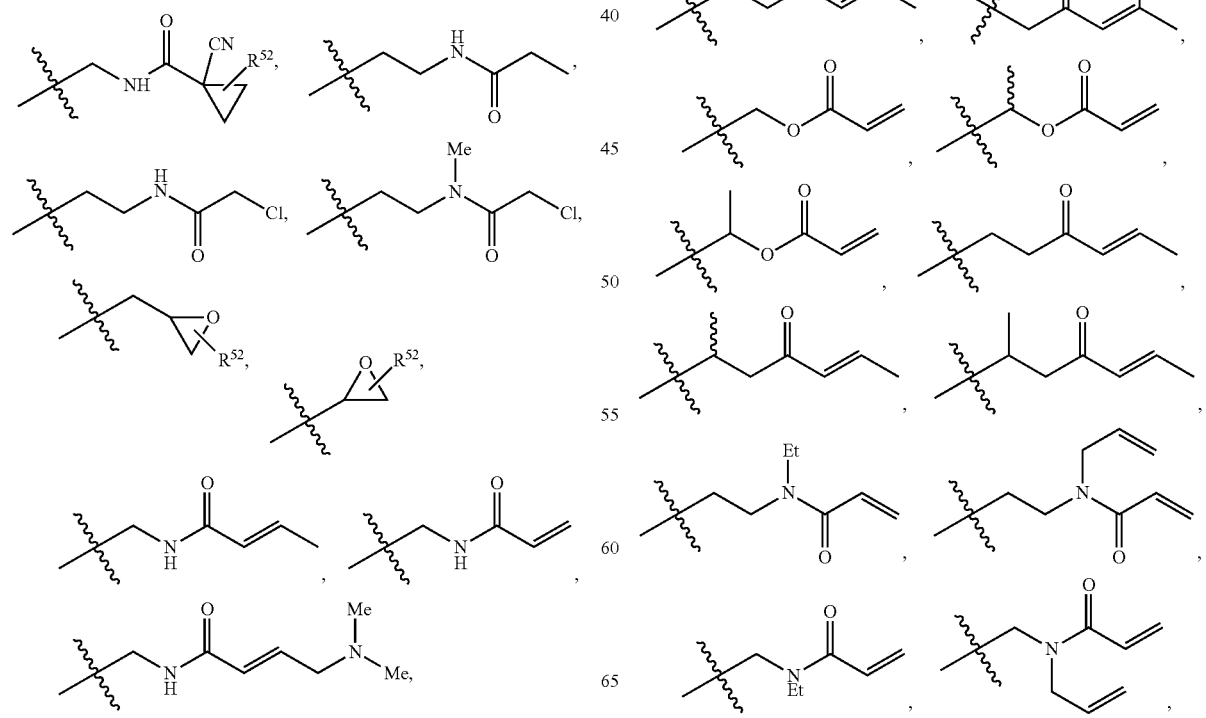

-continued
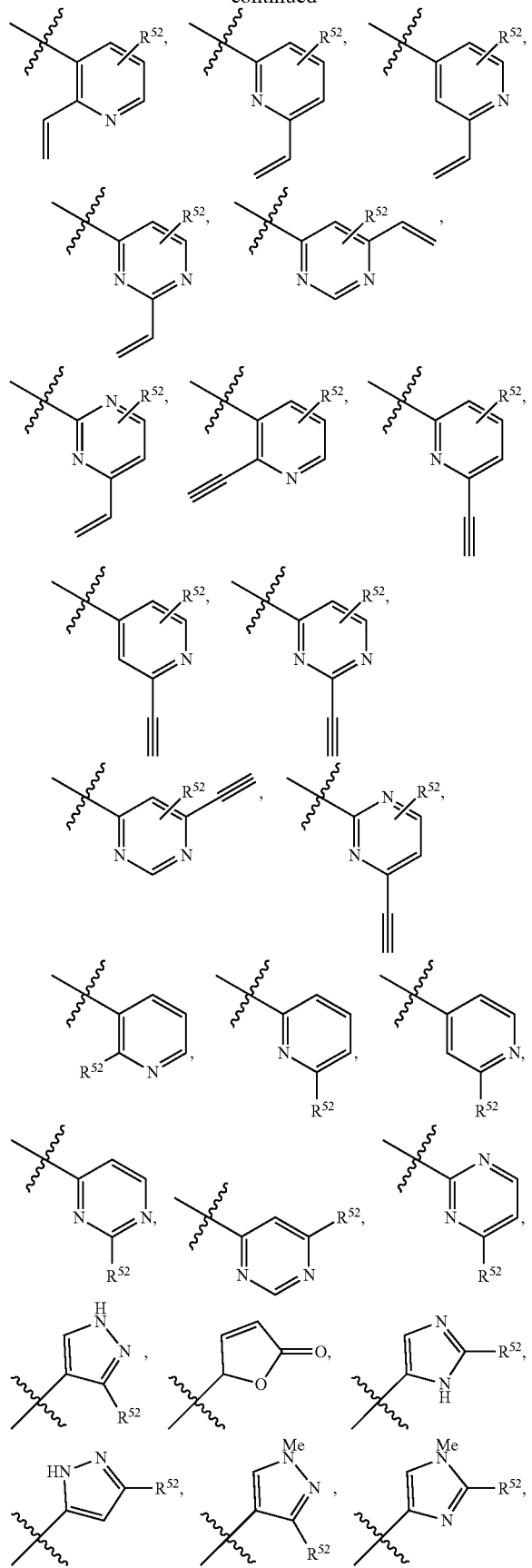
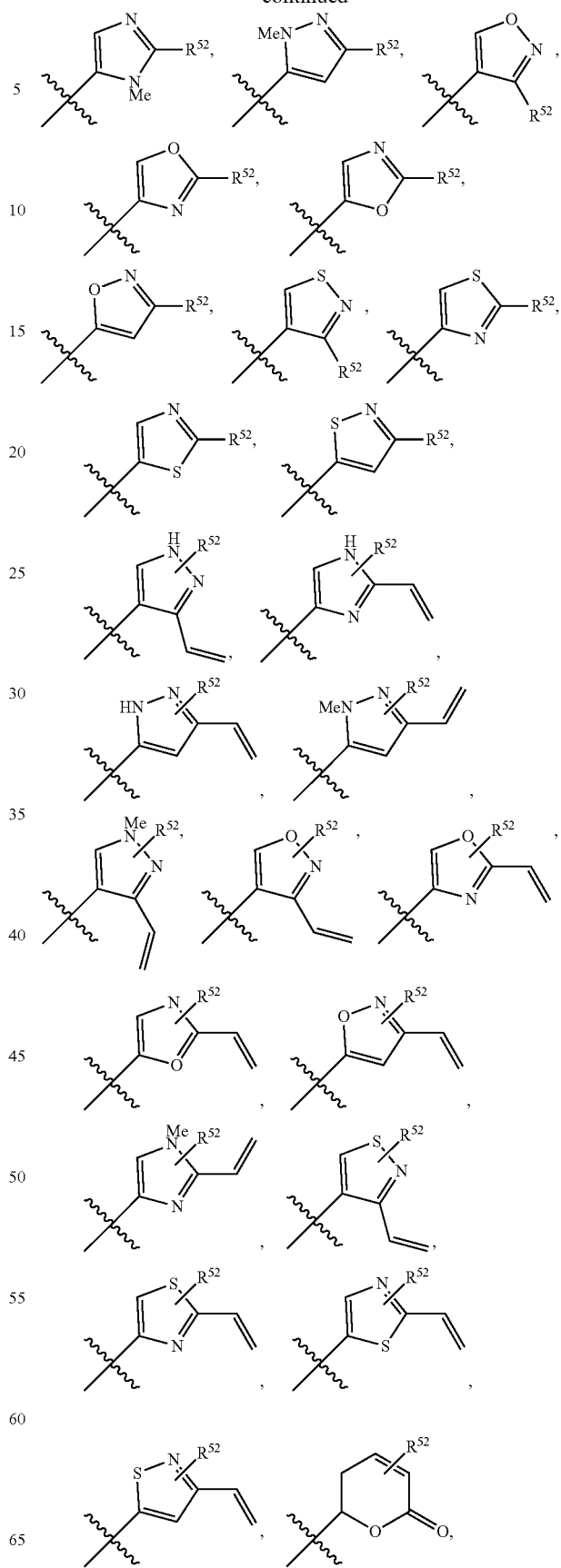

-continued
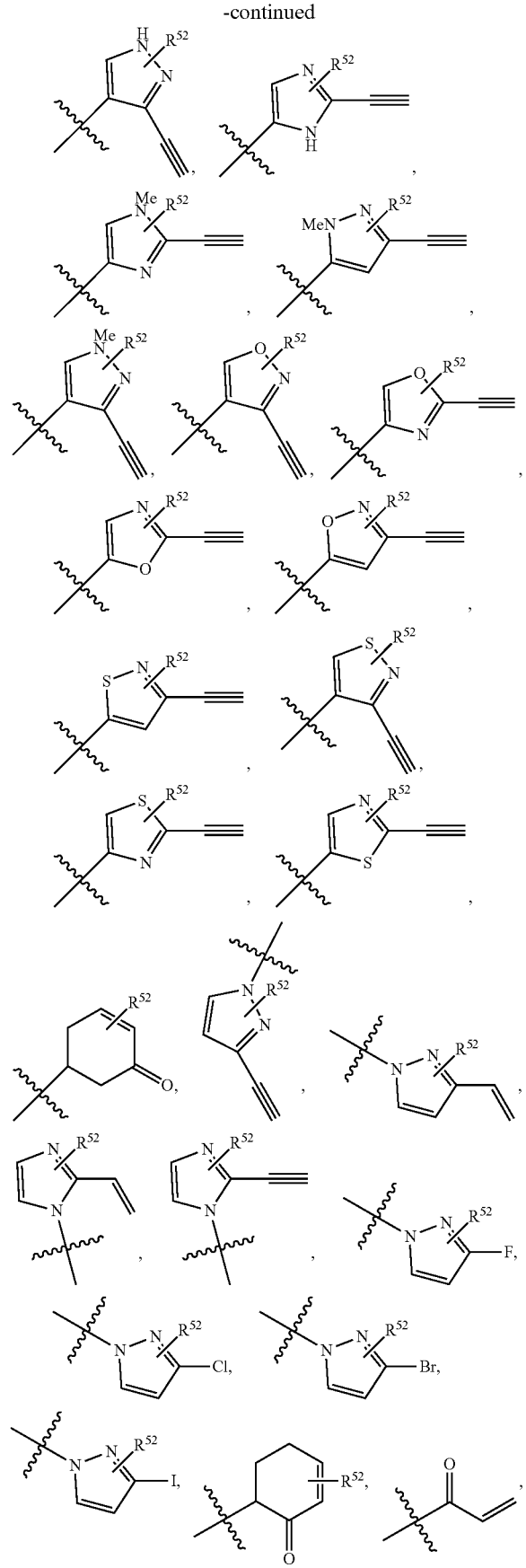
-continued
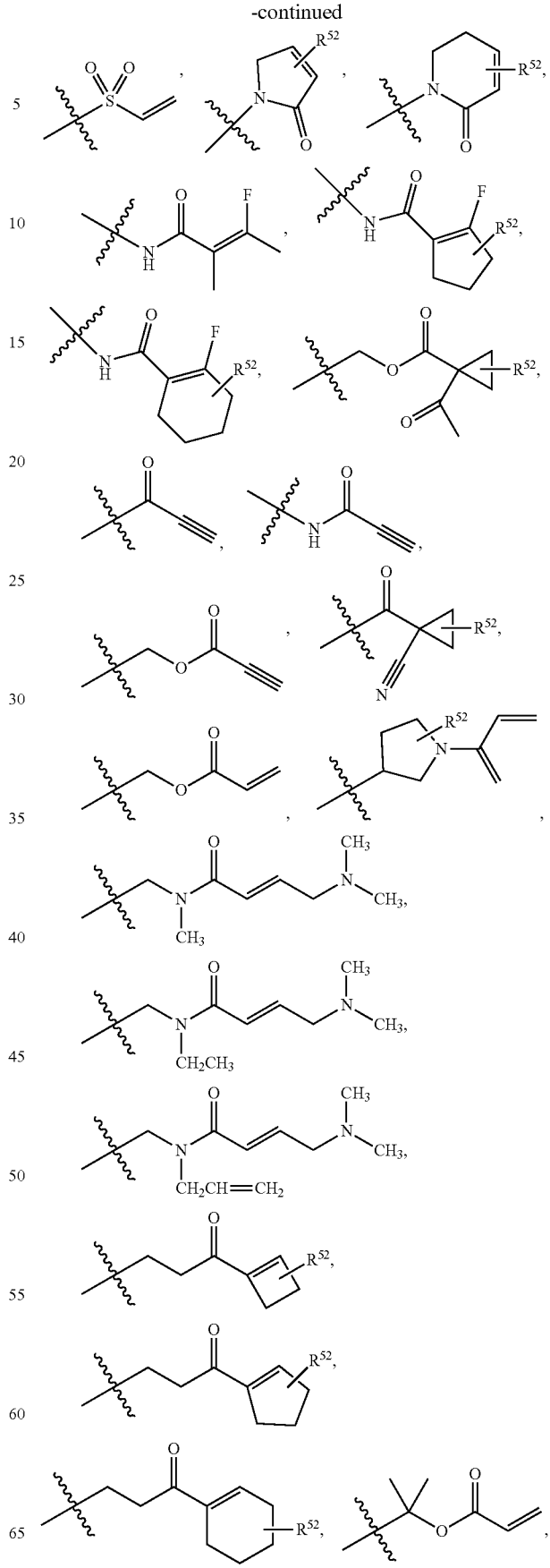

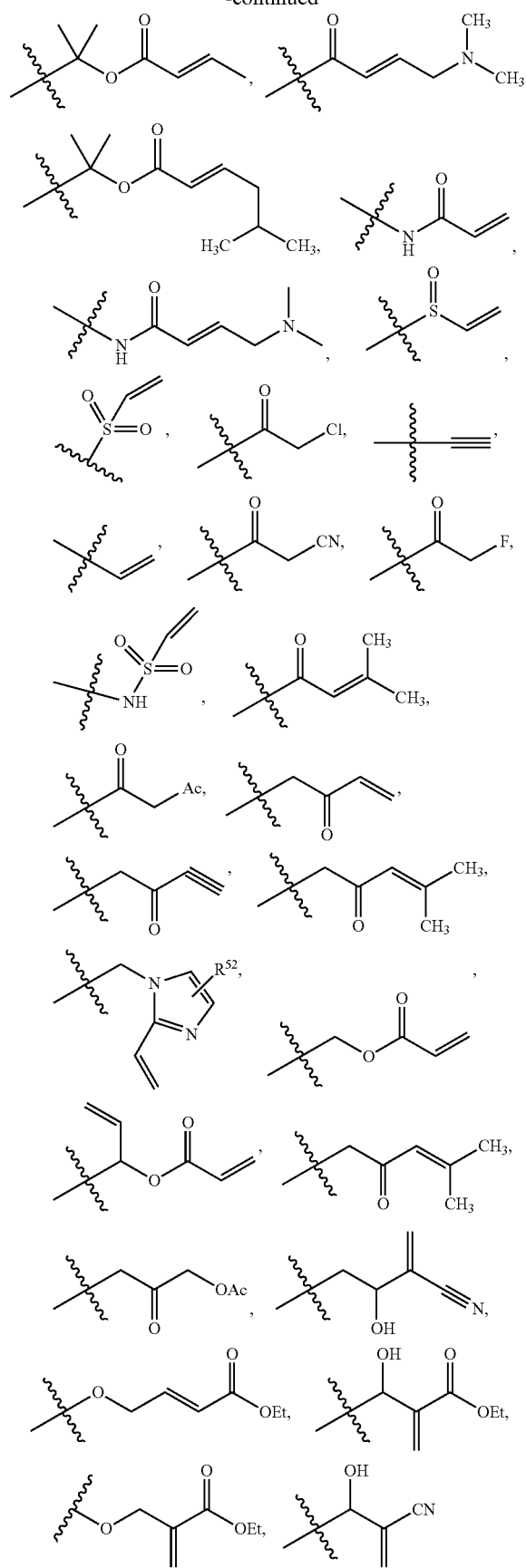
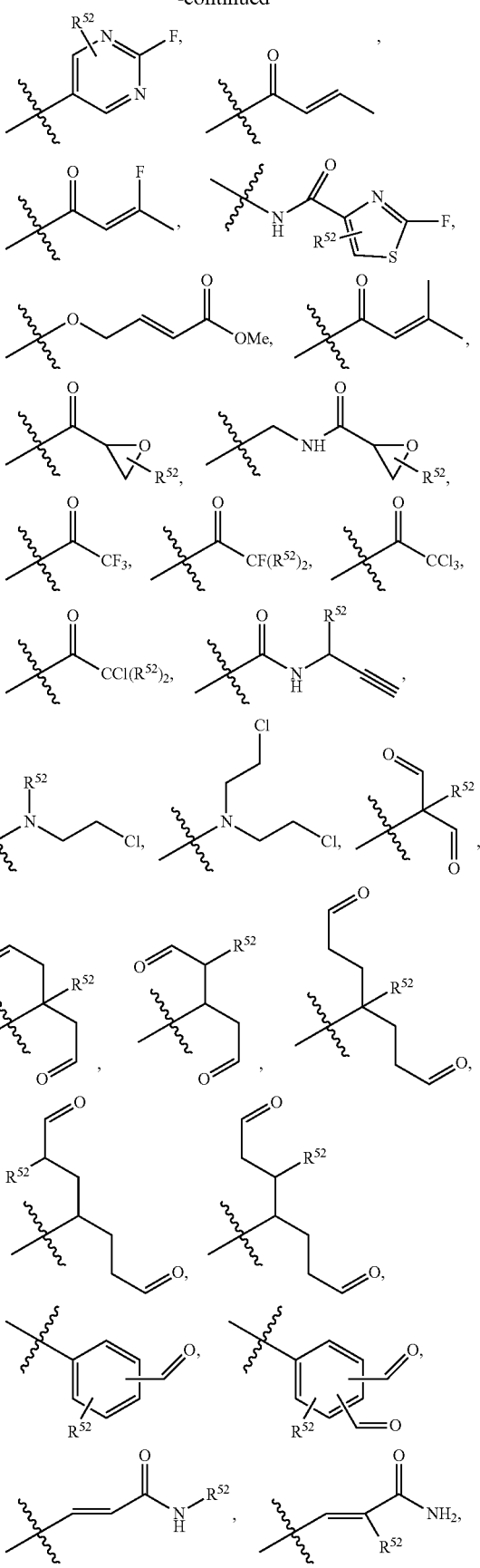

-continued

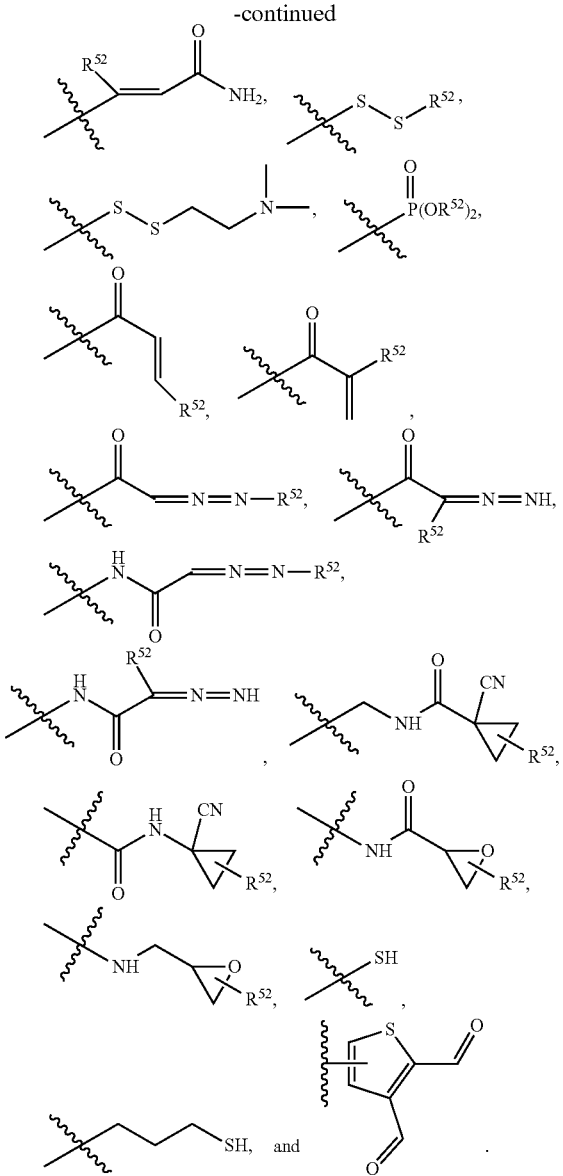

R⁵² is independently hydrogen, oxo, halogen, —CX$^b_3$, —CN, —SO₂Cl, —SO$_r$R⁵⁶, —SO$_p$NR⁵³R⁵⁴, —NHNH₂, —ONR⁵³R⁵⁴, —NHC═(O)NHNH₂, —NHC═(O)NR⁵³R⁵⁴, —N(O)$_q$, —NR⁵³R⁵⁴, —C(O)R⁵⁵, —C(O)—OR⁵⁵, —C(O)NR⁵³R⁵⁴, —OR⁵⁶, —NR⁵³SO₂R⁵⁶, —NR⁵³C═(O)R⁵⁵, —NR⁵³C(O)—OR⁵⁵, —NR⁵³OR⁵⁵, —OCX$^b_3$, —OCHX$^b_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent R⁵² substituents may optionally be joined to form a substituted or unsubstituted cycloalkyl, substituted or unsubstituted heterocycloalkyl, substituted or unsubstituted aryl, or substituted or unsubstituted heteroaryl. Two R⁵² substituents bonded to the same atom may optionally be joined to form a substituted or unsubstituted cycloalkyl or substituted or unsubstituted heterocycloalkyl. In some embodiments, R⁵² is hydrogen. In some embodiments, R⁵² is methyl. In some embodiments, R⁵² is ethyl. In some embodiments, R⁵² is —CN. In some embodiments, R⁵² is —NO₂.

R⁵³, R⁵⁴, R⁵⁵, and R⁵⁶ are independently hydrogen, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R⁵³ and R⁵⁴ substituents bonded to the same nitrogen atom may optionally be joined to form a substituted or unsubstituted heterocycloalkyl or substituted or unsubstituted heteroaryl. In some embodiments, R⁵³, R⁵⁴, R⁵⁵, and R⁵⁶ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol p is independently 1 or 2. In some embodiments, p is 1. In some embodiments, p is 2. The symbol q is independently an integer from 1 to 2. In some embodiments, q is 1. In some embodiments, q is 2. The symbol r is independently an integer from 0 to 4. In some embodiments, r is 0. In some embodiments, r is 1. In some embodiments, r is 2. In some embodiments, r is 3. In some embodiments, r is 4. X$^a$ is independently —Cl, —Br, —I, or —F. In some embodiments, X$^a$ is —Cl. In some embodiments, X$^a$ is —Br. In some embodiments, X$^a$ is —I. In some embodiments, X$^a$ is —F.

Examples of E include, but are not limited to, the following groups:

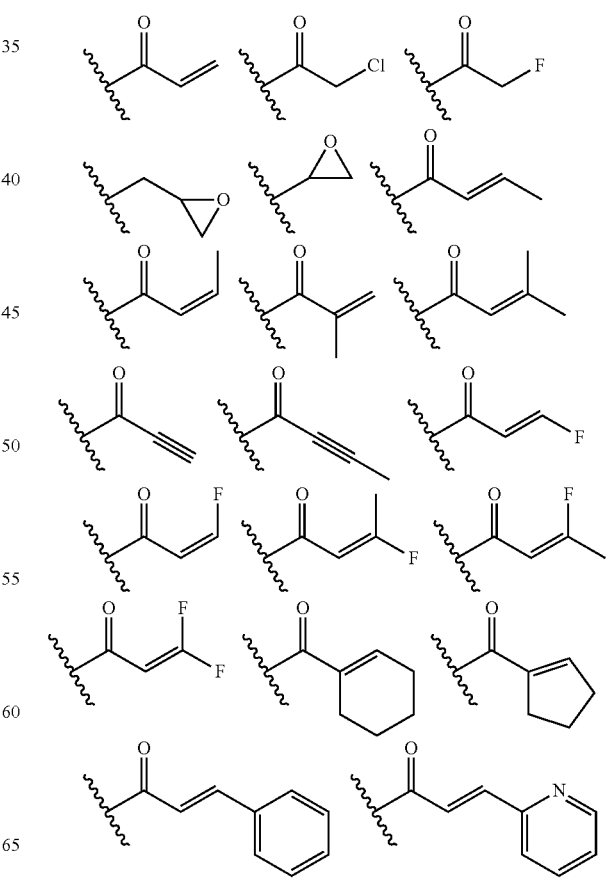

-continued

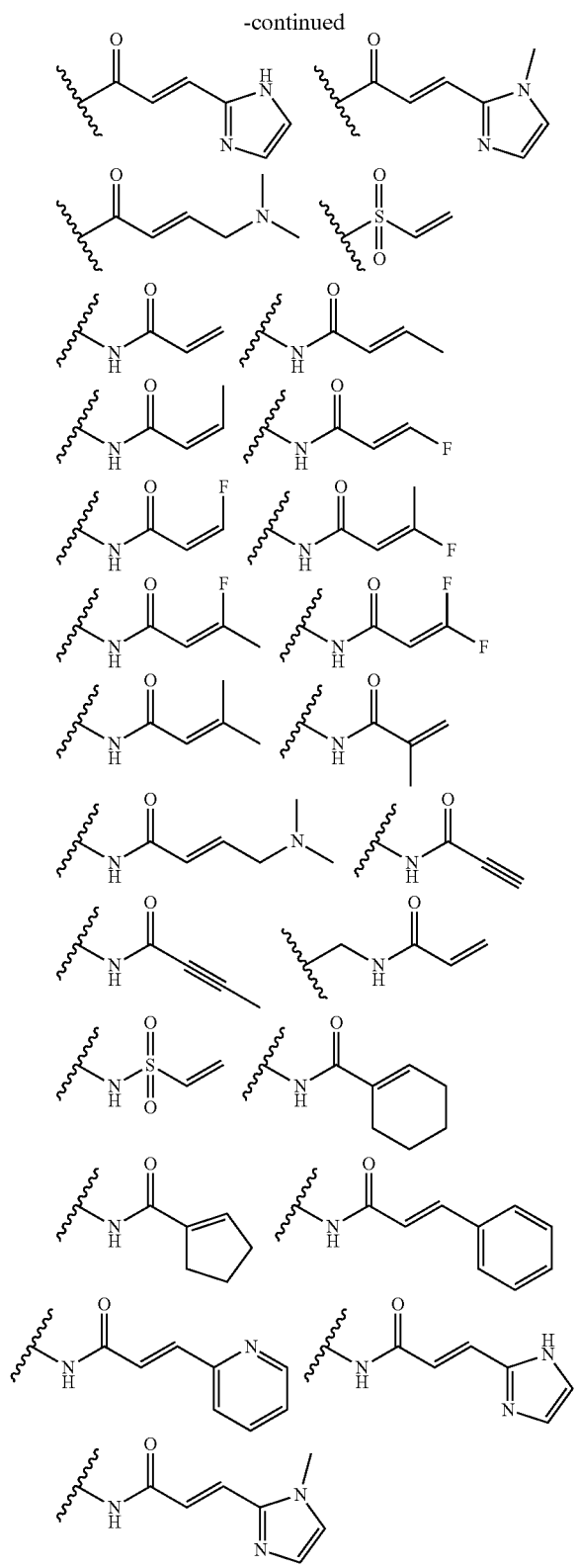

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to:

5- to 7-membered aromatic, monocyclic rings containing one or more, for example, from 1 to 4, or in certain embodiments, from 1 to 3, heteroatoms chosen from N, O, and S, with the remaining ring atoms being carbon; bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 4- to 8-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, pyridyl, pyrazinyl, pyrimidinyl, pyrazolinyl, imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein.

Substituted heteroaryl also includes ring systems substituted with one or more oxide (—O—) substituents, such as pyridinyl N-oxides.

As used herein, "heterocycloalkyl" refers to a single, non-aromatic ring, usually with 3 to 8 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include but are not limited to, for example, pyrrolidinyl, morpholinyl, piperidinyl, piperazinyl, azetidinyl, diazepanyl, diazocanyl, pyrrolidinyl, morpholinyl, piperidinyl, piperazinyl, imidazolidinyl, pyrazolidinyl, dihydrofuranyl, and tetrahydrofuranyl. Substituted heterocycloalkyl can also include ring systems substituted with one or more oxo (=O) or oxide (—O—) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 7 ring atoms, optionally contains 1-3 heteroatoms independently chosen from oxygen, sulfur, and nitrogen and is not aromatic.

As used herein, "sulfanyl" refers to the groups: —S-(optionally substituted ($C_1$-$C_6$)alkyl), —S-(optionally substituted cycloalkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

As used herein, "sulfinyl" refers to the groups: —S(O)-(optionally substituted ($C_1$-$C_6$)alkyl), —S(O)-(optionally substituted cycloalkyl), —S(O)-(optionally substituted aryl), —S(O)-optionally substituted heteroaryl), —S(O)-(optionally substituted heterocycloalkyl); and —S(O)-(optionally substituted amino).

As used herein, "sulfonyl" refers to the groups: —S($O_2$)-(optionally substituted ($C_1$-$C_6$)alkyl), —S($O_2$)-(optionally substituted cycloalkyl), —S($O_2$)-(optionally substituted aryl), —S($O_2$)-(optionally substituted heteroaryl), —S($O_2$)-(optionally substituted heterocycloalkyl), and —S($O_2$)-(optionally substituted amino).

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

As used herein, the terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently —$R^a$, —$OR^b$, optionally substituted amino (including —$NR^cOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, azido, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), or sulfonyl (such as —$SO_2R^a$ and —$SO_2NR^bR^c$), where $R^a$ is optionally substituted $C_1$-$C_6$ alkyl, optionally substituted cycloalkyl, optionally substituted heterocycloalkyl, optionally substituted alkenyl, optionally substituted alkynyl, optionally substituted aryl, or optionally substituted heteroaryl; $R^b$ is hydrogen, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), or —$NHSO_2(C_1$-$C_4$ haloalkyl).

As used herein, "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), or sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH ($C_1$-$C_4$ alkyl), —$SO_2$NH(phenyl), —$NHSO_2$($C_1$-$C_4$ alkyl), —$NHSO_2$(phenyl), or —$NHSO_2$($C_1$-$C_4$ haloalkyl).

As used herein, "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH ($C_1$-$C_4$ alkyl), —$SO_2$NH(phenyl), —$NHSO_2$($C_1$-$C_4$ alkyl), —$NHSO_2$(phenyl), or —$NHSO_2$($C_1$-$C_4$ haloalkyl).

In some embodiments, a substituted alkoxy group is "polyalkoxy" or —O-(optionally substituted alkylene)-(optionally substituted alkoxy), and includes groups such as —$OCH_2CH_2OCH_3$, and residues of glycol ethers such as polyethyleneglycol, and —O($CH_2CH_2O)_xCH_3$, where x is an integer of 2-20, such as 2-10, and for example, 2-5. Another substituted alkoxy group is hydroxyalkoxy or —$OCH_2(CH_2)_y$OH, where y is an integer of 1-10, such as 1-4.

As used herein, "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is optionally substituted $C_1$-$C_6$ alkyl, optionally substituted alkenyl, optionally substituted alkynyl, optionally substituted aryl, or optionally substituted heteroaryl;

$R^b$ is H, optionally substituted $C_1$-$C_6$ alkyl, optionally substituted cycloalkyl, optionally substituted heterocycloalkyl, optionally substituted aryl, or optionally substituted heteroaryl; and $R^c$ is hydrogen or optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH ($C_1$-$C_4$ alkyl), —$SO_2$NH(phenyl), —$NHSO_2$($C_1$-$C_4$ alkyl), —$NHSO_2$(phenyl), or —$NHSO_2$($C_1$-$C_4$ haloalkyl).

As used herein, "substituted amino" refers to the group —$NHR^d$ or —$NR^dR^e$ wherein $R^d$ is hydroxyl, formyl, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein $R^e$ is chosen from optionally substituted alkyl, optionally substituted cycloalkyl, optionally substituted aryl, optionally substituted heteroaryl, or optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$) OR$^c$, sulfanyl (such as SR$^b$), sulfinyl (such as —SOR$^a$), or sulfonyl (such as —SO$_2$R$^a$ and —SO$_2$NR$^b$R$^c$), wherein R$^a$ is optionally substituted C$_1$-C$_6$ alkyl, optionally substituted alkenyl, optionally substituted alkynyl, optionally substituted aryl, or optionally substituted heteroaryl;

R$^b$ is H, optionally substituted C$_1$-C$_6$ alkyl, optionally substituted cycloalkyl, optionally substituted heterocycloalkyl, optionally substituted aryl, or optionally substituted heteroaryl; and R$^c$ is hydrogen or optionally substituted C$_1$-C$_4$ alkyl; or R$^b$ and R$^c$, and the nitrogen to which they are attached, form an optionally substituted heterocycloalkyl group; and wherein each optionally substituted group is unsubstituted or independently substituted with one or more, such as one, two, or three, substituents independently chosen from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$- C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), or —NHSO$_2$(C$_1$-C$_4$ haloalkyl); and wherein optionally substituted acyl, optionally substituted alkoxycarbonyl, sulfinyl and sulfonyl are as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds described herein exist in various tautomeric forms, the term "compound" is intended to include all tautomeric forms of the compound.

Compounds of Formula I or II also include crystalline and amorphous forms of those compounds, including, for example, polymorphs, pseudopolymorphs, solvates (including hydrates), unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates (including hydrates), unsolvated polymorphs (including anhydrates), conformational polymorphs, and amorphous forms, as well as mixtures thereof, unless a particular crystalline or amorphous form is referred to. Similarly, "pharmaceutically acceptable forms" of compounds of Formula I or II also include crystalline and amorphous forms of those compounds, including, for example, polymorphs, pseudopolymorphs, solvates (including hydrates), unsolvated polymorphs (including anhydrates), conformational polymorphs, and amorphous forms of the pharmaceutically acceptable salts, as well as mixtures thereof.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates.

Compounds of Formula I also include other pharmaceutically acceptable forms of the recited compounds, including chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound". Similarly, pharmaceutically acceptable salts include "non-covalent complexes" of pharmaceutically acceptable salts.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is sp$^2$-hybridized, an ether oxygen, or the oxygen of a sulfoxide or N-oxide.

The term "hydrogen bond donor" refers to an oxygen, nitrogen, or heteroaromatic carbon that bears a hydrogen group containing a ring nitrogen or a heteroaryl group containing a ring nitrogen.

The compounds disclosed herein can be used in different enriched isotopic forms, e.g., enriched in the content of $^2$H, $^3$H, $^{11}$C, $^{13}$C and/or $^{14}$C. In one particular embodiment, the compound is deuterated at least one position. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

"Pharmaceutically acceptable salts" include, but are not limited to salts with inorganic acids, such as hydrochlorate, carbonate, phosphate, hydrogenphosphate, diphosphate, hydrobromate, sulfate, sulfinate, nitrate, and like salts; as well as salts with an organic acid, such as malate, malonate, maleate, fumarate, tartrate, succinate, citrate, acetate, lactate, gluconate, methanesulfonate, Tris (hydroxymethylaminomethane), p-toluenesulfonate, priopionate, 2-hydroxyethylsulfonate, benzoate, salicylate, stearate, oxalate, pamoate, and alkanoate such as acetate, $HOOC-(CH_2)_n-COOH$ where n is 0-4, and like salts. Other salts include sulfate, methasulfonate, bromide, trifluoracetate, picrate, sorbate, benzilate, salicilate, nitrate, phthalate or morpholine. Pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I or II when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in the compounds of Formula I or II. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, $(C_1-C_{18})$-alkyl, $(C_3-C_7)$-cycloalkyl, $(C_3-C_7)$-cycloalkyl-$(C_1-C_4)$-alkyl-, $(C_6-C_{14})$-aryl which is unsubstituted or substituted by a residue $(C_1-C_2)$-alkyl, $(C_1-C_2)$-alkoxy, fluoro, or chloro; heteroaryl-, $(C_6-C_{14})$-aryl-$(C_1-C_4)$-alkyl- where aryl is unsubstituted or substituted by a residue $(C_1-C_2)$-alkyl, $(C_1-C_2)$-alkoxy, fluoro, or chloro; or heteroaryl-$(C_1-C_4)$-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

As used herein, the terms "group", "radical" or "fragment" are synonymous and are intended to indicate functional groups or fragments of molecules attachable to a bond or other fragments of molecules.

As used herein, the term "leaving group" refers to the meaning conventionally associated with it in synthetic organic chemistry, i.e., an atom or group displaceable under nucleophilic displacement conditions. Examples of leaving groups include, but are not limited to, dimethylhydroxylamino (e.g. Weinreb amide), halogen, alkane- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

As used herein, the term "protective group" or "protecting group" refers to a group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block certain reactive sites present in the reactants. Examples of protecting groups can be found in Wuts et al., *Green's Protective Groups in Organic Synthesis*, (J. Wiley, 4th ed. 2006).

As used herein, the term "deprotection" or "deprotecting" refers to a process by which a protective group is removed after a selective reaction is completed. Certain protective groups may be preferred over others due to their convenience or relative ease of removal. Without being limiting, deprotecting reagents for protected amino or anilino group include strong acid such as trifluoroacetic acid (TFA), concentrated HCl, $H_2SO_4$, or HBr, and the like.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "active agent" is used to indicate a chemical entity which has biological activity. In certain embodiments, an "active agent" is a compound having pharmaceutical utility. For example an active agent may be an anti-cancer therapeutic.

As used herein, "significant" refers to any detectable change that is statistically significant in a standard parametric test of statistical significance such as Student's T-test, where $p<0.05$.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "therapeutically effective amount" of a chemical entity described herein refers to an amount effective, when administered to a human or non-human subject, to provide a therapeutic benefit such as amelioration of symptoms, slowing of disease progression, or prevention of disease.

"Treating" or "treatment" encompasses administration of at least one compound of Formula I or II, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, non-small cell lung, melanoma, mesothelioma, ovary, sarcoma, stomach, uterus and Medulloblastoma.

As used herein, "subject" refers to a mammal that has been or will be the object of treatment, observation or experiment. The methods described herein can be useful in both human therapy and veterinary applications. In some embodiments, the subject is a human.

The term "mammal" is intended to have its standard meaning, and encompasses humans, dogs, cats, sheep, and cows, for example.

As used herein, the term EGFR is used to refer the epidermal growth factor receptor (EGFR), a receptor tyrosine kinase of the ErbB family. The terms "EGFR", "Her", "ErbB1" and the like are used interchangeably to refer to the gene or protein product of the gene.

A. Compounds

In one aspect, provided is a compound of Formula I

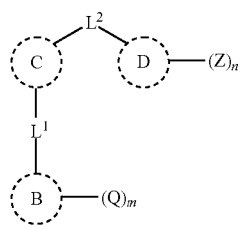

Formula I or a pharmaceutically acceptable salt thereof, wherein

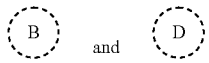

are each independently selected from the group consisting of aryl, heteroaryl and heterocycloalkyl;

is selected from the group consisting of:

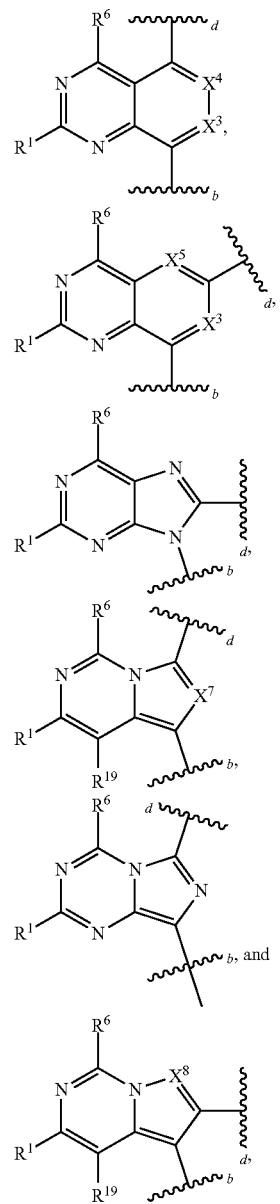

wherein ⌇b is a point of attachment for $L^1$ and ⌇d is a point of attachment for $L^2$;

$X^3$ is C—$R^3$ or N;
$X^4$ is C—$R^4$ or N;
$X^5$ is C—$R^5$ or N;
$X^7$ is C—$R^{20}$ or N;
$X^8$ is C—$R^{21}$ or N;
$L^1$ and $L^2$ are each independently selected from the group consisting of bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—, optionally substituted C$_{1-6}$ alkylene, optionally substituted C$_{2-6}$ alkenylene, optionally substituted C$_{2-6}$ alkynylene, optionally substituted 1- to 6-membered heteroalkylene, optionally substituted 2- to 6-membered heteroalkenylene, and optionally substituted 2- to 6-membered heteroalkynylene;

R$^1$, R$^3$, R$^4$, R$^5$, R$^6$, R$^{19}$, R$^{20}$ and R$^{21}$ are each independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl and optionally substituted carbamimidoyl;

R$^{51}$ is independently selected at each occurrence from hydrogen, sulfonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted acyl, optionally substituted alkoxycarbonyl, optionally substituted aminocarbonyl, optionally substituted aminosulfonyl and optionally substituted carbamimidoyl;

Q and Z are each independently selected at each occurrence from hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl and E; wherein E is an electrophilic group capable of forming a covalent bond with a nucleophile; and m and n are each independently 0, 1, 2, 3, 4 or 5;
wherein at least one of

is substituted with E.
In some embodiments,

is selected from the group consisting of:

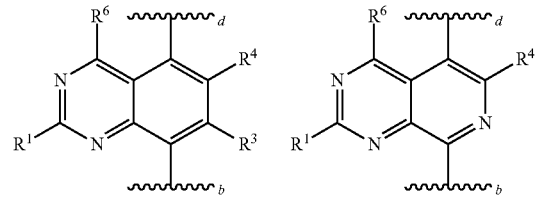

In some examples R$^3$ is H. In some examples R$^4$ is H. In some examples both R$^3$ and R$^4$ are H.

In some embodiments,

is selected from the group consisting of:

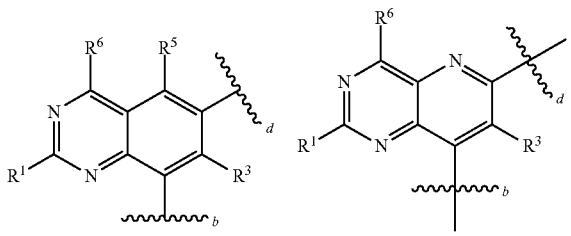

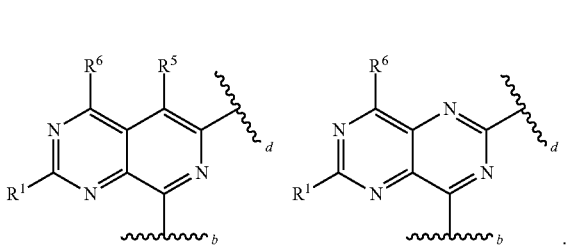

In some examples R$^3$ is H. In some examples R$^5$ is H. In some examples both R$^3$ and R$^5$ are H.

In some embodiments,

is selected from the group consisting of:

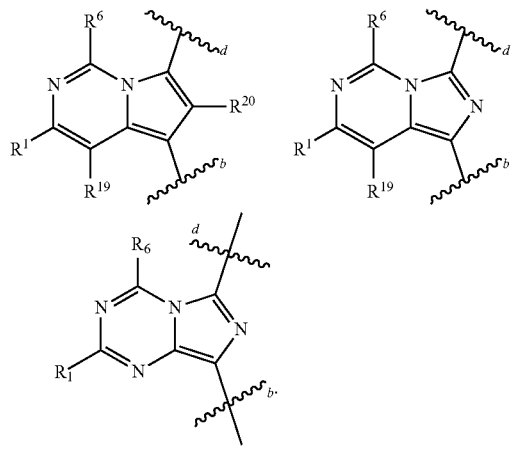

In some examples $R^{20}$ is H.

In some embodiments,

is selected from the group consisting of:

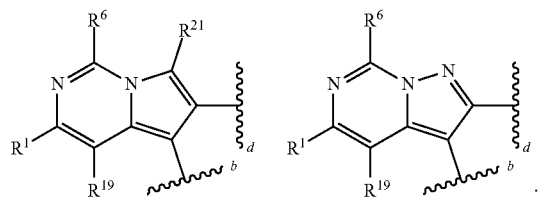

In some examples $R^{21}$ is H.

In some embodiments,

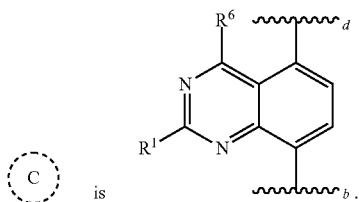

In some examples $R^1$ is H or $NH_2$. In some examples $R^6$ is H or $NH_2$. In some examples $R^1$ is H and $R^6$ is $NH_2$. In some examples $R^1$ is $NH_2$ and $R^6$ is H.

In some embodiments,

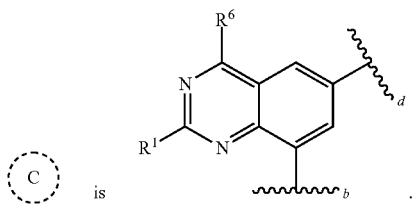

In some examples, $R^1$ is H or $NH_2$. In some examples $R^6$ is H or $NH_2$. In some examples $R^1$ is H and $R^6$ is $NH_2$. In some examples $R^1$ is $NH_2$ and $R^6$ is H.

In some embodiments,

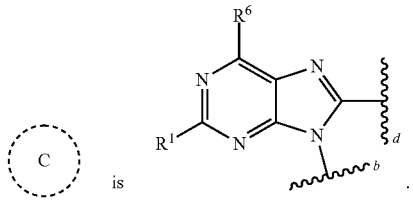 is

In some examples, $R^1$ is H or $NH_2$. In some examples $R^6$ is H or $NH_2$. In some examples $R^1$ is H and $R^6$ is $NH_2$. In some examples $R^1$ is $NH_2$ and $R^6$ is H.

In some embodiments,

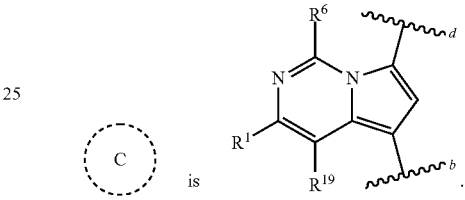 is

In some examples $R^1$ is H or $NH_2$. In some examples $R^6$ is H or $NH_2$. In some examples $R^1$ is H and $R^6$ is $NH_2$. In some examples $R^1$ is $NH_2$ and $R^6$ is H. In some examples $R^{19}$ is H. In some examples $R^1$ is H, $R^6$ is $NH_2$ and $R^{19}$ is H. In some examples $R^1$ is $NH_2$, $R^6$ is H and $R^{19}$ is H.

In some embodiments, $R^1$ is selected from the group consisting of hydrogen, cyano, halo, hydroxy, optionally substituted alkyl, optionally substituted aryl, optionally substituted heteroaryl, and optionally substituted amino. In some embodiments, $R^1$ is selected from hydrogen and —$NH_2$. In some embodiments, $R^6$ is selected from the group consisting of hydrogen, cyano, halo, hydroxy, optionally substituted alkyl, optionally substituted aryl, optionally substituted heteroaryl, and optionally substituted amino. In some embodiments, $R^6$ is selected from hydrogen and —$NH_2$. In some embodiments, $R^{19}$ is hydrogen.

In some embodiments, $L^1$ and $L^2$ are each independently selected from the group consisting of bond, —O—, —S—, —N($R^{51}$)—, —N($R^{51}$)$CH_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—. In some embodiments, $L^1$ and $L^2$ are each independently selected from the group consisting of optionally substituted $C_{1-6}$ alkylene, optionally substituted $C_{2-6}$ alkenylene, optionally substituted $C_{2-6}$ alkynylene, optionally substituted 1- to 6-membered heteroalkylene, optionally substituted 2- to 6-membered heteroalkenylene, and optionally substituted 2- to 6-membered heteroalkynylene. In some embodiments, $L^1$ and $L^2$ are each independently selected from the group consisting of —O—, —NH— and a bond. In some embodiments, $L^1$ and $L^2$ are each —NH—. In some embodiments, $L^1$ and $L^2$ are each —O—. In some embodiments $L^1$ and $L^2$ are each a bond.

In some embodiments, each Z is independently hydrogen, cyano, halo, optionally substituted amino, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted aryloxy, optionally substituted heterocycloalkyl, optionally substituted aminocarbonyl, or E.

In some embodiments, each Z is independently hydrogen, cyano, halo, optionally substituted alkoxy, optionally substituted heterocycloalkyloxy, optionally substituted heterocycloalkyl, or optionally substituted amino, optionally substituted aminocarbonyl, or E.

In some embodiments, each Q is independently hydrogen, cyano, halo, optionally substituted amino, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted aryloxy, optionally substituted heterocycloalkyl, optionally substituted aminocarbonyl, or E.

In some embodiments, each Q is independently hydrogen, cyano, halo, optionally substituted alkoxy, optionally substituted heterocycloalkyloxy, optionally substituted heterocycloalkyl, or optionally substituted amino, optionally substituted aminocarbonyl, or E.

In some embodiments, n is 0.

In some embodiments, n is 1, 2, 3, 4, or 5 and at least one Z is cyano, fluoro, chloro, methoxy, —CONH$_2$, 2-methoxyethoxy, 2-(dimethylamino)ethoxy, (1-methylpyrrolidin-3-yl)oxy, (1-methylpiperidin-4-yl)oxy, (1-methylpiperidin-3-yl)oxy, (1-methylazetidin-3-yl)oxy (2-(dimethylamino)ethyl)(methyl)amino, dimethylamino, methyl(1-methylazetidin-3-yl)amino, methyl(1-methylpyrrolidin-3-yl)amino, methyl(1-methylpiperidin-4-yl)amino, optionally substituted morpholinyl, optionally substituted piperazinyl, optionally substituted pyrrolidinyl, optionally substituted piperidinyl, optionally substituted azetidinyl or E.

In some embodiments, n is 1, 2, 3, 4, or 5 and each Z is selected independently from cyano, fluoro, chloro, optionally substituted amino, optionally substituted alkyl, optionally substituted alkoxy, optionally substituted aminocarbonyl.

In some embodiments, n is 1, 2, 3, 4, or 5 and each Z is selected independently from cyano, fluoro, chloro, methyl, —CF$_3$,

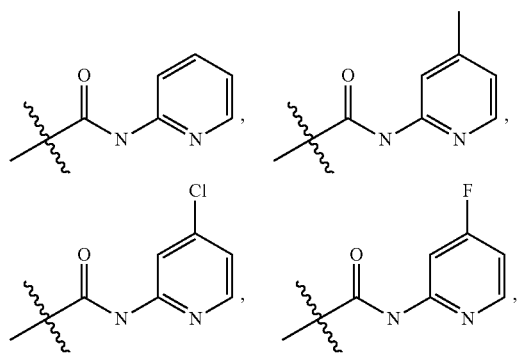

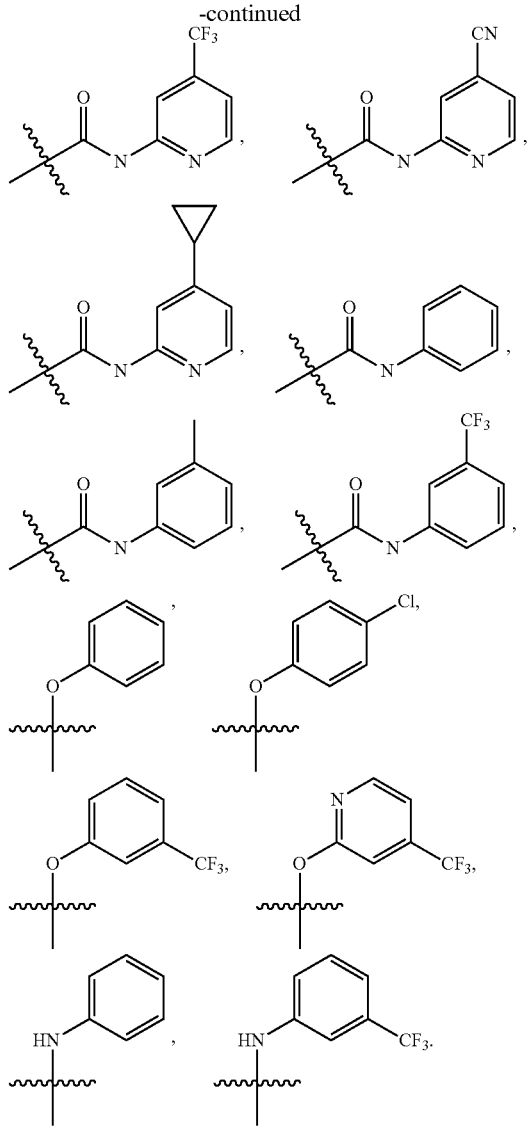

In some embodiments, m is 1, 2, 3, 4, or 5 and at least one Q is cyano, fluoro, chloro, methoxy, —CONH$_2$, 2-methoxyethoxy, 2-(dimethylamino)ethoxy, (1-methylpyrrolidin-3-yl)oxy, (1-methylpiperidin-4-yl)oxy, (1-methylpiperidin-3-yl)oxy, (1-methylazetidin-3-yl)oxy (2-(dimethylamino)ethyl)(methyl)amino, dimethylamino, methyl(1-methylazetidin-3-yl)amino, methyl(1-methylpyrrolidin-3-yl)amino, methyl(1-methylpiperidin-4-yl)amino, optionally substituted morpholinyl, optionally substituted piperazinyl, optionally substituted pyrrolidinyl, optionally substituted piperidinyl, optionally substituted azetidinyl or E.

In some embodiments, m is 1, 2, 3, 4, or 5 and at least one Q is E.

In some embodiments, each E is independently an electrophilic group capable of forming a covalent bond with a cysteine residue of a protein.

In some embodiments, E comprises a substituted or unsubstituted vinyl sulfone moiety, substituted or unsubstituted vinyl sulfonamide moiety, substituted or unsubstituted fluoro(C$_1$-C$_4$)alkylketone moiety, substituted or unsubstituted chloro(C$_1$-C$_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety.

In some embodiments, E is selected from a group consisting of

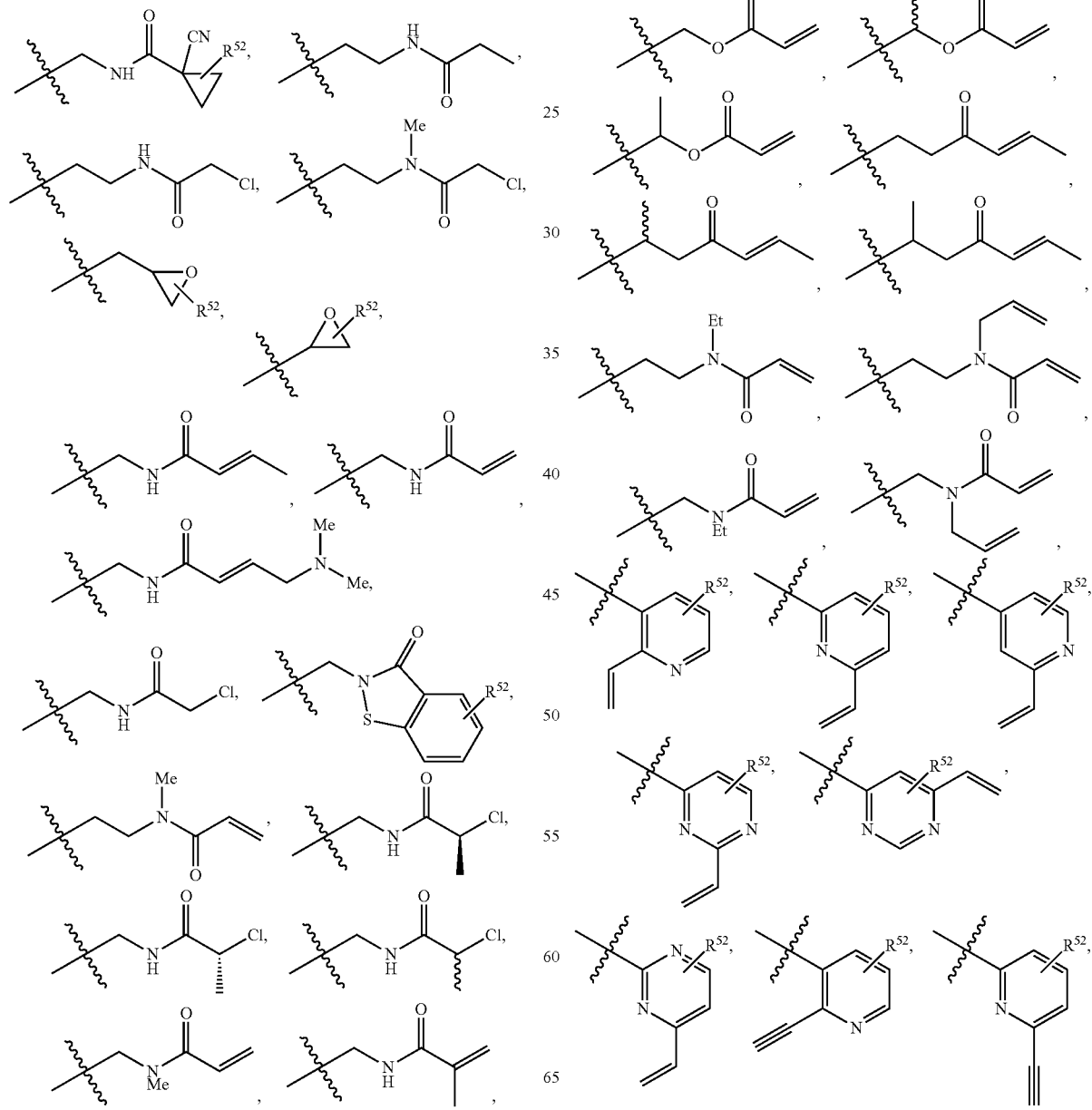

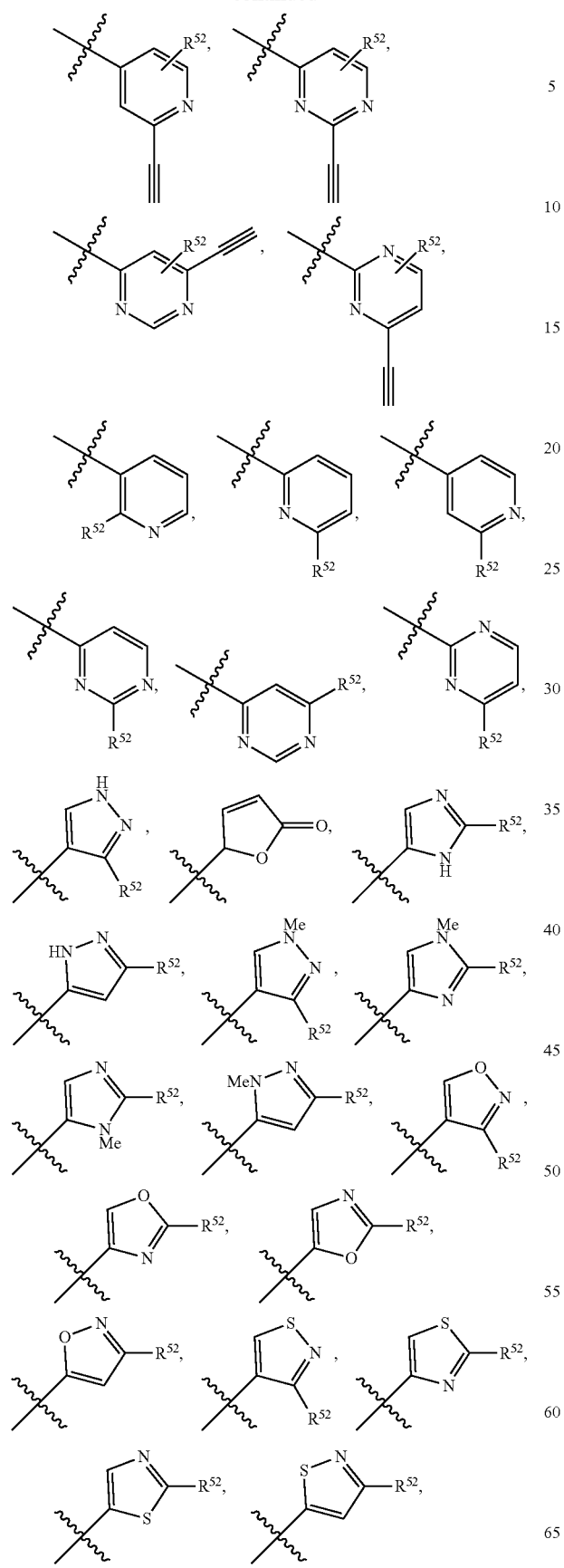
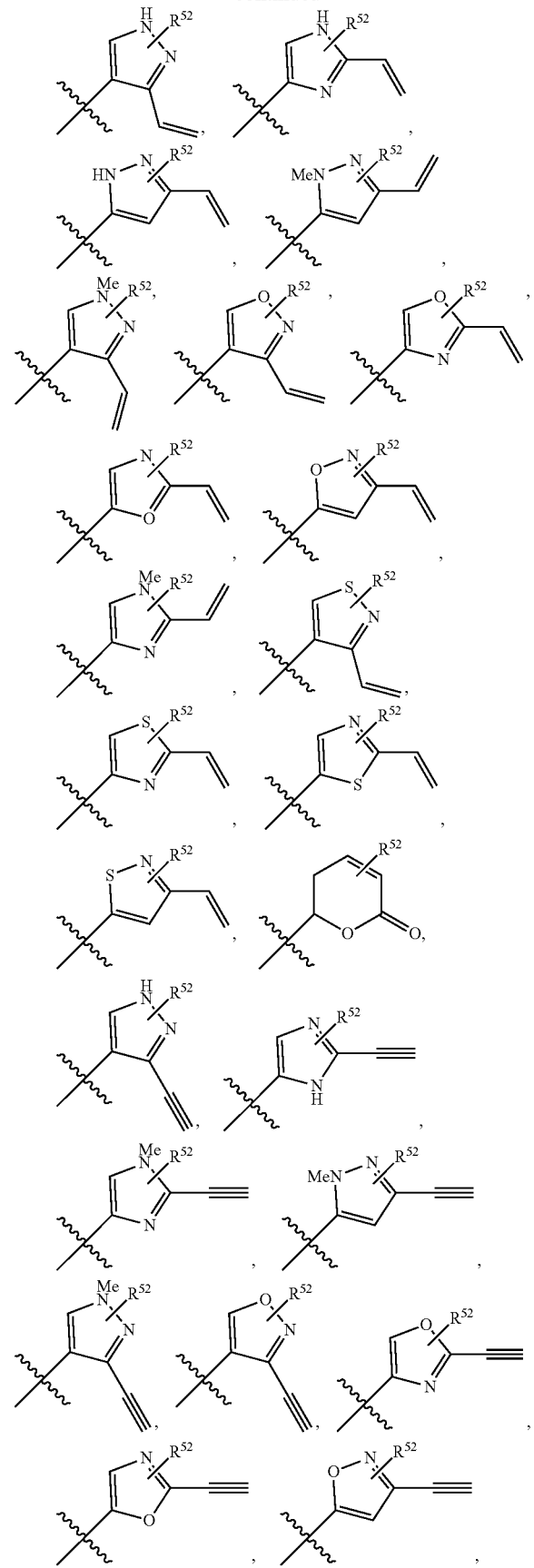

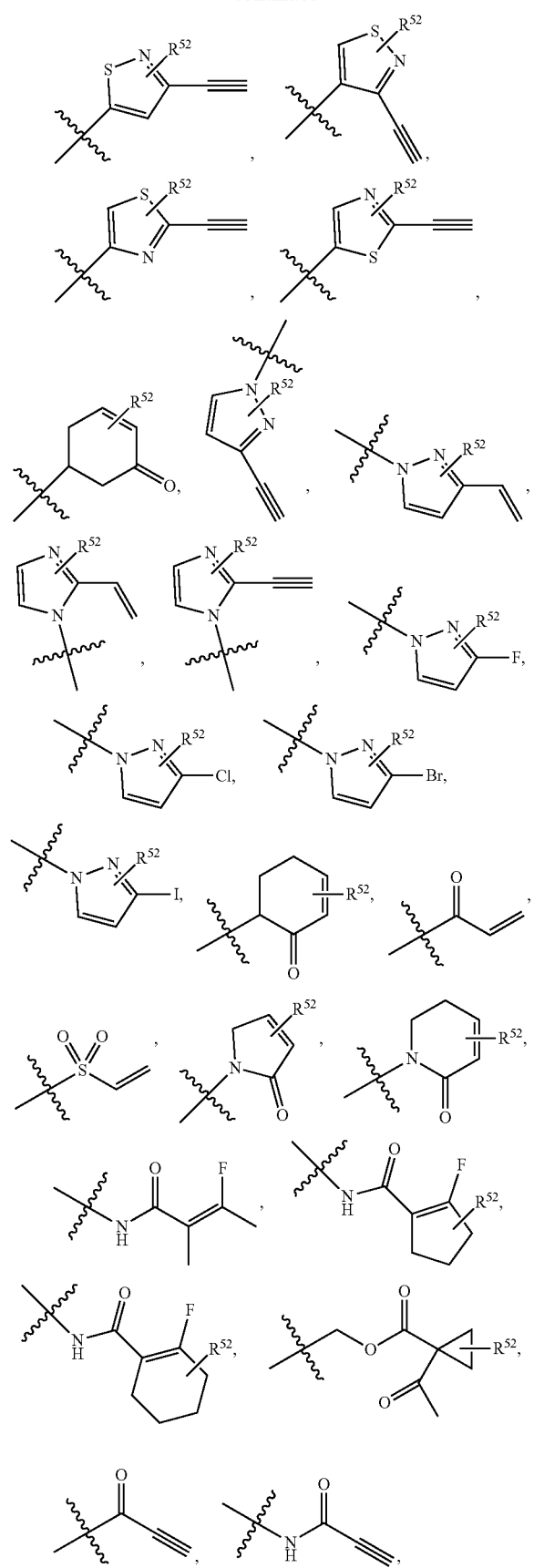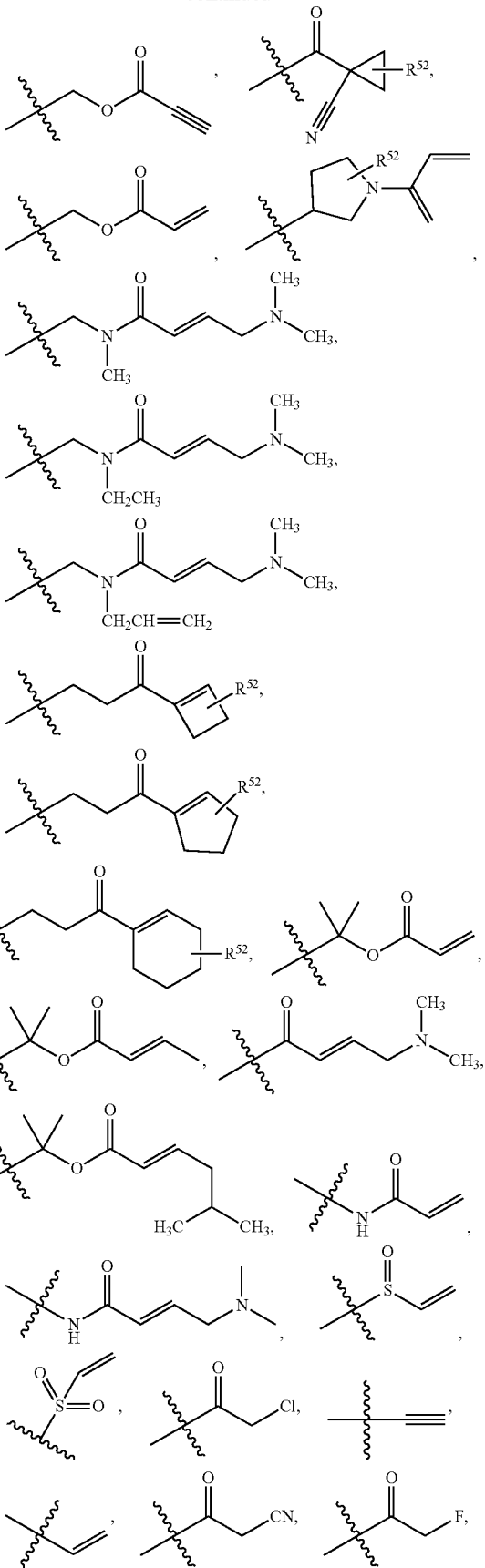

-continued
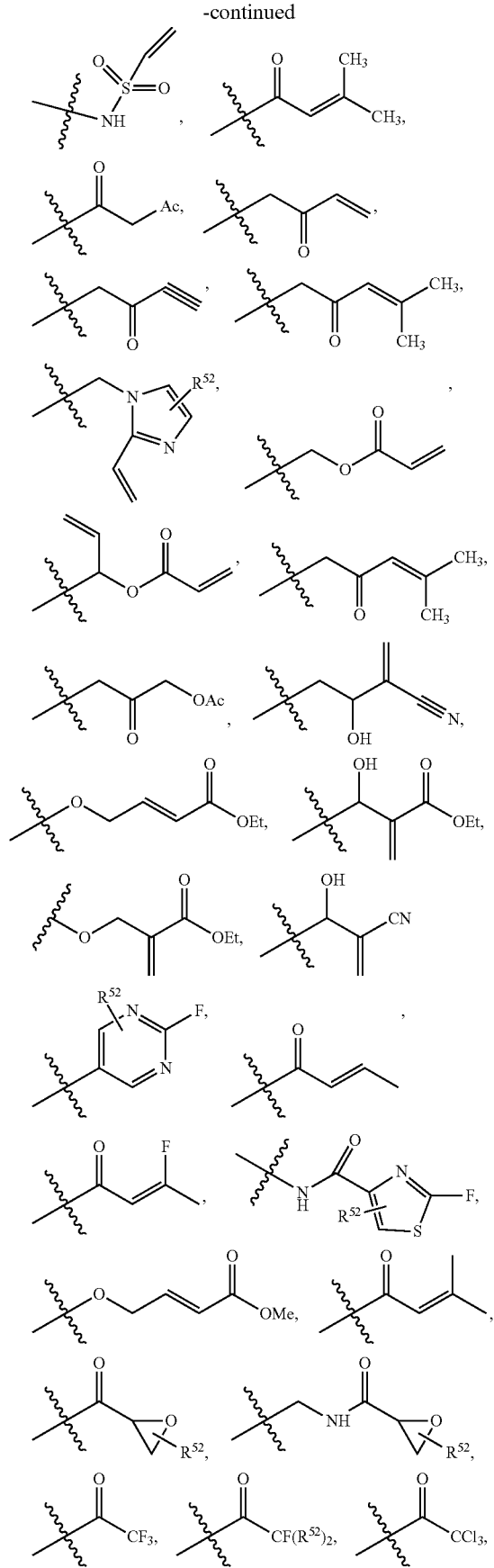
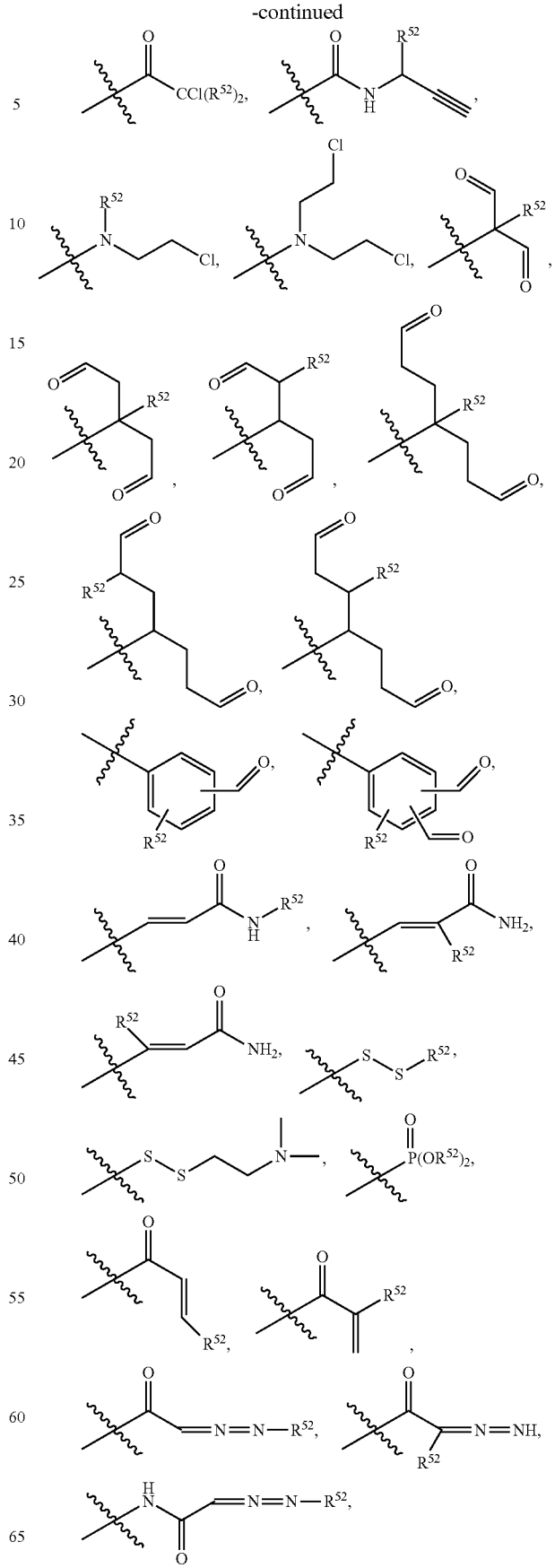

-continued

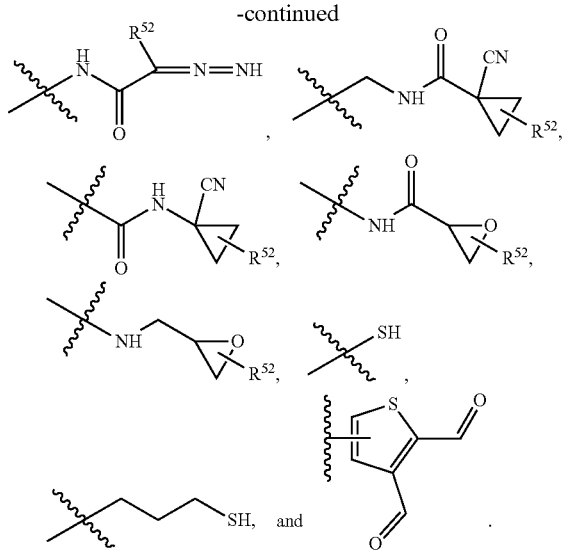

R[52] is independently hydrogen, oxo, halogen, —CX[b][3], —CN, —SO$_2$Cl, —SO$_r$R[56], —SO$_p$NR[53]R[54], —NHNH$_2$, —ONR[53]R[54], —NHC═(O)NHNH$_2$, —NHC═(O)NR[53]R[54], —N(O)$_q$, —NR[53]R[54], —C(O)R[55], —C(O)—OR[55], —C(O)NR[53]R[54], —OR[56], —NR[53]SO$_2$R[56], —NR[53]C═(O)R[55], —NR[53]C(O)—OR[55], —NR[53]OR[55], —OCX[b][3], —OCHX[b][2], substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent R[52] substituents may optionally be joined to form a substituted or unsubstituted cycloalkyl, substituted or unsubstituted heterocycloalkyl, substituted or unsubstituted aryl, or substituted or unsubstituted heteroaryl. Two R[52] substituents bonded to the same atom may optionally be joined to form a substituted or unsubstituted cycloalkyl or substituted or unsubstituted heterocycloalkyl. In some embodiments, R[52] is hydrogen. In some embodiments, R[52] is methyl. In some embodiments, R[52] is ethyl. In some embodiments, R[52] is —CN. In some embodiments, R[52] is —NO$_2$.

R[53], R[54], R[55], and R[56] are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R[53] and R[54] substituents bonded to the same nitrogen atom may optionally be joined to form a substituted or unsubstituted heterocycloalkyl or substituted or unsubstituted heteroaryl. In some embodiments, R[53], R[54], R[55], and R[56] are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol p is independently 1 or 2. In some embodiments, p is 1. In some embodiments, p is 2. The symbol q is independently an integer from 1 to 2. In some embodiments, q is 1. In some embodiments, q is 2. The symbol r is independently an integer from 0 to 4. In some embodiments, r is 0. In some embodiments, r is 1. In some embodiments, r is 2. In some embodiments, r is 3. In some embodiments, r is 4. X$^a$ is independently —Cl, —Br, —I, or —F. In some embodiments, X$^a$ is —Cl. In some embodiments, X$^a$ is —Br. In some embodiments, X$^a$ is —I. In some embodiments, X$^a$ is —F.

In some embodiments, each E is independently selected from a group consisting of

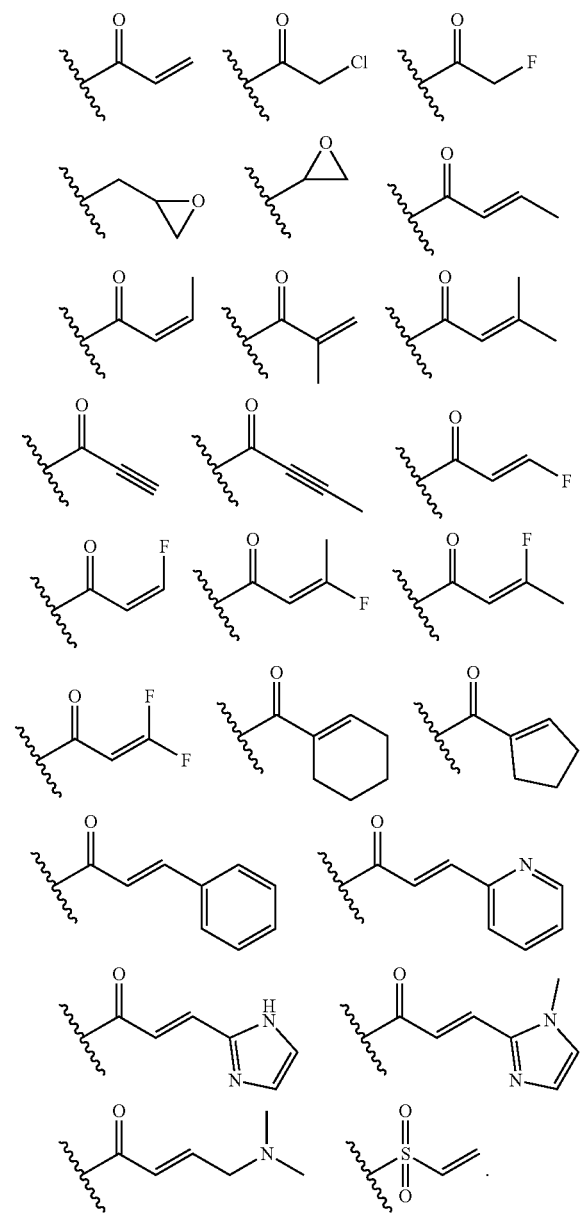

In some embodiments, each E is independently selected from a group consisting of

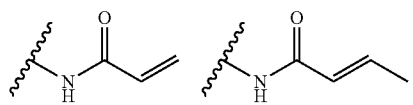

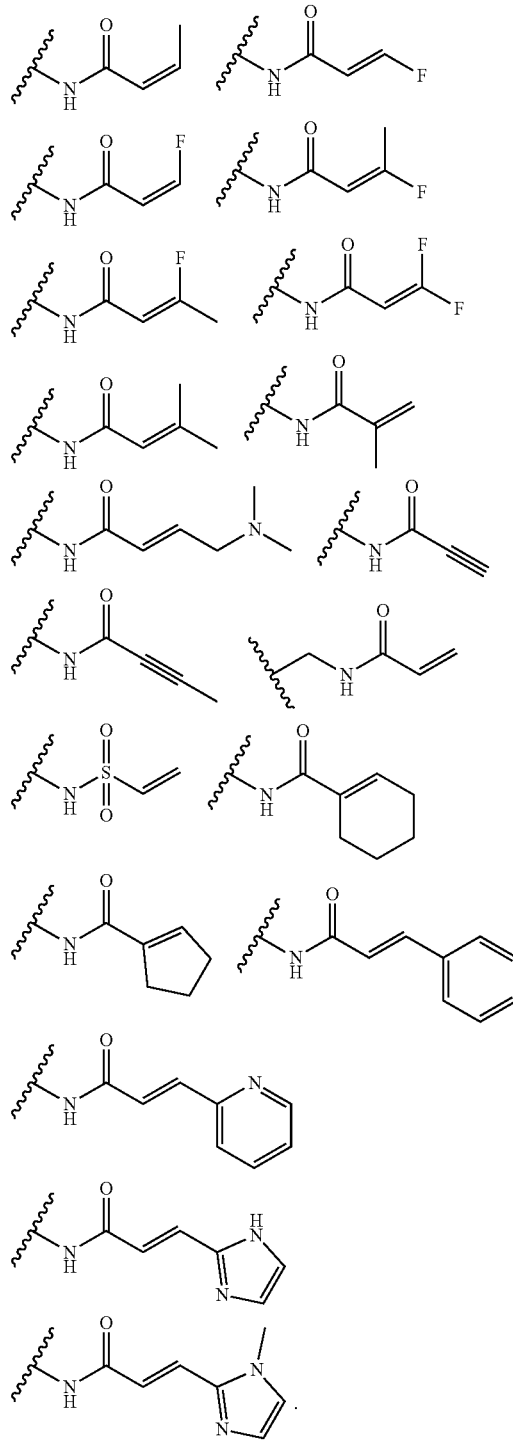
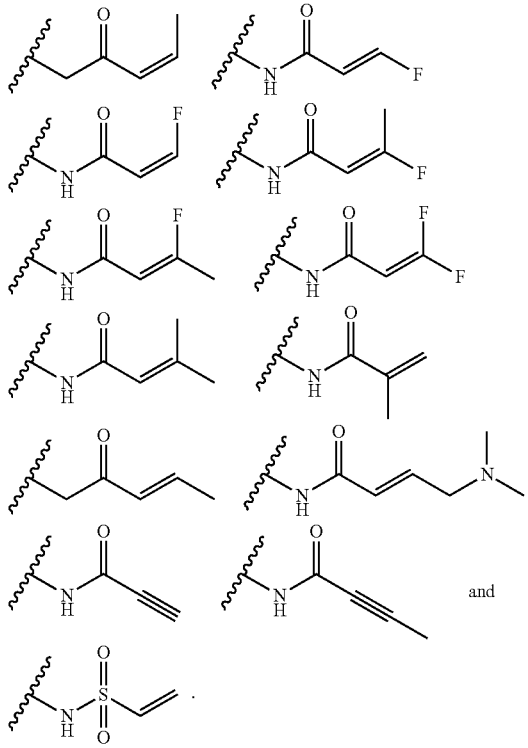

In some embodiments, at least one E is


In some embodiments, E at least one is

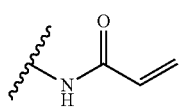

In some embodiments,

is selected from 5- to 7-membered aryl, 5- to 7-membered heteroaryl and 5- to 7-membered heterocycloalkyl.

In some embodiments,

is selected from the group consisting of pyrrolyl, furanyl, thienyl, imidazolyl, pyrazolyl, oxazolyl, isoxazolyl, thiaz- In some embodiments, each E is independently selected from a group consisting of

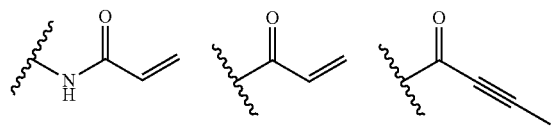

olyl, isothiazolyl, 1,2,3-triazolyl, 1,2,4-triazolyl, furazanyl, 1,2,3-oxadiazolyl, 1,2,4-oxadiazole, 1,2,5-oxadiazole, 1,3,4-oxadiazole, thiadiazolyl, dithiazolyl, tetrazolyl, pyridinyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl, tetrazinyl, phenyl, piperazinyl, morpholinyl, piperidinyl, thiomorpholinyl, pyrrolidinyl, tetrahydrofuranyl and diazepanyl;

For example

is selected from the group consisting of: phenyl, pyridinyl, pyrimidinyl, pyrazinyl, thiazolyl, oxazolyl, imidazolyl, pyrazolyl, isoxazolyl, and thienyl. In some examples,

is phenyl or pyridinyl.

In some embodiments,

is selected from the group consisting of:

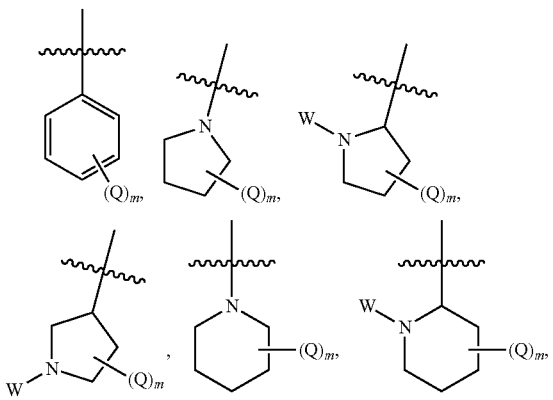

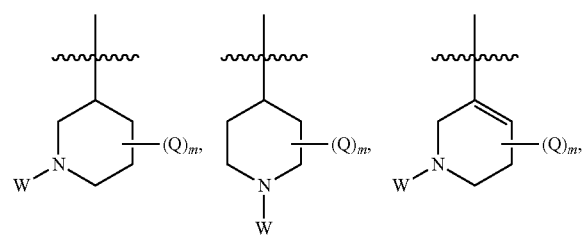

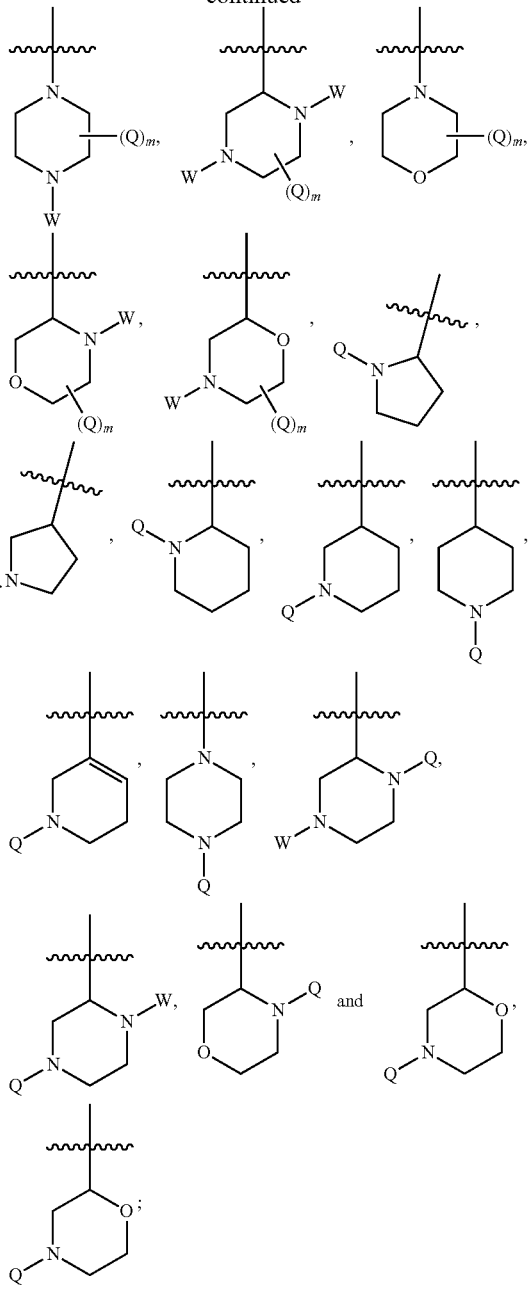

wherein each W is independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, or E; wherein each E is independently an electrophilic group capable of forming a covalent bond with a nucleophile.

In some embodiments,
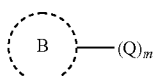
is selected from the group consisting of
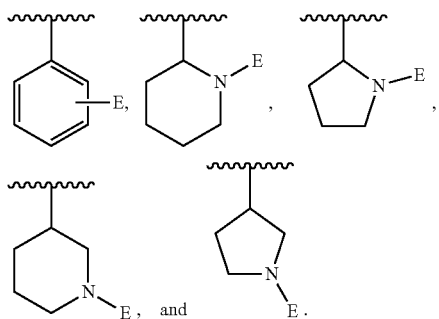
In some embodiments,
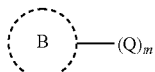
is selected from the group consisting of
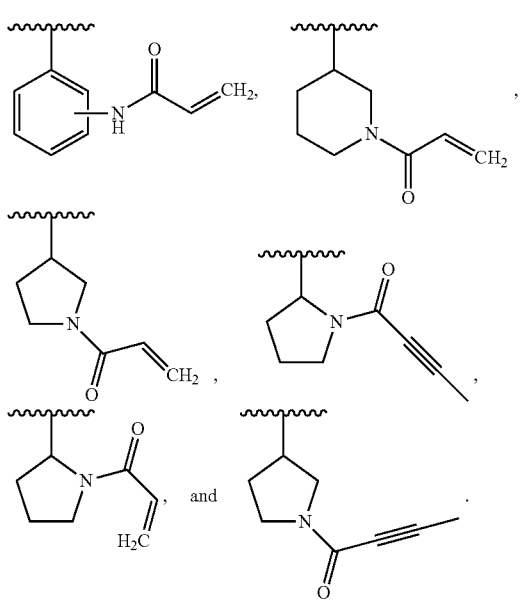
In some embodiments,
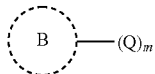
is selected from the group consisting of
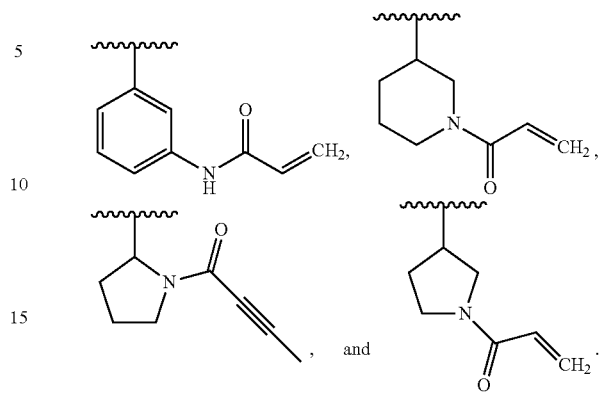
In some embodiments,
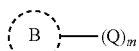
is selected from the group consisting of
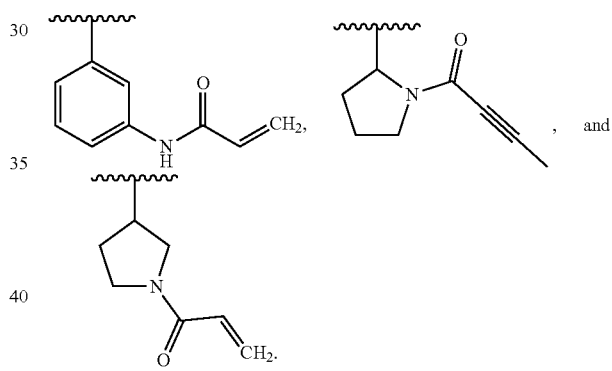
In some embodiments
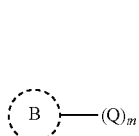 is 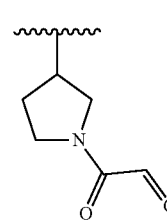
In some embodiments,
 is 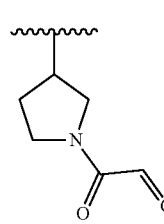

In some embodiments,

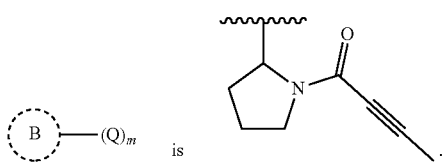 is

In some embodiments,

is 5- to 7-membered aryl or 5- to 7-membered heteroaryl.
In some embodiments,

is selected from the group consisting of pyrrolyl, furanyl, thienyl, imidazolyl, pyrazolyl, oxazolyl, isoxazolyl, thiazolyl, isothiazolyl, 1,2,3-triazolyl, 1,2,4-triazolyl, furazanyl, 1,2,3-oxadiazolyl, 1,2,4-oxadiazole, 1,2,5-oxadiazole, 1,3,4-oxadiazole, thiadiazolyl, dithiazolyl, tetrazolyl, pyridinyl, pyranyl, thiopyranyl, diazinyl, pyrazinyl, pyrimidinyl, pyridazinyl, oxazinyl, thiazinyl, dioxinyl, dithiinyl, 1,2,3-triazinyl, 1,2,4-triazinyl, 1,3,5-triazinyl, tetrazinyl, phenyl, piperazinyl, morpholinyl, piperidinyl, thiomorpholinyl, pyrrolidinyl, tetrahydrofuranyl and diazepanyl; For example

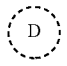

is selected from the group consisting of: phenyl, pyridinyl, pyrimidinyl, pyrazinyl, thiazolyl, oxazolyl, imidazolyl, pyrazolyl, isoxazolyl, and thienyl. In some embodiments,

is phenyl or pyridinyl.
In some embodiments,

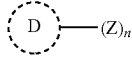

is selected from the group consisting of:

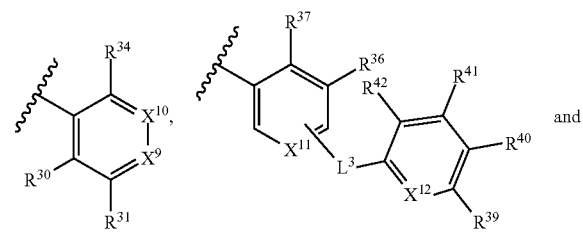 and

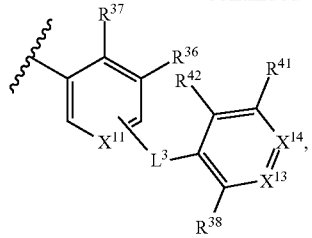

wherein:
$X^9$ is C—$R^{32}$ or N;
$X^{10}$ is C—$R^{33}$ or N;
$X^{11}$ is C—$R^{35}$ or N;
$X^{12}$ is C—$R^{38}$ or N;
$X^{11}$ is C—$R^{39}$ or N;
$X^{14}$ is C—$R^{40}$ or N;
$L^3$ is selected from the group consisting of bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—, optionally substituted C$_{1-6}$ alkylene, optionally substituted C$_{2-6}$ alkenylene, optionally substituted C$_{2-6}$ alkynylene, optionally substituted 1- to 6-membered heteroalkylene, optionally substituted 2- to 6-membered heteroalkenylene, and optionally substituted 2- to 6-membered heteroalkynylene;
$R^{51}$ is independently selected at each occurrence from hydrogen, sulfonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted acyl, optionally substituted alkoxycarbonyl, optionally substituted aminocarbonyl, optionally substituted aminosulfonyl and optionally substituted carbamimidoyl; and
$R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$ are each independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl and optionally substituted carbamimidoyl.
In some embodiments, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$ are each independently selected from the group consisting of hydrogen, cyano, halo, $C_1$-$C_3$ alkyl, $C_1$-$C_3$ haloalkyl, $C_1$-$C_3$ alkoxy, 3- to 6-membered cycloalkyl, aminocarbonyl and amino. In some embodiments, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$ and $R^{42}$ are each independently selected from the group consisting of hydrogen, halo, cyclopropyl, —CN, —CH$_3$, —CF$_3$, —CONH$_2$, —NH$_2$, and —OCH$_3$. In some embodiments, $R^{30}$, $R^{31}$, $R^{32}$ and $R^{41}$ are each independently selected from the group consisting of hydrogen, halo, cyclopropyl, —CN, —CH$_3$, —CF$_3$, —CONH$_2$, —NH$_2$, and —OCH$_3$; and $R^{33}$, $R^{34}$, $R^{35}$, $R^{36}$, $R^{37}$, $R^{38}$, $R^{39}$, $R^{40}$ and $R^{42}$ are each hydrogen.

In some embodiments, $L^3$ is selected from —O—, —N(R$^{51}$)—, —C(O)N(R$^{51}$)— and —N(R$^{51}$)C(O)—. In some examples, $L^3$ is selected from —O—, —NH— and —C(O)NH—. In some embodiments, $L^3$ is —O—. In some embodiments, $L^3$ is —NH—. In some embodiments, $L^3$ is —C(O)NH—.

In some embodiments,

is:

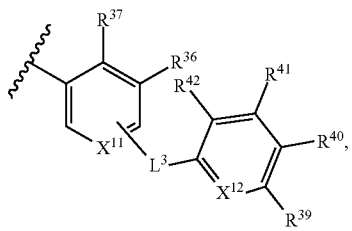

wherein:
$X^{11}$ is C—R$^{35}$ or N;
$X^{12}$ is C—R$^{38}$ or N;
$L^3$ is selected from the group consisting of bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—, optionally substituted C$_{1-6}$ alkylene, optionally substituted C$_{2-6}$ alkenylene, optionally substituted C$_{2-6}$ alkynylene, optionally substituted 1- to 6-membered heteroalkylene, optionally substituted 2- to 6-membered heteroalkenylene, and optionally substituted 2- to 6-membered heteroalkynylene;
$R^{51}$ is independently selected at each occurrence from hydrogen, sulfonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted acyl, optionally substituted alkoxycarbonyl, optionally substituted aminocarbonyl, optionally substituted aminosulfonyl and optionally substituted carbamimidoyl; and
$R^{35}$, $R^{36}$, $R^{37}$, $R^{38}$, $R^{39}$, $R^{40}$, $R^{41}$ and $R^{42}$ are each independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl and optionally substituted carbamimidoyl.

In some embodiments, $R^{35}$, $R^{36}$, $R^{37}$, $R^{38}$, $R^{39}$, $R^{40}$, $R^{41}$ and $R^{42}$ are each independently selected from the group consisting of hydrogen, cyano, halo, C$_1$-C$_3$ alkyl, C$_1$-C$_3$ haloalkyl, C$_1$-C$_3$ alkoxy, 3- to 6-membered cycloalkyl, aminocarbonyl and amino. In some embodiments, $R^{35}$, $R^{36}$, $R^{37}$, $R^{38}$, $R^{39}$, $R^{40}$, $R^{41}$ and $R^{42}$ are each independently selected from the group consisting of hydrogen, halo, cyclopropyl, —CN, —CH$_3$, —CF$_3$, —CONH$_2$, —NH$_2$, and —OCH$_3$. In some embodiments $R^{41}$ is selected from the group consisting of hydrogen, halo, cyclopropyl, —CN, —CH$_3$, —CF$_3$, —CONH$_2$, —NH$_2$, and —OCH$_3$; and $R^{35}$, $R^{36}$, $R^{37}$, $R^{38}$, $R^{39}$, $R^{40}$ and $R^{42}$ are each hydrogen.

In some embodiments, $L^3$ is selected from —O—, —N(R$^{51}$)—, —C(O)N(R$^{51}$)— and —N(R$^{51}$)C(O)—. In some examples, $L^3$ is selected from —O—, —NH— and —C(O)NH—. In some embodiments, $L^3$ is —O—. In some embodiments, $L^3$ is —NH—. In some embodiments, $L^3$ is —C(O)NH—.

In some embodiments,

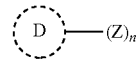

is:

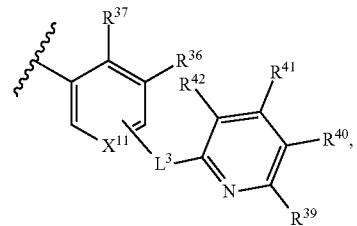

wherein:
$X^{11}$ is C—R$^{35}$ or N;
$L^3$ is selected from the group consisting of bond, —O—, —S—, —N(R$^{51}$)—, —N(R$^{51}$)CH$_2$—, —C(O)—, —C(O)O—, —OC(O)—, —OC(O)O—, —C(O)N(R$^{51}$)—, —C(O)N(R$^{51}$)C(O)—, —C(O)N(R$^{51}$)C(O)N(R$^{51}$)—, —N(R$^{51}$)C(O)—, —N(R$^{51}$)C(O)N(R$^{51}$)—, —N(R$^{51}$)C(O)O—, —OC(O)N(R$^{51}$)—, —C(NR$^{51}$)—, —N(R$^{51}$)C(NR$^{51}$)—, —C(NR$^{51}$)N(R$^{51}$)—, —N(R$^{51}$)C(NR$^{51}$)N(R$^{51}$)—, —S(O)$_2$—, —OS(O)—, —S(O)O—, —S(O)—, —OS(O)$_2$—, —S(O)$_2$O—, —N(R$^{51}$)S(O)$_2$—, —S(O)$_2$N(R$^{51}$)—, —N(R$^{51}$)S(O)—, —S(O)N(R$^{51}$)—, —N(R$^{51}$)S(O)$_2$N(R$^{51}$)—, —N(R$^{51}$)S(O)N(R$^{51}$)—, optionally substituted C$_{1-6}$ alkylene, optionally substituted C$_{2-6}$ alkenylene, optionally substituted C$_{2-6}$ alkynylene, optionally substituted 1- to 6-membered heteroalkylene, optionally substituted 2- to 6-membered heteroalkenylene, and optionally substituted 2- to 6-membered heteroalkynylene;

R$^{51}$ is independently selected at each occurrence from hydrogen, sulfonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted acyl, optionally substituted alkoxycarbonyl, optionally substituted aminocarbonyl, optionally substituted aminosulfonyl and optionally substituted carbamimidoyl; and R$^{35}$, R$^{36}$, R$^{37}$, R$^{39}$, R$^{40}$, R$^{41}$ and R$^{42}$ are each independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl and optionally substituted carbamimidoyl.

In some embodiments R$^{35}$, R$^{36}$, R$^{37}$, R$^{39}$, R$^{40}$, R$^{41}$ and R$^{42}$ are each independently selected from the group consisting of hydrogen, cyano, halo, C$_1$-C$_3$ alkyl, C$_1$-C$_3$ haloalkyl, C$_1$-C$_3$ alkoxy, 3- to 6-membered cycloalkyl, aminocarbonyl and amino. In some embodiments, R$^{35}$, R$^{36}$, R$^{37}$, R$^{39}$, R$^{40}$, R$^{41}$ and R$^{42}$ are each independently selected from the group consisting of hydrogen, halo, cyclopropyl, —CN, —CH$_3$, —CF$_3$, —CONH$_2$, —NH$_2$, and —OCH$_3$. In some embodiments R$^{41}$ is selected from the group consisting of hydrogen, halo, cyclopropyl, —CN, —CH$_3$, —CF$_3$, —CONH$_2$, —NH$_2$, and —OCH$_3$; and R$^{35}$, R$^{36}$, R$^{37}$, R$^{39}$, R$^{40}$ and R$^{42}$ are each hydrogen.

In some embodiments, L$^3$ is selected from —O—, —N(R$^{51}$)—, —C(O)N(R$^{51}$)— and —N(R$^{51}$)C(O)—. In some examples, L$^3$ is selected from —O—, —NH— and —C(O)NH—. In some embodiments, L$^3$ is —O—. In some embodiments, L$^3$ is —NH—. In some embodiments, L$^3$ is —C(O)NH—.

In some embodiments, the compound or pharmaceutically acceptable salt has the Formula Ia:

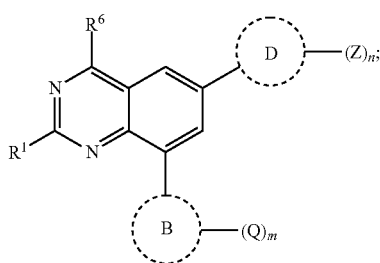

Formula Ia wherein

Z, Q, R$^1$, R$^6$, m and n are as defined for Formula I.

In some embodiments, the compound or pharmaceutically acceptable salt has the Formula Ib:

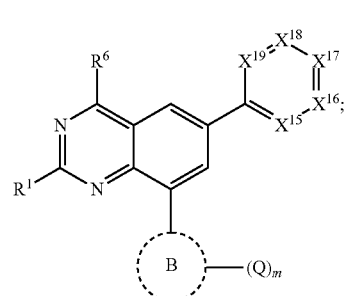

Formula Ib wherein

Q, R$^1$, R$^6$, and m are as defined for Formula I;

X$^{15}$ is N or CR$^{43}$;

X$^{16}$ is N or CR$^{44}$;

X$^{17}$ is N or CR$^{45}$;

X$^{18}$ is N or CR$^{46}$;

X$^{19}$ is N or CR$^{47}$; and

R$^{43}$, R$^{44}$, R$^{45}$, R$^{46}$ and R$^{47}$ are independently selected from hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl and E; wherein E is an electrophilic group capable of forming a covalent bond with a nucleophile.

In some embodiments,

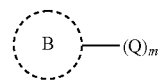

is selected from the group consisting of
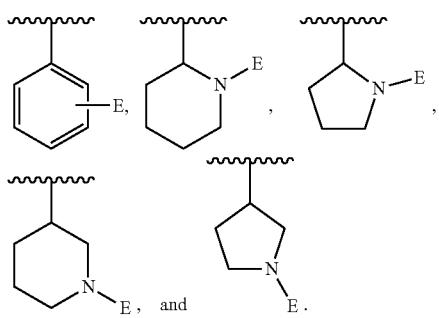
In some embodiments,
is selected from the group consisting of
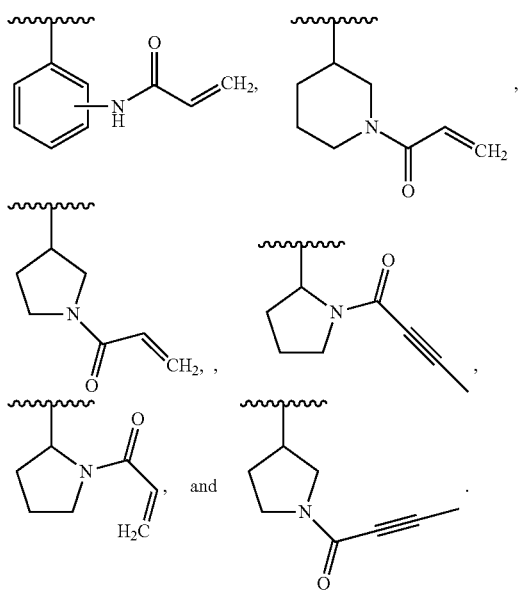
In some embodiments,
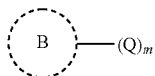
is selected from the group consisting of
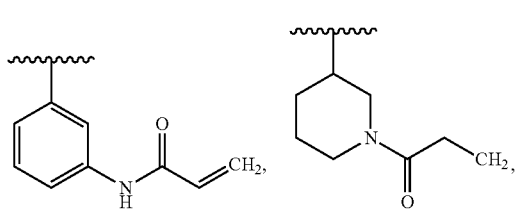
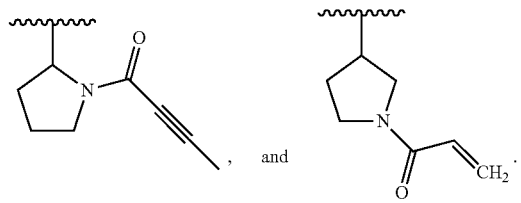
In some embodiments
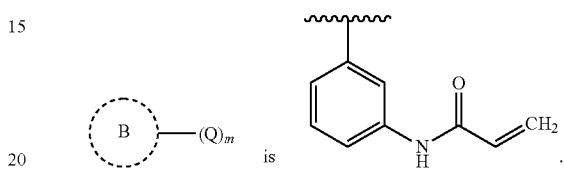
In some embodiments,
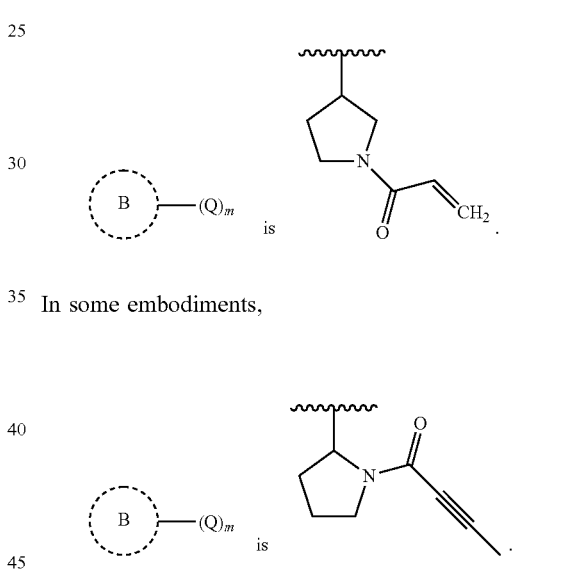
In some embodiments, the compound or pharmaceutically acceptable salt has the Formula Ic:
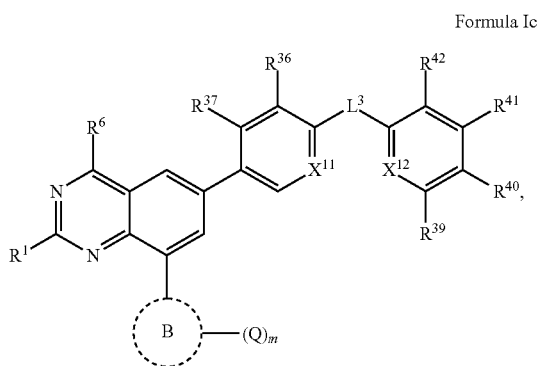
Formula Ic wherein

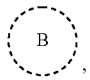

Q, $R^1$, $R^6$, and m are as described above for Formula I;
$X^{11}$ is C—$R^{35}$ or N;
$X^{12}$ is C—$R^{38}$ or N;
$L^3$ is selected from the group consisting of bond, —O—, —S—, —N($R^{51}$)—, —N($R^{51}$)$CH_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—, optionally substituted $C_{1-6}$ alkylene, optionally substituted $C_{2-6}$ alkenylene, optionally substituted $C_{2-6}$ alkynylene, optionally substituted 1- to 6-membered heteroalkylene, optionally substituted 2- to 6-membered heteroalkenylene, and optionally substituted 2- to 6-membered heteroalkynylene; and $R^{35}$, $R^{36}$, $R^{37}$, $R^{38}$, $R^{39}$, $R^{40}$, $R^{41}$ and $R^{42}$ are each independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl and optionally substituted carbamimidoyl.

In some embodiments, $R^{35}$, $R^{36}$, $R^{37}$, $R^{38}$, $R^{39}$, $R^{40}$, $R^{41}$ and $R^{42}$ are each independently selected from the group consisting of hydrogen, cyano, halo, $C_1$-$C_3$ alkyl, $C_1$-$C_3$ haloalkyl, $C_1$-$C_3$ alkoxy, 3- to 6-membered cycloalkyl, aminocarbonyl and amino. In some embodiments, $R^{35}$, $R^{36}$, $R^{37}$, $R^{38}$, $R^{39}$, $R^{40}$, $R^{41}$ and $R^{42}$ are each independently selected from the group consisting of hydrogen, halo, cyclopropyl, —CN, —$CH_3$, —$CF_3$, —$CONH_2$, —$NH_2$, and —$OCH_3$. In some embodiments, $R^{41}$ is selected from the group consisting of hydrogen, halo, cyclopropyl, —CN, —$CH_3$, —$CF_3$, —$CONH_2$, —$NH_2$, and —$OCH_3$; and $R^{31}$, $R^{36}$, $R^{37}$, $R^{38}$, $R^{39}$, $R^{40}$ and $R^{42}$ are each hydrogen.

In some embodiments, $L^3$ is selected from —O—, —N($R^{51}$)—, —C(O)N($R^{51}$)— and —N($R^{51}$)C(O)—. In some examples, $L^3$ is selected from —O—, —NH— and —C(O)NH—.

In some embodiments,

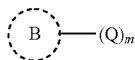

is selected from the group consisting of

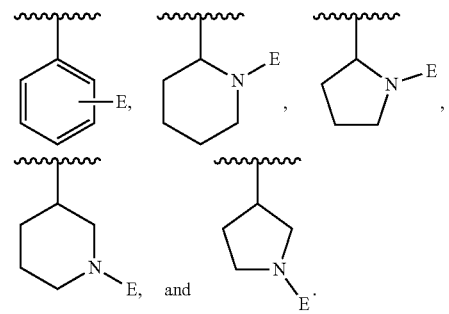

In some embodiments,

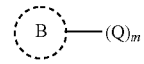

is selected from the group consisting of

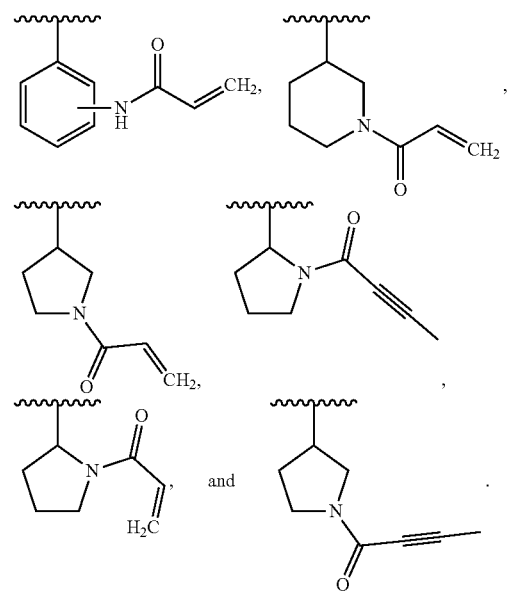

In some embodiments,

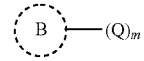

is selected from the group consisting of

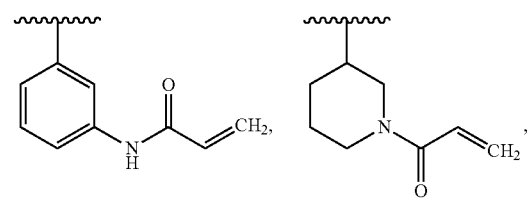

-continued

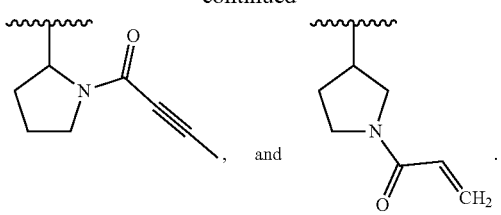
and

In some embodiments

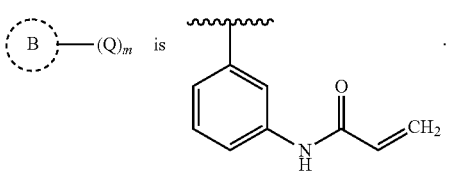 is

In some embodiments,

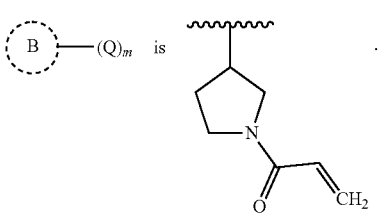 is

In some embodiments,

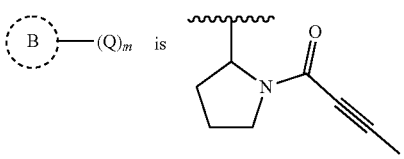 is

In some embodiments, the compounds have the Formula Id:

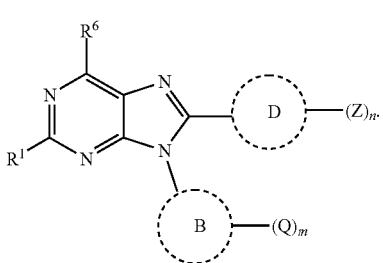

(Id)

In some embodiments, the compounds have the Formula Ie:

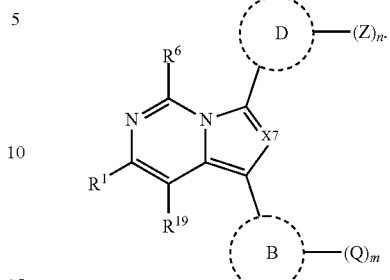

(Ie)

In some embodiments, the compounds have the Formula If:

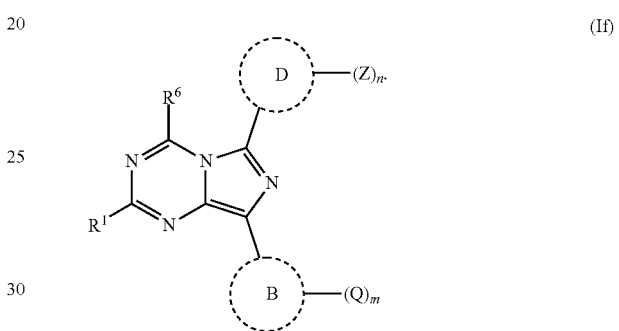

(If)

In some embodiments, the compounds have the Formula Ig:

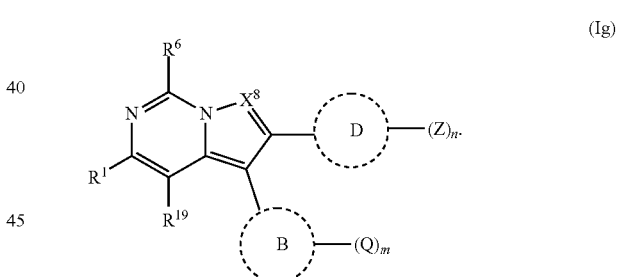

(Ig)

In some embodiments, for the compounds of Formula Ic, Id, Ie, If, and Ig,

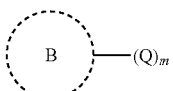

is selected from the group consisting of

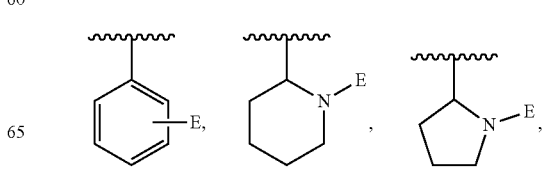

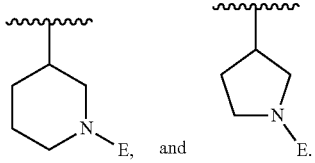 and

In some embodiments,

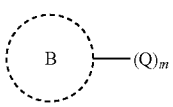

is selected from the group consisting of

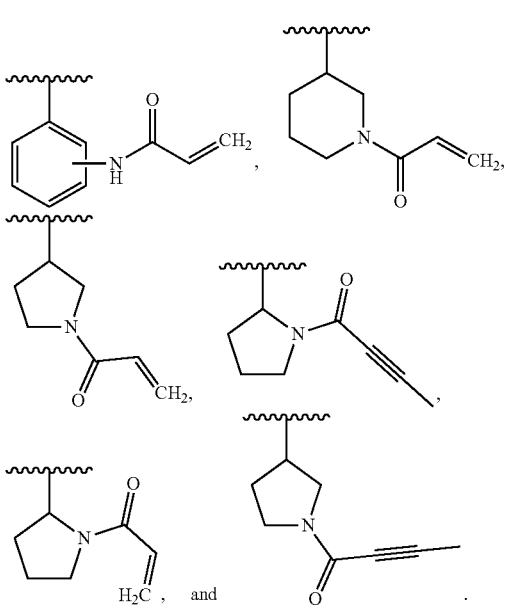

In some embodiments,

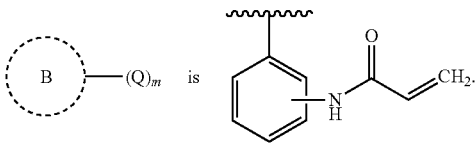 is 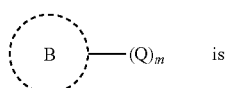

In some embodiments,

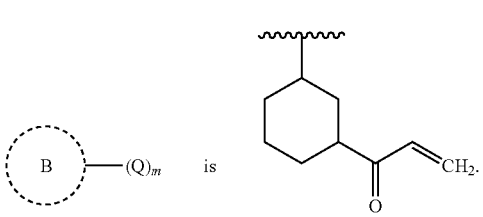

In some embodiments,

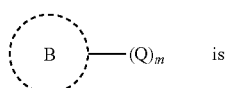 is 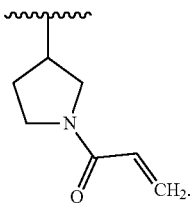

In some embodiments,

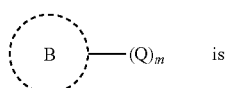 is 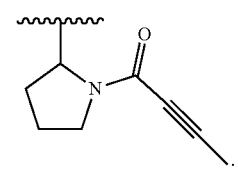

In some embodiments

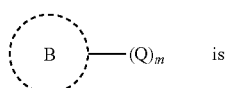 is 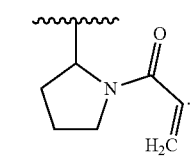

In some embodiments,

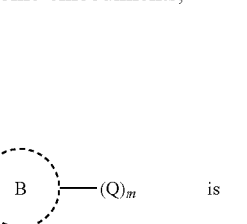 is 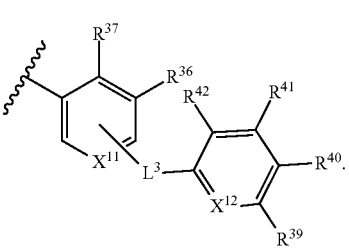

In some embodiments, for the compounds of Formula Ic, Id, Ie, If, and Ig,

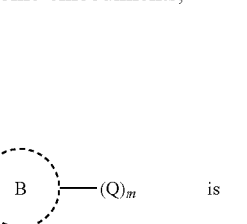 is:

In some embodiments, $L^3$ is selected from —O— and —C(O)NH—. In some embodiments, $L^3$ is —C(O)NH—. In some embodiments, $L^3$ is —O—. In some embodiments, $X^{11}$ is C—$R^{35}$. In some embodiments, $X^{12}$ is N. In some embodiments, $R^{35}$, $R^{36}$, $R^{37}$, $R^{38}$, $R^{39}$, $R^{40}$, $R^{41}$, and $R^{42}$ are each independently selected from the group consisting of hydrogen, chloro, fluoro, cyano, cyclopropyl, —$CH_3$, —$CF_3$, —$OCH_3$ and —OPh. In some embodiments, $R^{35}$, $R^{36}$, $R^{37}$, $R^{38}$, $R^{39}$, $R^{40}$, $R^{41}$, and $R^{42}$ are each independently selected from the group consisting of hydrogen, cyclopropyl, —CF$_3$, and —OCH$_3$.

In some embodiments, $R^1$ is selected from the group consisting of hydrogen, optionally substituted aryl and optionally substituted amino. In some embodiments, $R^1$ is selected from hydrogen and —NH$_2$. In some embodiments, $R^1$ is hydrogen. In some embodiments, $R^1$ is optionally substituted aryl. In some embodiments, $R^1$ is optionally substituted amino.

In some embodiments, $R^6$ is selected from the group consisting of hydrogen, cyano, halo, hydroxy, optionally substituted alkyl, optionally substituted aryl, optionally substituted heteroaryl, and optionally substituted amino. In some embodiments, $R^6$ is selected from the group consisting of hydrogen, optionally substituted aryl and optionally substituted amino. In some embodiments, $R^6$ is selected from hydrogen and —NH$_2$. In some embodiments, $R^6$ is hydrogen. In some embodiments, $R^6$ is optionally substituted aryl. In some embodiments, $R^6$ is optionally substituted amino.

In some embodiments, the compound or pharmaceutically acceptable salt has the Formula II:

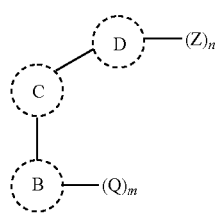

Formula II or a pharmaceutically acceptable salt thereof, wherein:

is selected from the group consisting of aryl, heteroaryl and heterocycloalkyl, each of which is substituted with E;

is optionally substituted heteroaryl;

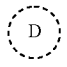

is selected from the group consisting of aryl, heteroaryl and heterocycloalkyl;

Q and Z are each independently selected at each occurrence from hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, and optionally substituted carbamimidoyl or E;

E is an electrophilic group capable of forming a covalent bond with a nucleophile; and m and n are each independently 0, 1, 2, 3, 4 or 5.

In another aspect, the present disclosure provides a compound or pharmaceutically acceptable salt thereof, wherein the compound is chosen from the group consisting of:

1-(2-(6-(2-fluorophenyl)quinazolin-8-yl)pyrrolidin-1-yl)but-2-yn-1-one,
1-(2-(6-phenylquinazolin-8-yl)pyrrolidin-1-yl)but-2-yn-1-one,
1-(2-(6-(2,6-difluorophenyl)quinazolin-8-yl)pyrrolidin-1-yl)but-2-yn-1-one,
1-(2-(2-amino-6-phenylquinazolin-8-yl)pyrrolidin-1-yl)but-2-yn-1-one,
1-(2-(2-amino-6-(2-fluorophenyl)quinazolin-8-yl)pyrrolidin-1-yl)but-2-yn-1-one,
4-(8-(1-(but-2-ynoyl)pyrrolidin-2-yl)quinazolin-6-yl)-N-phenylbenzamide,
4-(8-(1-(but-2-ynoyl)pyrrolidin-2-yl)quinazolin-6-yl)-N-(pyridin-2-yl)benzamide,
4-(8-(1-(but-2-ynoyl)pyrrolidin-2-yl)quinazolin-6-yl)-N-(4-(trifluoromethyl)pyridin-2-yl)benzamide,
4-(8-(1-(but-2-ynoyl)pyrrolidin-2-yl)quinazolin-6-yl)-N-(4-fluoropyridin-2-yl)benzamide,
4-(8-(1-(but-2-ynoyl)pyrrolidin-2-yl)quinazolin-6-yl)-3-chloro-N-(pyridin-2-yl)benzamide,
4-(8-(1-(but-2-ynoyl)pyrrolidin-2-yl)quinazolin-6-yl)-3-fluoro-N-(pyridin-2-yl)benzamide,
4-(8-(1-(but-2-ynoyl)pyrrolidin-2-yl)quinazolin-6-yl)-3,5-difluoro-N-(pyridin-2-yl)benzamide,
4-(8-(1-(but-2-ynoyl)pyrrolidin-2-yl)quinazolin-6-yl)-3-fluoro-N-(4-(trifluoromethyl)pyridin-2-yl)benzamide,
4-(8-(1-(but-2-ynoyl)pyrrolidin-2-yl)quinazolin-6-yl)-2,3-difluoro-N-(pyridin-2-yl)benzamide,
1-(2-(6-(4-phenoxyphenyl)quinazolin-8-yl)pyrrolidin-1-yl)but-2-yn-1-one,
1-(2-(6-(4-(pyridin-2-yloxy)phenyl)quinazolin-8-yl)pyrrolidin-1-yl)but-2-yn-1-one,
1-(2-(6-(4-((4-(trifluoromethyl)pyridin-2-yl)oxy)phenyl)quinazolin-8-yl)pyrrolidin-1-yl)but-2-yn-1-one,
1-(2-(6-(2-fluoro-4-(pyridin-2-yloxy)phenyl)quinazolin-8-yl)pyrrolidin-1-yl)but-2-yn-1-one,
1-(2-(6-(2-chloro-4-(pyridin-2-yloxy)phenyl)quinazolin-8-yl)pyrrolidin-1-yl)but-2-yn-1-one,
1-(2-(6-(2,6-difluoro-4-(pyridin-2-yloxy)phenyl)quinazolin-8-yl)pyrrolidin-1-yl)but-2-yn-1-one,
1-(2-(6-(2,3-difluoro-4-(pyridin-2-yloxy)phenyl)quinazolin-8-yl)pyrrolidin-1-yl)but-2-yn-1-one,
1-(2-(2-amino-6-(2,6-difluoro-4-(pyridin-2-yloxy)phenyl)quinazolin-8-yl)pyrrolidin-1-yl)but-2-yn-1-one,
1-(2-(2-amino-6-(4-(pyridin-2-yloxy)phenyl)quinazolin-8-yl)pyrrolidin-1-yl)but-2-yn-1-one,
1-(2-(2-amino-6-(2-fluoro-4-(pyridin-2-yloxy)phenyl)quinazolin-8-yl)pyrrolidin-1-yl)but-2-yn-1-one,
1-(2-(2-amino-6-(2-chloro-4-(pyridin-2-yloxy)phenyl)quinazolin-8-yl)pyrrolidin-1-yl)but-2-yn-1-one,
4-(5-(1-(but-2-ynoyl)pyrrolidin-2-yl)pyrrolo[1,2-c]pyrimidin-7-yl)-N-phenylbenzamide,
4-(5-(1-(but-2-ynoyl)pyrrolidin-2-yl)pyrrolo[1,2-c]pyrimidin-7-yl)-N-(pyridin-2-yl)benzamide,
4-(5-(1-(but-2-ynoyl)pyrrolidin-2-yl)pyrrolo[1,2-c]pyrimidin-7-yl)-N-(4-(trifluoromethyl)pyridin-2-yl)benzamide, 4-(5-(1-(but-2-ynoyl)pyrrolidin-2-yl)pyrrolo[1,2-c]pyrimidin-7-yl)-N-(3-chloropyridin-2-yl)benzamide,
4-(5-(1-(but-2-ynoyl)pyrrolidin-2-yl)pyrrolo[1,2-c]pyrimidin-7-yl)-N-(4-chloropyridin-2-yl)benzamide,
4-(5-(1-(but-2-ynoyl)pyrrolidin-2-yl)pyrrolo[1,2-c]pyrimidin-7-yl)-3-fluoro-N-(pyridin-2-yl)benzamide,
4-(5-(1-(but-2-ynoyl)pyrrolidin-2-yl)pyrrolo[1,2-c]pyrimidin-7-yl)-3-chloro-N-(pyridin-2-yl)benzamide,
4-(5-(1-(but-2-ynoyl)pyrrolidin-2-yl)pyrrolo[1,2-c]pyrimidin-7-yl)-2-fluoro-N-(pyridin-2-yl)benzamide,
4-(5-(1-(but-2-ynoyl)pyrrolidin-2-yl)pyrrolo[1,2-c]pyrimidin-7-yl)-3,5-dichloro-N-(pyridin-2-yl)benzamide,
4-(5-(1-(but-2-ynoyl)pyrrolidin-2-yl)pyrrolo[1,2-c]pyrimidin-7-yl)-3,5-difluoro-N-(pyridin-2-yl)benzamide,
4-(5-(1-(but-2-ynoyl)pyrrolidin-2-yl)pyrrolo[1,2-c]pyrimidin-7-yl)-3-fluoro-N-(4-(trifluoromethyl)pyridin-2-yl)benzamide,
4-(5-(1-(but-2-ynoyl)pyrrolidin-2-yl)pyrrolo[1,2-c]pyrimidin-7-yl)-3-chloro-N-(4-(trifluoromethyl)pyridin-2-yl)benzamide,
4-(5-(1-acryloylpyrrolidin-3-yl)pyrrolo[1,2-c]pyrimidin-7-yl)-N-phenylbenzamide,
4-(5-(1-acryloylpyrrolidin-3-yl)pyrrolo[1,2-c]pyrimidin-7-yl)-N-(pyridin-2-yl)benzamide,
4-(5-(1-acryloylpyrrolidin-3-yl)pyrrolo[1,2-c]pyrimidin-7-yl)-N-(4-(trifluoromethyl)pyridin-2-yl)benzamide,
4-(5-(1-acryloylpyrrolidin-3-yl)pyrrolo[1,2-c]pyrimidin-7-yl)-N-(4-cyanopyridin-2-yl)benzamide,
4-(5-(1-acryloylpyrrolidin-3-yl)pyrrolo[1,2-c]pyrimidin-7-yl)-N-(4-fluoropyridin-2-yl)benzamide,
4-(5-(1-acryloylpyrrolidin-3-yl)pyrrolo[1,2-c]pyrimidin-7-yl)-N-(4-chloropyridin-2-yl)benzamide,
4-(5-(1-acryloylpyrrolidin-3-yl)pyrrolo[1,2-c]pyrimidin-7-yl)-N-(3-chloropyridin-2-yl)benzamide,
4-(5-(1-acryloylpyrrolidin-3-yl)pyrrolo[1,2-c]pyrimidin-7-yl)-N-(3-fluoropyridin-2-yl)benzamide,
4-(5-(1-acryloylpyrrolidin-3-yl)pyrrolo[1,2-c]pyrimidin-7-yl)-N-(2-fluorophenyl)benzamide,
4-(5-(1-acryloylpyrrolidin-3-yl)pyrrolo[1,2-c]pyrimidin-7-yl)-N-(2-chlorophenyl)benzamide,
4-(5-(1-acryloylpyrrolidin-3-yl)pyrrolo[1,2-c]pyrimidin-7-yl)-N-(3-(trifluoromethyl)phenyl)benzamide,
4-(5-(1-acryloylpyrrolidin-3-yl)pyrrolo[1,2-c]pyrimidin-7-yl)-N-(3-fluorophenyl)benzamide,
4-(5-(1-acryloylpyrrolidin-3-yl)pyrrolo[1,2-c]pyrimidin-7-yl)-N-(3-chlorophenyl)benzamide,
4-(5-(1-acryloylpyrrolidin-3-yl)pyrrolo[1,2-c]pyrimidin-7-yl)-2-fluoro-N-(pyridin-2-yl)benzamide,
4-(5-(1-acryloylpyrrolidin-3-yl)pyrrolo[1,2-c]pyrimidin-7-yl)-2-chloro-N-(pyridin-2-yl)benzamide,
4-(5-(1-acryloylpyrrolidin-3-yl)pyrrolo[1,2-c]pyrimidin-7-yl)-3-fluoro-N-(pyridin-2-yl)benzamide,
4-(5-(1-acryloylpyrrolidin-3-yl)pyrrolo[1,2-c]pyrimidin-7-yl)-3-chloro-N-(pyridin-2-yl)benzamide,
4-(5-(1-acryloylpyrrolidin-3-yl)pyrrolo[1,2-c]pyrimidin-7-yl)-3-chloro-N-(4-(trifluoromethyl)pyridin-2-yl)benzamide,
4-(5-(1-acryloylpyrrolidin-3-yl)pyrrolo[1,2-c]pyrimidin-7-yl)-3-fluoro-N-(4-(trifluoromethyl)pyridin-2-yl)benzamide,
4-(5-(1-acryloylpyrrolidin-3-yl)pyrrolo[1,2-c]pyrimidin-7-yl)-2,3-difluoro-N-(pyridin-2-yl)benzamide,
4-(5-(1-acryloylpyrrolidin-3-yl)pyrrolo[1,2-c]pyrimidin-7-yl)-2-fluoro-N-(pyridin-2-yl)benzamide,
1-(3-(7-(4-(pyridin-2-yloxy)phenyl)pyrrolo[1,2-c]pyrimidin-5-yl)pyrrolidin-1-yl)prop-2-en-1-one,
1-(3-(7-(4-((4-(trifluoromethyl)pyridin-2-yl)oxy)phenyl)pyrrolo[1,2-c]pyrimidin-5-yl)pyrrolidin-1-yl)prop-2-en-1-one,
1-(3-(7-(4-((3-fluoropyridin-2-yl)oxy)phenyl)pyrrolo[1,2-c]pyrimidin-5-yl)pyrrolidin-1-yl)prop-2-en-1-one,
1-(3-(7-(4-((3-chloropyridin-2-yl)oxy)phenyl)pyrrolo[1,2-c]pyrimidin-5-yl)pyrrolidin-1-yl)prop-2-en-1-one,
1-(3-(7-(2-chloro-4-(pyridin-2-yloxy)phenyl)pyrrolo[1,2-c]pyrimidin-5-yl)pyrrolidin-1-yl)prop-2-en-1-one,
1-(3-(7-(2-fluoro-4-(pyridin-2-yloxy)phenyl)pyrrolo[1,2-c]pyrimidin-5-yl)pyrrolidin-1-yl)prop-2-en-1-one,
1-(3-(7-(2,3-difluoro-4-(pyridin-2-yloxy)phenyl)pyrrolo[1,2-c]pyrimidin-5-yl)pyrrolidin-1-yl)prop-2-en-1-one,
1-(3-(7-(3-fluoro-4-(pyridin-2-yloxy)phenyl)pyrrolo[1,2-c]pyrimidin-5-yl)pyrrolidin-1-yl)prop-2-en-1-one,
1-(3-(1-amino-7-(4-(pyridin-2-yloxy)phenyl)pyrrolo[1,2-c]pyrimidin-5-yl)pyrrolidin-1-yl)prop-2-en-1-one,
1-(3-(1-amino-7-(4-((4-(trifluoromethyl)pyridin-2-yl)oxy)phenyl)pyrrolo[1,2-c]pyrimidin-5-yl)pyrrolidin-1-yl)prop-2-en-1-one,
1-(3-(1-amino-7-(4-((3-fluoropyridin-2-yl)oxy)phenyl)pyrrolo[1,2-c]pyrimidin-5-yl)pyrrolidin-1-yl)prop-2-en-1-one,
1-(3-(1-amino-7-(4-((3-chloropyridin-2-yl)oxy)phenyl)pyrrolo[1,2-c]pyrimidin-5-yl)pyrrolidin-1-yl)prop-2-en-1-one,
1-(3-(1-amino-7-(2-fluoro-4-(pyridin-2-yloxy)phenyl)pyrrolo[1,2-c]pyrimidin-5-yl)pyrrolidin-1-yl)prop-2-en-1-one,
1-(3-(1-amino-7-(3-fluoro-4-(pyridin-2-yloxy)phenyl)pyrrolo[1,2-c]pyrimidin-5-yl)pyrrolidin-1-yl)prop-2-en-1-one,
4-(5-(1-acryloylpyrrolidin-3-yl)-1-aminopyrrolo[1,2-c]pyrimidin-7-yl)-N-(pyridin-2-yl)benzamide,
4-(5-(1-acryloylpyrrolidin-3-yl)-1-aminopyrrolo[1,2-c]pyrimidin-7-yl)-N-(4-(trifluoromethyl)pyridin-2-yl)benzamide,
4-(5-(1-acryloylpyrrolidin-3-yl)-1-aminopyrrolo[1,2-c]pyrimidin-7-yl)-N-(3-chloropyridin-2-yl)benzamide,
4-(5-(1-acryloylpyrrolidin-3-yl)-1-aminopyrrolo[1,2-c]pyrimidin-7-yl)-3-chloro-N-(pyridin-2-yl)benzamide,
4-(5-(1-acryloylpyrrolidin-3-yl)-1-aminopyrrolo[1,2-c]pyrimidin-7-yl)-2-fluoro-N-(pyridin-2-yl)benzamide,
4-(1-amino-5-(1-(but-2-ynoyl)pyrrolidin-2-yl)pyrrolo[1,2-c]pyrimidin-7-yl)-N-(pyridin-2-yl)benzamide,
4-(1-amino-5-(1-(but-2-ynoyl)pyrrolidin-2-yl)pyrrolo[1,2-c]pyrimidin-7-yl)-N-(4-(trifluoromethyl)pyridin-2-yl)benzamide,
4-(1-amino-5-(1-(but-2-ynoyl)pyrrolidin-2-yl)pyrrolo[1,2-c]pyrimidin-7-yl)-N-(3-chloropyridin-2-yl)benzamide,
4-(1-amino-5-(1-(but-2-ynoyl)pyrrolidin-2-yl)pyrrolo[1,2-c]pyrimidin-7-yl)-3-chloro-N-(pyridin-2-yl)benzamide,
4-(1-amino-5-(1-(but-2-ynoyl)pyrrolidin-2-yl)pyrrolo[1,2-c]pyrimidin-7-yl)-2-fluoro-N-(pyridin-2-yl)benzamide,
4-(1-amino-5-(1-(but-2-ynoyl)pyrrolidin-2-yl)pyrrolo[1,2-c]pyrimidin-7-yl)-N-(3-fluoropyridin-2-yl)benzamide,
1-(2-(1-amino-7-(4-phenoxyphenyl)pyrrolo[1,2-c]pyrimidin-5-yl)pyrrolidin-1-yl)but-2-yn-1-one,
1-(2-(1-amino-7-(4-(pyridin-2-yloxy)phenyl)pyrrolo[1,2-c]pyrimidin-5-yl)pyrrolidin-1-yl)but-2-yn-1-one,
1-(2-(1-amino-7-(4-((4-(trifluoromethyl)pyridin-2-yl)oxy)phenyl)pyrrolo[1,2-c]pyrimidin-5-yl)pyrrolidin-1-yl)but-2-yn-1-one,
1-(2-(1-amino-7-(4-((3-fluoropyridin-2-yl)oxy)phenyl)pyrrolo[1,2-c]pyrimidin-5-yl)pyrrolidin-1-yl)but-2-yn-1-one, 1-(2-(1-amino-7-(4-((3-chloropyridin-2-yl)oxy)phenyl)pyrrolo[1,2-c]pyrimidin-5-yl)pyrrolidin-1-yl)but-2-yn-1-one,
1-(2-(1-amino-7-(2-chloro-4-(pyridin-2-yloxy)phenyl)pyrrolo[1,2-c]pyrimidin-5-yl)pyrrolidin-1-yl)but-2-yn-1-one,
1-(2-(1-amino-7-(3-fluoro-4-(pyridin-2-yloxy)phenyl)pyrrolo[1,2-c]pyrimidin-5-yl)pyrrolidin-1-yl)but-2-yn-1-one,
1-(2-(1-amino-7-(2-fluoro-4-(pyridin-2-yloxy)phenyl)pyrrolo[1,2-c]pyrimidin-5-yl)pyrrolidin-1-yl)but-2-yn-1-one,
N-(3-(6-(3-((3-cyanophenyl)amino)phenyl)quinazolin-8-yl)phenyl)acrylamide,
N-(3-(6-(3-((3-cyclopropylphenyl)amino)phenyl)quinazolin-8-yl)phenyl)acrylamide,
N-(3-(6-(2-cyanopyridin-4-yl)quinazolin-8-yl)phenyl)acrylamide,
N-(3-(6-(2-cyclopropylpyridin-4-yl)quinazolin-8-yl)phenyl)acrylamide,
N-(3-(6-(4-((3-cyanophenyl)amino)phenyl)quinazolin-8-yl)phenyl)acrylamide,
N-(3-(6-(4-((3-cyclopropylphenyl)amino)phenyl)quinazolin-8-yl)phenyl)acrylamide,
3-((3-(8-(1-acryloylpiperidin-3-yl)quinazolin-6-yl)phenyl)amino)benzonitrile,
1-(3-(6-(3-((3-cyclopropylphenyl)amino)phenyl)quinazolin-8-yl)piperidin-1-yl)prop-2-en-1-one,
4-(8-(3-acrylamidophenyl)quinazolin-6-yl)-N-(3-cyanophenyl)benzamide,
4-(8-(3-acrylamidophenyl)quinazolin-6-yl)-N-(3-cyclopropylphenyl)benzamide,
N-(3-(6-(5-cyanopyridin-3-yl)quinazolin-8-yl)phenyl)acrylamide,
N-(3-(6-(5-cyclopropylpyridin-3-yl)quinazolin-8-yl)phenyl)acrylamide,
4-(5-(1-acryloylpyrrolidin-3-yl)pyrrolo[1,2-c]pyrimidin-7-yl)-N-(3-cyanophenyl)benzamide,
4-(5-(1-acryloylpyrrolidin-3-yl)pyrrolo[1,2-c]pyrimidin-7-yl)-N-(3-cyclopropylphenyl)benzamide,
5-(8-(1-acryloylpyrrolidin-3-yl)quinazolin-6-yl)nicotinonitrile,
1-(3-(6-(5-cyclopropylpyridin-3-yl)quinazolin-8-yl)pyrrolidin-1-yl)prop-2-en-1-one,
4-(8-(1-acryloylpyrrolidin-3-yl)quinazolin-6-yl)-N-(3-cyanophenyl)benzamide,
4-(8-(1-acryloylpyrrolidin-3-yl)quinazolin-6-yl)-N-(3-cyclopropylphenyl)benzamide,
5-(8-(3-acrylamidophenyl)quinazolin-6-yl)-N-(3-cyclopropylphenyl)picolinamide,
N-(3-(6-(6-(3-cyanophenoxy)pyridin-3-yl)quinazolin-8-yl)phenyl)acrylamide,
N-(3-(6-(6-(3-cyclopropylphenoxy)pyridin-3-yl)quinazolin-8-yl)phenyl)acrylamide,
3-((5-(8-(1-acryloylpyrrolidin-3-yl)quinazolin-6-yl)pyridin-2-yl)oxy)benzonitrile,
N-(3-(6-(2-chloro-4-((4-cyanopyridin-2-yl)oxy)phenyl)quinazolin-8-yl)phenyl)acrylamide,
N-(3-(6-(2-chloro-4-((4-cyclopropylpyridin-2-yl)oxy)phenyl)quinazolin-8-yl)phenyl)acrylamide,
2-(4-(8-(1-acryloylpyrrolidin-3-yl)quinazolin-6-yl)-3-fluorophenoxy)isonicotinonitrile,
1-(3-(6-(4-((4-cyclopropylpyridin-2-yl)oxy)-2-fluorophenyl)quinazolin-8-yl)pyrrolidin-1-yl)prop-2-en-1-one,
5-(8-(1-acryloylpyrrolidin-3-yl)quinazolin-6-yl)-N-(3-cyanophenyl)picolinamide,
5-(8-(1-acryloylpyrrolidin-3-yl)quinazolin-6-yl)-N-(3-cyclopropylphenyl)picolinamide,
N-(3-(2-amino-6-(4-((4-cyanopyridin-2-yl)oxy)phenyl)quinazolin-8-yl)phenyl)acrylamide,
N-(3-(2-amino-6-(4-((4-cyclopropylpyridin-2-yl)oxy)phenyl)quinazolin-8-yl)phenyl)acrylamide,
2-(4-(8-(1-acryloylpyrrolidin-3-yl)-2-aminoquinazolin-6-yl)phenoxy)isonicotinonitrile,
1-(3-(2-amino-6-(4-((4-cyclopropylpyridin-2-yl)oxy)phenyl)quinazolin-8-yl)pyrrolidin-1-yl)prop-2-en-1-one,
4-(8-(1-(but-2-ynoyl)pyrrolidin-2-yl)quinazolin-6-yl)-N-(4-cyanopyridin-2-yl)benzamide,
4-(8-(1-(but-2-ynoyl)pyrrolidin-2-yl)quinazolin-6-yl)-N-(4-cyclopropylpyridin-2-yl)benzamide,
4-(8-(1-(but-2-ynoyl)pyrrolidin-2-yl)quinazolin-6-yl)-N-(4-cyanopyridin-2-yl)-3-fluorobenzamide,
4-(8-(1-(but-2-ynoyl)pyrrolidin-2-yl)quinazolin-6-yl)-N-(4-cyclopropylpyridin-2-yl)-3-fluorobenzamide,
2-(4-(8-(1-(but-2-ynoyl)pyrrolidin-2-yl)quinazolin-6-yl)phenoxy)isonicotinonitrile,
1-(2-(6-(4-((4-cyclopropylpyridin-2-yl)oxy)phenyl)quinazolin-8-yl)pyrrolidin-1-yl)but-2-yn-1-one,
4-(5-(1-(but-2-ynoyl)pyrrolidin-2-yl)pyrrolo[1,2-c]pyrimidin-7-yl)-N-(4-cyanopyridin-2-yl)benzamide,
4-(5-(1-(but-2-ynoyl)pyrrolidin-2-yl)pyrrolo[1,2-c]pyrimidin-7-yl)-N-(4-cyclopropylpyridin-2-yl)benzamide,
4-(5-(1-(but-2-ynoyl)pyrrolidin-2-yl)pyrrolo[1,2-c]pyrimidin-7-yl)-N-(4-cyanopyridin-2-yl)-3-fluorobenzamide,
4-(5-(1-(but-2-ynoyl)pyrrolidin-2-yl)pyrrolo[1,2-c]pyrimidin-7-yl)-N-(4-cyclopropylpyridin-2-yl)-3-fluorobenzamide,
4-(5-(1-(but-2-ynoyl)pyrrolidin-2-yl)pyrrolo[1,2-c]pyrimidin-7-yl)-3-chloro-N-(4-cyanopyridin-2-yl)benzamide,
4-(5-(1-(but-2-ynoyl)pyrrolidin-2-yl)pyrrolo[1,2-c]pyrimidin-7-yl)-3-chloro-N-(4-cyclopropylpyridin-2-yl)benzamide,
4-(5-(1-acryloylpyrrolidin-3-yl)pyrrolo[1,2-c]pyrimidin-7-yl)-N-(4-cyanopyridin-2-yl)benzamide,
4-(5-(1-acryloylpyrrolidin-3-yl)pyrrolo[1,2-c]pyrimidin-7-yl)-N-(4-cyclopropylpyridin-2-yl)benzamide,
4-(5-(1-acryloylpyrrolidin-3-yl)pyrrolo[1,2-c]pyrimidin-7-yl)-N-(4-cyclopropylpyridin-2-yl)benzamide,
4-(5-(1-acryloylpyrrolidin-3-yl)pyrrolo[1,2-c]pyrimidin-7-yl)-N-(3-cyanophenyl)benzamide,
4-(5-(1-acryloylpyrrolidin-3-yl)pyrrolo[1,2-c]pyrimidin-7-yl)-N-(3-cyclopropylphenyl)benzamide,
4-(5-(1-acryloylpyrrolidin-3-yl)pyrrolo[1,2-c]pyrimidin-7-yl)-3-chloro-N-(4-cyanopyridin-2-yl)benzamide,
4-(5-(1-acryloylpyrrolidin-3-yl)pyrrolo[1,2-c]pyrimidin-7-yl)-N-(4-cyanopyridin-2-yl)-3-fluorobenzamide,
4-(5-(1-acryloylpyrrolidin-3-yl)pyrrolo[1,2-c]pyrimidin-7-yl)-N-(4-cyclopropylpyridin-2-yl)-3-fluorobenzamide,
2-(4-(5-(1-acryloylpyrrolidin-3-yl)pyrrolo[1,2-c]pyrimidin-7-yl)phenoxy)isonicotinonitrile,
1-(3-(7-(4-((4-cyclopropylpyridin-2-yl)oxy)phenyl)pyrrolo[1,2-c]pyrimidin-5-yl)pyrrolidin-1-yl)prop-2-en-1-one,
2-(4-(5-(1-acryloylpyrrolidin-3-yl)-1-aminopyrrolo[1,2-c]pyrimidin-7-yl)phenoxy)isonicotinonitrile,
1-(3-(1-amino-7-(4-((4-cyclopropylpyridin-2-yl)oxy)phenyl)pyrrolo[1,2-c]pyrimidin-5-yl)pyrrolidin-1-yl)prop-2-en-1-one,
4-(5-(1-acryloylpyrrolidin-3-yl)-1-aminopyrrolo[1,2-c]pyrimidin-7-yl)-N-(4-cyanopyridin-2-yl)benzamide,
4-(5-(1-acryloylpyrrolidin-3-yl)-1-aminopyrrolo[1,2-c]pyrimidin-7-yl)-N-(4-cyclopropylpyridin-2-yl)benzamide,
4-(1-amino-5-(1-(but-2-ynoyl)pyrrolidin-2-yl)pyrrolo[1,2-c]pyrimidin-7-yl)-N-(4-cyanopyridin-2-yl)benzamide, 4-(1-amino-5-(1-(but-2-ynoyl)pyrrolidin-2-yl)pyrrolo[1,2-c]pyrimidin-7-yl)-N-(4-cyclopropylpyridin-2-yl)benzamide,
2-(4-(1-amino-5-(1-(but-2-ynoyl)pyrrolidin-2-yl)pyrrolo[1,2-c]pyrimidin-7-yl)phenoxy)isonicotinonitrile,
1-(2-(1-amino-7-(4-((4-cyclopropylpyridin-2-yl)oxy)phenyl)pyrrolo[1,2-c]pyrimidin-5-yl)pyrrolidin-1-yl)but-2-yn-1-one,
4-(8-(1-acryloylpyrrolidin-3-yl)quinazolin-6-yl)-3-fluoro-N-(4-(trifluoromethyl)pyridin-2-yl)benzamide,
4-(8-(1-acryloylpyrrolidin-3-yl)quinazolin-6-yl)-N-(4-cyanopyridin-2-yl)-3-fluorobenzamide,
4-(8-(1-acryloylpyrrolidin-3-yl)quinazolin-6-yl)-N-(4-cyclopropylpyridin-2-yl)-3-fluorobenzamide,
4-(8-(3-acrylamidophenyl)quinazolin-6-yl)-3-fluoro-N-(4-(trifluoromethyl)pyridin-2-yl)benzamide,
4-(8-(3-acrylamidophenyl)quinazolin-6-yl)-N-(4-cyanopyridin-2-yl)-3-fluorobenzamide,
4-(8-(3-acrylamidophenyl)quinazolin-6-yl)-N-(4-cyclopropylpyridin-2-yl)-3-fluorobenzamide,
4-(8-(1-acryloylpyrrolidin-3-yl)quinazolin-6-yl)-3-chloro-N-(4-(trifluoromethyl)pyridin-2-yl)benzamide,
4-(8-(1-acryloylpyrrolidin-3-yl)quinazolin-6-yl)-3-chloro-N-(4-cyanopyridin-2-yl)benzamide,
4-(8-(1-acryloylpyrrolidin-3-yl)quinazolin-6-yl)-3-chloro-N-(4-cyclopropylpyridin-2-yl)benzamide,
4-(8-(3-acrylamidophenyl)quinazolin-6-yl)-3-chloro-N-(4-(trifluoromethyl)pyridin-2-yl)benzamide,
4-(8-(3-acrylamidophenyl)quinazolin-6-yl)-3-chloro-N-(4-cyanopyridin-2-yl)benzamide,
4-(8-(3-acrylamidophenyl)quinazolin-6-yl)-3-chloro-N-(4-cyclopropylpyridin-2-yl)benzamide,
4-(8-(1-acryloylpyrrolidin-3-yl)quinazolin-6-yl)-3-methoxy-N-(4-(trifluoromethyl)pyridin-2-yl)benzamide,
4-(8-(1-acryloylpyrrolidin-3-yl)quinazolin-6-yl)-N-(4-cyanopyridin-2-yl)-3-methoxybenzamide,
4-(8-(1-acryloylpyrrolidin-3-yl)quinazolin-6-yl)-N-(4-cyclopropylpyridin-2-yl)-3-methoxybenzamide,
4-(8-(3-acrylamidophenyl)quinazolin-6-yl)-3-methoxy-N-(4-(trifluoromethyl)pyridin-2-yl)benzamide,
4-(8-(3-acrylamidophenyl)quinazolin-6-yl)-N-(4-cyanopyridin-2-yl)-3-methoxybenzamide,
4-(8-(3-acrylamidophenyl)quinazolin-6-yl)-N-(4-cyclopropylpyridin-2-yl)-3-methoxybenzamide,
4-(8-(1-acryloylpyrrolidin-3-yl)quinazolin-6-yl)-2-fluoro-N-(4-(trifluoromethyl)pyridin-2-yl)benzamide,
4-(8-(1-acryloylpyrrolidin-3-yl)quinazolin-6-yl)-N-(4-cyanopyridin-2-yl)-2-fluorobenzamide,
4-(8-(1-acryloylpyrrolidin-3-yl)quinazolin-6-yl)-N-(4-cyclopropylpyridin-2-yl)-2-fluorobenzamide,
4-(8-(3-acrylamidophenyl)quinazolin-6-yl)-2-fluoro-N-(4-(trifluoromethyl)pyridin-2-yl)benzamide,
4-(8-(3-acrylamidophenyl)quinazolin-6-yl)-N-(4-cyanopyridin-2-yl)-2-fluorobenzamide,
4-(8-(3-acrylamidophenyl)quinazolin-6-yl)-N-(4-cyclopropylpyridin-2-yl)-2-fluorobenzamide,
4-(8-(1-acryloylpyrrolidin-3-yl)quinazolin-6-yl)-2-chloro-N-(4-(trifluoromethyl)pyridin-2-yl)benzamide,
4-(8-(1-acryloylpyrrolidin-3-yl)quinazolin-6-yl)-2-chloro-N-(4-cyanopyridin-2-yl)benzamide,
4-(8-(1-acryloylpyrrolidin-3-yl)quinazolin-6-yl)-2-chloro-N-(4-cyclopropylpyridin-2-yl)benzamide,
4-(8-(3-acrylamidophenyl)quinazolin-6-yl)-2-chloro-N-(4-(trifluoromethyl)pyridin-2-yl)benzamide
4-(8-(3-acrylamidophenyl)quinazolin-6-yl)-2-chloro-N-(4-cyanopyridin-2-yl)benzamide,
4-(8-(3-acrylamidophenyl)quinazolin-6-yl)-2-chloro-N-(4-cyclopropylpyridin-2-yl)benzamide,
4-(8-(1-acryloylpyrrolidin-3-yl)quinazolin-6-yl)-2-methoxy-N-(4-(trifluoromethyl)pyridin-2-yl)benzamide,
4-(8-(1-acryloylpyrrolidin-3-yl)quinazolin-6-yl)-N-(4-cyanopyridin-2-yl)-2-methoxybenzamide,
4-(8-(1-acryloylpyrrolidin-3-yl)quinazolin-6-yl)-N-(4-cyclopropylpyridin-2-yl)-2-methoxybenzamide,
4-(8-(3-acrylamidophenyl)quinazolin-6-yl)-2-methoxy-N-(4-(trifluoromethyl)pyridin-2-yl)benzamide,
4-(8-(3-acrylamidophenyl)quinazolin-6-yl)-N-(4-cyanopyridin-2-yl)-2-methoxybenzamide,
4-(8-(3-acrylamidophenyl)quinazolin-6-yl)-N-(4-cyclopropylpyridin-2-yl)-2-methoxybenzamide,
1-(3-(6-(4-(pyridin-2-yloxy)phenyl)quinazolin-8-yl)pyrrolidin-1-yl)prop-2-en-1-one,
1-(3-(6-(2-fluoro-4-((3-fluoropyridin-2-yl)oxy)phenyl)quinazolin-8-yl)pyrrolidin-1-yl)prop-2-en-1-one,
4-(8-(3-acrylamidophenyl)quinazolin-6-yl)-N-(4-cyanopyridin-2-yl)benzamide,
N-(3-(2-amino-6-(5-methoxypyridin-3-yl)quinazolin-8-yl)phenyl)acrylamide,
N-(3-(2-amino-6-(5-fluoropyridin-3-yl)quinazolin-8-yl)phenyl)acrylamide,
N-(3-(6-(2-fluoro-4-(pyridin-2-yloxy)phenyl)quinazolin-8-yl)phenyl)acrylamide,
4-(8-(3-acrylamidophenyl)quinazolin-6-yl)-N-(pyridin-3-yl)benzamide,
1-(3-(6-(2-fluoro-4-(pyridin-2-yloxy)phenyl)quinazolin-8-yl)pyrrolidin-1-yl)prop-2-en-1-one,
4-(8-(1-acryloylpyrrolidin-3-yl)quinazolin-6-yl)-N-(pyridin-3-yl)benzamide,
N-(3-(6-(4-(pyridin-3-yloxy)phenyl)quinazolin-8-yl)phenyl)acrylamide,
N-(3-(6-(pyridin-2-yl)quinazolin-8-yl)phenyl)acrylamide,
N-(3-(6-(3-methoxy-4-(pyridin-2-yloxy)phenyl)quinazolin-8-yl)phenyl)acrylamide,
N-(3-(6-(2-methoxy-4-(pyridin-2-yloxy)phenyl)quinazolin-8-yl)phenyl)acrylamide,
4-(8-(1-acryloylpyrrolidin-3-yl)quinazolin-6-yl)-N-(4-cyclopropylpyridin-2-yl)benzamide,
4-(8-(1-acryloylpyrrolidin-3-yl)quinazolin-6-yl)-N-(4-cyanopyridin-2-yl)benzamide,
4-(8-(1-acryloylpyrrolidin-3-yl)quinazolin-6-yl)-N-(4-(trifluoromethyl)pyridin-2-yl)benzamide,
2-(4-(8-(1-acryloylpyrrolidin-3-yl)quinazolin-6-yl)benzamido)isonicotinamide,
4-(8-(3-acrylamidophenyl)quinazolin-6-yl)-N-(4-cyclopropylpyridin-2-yl)benzamide,
4-(8-(3-acrylamidophenyl)quinazolin-6-yl)-2-fluoro-N-(pyridin-2-yl)benzamide,
1-(3-(6-(2-methoxy-4-(pyridin-2-yloxy)phenyl)quinazolin-8-yl)pyrrolidin-1-yl)prop-2-en-1-one,
2-(4-(8-(3-acrylamidophenyl)quinazolin-6-yl)-3-chlorobenzamido)isonicotinamide,
N-(3-(6-(3-fluoro-4-(pyridin-2-yloxy)phenyl)quinazolin-8-yl)phenyl)acrylamide,
4-(8-(3-acrylamidophenyl)quinazolin-6-yl)-N-(4-(trifluoromethyl)pyridin-2-yl)benzamide,
2-(4-(8-(3-acrylamidophenyl)quinazolin-6-yl)benzamido)isonicotinamide,
4-(8-(3-acrylamidophenyl)quinazolin-6-yl)-2-methoxy-N-(pyridin-2-yl)benzamide,
4-(8-(1-acryloylpyrrolidin-3-yl)quinazolin-6-yl)-N-(5-(trifluoromethyl)pyridin-2-yl)benzamide,
1-(3-(2-amino-6-(2-fluoro-4-(pyridin-2-yloxy)phenyl)quinazolin-8-yl)pyrrolidin-1-yl)prop-2-en-1-one, 1-(3-(6-(3-methoxy-4-(pyridin-2-yloxy)phenyl)quinazolin-8-yl)pyrrolidin-1-yl)prop-2-en-1-one,
4-(8-(1-acryloylpyrrolidin-3-yl)quinazolin-6-yl)-N-(pyridazin-4-yl)benzamide,
4-(5-(1-acryloylpyrrolidin-3-yl)pyrrolo[1,2-c]pyrimidin-7-yl)-2-fluoro-N-(4-methoxypyridin-2-yl)benzamide,
4-(5-(1-acryloylpyrrolidin-3-yl)pyrrolo[1,2-c]pyrimidin-7-yl)-3-fluoro-N-(4-methoxypyridin-2-yl)benzamide,
4-(5-(1-acryloylpyrrolidin-3-yl)pyrrolo[1,2-c]pyrimidin-7-yl)-2-fluoro-N-(4-(trifluoromethyl)pyridin-2-yl)benzamide,
4-(8-(3-acrylamidophenyl)quinazolin-6-yl)-N-(4-cyanopyridin-2-yl)-3-fluorobenzamide,
4-(8-(1-acryloylpyrrolidin-3-yl)quinazolin-6-yl)-N-(pyridin-4-yl)benzamide,
4-(8-(3-acrylamidophenyl)quinazolin-6-yl)-N-(4-cyanopyridin-2-yl)-2-methoxybenzamide,
N-(3-(2-amino-6-(2-fluoro-4-(pyridin-2-yloxy)phenyl)quinazolin-8-yl)phenyl)acrylamide,
N-(3-(2-amino-6-(3-fluoro-4-(pyridin-2-yloxy)phenyl)quinazolin-8-yl)phenyl)acrylamide,
1-(3-(7-(2-fluoro-4-(pyridin-2-yloxy)phenyl)pyrrolo[1,2-c]pyrimidin-5-yl)pyrrolidin-1-yl)prop-2-en-1-one,
1-(3-(6-(3-fluoro-4-(pyridin-2-yloxy)phenyl)quinazolin-8-yl)pyrrolidin-1-yl)prop-2-en-1-one,
4-(5-(1-acryloylpyrrolidin-3-yl)pyrrolo[1,2-c]pyrimidin-7-yl)-N-(4-cyanopyridin-2-yl)benzamide,
4-(5-(1-acryloylpyrrolidin-3-yl)pyrrolo[1,2-c]pyrimidin-7-yl)-N-(4-methoxypyridin-2-yl)benzamide,
4-(8-(3-acrylamidophenyl)quinazolin-6-yl)-2-chloro-N-(pyridin-2-yl)benzamide,
4-(5-(1-acryloylpyrrolidin-3-yl)pyrrolo[1,2-c]pyrimidin-7-yl)-N-(4-cyclopropylpyridin-2-yl)benzamide,
4-(5-(1-acryloylpyrrolidin-3-yl)pyrrolo[1,2-c]pyrimidin-7-yl)-N-(4-cyclopropylpyridin-2-yl)-2-fluorobenzamide,
N-(3-(2-amino-6-(2-methoxy-4-(pyridin-2-yloxy)phenyl)quinazolin-8-yl)phenyl)acrylamide,
1-(3-(7-(3-methoxy-4-(pyridin-2-yloxy)phenyl)pyrrolo[1,2-c]pyrimidin-5-yl)pyrrolidin-1-yl)prop-2-en-1-one,
1-(3-(2-amino-6-(2-methoxy-4-(pyridin-2-yloxy)phenyl)quinazolin-8-yl)pyrrolidin-1-yl)prop-2-en-1-one,
1-(3-(7-(2-methoxy-4-(pyridin-2-yloxy)phenyl)pyrrolo[1,2-c]pyrimidin-5-yl)pyrrolidin-1-yl)prop-2-en-1-one,
4-(8-(3-acrylamidophenyl)-5-aminoquinazolin-6-yl)-N-(pyridin-2-yl)benzamide,
4-(8-(3-acrylamidophenyl)-5-aminoquinazolin-6-yl)-N-(4-cyclopropylpyridin-2-yl)benzamide,
4-(5-(1-acryloylpyrrolidin-3-yl)pyrrolo[1,2-c]pyrimidin-7-yl)-N-(4-cyanopyridin-2-yl)-2-fluorobenzamide,
N-(3-(5-amino-6-(2-fluoro-4-(pyridin-2-yloxy)phenyl)quinazolin-8-yl)phenyl)acrylamide,
1-(3-(5-amino-6-(2-fluoro-4-(pyridin-2-yloxy)phenyl)quinazolin-8-yl)pyrrolidin-1-yl)prop-2-en-1-one,
N-(3-(6-(4-((4-(trifluoromethyl)pyridin-2-yl)oxy)phenyl)quinazolin-8-yl)phenyl)acrylamide,
4-(8-(3-acrylamidophenyl)-5-aminoquinazolin-6-yl)-N-(4-cyanopyridin-2-yl)benzamide,
4-(8-(3-acrylamidophenyl)-5-aminoquinazolin-6-yl)-3-fluoro-N-(pyridin-2-yl)benzamide,
4-(8-(3-acrylamidophenyl)-2,5-diaminoquinazolin-6-yl)-N-(pyridin-2-yl)benzamide,
N-(3-(5-amino-6-(4-(pyridin-2-yloxy)phenyl)quinazolin-8-yl)phenyl)acrylamide,
N-(3-(6-(2-fluoro-4-((4-(trifluoromethyl)pyridin-2-yl)oxy)phenyl)quinazolin-8-yl)phenyl)acrylamide,
1-(3-(5-amino-6-(4-(pyridin-2-yloxy)phenyl)quinazolin-8-yl)pyrrolidin-1-yl)prop-2-en-1-one,
N-(3-(5-amino-6-(4-phenoxyphenyl)quinazolin-8-yl)phenyl)acrylamide,
N-(3-(6-(4-((4-cyclopropylpyridin-2-yl)oxy)phenyl)quinazolin-8-yl)phenyl)acrylamide,
N-(3-(6-(4-((4-cyanopyridin-2-yl)oxy)phenyl)quinazolin-8-yl)phenyl)acrylamide,
4-(1-(1-acryloylpyrrolidin-3-yl)-5-aminoimidazo[1,5-c]pyrimidin-3-yl)-N-(pyridin-2-yl)benzamide,
1-(3-(5-amino-3-(4-(pyridin-2-yloxy)phenyl)imidazo[1,5-c]pyrimidin-1-yl)pyrrolidin-1-yl)prop-2-en-1-one,
N-(3-(5-amino-6-(2-fluoro-4-((4-(trifluoromethyl)pyridin-2-yl)oxy)phenyl)quinazolin-8-yl)phenyl)acrylamide,
N-(3-(5-amino-6-(4-((4-(trifluoromethyl)pyridin-2-yl)oxy)phenyl)quinazolin-8-yl)phenyl)acrylamide,
N-(3-(6-(4-((4-cyanopyridin-2-yl)oxy)-2-fluorophenyl)quinazolin-8-yl)phenyl)acrylamide,
4-(8-(3-acrylamidophenyl)-5-aminoquinazolin-6-yl)-3-chloro-N-(pyridin-2-yl)benzamide,
2-(4-(8-(3-acrylamidophenyl)quinazolin-6-yl)phenoxy)isonicotinamide,
1-(3-(5-amino-6-(4-phenoxyphenyl)quinazolin-8-yl)pyrrolidin-1-yl)prop-2-en-1-one,
1-(3-(5-amino-6-(4-((4-(trifluoromethyl)pyridin-2-yl)oxy)phenyl)quinazolin-8-yl)pyrrolidin-1-yl)prop-2-en-1-one,
2-(4-(8-(3-acrylamidophenyl)quinazolin-6-yl)-3-fluorophenoxy)isonicotinamide,
1-(3-(5-amino-6-(2-fluoro-4-((4-(trifluoromethyl)pyridin-2-yl)oxy)phenyl)quinazolin-8-yl)pyrrolidin-1-yl)prop-2-en-1-one,
1-(3-(5-amino-3-(4-((4-(trifluoromethyl)pyridin-2-yl)oxy)phenyl)imidazo[1,5-c]pyrimidin-1-yl)pyrrolidin-1-yl)prop-2-en-1-one,
4-(8-(1-acryloylpyrrolidin-3-yl)-4-aminoimidazo[1,5-a][1,3,5]triazin-6-yl)-N-(pyridin-2-yl)benzamide,
N-(3-(6-(4-((4-cyclopropylpyridin-2-yl)oxy)-2-fluorophenyl)quinazolin-8-yl)phenyl)acrylamide,
4-(8-(1-acryloylpyrrolidin-3-yl)-4-aminoimidazo[1,5-a][1,3,5]triazin-6-yl)-N-(4-cyclopropylpyridin-2-yl)benzamide,
4-(8-(3-acrylamidophenyl)-5-aminoquinazolin-6-yl)-3-chloro-N-(4-cyclopropylpyridin-2-yl)benzamide,
4-(8-(3-acrylamidophenyl)quinazolin-6-yl)-3-cyano-N-(pyridin-2-yl)benzamide,
4-(8-(3-acrylamidophenyl)-5-aminoquinazolin-6-yl)-N-(4-cyclopropylpyridin-2-yl)-3-fluorobenzamide,
N-(3-(5-amino-6-(2-chloro-4-(pyridin-2-yloxy)phenyl)quinazolin-8-yl)phenyl)acrylamide,
4-(5-amino-1-(1-(but-2-ynoyl)pyrrolidin-3-yl)imidazo[1,5-c]pyrimidin-3-yl)-N-(pyridin-2-yl)benzamide,
4-(4-amino-8-(1-(but-2-ynoyl)pyrrolidin-3-yl)imidazo[1,5-a][1,3,5]triazin-6-yl)-N-(pyridin-2-yl)benzamide,
1-(3-(5-amino-3-(3-fluoro-4-((4-(trifluoromethyl)pyridin-2-yl)oxy)phenyl)imidazo[1,5-c]pyrimidin-1-yl)pyrrolidin-1-yl)prop-2-en-1-one,
1-(3-(5-amino-3-(3-fluoro-4-((4-(trifluoromethyl)pyridin-2-yl)oxy)phenyl)imidazo[1,5-c]pyrimidin-1-yl)pyrrolidin-1-yl)but-2-yn-1-one,
1-(3-(5-amino-3-(3-fluoro-4-(pyridin-2-yloxy)phenyl)imidazo[1,5-c]pyrimidin-1-yl)pyrrolidin-1-yl)prop-2-en-1-one,
1-(3-(5-amino-3-(3-fluoro-4-(pyridin-2-yloxy)phenyl)imidazo[1,5-c]pyrimidin-1-yl)pyrrolidin-1-yl)but-2-yn-1-one,
1-(3-(5-amino-3-(4-((4-methoxypyridin-2-yl)oxy)phenyl)imidazo[1,5-c]pyrimidin-1-yl)pyrrolidin-1-yl)prop-2-en-1-one, 4-(8-(3-acrylamidophenyl)-5-aminoquinazolin-6-yl)-N-(3-fluoropyridin-2-yl)benzamide,
1-(3-(5-amino-3-(3-methoxy-4-(pyridin-2-yloxy)phenyl)imidazo[1,5-c]pyrimidin-1-yl)pyrrolidin-1-yl)prop-2-en-1-one,
1-(3-(5-amino-3-(3-methoxy-4-(pyridin-2-yloxy)phenyl)imidazo[1,5-c]pyrimidin-1-yl)pyrrolidin-1-yl)but-2-yn-1-one,
1-(3-(5-amino-3-(4-((4-methoxypyridin-2-yl)oxy)phenyl)imidazo[1,5-c]pyrimidin-1-yl)pyrrolidin-1-yl)but-2-yn-1-one,
4-(8-(1-acryloylpyrrolidin-3-yl)-5-aminoquinazolin-6-yl)-N-(3-fluoropyridin-2-yl)benzamide,
1-(3-(5-amino-3-(3-fluoro-4-((4-methoxypyridin-2-yl)oxy)phenyl)imidazo[1,5-c]pyrimidin-1-yl)pyrrolidin-1-yl)prop-2-en-1-one,
4-(8-(3-acrylamidophenyl)-5-aminoquinazolin-6-yl)-3-chloro-N-(3-fluoropyridin-2-yl)benzamide,
1-(3-(5-amino-3-(4-((3-(trifluoromethyl)pyridin-2-yl)oxy)phenyl)imidazo[1,5-c]pyrimidin-1-yl)pyrrolidin-1-yl)prop-2-en-1-one,
1-(3-(5-amino-3-(4-((3-(trifluoromethyl)pyridin-2-yl)oxy)phenyl)imidazo[1,5-c]pyrimidin-1-yl)pyrrolidin-1-yl)but-2-yn-1-one,
N-(3-(5-amino-3-(4-((3-(trifluoromethyl)pyridin-2-yl)oxy)phenyl)imidazo[1,5-c]pyrimidin-1-yl)phenyl)acrylamide,
1-(3-(5-amino-3-(3-methoxy-4-((4-(trifluoromethyl)pyridin-2-yl)oxy)phenyl)imidazo[1,5-c]pyrimidin-1-yl)pyrrolidin-1-yl)prop-2-en-1-one,
1-(3-(5-amino-3-(3-methoxy-4-((4-(trifluoromethyl)pyridin-2-yl)oxy)phenyl)imidazo[1,5-c]pyrimidin-1-yl)pyrrolidin-1-yl)but-2-yn-1-one,
1-(3-(5-amino-3-(3-fluoro-4-((3-(trifluoromethyl)pyridin-2-yl)oxy)phenyl)imidazo[1,5-c]pyrimidin-1-yl)pyrrolidin-1-yl)prop-2-en-1-one,
(R/S))-1-(3-(5-amino-3-(4-(pyridin-2-yloxy)phenyl)imidazo[1,5-c]pyrimidin-1-yl)pyrrolidin-1-yl)prop-2-en-1-one,
(S/R)-1-(3-(5-amino-3-(4-(pyridin-2-yloxy)phenyl)imidazo[1,5-c]pyrimidin-1-yl)pyrrolidin-1-yl)prop-2-en-1-one,
1-(3-(5-amino-3-(4-((3-fluoropyridin-2-yl)oxy)phenyl)imidazo[1,5-c]pyrimidin-1-yl)pyrrolidin-1-yl)prop-2-en-1-one,
2-(4-(1-(1-acryloylpyrrolidin-3-yl)-5-aminoimidazo[1,5-c]pyrimidin-3-yl)phenoxy)nicotinonitrile,
1-(3-(5-amino-3-(4-((3-fluoropyridin-2-yl)oxy)phenyl)imidazo[1,5-c]pyrimidin-1-yl)pyrrolidin-1-yl)but-2-yn-1-one,
2-(4-(5-amino-1-(1-(but-2-ynoyl)pyrrolidin-3-yl)imidazo[1,5-c]pyrimidin-3-yl)phenoxy)nicotinonitrile,
4-(1-(1-acryloylpyrrolidin-3-yl)-5-aminoimidazo[1,5-c]pyrimidin-3-yl)-2-fluoro-N-(pyridin-2-yl)benzamide,
4-(5-amino-1-(1-(but-2-ynoyl)pyrrolidin-3-yl)imidazo[1,5-c]pyrimidin-3-yl)-2-fluoro-N-(pyridin-2-yl)benzamide,
1-(3-(5-amino-3-(4-((3-fluoropyridin-2-yl)oxy)-3-methoxyphenyl)imidazo[1,5-c]pyrimidin-1-yl)piperidin-1-yl)prop-2-en-1-one,
1-(3-(5-amino-3-(4-((3-fluoropyridin-2-yl)oxy)-3-methoxyphenyl)imidazo[1,5-c]pyrimidin-1-yl)pyrrolidin-1-yl)prop-2-en-1-one,
2-(4-(1-(1-acryloylpiperidin-3-yl)-5-aminoimidazo[1,5-c]pyrimidin-3-yl)-2-fluorophenoxy)nicotinonitrile,
4-(1-(1-acryloylpiperidin-3-yl)-5-aminoimidazo[1,5-c]pyrimidin-3-yl)-N-(pyridin-2-yl)benzamide,
4-(5-amino-1-(1-(but-2-ynoyl)piperidin-3-yl)imidazo[1,5-c]pyrimidin-3-yl)-N-(pyridin-2-yl)benzamide,
4-(4-amino-8-(1-(but-2-ynoyl)pyrrolidin-3-yl)imidazo[1,5-a][1,3,5]triazin-6-yl)-N-(4-cyclopropylpyridin-2-yl)benzamide,
4-(1-(1-acryloylpyrrolidin-3-yl)-5-aminoimidazo[1,5-c]pyrimidin-3-yl)-N-(4-cyclopropylpyridin-2-yl)benzamide,
4-(5-amino-1-(1-(but-2-ynoyl)pyrrolidin-3-yl)imidazo[1,5-c]pyrimidin-3-yl)-N-(4-cyclopropylpyridin-2-yl)benzamide,
4-(1-(1-acryloylpyrrolidin-3-yl)-5-aminoimidazo[1,5-c]pyrimidin-3-yl)-N-(4-methoxypyridin-2-yl)benzamide,
4-(5-amino-1-(1-(but-2-ynoyl)pyrrolidin-3-yl)imidazo[1,5-c]pyrimidin-3-yl)-N-(4-methoxypyridin-2-yl)benzamide,
4-(1-(1-acryloylpyrrolidin-3-yl)-5-aminoimidazo[1,5-c]pyrimidin-3-yl)-N-(4-(trifluoromethyl)pyridin-2-yl)benzamide,
1-(3-(5-amino-3-(4-(pyridin-2-yloxy)phenyl)imidazo[1,5-c]pyrimidin-1-yl)piperidin-1-yl)prop-2-en-1-one,
1-(3-(5-amino-3-(4-(pyridin-2-yloxy)phenyl)imidazo[1,5-c]pyrimidin-1-yl)piperidin-1-yl)but-2-yn-1-one,
4-(1-(1-acryloylpyrrolidin-3-yl)-5-aminoimidazo[1,5-c]pyrimidin-3-yl)-N-(pyridin-2-yl)-3-(trifluoromethyl)benzamide,
4-(5-amino-1-(1-(but-2-ynoyl)pyrrolidin-3-yl)imidazo[1,5-c]pyrimidin-3-yl)-N-(pyridin-2-yl)-3-(trifluoromethyl)benzamide,
4-(5-amino-1-(1-(but-2-ynoyl)pyrrolidin-3-yl)imidazo[1,5-c]pyrimidin-3-yl)-N-(4-cyclopropylpyridin-2-yl)-2-fluorobenzamide,
4-(1-(1-acryloylpyrrolidin-3-yl)-5-aminoimidazo[1,5-c]pyrimidin-3-yl)-N-(4-cyclopropylpyridin-2-yl)-2-fluorobenzamide,
4-(5-amino-1-(1-(but-2-ynoyl)pyrrolidin-2-yl)imidazo[1,5-c]pyrimidin-3-yl)-N-(pyridin-2-yl)benzamide,
(S)-4-(5-amino-1-(1-(but-2-ynoyl)pyrrolidin-2-yl)imidazo[1,5-c]pyrimidin-3-yl)-N-(pyridin-2-yl)benzamide,
(R)-4-(5-amino-1-(1-(but-2-ynoyl)pyrrolidin-2-yl)imidazo[1,5-c]pyrimidin-3-yl)-N-(pyridin-2-yl)benzamide,
(R)-4-(5-amino-1-(1-(but-2-ynoyl)pyrrolidin-3-yl)imidazo[1,5-c]pyrimidin-3-yl)-N-(pyridin-2-yl)benzamide,
(S)-4-(5-amino-1-(1-(but-2-ynoyl)pyrrolidin-3-yl)imidazo[1,5-c]pyrimidin-3-yl)-N-(pyridin-2-yl)benzamide,
(R)-4-(1-(1-acryloylpyrrolidin-3-yl)-5-aminoimidazo[1,5-c]pyrimidin-3-yl)-N-(pyridin-2-yl)benzamide,
(S)-4-(1-(1-acryloylpyrrolidin-3-yl)-5-aminoimidazo[1,5-c]pyrimidin-3-yl)-N-(pyridin-2-yl)benzamide,
(R)-4-(1-(1-acryloylpiperidin-3-yl)-5-aminoimidazo[1,5-c]pyrimidin-3-yl)-N-(pyridin-2-yl)benzamide,
(S)-4-(1-(1-acryloylpiperidin-3-yl)-5-aminoimidazo[1,5-c]pyrimidin-3-yl)-N-(pyridin-2-yl)benzamide,
(R)-4-(5-amino-1-(1-(but-2-ynoyl)piperidin-3-yl)imidazo[1,5-c]pyrimidin-3-yl)-N-(pyridin-2-yl)benzamide,
(S)-4-(5-amino-1-(1-(but-2-ynoyl)piperidin-3-yl)imidazo[1,5-c]pyrimidin-3-yl)-N-(pyridin-2-yl)benzamide,
4-(1-(1-acryloylpyrrolidin-3-yl)-5-aminoimidazo[1,5-c]pyrimidin-3-yl)-N-(4-cyanopyridin-2-yl)benzamide,
4-(1-(1-acryloylpiperidin-3-yl)-5-aminoimidazo[1,5-c]pyrimidin-3-yl)-N-(4-cyanopyridin-2-yl)benzamide,
4-(5-amino-1-(1-(but-2-ynoyl)piperidin-3-yl)imidazo[1,5-c]pyrimidin-3-yl)-N-(4-cyanopyridin-2-yl)benzamide,
4-(5-amino-1-(1-(but-2-ynoyl)pyrrolidin-3-yl)imidazo[1,5-c]pyrimidin-3-yl)-N-(4-cyanopyridin-2-yl)benzamide,
4-(1-(1-acryloylpyrrolidin-3-yl)-5-aminoimidazo[1,5-c]pyrimidin-3-yl)-N-(4-cyanopyridin-2-yl)-2-fluorobenzamide,
4-(1-(1-acryloylpiperidin-3-yl)-5-aminoimidazo[1,5-c]pyrimidin-3-yl)-N-(4-cyanopyridin-2-yl)-2-fluorobenzamide, 4-(5-amino-1-(1-(but-2-ynoyl)piperidin-3-yl)imidazo[1,5-c]pyrimidin-3-yl)-N-(4-cyanopyridin-2-yl)-2-fluorobenzamide, 4-(5-amino-1-(1-(but-2-ynoyl)pyrrolidin-3-yl)imidazo[1,5-c]pyrimidin-3-yl)-N-(4-cyanopyridin-2-yl)-2-fluorobenzamide, 4-(1-(1-acryloylpyrrolidin-3-yl)-5-aminoimidazo[1,5-c]pyrimidin-3-yl)-2-chloro-N-(4-cyanopyridin-2-yl)benzamide, 4-(5-amino-1-(1-(but-2-ynoyl)pyrrolidin-3-yl)imidazo[1,5-c]pyrimidin-3-yl)-2-chloro-N-(4-cyanopyridin-2-yl)benzamide, 4-(1-(1-acryloylpiperidin-3-yl)-5-aminoimidazo[1,5-c]pyrimidin-3-yl)-2-chloro-N-(4-cyanopyridin-2-yl)benzamide, 4-(5-amino-1-(1-(but-2-ynoyl)piperidin-3-yl)imidazo[1,5-c]pyrimidin-3-yl)-2-chloro-N-(4-cyanopyridin-2-yl)benzamide, 4-(1-(1-acryloylpyrrolidin-3-yl)-5-aminoimidazo[1,5-c]pyrimidin-3-yl)-2-cyano-N-(4-cyanopyridin-2-yl)benzamide, 4-(5-amino-1-(1-(but-2-ynoyl)pyrrolidin-3-yl)imidazo[1,5-c]pyrimidin-3-yl)-2-cyano-N-(4-cyanopyridin-2-yl)benzamide, 4-(1-(1-acryloylpiperidin-3-yl)-5-aminoimidazo[1,5-c]pyrimidin-3-yl)-2-cyano-N-(4-cyanopyridin-2-yl)benzamide, 4-(5-amino-1-(1-(but-2-ynoyl)piperidin-3-yl)imidazo[1,5-c]pyrimidin-3-yl)-2-cyano-N-(4-cyanopyridin-2-yl)benzamide, 4-(1-(1-acryloylpyrrolidin-3-yl)-5-aminoimidazo[1,5-c]pyrimidin-3-yl)-N-(4-cyanopyridin-2-yl)-2-(trifluoromethyl)benzamide, 4-(5-amino-1-(1-(but-2-ynoyl)pyrrolidin-3-yl)imidazo[1,5-c]pyrimidin-3-yl)-N-(4-cyanopyridin-2-yl)-2-(trifluoromethyl)benzamide, 4-(1-(1-acryloylpiperidin-3-yl)-5-aminoimidazo[1,5-c]pyrimidin-3-yl)-N-(4-cyanopyridin-2-yl)-2-(trifluoromethyl)benzamide, 4-(5-amino-1-(1-(but-2-ynoyl)piperidin-3-yl)imidazo[1,5-c]pyrimidin-3-yl)-N-(4-cyanopyridin-2-yl)-2-(trifluoromethyl)benzamide, 4-(1-(1-acryloylpyrrolidin-3-yl)-5-aminoimidazo[1,5-c]pyrimidin-3-yl)-N-(4-cyanopyridin-2-yl)-3-fluorobenzamide, 4-(5-amino-1-(1-(but-2-ynoyl)pyrrolidin-3-yl)imidazo[1,5-c]pyrimidin-3-yl)-N-(4-cyanopyridin-2-yl)-3-fluorobenzamide, 4-(1-(1-acryloylpiperidin-3-yl)-5-aminoimidazo[1,5-c]pyrimidin-3-yl)-N-(4-cyanopyridin-2-yl)-3-fluorobenzamide, 4-(5-amino-1-(1-(but-2-ynoyl)piperidin-3-yl)imidazo[1,5-c]pyrimidin-3-yl)-N-(4-cyanopyridin-2-yl)-3-fluorobenzamide, 4-(1-(1-acryloylpyrrolidin-3-yl)-5-aminoimidazo[1,5-c]pyrimidin-3-yl)-3-chloro-N-(4-cyanopyridin-2-yl)benzamide, 4-(5-amino-1-(1-(but-2-ynoyl)pyrrolidin-3-yl)imidazo[1,5-c]pyrimidin-3-yl)-3-chloro-N-(4-cyanopyridin-2-yl)benzamide, 4-(1-(1-acryloylpyrrolidin-3-yl)-5-aminoimidazo[1,5-c]pyrimidin-3-yl)-3-cyano-N-(4-cyanopyridin-2-yl)benzamide, 4-(5-amino-1-(1-(but-2-ynoyl)pyrrolidin-3-yl)imidazo[1,5-c]pyrimidin-3-yl)-3-cyano-N-(4-cyanopyridin-2-yl)benzamide, 4-(1-(1-acryloylpiperidin-3-yl)-5-aminoimidazo[1,5-c]pyrimidin-3-yl)-3-cyano-N-(4-cyanopyridin-2-yl)benzamide, 4-(5-amino-1-(1-(but-2-ynoyl)piperidin-3-yl)imidazo[1,5-c]pyrimidin-3-yl)-3-cyano-N-(4-cyanopyridin-2-yl)benzamide, 4-(1-(1-acryloylpyrrolidin-3-yl)-5-aminoimidazo[1,5-c]pyrimidin-3-yl)-N-(4-cyanopyridin-2-yl)-3-(trifluoromethyl)benzamide, 4-(5-amino-1-(1-(but-2-ynoyl)pyrrolidin-3-yl)imidazo[1,5-c]pyrimidin-3-yl)-N-(4-cyanopyridin-2-yl)-3-(trifluoromethyl)benzamide, 4-(1-(1-acryloylpiperidin-3-yl)-5-aminoimidazo[1,5-c]pyrimidin-3-yl)-N-(4-cyanopyridin-2-yl)-3-(trifluoromethyl)benzamide, 4-(5-amino-1-(1-(but-2-ynoyl)piperidin-3-yl)imidazo[1,5-c]pyrimidin-3-yl)-N-(4-cyanopyridin-2-yl)-3-(trifluoromethyl)benzamide, 5-(1-(1-acryloylpyrrolidin-3-yl)-5-aminoimidazo[1,5-c]pyrimidin-3-yl)-N-(4-cyanopyridin-2-yl)picolinamide, 5-(5-amino-1-(1-(but-2-ynoyl)pyrrolidin-3-yl)imidazo[1,5-c]pyrimidin-3-yl)-N-(4-cyanopyridin-2-yl)picolinamide, 5-(1-(1-acryloylpiperidin-3-yl)-5-aminoimidazo[1,5-c]pyrimidin-3-yl)-N-(4-cyanopyridin-2-yl)picolinamide, 5-(5-amino-1-(1-(but-2-ynoyl)piperidin-3-yl)imidazo[1,5-c]pyrimidin-3-yl)-N-(4-cyanopyridin-2-yl)picolinamide, 6-(1-(1-acryloylpyrrolidin-3-yl)-5-aminoimidazo[1,5-c]pyrimidin-3-yl)-N-(4-cyanopyridin-2-yl)nicotinamide, 6-(5-amino-1-(1-(but-2-ynoyl)pyrrolidin-3-yl)imidazo[1,5-c]pyrimidin-3-yl)-N-(4-cyanopyridin-2-yl)nicotinamide, 6-(1-(1-acryloylpiperidin-3-yl)-5-aminoimidazo[1,5-c]pyrimidin-3-yl)-N-(4-cyanopyridin-2-yl)nicotinamide, 6-(5-amino-1-(1-(but-2-ynoyl)piperidin-3-yl)imidazo[1,5-c]pyrimidin-3-yl)-N-(4-cyanopyridin-2-yl)nicotinamide, 4-(1-(1-acryloylpiperidin-3-yl)-5-aminoimidazo[1,5-c]pyrimidin-3-yl)-N-(pyridin-2-yl)-2-(trifluoromethyl)benzamide, 4-(5-amino-1-(1-(but-2-ynoyl)piperidin-3-yl)imidazo[1,5-c]pyrimidin-3-yl)-N-(pyridin-2-yl)-2-(trifluoromethyl)benzamide, 4-(1-(1-acryloylpiperidin-3-yl)-5-aminoimidazo[1,5-c]pyrimidin-3-yl)-N-(pyridin-2-yl)-3-(trifluoromethyl)benzamide, 4-(5-amino-1-(1-(but-2-ynoyl)piperidin-3-yl)imidazo[1,5-c]pyrimidin-3-yl)-N-(pyridin-2-yl)-3-(trifluoromethyl)benzamide, 4-(1-(1-acryloylpyrrolidin-3-yl)-5-aminoimidazo[1,5-c]pyrimidin-3-yl)-3-cyano-N-(pyridin-2-yl)benzamide, 4-(5-amino-1-(1-(but-2-ynoyl)pyrrolidin-3-yl)imidazo[1,5-c]pyrimidin-3-yl)-3-cyano-N-(pyridin-2-yl)benzamide, 4-(1-(1-acryloylpiperidin-3-yl)-5-aminoimidazo[1,5-c]pyrimidin-3-yl)-3-cyano-N-(pyridin-2-yl)benzamide, 4-(5-amino-1-(1-(but-2-ynoyl)piperidin-3-yl)imidazo[1,5-c]pyrimidin-3-yl)-3-cyano-N-(pyridin-2-yl)benzamide, 4-(1-(1-acryloylpyrrolidin-3-yl)-5-aminoimidazo[1,5-c]pyrimidin-3-yl)-3-chloro-N-(pyridin-2-yl)benzamide, 4-(5-amino-1-(1-(but-2-ynoyl)pyrrolidin-3-yl)imidazo[1,5-c]pyrimidin-3-yl)-3-chloro-N-(pyridin-2-yl)benzamide, 4-(1-(1-acryloylpiperidin-3-yl)-5-aminoimidazo[1,5-c]pyrimidin-3-yl)-3-chloro-N-(pyridin-2-yl)benzamide, 4-(5-amino-1-(1-(but-2-ynoyl)piperidin-3-yl)imidazo[1,5-c]pyrimidin-3-yl)-3-chloro-N-(pyridin-2-yl)benzamide, 4-(1-(1-acryloylpyrrolidin-3-yl)-5-aminoimidazo[1,5-c]pyrimidin-3-yl)-3-fluoro-N-(pyridin-2-yl)benzamide, 4-(5-amino-1-(1-(but-2-ynoyl)pyrrolidin-3-yl)imidazo[1,5-c]pyrimidin-3-yl)-3-fluoro-N-(pyridin-2-yl)benzamide, 4-(1-(1-acryloylpiperidin-3-yl)-5-aminoimidazo[1,5-c]pyrimidin-3-yl)-3-fluoro-N-(pyridin-2-yl)benzamide,
4-(5-amino-1-(1-(but-2-ynoyl)piperidin-3-yl)imidazo[1,5-c]pyrimidin-3-yl)-3-fluoro-N-(pyridin-2-yl)benzamide,
6-(1-(1-acryloylpyrrolidin-3-yl)-5-aminoimidazo[1,5-c]pyrimidin-3-yl)-N-(pyridin-2-yl)nicotinamide,
6-(5-amino-1-(1-(but-2-ynoyl)pyrrolidin-3-yl)imidazo[1,5-c]pyrimidin-3-yl)-N-(pyridin-2-yl)nicotinamide,
6-(1-(1-acryloylpiperidin-3-yl)-5-aminoimidazo[1,5-c]pyrimidin-3-yl)-N-(pyridin-2-yl)nicotinamide,
6-(5-amino-1-(1-(but-2-ynoyl)piperidin-3-yl)imidazo[1,5-c]pyrimidin-3-yl)-N-(pyridin-2-yl)nicotinamide,
5-(1-(1-acryloylpyrrolidin-3-yl)-5-aminoimidazo[1,5-c]pyrimidin-3-yl)-N-(pyridin-2-yl)picolinamide,
5-(5-amino-1-(1-(but-2-ynoyl)pyrrolidin-3-yl)imidazo[1,5-c]pyrimidin-3-yl)-N-(pyridin-2-yl)picolinamide,
5-(1-(1-acryloylpiperidin-3-yl)-5-aminoimidazo[1,5-c]pyrimidin-3-yl)-N-(pyridin-2-yl)picolinamide,
5-(5-amino-1-(1-(but-2-ynoyl)piperidin-3-yl)imidazo[1,5-c]pyrimidin-3-yl)-N-(pyridin-2-yl)picolinamide,
4-(1-(1-acryloylpiperidin-3-yl)-5-aminoimidazo[1,5-c]pyrimidin-3-yl)-N-(4-cyclopropylpyridin-2-yl)benzamide,
4-(5-amino-1-(1-(but-2-ynoyl)piperidin-3-yl)imidazo[1,5-c]pyrimidin-3-yl)-N-(4-cyclopropylpyridin-2-yl)benzamide,
4-(1-(1-acryloylpiperidin-3-yl)-5-aminoimidazo[1,5-c]pyrimidin-3-yl)-N-(4-cyclopropylpyridin-2-yl)-2-fluorobenzamide,
4-(5-amino-1-(1-(but-2-ynoyl)piperidin-3-yl)imidazo[1,5-c]pyrimidin-3-yl)-N-(4-cyclopropylpyridin-2-yl)-2-fluorobenzamide,
4-(1-(1-acryloylpyrrolidin-3-yl)-5-aminoimidazo[1,5-c]pyrimidin-3-yl)-2-chloro-N-(4-cyclopropylpyridin-2-yl)benzamide,
4-(5-amino-1-(1-(but-2-ynoyl)pyrrolidin-3-yl)imidazo[1,5-c]pyrimidin-3-yl)-2-chloro-N-(4-cyclopropylpyridin-2-yl)benzamide,
4-(1-(1-acryloylpiperidin-3-yl)-5-aminoimidazo[1,5-c]pyrimidin-3-yl)-2-chloro-N-(4-cyclopropylpyridin-2-yl)benzamide,
4-(5-amino-1-(1-(but-2-ynoyl)piperidin-3-yl)imidazo[1,5-c]pyrimidin-3-yl)-2-chloro-N-(4-cyclopropylpyridin-2-yl)benzamide,
4-(1-(1-acryloylpyrrolidin-3-yl)-5-aminoimidazo[1,5-c]pyrimidin-3-yl)-2-cyano-N-(4-cyclopropylpyridin-2-yl)benzamide,
4-(5-amino-1-(1-(but-2-ynoyl)pyrrolidin-3-yl)imidazo[1,5-c]pyrimidin-3-yl)-2-cyano-N-(4-cyclopropylpyridin-2-yl)benzamide,
4-(1-(1-acryloylpiperidin-3-yl)-5-aminoimidazo[1,5-c]pyrimidin-3-yl)-2-cyano-N-(4-cyclopropylpyridin-2-yl)benzamide,
4-(5-amino-1-(1-(but-2-ynoyl)piperidin-3-yl)imidazo[1,5-c]pyrimidin-3-yl)-2-cyano-N-(4-cyclopropylpyridin-2-yl)benzamide,
4-(1-(1-acryloylpyrrolidin-3-yl)-5-aminoimidazo[1,5-c]pyrimidin-3-yl)-N-(4-cyclopropylpyridin-2-yl)-2-(trifluoromethyl)benzamide,
4-(5-amino-1-(1-(but-2-ynoyl)pyrrolidin-3-yl)imidazo[1,5-c]pyrimidin-3-yl)-N-(4-cyclopropylpyridin-2-yl)-2-(trifluoromethyl)benzamide,
4-(1-(1-acryloylpiperidin-3-yl)-5-aminoimidazo[1,5-c]pyrimidin-3-yl)-N-(4-cyclopropylpyridin-2-yl)-2-(trifluoromethyl)benzamide,
4-(5-amino-1-(1-(but-2-ynoyl)piperidin-3-yl)imidazo[1,5-c]pyrimidin-3-yl)-N-(4-cyclopropylpyridin-2-yl)-2-(trifluoromethyl)benzamide,
6-(1-(1-acryloylpyrrolidin-3-yl)-5-aminoimidazo[1,5-c]pyrimidin-3-yl)-N-(4-cyclopropylpyridin-2-yl)nicotinamide,
6-(5-amino-1-(1-(but-2-ynoyl)pyrrolidin-3-yl)imidazo[1,5-c]pyrimidin-3-yl)-N-(4-cyclopropylpyridin-2-yl)nicotinamide,
6-(1-(1-acryloylpiperidin-3-yl)-5-aminoimidazo[1,5-c]pyrimidin-3-yl)-N-(4-cyclopropylpyridin-2-yl)nicotinamide,
6-(5-amino-1-(1-(but-2-ynoyl)piperidin-3-yl)imidazo[1,5-c]pyrimidin-3-yl)-N-(4-cyclopropylpyridin-2-yl)nicotinamide,
5-(1-(1-acryloylpyrrolidin-3-yl)-5-aminoimidazo[1,5-c]pyrimidin-3-yl)-N-(4-cyclopropylpyridin-2-yl)picolinamide,
5-(5-amino-1-(1-(but-2-ynoyl)pyrrolidin-3-yl)imidazo[1,5-c]pyrimidin-3-yl)-N-(4-cyclopropylpyridin-2-yl)picolinamide,
5-(1-(1-acryloylpiperidin-3-yl)-5-aminoimidazo[1,5-c]pyrimidin-3-yl)-N-(4-cyclopropylpyridin-2-yl)picolinamide,
5-(5-amino-1-(1-(but-2-ynoyl)piperidin-3-yl)imidazo[1,5-c]pyrimidin-3-yl)-N-(4-cyclopropylpyridin-2-yl)picolinamide,
4-(5-amino-1-(1-(but-2-ynoyl)pyrrolidin-3-yl)imidazo[1,5-c]pyrimidin-3-yl)-N-(4-(trifluoromethyl)pyridin-2-yl)benzamide,
4-(1-(1-acryloylpiperidin-3-yl)-5-aminoimidazo[1,5-c]pyrimidin-3-yl)-N-(4-(trifluoromethyl)pyridin-2-yl)benzamide,
4-(5-amino-1-(1-(but-2-ynoyl)piperidin-3-yl)imidazo[1,5-c]pyrimidin-3-yl)-N-(4-(trifluoromethyl)pyridin-2-yl)benzamide,
4-(1-(1-acryloylpyrrolidin-3-yl)-5-aminoimidazo[1,5-c]pyrimidin-3-yl)-2-fluoro-N-(4-(trifluoromethyl)pyridin-2-yl)benzamide,
4-(5-amino-1-(1-(but-2-ynoyl)pyrrolidin-3-yl)imidazo[1,5-c]pyrimidin-3-yl)-2-fluoro-N-(4-(trifluoromethyl)pyridin-2-yl)benzamide,
4-(1-(1-acryloylpiperidin-3-yl)-5-aminoimidazo[1,5-c]pyrimidin-3-yl)-2-fluoro-N-(4-(trifluoromethyl)pyridin-2-yl)benzamide,
4-(5-amino-1-(1-(but-2-ynoyl)piperidin-3-yl)imidazo[1,5-c]pyrimidin-3-yl)-2-fluoro-N-(4-(trifluoromethyl)pyridin-2-yl)benzamide,
4-(1-(1-acryloylpyrrolidin-3-yl)-5-aminoimidazo[1,5-c]pyrimidin-3-yl)-2-chloro-N-(4-(trifluoromethyl)pyridin-2-yl)benzamide,
4-(5-amino-1-(1-(but-2-ynoyl)pyrrolidin-3-yl)imidazo[1,5-c]pyrimidin-3-yl)-2-chloro-N-(4-(trifluoromethyl)pyridin-2-yl)benzamide,
4-(1-(1-acryloylpiperidin-3-yl)-5-aminoimidazo[1,5-c]pyrimidin-3-yl)-2-chloro-N-(4-(trifluoromethyl)pyridin-2-yl)benzamide,
4-(5-amino-1-(1-(but-2-ynoyl)piperidin-3-yl)imidazo[1,5-c]pyrimidin-3-yl)-2-chloro-N-(4-(trifluoromethyl)pyridin-2-yl)benzamide,
4-(1-(1-acryloylpyrrolidin-3-yl)-5-aminoimidazo[1,5-c]pyrimidin-3-yl)-2-cyano-N-(4-(trifluoromethyl)pyridin-2-yl)benzamide,
4-(5-amino-1-(1-(but-2-ynoyl)pyrrolidin-3-yl)imidazo[1,5-c]pyrimidin-3-yl)-2-cyano-N-(4-(trifluoromethyl)pyridin-2-yl)benzamide,
4-(1-(1-acryloylpiperidin-3-yl)-5-aminoimidazo[1,5-c]pyrimidin-3-yl)-2-cyano-N-(4-(trifluoromethyl)pyridin-2-yl)benzamide, 4-(5-amino-1-(1-(but-2-ynoyl)piperidin-3-yl)imidazo[1,5-c]pyrimidin-3-yl)-2-cyano-N-(4-(trifluoromethyl)pyridin-2-yl)benzamide,
4-(1-(1-acryloylpyrrolidin-3-yl)-5-aminoimidazo[1,5-c]pyrimidin-3-yl)-2-(trifluoromethyl)-N-(4-(trifluoromethyl)pyridin-2-yl)benzamide,
4-(5-amino-1-(1-(but-2-ynoyl)pyrrolidin-3-yl)imidazo[1,5-c]pyrimidin-3-yl)-2-(trifluoromethyl)-N-(4-(trifluoromethyl)pyridin-2-yl)benzamide,
4-(1-(1-acryloylpiperidin-3-yl)-5-aminoimidazo[1,5-c]pyrimidin-3-yl)-2-(trifluoromethyl)-N-(4-(trifluoromethyl)pyridin-2-yl)benzamide,
4-(5-amino-1-(1-(but-2-ynoyl)piperidin-3-yl)imidazo[1,5-c]pyrimidin-3-yl)-2-(trifluoromethyl)-N-(4-(trifluoromethyl)pyridin-2-yl)benzamide,
4-(1-(1-acryloylpyrrolidin-3-yl)-5-aminoimidazo[1,5-c]pyrimidin-3-yl)-3-fluoro-N-(4-(trifluoromethyl)pyridin-2-yl)benzamide,
4-(5-amino-1-(1-(but-2-ynoyl)pyrrolidin-3-yl)imidazo[1,5-c]pyrimidin-3-yl)-3-fluoro-N-(4-(trifluoromethyl)pyridin-2-yl)benzamide,
4-(1-(1-acryloylpiperidin-3-yl)-5-aminoimidazo[1,5-c]pyrimidin-3-yl)-3-fluoro-N-(4-(trifluoromethyl)pyridin-2-yl)benzamide,
4-(5-amino-1-(1-(but-2-ynoyl)piperidin-3-yl)imidazo[1,5-c]pyrimidin-3-yl)-3-fluoro-N-(4-(trifluoromethyl)pyridin-2-yl)benzamide,
4-(1-(1-acryloylpyrrolidin-3-yl)-5-aminoimidazo[1,5-c]pyrimidin-3-yl)-3-chloro-N-(4-(trifluoromethyl)pyridin-2-yl)benzamide,
4-(5-amino-1-(1-(but-2-ynoyl)pyrrolidin-3-yl)imidazo[1,5-c]pyrimidin-3-yl)-3-chloro-N-(4-(trifluoromethyl)pyridin-2-yl)benzamide,
4-(1-(1-acryloylpiperidin-3-yl)-5-aminoimidazo[1,5-c]pyrimidin-3-yl)-3-chloro-N-(4-(trifluoromethyl)pyridin-2-yl)benzamide,
4-(5-amino-1-(1-(but-2-ynoyl)piperidin-3-yl)imidazo[1,5-c]pyrimidin-3-yl)-3-chloro-N-(4-(trifluoromethyl)pyridin-2-yl)benzamide,
4-(1-(1-acryloylpyrrolidin-3-yl)-5-aminoimidazo[1,5-c]pyrimidin-3-yl)-3-cyano-N-(4-(trifluoromethyl)pyridin-2-yl)benzamide,
4-(5-amino-1-(1-(but-2-ynoyl)pyrrolidin-3-yl)imidazo[1,5-c]pyrimidin-3-yl)-3-cyano-N-(4-(trifluoromethyl)pyridin-2-yl)benzamide,
4-(1-(1-acryloylpiperidin-3-yl)-5-aminoimidazo[1,5-c]pyrimidin-3-yl)-3-cyano-N-(4-(trifluoromethyl)pyridin-2-yl)benzamide,
4-(5-amino-1-(1-(but-2-ynoyl)piperidin-3-yl)imidazo[1,5-c]pyrimidin-3-yl)-3-cyano-N-(4-(trifluoromethyl)pyridin-2-yl)benzamide,
4-(1-(1-acryloylpyrrolidin-3-yl)-5-aminoimidazo[1,5-c]pyrimidin-3-yl)-3-(trifluoromethyl)-N-(4-(trifluoromethyl)pyridin-2-yl)benzamide,
4-(5-amino-1-(1-(but-2-ynoyl)pyrrolidin-3-yl)imidazo[1,5-c]pyrimidin-3-yl)-3-(trifluoromethyl)-N-(4-(trifluoromethyl)pyridin-2-yl)benzamide,
4-(1-(1-acryloylpiperidin-3-yl)-5-aminoimidazo[1,5-c]pyrimidin-3-yl)-3-(trifluoromethyl)-N-(4-(trifluoromethyl)pyridin-2-yl)benzamide,
4-(5-amino-1-(1-(but-2-ynoyl)piperidin-3-yl)imidazo[1,5-c]pyrimidin-3-yl)-3-(trifluoromethyl)-N-(4-(trifluoromethyl)pyridin-2-yl)benzamide,
6-(1-(1-acryloylpyrrolidin-3-yl)-5-aminoimidazo[1,5-c]pyrimidin-3-yl)-N-(4-(trifluoromethyl)pyridin-2-yl)nicotinamide,
6-(5-amino-1-(1-(but-2-ynoyl)pyrrolidin-3-yl)imidazo[1,5-c]pyrimidin-3-yl)-N-(4-(trifluoromethyl)pyridin-2-yl)nicotinamide,
6-(1-(1-acryloylpiperidin-3-yl)-5-aminoimidazo[1,5-c]pyrimidin-3-yl)-N-(4-(trifluoromethyl)pyridin-2-yl)nicotinamide,
6-(5-amino-1-(1-(but-2-ynoyl)piperidin-3-yl)imidazo[1,5-c]pyrimidin-3-yl)-N-(4-(trifluoromethyl)pyridin-2-yl)nicotinamide,
5-(1-(1-acryloylpyrrolidin-3-yl)-5-aminoimidazo[1,5-c]pyrimidin-3-yl)-N-(4-(trifluoromethyl)pyridin-2-yl)picolinamide,
5-(5-amino-1-(1-(but-2-ynoyl)pyrrolidin-3-yl)imidazo[1,5-c]pyrimidin-3-yl)-N-(4-(trifluoromethyl)pyridin-2-yl)picolinamide,
5-(1-(1-acryloylpiperidin-3-yl)-5-aminoimidazo[1,5-c]pyrimidin-3-yl)-N-(4-(trifluoromethyl)pyridin-2-yl)picolinamide,
5-(5-amino-1-(1-(but-2-ynoyl)piperidin-3-yl)imidazo[1,5-c]pyrimidin-3-yl)-N-(4-(trifluoromethyl)pyridin-2-yl)picolinamide,
1-(3-(5-amino-3-(6-(pyridin-2-yloxy)pyridin-3-yl)imidazo[1,5-c]pyrimidin-1-yl)pyrrolidin-1-yl)but-2-yn-1-one,
1-(3-(5-amino-3-(6-(pyridin-2-yloxy)pyridin-3-yl)imidazo[1,5-c]pyrimidin-1-yl)pyrrolidin-1-yl)prop-2-en-1-one,
1-(3-(5-amino-3-(5-(pyridin-2-yloxy)pyridin-2-yl)imidazo[1,5-c]pyrimidin-1-yl)pyrrolidin-1-yl)but-2-yn-1-one,
1-(3-(5-amino-3-(5-(pyridin-2-yloxy)pyridin-2-yl)imidazo[1,5-c]pyrimidin-1-yl)pyrrolidin-1-yl)prop-2-en-1-one,
1-(3-(5-amino-3-(6-(pyridin-2-yloxy)pyridin-3-yl)imidazo[1,5-c]pyrimidin-1-yl)piperidin-1-yl)but-2-yn-1-one,
1-(3-(5-amino-3-(6-(pyridin-2-yloxy)pyridin-3-yl)imidazo[1,5-c]pyrimidin-1-yl)piperidin-1-yl)prop-2-en-1-one,
1-(3-(5-amino-3-(5-(pyridin-2-yloxy)pyridin-2-yl)imidazo[1,5-c]pyrimidin-1-yl)piperidin-1-yl)but-2-yn-1-one,
1-(3-(5-amino-3-(5-(pyridin-2-yloxy)pyridin-2-yl)imidazo[1,5-c]pyrimidin-1-yl)piperidin-1-yl)prop-2-en-1-one,
1-(3-(5-amino-3-(2-chloro-4-(pyridin-2-yloxy)phenyl)imidazo[1,5-c]pyrimidin-1-yl)pyrrolidin-1-yl)but-2-yn-1-one,
1-(3-(5-amino-3-(2-chloro-4-(pyridin-2-yloxy)phenyl)imidazo[1,5-c]pyrimidin-1-yl)pyrrolidin-1-yl)prop-2-en-1-one,
1-(3-(5-amino-3-(2-chloro-4-(pyridin-2-yloxy)phenyl)imidazo[1,5-c]pyrimidin-1-yl)piperidin-1-yl)but-2-yn-1-one,
1-(3-(5-amino-3-(2-chloro-4-(pyridin-2-yloxy)phenyl)imidazo[1,5-c]pyrimidin-1-yl)piperidin-1-yl)prop-2-en-1-one,
1-(3-(5-amino-3-(3-chloro-4-(pyridin-2-yloxy)phenyl)imidazo[1,5-c]pyrimidin-1-yl)pyrrolidin-1-yl)but-2-yn-1-one,
1-(3-(5-amino-3-(3-chloro-4-(pyridin-2-yloxy)phenyl)imidazo[1,5-c]pyrimidin-1-yl)pyrrolidin-1-yl)prop-2-en-1-one,
1-(3-(5-amino-3-(3-chloro-4-(pyridin-2-yloxy)phenyl)imidazo[1,5-c]pyrimidin-1-yl)piperidin-1-yl)but-2-yn-1-one,
1-(3-(5-amino-3-(3-chloro-4-(pyridin-2-yloxy)phenyl)imidazo[1,5-c]pyrimidin-1-yl)piperidin-1-yl)prop-2-en-1-one,
1-(3-(5-amino-3-(3-fluoro-4-(pyridin-2-yloxy)phenyl)imidazo[1,5-c]pyrimidin-1-yl)piperidin-1-yl)but-2-yn-1-one,
1-(3-(5-amino-3-(3-fluoro-4-(pyridin-2-yloxy)phenyl)imidazo[1,5-c]pyrimidin-1-yl)piperidin-1-yl)prop-2-en-1-one,
1-(3-(5-amino-3-(2-fluoro-4-(pyridin-2-yloxy)phenyl)imidazo[1,5-c]pyrimidin-1-yl)pyrrolidin-1-yl)but-2-yn-1-one, 1-(3-(5-amino-3-(2-fluoro-4-(pyridin-2-yloxy)phenyl)imidazo[1,5-c]pyrimidin-1-yl)pyrrolidin-1-yl)prop-2-en-1-one,
1-(3-(5-amino-3-(2-fluoro-4-(pyridin-2-yloxy)phenyl)imidazo[1,5-c]pyrimidin-1-yl)piperidin-1-yl)but-2-yn-1-one,
1-(3-(5-amino-3-(2-fluoro-4-(pyridin-2-yloxy)phenyl)imidazo[1,5-c]pyrimidin-1-yl)piperidin-1-yl)prop-2-en-1-one,
1-(3-(5-amino-3-(2-fluoro-4-((4-methoxypyridin-2-yl)oxy)phenyl)imidazo[1,5-c]pyrimidin-1-yl)pyrrolidin-1-yl)but-2-yn-1-one,
1-(3-(5-amino-3-(2-fluoro-4-((4-methoxypyridin-2-yl)oxy)phenyl)imidazo[1,5-c]pyrimidin-1-yl)pyrrolidin-1-yl)prop-2-en-1-one,
1-(3-(5-amino-3-(2-fluoro-4-((4-methoxypyridin-2-yl)oxy)phenyl)imidazo[1,5-c]pyrimidin-1-yl)piperidin-1-yl)but-2-yn-1-one,
1-(3-(5-amino-3-(2-fluoro-4-((4-methoxypyridin-2-yl)oxy)phenyl)imidazo[1,5-c]pyrimidin-1-yl)piperidin-1-yl)prop-2-en-1-one,
1-(3-(5-amino-3-(2-chloro-4-((4-methoxypyridin-2-yl)oxy)phenyl)imidazo[1,5-c]pyrimidin-1-yl)pyrrolidin-1-yl)but-2-yn-1-one,
1-(3-(5-amino-3-(2-chloro-4-((4-methoxypyridin-2-yl)oxy)phenyl)imidazo[1,5-c]pyrimidin-1-yl)pyrrolidin-1-yl)prop-2-en-1-one,
1-(3-(5-amino-3-(2-chloro-4-((4-methoxypyridin-2-yl)oxy)phenyl)imidazo[1,5-c]pyrimidin-1-yl)piperidin-1-yl)but-2-yn-1-one,
1-(3-(5-amino-3-(2-chloro-4-((4-methoxypyridin-2-yl)oxy)phenyl)imidazo[1,5-c]pyrimidin-1-yl)piperidin-1-yl)prop-2-en-1-one,
1-(3-(5-amino-3-(3-fluoro-4-((4-methoxypyridin-2-yl)oxy)phenyl)imidazo[1,5-c]pyrimidin-1-yl)pyrrolidin-1-yl)but-2-yn-1-one,
1-(3-(5-amino-3-(3-fluoro-4-((4-methoxypyridin-2-yl)oxy)phenyl)imidazo[1,5-c]pyrimidin-1-yl)piperidin-1-yl)but-2-yn-1-one,
1-(3-(5-amino-3-(3-fluoro-4-((4-methoxypyridin-2-yl)oxy)phenyl)imidazo[1,5-c]pyrimidin-1-yl)piperidin-1-yl)prop-2-en-1-one,
1-(3-(5-amino-3-(3-chloro-4-((4-methoxypyridin-2-yl)oxy)phenyl)imidazo[1,5-c]pyrimidin-1-yl)pyrrolidin-1-yl)but-2-yn-1-one,
1-(3-(5-amino-3-(3-chloro-4-((4-methoxypyridin-2-yl)oxy)phenyl)imidazo[1,5-c]pyrimidin-1-yl)pyrrolidin-1-yl)prop-2-en-1-one,
1-(3-(5-amino-3-(3-chloro-4-((4-methoxypyridin-2-yl)oxy)phenyl)imidazo[1,5-c]pyrimidin-1-yl)piperidin-1-yl)but-2-yn-1-one,
1-(3-(5-amino-3-(3-chloro-4-((4-methoxypyridin-2-yl)oxy)phenyl)imidazo[1,5-c]pyrimidin-1-yl)piperidin-1-yl)prop-2-en-1-one,
1-(3-(5-amino-3-(4-((4-methoxypyridin-2-yl)oxy)phenyl)imidazo[1,5-c]pyrimidin-1-yl)piperidin-1-yl)but-2-yn-1-one,
1-(3-(5-amino-3-(4-((4-methoxypyridin-2-yl)oxy)phenyl)imidazo[1,5-c]pyrimidin-1-yl)piperidin-1-yl)prop-2-en-1-one,
1-(3-(5-amino-3-(6-((4-methoxypyridin-2-yl)oxy)pyridin-3-yl)imidazo[1,5-c]pyrimidin-1-yl)pyrrolidin-1-yl)but-2-yn-1-one,
1-(3-(5-amino-3-(6-((4-methoxypyridin-2-yl)oxy)pyridin-3-yl)imidazo[1,5-c]pyrimidin-1-yl)pyrrolidin-1-yl)prop-2-en-1-one,
1-(3-(5-amino-3-(6-((4-methoxypyridin-2-yl)oxy)pyridin-3-yl)imidazo[1,5-c]pyrimidin-1-yl)piperidin-1-yl)but-2-yn-1-one,
1-(3-(5-amino-3-(6-((4-methoxypyridin-2-yl)oxy)pyridin-3-yl)imidazo[1,5-c]pyrimidin-1-yl)piperidin-1-yl)prop-2-en-1-one,
1-(3-(5-amino-3-(5-((4-methoxypyridin-2-yl)oxy)pyridin-2-yl)imidazo[1,5-c]pyrimidin-1-yl)pyrrolidin-1-yl)but-2-yn-1-one,
1-(3-(5-amino-3-(5-((4-methoxypyridin-2-yl)oxy)pyridin-2-yl)imidazo[1,5-c]pyrimidin-1-yl)pyrrolidin-1-yl)prop-2-en-1-one,
1-(3-(5-amino-3-(5-((4-methoxypyridin-2-yl)oxy)pyridin-2-yl)imidazo[1,5-c]pyrimidin-1-yl)piperidin-1-yl)but-2-yn-1-one,
1-(3-(5-amino-3-(5-((4-methoxypyridin-2-yl)oxy)pyridin-2-yl)imidazo[1,5-c]pyrimidin-1-yl)piperidin-1-yl)prop-2-en-1-one,
2-((6-(5-amino-1-(1-(but-2-ynoyl)pyrrolidin-3-yl)imidazo[1,5-c]pyrimidin-3-yl)pyridin-3-yl)oxy)isonicotinonitrile,
2-((6-(1-(1-acryloylpyrrolidin-3-yl)-5-aminoimidazo[1,5-c]pyrimidin-3-yl)pyridin-3-yl)oxy)isonicotinonitrile,
2-((6-(5-amino-1-(1-(but-2-ynoyl)piperidin-3-yl)imidazo[1,5-c]pyrimidin-3-yl)pyridin-3-yl)oxy)isonicotinonitrile,
2-((6-(1-(1-acryloylpiperidin-3-yl)-5-aminoimidazo[1,5-c]pyrimidin-3-yl)pyridin-3-yl)oxy)isonicotinonitrile,
2-(4-(5-amino-1-(1-(but-2-ynoyl)pyrrolidin-3-yl)imidazo[1,5-c]pyrimidin-3-yl)phenoxy)isonicotinonitrile,
2-(4-(1-(1-acryloylpyrrolidin-3-yl)-5-aminoimidazo[1,5-c]pyrimidin-3-yl)phenoxy)isonicotinonitrile,
2-(4-(5-amino-1-(1-(but-2-ynoyl)piperidin-3-yl)imidazo[1,5-c]pyrimidin-3-yl)phenoxy)isonicotinonitrile,
2-(4-(1-(1-acryloylpiperidin-3-yl)-5-aminoimidazo[1,5-c]pyrimidin-3-yl)phenoxy)isonicotinonitrile,
2-((5-(5-amino-1-(1-(but-2-ynoyl)pyrrolidin-3-yl)imidazo[1,5-c]pyrimidin-3-yl)pyridin-2-yl)oxy)isonicotinonitrile,
2-((5-(1-(1-acryloylpyrrolidin-3-yl)-5-aminoimidazo[1,5-c]pyrimidin-3-yl)pyridin-2-yl)oxy)isonicotinonitrile,
2-((5-(5-amino-1-(1-(but-2-ynoyl)piperidin-3-yl)imidazo[1,5-c]pyrimidin-3-yl)pyridin-2-yl)oxy)isonicotinonitrile,
2-((5-(1-(1-acryloylpiperidin-3-yl)-5-aminoimidazo[1,5-c]pyrimidin-3-yl)pyridin-2-yl)oxy)isonicotinonitrile,
2-(4-(5-amino-1-(1-(but-2-ynoyl)pyrrolidin-3-yl)imidazo[1,5-c]pyrimidin-3-yl)-2-fluorophenoxy)isonicotinonitrile,
2-(4-(1-(1-acryloylpyrrolidin-3-yl)-5-aminoimidazo[1,5-c]pyrimidin-3-yl)-2-fluorophenoxy)isonicotinonitrile,
2-(4-(5-amino-1-(1-(but-2-ynoyl)piperidin-3-yl)imidazo[1,5-c]pyrimidin-3-yl)-2-fluorophenoxy)isonicotinonitrile,
2-(4-(1-(1-acryloylpiperidin-3-yl)-5-aminoimidazo[1,5-c]pyrimidin-3-yl)-2-fluorophenoxy)isonicotinonitrile,
2-(4-(5-amino-1-(1-(but-2-ynoyl)pyrrolidin-3-yl)imidazo[1,5-c]pyrimidin-3-yl)-2-chlorophenoxy)isonicotinonitrile,
2-(4-(1-(1-acryloylpyrrolidin-3-yl)-5-aminoimidazo[1,5-c]pyrimidin-3-yl)-2-chlorophenoxy)isonicotinonitrile,
2-(4-(5-amino-1-(1-(but-2-ynoyl)piperidin-3-yl)imidazo[1,5-c]pyrimidin-3-yl)-2-chlorophenoxy)isonicotinonitrile,
2-(4-(1-(1-acryloylpiperidin-3-yl)-5-aminoimidazo[1,5-c]pyrimidin-3-yl)-2-chlorophenoxy)isonicotinonitrile,
2-(4-(5-amino-1-(1-(but-2-ynoyl)pyrrolidin-3-yl)imidazo[1,5-c]pyrimidin-3-yl)-3-fluorophenoxy)isonicotinonitrile,
2-(4-(1-(1-acryloylpyrrolidin-3-yl)-5-aminoimidazo[1,5-c]pyrimidin-3-yl)-3-fluorophenoxy)isonicotinonitrile,
2-(4-(5-amino-1-(1-(but-2-ynoyl)piperidin-3-yl)imidazo[1,5-c]pyrimidin-3-yl)-3-fluorophenoxy)isonicotinonitrile,
2-(4-(1-(1-acryloylpiperidin-3-yl)-5-aminoimidazo[1,5-c]pyrimidin-3-yl)-3-fluorophenoxy)isonicotinonitrile, 2-(4-(5-amino-1-(1-(but-2-ynoyl)pyrrolidin-3-yl)imidazo[1,5-c]pyrimidin-3-yl)-3-chlorophenoxy)isonicotinonitrile,
2-(4-(1-(1-acryloylpyrrolidin-3-yl)-5-aminoimidazo[1,5-c]pyrimidin-3-yl)-3-chlorophenoxy)isonicotinonitrile,
2-(4-(5-amino-1-(1-(but-2-ynoyl)piperidin-3-yl)imidazo[1,5-c]pyrimidin-3-yl)-3-chlorophenoxy)isonicotinonitrile,
2-(4-(1-(1-acryloylpiperidin-3-yl)-5-aminoimidazo[1,5-c]pyrimidin-3-yl)-3-chlorophenoxy)isonicotinonitrile,
1-(3-(5-amino-3-(2-chloro-4-((4-cyclopropylpyridin-2-yl)oxy)phenyl)imidazo[1,5-c]pyrimidin-1-yl)pyrrolidin-1-yl)but-2-yn-1-one,
1-(3-(5-amino-3-(2-chloro-4-((4-cyclopropylpyridin-2-yl)oxy)phenyl)imidazo[1,5-c]pyrimidin-1-yl)pyrrolidin-1-yl)prop-2-en-1-one,
1-(3-(5-amino-3-(2-chloro-4-((4-cyclopropylpyridin-2-yl)oxy)phenyl)imidazo[1,5-c]pyrimidin-1-yl)piperidin-1-yl)but-2-yn-1-one,
1-(3-(5-amino-3-(2-chloro-4-((4-cyclopropylpyridin-2-yl)oxy)phenyl)imidazo[1,5-c]pyrimidin-1-yl)piperidin-1-yl)prop-2-en-1-one,
1-(3-(5-amino-3-(4-((4-cyclopropylpyridin-2-yl)oxy)-2-fluorophenyl)imidazo[1,5-c]pyrimidin-1-yl)pyrrolidin-1-yl)but-2-yn-1-one,
1-(3-(5-amino-3-(4-((4-cyclopropylpyridin-2-yl)oxy)-2-fluorophenyl)imidazo[1,5-c]pyrimidin-1-yl)pyrrolidin-1-yl)prop-2-en-1-one,
1-(3-(5-amino-3-(4-((4-cyclopropylpyridin-2-yl)oxy)-2-fluorophenyl)imidazo[1,5-c]pyrimidin-1-yl)piperidin-1-yl)but-2-yn-1-one,
1-(3-(5-amino-3-(4-((4-cyclopropylpyridin-2-yl)oxy)-2-fluorophenyl)imidazo[1,5-c]pyrimidin-1-yl)piperidin-1-yl)prop-2-en-1-one,
1-(3-(5-amino-3-(4-((4-cyclopropylpyridin-2-yl)oxy)-3-fluorophenyl)imidazo[1,5-c]pyrimidin-1-yl)pyrrolidin-1-yl)but-2-yn-1-one,
1-(3-(5-amino-3-(4-((4-cyclopropylpyridin-2-yl)oxy)-3-fluorophenyl)imidazo[1,5-c]pyrimidin-1-yl)pyrrolidin-1-yl)prop-2-en-1-one,
1-(3-(5-amino-3-(4-((4-cyclopropylpyridin-2-yl)oxy)-3-fluorophenyl)imidazo[1,5-c]pyrimidin-1-yl)piperidin-1-yl)but-2-yn-1-one,
1-(3-(5-amino-3-(4-((4-cyclopropylpyridin-2-yl)oxy)-3-fluorophenyl)imidazo[1,5-c]pyrimidin-1-yl)piperidin-1-yl)prop-2-en-1-one,
1-(3-(5-amino-3-(3-chloro-4-((4-cyclopropylpyridin-2-yl)oxy)phenyl)imidazo[1,5-c]pyrimidin-1-yl)pyrrolidin-1-yl)but-2-yn-1-one,
1-(3-(5-amino-3-(3-chloro-4-((4-cyclopropylpyridin-2-yl)oxy)phenyl)imidazo[1,5-c]pyrimidin-1-yl)pyrrolidin-1-yl)prop-2-en-1-one,
1-(3-(5-amino-3-(3-chloro-4-((4-cyclopropylpyridin-2-yl)oxy)phenyl)imidazo[1,5-c]pyrimidin-1-yl)piperidin-1-yl)but-2-yn-1-one,
1-(3-(5-amino-3-(3-chloro-4-((4-cyclopropylpyridin-2-yl)oxy)phenyl)imidazo[1,5-c]pyrimidin-1-yl)piperidin-1-yl)prop-2-en-1-one,
1-(3-(5-amino-3-(4-((4-cyclopropylpyridin-2-yl)oxy)phenyl)imidazo[1,5-c]pyrimidin-1-yl)pyrrolidin-1-yl)but-2-yn-1-one,
1-(3-(5-amino-3-(4-((4-cyclopropylpyridin-2-yl)oxy)phenyl)imidazo[1,5-c]pyrimidin-1-yl)pyrrolidin-1-yl)prop-2-en-1-one,
1-(3-(5-amino-3-(4-((4-cyclopropylpyridin-2-yl)oxy)phenyl)imidazo[1,5-c]pyrimidin-1-yl)piperidin-1-yl)but-2-yn-1-one,
1-(3-(5-amino-3-(4-((4-cyclopropylpyridin-2-yl)oxy)phenyl)imidazo[1,5-c]pyrimidin-1-yl)piperidin-1-yl)prop-2-en-1-one,
1-(3-(5-amino-3-(6-((4-cyclopropylpyridin-2-yl)oxy)pyridin-3-yl)imidazo[1,5-c]pyrimidin-1-yl)pyrrolidin-1-yl)but-2-yn-1-one,
1-(3-(5-amino-3-(6-((4-cyclopropylpyridin-2-yl)oxy)pyridin-3-yl)imidazo[1,5-c]pyrimidin-1-yl)pyrrolidin-1-yl)prop-2-en-1-one,
1-(3-(5-amino-3-(6-((4-cyclopropylpyridin-2-yl)oxy)pyridin-3-yl)imidazo[1,5-c]pyrimidin-1-yl)piperidin-1-yl)but-2-yn-1-one,
1-(3-(5-amino-3-(6-((4-cyclopropylpyridin-2-yl)oxy)pyridin-3-yl)imidazo[1,5-c]pyrimidin-1-yl)piperidin-1-yl)prop-2-en-1-one,
1-(3-(5-amino-3-(5-((4-cyclopropylpyridin-2-yl)oxy)pyridin-2-yl)imidazo[1,5-c]pyrimidin-1-yl)pyrrolidin-1-yl)but-2-yn-1-one,
1-(3-(5-amino-3-(5-((4-cyclopropylpyridin-2-yl)oxy)pyridin-2-yl)imidazo[1,5-c]pyrimidin-1-yl)pyrrolidin-1-yl)prop-2-en-1-one,
1-(3-(5-amino-3-(5-((4-cyclopropylpyridin-2-yl)oxy)pyridin-2-yl)imidazo[1,5-c]pyrimidin-1-yl)piperidin-1-yl)but-2-yn-1-one,
1-(3-(5-amino-3-(5-((4-cyclopropylpyridin-2-yl)oxy)pyridin-2-yl)imidazo[1,5-c]pyrimidin-1-yl)piperidin-1-yl)prop-2-en-1-one,
1-(3-(5-amino-3-(5-((4-(trifluoromethyl)pyridin-2-yl)oxy)pyridin-2-yl)imidazo[1,5-c]pyrimidin-1-yl)pyrrolidin-1-yl)but-2-yn-1-one,
1-(3-(5-amino-3-(5-((4-(trifluoromethyl)pyridin-2-yl)oxy)pyridin-2-yl)imidazo[1,5-c]pyrimidin-1-yl)pyrrolidin-1-yl)prop-2-en-1-one,
1-(3-(5-amino-3-(5-((4-(trifluoromethyl)pyridin-2-yl)oxy)pyridin-2-yl)imidazo[1,5-c]pyrimidin-1-yl)piperidin-1-yl)but-2-yn-1-one,
1-(3-(5-amino-3-(5-((4-(trifluoromethyl)pyridin-2-yl)oxy)pyridin-2-yl)imidazo[1,5-c]pyrimidin-1-yl)piperidin-1-yl)prop-2-en-1-one,
1-(3-(5-amino-3-(4-((4-(trifluoromethyl)pyridin-2-yl)oxy)phenyl)imidazo[1,5-c]pyrimidin-1-yl)pyrrolidin-1-yl)but-2-yn-1-one,
1-(3-(5-amino-3-(4-((4-(trifluoromethyl)pyridin-2-yl)oxy)phenyl)imidazo[1,5-c]pyrimidin-1-yl)piperidin-1-yl)but-2-yn-1-one,
1-(3-(5-amino-3-(4-((4-(trifluoromethyl)pyridin-2-yl)oxy)phenyl)imidazo[1,5-c]pyrimidin-1-yl)piperidin-1-yl)prop-2-en-1-one,
1-(3-(5-amino-3-(6-((4-(trifluoromethyl)pyridin-2-yl)oxy)pyridin-3-yl)imidazo[1,5-c]pyrimidin-1-yl)pyrrolidin-1-yl)but-2-yn-1-one,
1-(3-(5-amino-3-(6-((4-(trifluoromethyl)pyridin-2-yl)oxy)pyridin-3-yl)imidazo[1,5-c]pyrimidin-1-yl)pyrrolidin-1-yl)prop-2-en-1-one,
1-(3-(5-amino-3-(6-((4-(trifluoromethyl)pyridin-2-yl)oxy)pyridin-3-yl)imidazo[1,5-c]pyrimidin-1-yl)piperidin-1-yl)but-2-yn-1-one,
1-(3-(5-amino-3-(6-((4-(trifluoromethyl)pyridin-2-yl)oxy)pyridin-3-yl)imidazo[1,5-c]pyrimidin-1-yl)piperidin-1-yl)prop-2-en-1-one,
1-(3-(5-amino-3-(3-fluoro-4-((4-(trifluoromethyl)pyridin-2-yl)oxy)phenyl)imidazo[1,5-c]pyrimidin-1-yl)piperidin-1-yl)but-2-yn-1-one,
1-(3-(5-amino-3-(3-fluoro-4-((4-(trifluoromethyl)pyridin-2-yl)oxy)phenyl)imidazo[1,5-c]pyrimidin-1-yl)piperidin-1-yl)prop-2-en-1-one, 1-(3-(5-amino-3-(3-chloro-4-((4-(trifluoromethyl)pyridin-2-yl)oxy)phenyl)imidazo[1,5-c]pyrimidin-1-yl)pyrrolidin-1-yl)but-2-yn-1-one,
1-(3-(5-amino-3-(3-chloro-4-((4-(trifluoromethyl)pyridin-2-yl)oxy)phenyl)imidazo[1,5-c]pyrimidin-1-yl)pyrrolidin-1-yl)prop-2-en-1-one,
1-(3-(5-amino-3-(3-chloro-4-((4-(trifluoromethyl)pyridin-2-yl)oxy)phenyl)imidazo[1,5-c]pyrimidin-1-yl)piperidin-1-yl)but-2-yn-1-one,
1-(3-(5-amino-3-(3-chloro-4-((4-(trifluoromethyl)pyridin-2-yl)oxy)phenyl)imidazo[1,5-c]pyrimidin-1-yl)piperidin-1-yl)prop-2-en-1-one,
1-(3-(5-amino-3-(2-fluoro-4-((4-(trifluoromethyl)pyridin-2-yl)oxy)phenyl)imidazo[1,5-c]pyrimidin-1-yl)pyrrolidin-1-yl)but-2-yn-1-one,
1-(3-(5-amino-3-(2-fluoro-4-((4-(trifluoromethyl)pyridin-2-yl)oxy)phenyl)imidazo[1,5-c]pyrimidin-1-yl)pyrrolidin-1-yl)prop-2-en-1-one,
1-(3-(5-amino-3-(2-fluoro-4-((4-(trifluoromethyl)pyridin-2-yl)oxy)phenyl)imidazo[1,5-c]pyrimidin-1-yl)piperidin-1-yl)but-2-yn-1-one,
1-(3-(5-amino-3-(2-fluoro-4-((4-(trifluoromethyl)pyridin-2-yl)oxy)phenyl)imidazo[1,5-c]pyrimidin-1-yl)piperidin-1-yl)prop-2-en-1-one,
1-(3-(5-amino-3-(2-chloro-4-((4-(trifluoromethyl)pyridin-2-yl)oxy)phenyl)imidazo[1,5-c]pyrimidin-1-yl)pyrrolidin-1-yl)but-2-yn-1-one,
1-(3-(5-amino-3-(2-chloro-4-((4-(trifluoromethyl)pyridin-2-yl)oxy)phenyl)imidazo[1,5-c]pyrimidin-1-yl)pyrrolidin-1-yl)prop-2-en-1-one,
1-(3-(5-amino-3-(2-chloro-4-((4-(trifluoromethyl)pyridin-2-yl)oxy)phenyl)imidazo[1,5-c]pyrimidin-1l-yl)piperidin-1-yl)but-2-yn-1l-one,
1-(3-(5-amino-3-(2-chloro-4-((4-(trifluoromethyl)pyridin-2-yl)oxy)phenyl)imidazo[1,5-c]pyrimidin-1-yl)piperidin-1-yl)prop-2-en-1-one,
4-(8-(1-acryloylpyrrolidin-3-yl)-4-aminoimidazo[1,5-a][1,3,5]triazin-6-yl)-N-(4-cyanopyridin-2-yl)benzamide,
4-(4-amino-8-(1-(but-2-ynoyl)pyrrolidin-3-yl)imidazo[1,5-a][1,3,5]triazin-6-yl)-N-(4-cyanopyridin-2-yl)benzamide, and
4-(8-(1-acryloylpiperidin-3-yl)-4-aminoimidazo[1,5-a][1,3,5]triazin-6-yl)-N-(4-cyanopyridin-2-yl)benzamide,
or a pharmaceutically acceptable salt thereof.

In yet another aspect, the present disclosure provides a compound chosen from the compounds set forth in Table 1 below and pharmaceutically acceptable salts thereof.

TABLE 1

Illustrative Compounds of the Present Invention

| Compound No. | Structure | Name |
|---|---|---|
| C001 | 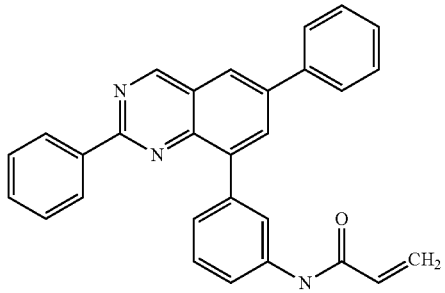 [SMILES: C=CC(=O)Nc1cccc(-c2cc(-c3ccccc3)cc3cnc(-c4ccccc4)nc23)c1] | N-(3-(2,6-diphenylquinazolin-8-yl)phenyl)acrylamide |
| C002 | 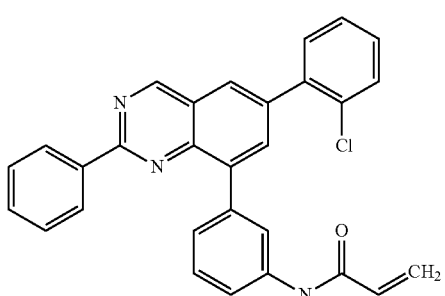 | N-(3-(6-(2-chlorophenyl)-2-phenylquinazolin-8yl)phenyl)-acrylamide |
| C003 | 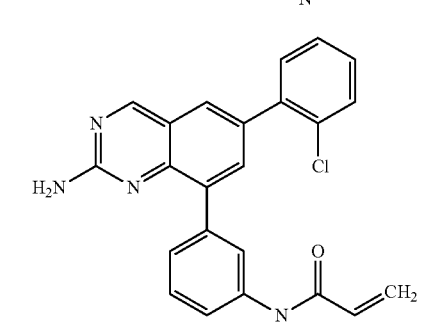 | N-(3-(2-amino-6-(2-chloro-phenyl)quinazolin-8-yl)phenyl)acrylamide |

TABLE 1-continued
Illustrative Compounds of the Present Invention
| Compound No. | Structure | Name |
|---|---|---|
| C004 | 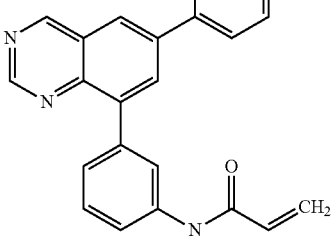 | N-(3-(6-phenylquinazolin-8-yl)phenyl)acrylamide |
| C005 | 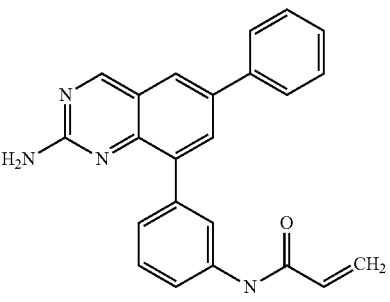 | N-(3-(2-amino-6-phenyl-quinazolin-8-yl)phenyl)acrylamide |
| C006 | 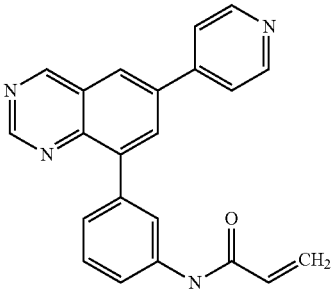 [SMILES: C=CC(=O)Nc1cccc(-c2cc(-c3ccccc3)cc3cncnc23)c1] | N-(3-(6-(pyridin-4-yl)-quinazolin-8-yl)phenyl)acrylamide |
| C007 | 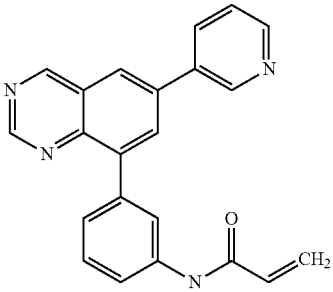 [SMILES: C=CC(=O)Nc1cccc(-c2cc(-c3cccnc3)cc3cncnc23)c1] | N-(3-(6-(pyridin-3-yl)-quinazolin-8-yl)phenyl)acrylamide |

TABLE 1-continued

Illustrative Compounds of the Present Invention

| Compound No. | Structure | Name |
|---|---|---|
| C008 | 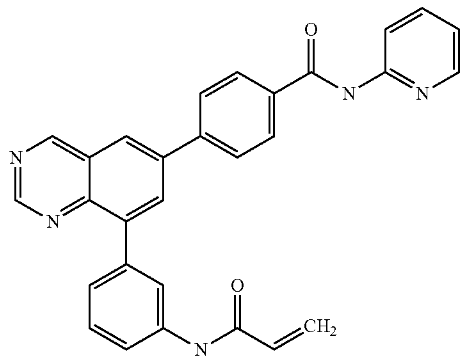 [SMILES: C=CC(=O)Nc1cccc(-c2cc(-c3ccc(C(=O)Nc4ccccn4)cc3)cc3cncnc23)c1] | 4-(8-(3-acrylamidophenyl)-quinazolin-6-yl)-N-(pyridin-2-yl)benzamide |
| C009 | 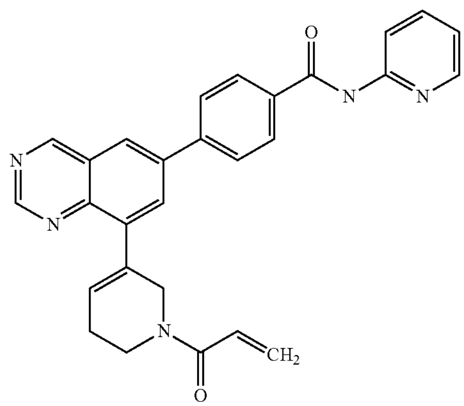 [SMILES: C=CC(=O)N1CCC=C(c2cc(-c3ccc(C(=O)Nc4ccccn4)cc3)cc3cncnc23)C1] | 4-(8-(1-acryloyl-1,2,5,6-tetrahydropyridin-3-yl)quinazolin-6-yl)-N-(pyridin-2-yl)benzamide |
| C010 | 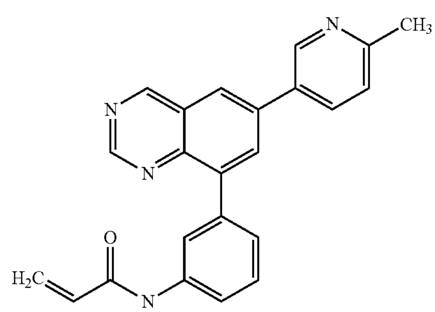 [SMILES: C=CC(=O)Nc1cccc(-c2cc(-c3ccc(C)nc3)cc3cncnc23)c1] | N-(3-(6-(6-methylpyridin-3-yl)quinazolin-8-yl)phenyl)acrylamide |
| C011 | 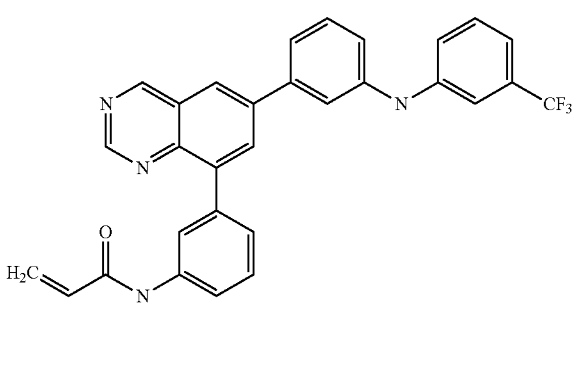 [SMILES: C=CC(=O)Nc1cccc(-c2cc(-c3cccc(Nc4cccc(C(F)(F)F)c4)c3)cc3cncnc23)c1] | N-(3-(6-(3-((3-(trifluoromethyl)phenyl)amino)phenyl)quinazolin-8-yl)phenyl)acrylamide |

TABLE 1-continued

Illustrative Compounds of the Present Invention

| Compound No. | Structure | Name |
|---|---|---|
| C012 | 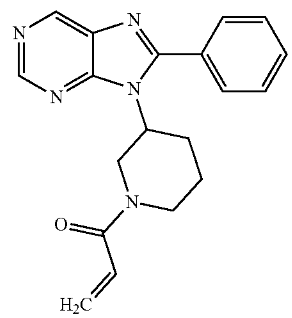 [SMILES: C=CC(=O)N1CCCC(n2c(-c3ccccc3)nc3cncnc32)C1] | 1-(3-(8-phenyl-9H-purin-9-yl)piperidin-1-yl)prop-2-en-1-one |
| C013 | 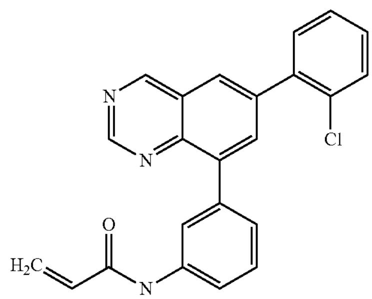 [SMILES: C=CC(=O)Nc1cccc(-c2cc(-c3ccccc3Cl)cc3cncnc23)c1] | N-(3-(6-(2-chlorophenyl)-quinazolin-8-yl)phenyl)acrylamide |
| C014 | 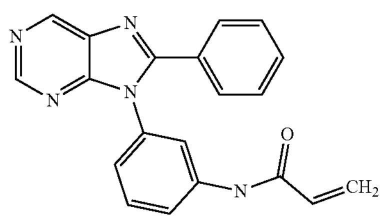 [SMILES: C=CC(=O)Nc1cccc(-n2c(-c3ccccc3)nc3cncnc32)c1] | N-(3-(8-phenyl-9H-purin-9-yl)phenyl)acrylamide |
| C015 | 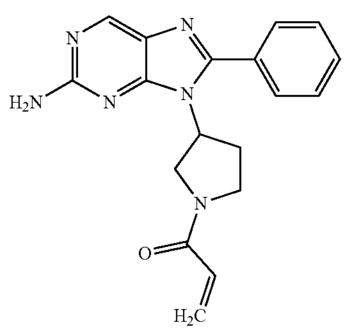 [SMILES: C=CC(=O)N1CCC(n2c(-c3ccccc3)nc3cnc(N)nc32)C1] | 1-(3-(2-amino-8-phenyl-9H-purin-9-yl)pyrrolidin-1-yl)prop-2-en-1-one |
| C016 | 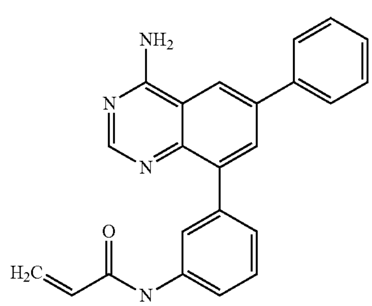 [SMILES: C=CC(=O)Nc1cccc(-c2cc(-c3ccccc3)cc3c(N)ncnc23)c1] | N-(3-(4-amino-6-phenylquinazolin-8-yl)phenyl)acrylamide |

TABLE 1-continued

Illustrative Compounds of the Present Invention

| Compound No. | Structure | Name |
|---|---|---|
| C017 | 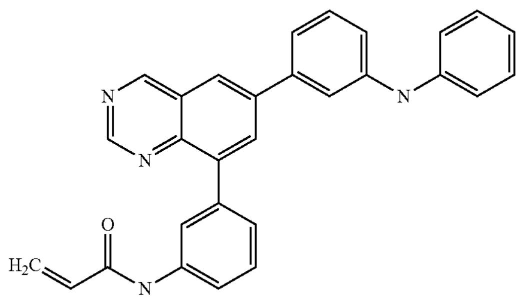 [SMILES: C=CC(=O)Nc1cccc(-c2cc(-c3cccc(Nc4ccccc4)c3)cc3cncnc23)c1] | N-(3-(6-(3-(phenylamino)phenyl)quinazolin-8-yl)-phenyl)acrylamide |
| C018 | 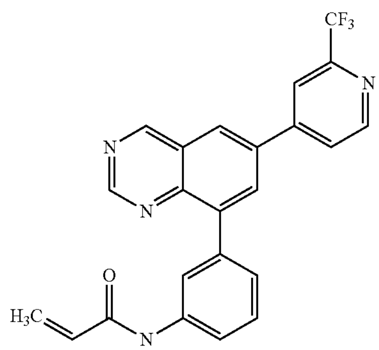 [SMILES: C=CC(=O)Nc1cccc(-c2cc(-c3ccnc(C(F)(F)F)c3)cc3cncnc23)c1] | N-(3-(6-(2-(trifluoromethyl)pyridin-4-yl)quinazolin-8-yl)phenyl)acrylamide |
| C019 | 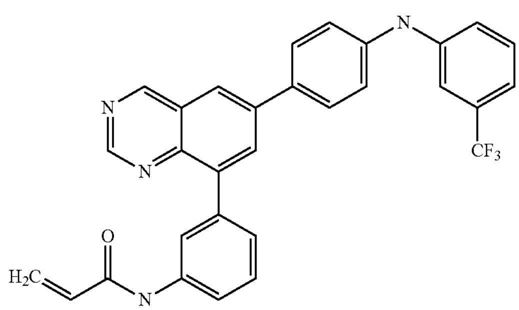 [SMILES: C=CC(=O)Nc1cccc(-c2cc(-c3ccc(Nc4cccc(C(F)(F)F)c4)cc3)cc3cncnc23)c1] | N-(3-(6-(4-((3-(trifluoromethyl)phenyl)amino)phenyl)quinazolin-8-yl)-phenyl)acrylamide |
| C020 | 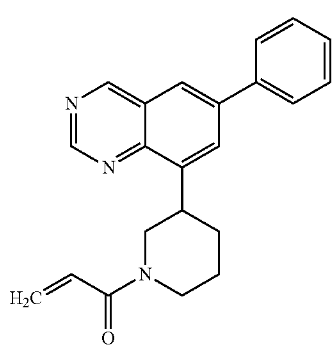 [SMILES: C=CC(=O)N1CCCC(c2cc(-c3ccccc3)cc3cncnc23)C1] | 1-(3-(6-phenylquinazolin-8-yl)piperidin-1-yl)prop-2-en-1-one |

TABLE 1-continued

Illustrative Compounds of the Present Invention

| Compound No. | Structure | Name |
| --- | --- | --- |
| C021 | 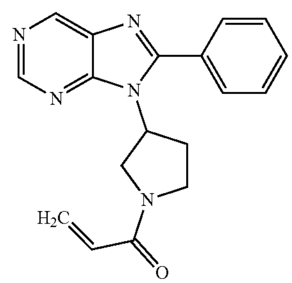 [SMILES: C=CC(=O)N1CCC(n2c(-c3ccccc3)nc3cncnc32)C1] | 1-(3-(8-phenyl-9H-purin-9-yl)pyrrolidin-1-yl)prop-2-en-1-one |
| C022 | 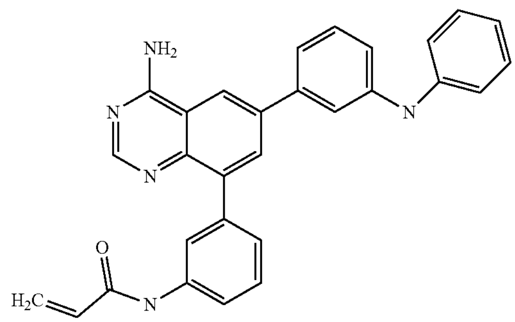 [SMILES: C=CC(=O)Nc1cccc(-c2cc(-c3cccc(Nc4ccccc4)c3)cc3c(N)ncnc23)c1] | N-(3-(4-amino-6-(3-(phenyl-amino)phenyl)quinazolin-8-yl)phenyl)acrylamide |
| C023 | 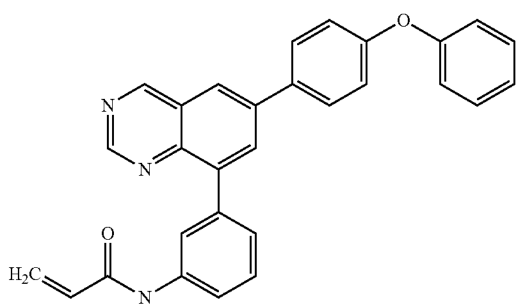 [SMILES: C=CC(=O)Nc1cccc(-c2cc(-c3ccc(Oc4ccccc4)cc3)cc3cncnc23)c1] | N-(3-(6-(4-phenoxyphenyl)quinazolin-8-yl)phenyl)acrylamide |
| C024 | 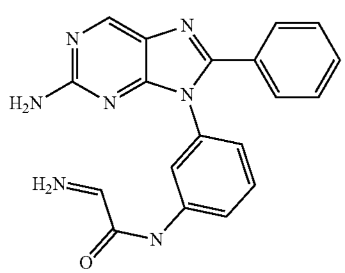 [SMILES: N=CC(=O)Nc1cccc(-n2c(-c3ccccc3)nc3cnc(N)nc32)c1] | N-(3-(2-amino-8-phenyl-9H-purin-9-yl)phenyl)acrylamide |
| C025 | 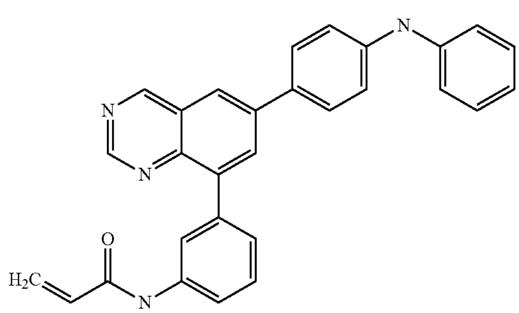 [SMILES: C=CC(=O)Nc1cccc(-c2cc(-c3ccc(Nc4ccccc4)cc3)cc3cncnc23)c1] | N-(3-(6-(4-(phenylamino)phenyl)quinazolin-8-yl)phenyl)acrylamide |

TABLE 1-continued

Illustrative Compounds of the Present Invention

| Compound No. | Structure | Name |
|---|---|---|
| C026 | 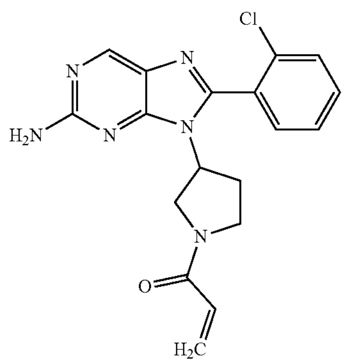 [SMILES: C=CC(=O)N1CCC(n2c(-c3ccccc3Cl)nc3cnc(N)nc32)C1] | 1-(3-(2-amino-8-(2-chlorophenyl)-9H-purin-9-yl)pyrrolidin-1-yl)prop-2-en-1-one |
| C027 | 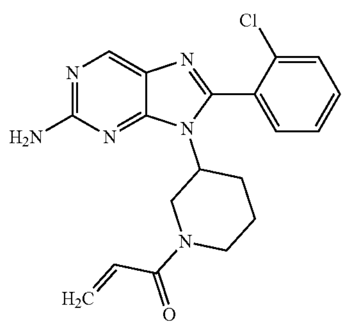 [SMILES: C=CC(=O)N1CCCC(n2c(-c3ccccc3Cl)nc3cnc(N)nc32)C1] | 1-(3-(2-amino-8-(2-chlorophenyl)-9H-purin-9-yl)piperidin-1-yl)prop-2-en-1-one |
| C028 | 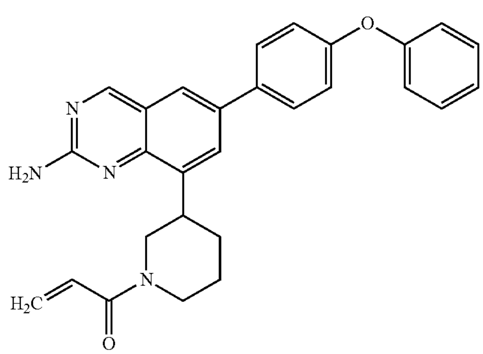 [SMILES: C=CC(=O)N1CCCC(c2cc(-c3ccc(Oc4ccccc4)cc3)cc3cnc(N)nc23)C1] | 1-(3-(2-amino-6-(4-phenoxyphenyl)quinazolin-8-yl)piperidin-1-yl)prop-2-en-1-one |
| C029 | 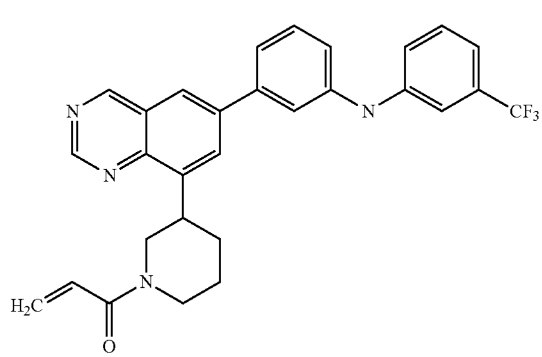 [SMILES: C=CC(=O)N1CCCC(c2cc(-c3cccc(Nc4cccc(C(F)(F)F)c4)c3)cc3cncnc23)C1] | 1-(3-(6-(3-((3-(trifluoromethyl)phenyl)amino)phenyl)quinazolin-8-yl)-piperidin-1-yl)prop-2-en-1-one |

TABLE 1-continued

Illustrative Compounds of the Present Invention

| Compound No. | Structure | Name |
|---|---|---|
| C030 | 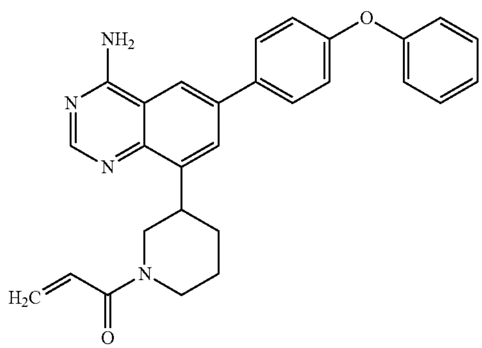 [SMILES: C=CC(=O)N1CCCC(c2cc(-c3ccc(Oc4ccccc4)cc3)cc3c(N)ncnc23)C1] | 1-(3-(4-amino-6-(4-phenoxyphenyl)quinazolin-8-yl)-piperidin-1-yl)prop-2-en-1-one |
| C031 | 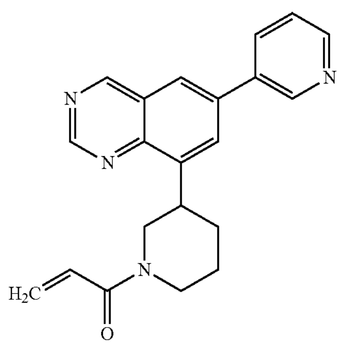 [SMILES: C=CC(=O)N1CCCC(c2cc(-c3cccnc3)cc3cncnc23)C1] | 1-(3-(6-(pyridin-3-yl)quinazolin-8-yl)piperidin-1-yl)prop-2-en-1-one |
| C032 | 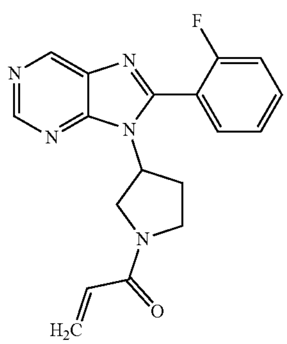 | 1-(3-(8-(2-fluorophenyl)-9H-purin-9-yl)pyrrolidin-1-yl)prop-2-en-1-one |
| C033 | 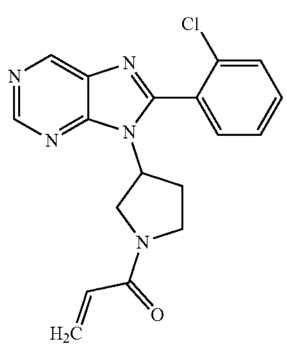 [SMILES: C=CC(=O)N1CCC(n2c(-c3ccccc3Cl)nc3cncnc32)C1] | 1-(3-(8-(2-chlorophenyl)-9H-purin-9-yl)pyrrolidin-1-yl)prop-2-en-1-one |

TABLE 1-continued
Illustrative Compounds of the Present Invention
| Compound No. | Structure | Name |
|---|---|---|
| C034 | 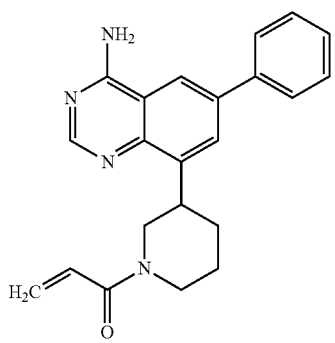 [SMILES: C=CC(=O)N1CCCC(c2cc(-c3ccccc3)cc3c(N)ncnc23)C1] | 1-(3-(4-amino-6-phenylquinazolin-8-yl)piperidin-1-yl)prop-2-en-1-one |
| C035 | 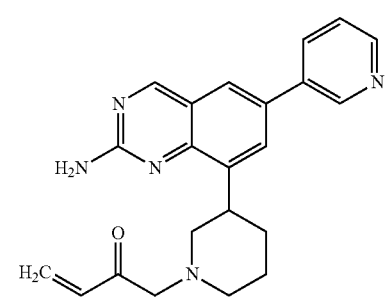 [SMILES: C=CC(=O)CN1CCCC(c2cc(-c3cccnc3)cc3cnc(N)nc23)C1] | N-(3-(2-amino-6-(pyridin-3-yl)quinazolin-8-yl)phenyl)acrylamide |
| C036 | 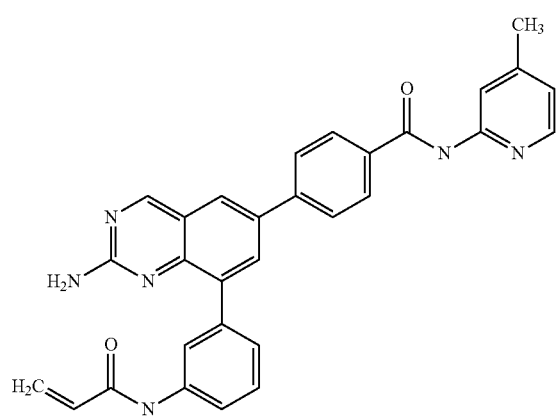 [SMILES: C=CC(=O)Nc1cccc(-c2cc(-c3ccc(C(=O)Nc4cc(C)ccn4)cc3)cc3cnc(N)nc23)c1] | 4-(8-(3-acrylamidophenyl)-2-aminoquinazolin-6-yl)-N-(4-methylpyridin-2-yl)benzamide |

TABLE 1-continued
Illustrative Compounds of the Present Invention
| Compound No. | Structure | Name |
|---|---|---|
| C037 | 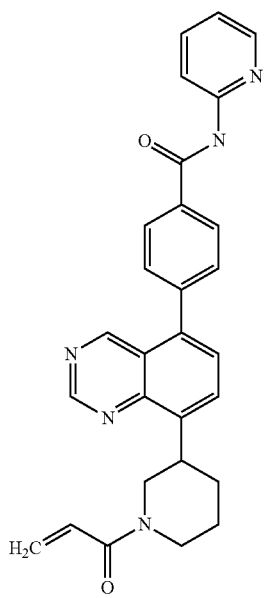 [SMILES: C=CC(=O)N1CCCC(c2ccc(-c3ccc(C(=O)Nc4ccccn4)cc3)c3cncnc23)C1] | 4-(8-(1-acryloylpiperidin-3-yl)quinazolin-5-yl)-N-(pyridin-2-yl)benzamide |
| C038 | 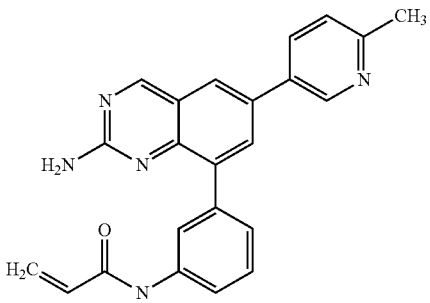 [SMILES: C=CC(=O)Nc1cccc(-c2cc(-c3ccc(C)nc3)cc3cnc(N)nc23)c1] | N-(3-(2-amino-6-(6-methylpyridin-3-yl)quinazolin-8-yl)phenyl)acrylamide |
| C039 | 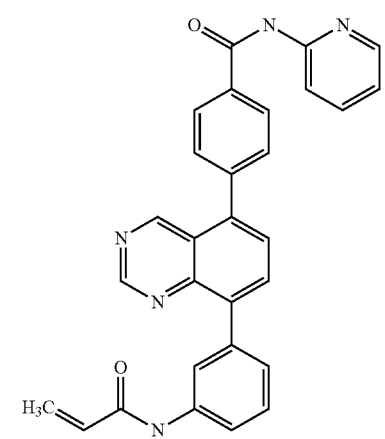 [SMILES: C=CC(=O)Nc1cccc(-c2ccc(-c3ccc(C(=O)Nc4ccccn4)cc3)c3cncnc23)c1] | 4-(8-(3-acrylamidophenyl)quinazolin-5-yl)-N-(pyridin-2-yl)benzamide |

TABLE 1-continued

Illustrative Compounds of the Present Invention

| Compound No. | Structure | Name |
|---|---|---|
| C040 | 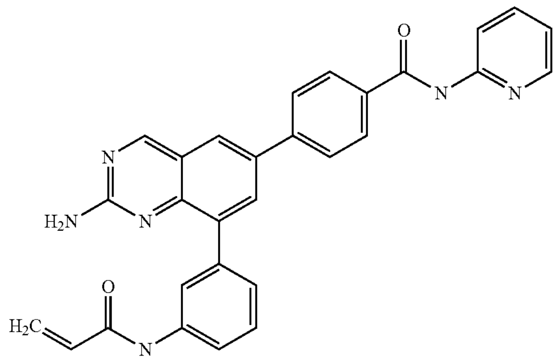 [SMILES: C=CC(=O)Nc1cccc(-c2cc(-c3ccc(C(=O)Nc4ccccn4)cc3)cc3cnc(N)nc23)c1] | 4-(8-(3-acrylamidophenyl)-2-aminoquinazolin-6-yl)-N-(pyridin-2-yl)benzamide |
| C041 | 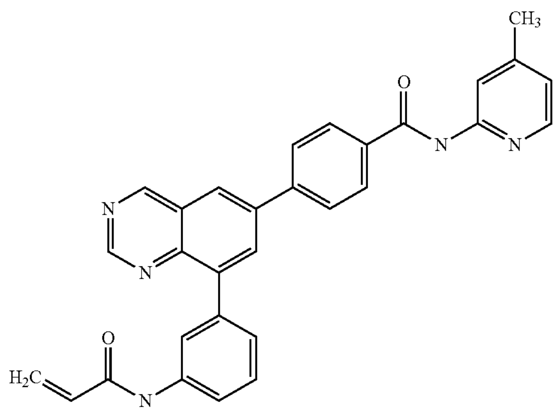 [SMILES: C=CC(=O)Nc1cccc(-c2cc(-c3ccc(C(=O)Nc4cc(C)ccn4)cc3)cc3cncnc23)c1] | 4-(8-(3-acrylamidophenyl)quinazolin-6-yl)-N-(4-methylpyridin-2-yl)benzamide |
| C042 | 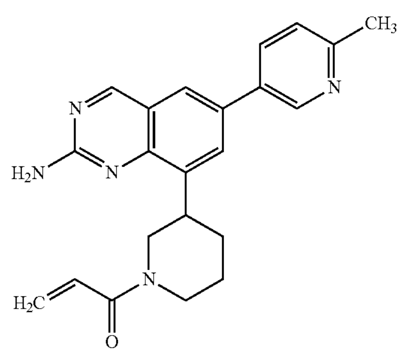 [SMILES: C=CC(=O)N1CCCC(c2cc(-c3ccc(C)nc3)cc3cnc(N)nc23)C1] | 1-(3-(2-amino-6-(6-methylpyridin-3-yl)quinazolin-8-yl)piperidin-1-yl)prop-2-en-1-one |
| C043 | 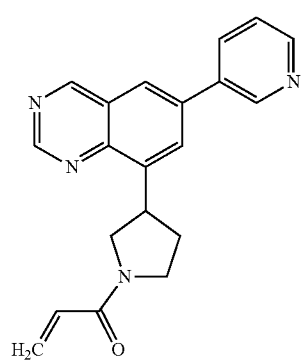 [SMILES: C=CC(=O)N1CCC(c2cc(-c3cccnc3)cc3cncnc23)C1] | 1-(3-(6-(pyridin-3-yl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C044 | 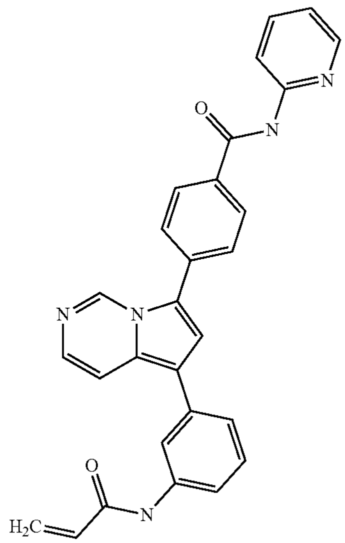 [SMILES: C=CC(=O)Nc1cccc(-c2cc(-c3ccc(C(=O)Nc4ccccn4)cc3)n3cnccc23)c1] | 4-(5-(3-acrylamidophenyl)pyrrolo[1,2-c]pyrimidin-7-yl)-N-(pyridin-2-yl)benzamide |
| C045 | 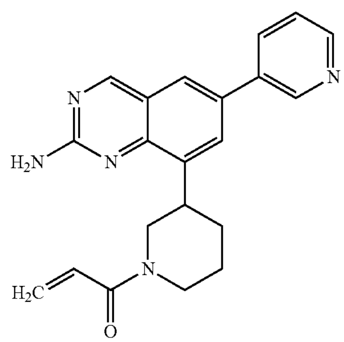 | 1-(3-(2-amino-6-(pyridin-3-yl)quinazolin-8-yl)piperidin-1-yl)prop-2-en-1-one |
| C046 | 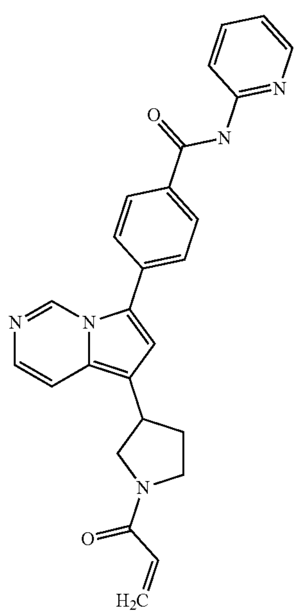 [SMILES: C=CC(=O)N1CCC(c2cc(-c3ccc(C(=O)Nc4ccccn4)cc3)n3cnccc23)C1] | 4-(5-(1-acryloylpyrrolidin-3-yl)pyrrolo[1,2-c]pyrimidin-7-yl)-N-(pyridin-2-yl)benzamide |

TABLE 1-continued

Illustrative Compounds of the Present Invention

| Compound No. | Structure | Name |
|---|---|---|
| C047 | 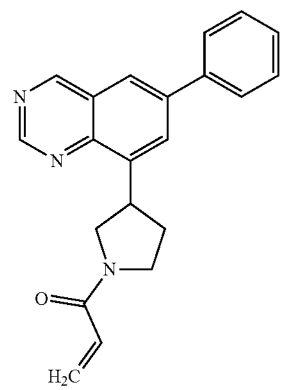 [SMILES: C=CC(=O)N1CCC(c2cc(-c3ccccc3)cc3cncnc23)C1] | 1-(3-(6-phenylquinazolin-8-yl)pyrrolidin-1-yl)prop-2-en-1-one |
| C048 | 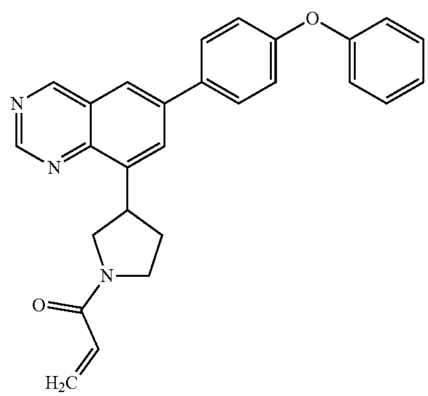 [SMILES: C=CC(=O)N1CCC(c2cc(-c3ccc(Oc4ccccc4)cc3)cc3cncnc23)C1] | 1-(3-(6-(4-phenoxyphenyl)quinazolin-8-yl)pyrrolidin-1-yl)prop-2-en-1-one |
| C049 | 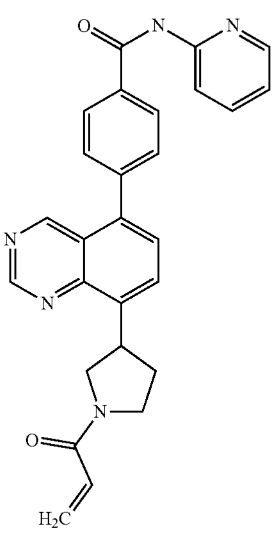 [SMILES: C=CC(=O)N1CCC(c2ccc(-c3ccc(C(=O)Nc4ccccn4)cc3)c3cncnc23)C1] | 4-(8-(1-acryloylpyrrolidin-3-yl)quinazolin-5-yl)-N-(pyridin-2-yl)benzamide |

TABLE 1-continued

Illustrative Compounds of the Present Invention

| Compound No. | Structure | Name |
|---|---|---|
| C050 | 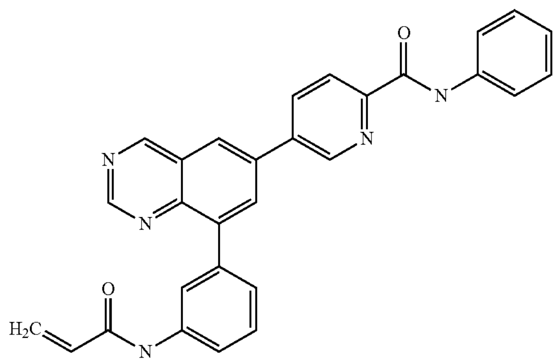 [SMILES: C=CC(=O)Nc1cccc(-c2cc(-c3ccc(C(=O)Nc4ccccc4)nc3)cc3cncnc23)c1] | 5-(8-(3-acrylamidophenyl)quinazolin-6-yl)-N-phenyl-picolinamide |
| C051 | 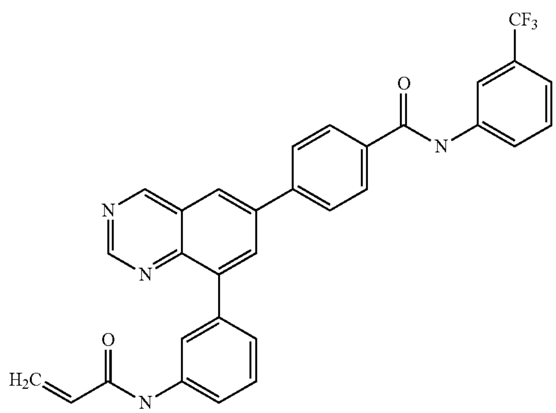 [SMILES: C=CC(=O)Nc1cccc(-c2cc(-c3ccc(C(=O)Nc4cccc(C(F)(F)F)c4)cc3)cc3cncnc23)c1] | 4-(8-(3-acrylamidophenyl)quinazolin-6-yl)-N-(3-(trifluoromethyl)phenyl)-benzamide |
| C052 | 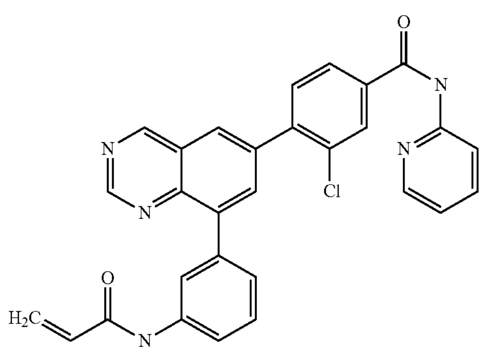 [SMILES: C=CC(=O)Nc1cccc(-c2cc(-c3ccc(C(=O)Nc4ccccn4)cc3Cl)cc3cncnc23)c1] | 4-(8-(3-acrylamidophenyl)quinazolin-6-yl)-3-chloro-N-(pyridin-2-yl)benzamide |
| C053 | 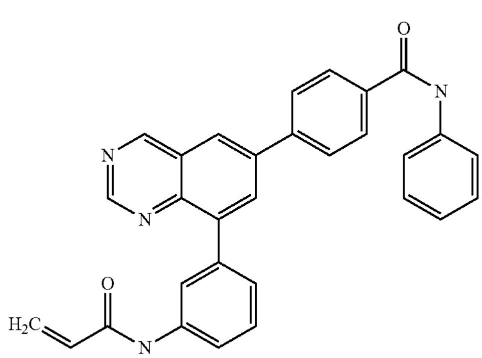 [SMILES: C=CC(=O)Nc1cccc(-c2cc(-c3ccc(C(=O)Nc4ccccc4)cc3)cc3cncnc23)c1] | 4-(8-(3-acrylamidophenyl)quinazolin-6-yl)-N-phenylbenzamide |

TABLE 1-continued
Illustrative Compounds of the Present Invention
| Compound No. | Structure | Name |
|---|---|---|
| C054 | 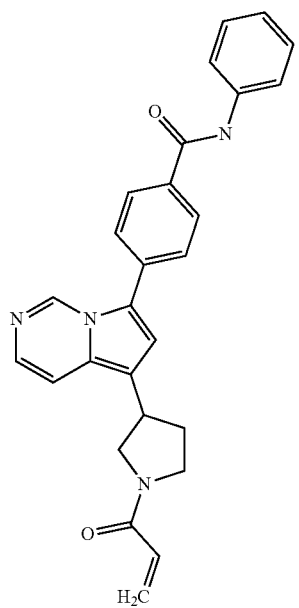 | 4-(5-(1-acryloylpyrrolidin-3-yl)pyrrolo[1,2-c]pyrimidin-7-yl)-N-phenylbenzamide |
| C055 | 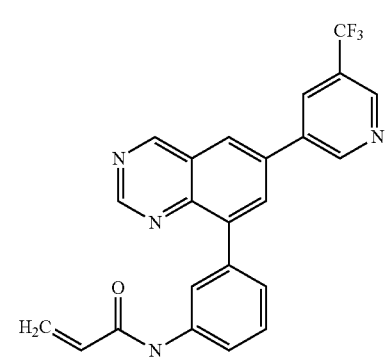 | N-(3-(6-(5-(trifluoromethyl)pyridin-3-yl)quinazolin-8-yl)phenyl)acrylamide |

TABLE 1-continued
Illustrative Compounds of the Present Invention
| Compound No. | Structure | Name |
|---|---|---|
| C056 | 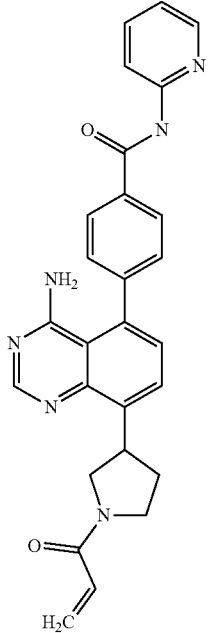 [SMILES: C=CC(=O)N1CCC(c2ccc(-c3ccc(C(=O)Nc4ccccn4)cc3)c3c(N)ncnc23)C1] | 4-(8-(1-acryloylpyrrolidin-3-yl)-4-aminoquinazolin-5-yl)-N-(pyridin-2-yl)benzamide |
| C057 | 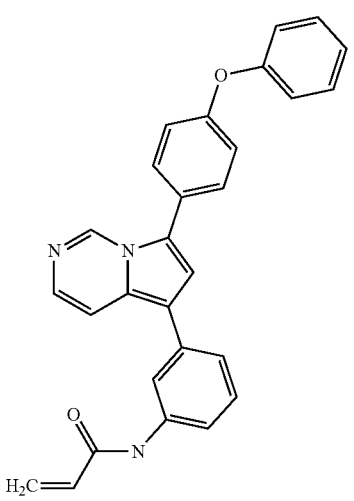 [SMILES: C=CC(=O)Nc1cccc(-c2cc(-c3ccc(Oc4ccccc4)cc3)n3cnccc23)c1] | N-(3-(7-(4-phenoxyphenyl)pyrrolo[1,2-c]pyrimidin-5-yl)phenyl)acrylamide |

TABLE 1-continued
Illustrative Compounds of the Present Invention
| Compound No. | Structure | Name |
|---|---|---|
| C058 | 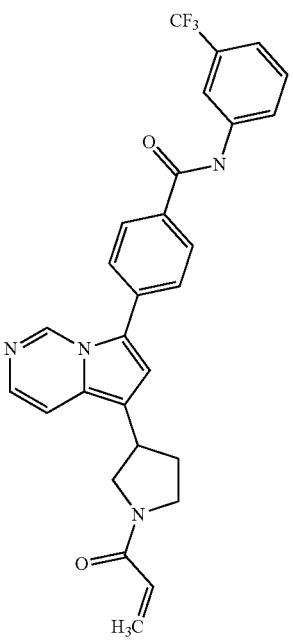 [SMILES: C=CC(=O)N1CCC(c2cc(-c3ccc(C(=O)Nc4cccc(C(F)(F)F)c4)cc3)n3cnccc23)C1] | 4-(5-(1-acryloylpyrrolidin-3-yl)pyrrolo[1,2-c]pyrimidin-7-yl)-N-(3-(trifluoromethyl)phenyl)benzamide |
| C059 | 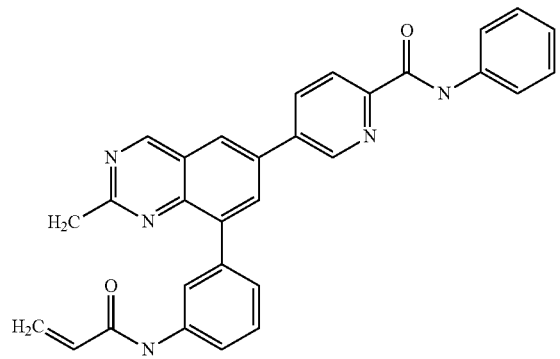 | 5-(8-(3-acrylamidophenyl)-2-aminoquinazolin-6-yl)-N-phenylpicolinamide |
| C060 | 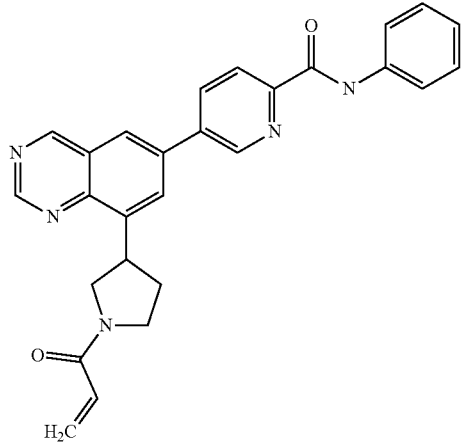 [SMILES: C=CC(=O)N1CCC(c2cc(-c3ccc(C(=O)Nc4ccccc4)nc3)cc3cncnc23)C1] | 5-(8-(1-acryloylpyrrolidin-3-yl)quinazolin-6-yl)-N-phenylpicolinamide |

TABLE 1-continued

Illustrative Compounds of the Present Invention

| Compound No. | Structure | Name |
|---|---|---|
| C061 | 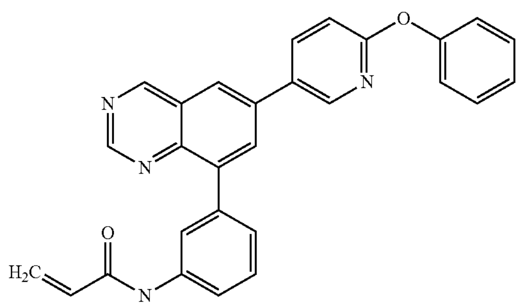 | N-(3-(6-(6-phenoxypyridin-3-yl)quinazolin-8-yl)phenyl)acrylamide |
| C062 | 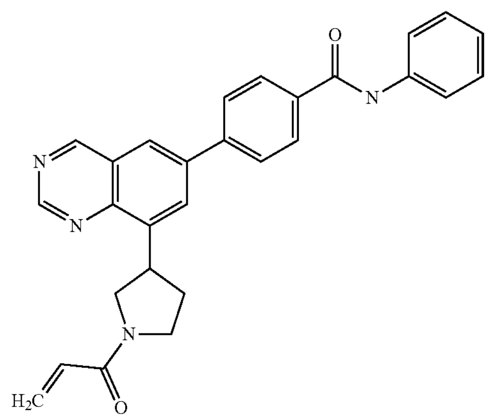 [SMILES: C=CC(=O)N1CCC(c2cc(-c3ccc(C(=O)Nc4ccccc4)cc3)cc3cncnc23)C1] | 4-(8-(1-acryloylpyrrolidin-3-yl)quinazolin-6-yl)-N-phenylbenzamide |
| C063 | 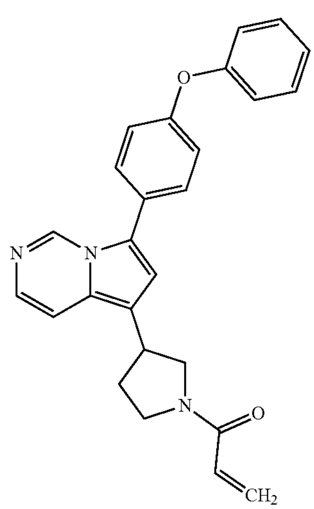 [SMILES: C=CC(=O)N1CCC(c2cc(-c3ccc(Oc4ccccc4)cc3)n3cnccc23)C1] | 1-(3-(7-(4-phenoxyphenyl)pyrrolo[1,2-c]pyrimidin-5-yl)pyrrolidin-1-yl)prop-2-en-1-one |

TABLE 1-continued

Illustrative Compounds of the Present Invention

| Compound No. | Structure | Name |
|---|---|---|
| C064 | 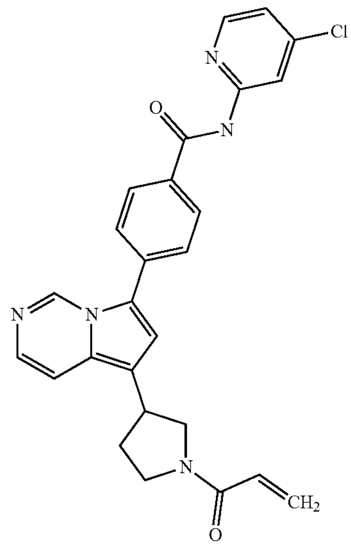 [SMILES: C=CC(=O)N1CCC(c2cc(-c3ccc(C(=O)Nc4cc(Cl)ccn4)cc3)n3cnccc23)C1] | 4-(5-(1-acryloylpyrrolidin-3-yl)pyrrolo[1,2-c]pyrimidin-7-yl)-N-(4-chloropyridin-2-yl)benzamide |
| C065 | 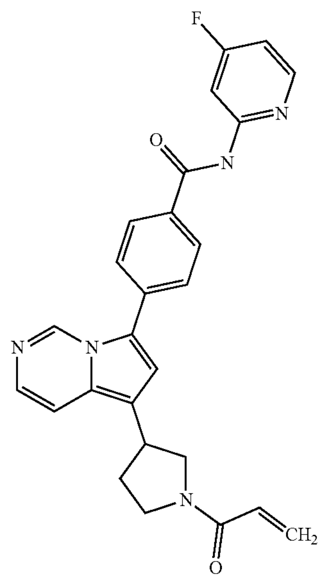 [SMILES: C=CC(=O)N1CCC(c2cc(-c3ccc(C(=O)Nc4cc(F)ccn4)cc3)n3cnccc23)C1] | 4-(5-(1-acryloylpyrrolidin-3-yl)pyrrolo[1,2-c]pyrimidin-7-yl)-N-(4-fluoropyridin-2-yl)benzamide |
| C066 | 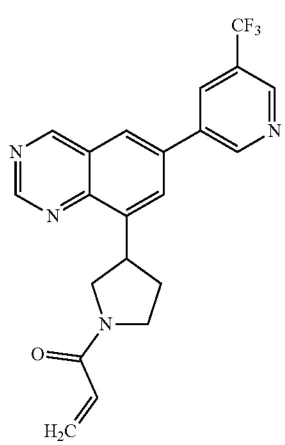 [SMILES: C=CC(=O)N1CCC(c2cc(-c3cncc(C(F)(F)F)c3)cc3cncnc23)C1] | 1-(3-(6-(5-(trifluoromethyl)pyridin-3-yl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C067 | 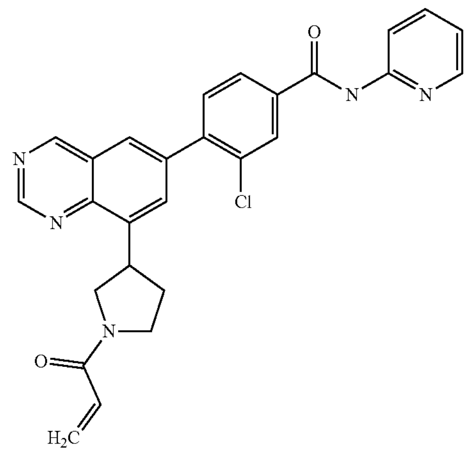 [SMILES: C=CC(=O)N1CCC(c2cc(-c3ccc(C(=O)Nc4ccccn4)cc3Cl)cc3cncnc23)C1] | 4-(8-(1-acryloylpyrrolidin-3-yl)quinazolin-6-yl)-3-chloro-N-(pyridin-2-yl)benzamide |
| C068 | 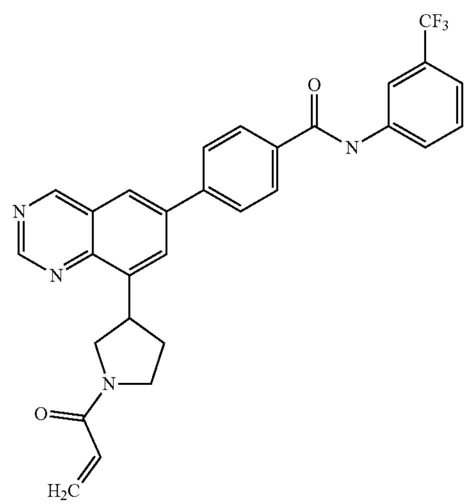 [SMILES: C=CC(=O)N1CCC(c2cc(-c3ccc(C(=O)Nc4cccc(C(F)(F)F)c4)cc3)cc3cncnc23)C1] | 4-(8-(1-acryloylpyrrolidin-3-yl)quinazolin-6-yl)-N-(3-(trifluoromethyl)phenyl)benzamide |
| C069 | 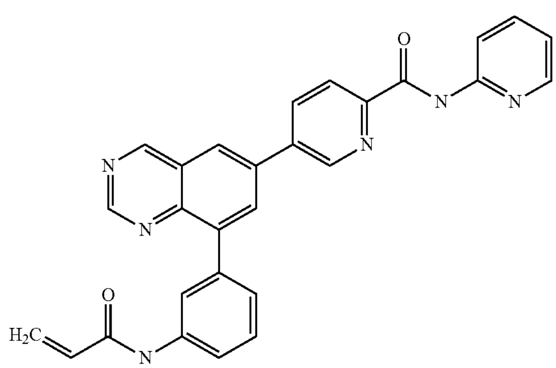 [SMILES: C=CC(=O)Nc1cccc(-c2cc(-c3ccc(C(=O)Nc4ccccn4)nc3)cc3cncnc23)c1] | 5-(8-(3-acrylamidophenyl)quinazolin-6-yl)-N-(pyridin-2-yl)picolinamide |

TABLE 1-continued

Illustrative Compounds of the Present Invention

| Compound No. | Structure | Name |
|---|---|---|
| C070 | 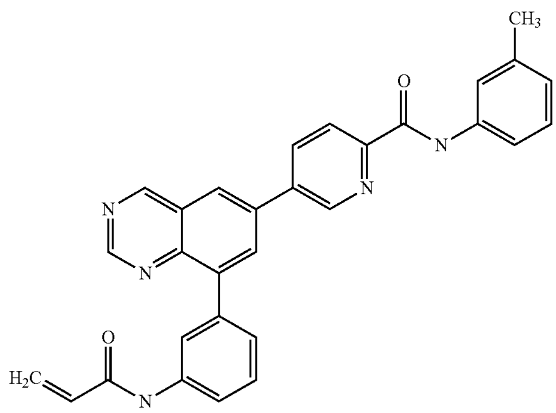 | 5-(8-(3-acrylamidophenyl)quinazolin-6-yl)-N-(m-tolyl)picolinamide |
| C071 | 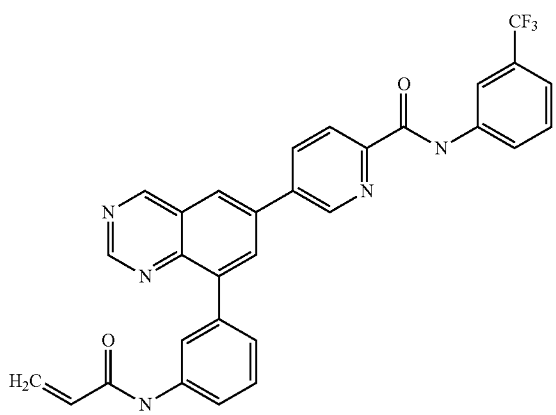 | 5-(8-(3-acrylamidophenyl)quinazolin-6-yl)-N-(3-trifluoromethyl)phenyl)picolinamide |
| C072 | 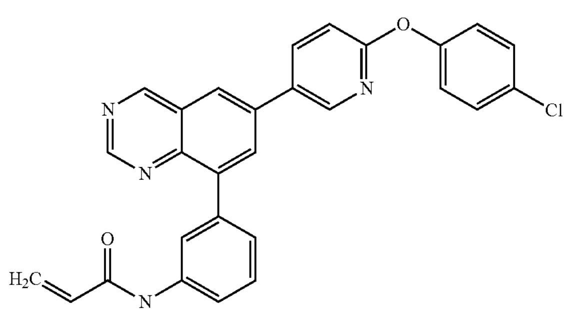 [SMILES: C=CC(=O)Nc1cccc(-c2cc(-c3ccc(Oc4ccc(Cl)cc4)nc3)cc3cncnc23)c1] | N-(3-(6-(6-(4-chlorophenoxy)pyridin-3-yl)quinazolin-8-yl)phenyl)acrylamide |
| C073 | 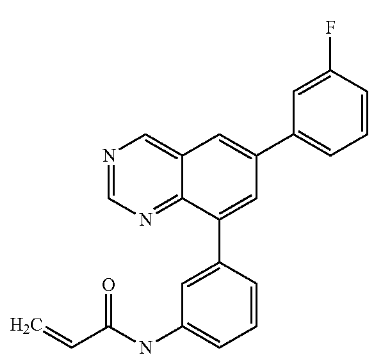 [SMILES: C=CC(=O)Nc1cccc(-c2cc(-c3cccc(F)c3)cc3cncnc23)c1] | N-(3-(6-(3-fluorophenyl)quinazolin-8-yl)phenyl)acrylamide |

TABLE 1-continued

Illustrative Compounds of the Present Invention

| Compound No. | Structure | Name |
|---|---|---|
| C074 | 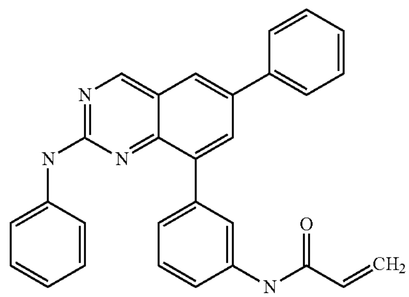 [SMILES: C=CC(=O)Nc1cccc(-c2cc(-c3ccccc3)cc3cnc(Nc4ccccc4)nc23)c1] | N-(3-(6-phenyl-2-(phenylamino)quinazolin-8-yl)phenyl)acrylamide |
| C075 | 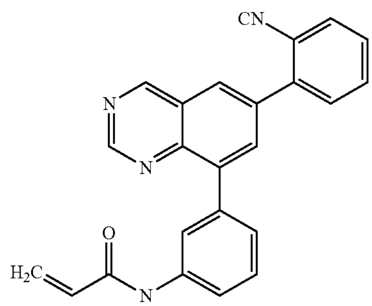 | N-(3-(6-(2-cyanophenyl)quinazolin-8-yl)phenyl)acrylamide |
| C076 | 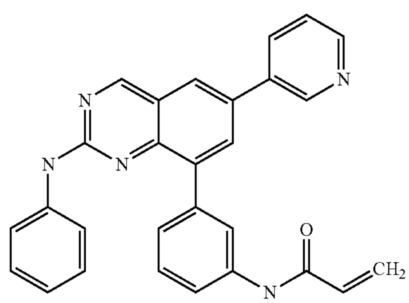 [SMILES: C=CC(=O)Nc1cccc(-c2cc(-c3cccnc3)cc3cnc(Nc4ccccc4)nc23)c1] | N-(3-(2-(phenylamino)-6-(pyridin-3-yl)quinazolin-8-yl)phenyl)acrylamide |
| C077 | 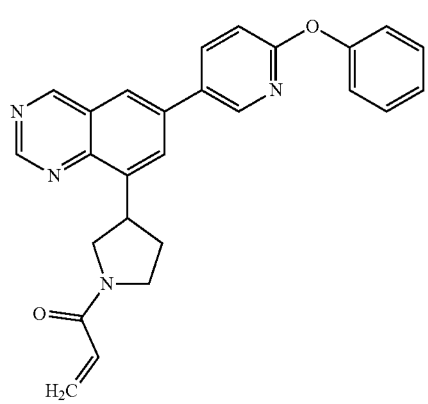 [SMILES: C=CC(=O)N1CCC(c2cc(-c3ccc(Oc4ccccc4)nc3)cc3cncnc23)C1] | 1-(3-(6-(6-phenoxypyridin-3-yl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C078 | 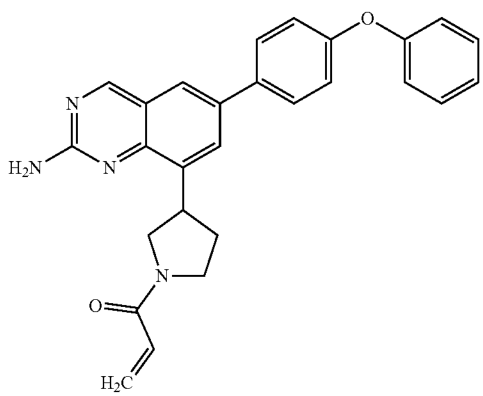 [SMILES: C=CC(=O)N1CCC(c2cc(-c3ccc(Oc4ccccc4)cc3)cc3cnc(N)nc23)C1] | 1-(3-(2-amino-6-(4-phenoxyphenyl)quinazolin-8-yl)pyrrolidin-1-yl)prop-2-en-1-one |
| C079 | 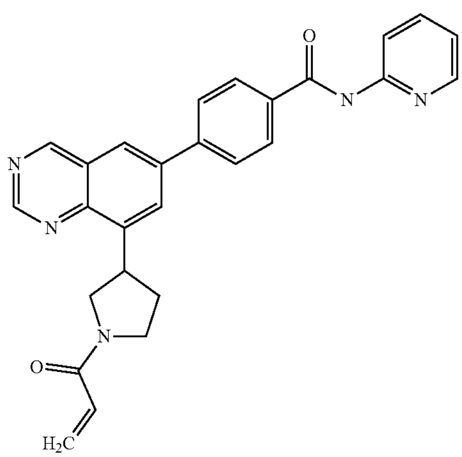 | 4-(8-(1-acryloylpyrrolidin-3-yl)quinazolin-6-yl)-N-(pyridin-2-yl)benzamide |
| C080 | 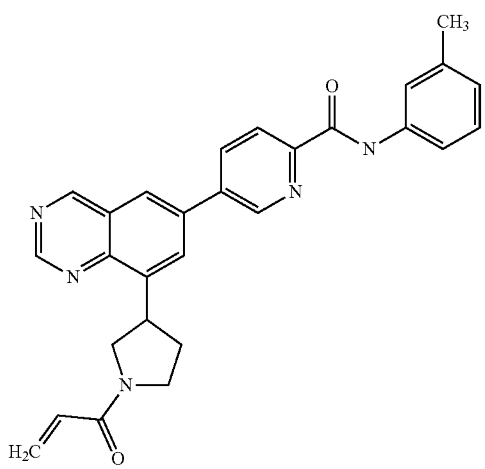 [SMILES: C=CC(=O)N1CCC(c2cc(-c3ccc(C(=O)Nc4cccc(C)c4)nc3)cc3cncnc23)C1] | 5-(8-(1-acryloylpyrrolidin-3-yl)quinazolin-6-yl)-N-(m-tolyl)picolinamide |

TABLE 1-continued

Illustrative Compounds of the Present Invention

| Compound No. | Structure | Name |
|---|---|---|
| C081 | 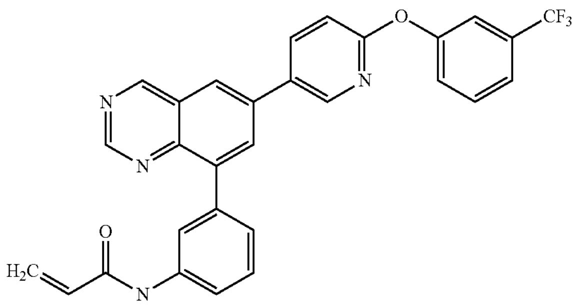 [SMILES: C=CC(=O)Nc1cccc(-c2cc(-c3ccc(Oc4cccc(C(F)(F)F)c4)nc3)cc3cncnc23)c1] | N-(3-(6-(6-(3-(trifluoromethyl)phenoxy)pyridin-3-yl)quinazolin-8-yl)phenyl)acrylamide |
| C082 | 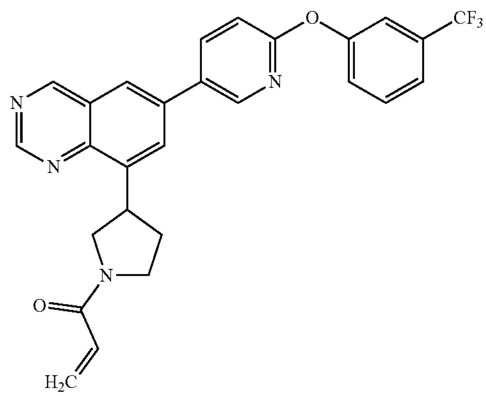 [SMILES: C=CC(=O)N1CCC(c2cc(-c3ccc(Oc4cccc(C(F)(F)F)c4)nc3)cc3cncnc23)C1] | 1-(3-(6-(6-(3-(trifluoromethyl)phenoxy)pyridin-3-yl)quinazolin-8-yl)pyrrolidin-1-yl)prop-2-en-1-one |
| C083 | 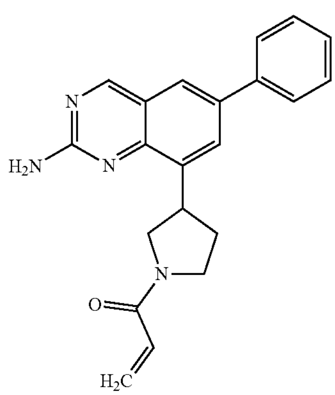 [SMILES: C=CC(=O)N1CCC(c2cc(-c3ccccc3)cc3cnc(N)nc23)C1] | 1-(3-(2-amino-6-phenylquinazolin-8-yl)pyrrolidin-1-yl)prop-2-en-1-one |
| C084 | 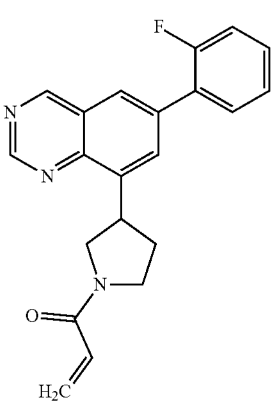 [SMILES: C=CC(=O)N1CCC(c2cc(-c3ccccc3F)cc3cncnc23)C1] | 1-(3-(6-(2-fluorophenyl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C085 | 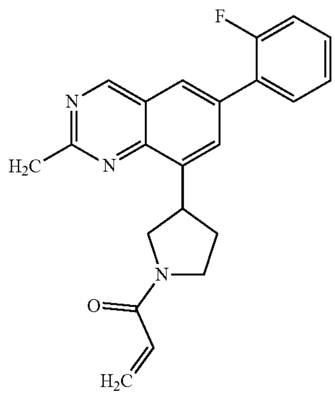 [SMILES: C=CC(=O)N1CCC(c2cc(-c3ccccc3F)cc3cnc(C)nc23)C1] | 1-(3-(2-amino-6-(2-fluorophenyl)quinazolin-8-yl)pyrrolidin-1-yl)prop-2-en-1-one |
| C086 | 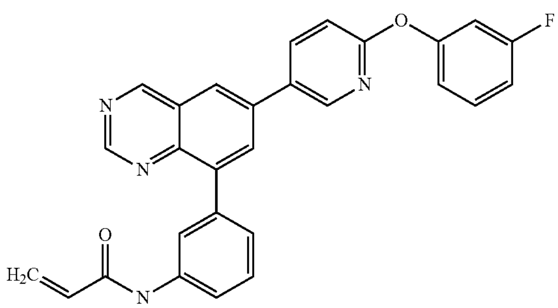 [SMILES: C=CC(=O)Nc1cccc(-c2cc(-c3ccc(Oc4cccc(F)c4)nc3)cc3cncnc23)c1] | N-(3-(6-(6-(3-fluorophenoxy)pyridin-3-yl)quinazolin-8-yl)phenyl)acrylamide |
| C087 | 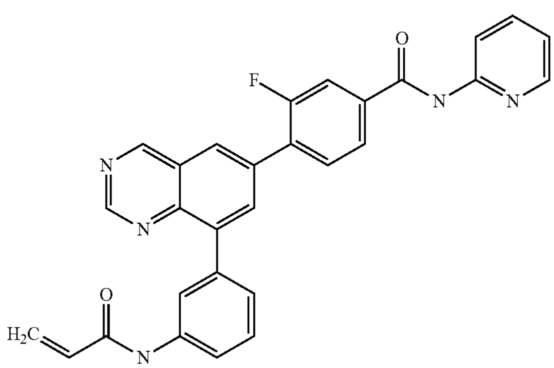 [SMILES: C=CC(=O)Nc1cccc(-c2cc(-c3ccc(C(=O)Nc4ccccn4)cc3F)cc3cncnc23)c1] | 4-(8-(3-Acrylamidophenyl)quinazolin-6-yl)-3-fluoro-N-(pyridin-2-yl)benzamide |
| C088 | 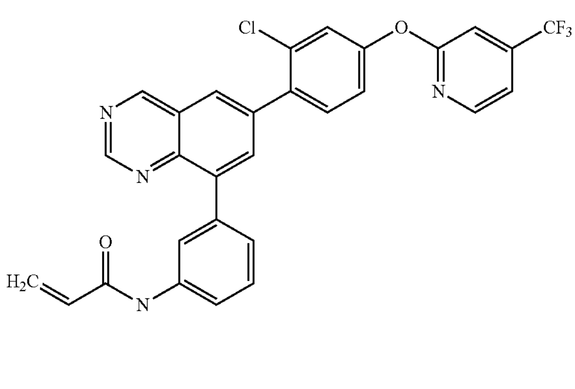 [SMILES: C=CC(=O)Nc1cccc(-c2cc(-c3ccc(Oc4cc(C(F)(F)F)ccn4)cc3Cl)cc3cncnc23)c1] | N-(3-(6-(2-chloro-4-((4-trifluoromethyl)pyridin-2-yl)oxy)phenyl)quinazolin-8-yl)phenyl)acrylamide |

TABLE 1-continued

Illustrative Compounds of the Present Invention

| Compound No. | Structure | Name |
|---|---|---|
| C089 | 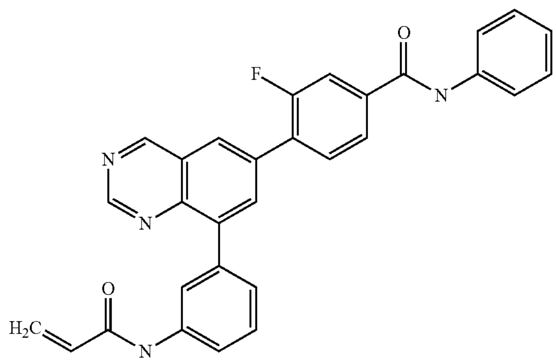 [SMILES: C=CC(=O)Nc1cccc(-c2cc(-c3ccc(C(=O)Nc4ccccc4)cc3F)cc3cncnc23)c1] | 4-(8-(3-Acrylamidophenyl)quinazolin-6-yl)-3-fluoro-N-phenylbenzamide |
| C090 | 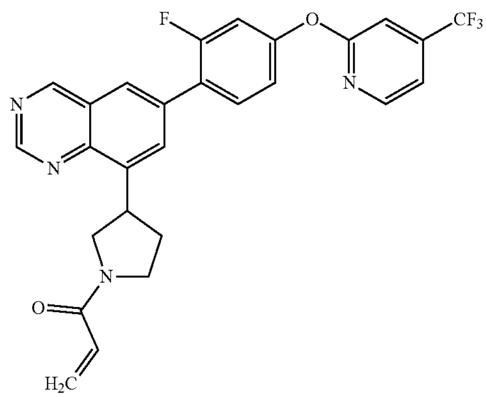 [SMILES: C=CC(=O)N1CCC(c2cc(-c3ccc(Oc4cc(C(F)(F)F)ccn4)cc3F)cc3cncnc23)C1] | 1-(3-(6-(2-Fluoro-4-((4-(trifluoromethyl)pyridin-2-yl)oxy)phenyl)quinazolin-8-yl)pyrrolidin-1-yl)prop-2-en-1-one |
| C091 | 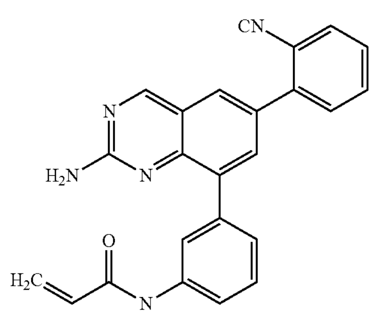 | N-(3-(2-amino-6-(2-cyanophenyl)quinazolin-8-yl)phenyl)acrylamide |
| C092 | 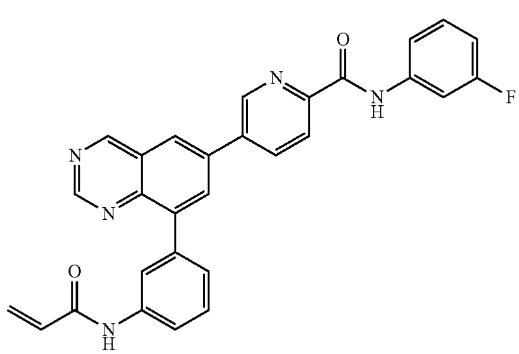 [SMILES: C=CC(=O)Nc1cccc(-c2cc(-c3ccc(C(=O)Nc4cccc(F)c4)nc3)cc3cncnc23)c1] | 5-(8-(3-acrylamidophenyl)quinazolin-6-yl)-N-(3-fluorophenyl)picolinamide |

TABLE 1-continued

Illustrative Compounds of the Present Invention

| Compound No. | Structure | Name |
|---|---|---|
| C093 | 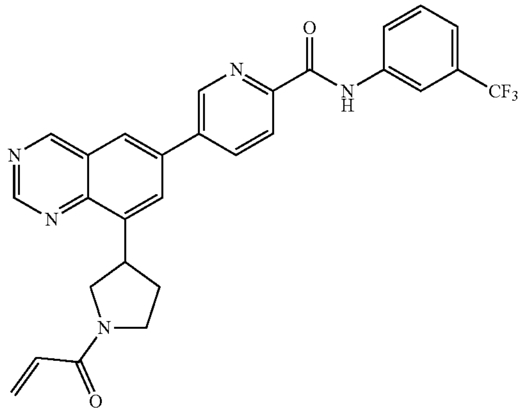 [SMILES: C=CC(=O)N1CCC(c2cc(-c3ccc(C(=O)Nc4cccc(C(F)(F)F)c4)nc3)cc3cncnc23)C1] | 5-(8-(1-acryloylpyrrolidin-3-yl)quinazolin-6-yl)-N-(3-(trifluoromethyl)phenyl)picolinamide |
| C094 | 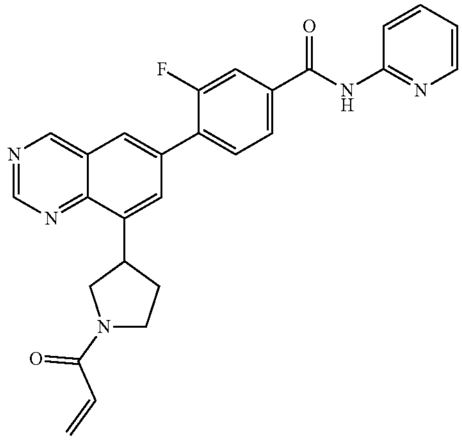 [SMILES: C=CC(=O)N1CCC(c2cc(-c3ccc(C(=O)Nc4ccccn4)cc3F)cc3cncnc23)C1] | 4-(8-(1-acryloylpyrrolidin-3-yl)quinazolin-6-yl)-3-fluoro-N-(pyridin-2-yl)benzamide |
| C095 | 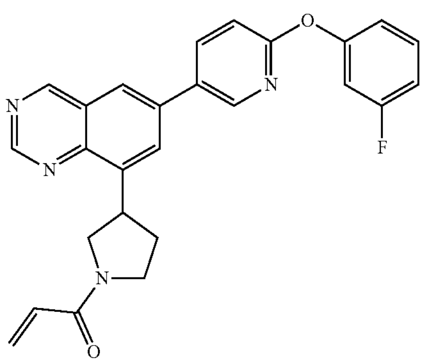 [SMILES: C=CC(=O)N1CCC(c2cc(-c3ccc(Oc4cccc(F)c4)nc3)cc3cncnc23)C1] | 1-(3-(6-(6-(3-fluorophenoxy)pyridin-3-yl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C096 | 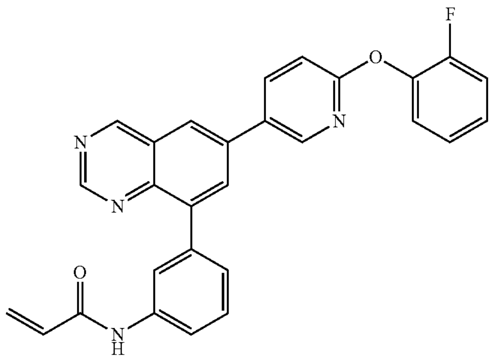 [SMILES: C=CC(=O)Nc1cccc(-c2cc(-c3ccc(Oc4ccccc4F)nc3)cc3cncnc23)c1] | N-(3-(6-(6-(2-fluorophenoxy)pyridin-3-yl)quinazolin-8-yl)phenyl)acrylamide |
| C097 | 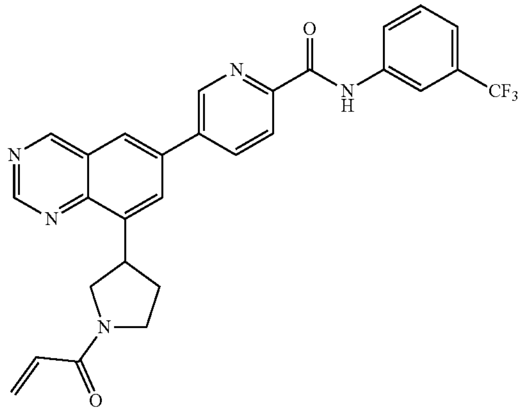 [SMILES: C=CC(=O)N1CCC(c2cc(-c3ccc(C(=O)Nc4cccc(C(F)(F)F)c4)nc3)cc3cncnc23)C1] | 5-(8-(1-acryloylpyrrolidin-3-yl)quinazolin-6-yl)-N-(3-fluorophenyl)picolinamide |
| C098 | 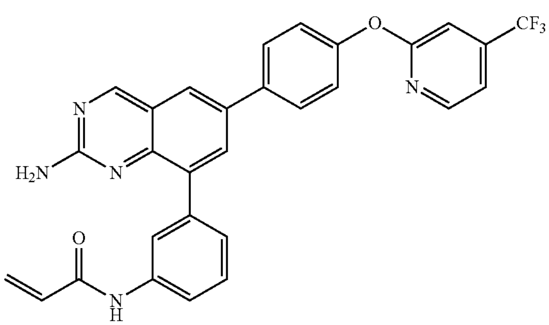 [SMILES: C=CC(=O)Nc1cccc(-c2cc(-c3ccc(Oc4cc(C(F)(F)F)ccn4)cc3)cc3cnc(N)nc23)c1] | N-(3-(2-amino-6-(4-((4-(trifluoromethyl)pyridin-2-yl)oxy)phenyl)quinazolin-8-yl)phenyl)acrylamide |
| C099 | 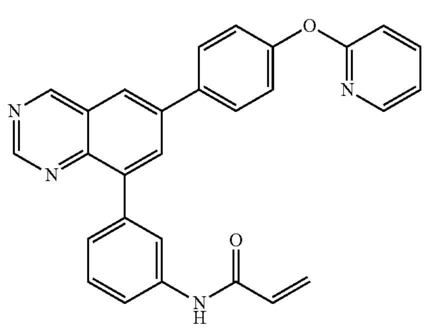 [SMILES: C=CC(=O)Nc1cccc(-c2cc(-c3ccc(Oc4ccccn4)cc3)cc3cncnc23)c1] | N-(3-(6-(4-(pyridin-2-yloxy)phenyl)quinazolin-8-yl)phenyl)acrylamide |

TABLE 1-continued

Illustrative Compounds of the Present Invention

| Compound No. | Structure | Name |
|---|---|---|
| C100 | 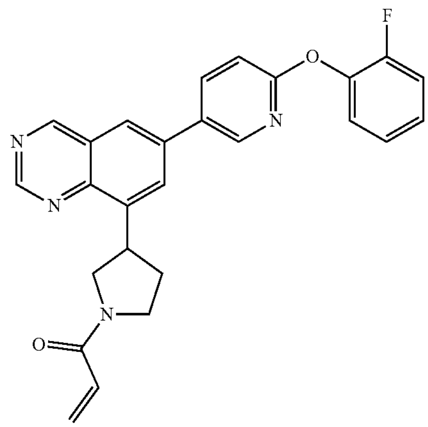 [SMILES: C=CC(=O)N1CCC(c2cc(-c3ccc(Oc4ccccc4F)nc3)cc3cncnc23)C1] | 1-(3-(6-(6-(2-fluorophenoxy)pyridin-3-yl)quinazolin-8-yl)pyrrolidin-1-yl)prop-2-en-1-one |
| C101 | 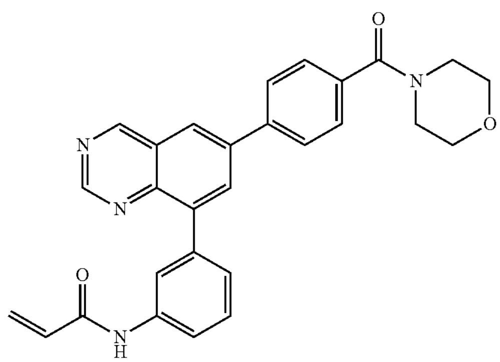 [SMILES: C=CC(=O)Nc1cccc(-c2cc(-c3ccc(C(=O)N4CCOCC4)cc3)cc3cncnc23)c1] | N-(3-(6-(4-morpholine-4-carbonyl)phenyl)quinazolin-8-yl)phenyl)acrylamide |
| C102 | 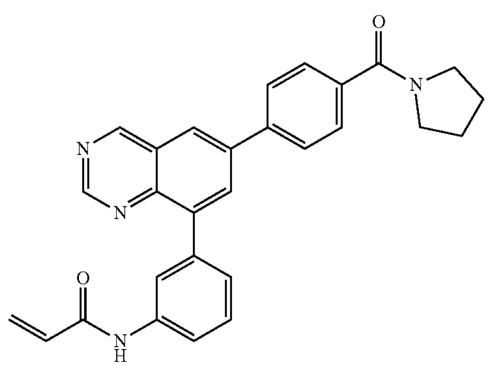 [SMILES: C=CC(=O)Nc1cccc(-c2cc(-c3ccc(C(=O)N4CCCC4)cc3)cc3cncnc23)c1] | N-(3-(6-(4-pyrrolidine-1-carbonyl)phenyl)quinazolin-8-yl)phenyl)acrylamide |
| C103 | 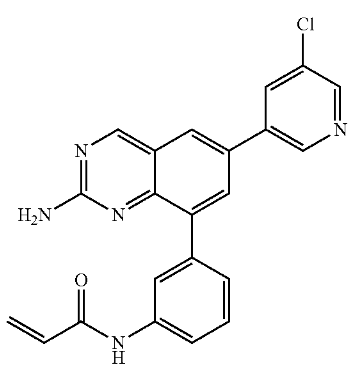 [SMILES: C=CC(=O)Nc1cccc(-c2cc(-c3cncc(Cl)c3)cc3cnc(N)nc23)c1] | N-(3-(2-amino-6-(5-chloropyridin-3-yl)-quinazolin-8-yl)phenyl)acrylamide |

TABLE 1-continued

Illustrative Compounds of the Present Invention

| Compound No. | Structure | Name |
|---|---|---|
| C104 | 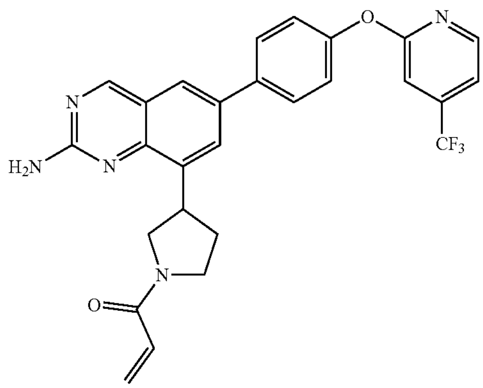 [SMILES: C=CC(=O)N1CCC(c2cc(-c3ccc(Oc4cc(C(F)(F)F)ccn4)cc3)cc3cnc(N)nc23)C1] | 1-(3-(2-amino-6-(4-((4-(trifluoromethyl)pyridin-2-yl)oxy)phenyl)quinazolin-8-yl)pyrrolidin-1-yl)prop-2-en-1-one |
| C105 | 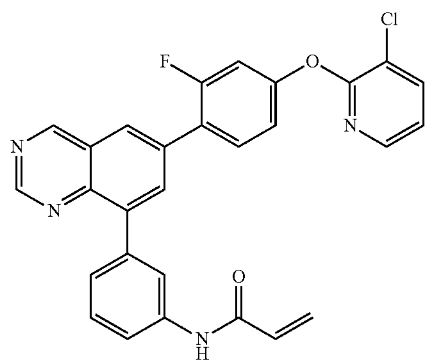 [SMILES: C=CC(=O)Nc1cccc(-c2cc(-c3ccc(Oc4ncccc4Cl)cc3F)cc3cncnc23)c1] | N-(3-(6-(2-fluoro-4-((3-fluoropyridin-2-yl)oxy)phenyl)quinazolin-8-yl)phenyl)acrylamide |
| C106 | 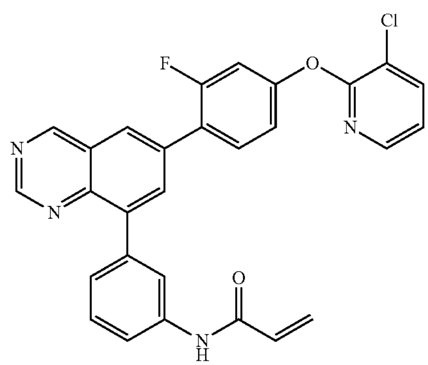 [SMILES: C=CC(=O)Nc1cccc(-c2cc(-c3ccc(Oc4ncccc4Cl)cc3F)cc3cncnc23)c1] | N-(3-(6-(4-((3-chloropyridin-2-yl)oxy)-2-fluorophenyl)quinazolin-8-yl)phenyl)acrylamide |
| C107 | 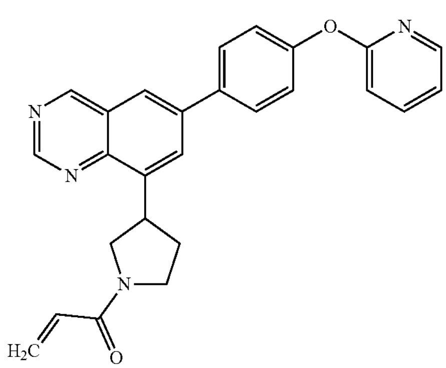 [SMILES: C=CC(=O)N1CCC(c2cc(-c3ccc(Oc4ccccn4)cc3)cc3cncnc23)C1] | 1-(3-(6-(4-(pyridin-2-yloxy)phenyl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C108 | 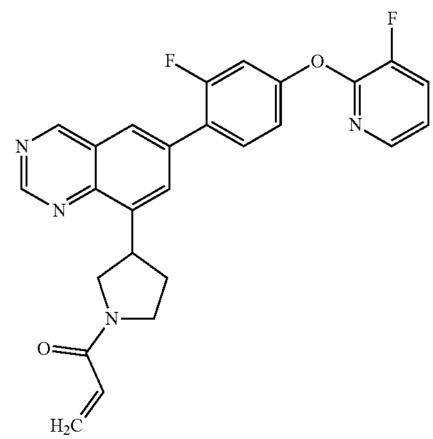 [SMILES: C=CC(=O)N1CCC(c2cc(-c3ccc(Oc4ncccc4F)cc3F)cc3cncnc23)C1] | 1-(3-(6-(2-fluoro-4-((3-fluoropyridin-2-yl)oxy)phenyl)quinazolin-8-yl)pyrrolidin-1-yl)prop-2-en-1-one |
| C109 | 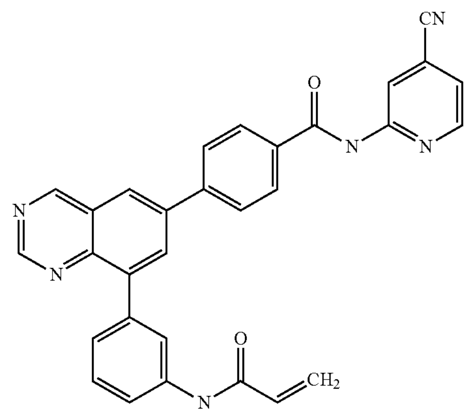 [SMILES: C=CC(=O)Nc1cccc(-c2cc(-c3ccc(C(=O)Nc4cc(C#N)ccn4)cc3)cc3cncnc23)c1] | 4-(8-(3-acrylamidophenyl)quinazolin-6-yl)-N-(4-cyanopyridin-2-yl)benzamide |
| C110 | 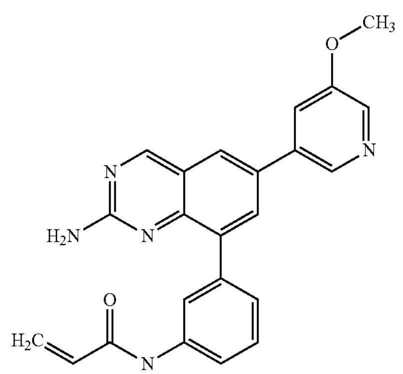 [SMILES: C=CC(=O)Nc1cccc(-c2cc(-c3cncc(OC)c3)cc3cnc(N)nc23)c1] | N-(3-(2-amino-6-(5-methoxypyridin-3-yl)quinazolin-8-yl)phenyl)acrylamide |
| C111 | 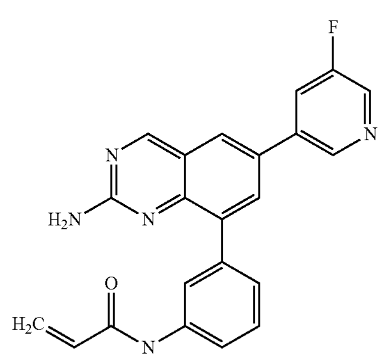 [SMILES: C=CC(=O)Nc1cccc(-c2cc(-c3cncc(F)c3)cc3cnc(N)nc23)c1] | N-(3-(2-amino-6-(5-fluoropyridin-3-yl)quinazolin-8-yl)phenyl)acrylamide |

TABLE 1-continued

Illustrative Compounds of the Present Invention

| Compound No. | Structure | Name |
|---|---|---|
| C112 | 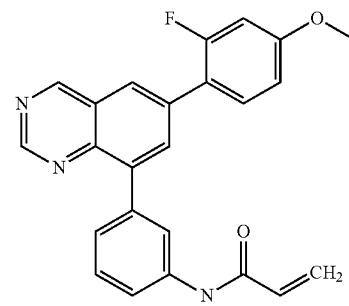 | N-(3-(6-(2-fluoro-4-(pyridin-2-yloxy)phenyl)quinazolin-8-yl)phenyl)acrylamide |
| C113 | 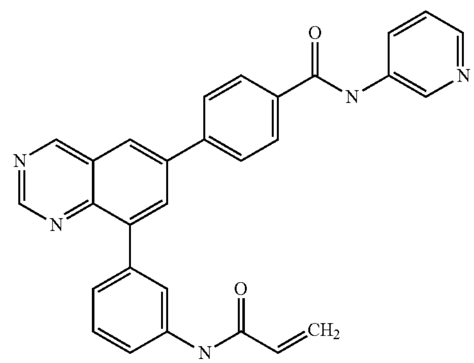 [SMILES: C=CC(=O)Nc1cccc(-c2cc(-c3ccc(C(=O)Nc4cccnc4)cc3)cc3cncnc23)c1] | 4-(8-(3-acrylamidophenyl)quinazolin-6-yl)-N-(pyridin-3-yl)benzamide |
| C114 | 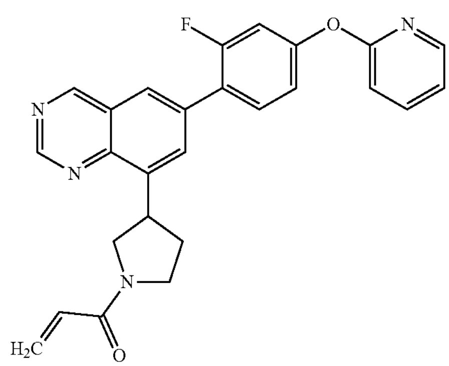 [SMILES: C=CC(=O)N1CCC(c2cc(-c3ccc(Oc4ccccn4)cc3F)cc3cncnc23)C1] | 1-(3-(6-(2-fluoro-4-(pyridin-2-yloxy)phenyl)quinazolin-8-yl)pyrrolidin-1-yl)prop-2-en-1-one |
| C115 | 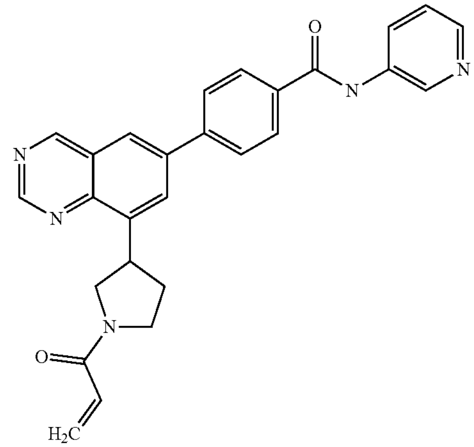 [SMILES: C=CC(=O)N1CCC(c2cc(-c3ccc(C(=O)Nc4cccnc4)cc3)cc3cncnc23)C1] | 4-(8-(1-acryloylpyrrolidin-3-yl)quinazolin-6-yl)-N-(pyridin-3-yl)benzamide |

TABLE 1-continued
Illustrative Compounds of the Present Invention
| Compound No. | Structure | Name |
|---|---|---|
| C116 | 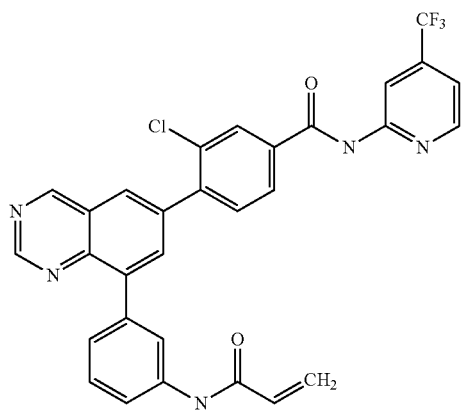 | 4-(8-(3-acrylamidophenyl)quinazolin-6-yl)-3-chloro-N-(4-(trifluoromethyl)pyridin-2-yl)benzamide |
| C117 | 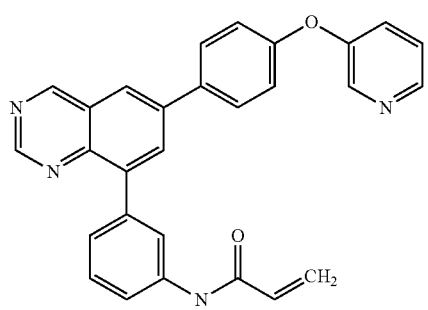 [SMILES: C=CC(=O)Nc1cccc(-c2cc(-c3ccc(Oc4cccnc4)cc3)cc3cncnc23)c1] | N-(3-(6-(4-(pyridin-3-yloxy)phenyl)quinazolin-8-yl)phenyl)acrylamide |
| C118 | 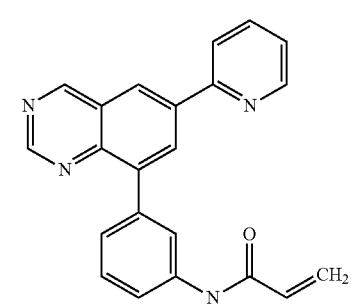 | N-(3-(6-(pyridin-2-yl)quinazolin-8-yl)phenyl)acrylamide |
| C119 | 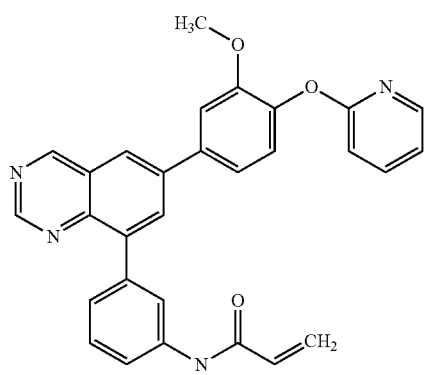 [SMILES: C=CC(=O)Nc1cccc(-c2cc(-c3ccc(Oc4ccccn4)c(OC)c3)cc3cncnc23)c1] | N-(3-(6-(3-methoxy-4-(pyridin-2-yloxy)phenyl)quinazolin-8-yl)phenyl)acrylamide |

TABLE 1-continued

Illustrative Compounds of the Present Invention

| Compound No. | Structure | Name |
|---|---|---|
| C120 | 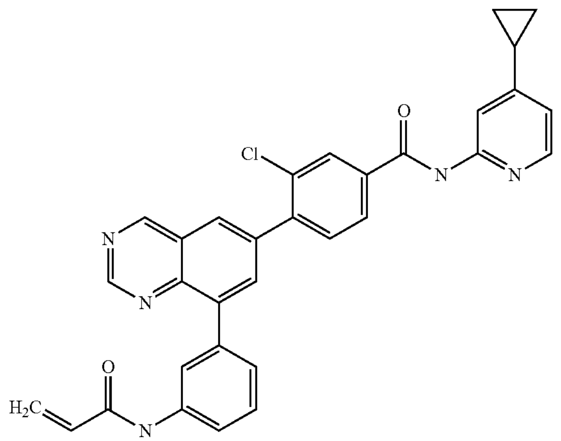 [SMILES: C=CC(=O)Nc1cccc(-c2cc(-c3ccc(C(=O)Nc4cc(C5CC5)ccn4)cc3Cl)cc3cncnc23)c1] | 4-(8-(3-acrylamidophenyl)quinazolin-6-yl)-3-chloro-N-(4-cyclopropylpyridin-2-yl)benzamide |
| C121 | 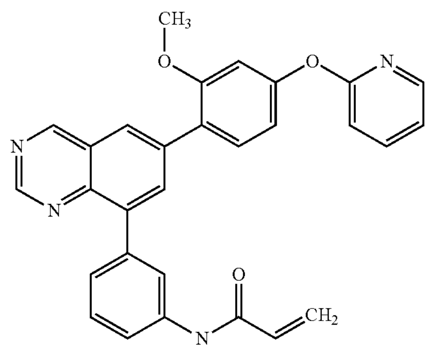 [SMILES: C=CC(=O)Nc1cccc(-c2cc(-c3ccc(Oc4ccccn4)cc3OC)cc3cncnc23)c1] | N-(3-(6-(2-methoxy-4-(pyridin-2-yloxy)phenyl)quinazolin-8-yl)phenyl)acrylamide |
| C122 | 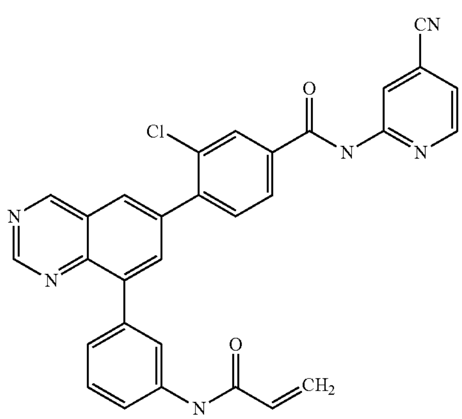 [SMILES: C=CC(=O)Nc1cccc(-c2cc(-c3ccc(C(=O)Nc4cc(C#N)ccn4)cc3Cl)cc3cncnc23)c1] | 4-(8-(3-acrylamidophenyl)quinazolin-6-yl)-3-chloro-N-(4-cyanopyridin-2-yl)benzamide |

TABLE 1-continued

Illustrative Compounds of the Present Invention

| Compound No. | Structure | Name |
|---|---|---|
| C123 | 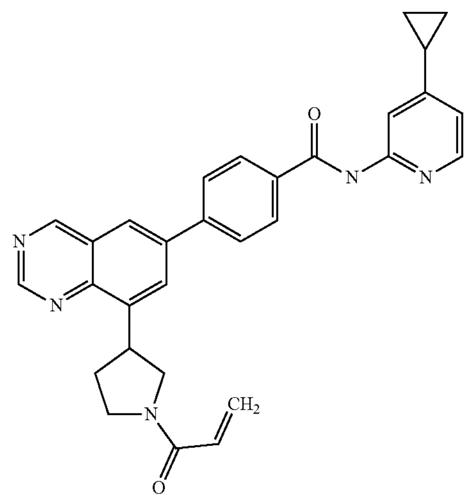 [SMILES: C=CC(=O)N1CCC(c2cc(-c3ccc(C(=O)Nc4cc(C5CC5)ccn4)cc3)cc3cncnc23)C1] | 4-(8-(1-acryloylpyrrolidin-3-yl)quinazolin-6-yl)-N-(4-cyclopropylpyridin-2-yl)benzamide |
| C124 | 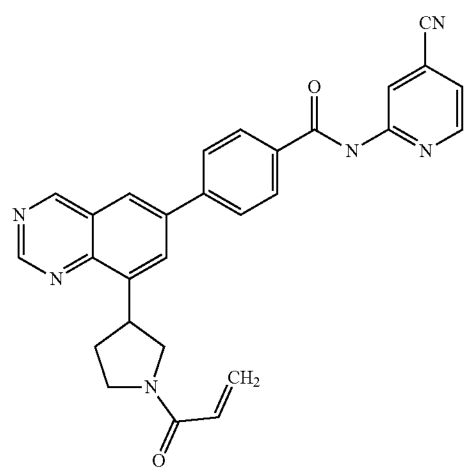 [SMILES: C=CC(=O)N1CCC(c2cc(-c3ccc(C(=O)Nc4cc(C#N)ccn4)cc3)cc3cncnc23)C1] | 4-(8-(1-acryloylpyrrolidin-3-yl)quinazolin-6-yl)-N-(4-cyanopyridin-2-yl)benzamide |
| C125 | 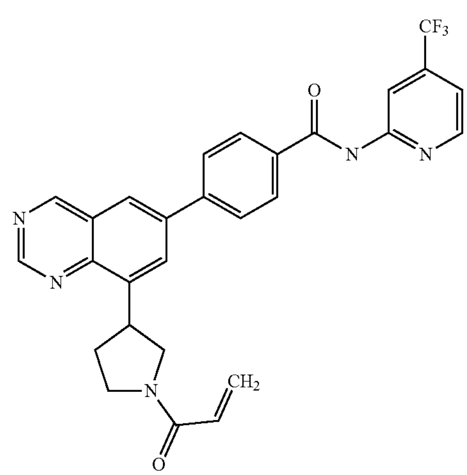 | 4-(8-(1-acryloylpyrrolidin-3-yl)quinazolin-6-yl)-N-(4-(trifluoromethyl)pyridin-2-yl)benzamide |

TABLE 1-continued

Illustrative Compounds of the Present Invention

| Compound No. | Structure | Name |
|---|---|---|
| C126 | 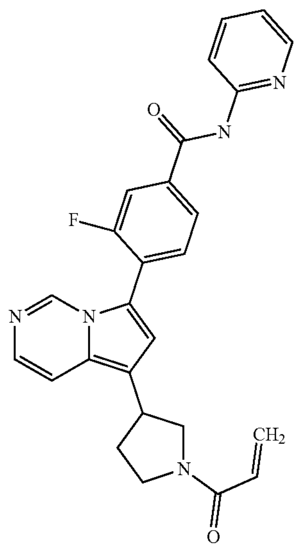 [SMILES: C=CC(=O)N1CCC(c2cc(-c3ccc(C(=O)Nc4ccccn4)cc3F)n3cnccc23)C1] | 4-(5-(1-acryloylpyrrolidin-3-yl)pyrrolo[1,2-c]pyrimidin-7-yl)-3-fluoro-N-(pyridin-2-yl)benzamide |
| C127 | 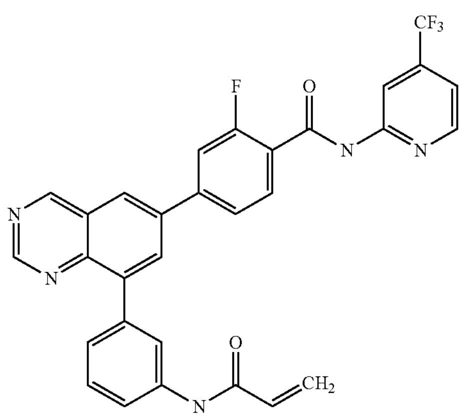 [SMILES: C=CC(=O)Nc1cccc(-c2cc(-c3ccc(C(=O)Nc4cc(C(F)(F)F)ccn4)c(F)c3)cc3cncnc23)c1] | 4-(8-(3-acrylamidophenyl)quinazolin-6-yl)-2-fluoro-N-(4-(trifluoromethyl)pyridin-2-yl)benzamide |
| C128 | 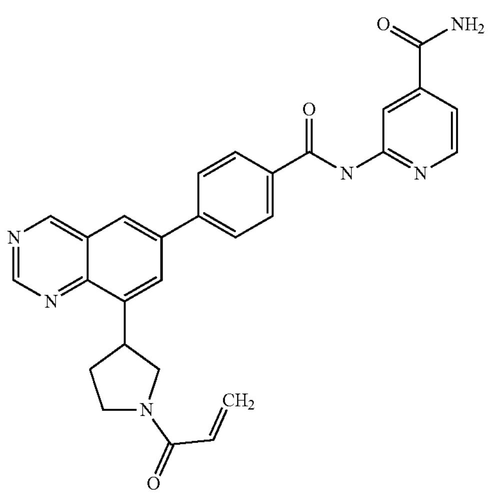 [SMILES: C=CC(=O)N1CCC(c2cc(-c3ccc(C(=O)Nc4cc(C(N)=O)ccn4)cc3)cc3cncnc23)C1] | 2-(4-(8-(1-acryloylpyrrolidin-3-yl)quinazolin-6-yl)benzamido)isonicotinamide |

TABLE 1-continued

Illustrative Compounds of the Present Invention

| Compound No. | Structure | Name |
|---|---|---|
| C129 | 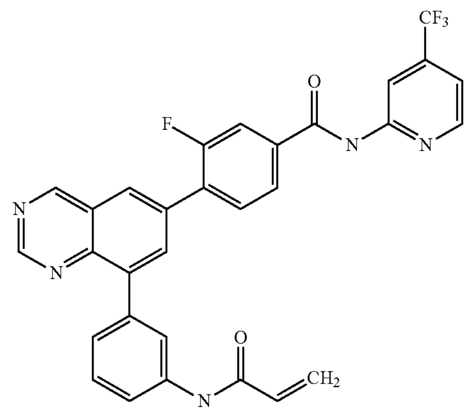 | 4-(8-(3-acrylamidophenyl)quinazolin-6-yl)-3-fluoro-N-(4-(trifluoromethyl)pyridin-2-yl)benzamide |
| C130 | 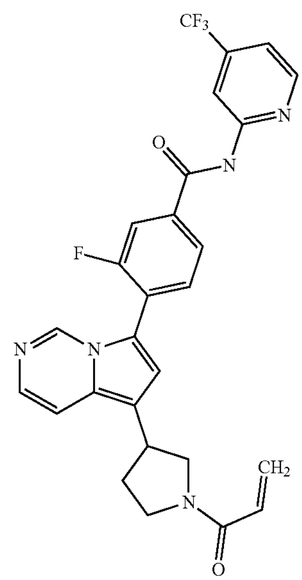 [SMILES: C=CC(=O)N1CCC(c2cc(-c3ccc(C(=O)Nc4cc(C(F)(F)F)ccn4)cc3F)n3cnccc23)C1] | 4-(5-(1-acryloylpyrrolidin-3-yl)pyrrolo[1,2-c]pyrimidin-7-yl)-3-fluoro-N-(4-(trifluoromethyl)pyridin-2-yl)benzamide |
| C131 | 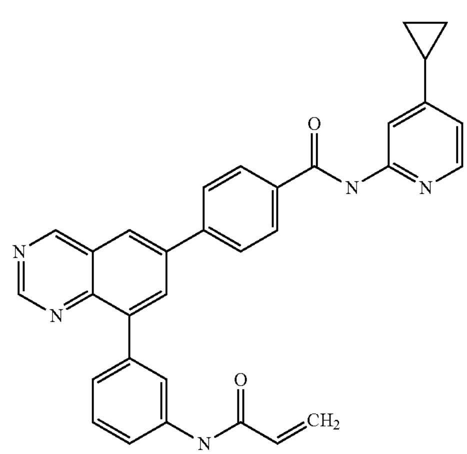 [SMILES: C=CC(=O)Nc1cccc(-c2cc(-c3ccc(C(=O)Nc4cc(C5CC5)ccn4)cc3)cc3cncnc23)c1] | 4-(8-(3-acrylamidophenyl)quinazolin-6-yl)-N-(4-cyclopropylpyridin-2-yl)benzamide |

TABLE 1-continued

Illustrative Compounds of the Present Invention

| Compound No. | Name |
|---|---|
| C132 | 4-(8-(3-acrylamidophenyl)quinazolin-6-yl)-2-fluoro-N-(pyridin-2-yl)benzamide |
| C133 | 1-(3-(6-(2-methoxy-4-(pyridin-2-yloxy)phenyl)quinazolin-8-yl)pyrrolidin-1-yl)prop-2-en-1-one |
| C134 | 2-(4-(8-(3-acrylamidophenyl)quinazolin-6-yl)-3-chlorobenzamido)isonicotinamide |
| C135 | N-(3-(6-(3-fluoro-4-(pyridin-2-yloxy)phenyl)quinazolin-8-yl)phenyl)acrylamide |

TABLE 1-continued

Illustrative Compounds of the Present Invention

| Compound No. | Structure | Name |
|---|---|---|
| C136 | 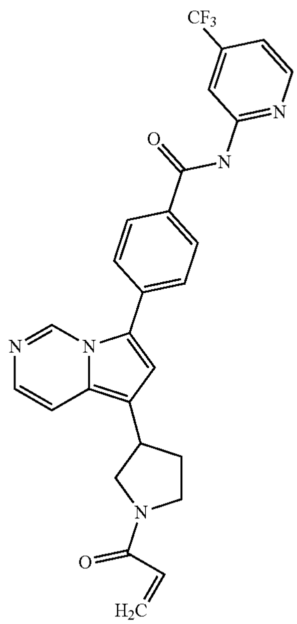 [SMILES: C=CC(=O)N1CCC(c2cc(-c3ccc(C(=O)Nc4cc(C(F)(F)F)ccn4)cc3)n3cnccc23)C1] | 4-(5-(1-acryloylpyrrolidin-3-yl)pyrrolo[1,2-c]pyrimidin-7-yl)-N-(4-(trifluoromethyl)pyridin-2-yl)benzamide |
| C137 | 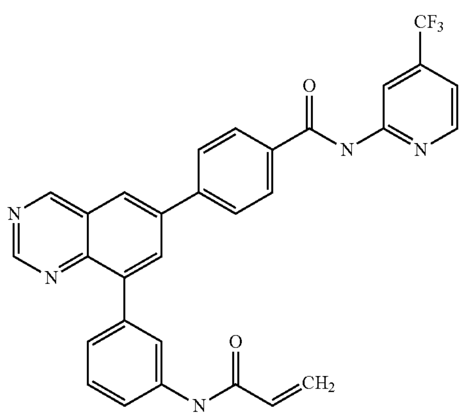 | 4-(8-(3-acrylamidophenyl)quinazolin-6-yl)-N-(4-(trifluoromethyl)pyridin-2-yl)benzamide |
| C138 | 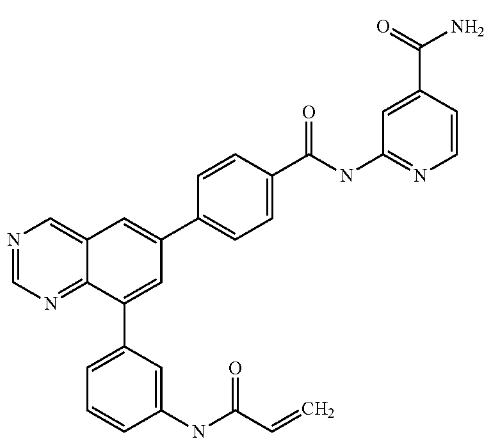 [SMILES: C=CC(=O)Nc1cccc(-c2cc(-c3ccc(C(=O)Nc4cc(C(N)=O)ccn4)cc3)cc3cncnc23)c1] | 2-(4-(8-(3-acrylamidophenyl)quinazolin-6-yl)benzamido)isonicotinamide |

TABLE 1-continued
Illustrative Compounds of the Present Invention
| Compound No. | Structure | Name |
|---|---|---|
| C139 | 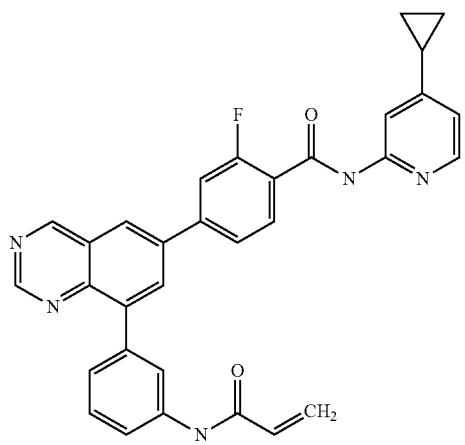 [SMILES: C=CC(=O)Nc1cccc(-c2cc(-c3ccc(C(=O)Nc4cc(C5CC5)ccn4)c(F)c3)cc3cncnc23)c1] | 4-(8-(3-acrylamidophenyl)quinazolin-6-yl)-N-(4-cyclopropylpyridin-2-yl)-2-fluorobenzamide |
| C140 | 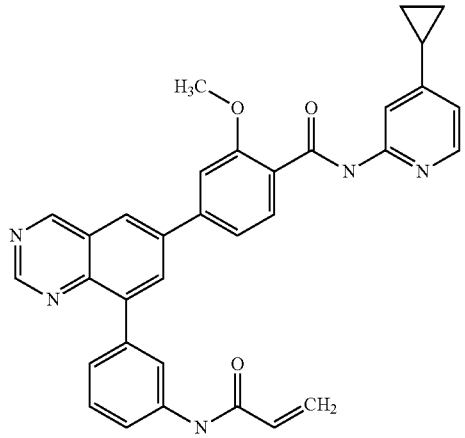 [SMILES: C=CC(=O)Nc1cccc(-c2cc(-c3ccc(C(=O)Nc4cc(C5CC5)ccn4)c(OC)c3)cc3cncnc23)c1] | 4-(8-(3-acrylamidophenyl)quinazolin-6-yl)-N-(4-cyclopropylpyridin-2-yl)-2-methoxybenzamide |
| C141 | 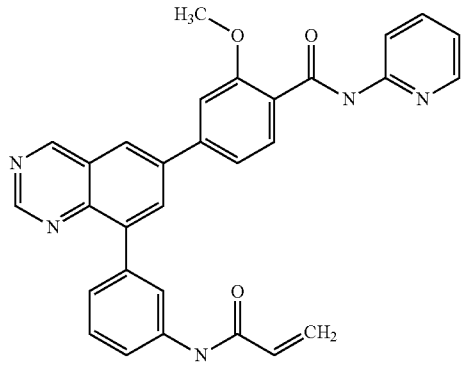 [SMILES: C=CC(=O)Nc1cccc(-c2cc(-c3ccc(C(=O)Nc4ccccn4)c(OC)c3)cc3cncnc23)c1] | 4-(8-(3-acrylamidophenyl)quinazolin-6-yl)-2-methoxy-N-(pyridin-2-yl)benzamide |

TABLE 1-continued

Illustrative Compounds of the Present Invention

| Compound No. | Structure | Name |
|---|---|---|
| C142 | 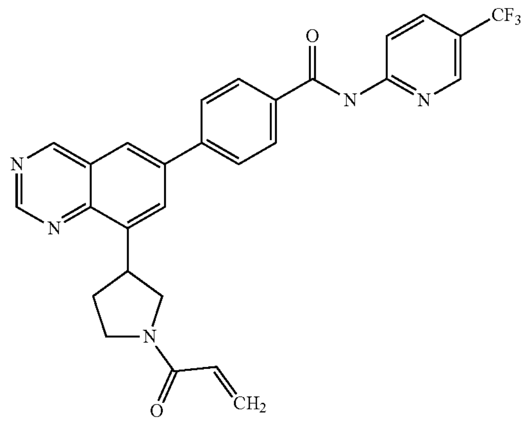 [SMILES: C=CC(=O)N1CCC(c2cc(-c3ccc(C(=O)Nc4ccc(C(F)(F)F)cn4)cc3)cc3cncnc23)C1] | 4-(8-(1-acryloylpyrrolidin-3-yl)quinazolin-6-yl)-N-(5-(trifluoromethyl)pyridin-2-yl)benzamide |
| C143 | 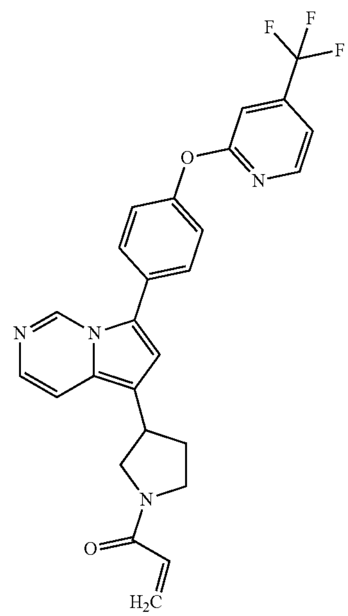 [SMILES: C=CC(=O)N1CCC(c2cc(-c3ccc(Oc4cc(C(F)(F)F)ccn4)cc3)n3cnccc23)C1] | 1-(3-(7-(4-((4-(trifluoromethyl)pyridin-2-yl)oxy)phenyl)pyrrolo[1,2-c]pyrimidin-5-yl)pyrrolidin-1-yl)prop-2-en-1-one |
| C144 | 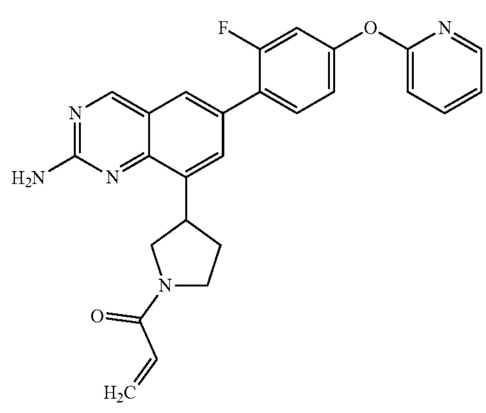 [SMILES: C=CC(=O)N1CCC(c2cc(-c3ccc(Oc4ccccn4)cc3F)cc3cnc(N)nc23)C1] | 1-(3-(2-amino-6-(2-fluoro-4-(pyridin-2-yloxy)phenyl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C145 | 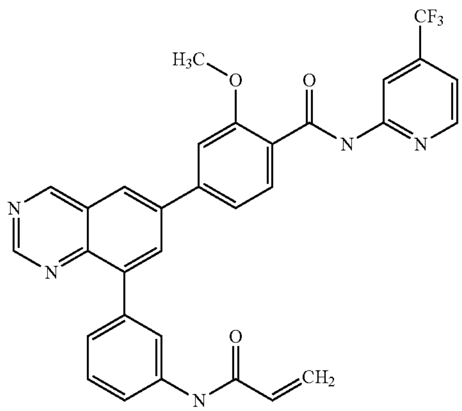 [SMILES: C=CC(=O)Nc1cccc(-c2cc(-c3ccc(C(=O)Nc4cc(C(F)(F)F)ccn4)c(OC)c3)cc3cncnc23)c1] | 4-(8-(3-acrylamidophenyl)quinazolin-6-yl)-2-methoxy-N-(4-(trifluoromethyl)pyridin-2-yl)benzamide |
| C146 | 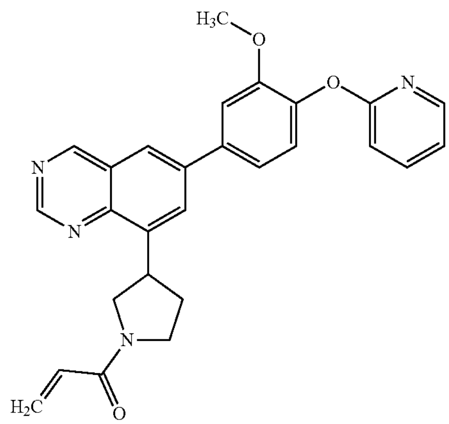 [SMILES: C=CC(=O)N1CCC(c2cc(-c3ccc(Oc4ccccn4)c(OC)c3)cc3cncnc23)C1] | 1-(3-(6-(3-methoxy-4-(pyridin-2-yloxy)phenyl)quinazolin-8-yl)pyrrolidin-1-yl)prop-2-en-1-one |
| C147 | 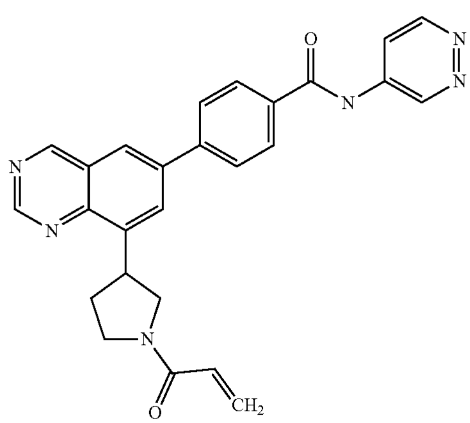 | 4-(8-(1-acryloylpyrrolidin-3-yl)quinazolin-6-yl)-N-(pyridazin-4-yl)benzamide |

TABLE 1-continued
Illustrative Compounds of the Present Invention
| Compound No. | Structure | Name |
|---|---|---|
| C148 | 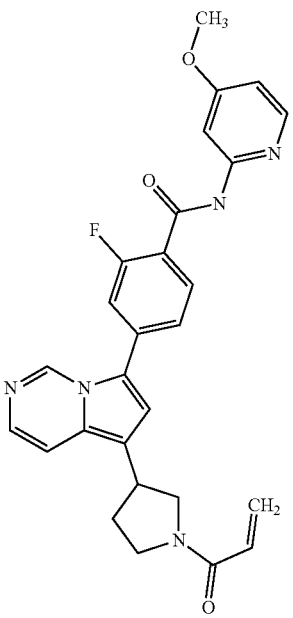 [SMILES: C=CC(=O)N1CCC(c2cc(-c3ccc(C(=O)Nc4cc(OC)ccn4)c(F)c3)n3cnccc23)C1] | 4-(5-(1-acryloylpyrrolidin-3-yl)pyrrolo[1,2-c]pyrimidin-7-yl)-2-fluoro-N-(4-methoxypyridin-2-yl)benzamide |
| C149 | 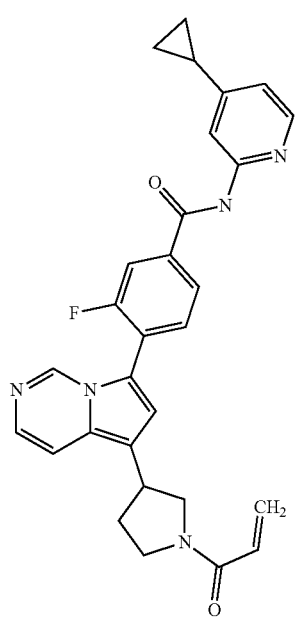 [SMILES: C=CC(=O)N1CCC(c2cc(-c3ccc(C(=O)Nc4cc(C5CC5)ccn4)cc3F)n3cnccc23)C1] | 4-(5-(1-acryloylpyrrolidin-3-yl)pyrrolo[1,2-c]pyrimidin-7-yl)-N-(4-cyclopropylpyridin-2-yl)-3-fluorobenzamide |

TABLE 1-continued
Illustrative Compounds of the Present Invention
| Compound No. | Structure | Name |
|---|---|---|
| C150 | 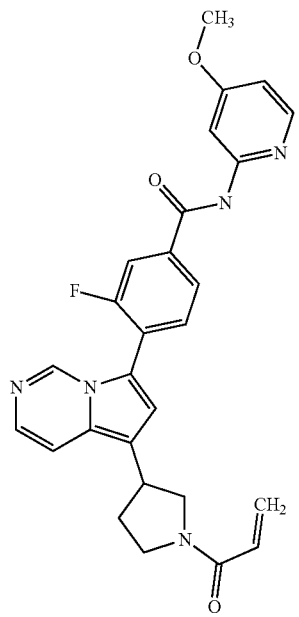 [SMILES: C=CC(=O)N1CCC(c2cc(-c3ccc(C(=O)Nc4cc(OC)ccn4)cc3F)n3cnccc23)C1] | 4-(5-(1-acryloylpyrrolidin-3-yl)pyrrolo[1,2-c]pyrimidin-7-yl)-3-fluoro-N-(4-methoxypyridin-2-yl)benzamide |
| C151 | 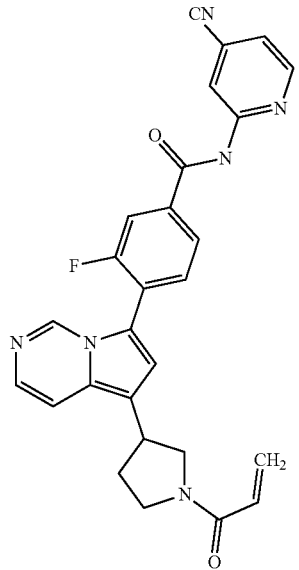 [SMILES: C=CC(=O)N1CCC(c2cc(-c3ccc(C(=O)Nc4cc(C#N)ccn4)cc3F)n3cnccc23)C1] | 4-(5-(1-acryloylpyrrolidin-3-yl)pyrrolo[1,2-c]pyrimidin-7-yl)-N-(4-cyanopyridin-2-yl)-3-fluorobenzamide |

TABLE 1-continued
Illustrative Compounds of the Present Invention
| Compound No. | Structure | Name |
|---|---|---|
| C152 | 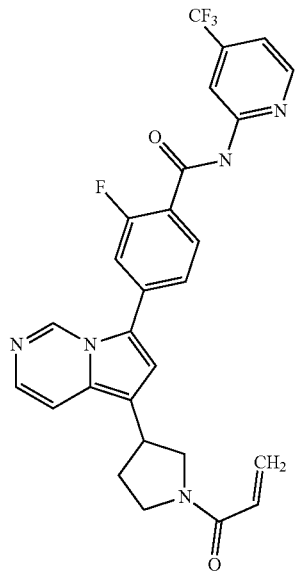 [SMILES: C=CC(=O)N1CCC(c2cc(-c3ccc(C(=O)Nc4cc(C(F)(F)F)ccn4)c(F)c3)n3cnccc23)C1] | 4-(5-(1-acryloylpyrrolidin-3-yl)pyrrolo[1,2-c]pyrimidin-7-yl)-2-fluoro-N-(4-(trifluoromethyl)pyridin-2-yl)benzamide |
| C153 | 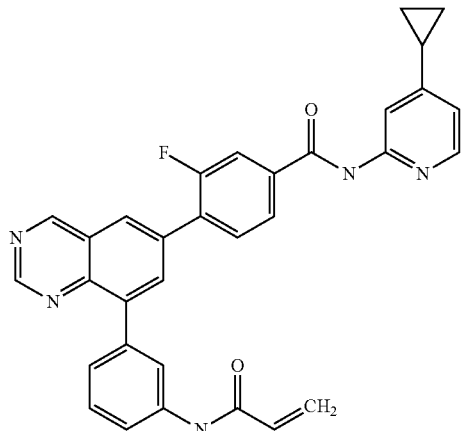 | 4-(8-(3-acrylamidophenyl)quinazolin-6-yl)-N-(4-cyclopropylpyridin-2-yl)-3-fluorobenzamide |
| C154 | 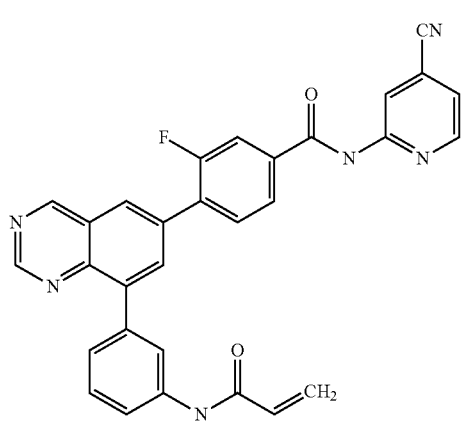 [SMILES: C=CC(=O)Nc1cccc(-c2cc(-c3ccc(C(=O)Nc4cc(C#N)ccn4)cc3F)cc3cncnc23)c1] | 4-(8-(3-acrylamidophenyl)quinazolin-6-yl)-N-(4-cyanopyridin-2-yl)-3-fluorobenzamide |

TABLE 1-continued

Illustrative Compounds of the Present Invention

| Compound No. | Structure | Name |
|---|---|---|
| C155 | 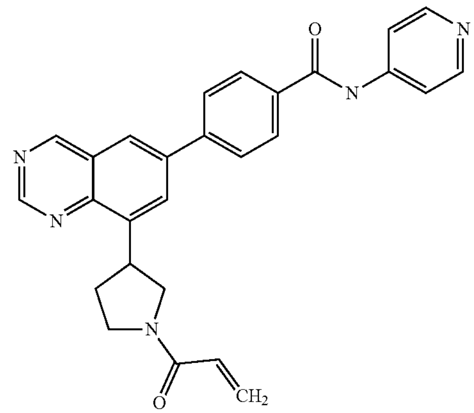 [SMILES: C=CC(=O)N1CCC(c2cc(-c3ccc(C(=O)Nc4ccncc4)cc3)cc3cncnc23)C1] | 4-(8-(1-acryloylpyrrolidin-3-yl)quinazolin-6-yl)-N-(pyridin-4-yl)benzamide |
| C156 | 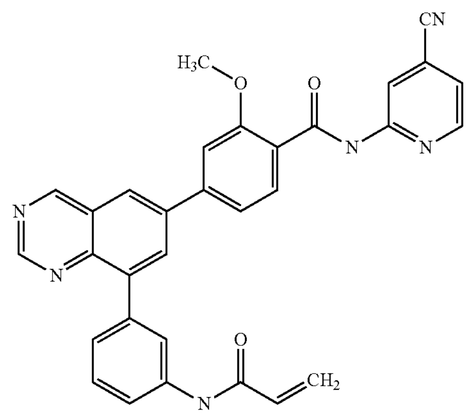 [SMILES: C=CC(=O)Nc1cccc(-c2cc(-c3ccc(C(=O)Nc4cc(C#N)ccn4)c(OC)c3)cc3cncnc23)c1] | 4-(8-(3-acrylamidophenyl)quinazolin-6-yl)-N-(4-cyanopyridin-2-yl)-2-methoxybenzamide |
| C157 | 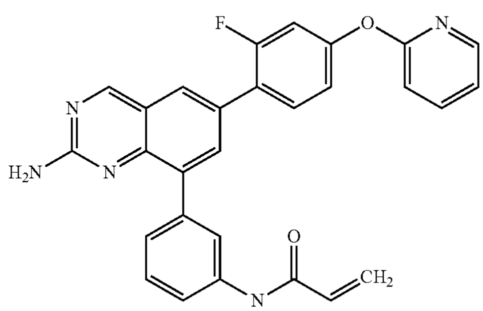 [SMILES: C=CC(=O)Nc1cccc(-c2cc(-c3ccc(Oc4ccccn4)cc3F)cc3cnc(N)nc23)c1] | N-(3-(2-amino-6-(2-fluoro-4-(pyridin-2-yloxy)phenyl)quinazolin-8-yl)phenyl)acrylamide |
| C158 | 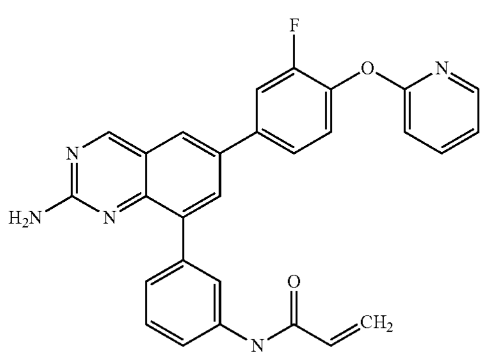 [SMILES: C=CC(=O)Nc1cccc(-c2cc(-c3ccc(Oc4ccccn4)c(F)c3)cc3cnc(N)nc23)c1] | N-(3-(2-amino-6-(3-fluoro-4-(pyridin-2-yloxy)phenyl)quinazolin-8-yl)phenyl)acrylamide |

TABLE 1-continued

Illustrative Compounds of the Present Invention

| Compound No. | Structure | Name |
|---|---|---|
| C159 | 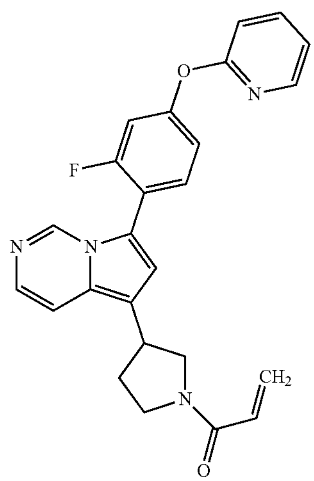 [SMILES: C=CC(=O)N1CCC(c2cc(-c3ccc(Oc4ccccn4)cc3F)n3cnccc23)C1] | 1-(3-(7-(2-fluoro-4-(pyridin-2-yloxy)phenyl)pyrrolo[1,2-c]pyrimidin-5-yl)pyrrolidin-1-yl)prop-2-en-1-one |
| C160 | 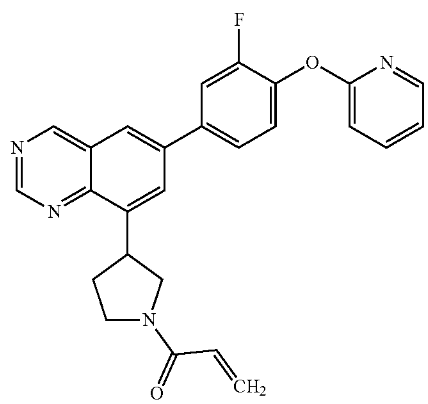 [SMILES: C=CC(=O)N1CCC(c2cc(-c3ccc(Oc4ccccn4)c(F)c3)cc3cncnc23)C1] | 1-(3-(6-(3-fluoro-4-(pyridin-2-yloxy)phenyl)quinazolin-8-yl)pyrrolidin-1-yl)prop-2-en-1-one |
| C161 | 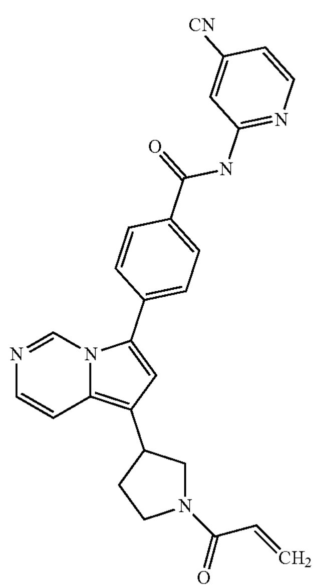 [SMILES: C=CC(=O)N1CCC(c2cc(-c3ccc(C(=O)Nc4cc(C#N)ccn4)cc3)n3cnccc23)C1] | 4-(5-(1-acryloylpyrrolidin-3-yl)pyrrolo[1,2-c]pyrimidin-7-yl)-N-(4-cyanopyridin-2-yl)benzamide |

TABLE 1-continued

Illustrative Compounds of the Present Invention

| Compound No. | Structure | Name |
|---|---|---|
| C162 | 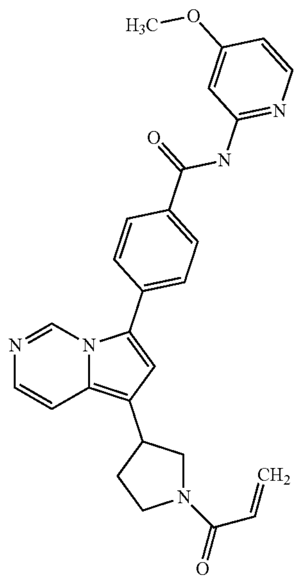 [SMILES: C=CC(=O)N1CCC(c2cc(-c3ccc(C(=O)Nc4cc(OC)ccn4)cc3)n3cnccc23)C1] | 4-(5-(1-acryloylpyrrolidin-3-yl)pyrrolo[1,2-c]pyrimidin-7-yl)-N-(4-methoxypyridin-2-yl)benzamide |
| C163 | 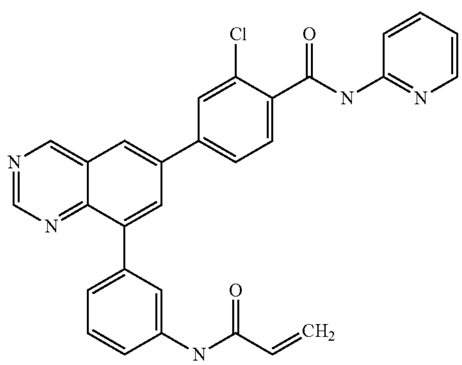 [SMILES: C=CC(=O)Nc1cccc(-c2cc(-c3ccc(C(=O)Nc4ccccn4)c(Cl)c3)cc3cncnc23)c1] | 4-(8-(3-acrylamidophenyl)quinazolin-6-yl)-2-chloro-N-(pyridin-2-yl)benzamide |
| C164 | 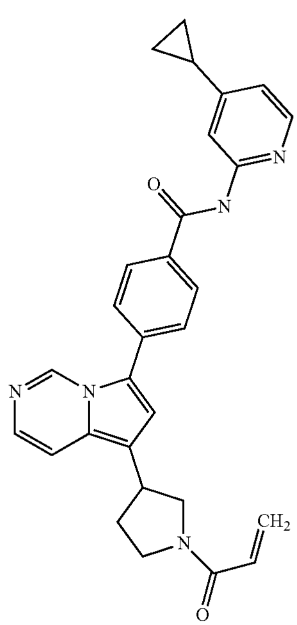 [SMILES: C=CC(=O)N1CCC(c2cc(-c3ccc(C(=O)Nc4cc(C5CC5)ccn4)cc3)n3cnccc23)C1] | 4-(5-(1-acryloylpyrrolidin-3-yl)pyrrolo[1,2-c]pyrimidin-7-yl)-N-(4-cyclopropylpyridin-2-yl)benzamide |

TABLE 1-continued

Illustrative Compounds of the Present Invention

| Compound No. | Structure | Name |
|---|---|---|
| C165 | 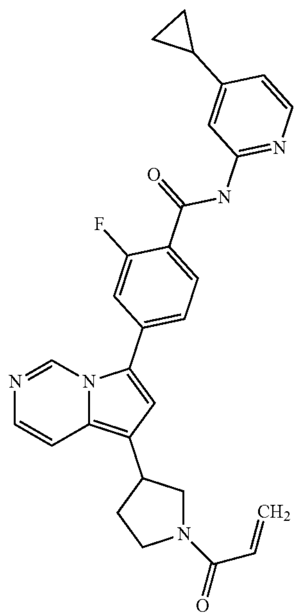 [SMILES: C=CC(=O)N1CCC(c2cc(-c3ccc(C(=O)Nc4cc(C5CC5)ccn4)c(F)c3)n3cnccc23)C1] | 4-(5-(1-acryloylpyrrolidin-3-yl)pyrrolo[1,2-c]pyrimidin-7-yl)-N-(4-cyclopropylpyridin-2-yl)-2-fluorobenzamide |
| C166 | 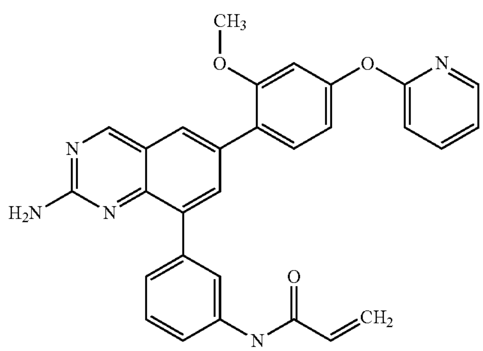 [SMILES: C=CC(=O)Nc1cccc(-c2cc(-c3ccc(Oc4ccccn4)cc3OC)cc3cnc(N)nc23)c1] | N-(3-(2-amino-6-(2-methoxy-4-(pyridin-2-yloxy)phenyl)quinazolin-8-yl)phenyl)acrylamide |
| C167 | 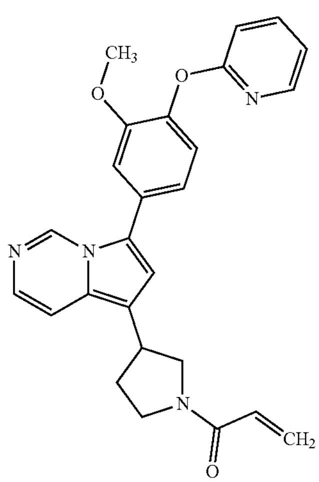 [SMILES: C=CC(=O)N1CCC(c2cc(-c3ccc(Oc4ccccn4)c(OC)c3)n3cnccc23)C1] | 1-(3-(7-(3-methoxy-4-(pyridin-2-yloxy)phenyl)pyrrolo[1,2-c]pyrimidin-5-yl)pyrrolidin-1-yl)prop-2-en-1-one |

TABLE 1-continued
Illustrative Compounds of the Present Invention
| Compound No. | Structure | Name |
|---|---|---|
| C168 | 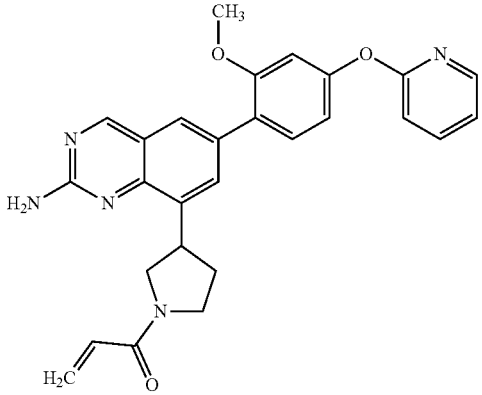 [SMILES: C=CC(=O)N1CCC(c2cc(-c3ccc(Oc4ccccn4)cc3OC)cc3cnc(N)nc23)C1] | 1-(3-(2-amino-6-(2-methoxy-4-(pyridin-2-yloxy)phenyl)quinazolin-8-yl)pyrrolidin-1-yl)prop-2-en-1-one |
| C169 | 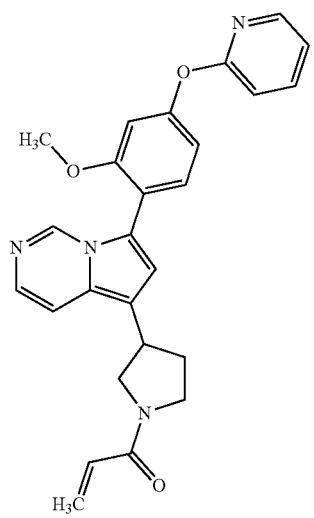 [SMILES: C=CC(=O)N1CCC(c2cc(-c3ccc(Oc4ccccn4)cc3OC)n3cnccc23)C1] | 1-(3-(7-(2-methoxy-4-(pyridin-2-yloxy)phenyl)pyrrolo[1,2-c]pyrimidin-5-yl)pyrrolidin-1-yl)prop-2-en-1-one |
| C170 | 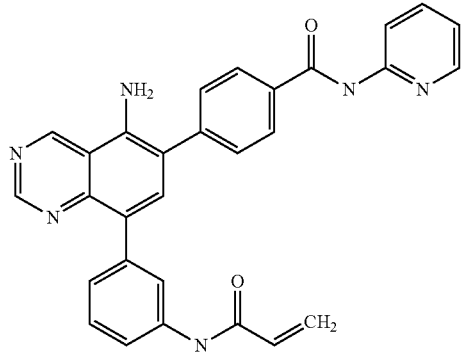 [SMILES: C=CC(=O)Nc1cccc(-c2cc(-c3ccc(C(=O)Nc4ccccn4)cc3)c(N)c3cncnc23)c1] | 4-(8-(3-acrylamidophenyl)-5-aminoquinazolin-6-yl)-N-(pyridin-2-yl)benzamide |

TABLE 1-continued

Illustrative Compounds of the Present Invention

| Compound No. | Structure | Name |
|---|---|---|
| C171 | 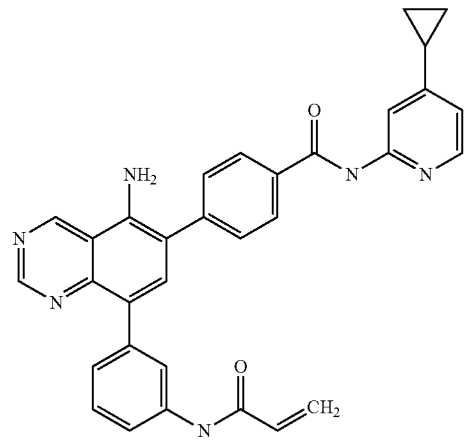 [SMILES: C=CC(=O)Nc1cccc(-c2cc(-c3ccc(C(=O)Nc4cc(C5CC5)ccn4)cc3)c(N)c3cncnc23)c1] | 4-(8-(3-acrylamidophenyl)-5-aminoquinazolin-6-yl)-N-(4-cyclopropylpyridin-2-yl)benzamide |
| C172 | 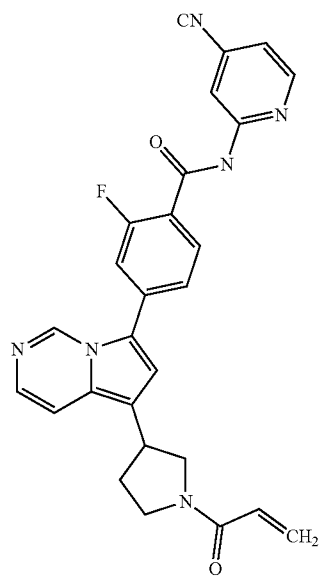 | 4-(5-(1-acryloylpyrrolidin-3-yl)pyrrolo[1,2-c]pyrimidin-7-yl)-N-(4-cyanopyridin-2-yl)-2-fluorobenzamide |
| C173 | 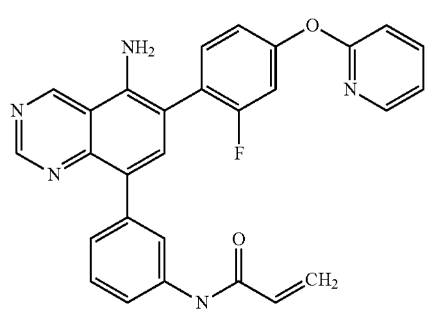 | N-(3-(5-amino-6-(2-fluoro-4-(pyridin-2-yloxy)phenyl)quinazolin-8-yl)phenyl)acrylamide |

TABLE 1-continued

Illustrative Compounds of the Present Invention

| Compound No. | Structure | Name |
|---|---|---|
| C174 | 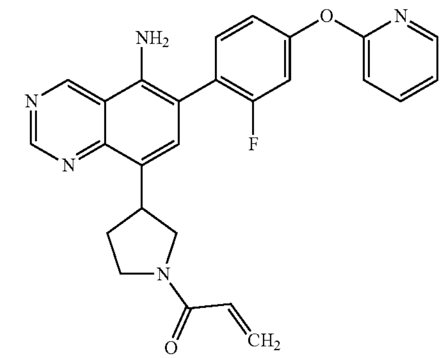 [SMILES: C=CC(=O)N1CCC(c2cc(-c3ccc(Oc4ccccn4)cc3F)c(N)c3cncnc23)C1] | 1-(3-(5-amino-6-(2-fluoro-4-(pyridin-2-yloxy)phenyl)qui-nazolin-8-yl)pyrrolidin-1-yl)prop-2-en-1-one |
| C175 | 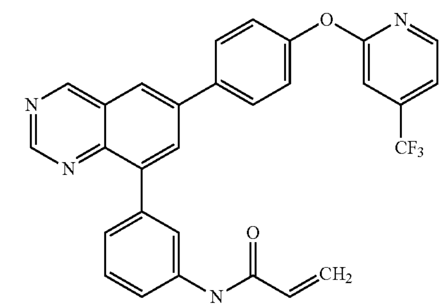 | N-(3-(6-(4-((4-(trifluoromethyl)pyridin-2-yl)oxy)phenyl)quinazolin-8-yl)phenyl)acrylamide |
| C176 | 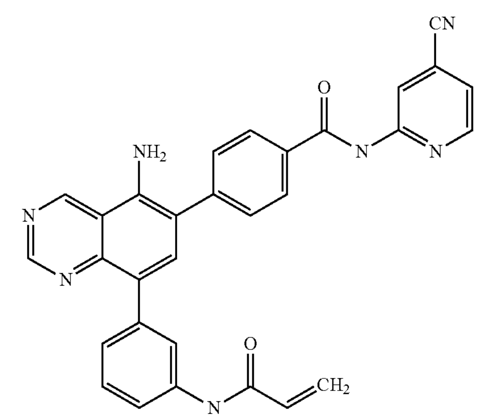 [SMILES: C=CC(=O)Nc1cccc(-c2cc(-c3ccc(C(=O)Nc4cc(C#N)ccn4)cc3)c(N)c3cncnc23)c1] | 4-(8-(3-acrylamidophenyl)-5-aminoquinazolin-6-yl)-N-(4-cyanopyridin-2-yl)benzamide |
| C177 | 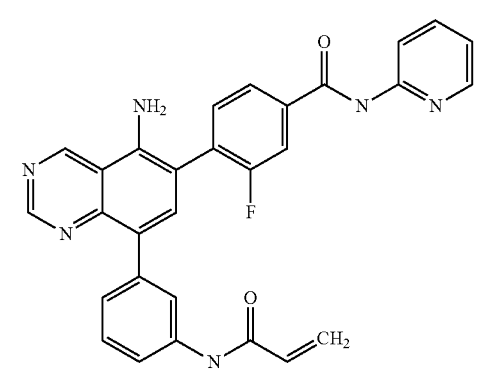 | 4-(8-(3-acrylamidophenyl)-5-aminoquinazolin-6-yl)-3-fluoro-N-(pyridin-2-yl)benzamide |

TABLE 1-continued

Illustrative Compounds of the Present Invention

| Compound No. | Structure | Name |
|---|---|---|
| C178 | 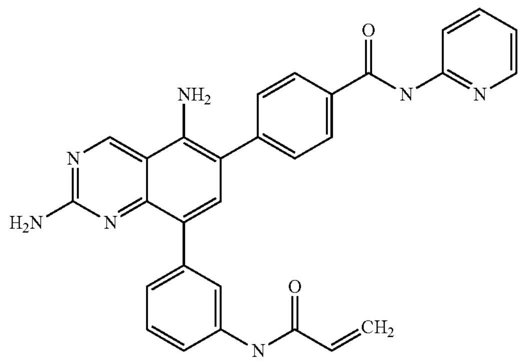 [SMILES: C=CC(=O)Nc1cccc(-c2cc(-c3ccc(C(=O)Nc4ccccn4)cc3)c(N)c3cnc(N)nc23)c1] | 4-(8-(3-acrylamidophenyl)-2,5-diaminoquinazolin-6-yl)-N-(pyridin-2-yl)benzamide |
| C179 | 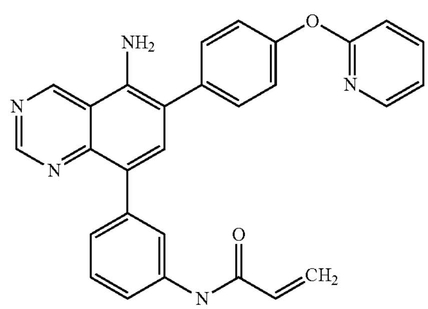 [SMILES: C=CC(=O)Nc1cccc(-c2cc(-c3ccc(Oc4ccccn4)cc3)c(N)c3cncnc23)c1] | N-(3-(5-amino-6-(4-(pyridin-2-yloxy)phenyl)quinazolin-8-yl)phenyl)acrylamide |
| C180 | 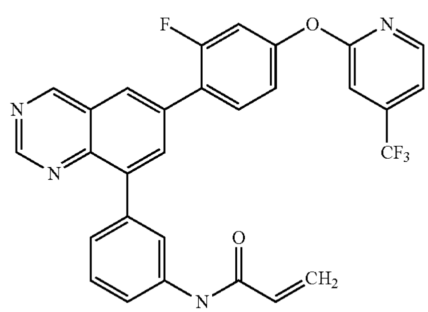 [SMILES: C=CC(=O)Nc1cccc(-c2cc(-c3ccc(Oc4cc(C(F)(F)F)ccn4)cc3F)cc3cncnc23)c1] | N-(3-(6-(2-fluoro-4-((4-(trifluoromethyl)pyridin-2-yl)oxy)phenyl)quinazolin-8-yl)phenyl)acrylamide |
| C181 | 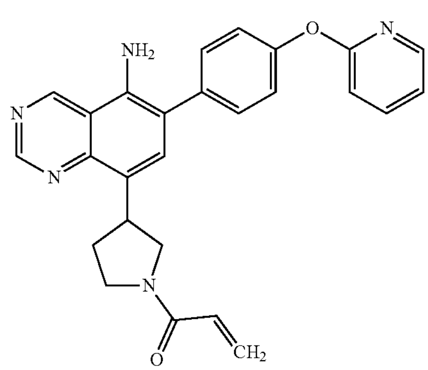 [SMILES: C=CC(=O)N1CCC(c2cc(-c3ccc(Oc4ccccn4)cc3)c(N)c3cncnc23)C1] | 1-(3-(5-amino-6-(4-(pyridin-2-yloxy)phenyl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C182 | 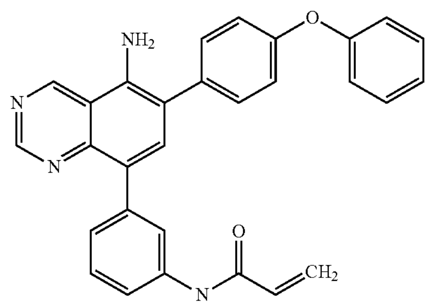 [SMILES: C=CC(=O)Nc1cccc(-c2cc(-c3ccc(Oc4ccccc4)cc3)c(N)c3cncnc23)c1] | N-(3-(5-amino-6-(4-phenoxyphenyl)quinazolin-8-yl)phenyl)acrylamide |
| C183 | 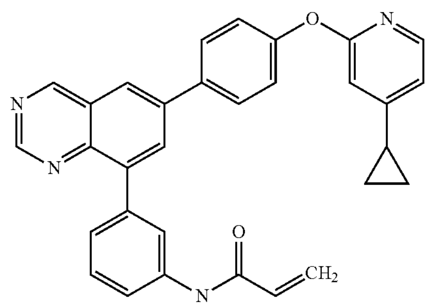 [SMILES: C=CC(=O)Nc1cccc(-c2cc(-c3ccc(Oc4cc(C5CC5)ccn4)cc3)cc3cncnc23)c1] | N-(3-(6-(4-((4-cyclopropylpyridin-2-yl)oxy)phenyl)quinazolin-8-yl)phenyl)acrylamide |
| C184 | 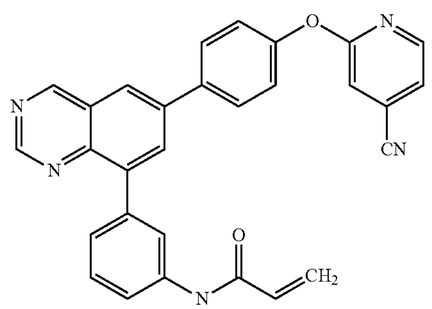 [SMILES: C=CC(=O)Nc1cccc(-c2cc(-c3ccc(Oc4cc(C#N)ccn4)cc3)cc3cncnc23)c1] | N-(3-(6-(4-((4-cyanopyridin-2-yl)oxy)phenyl)quinazolin-8-yl)phenyl)acrylamide |
| C185 | 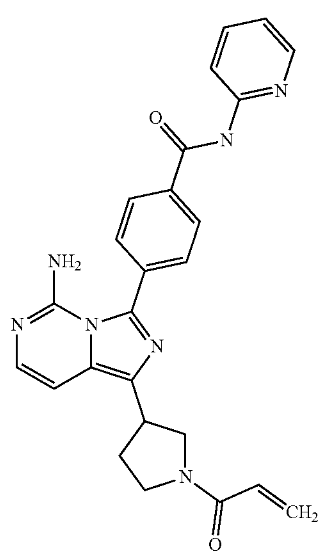 [SMILES: C=CC(=O)N1CCC(c2nc(-c3ccc(C(=O)Nc4ccccn4)cc3)n3c(N)nccc23)C1] | 4-(1-(1-acryloylpyrrolidin-3-yl)-5-aminoimidazo[1,5-c]pyrimidin-3-yl)-N-(pyridin-2-yl)benzamide |

TABLE 1-continued

Illustrative Compounds of the Present Invention

| Compound No. | Structure | Name |
|---|---|---|
| C186 | 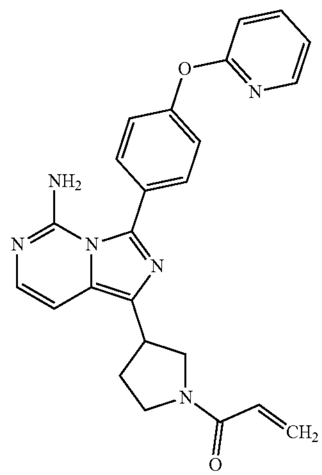 [SMILES: C=CC(=O)N1CCC(c2nc(-c3ccc(Oc4ccccn4)cc3)n3c(N)nccc23)C1] | 1-(3-(5-amino-3-(4-(pyridin-2-yloxy)phenyl)imidazo[1,5-c]pyrimidin-1-yl)pyrrolidin-1-yl)prop-2-en-1-one |
| C187 | 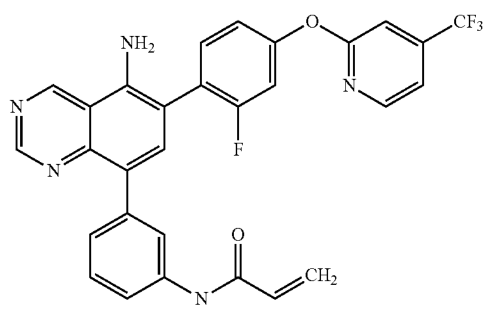 [SMILES: C=CC(=O)Nc1cccc(-c2cc(-c3ccc(Oc4cc(C(F)(F)F)ccn4)cc3F)c(N)c3cncnc23)c1] | N-(3-(5-amino-6-(2-fluoro-4-((4-(trifluoromethyl)pyridin-2-yl)oxy)phenyl)quinazolin-8-yl)phenyl)acrylamide |
| C188 | 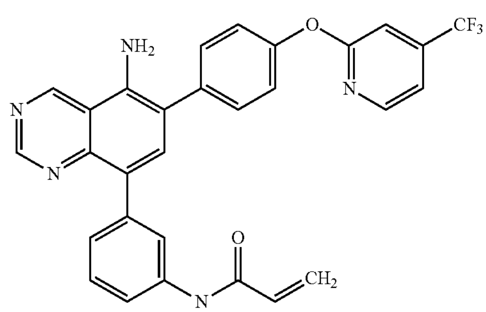 [SMILES: C=CC(=O)Nc1cccc(-c2cc(-c3ccc(Oc4cc(C(F)(F)F)ccn4)cc3)c(N)c3cncnc23)c1] | N-(3-(5-amino-6-(4-((4-(trifluoromethyl)pyridin-2-yl)oxy)phenyl)quinazolin-8-yl)phenyl)acrylamide |
| C189 | 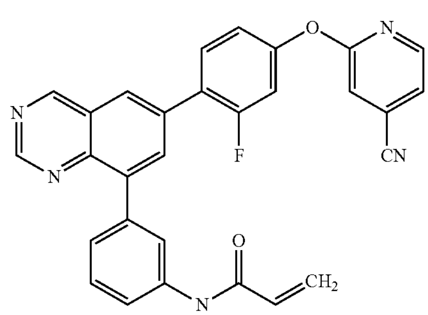 [SMILES: C=CC(=O)Nc1cccc(-c2cc(-c3ccc(Oc4cc(C#N)ccn4)cc3F)cc3cncnc23)c1] | N-(3-(6-(4-((4-cyanopyridin-2-yl)oxy)-2-fluorophenyl)quinazolin-8-yl)phenyl)acrylamide |

TABLE 1-continued

Illustrative Compounds of the Present Invention

| Compound No. | Structure | Name |
|---|---|---|
| C190 | 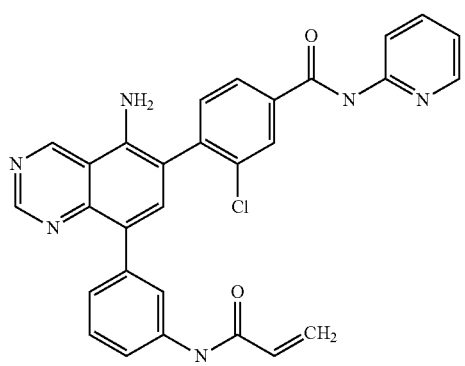 [SMILES: C=CC(=O)Nc1cccc(-c2cc(-c3ccc(C(=O)Nc4ccccn4)cc3Cl)c(N)c3cncnc23)c1] | 4-(8-(3-acrylamidophenyl)-5-aminoquinazolin-6-yl)-3-chloro-N-(pyridin-2-yl)benzamide |
| C191 | 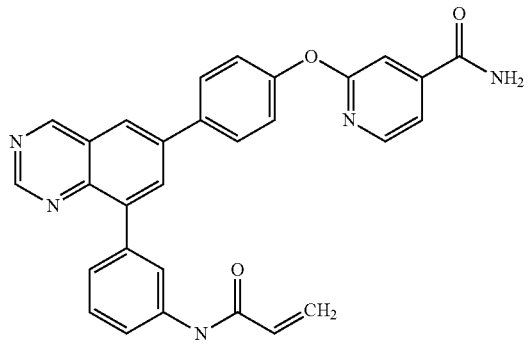 [SMILES: C=CC(=O)Nc1cccc(-c2cc(-c3ccc(Oc4cc(C(N)=O)ccn4)cc3)cc3cncnc23)c1] | 2-(4-(8-(3-acrylamidophenyl)quinazolin-6-yl)phenoxy)isonicotinamide |
| C192 | 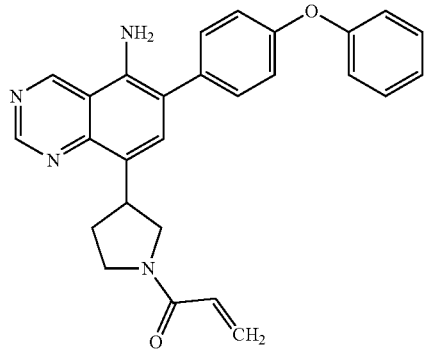 [SMILES: C=CC(=O)N1CCC(c2cc(-c3ccc(Oc4ccccc4)cc3)c(N)c3cncnc23)C1] | 1-(3-(5-amino-6-(4-phenoxyphenyl)quinazolin-8-yl)pyrrolidin-1-yl)prop-2-en-1-one |
| C193 | 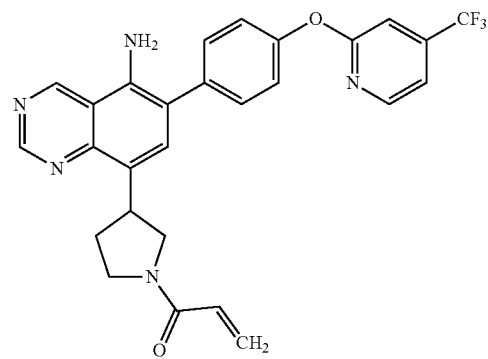 [SMILES: C=CC(=O)N1CCC(c2cc(-c3ccc(Oc4cc(C(F)(F)F)ccn4)cc3)c(N)c3cncnc23)C1] | 1-(3-(5-amino-6-(4-((4-(trifluoromethyl)pyridin-2-yl)oxy)phenyl)quinazolin-8-yl)pyrrolidin-1-yl)prop-2-en-1-one |

TABLE 1-continued

Illustrative Compounds of the Present Invention

| Compound No. | Structure | Name |
|---|---|---|
| C194 | 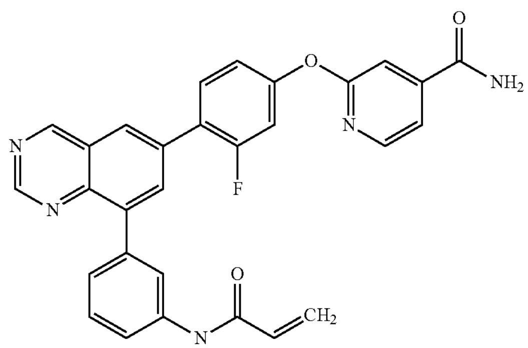 [SMILES: C=CC(=O)Nc1cccc(-c2cc(-c3ccc(Oc4cc(C(N)=O)ccn4)cc3F)cc3cncnc23)c1] | 2-(4-(8-(3-acrylamidophenyl)quinazolin-6-yl)-3-fluorophenoxy)isonicotinamide |
| C195 | 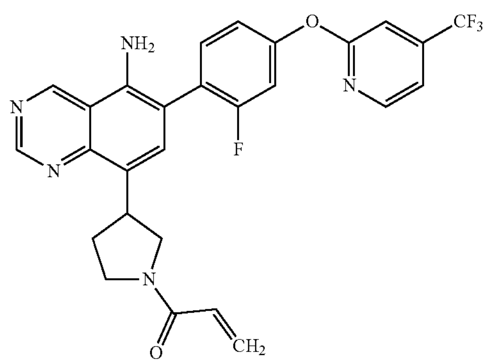 [SMILES: C=CC(=O)N1CCC(c2cc(-c3ccc(Oc4cc(C(F)(F)F)ccn4)cc3F)c(N)c3cncnc23)C1] | 1-(3-(5-amino-6-(2-fluoro-4-((4-(trifluoromethyl)pyridin-2-yl)oxy)phenyl)quinazolin-8-yl)pyrrolidin-1-yl)prop-2-en-1-one |
| C196 | 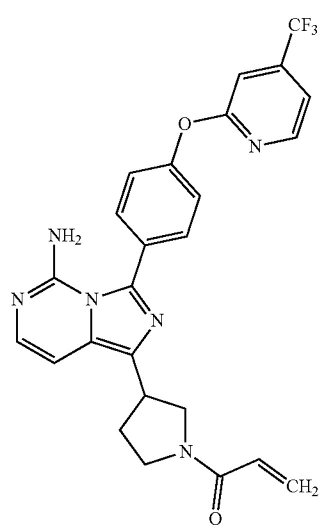 [SMILES: C=CC(=O)N1CCC(c2nc(-c3ccc(Oc4cc(C(F)(F)F)ccn4)cc3)n3c(N)nccc23)C1] | 1-(3-(5-amino-3-(4-((4-(trifluoromethyl)pyridin-2-yl)oxy)phenyl)imidazo[1,5-c]pyrimidin-1-yl)pyrrolidin-1-yl)prop-2-en-1-one |

TABLE 1-continued

Illustrative Compounds of the Present Invention

| Compound No. | Structure | Name |
|---|---|---|
| C197 | 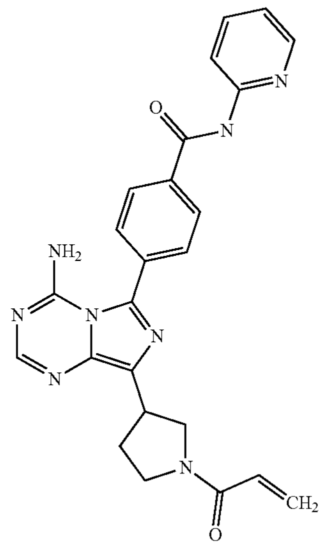 [SMILES: C=CC(=O)N1CCC(c2nc(-c3ccc(C(=O)Nc4ccccn4)cc3)n3c(N)ncnc23)C1] | 4-(8-(1-acryloylpyrrolidin-3-yl)-4-aminoimidazo[1,5-a][1,3,5]triazin-6-yl)-N-(pyridin-2-yl)benzamide |
| C198 | 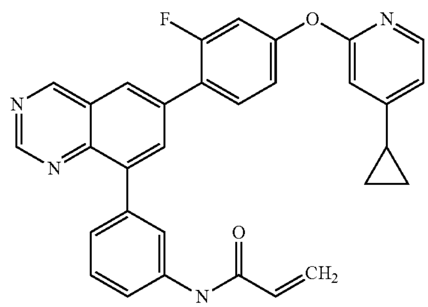 [SMILES: C=CC(=O)Nc1cccc(-c2cc(-c3ccc(Oc4cc(C5CC5)ccn4)cc3F)cc3cncnc23)c1] | N-(3-(6-(4-((4-cyclopropylpyridin-2-yl)oxy)-2-fluorophenyl)quinazolin-8-yl)phenyl)acrylamide |
| C199 | 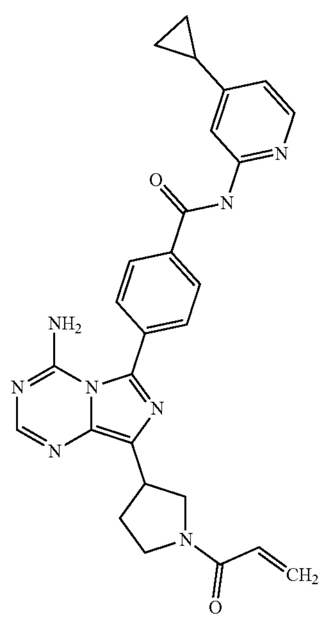 [SMILES: C=CC(=O)N1CCC(c2nc(-c3ccc(C(=O)Nc4cc(C5CC5)ccn4)cc3)n3c(N)ncnc23)C1] | 4-(8-(1-acryloylpyrrolidin-3-yl)-4-aminoimidazo[1,5-a][1,3,5]triazin-6-yl)-N-(4-cyclopropylpyridin-2-yl)benzamide |

TABLE 1-continued

Illustrative Compounds of the Present Invention

| Compound No. | Structure | Name |
|---|---|---|
| C200 | 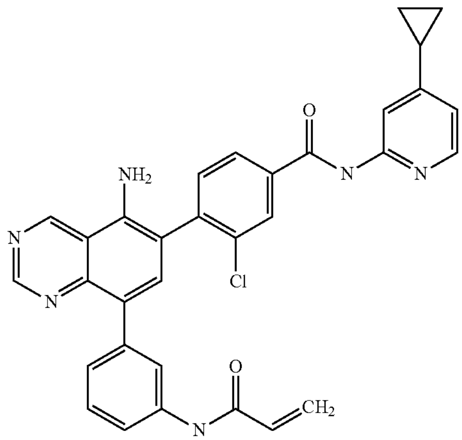 | 4-(8-(3-acrylamidophenyl)-5-aminoquinazolin-6-yl)-3-chloro-N-(4-cyclopropylpyridin-2-yl)benzamide |
| C201 | 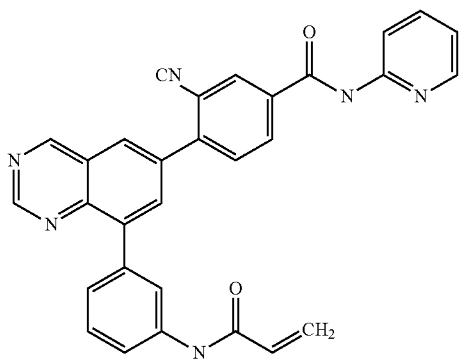 [SMILES: C=CC(=O)Nc1cccc(-c2cc(-c3ccc(C(=O)Nc4ccccn4)cc3C#N)cc3cncnc23)c1] | 4-(8-(3-acrylamidophenyl)quinazolin-6-yl)-3-cyano-N-(pyridin-2-yl)benzamide |
| C202 | 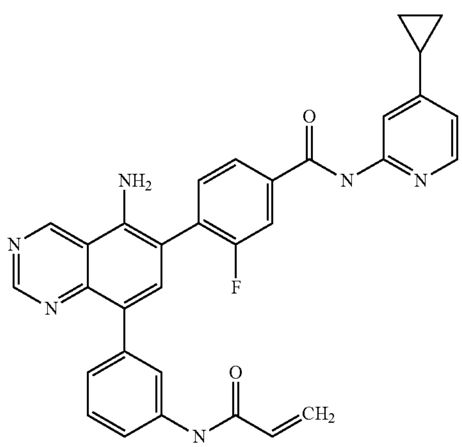 [SMILES: C=CC(=O)Nc1cccc(-c2cc(-c3ccc(C(=O)Nc4cc(C5CC5)ccn4)cc3F)c(N)c3cncnc23)c1] | 4-(8-(3-acrylamidophenyl)-5-aminoquinazolin-6-yl)-N-(4-cyclopropylpyridin-2-yl)-3-fluorobenzamide |
| C203 | 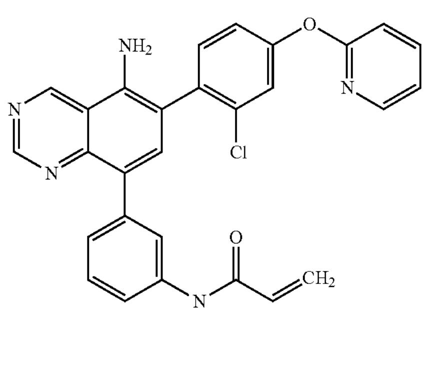 [SMILES: C=CC(=O)Nc1cccc(-c2cc(-c3ccc(Oc4ccccn4)cc3Cl)c(N)c3cncnc23)c1] | N-(3-(5-amino-6-(2-chloro-4-(pyridin-2-yloxy)phenyl)quinazolin-8-yl)phenyl)acrylamide |

TABLE 1-continued

Illustrative Compounds of the Present Invention

| Compound No. | Structure | Name |
|---|---|---|
| C204 | 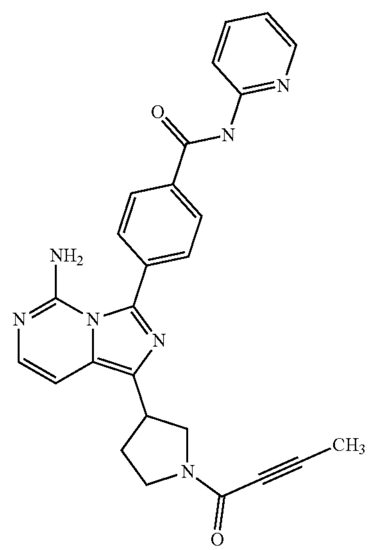 [SMILES: CC#CC(=O)N1CCC(c2nc(-c3ccc(C(=O)Nc4ccccn4)cc3)n3c(N)nccc23)C1] | 4-(5-amino-1-(1-(but-2-ynoyl)pyrrolidin-3-yl)imidazo[1,5-c]pyrimidin-3-yl)-N-(pyridin-2-yl)benzamide |
| C205 | 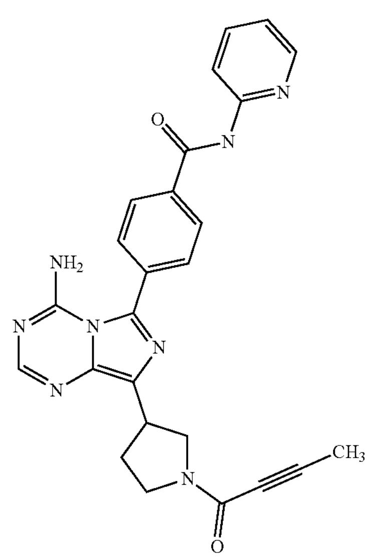 [SMILES: CC#CC(=O)N1CCC(c2nc(-c3ccc(C(=O)Nc4ccccn4)cc3)n3c(N)ncnc23)C1] | 4-(4-amino-8-(1-(but-2-ynoyl)pyrrolidin-3-yl)imidazo[1,5-a][1,3,5]triazin-6-yl)-N-(pyridin-2-yl)benzamide |

TABLE 1-continued

Illustrative Compounds of the Present Invention

| Compound No. | Structure | Name |
|---|---|---|
| C206 | 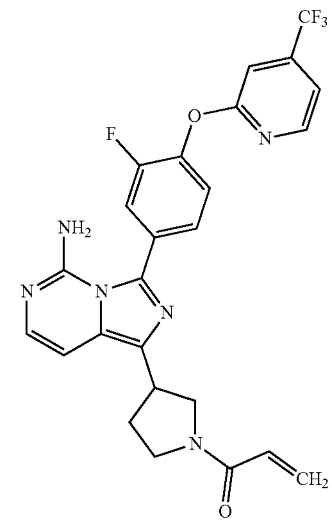 [SMILES: C=CC(=O)N1CCC(c2nc(-c3ccc(Oc4cc(C(F)(F)F)ccn4)c(F)c3)n3c(N)nccc23)C1] | 1-(3-(5-amino-3-(3-fluoro-4-((4-(trifluoromethyl)pyridin-2-yl)oxy)phenyl)imidazo[1,5-c]pyrimidin-1-yl)pyrrolidin-1-yl)prop-2-en-1-one |
| C207 | 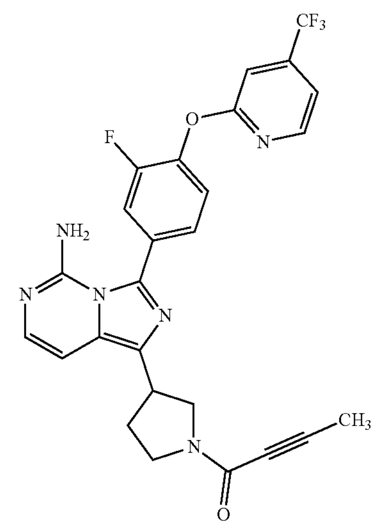 [SMILES: CC#CC(=O)N1CCC(c2nc(-c3ccc(Oc4cc(C(F)(F)F)ccn4)c(F)c3)n3c(N)nccc23)C1] | 1-(3-(5-amino-3-(3-fluoro-4-((4-(trifluoromethyl)pyridin-2-yl)oxy)phenyl)imidazo[1,5-c]pyrimidin-1-yl)pyrrolidin-1-yl)but-2-yn-1-one |
| C208 | 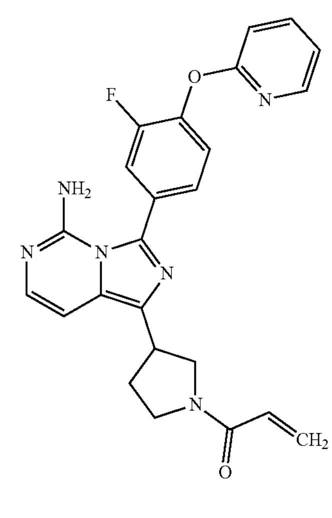 [SMILES: C=CC(=O)N1CCC(c2nc(-c3ccc(Oc4ccccn4)c(F)c3)n3c(N)nccc23)C1] | 1-(3-(5-amino-3-(3-fluoro-4-(pyridin-2-yloxy)phenyl)imidazo[1,5-c]pyrimidin-1-yl)pyrrolidin-1-yl)prop-2-en-1-one |

TABLE 1-continued

Illustrative Compounds of the Present Invention

| Compound No. | Structure | Name |
|---|---|---|
| C209 | 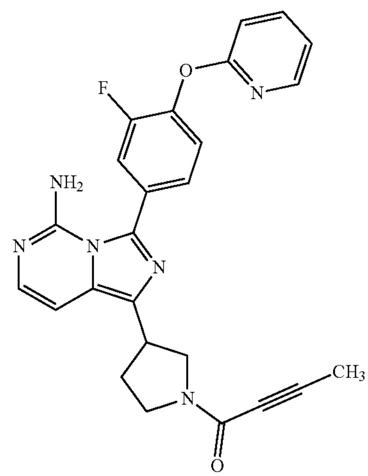 [SMILES: CC#CC(=O)N1CCC(c2nc(-c3ccc(Oc4ccccn4)c(F)c3)n3c(N)nccc23)C1] | 1-(3-(5-amino-3-(3-fluoro-4-(pyridin-2-yloxy)phenyl)imidazo[1,5-c]pyrimidin-1-yl)pyrrolidin-1-yl)but-2-yn-1-one |
| C210 | 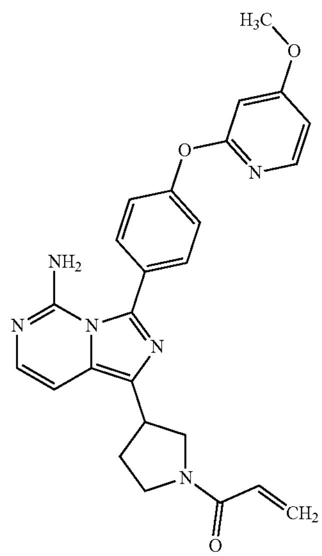 [SMILES: C=CC(=O)N1CCC(c2nc(-c3ccc(Oc4cc(OC)ccn4)cc3)n3c(N)nccc23)C1] | 1-(3-(5-amino-3-(4-((4-methoxypyridin-2-yl)oxy)phenyl)imidazo[1,5-c]pyrimidin-1-yl)pyrrolidin-1-yl)prop-2-en-1-one |
| C211 | 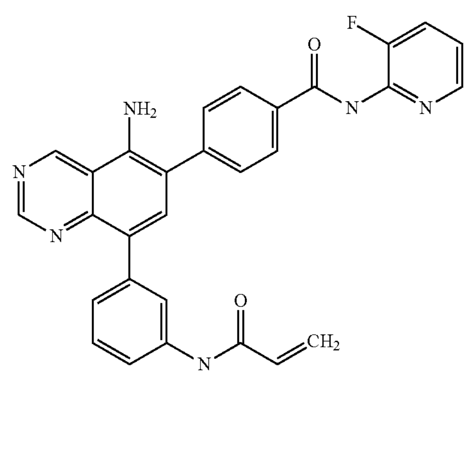 [SMILES: C=CC(=O)Nc1cccc(-c2cc(-c3ccc(C(=O)Nc4ncccc4F)cc3)c(N)c3cncnc23)c1] | 4-(8-(3-acrylamidophenyl)-5-aminoquinazolin-6-yl)-N-(3-fluoropyridin-2-yl)benzamide |

TABLE 1-continued

Illustrative Compounds of the Present Invention

| Compound No. | Structure | Name |
|---|---|---|
| C212 | 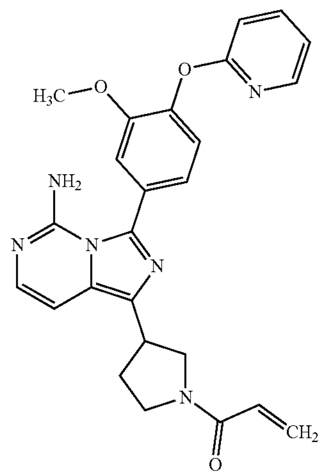 [SMILES: C=CC(=O)N1CCC(c2nc(-c3ccc(Oc4ccccn4)c(OC)c3)n3c(N)nccc23)C1] | 1-(3-(5-amino-3-(3-methoxy-4-(pyridin-2-yloxy)phenyl)imidazo[1,5-c]pyrimidin-1-yl)pyrrolidin-1-yl)prop-2-en-1-one |
| C213 | 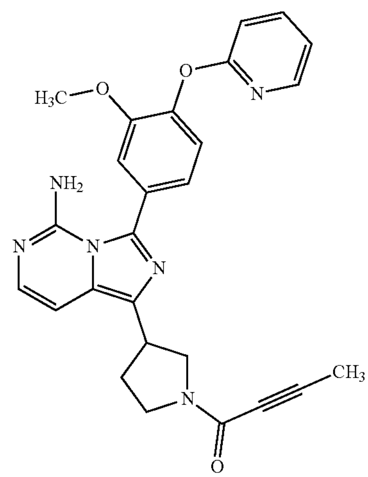 [SMILES: CC#CC(=O)N1CCC(c2nc(-c3ccc(Oc4ccccn4)c(OC)c3)n3c(N)nccc23)C1] | 1-(3-(5-amino-3-(3-methoxy-4-(pyridin-2-yloxy)phenyl)imidazo[1,5-c]pyrimidin-1-yl)pyrrolidin-1-yl)but-2-yn-1-one |
| C214 | 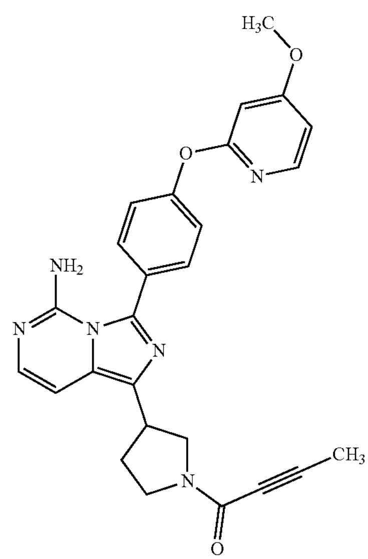 [SMILES: CC#CC(=O)N1CCC(c2nc(-c3ccc(Oc4cc(OC)ccn4)cc3)n3c(N)nccc23)C1] | 1-(3-(5-amino-3-(4-((4-methoxypyridin-2-yl)oxy)phenyl)imidazo[1,5-c]pyrimidin-1-yl)pyrrolidin-1-yl)but-2-yn-1-one |

TABLE 1-continued

Illustrative Compounds of the Present Invention

| Compound No. | Structure | Name |
|---|---|---|
| C215 | 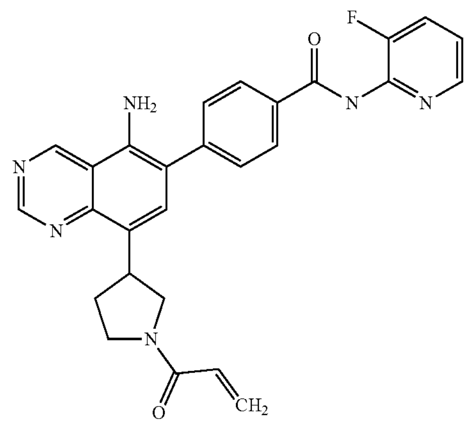 [SMILES: C=CC(=O)N1CCC(c2cc(-c3ccc(C(=O)Nc4ncccc4F)cc3)c(N)c3cncnc23)C1] | 4-(8-(1-acryloylpyrrolidin-3-yl)-5-aminoquinazolin-6-yl)-N-(3-fluoropyridin-2-yl)benzamide |
| C216 | 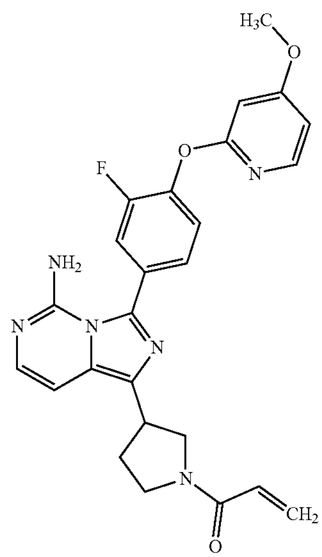 [SMILES: C=CC(=O)N1CCC(c2nc(-c3ccc(Oc4cc(OC)ccn4)c(F)c3)n3c(N)nccc23)C1] | 1-(3-(5-amino-3-(3-fluoro-4-((4-methoxypyridin-2-yl)oxy)phenyl)imidazo[1,5-c]pyrimidin-1-yl)pyrrolidin-1-yl)prop-2-en-1-one |
| C217 | 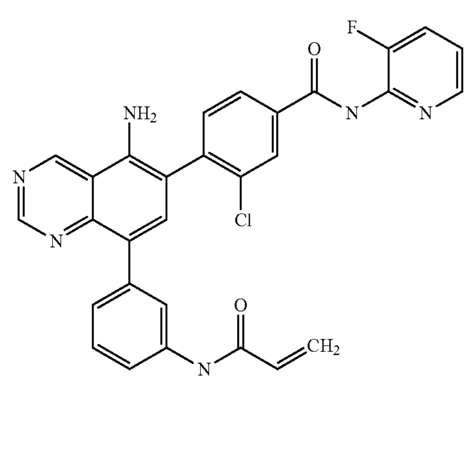 [SMILES: C=CC(=O)Nc1cccc(-c2cc(-c3ccc(C(=O)Nc4ncccc4F)cc3Cl)c(N)c3cncnc23)c1] | 4-(8-(3-acrylamidophenyl)-5-aminoquinazolin-6-yl)-3-chloro-N-(3-fluoropyridin-2-yl)benzamide |

TABLE 1-continued

Illustrative Compounds of the Present Invention

| Compound No. | Structure | Name |
|---|---|---|
| C218 | 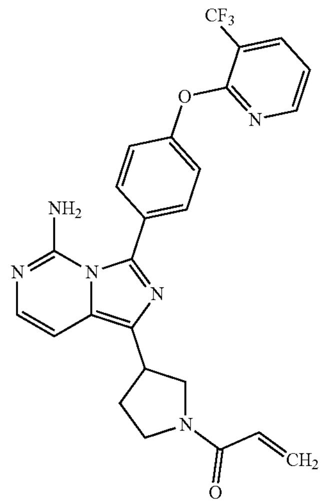 [SMILES: C=CC(=O)N1CCC(c2nc(-c3ccc(Oc4ncccc4C(F)(F)F)cc3)n3c(N)nccc23)C1] | 1-(3-(5-amino-3-(4-((3-(trifluoromethyl)pyridin-2-yl)oxy)phenyl)imidazo[1,5-c]pyrimidin-1-yl)pyrrolidin-1-yl)prop-2-en-1-one |
| C219 | 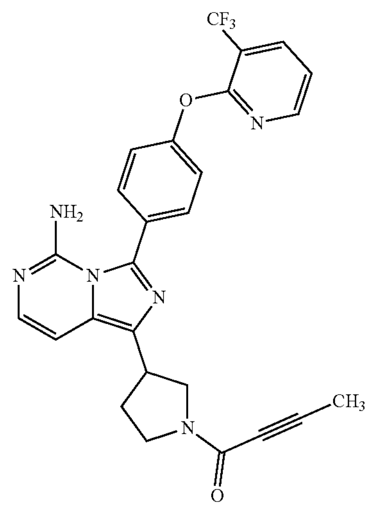 [SMILES: CC#CC(=O)N1CCC(c2nc(-c3ccc(Oc4ncccc4C(F)(F)F)cc3)n3c(N)nccc23)C1] | 1-(3-(5-amino-3-(4-((3-(trifluoromethyl)pyridin-2-yl)oxy)phenyl)imidazo[1,5-c]pyrimidin-1-yl)pyrrolidin-1-yl)but-2-yn-1-one |
| C220 | 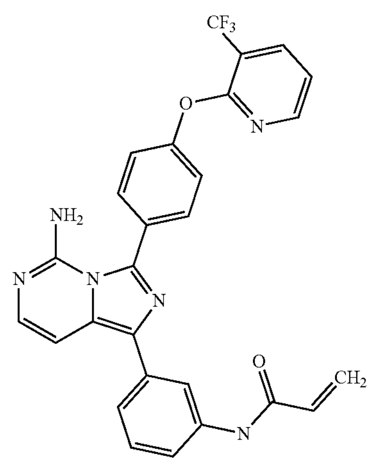 [SMILES: C=CC(=O)Nc1cccc(-c2nc(-c3ccc(Oc4ncccc4C(F)(F)F)cc3)n3c(N)nccc23)c1] | N-(3-(5-amino-3-(4-((3-(trifluoromethyl)pyridin-2-yl)oxy)phenyl)imidazo[1,5-c]pyrimidin-1-yl)phenyl)acrylamide |

TABLE 1-continued

Illustrative Compounds of the Present Invention

| Compound No. | Structure | Name |
|---|---|---|
| C221 | 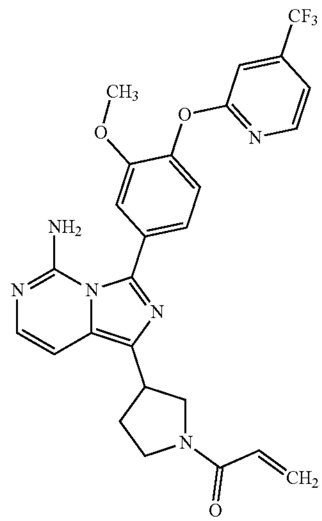 [SMILES: C=CC(=O)N1CCC(c2nc(-c3ccc(Oc4cc(C(F)(F)F)ccn4)c(OC)c3)n3c(N)nccc23)C1] | 1-(3-(5-amino-3-(3-methoxy-4-((4-(trifluoromethyl)pyridin-2-yl)oxy)phenyl)imidazo[1,5-c]pyrimidin-1-yl)pyrrolidin-1-yl)prop-2-en-1-one |
| C222 | 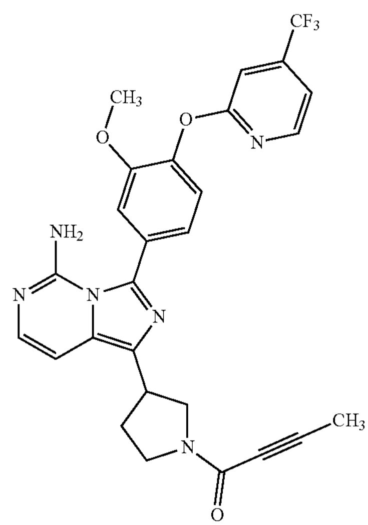 [SMILES: CC#CC(=O)N1CCC(c2nc(-c3ccc(Oc4cc(C(F)(F)F)ccn4)c(OC)c3)n3c(N)nccc23)C1] | 1-(3-(5-amino-3-(3-methoxy-4-((4-(trifluoromethyl)pyridin-2-yl)oxy)phenyl)imidazo[1,5-c]pyrimidin-1-yl)pyrrolidin-1-yl)but-2-yn-1-one |
| C223 | 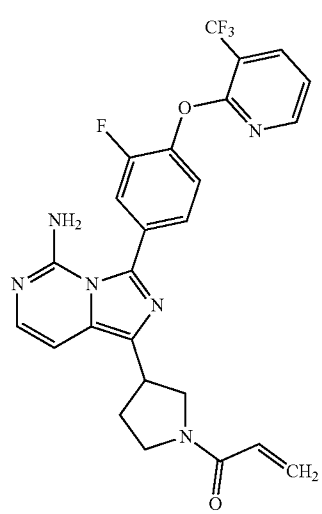 [SMILES: C=CC(=O)N1CCC(c2nc(-c3ccc(Oc4ncccc4C(F)(F)F)c(F)c3)n3c(N)nccc23)C1] | 1-(3-(5-amino-3-(3-fluoro-4-((3-(trifluoromethyl)pyridin-2-yl)oxy)phenyl)imidazo[1,5-c]pyrimidin-1-yl)pyrrolidin-1-yl)prop-2-en-1-one |

TABLE 1-continued

Illustrative Compounds of the Present Invention

| Compound No. | Structure | Name |
|---|---|---|
| C224 | 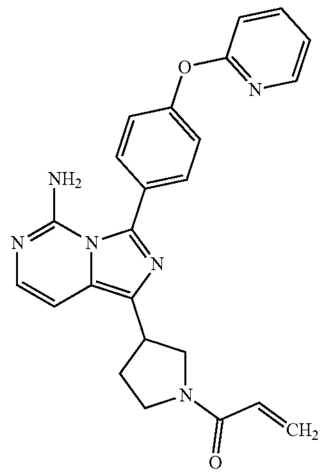 [SMILES: C=CC(=O)N1CCC(c2nc(-c3ccc(Oc4ccccn4)cc3)n3c(N)nccc23)C1] | (R/S))-1-(3-(5-amino-3-(4-(pyridin-2-yloxy)phenyl)imidazo[1,5-c]pyrimidin-1-yl)pyrrolidin-1-yl)prop-2-en-1-one |
| C225 | 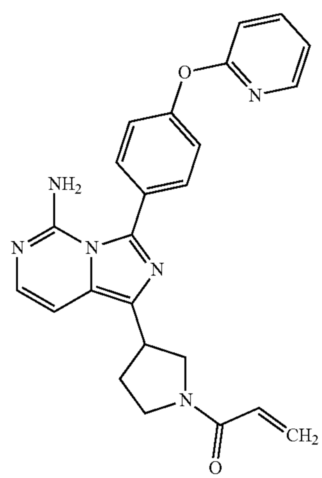 [SMILES: C=CC(=O)N1CCC(c2nc(-c3ccc(Oc4ccccn4)cc3)n3c(N)nccc23)C1] | (S/R)-1-(3-(5-amino-3-(4-(pyridin-2-yloxy)phenyl)imidazo[1,5-c]pyrimidin-1-yl)pyrrolidin-1-yl)prop-2-en-1-one |
| C226 | 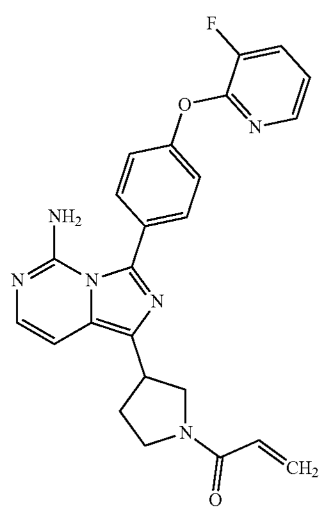 [SMILES: C=CC(=O)N1CCC(c2nc(-c3ccc(Oc4ncccc4F)cc3)n3c(N)nccc23)C1] | 1-(3-(5-amino-3-(4-((3-fluoropyridin-2-yl)oxy)phenyl)imidazo[1,5-c]pyrimidin-1-yl)pyrrolidin-1-yl)prop-2-en-1-one |

TABLE 1-continued

Illustrative Compounds of the Present Invention

| Compound No. | Structure | Name |
|---|---|---|
| C227 | 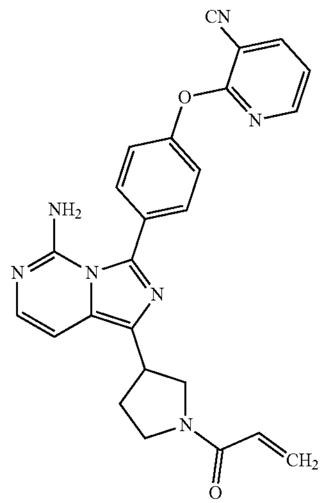 [SMILES: C=CC(=O)N1CCC(c2nc(-c3ccc(Oc4ncccc4C#N)cc3)n3c(N)nccc23)C1] | 2-(4-(1-(1-acryloylpyrrolidin-3-yl)-5-aminoimidazo[1,5-c]pyrimidin-3-yl)phenoxy)nicotinonitrile |
| C228 | 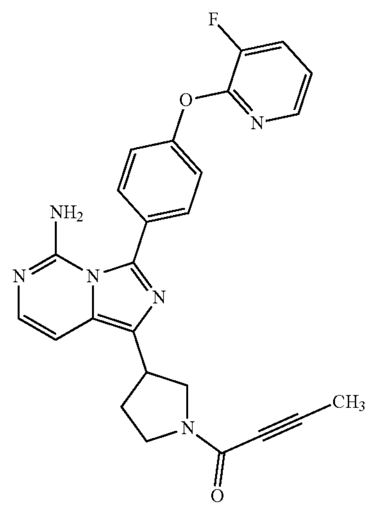 [SMILES: CC#CC(=O)N1CCC(c2nc(-c3ccc(Oc4ncccc4F)cc3)n3c(N)nccc23)C1] | 1-(3-(5-amino-3-(4-((3-fluoropyridin-2-yl)oxy)phenyl)imidazo[1,5-c]pyrimidin-1-yl)pyrrolidin-1-yl)but-2-yn-1-one |
| C229 | 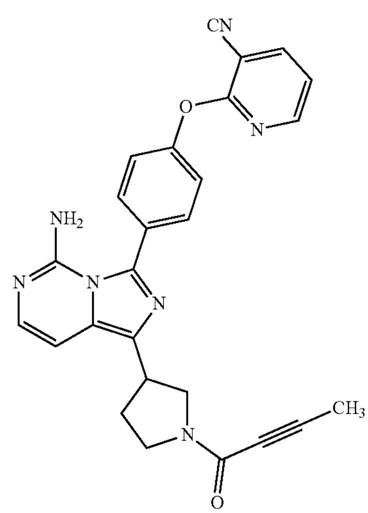 [SMILES: CC#CC(=O)N1CCC(c2nc(-c3ccc(Oc4ncccc4C#N)cc3)n3c(N)nccc23)C1] | 2-(4-(5-amino-1-(1-(but-2-ynoyl)pyrrolidin-3-yl)imidazo[1,5-c]pyrimidin-3-yl)phenoxy)nicotinonitrile |

TABLE 1-continued

Illustrative Compounds of the Present Invention

| Compound No. | Structure | Name |
|---|---|---|
| C230 | 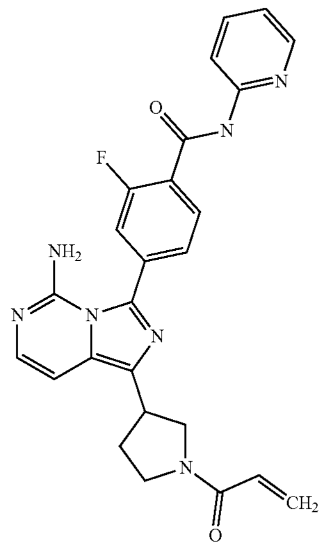 [SMILES: C=CC(=O)N1CCC(c2nc(-c3ccc(C(=O)Nc4ccccn4)c(F)c3)n3c(N)nccc23)C1] | 4-(1-(1-acryloylpyrrolidin-3-yl)-5-aminoimidazo[1,5-c]pyrimidin-3-yl)-2-fluoro-N-(pyridin-2-yl)benzamide |
| C231 | 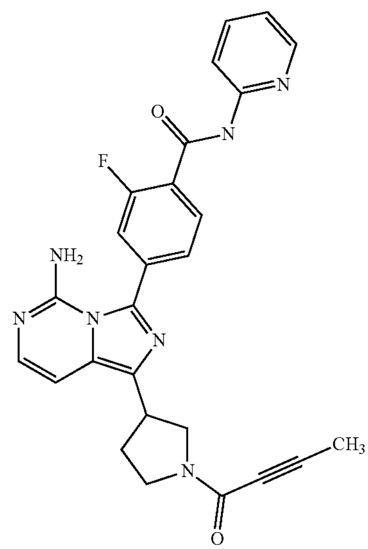 [SMILES: CC#CC(=O)N1CCC(c2nc(-c3ccc(C(=O)Nc4ccccn4)c(F)c3)n3c(N)nccc23)C1] | 4-(5-amino-1-(1-(but-2-ynoyl)pyrrolidin-3-yl)imidazo[1,5-c]pyrimidin-3-yl)-2-fluoro-N-(pyridin-2-yl)benzamide |
| C232 | 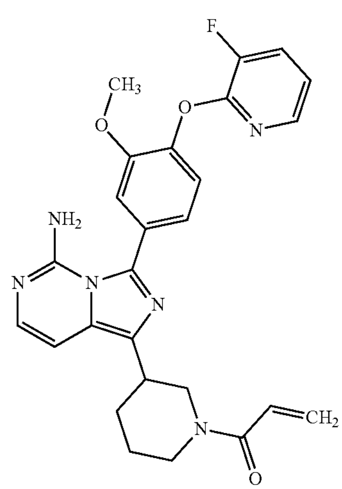 [SMILES: C=CC(=O)N1CCCC(c2nc(-c3ccc(Oc4ncccc4F)c(OC)c3)n3c(N)nccc23)C1] | 1-(3-(5-amino-3-(4-((3-fluoropyridin-2-yl)oxy)-3-methoxyphenyl)imidazo[1,5-c]pyrimidin-1-yl)piperidin-1-yl)prop-2-en-1-one |

TABLE 1-continued

Illustrative Compounds of the Present Invention

| Compound No. | Structure | Name |
|---|---|---|
| C233 | 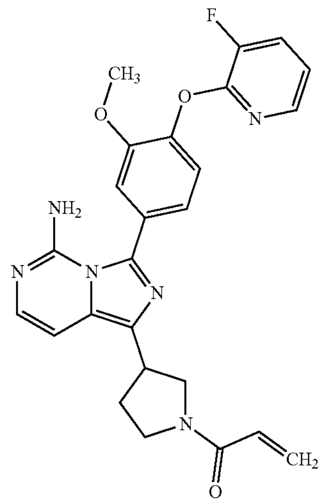 [SMILES: C=CC(=O)N1CCC(c2nc(-c3ccc(Oc4ncccc4F)c(OC)c3)n3c(N)nccc23)C1] | 1-(3-(5-amino-3-(4-((3-fluoropyridin-2-yl)oxy)-3-methoxyphenyl)imidazo[1,5-c]pyrimidin-1-yl)pyrrolidin-1-yl)prop-2-en-1-one |
| C234 | 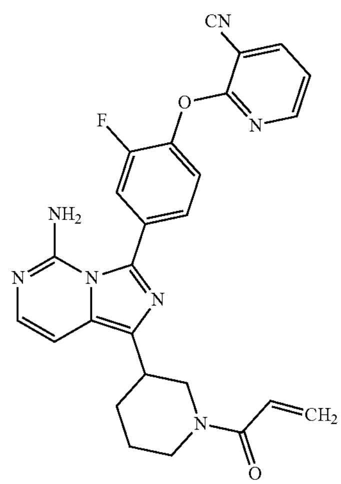 [SMILES: C=CC(=O)N1CCCC(c2nc(-c3ccc(Oc4ncccc4C#N)c(F)c3)n3c(N)nccc23)C1] | 2-(4-(1-(1-acryloylpiperidin-3-yl)-5-aminoimidazo[1,5-c]pyrimidin-3-yl)-2-fluorophenoxy)nicotinonitrile |
| C235 | 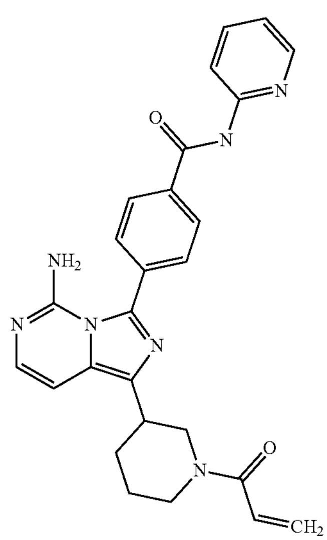 [SMILES: C=CC(=O)N1CCCC(c2nc(-c3ccc(C(=O)Nc4ccccn4)cc3)n3c(N)nccc23)C1] | 4-(1-(1-acryloylpiperidin-3-yl)-5-aminoimidazo[1,5-c]pyrimidin-3-yl)-N-(pyridin-2-yl)benzamide |

TABLE 1-continued
Illustrative Compounds of the Present Invention
| Compound No. | Structure | Name |
|---|---|---|
| C236 | 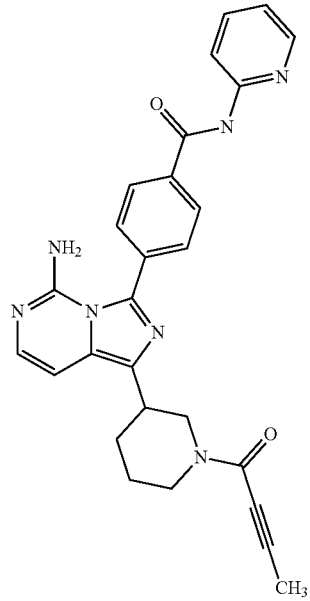 [SMILES: CC#CC(=O)N1CCCC(c2nc(-c3ccc(C(=O)Nc4ccccn4)cc3)n3c(N)nccc23)C1] | 4-(5-amino-1-(1-(but-2-ynoyl)piperidin-3-yl)imidazo[1,5-c]pyrimidin-3-yl)-N-(pyridin-2-yl)benzamide |
| C237 | 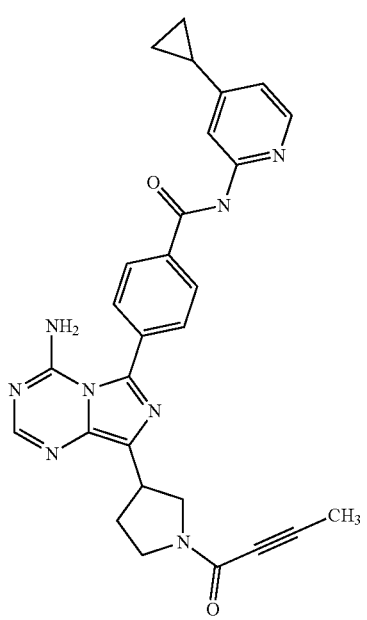 [SMILES: CC#CC(=O)N1CCC(c2nc(-c3ccc(C(=O)Nc4cc(C5CC5)ccn4)cc3)n3c(N)ncnc23)C1] | 4-(4-amino-8-(1-(but-2-ynoyl)pyrrolidin-3-yl)imidazo[1,5-a][1,3,5]triazin-6-yl)-N-(4-cyclopropylpyridin-2-yl)benzamide |

TABLE 1-continued
Illustrative Compounds of the Present Invention
| Compound No. | Structure | Name |
|---|---|---|
| C238 | 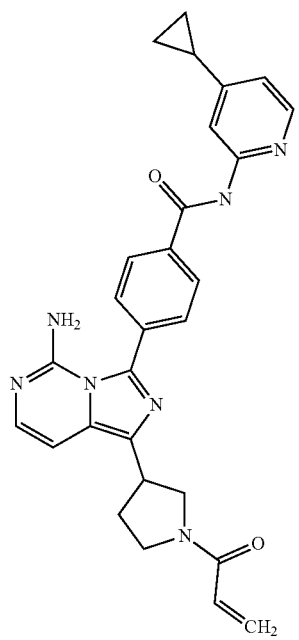 [SMILES: C=CC(=O)N1CCC(c2nc(-c3ccc(C(=O)Nc4cc(C5CC5)ccn4)cc3)n3c(N)nccc23)C1] | 4-(1-(1-acryloylpyrrolidin-3-yl)-5-aminoimidazo[1,5-c]pyrimidin-3-yl)-N-(4-cyclopropylpyridin-2-yl)benzamide |
| C239 | 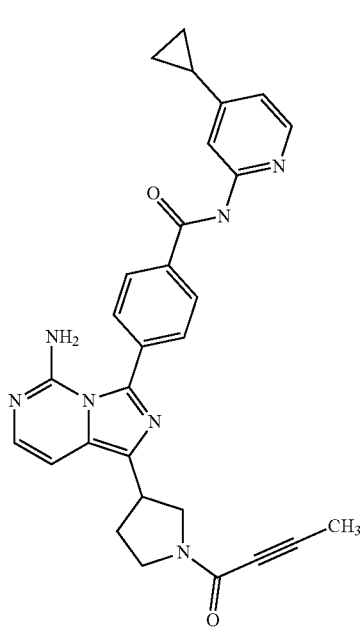 [SMILES: CC#CC(=O)N1CCC(c2nc(-c3ccc(C(=O)Nc4cc(C5CC5)ccn4)cc3)n3c(N)nccc23)C1] | 4-(5-amino-1-(1-(but-2-ynoyl)pyrrolidin-3-yl)imidazo[1,5-c]pyrimidin-3-yl)-N-(4-cyclopropylpyridin-2-yl)benzamide |

TABLE 1-continued

Illustrative Compounds of the Present Invention

| Compound No. | Structure | Name |
|---|---|---|
| C240 | 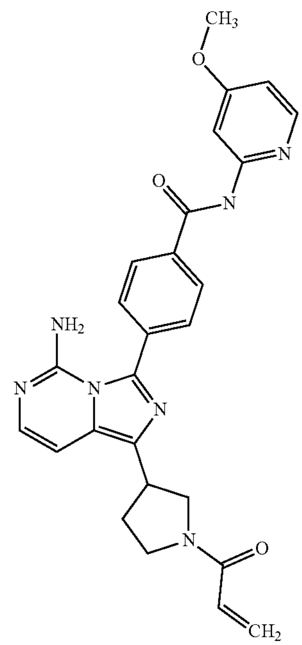 [SMILES: C=CC(=O)N1CCC(c2nc(-c3ccc(C(=O)Nc4cc(OC)ccn4)cc3)n3c(N)nccc23)C1] | 4-(1-(1-acryloylpyrrolidin-3-yl)-5-aminoimidazo[1,5-c]pyrimidin-3-yl)-N-(4-methoxypyridin-2-yl)benzamide |
| C241 | 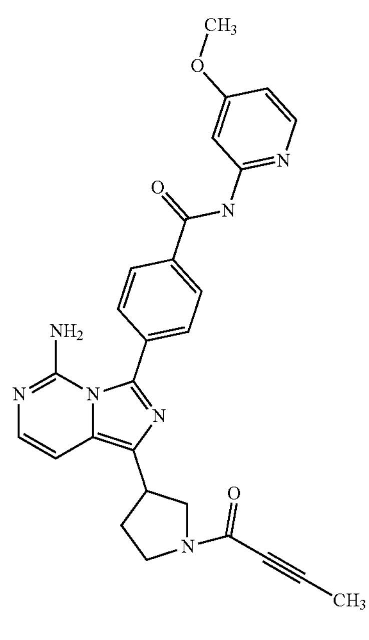 [SMILES: CC#CC(=O)N1CCC(c2nc(-c3ccc(C(=O)Nc4cc(OC)ccn4)cc3)n3c(N)nccc23)C1] | 4-(5-amino-1-(1-(but-2-ynoyl)pyrrolidin-3-yl)imidazo[1,5-c]pyrimidin-3-yl)-N-(4-methoxypyridin-2-yl)benzamide |

TABLE 1-continued
Illustrative Compounds of the Present Invention
| Compound No. | Structure | Name |
|---|---|---|
| C242 | 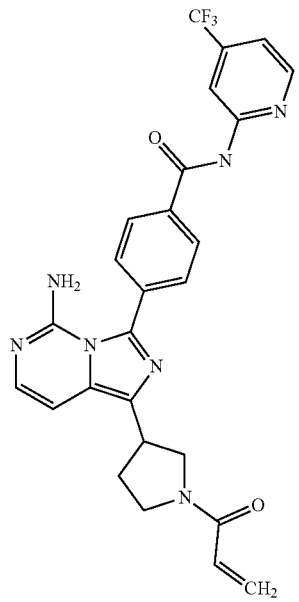 [SMILES: C=CC(=O)N1CCC(c2nc(-c3ccc(C(=O)Nc4cc(C(F)(F)F)ccn4)cc3)n3c(N)nccc23)C1] | 4-(1-(1-acryloylpyrrolidin-3-yl)-5-aminoimidazo[1,5-c]pyrimidin-3-yl)-N-(4-(trifluoromethyl)pyridin-2-yl)benzamide |
| C243 | 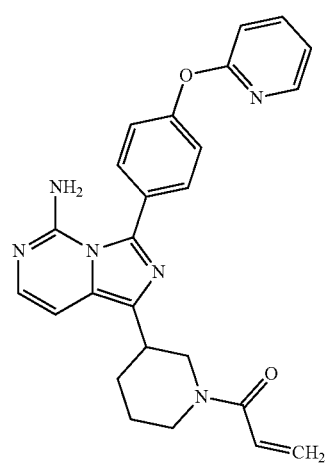 [SMILES: C=CC(=O)N1CCCC(c2nc(-c3ccc(Oc4ccccn4)cc3)n3c(N)nccc23)C1] | 1-(3-(5-amino-3-(4-(pyridin-2-yloxy)phenyl)imidazo[1,5-c]pyrimidin-1-yl)piperidin-1-yl)prop-2-en-1-one |

TABLE 1-continued
Illustrative Compounds of the Present Invention
| Compound No. | Structure | Name |
|---|---|---|
| C244 | 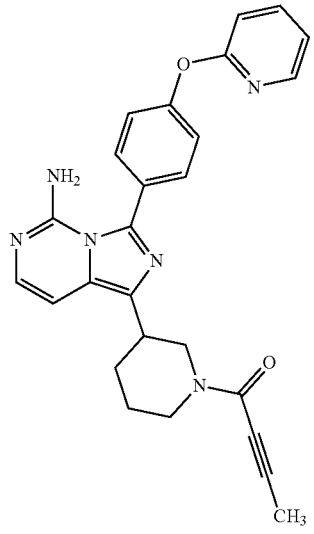 [SMILES: CC#CC(=O)N1CCCC(c2nc(-c3ccc(Oc4ccccn4)cc3)n3c(N)nccc23)C1] | 1-(3-(5-amino-3-(4-(pyridin-2-yloxy)phenyl)imidazo[1,5-c]pyrimidin-1-yl)piperidin-1-yl)but-2-yn-1-one |
| C245 | 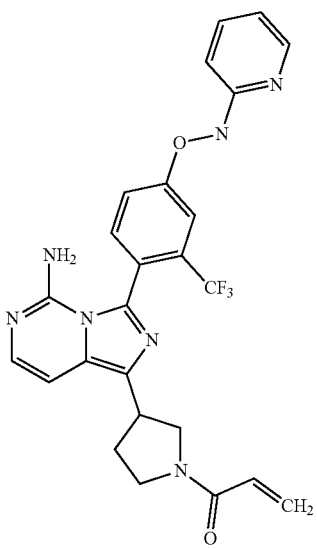 [SMILES: C=CC(=O)N1CCC(c2nc(-c3ccc(ONc4ccccn4)cc3C(F)(F)F)n3c(N)nccc23)C1] | 4-(1-(1-acryloylpyrrolidin-3-yl)-5-aminoimidazo[1,5-c]pyrimidin-3-yl)-N-(pyridin-2-yl)-3-(trifluoromethyl)benzamide |

TABLE 1-continued
Illustrative Compounds of the Present Invention
| Compound No. | Structure | Name |
|---|---|---|
| C246 | 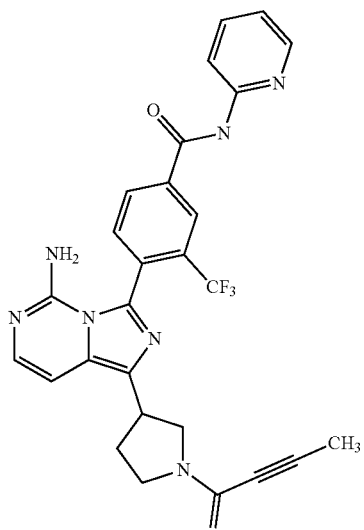 | 4-(5-amino-1-(1-(but-2-ynoyl)pyrrolidin-3-yl)imidazo[1,5-c]pyrimidin-3-yl)-N-(pyridin-2-yl)-3-(trifluoromethyl)benzamide |
| C247 | 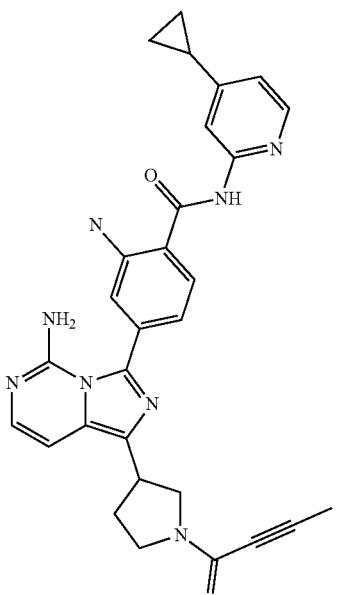 | 4-(5-amino-1-(1-(but-2-ynoyl)pyrrolidin-3-yl)imidazo[1,5-c]pyrimidin-3-yl)-N-(4-cyclopropylpyridin-2-yl)-2-fluorobenzamide |

TABLE 1-continued

Illustrative Compounds of the Present Invention

| Compound No. | Structure | Name |
|---|---|---|
| C248 | 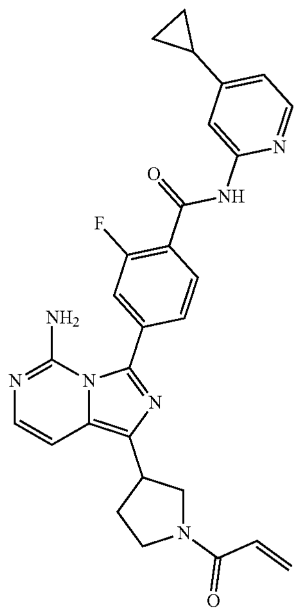 [SMILES: C=CC(=O)N1CCC(c2nc(-c3ccc(C(=O)Nc4cc(C5CC5)ccn4)c(F)c3)n3c(N)nccc23)C1] | 4-(1-(1-acryloylpyrrolidin-3-yl)-5-aminoimidazo[1,5-c]pyrimidin-3-yl)-N-(4-cyclopropylpyridin-2-yl)-2-fluorobenzamide |

In some embodiments, a compound of Formula I or II binds to a kinase including, but not limited to, Abl, Akt1, Akt2, Akt3, ALK, Alk5, A-Raf, B-Raf, Brk, BTK, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I or II binds to a kinase selected from the group consisting of EGFR, HER2, HER4, KDR, ALK, ARK5, BLK, BTK, FMS, ITK, JAK1, JAK2, JAK3, PLK1, PLK2, PLK3, PLK4, FAK, and SNARK In some embodiments, the compound of Formula I or II binds to a kinase selected from the group consisting of EGFR mutants such as EGFR del E746-A750, EGFR del E747-E749/A750P, EGFR del E747-S752/P753S, EGFR del E747-T751/Sins/A750P, EGFR del S752-1759, EGFR G719S, EGFR G719C, EGFR L861Q, EGFR L858R, EGFR T790M, EGFR L858R/T790M. For example, the compound of Formula I or II binds to a kinase which is EGFR L858R, EGFR T790M or EGFR L858R/T790M mutant. In some embodiments, a compound of Formula I or II binds to a kinase including, but not limited to, Abl, Akt1, Akt2, Akt3, ALK, Alk5, A-Raf, B-Raf, Brk, BTK, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof, with a Kd which is lower than 50 µM, 25 µM, 10 µM, 5 µM, or 1 µM as measured in an in vitro assay. For example, the compound of Formula I or II binds to a kinase selected from the group consisting of EGFR, EGFR L858R, EGFR T790M, EGFR del E746-A750, or EGFR L858R/T790M mutant, Her2, Her4, Fak, FGFR1, FGFR2, FGFR3, FGFR4, BTK, Met, Pim1, Pim2, Pim3, Pyk2, KDR, Src and Ret, and any mutated versions thereof with a Kd which is lower than 50 µM, 25 µM, 10 µM, 5 µM, or 1 µM as measured in an in vitro assay. In some embodiments, the compound of Formula I or II binds to a kinase selected from the group consisting of BTK, KDR, EGFR, EGFR L858R, EGFR T790M or EGFR L858R/T790M mutant with a Kd which is lower than 50 µM, 25 µM, 10 µM, 5 µM, or 1 µM as measured in an in vitro assay. For example, the compound of Formula I or II binds to a kinase which is EGFR, EGFR L858R, EGFR T790M, EGFR del E746-A750, EGFR L858R/T790M mutant with a Kd which is lower than 50 µM, 25 µM, 10 µM, 5 µM, or 1 µM as measured in an in vitro assay.

In some embodiments, a compound of Formula I or II inhibits a kinase including, but not limited to, Abl, Akt1, Akt2, Akt3, ALK, Alk5, A-Raf, B-Raf, Brk, BTK, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I or II inhibits a kinase selected from the group consisting of EGFR, BTK, Fak, FGFR1, FGFR2, FGFR3, FGFR4, Jnk1, Jnk2, Jnk3, Lck, Lyn, Met, Pim1, Pim2, Pim3, Pyk2, KDR, Src and Ret, and any mutated versions thereof. In some embodiments, the compound of Formula I or II inhibits a kinase selected from the group consisting of BTK, EGFR, EGFR L858R, EGFR del E746-A750, EGFR T790M or EGFR L858R/T790M mutant. For example, the compound of Formula I or II inhibits a kinase which is EGFR or EGFR L858R/T790M mutant. In some embodiments, a compound of Formula I or II inhibits a kinase including, but not limited to, Abl, Akt1, Akt2, Akt3, ALK, Alk5, A-Raf, B-Raf, Brk, BTK, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof with an $IC_{50}$ in an in vitro assay of M, 5 µM, 2 µM, 1 µM, 500 nM, 200 nM, 100 nM or less as ascertained in an in vitro kinase assay. For example, the compound of Formula I or II inhibits a kinase selected from the group consisting of EGFR, HER2, HER3, HER4, KDR, ALK, ARK5, BLK, BTK, FGFR1, FGFR2, FGFR3, FMS, ITK, JAK1, JAK2, JAK3, PLK1, PLK2, PLK3, PLK4, FAK, and SNARK, Src and Ret, and any mutated versions thereof with an $IC_{50}$ in an in vitro assay of 10 µM, 5 µM, 2 µM, 1 µM, 500 nM, 200 nM, 100 nM or less as ascertained in an in vitro kinase assay. In some embodiments, the compound of Formula I or II inhibits a kinase selected from the group consisting of EGFR, EGFR L858R, EGFR del E746-A750, EGFR T790M or EGFR L858R/T790M mutant with an $IC_{50}$ in an in vitro assay of 10 µM, 5 µM, 2 µM, 1 µM, 500 nM, 200 nM, 100 nM or less as ascertained in an in vitro kinase assay. For example, the compound of Formula I or II inhibits a kinase which is EGFR or EGFR L858R/T790M mutant with an $IC_{50}$ in an in vitro assay of 10 µM, 5 µM, 2 µM, 1 µM, 500 nM, 200 nM, 100 nM or less as ascertained in an in vitro kinase assay.

In some embodiments, the compound of Formula I or II inhibits the activity of one or more kinases selected from the group consisting of BTK, EGFR, EGFR L858R, EGFR T790M or EGFR L858R/T790M with an $IC_{50}$ in an in vitro assay of 1 µM, 500 nM, 200 nM, 100 nM, 50 nM, 25 nM or less as ascertained in an in vitro kinase assay.

In some embodiments, the compound of Formula I or II selectively inhibits the activity of one or more kinases selected from the group consisting of Abl, Akt1, Akt2, Akt3, ALK, Alk5, A-Raf, B-Raf, Brk, BTK, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3alpha, Gsk3beta, HCK, Her2/Erbb2, Her4/Erbb4, IGFIR, IKK beta, Irak4, Itk, Jak1, Jak2, Jak3, Jnk1, Jnk2, Jnk3, KDR, Kit, Lek, Lyn, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutated versions thereof. For example, the compound of Formula I or II selectively inhibits the activity of one or more kinases selected from the group consisting of EGFR, EGFR L858R, EGFR T790M, EGFR del E746-A750 or EGFR L858R/T790M, HER2, HER3, HER4, KDR, ALK, ARK5, BLK, BTK, FGFR1, FGFR2, FGFR3, FMS, ITK, JAK1, JAK2, JAK3, PLK1, PLK2, PLK3, PLK4, FAK, and SNARK, Src and Ret, In some embodiments, the compound of Formula I or II selectively inhibits the activity of one or more kinases selected from the group consisting of EGFR, EGFR L858R, EGFR T790M, EGFR del E746-A750 or EGFR L858R/T790M mutant.

In some embodiments, the compound of Formula I or II selectively inhibits the activity of, EGFR L858R, EGFR T790M, EGFR del E746-A750, or EGFR L858R/T790M mutant relative to one or more kinases selected from the group consisting of ABL1, AKT1 (PKB alpha), AURKB (Aurora B), BLK, BTK, CDK1/cyclin B, CHEK1 (CHK1), CSF1R (FMS), CSNKIG2 (CK1 gamma 2), EGFR (ErbB1), FGFR1, FGFR2, FGFR3, FGR, FLT3, FRAP1 (mTOR), FYN, IGFIR, IKBKB (IKK beta), INSR, JAK1, JAK2, JAK3, KDR, KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRC, SRMS (Srm), and YES1. In some embodiments, the compound of Formula I or II selectively inhibits the activity of one or more kinases selected from the group consisting of BTK, EGFR L858R, EGFR T790M EGFR del E746-A750, or EGFR L858R/T790M with an $IC_{50}$ which is ½, ⅓$^{rd}$, ¼$^{th}$, ⅕$^{th}$, 1/7$^{th}$, 1/10$^{th}$, 1/15$^{th}$, 1/20$^{th}$, 1/25$^{th}$, 1/30$^{th}$, 1/40$^{th}$, 1/50$^{th}$, 1/100$^{th}$, 1/150$^{th}$, 1/200$^{th}$, 1/300$^{th}$, 1/400$^{th}$, 1/500$^{th}$, 1/1000$^{th}$, 1/2000$^{th}$ or less than the $IC_{50}$ for a kinase selected from the group consisting of ABL1, AKT1 (PKB alpha), AURKB (Aurora B), BLK, BTK, CDK1/cyclin B, CHEK1 (CHK1), CSNK1G2 (CK1 gamma 2), EGFR (ErbB1), FGFR1, FGFR2, FGFR3, FGR, FLT3, FRAP1 (mTOR), FYN, IGF1R, IKBKB (IKK beta), INSR, JAK1, JAK2, JAK3, KDR, KIT, LCK, LYN A, MAP2K1 (MEK1), MAP4K5 (KHS1), MAPK1 (ERK2), MAPK14 (p38 alpha), MAPKAPK2, MET (cMet), PDGFRB (PDGFR beta), PIK3CA/PIK3R1 (p110 alpha/p85 alpha)PRKCB2 (PKC beta II), PTK2B (FAK2), PTK6 (Brk), RAF1 (cRAF) Y340D Y341D, RET, RPS6KB1 (p70S6K), SRC, SRMS (Srm), and YES1.

In some embodiments, one or more compounds of Formula I or II are capable of inhibiting cellular proliferation. For example, In some embodiments, one or more compounds of Formula I or II inhibit proliferation of tumor cells or tumor cell lines. For example, such cell lines express a kinase which is EGFR L858R, EGFR T790M, EGFR del E746-A750, or EGFR L858R/T790M mutant. In some embodiments, the compounds of Formula I or II inhibit A549, A431, HCC827 or H1975 cell proliferation in vitro or in an in vivo model such as a xenograft mouse model. In some embodiments, in vitro cultured HCC827 or H1975 cell proliferation may be inhibited with an $IC_{50}$ of less than 100 µM, 75 µM, 50 µM, 25 µM, 15 µM, 10 µM, 5 µM, 3 µM, 2 µM, 1 µM or less by one or more compounds of Formula I or II.

B. Methods of Making

Compounds disclosed herein may be prepared by the routes described below. Materials used herein are either commercially available or prepared by synthetic methods generally known in the art. These schemes are not limited to the compounds listed or by any particular substituents, which are employed for illustrative purposes. Although various steps of are described and depicted in Scheme A, the steps in some cases may be performed in a different order than the order shown in Scheme A. Various modifications to these synthetic reaction schemes may be made and will be suggested to one skilled in the art having referred to the disclosure contained in this Application. Numbering does not necessarily correspond to that of claims or other tables.

Scheme A

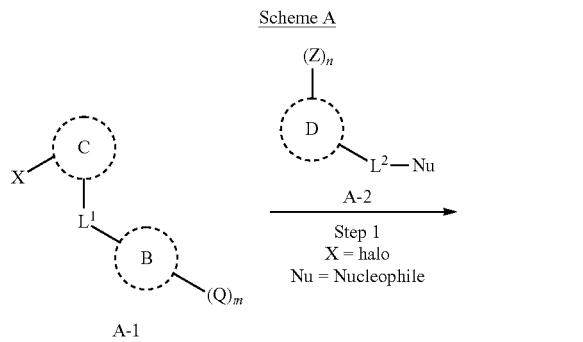

In Scheme A, A-1 is reacted with A-2 in the presence of a base or acid gives compounds of Formula I. Suitable bases include, but are not limited to, $Cs_2CO_3$, NaH, KH, t-BuOK, LiH, and $CaH_2$. Suitable acids include, but are not limited to, HCl, TFA, acetic acid, $MeSO_3H$, and p-toluenesulfonic acid. Suitable solvents include, but are not limited to, DMF, DMSO, DMA, and N-methyl piperidone. The reaction are generally carried out at a temperature ranging from 25 to 240° C.

Scheme B

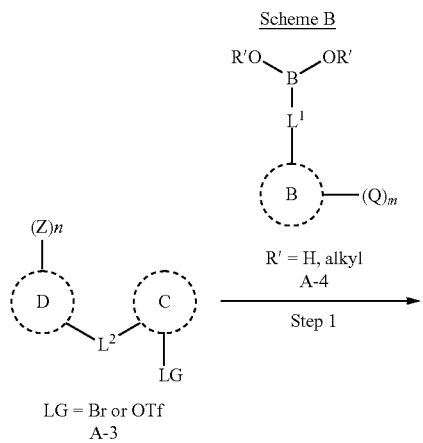

-continued

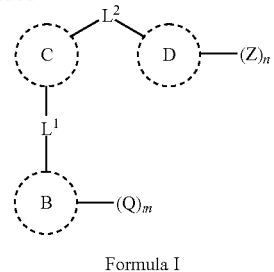

In Scheme B, Suzuki cross-coupling reaction of A-3 with boronic acid or ester A-4 in the presence of a base, such as $Na_2CO_3$, $K_2CO_3$, $Cs_2CO_3$, and a Pd catalyst, gives compounds of Formula I. The reaction is generally carried out at a temperature ranging from 25 to 180° C. in a suitable solvent such as 1,4-dioxane, water, tetrahydrofuran, or a mixture thereof.

C. Pharmaceutical Compositions and Formulations

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound of Formula I or II, and a pharmaceutically acceptable diluent(s), excipient(s), or carrier(s). In certain embodiments, the compounds described are administered as pharmaceutical compositions in which compounds of Formula I or II, are mixed with other active ingredients, as in combination therapy. Encompassed herein are all combinations of actives set forth in the combination therapies section below and throughout this disclosure. In specific embodiments, the pharmaceutical compositions include one or more compounds of Formula I or II.

A pharmaceutical composition, as used herein, refers to a mixture of a compound of Formula I or II, with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of Formula I or II, provided herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of Formula I or II, is formulated in an aqueous solution. In specific embodiments, the aqueous solution is selected from, by way of example only, a physiologically compatible buffer, such as Hank's solution, Ringer's solution, or physiological saline buffer. In other embodiments, one or more compound of Formula I or II, is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein, including compounds of Formula I or II, are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of a compound of Formula I or II is formulated in a form suitable for parenteral injection as sterile suspension, solution or emulsion in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of Formula I or II are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Formula I or II are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Formula I or II, is accomplished by means of iontophoretic patches and the like. In certain embodiments, transdermal patches provide controlled delivery of the compounds of Formula I or II. In specific embodiments, the rate of absorption is slowed by using rate-controlling membranes or by trapping the compound within a polymer matrix or gel. In alternative embodiments, absorption enhancers are used to increase absorption.

Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of Formula I or II, are formulated for administration by inhalation. Various forms suitable for administration by inhalation include, but are not limited to, aerosols, mists or powders. Pharmaceutical compositions of Formula I or II, are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of Formula I or II, are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of Formula I or II, are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Formula I or II, described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, a pharmaceutical composition comprising at least one compound of Formula I or II, illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of Formula I or II. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

D. Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

E. Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products Include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack.

Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

F. Methods of Use

The chemical entities described herein are useful in the treatment, or in the preparation of a medicament for the treatment of various disorders. For example, compounds of Formula I or II are useful as inhibitors of protein kinases. In some embodiments, the chemical entities described herein are inhibitors of one or more kinases. For example, compounds of Formula I or II are inhibitors of BTK or EGFR or mutants of such kinases, including the EGFR del E746-A750, EGFR del E747-E749/A750P, EGFR del E747-S752/P753S, EGFR del E747-T751/Sins/A750P, EGFR del S752-I759, EGFR G719S, EGFR G719C, EGFR L861Q, EGFR L858R, EGFR T790M or EGFR L858R/T790M mutant. Thus, without wishing to be bound by any particular theory, the compounds of Formula I or II are particularly useful for treating or lessening the severity of a disease, condition, or disorder where activation of one or more kinases, such as EGFR, which is implicated in the disease, condition, or disorder. When activation of EGFR kinase is implicated in a particular disease, condition, or disorder, the disease, condition, or disorder may also be referred to as "EGFR-mediated disease" or disease symptom. Accordingly, in another aspect, the present invention provides a method for treating or lessening the severity of a disease, condition, or disorder where activation of EGFR and/or other kinases is implicated in the disease state.

The inhibition of kinases may be assayed in vitro, in vivo or in a cell line. In vitro assays include assays that determine inhibition of either the phosphorylation activity or ATPase activity of activated kinase. Alternate in vitro assays quantitate the ability of the inhibitor to bind to kinase. Inhibitor binding may be measured by radiolabelling the inhibitor prior to binding, isolating the inhibitor, complex and determining the amount of radiolabel bound. Alternatively, inhibitor binding may be determined by running a competition experiment where new inhibitors are incubated with kinase bound to known radioligands. At 1 micro-molar concentration, one or more compounds of the present invention exhibits at least about 50%, 60%, 70, 80%, 90% or even higher inhibition of kinases including BTK, EGFR, EGFR L858R, EGFR del E746-A750, EGFR T790M or EGFR L858R/T790M.

The chemical entities described herein may be prepared in substantially pure form, typically by standard chromatographic methods, prior to formulation in a pharmaceutically acceptable form.

The chemical entities described herein may be used in treating a variety of cancers. Cancers that can be prevented and/or treated by the chemical entities, compositions, and methods described herein include, but are not limited to, human sarcomas and carcinomas, e.g. carcinomas, e.g., colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the chemical entities described herein are used for the treatment of cancers of the
  i. digestive system including, without limitation, the esophagus, stomach, small intestine, colon (including colorectal), liver & intrahepatic bile duct, gallbladder & other biliary, pancreas, and other digestive organs;
  ii. respiratory system, including without limitation, larynx, lung & bronchus, and other respiratory organs;
  iii. skin;
  iv. thyroid;
  v. breast;
  vi. genital system, including without limitation, uterine cervix, ovary, and prostate;
  vii. urinary system, including without limitation, urinary bladder and kidney and renal pelvis; and
  viii. oral cavity & pharynx, including without limitation, tongue, mouth, pharynx, and other oral cavity.

In some embodiments, the chemical entities described herein are used for the treatment of colon cancer, liver cancer, lung cancer, melanoma, thyroid cancer, breast cancer, ovarian cancer, and oral cancer.

In some embodiments, the methods described herein can be used to treat a B-cell proliferative disorder, which include, but are not limited to diffuse large B cell lymphoma, follicular lymphoma, chronic lymphocytic lymphoma, chronic lymphocytic leukemia, B-cell prolymphocytic leukemia, lymphoplamacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

The chemical entities described herein may also be used in conjunction with other well known therapeutic agents that are selected for their particular usefulness against the condition that is being treated. For example, the chemical entities described herein may be useful in combination with at least one additional anti-cancer and/or cytotoxic agents. Further, the chemical entities described herein may also be useful in combination with other inhibitors of parts of the signaling pathway that links cell surface growth factor receptors to nuclear signals initiating cellular proliferation.

Such known anti-cancer and/or cytotoxic agents that may be used in combination with the chemical entities described herein include:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycinC, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3methylenedioxyanilino)-7-[2-(4-methylpiperazin-1-yl)ethoxy]-5-tetrahydropyran-4yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4ylamino}thiazole-5-carboxamide (dasatinib, BMS-354825; J. Med. Chem., 2004, 47, 66586661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifamib (RI15777) and lonafarmib (SCH66336)), inhibitors of cell signalling through MEK and/or AKT kinases, c-kit inhibitors, abl kinase inhibitors, P13 kinase inhibitors, Plt3 kinase inhibitors, CSF-IR kinase inhibitors, IGF receptor (insulin like growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4•{4-fluoro-2-methylindol-5-yloxy)-6-methoxy-7-(3pyrrolidin-1-ylpropoxy)quinazoline (AZD2171; Example 240 within WO 00/47212), compounds such as those disclosed in International Patent Applications WO 97/22596, WO 97/30035, WO 97/32856 and WO 98/13354 and compounds that work by other mechanisms (for example linomide, inhibitors of integrin av~3 function and angiostatin));

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase subject tolerance to chemotherapy or radiotherapy such as multi-drug resistance gene therapy; and (x) immunotherapy approaches, including for example ex-vivo and in-vivo approaches to increase the immunogenicity of subject's tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

(xi) checkpoint inhibitors, including for example inhibitors of checkpoint proteins such as PD-1, PD-L1 or TCLA-4. Some examples of checkpoint inhibitors are pembrolizumab, nivoluma and Ipilimumab.

In certain embodiments, the at least one chemical entity is administered in combination with one or more agents chosen from pacliataxel, bortezomib, dacarbazine, gemcitabine, trastuzumab, bevacizumab, capecitabine, docetaxel, erlotinib, aromatase inhibitors, such as AROMASIN™ (exemestane), and estrogen receptor inhibitors, such as FASLODEX™ (fulvestrant).

When a chemical entity described herein is administered into a human subject, the daily dosage will normally be determined by the prescribing physician with the dosage generally varying according to the age, weight, and response of the individual subject, as well as the severity of the subject's symptoms.

In one exemplary application, a suitable amount of at least one chemical entity is administered to a mammal undergoing treatment for cancer, for example, breast cancer. Administration typically occurs in an amount of between about 0.01 mg/kg of body weight to about 100 mg/kg of body weight per day (administered in single or divided doses), such as at least about 0.1 mg/kg of body weight per day. A particular therapeutic dosage can include, e.g., from about 0.01 mg to about 1000 mg of the chemical entity, such as including, e.g., from about 1 mg to about 1000 mg. The quantity of the at least one chemical entity in a unit dose of preparation may be varied or adjusted from about 0.1 mg to 1000 mg, such as from about 1 mg to 300 mg, for example 10 mg to 200 mg, according to the particular application. The amount administered will vary depending on the particular $IC_{50}$ value of the at least one chemical entity used and the judgment of the attending clinician taking into consideration factors such as health, weight, and age. In combinational applications in which the at least one chemical entity described herein is not the sole active ingredient, it may be possible to administer lesser amounts of the at least one chemical entity and still have therapeutic or prophylactic effect.

In some embodiments, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one chemical entity. Thereafter, the dosage is increased by small amounts until the optimum effect under the circumstances is reached. For convenience, the total daily dosage may be divided and administered in portions during the day if desired.

The amount and frequency of administration of the at least one chemical entities described herein, and if applicable other chemotherapeutic agents and/or radiation therapy, will be regulated according to the judgment of the attending clinician (physician) considering such factors as age, condition and size of the subject as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the subject, and in view of the observed responses of the disease to the administered therapeutic agents.

Also, in general, the at least one chemical entities described herein need not be administered in the same pharmaceutical composition as a chemotherapeutic agent, and may, because of different physical and chemical characteristics, be administered by a different route. For example, the chemical entities/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemical entity (and where appropriate, chemotherapeutic agent and/or radiation) will depend upon the diagnosis of the attending physicians and their judgment of the condition of the subject and the appropriate treatment protocol.

The chemical entities described herein (and where appropriate chemotherapeutic agent and/or radiation) may be administered concurrently (e.g., simultaneously, essentially simultaneously or within the same treatment protocol) or sequentially, depending upon the nature of the proliferative disease, the condition of the subject, and the actual choice of chemotherapeutic agent and/or radiation to be administered in conjunction (i.e., within a single treatment protocol) with the chemical entity/composition.

In combinational applications and uses, the chemical entity/composition and the chemotherapeutic agent and/or radiation need not be administered simultaneously or essentially simultaneously, and the initial order of administration of the chemical entity/composition, and the chemotherapeutic agent and/or radiation, may not be important. Thus, the at least one chemical entity described herein may be administered first followed by the administration of the chemotherapeutic agent and/or radiation; or the chemotherapeutic agent and/or radiation may be administered first followed by the administration of the at least one chemical entity described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject. For example, the chemotherapeutic agent and/or radiation may be administered first, and then the treatment continued with the administration of the at least one chemical entity described herein followed, where determined advantageous, by the administration of the chemotherapeutic agent and/or radiation, and so on until the treatment protocol is complete.

Thus, in accordance with experience and knowledge, the practicing physician can modify each protocol for the administration of a chemical entity/composition for treatment according to the individual subject's needs, as the treatment proceeds.

The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

The following examples serve to more fully describe the manner of using the invention. These examples are presented for illustrative purposes and should not serve to limit the true scope of the invention.

In carrying out the procedures of the methods described herein, it is of course to be understood that references to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Example 1: Preparation of N-(3-(2,6-diphenylquinazolin-8-yl)phenyl)acrylamide

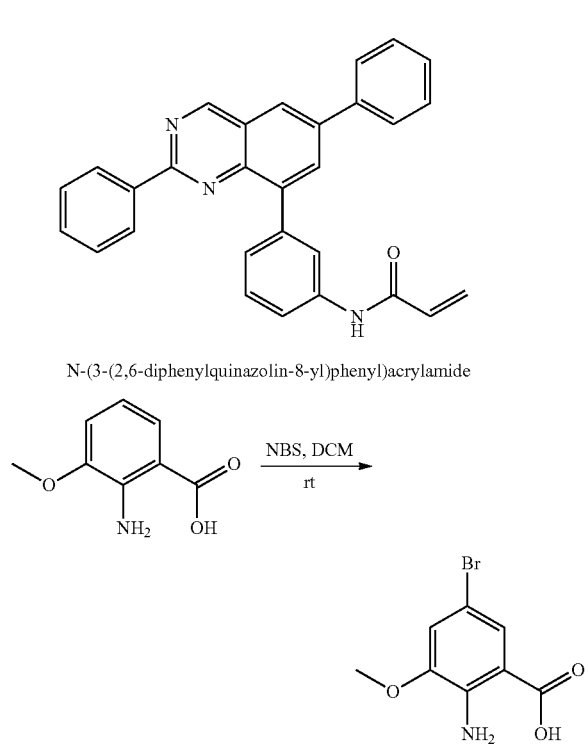

N-(3-(2,6-diphenylquinazolin-8-yl)phenyl)acrylamide

To a solution of 2-amino-3-methoxybenzoic acid (10.0 g, 59.8 mmol, 1.0 eq) in DCM (150 mL) was added NBS (10.6 g, 59.8 mmol, 1.0 eq) and the mixture was stirred at rt for 2 h. The solid was filtered and washed with DCM (100 mL×2) to provide 2-amino-5-bromo-3-methoxybenzoic acid as a grey solid (12.1 g, 82.2%).

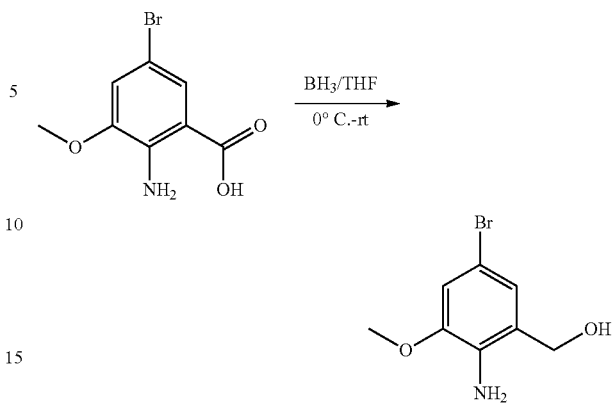

To a solution of 2-amino-5-bromo-3-methoxybenzoic acid (6.0 g, 29.3 mmol, 1.0 eq) in THF (130 mL) was added borohydride in THF (140.8 mL, 1N) under ice/water bath and the reaction mixture was stirred at 50° C. overnight. Then the mixture was cooled to 0° C., quenched with MeOH (50 mL) and concentrated to 25 mL. The residue was diluted with aqueous $Na_2CO_3$ (200 mL) and extracted with EA (100 mL×3). The organic layers were separated, combined, dried over $Na_2SO_4$, filtered and concentrated to afford (2-amino-5-bromo-3-methoxyphenyl)methanol (5.1 g, 91%).

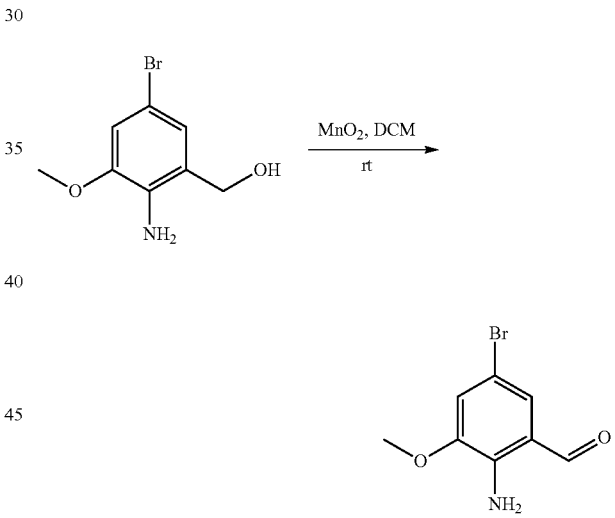

A mixture of (2-amino-5-bromo-3-methoxyphenyl)methanol (5.1 g, 22 mmol, 1.0 eq) and $MnO_2$ (9.6 g, 110 mmol, 5 eq) in DCM (200 mL) was stirred at rt overnight. The solid was filtered off and the filtrate was concentrated to provide 2-amino-5-bromo-3-methoxybenzaldehyde as a brown solid (4.9 g, 96.8%).

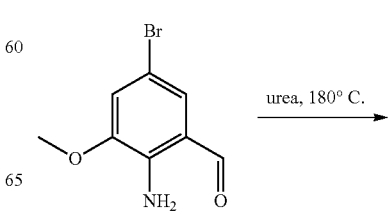

-continued

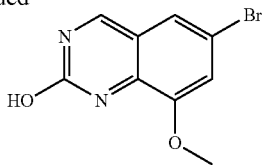

A mixture of 2-amino-5-bromo-3-methoxybenzaldehyde (4.9 g, 21.3 mmol, 1.0 eq) and urea (19.2 g, 320 mmol, 15.0 eq) was stirred at 180° C. for 2 h, then cooled and poured into ice-water. The solid was collected by filtration, washed with H$_2$O for three times, and dried in vacuo to afford 6-bromo-8-methoxyquinazolin-2-ol as a grey solid (4.1 g, 75.5%).

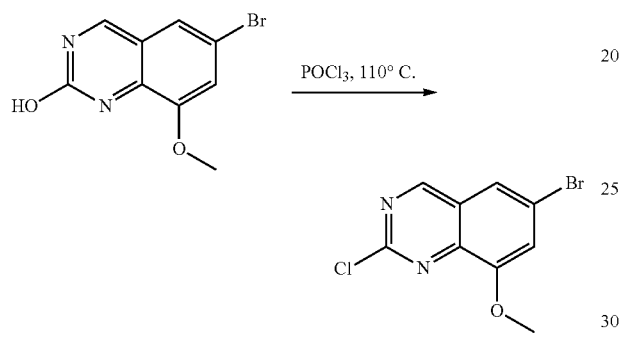

A solution of 6-bromo-8-methoxyquinazolin-2-ol (3.9 g, 15.3 mmol, 1.0 eq) in POCl$_3$ (30 mL) was refluxed for 5 h, then cooled to rt and concentrated. The resulting residue was dissolved in EA (100 mL) and poured into ice-water with vigorous stirring. The organic phase was separated and washed with brine, dried over anhydrous Na$_2$SO$_4$ and concentrated. The resulting residue was purified by column chromatography (PE/EA=4:1, v/v) to afford 6-bromo-2-chloro-8-methoxyquinazoline as a yellow solid (1.3 g, 31.2%).

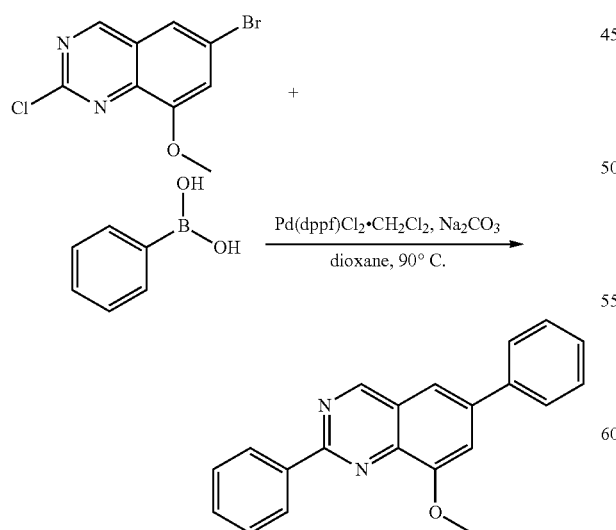

To a solution of 6-bromo-2-chloro-8-methoxyquinazoline (500.0 mg, 1.8 mmol, 1.0 eq) and phenylboronic acid (672.0 mg, 5.5 mmol, 3.0 eq) in dioxane (20 mL) was added Na$_2$CO$_3$ (389.0 mg, 3.7 mmol, 2.0 eq), followed by Pd(dppf)Cl$_2$ (75 mg, 0.092 mmol, 0.05 eq) under N$_2$. The mixture was stirred at 90° C. for 12 h, then cooled to rt, diluted with EA (40 mL) and filtered. The filtrate was concentrated and the resulting residue was purified by column chromatography (PE/EA=4/1, v/v) to afford 8-methoxy-2,6-diphenylquinazoline as a yellow solid (230.0 mg, 40.2%).

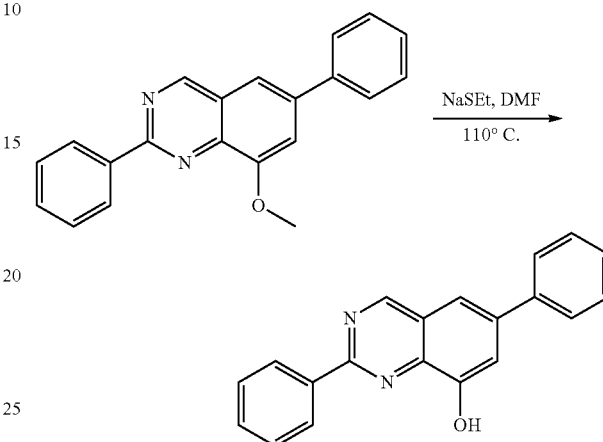

To a solution of 8-methoxy-2,6-diphenylquinazoline (130.0 mg, 0.4 mmol, 1.0 eq) in DMF (8.0 mL) was added sodium ethanethiolate (109.2 mg, 1.3 mmol, 3.0 eq). The mixture was heated at 110° C. overnight under N$_2$, then cooled and concentrated. The residue was diluted with MeOH (4.0 mL) and EA (60.0 mL), washed with 1N HCl (5.0 mL×2). The combined organic layer was dried over anhydrous Na$_2$SO$_4$ and concentrated. The residue was purified by column chromatography to provide 2,6-diphenylquinazolin-8-ol as a yellow solid (100.0 mg, 80.6%).

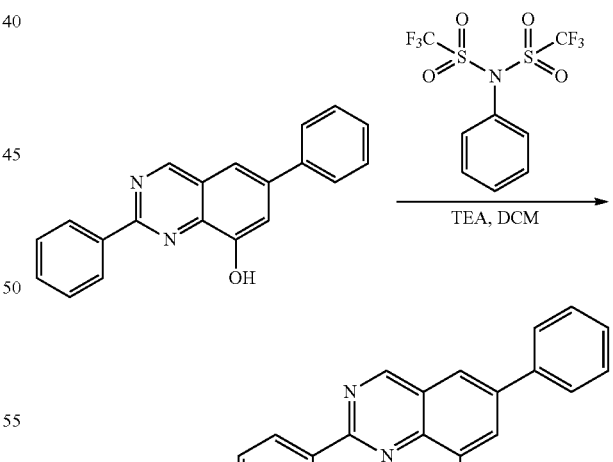

To a solution of 2,6-diphenylquinazolin-8-ol (320.0 mg, 1.1 mmol, 1.0 eq) and TEA (0.8 mL, 5.4 mmol, 5.0 eq) in DCM (15.0 mL) was added PhN(OTf)$_2$ (1.2 g, 3.2 mmol, 3.0 eq). The mixture was stirred at rt overnight, then concentrated. The residue was purified by column chromatography (PE/EA=4/1) to provide 2,6-diphenylquinazolin-8-yl trifluoromethanesulfonate as a yellow solid (434.0 mg, 94.0%).

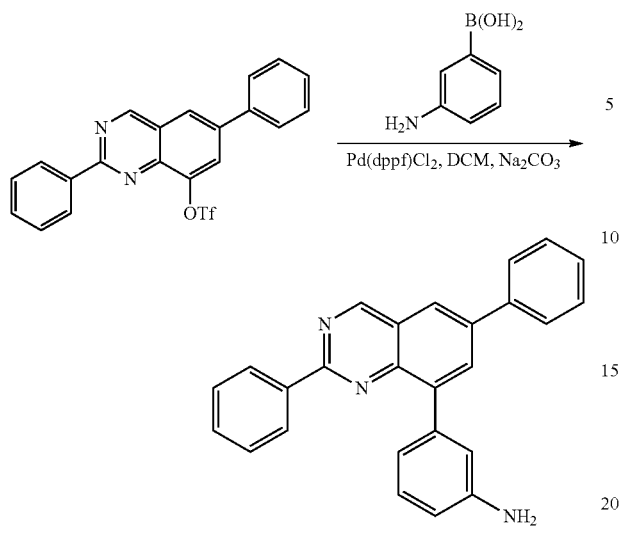

To a solution of 2,6-diphenylquinazolin-8-yl trifluoromethanesulfonate (434.0 mg, 1.0.0 mmol, 1.0 q.) and (3-aminophenyl)boronic acid (165.9 mg, 1.21 mmol, 1.2 eq) in dioxane (15 mL) and H₂O (1.5 mL) was added Na₂CO₃ (214.0 mg, 2.0 mmol, 2.0 eq), followed by Pd(dppf)Cl₂ (41.0 mg, 0.1 mmol, 0.1 eq) under N₂. The mixture was stirred at 90° C. for 12 h, then cooled to rt, diluted with EA (40.0 mL) and filtered. The filtrate was concentrated and the resulting residue was purified by column chromatography (PE/EA=10/1, v/v) to afford 3-(2,6-diphenylquinazolin-8-yl)aniline as a yellow solid (280.0 mg, 74%).

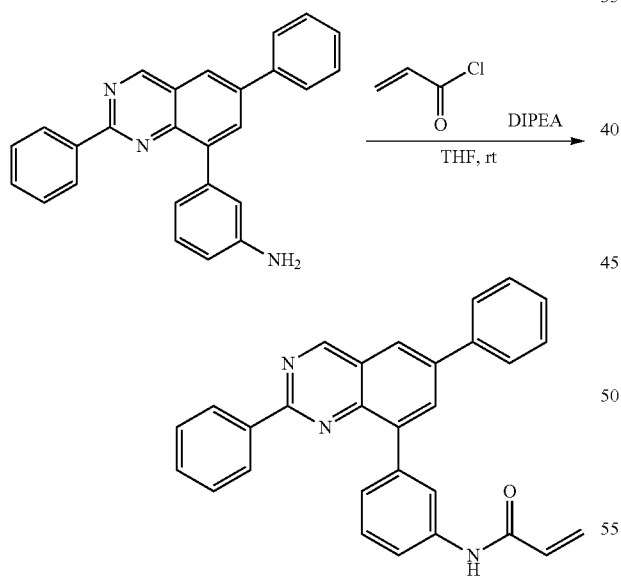

To a solution of 3-(2,6-diphenylquinazolin-8-yl)aniline (280.0 mg, 0.8 mmol, 1.0 eq) in THF (10.0 mL) was added DIPEA (0.6 mL, 3.0 mmol, 4.0 eq), followed by acryloyl chloride (135.0 mg, 1.5 mmol, 2.0 eq). The resulting mixture was stirred at rt for 1 h, then washed with brine, dried over anhydrous Na₂SO₄, concentrated and purified by column chromatography (PE/EA=4:1, v/v) to afford N-(3-(2,6-diphenylquinazolin-8-yl)phenyl)acrylamide as a yellow solid (50.0 mg, 35%). LR-MS (M+H⁺) m/z calculated 428.2, found 428.6. ¹H NMR (DMSO-d6, 400 MHz) δ 10.32 (s, 1H), 9.82 (s, 1H), 8.52 (t, 3H), 8.36 (s, 1H), 8.26 (s, 1H), 7.96 (d, 2H), 7.84 (d, 1H), 7.67 (d, 1H), 7.47-7.60 (m, 7H), 6.50 (dd, 1H), 6.29 (d, 1H), 5.79 (d, 1H).

Example 2: Preparation of N-(3-(6-(2-chlorophenyl)-2-phenylquinazolin-8-yl)phenyl)acrylamide N-(3-(6-(2-chlorophenyl)-2-phenylquinazolin-8-yl)phenyl)acrylamide

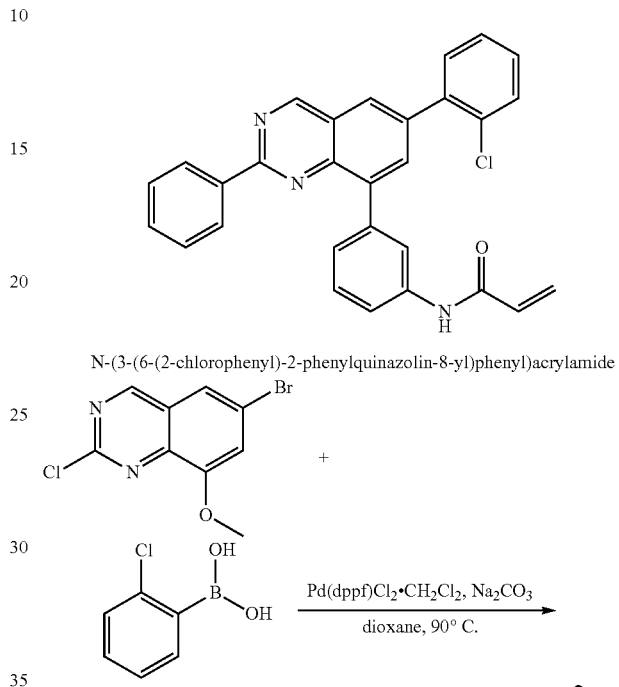

To a solution of 6-bromo-2-chloro-8-methoxyquinazoline (900.0 mg, 3.3 mmol, 1.0 eq) and (2-chlorophenyl)boronic acid (515.0 mg, 3.3 mmol, 1.0 eq) in dioxane (20 mL) was added Na₂CO₃ (700.0 mg, 6.6 mmol, 2.0 eq), followed by Pd(dppf)Cl₂ (135.0 mg, 0.17 mmol, 0.1 eq) under N₂. The mixture was stirred at 90° C. for 12 h, then cooled to rt, diluted with EA (40.0 mL) and filtered. The filtrate was concentrated. The resulting residue was purified by column chromatography (PE/EA=4/1, v/v) to afford 2-chloro-6-(2-chlorophenyl)-8-methoxyquinazoline as a yellow solid (500.0 mg, 50%).

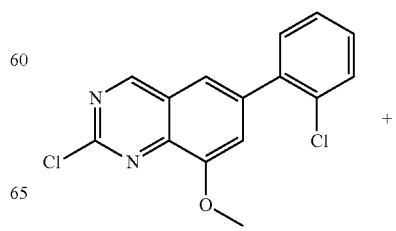

-continued

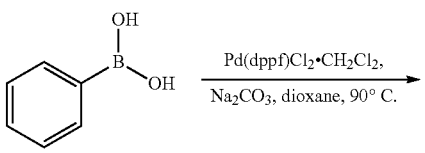

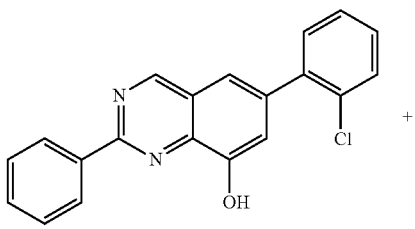

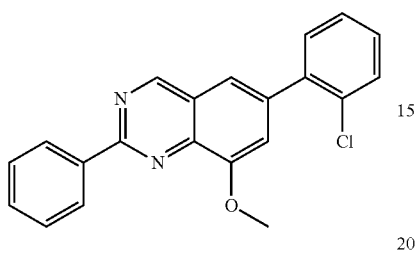

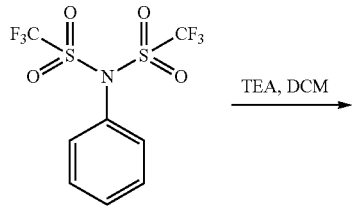

To a solution of 2-chloro-6-(2-chlorophenyl)-8-methoxyquinazoline (150.0 mg, 0.5 mmol, 1.0 eq) and phenylboronic acid (90.0 mg, 0.7 mmol, 1.5 eq) in dioxane (10.0 mL) was added Na$_2$CO$_3$ (104.0 mg, 1.0 mmol, 2.0 eq), followed by Pd(dppf)Cl$_2$ (20.0 mg, 0.025 mmol, 0.05 eq) under N$_2$. The mixture was stirred at 90° C. for 12 h, then cooled to rt, diluted with EA (20.0 mL) and filtered. The filtrate was concentrated. The resulting residue was purified by column chromatography (PE/EA=4/1, v/v) to afford 6-(2-chlorophenyl)-8-methoxy-2-phenylquinazoline as a yellow solid (136.0 mg, 80.5%).

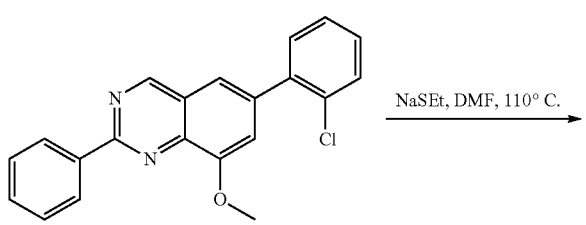

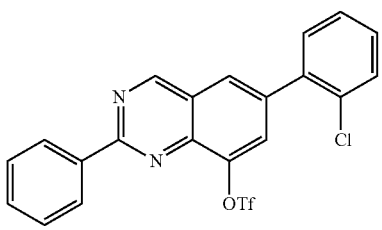

To a solution of 6-(2-chlorophenyl)-2-phenylquinazolin-8-ol (147.0 mg, 0.4 mmol, 1.0 eq) and TEA (0.3 mL, 2.2 mmol, 5.0 eq) in DCM (10 mL) was added PhN(OTf)$_2$ (471.0 mg, 1.3 mmol, 3.0 eq). The mixture was stirred at rt overnight, then concentrated. The resulting residue was purified by column chromatography (PE/EA=10/1) to provide 6-(2-chlorophenyl)-2-phenylquinazolin-8-yl trifluoromethanesulfonate as a yellow solid (183.0 mg, 90%).

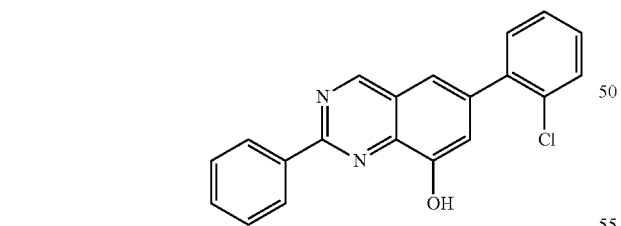

To a solution of 6-(2-chlorophenyl)-8-methoxy-2-phenylquinazoline (136.0 mg, 0.4 mmol, 1.0 eq) in DMF (8.0 mL) was added sodium ethanethiolate (114.2 mg, 1.3 mmol, 3.0 eq). The mixture was heated at 110° C. for 5 h under N$_2$. The mixture was concentrated and the residue was diluted with MeOH (4.0 mL) and EA (60.0 mL), then washed with 1N HCl (5.0 mL×2). The EA layer was concentrated and the residue was purified by column chromatography to provide 6-(2-chlorophenyl)-2-phenylquinazolin-8-ol as a brown solid (147.0 mg, quant.).

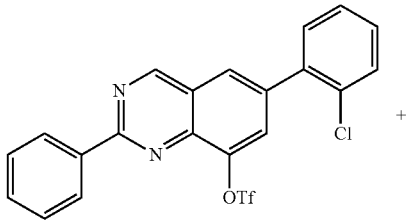

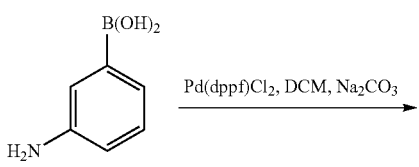

-continued

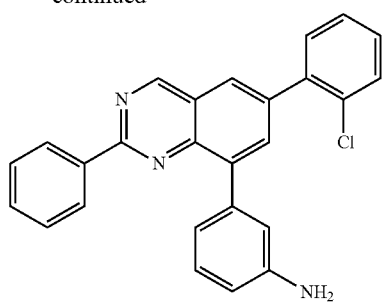

To a solution of 6-(2-chlorophenyl)-2-phenylquinazolin-8-yl trifluoromethanesulfonate (183.0 mg, 0.4 mmol, 1.0 eq) and (3-aminophenyl)boronic acid (65.0 mg, 0.5 mmol, 1.2 eq) in dioxane (10.0 mL) and H$_2$O (1.0 mL) was added Na$_2$CO$_3$ (84.0 mg, 0.8 mmol, 2.0 eq), followed by Pd(dppf)Cl$_2$ (16.0 mg, 0.02 mmol, 0.05 eq) under N$_2$. The mixture was stirred at 90° C. for 12 h, then cooled to rt, diluted with EA (40.0 mL) and filtered. The filtrate was concentrated and the resulting residue was purified by column chromatography (PE/EA=4/1, v/v) to afford 3-(6-(2-chlorophenyl)-2-phenylquinazolin-8-yl)aniline as a yellow solid (110.0 mg, 68.5%).

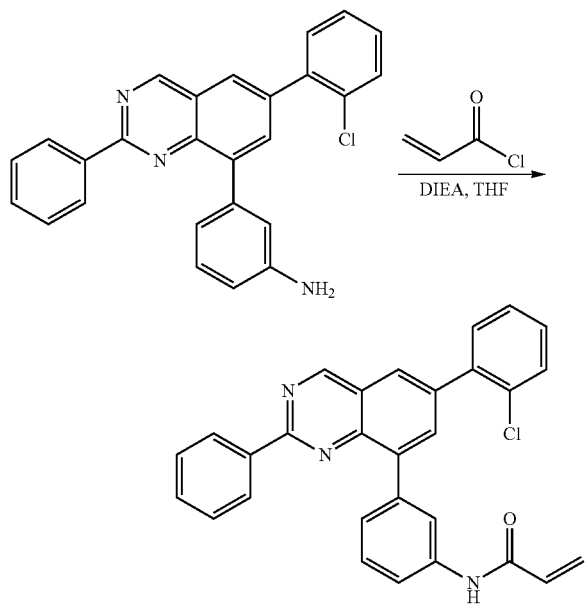

To a solution of 3-(6-(2-chlorophenyl)-2-phenylquinazolin-8-yl)aniline (110.0 mg, 0.3 mmol, 1.0 eq) in THF (8.0 mL) was added DIPEA (0.1 mL, 1.1 mmol, 4 eq), followed by acryloyl chloride (49.0 mg, 0.5 mmol, 2.0 eq). The resulting mixture was stirred at rt for 1 h, then washed with brine, dried over anhydrous Na$_2$SO$_4$, concentrated and purified by column chromatography (PE/EA=4:1, v/v) to afford N-(3-(6-(2-chlorophenyl)-2-phenylquinazolin-8-yl)phenyl)acrylamide as a white solid (50.9 mg, 40.9%.) LRMS (M+H$^+$) m/z calculated 462.1, found 462.6. $^1$H NMR (DMSO-d$_6$, 400 MHz) δ 10.31 (s, 1H), 9.84 (s, 1H), 8.53 (t, 2H), 8.27 (d, 2H), 8.13 (s, 1H), 7.82 (d, 1H), 7.64-7.70 (m, 3H), 7.54-7.61 (m, 6H), 6.50 (dd, 1H), 6.29 (d, 1H), 5.78 (d, 1H).

Example 3: Preparation of N-(3-(6-phenyl-2-(phenylamino)quinazolin-8-yl)phenyl)acrylamide

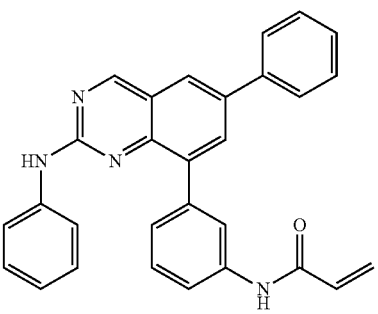

N-(3-(6-phenyl-2-(phenylamino)quinazolin-8-yl)phenyl)acrylamide

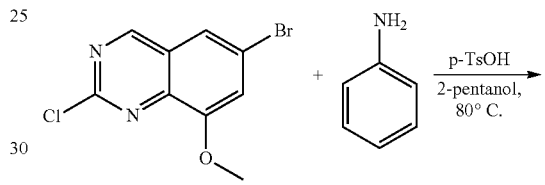

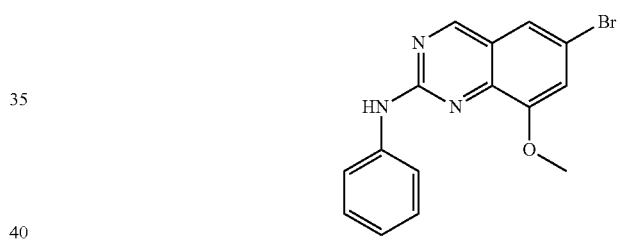

To a solution of 6-bromo-2-chloro-8-methoxyquinazoline (500.0 mg, 1.8 mmol, 1.0 eq) and aniline (256.0 mg, 2.8 mmol, 1.5 eq) in 2-pentanol (10 mL) was added p-TsOH (35.0 mg, 0.2 mmol, 0.1 eq). The mixture was stirred at 80° C. overnight. then cooled to rt and concentrated. The resulting residue was purified by column chromatography (PE/EA=2:1, v/v) to afford 6-bromo-8-methoxy-N-phenylquinazolin-2-amine as a yellow solid (400.0 mg, 66.2%).

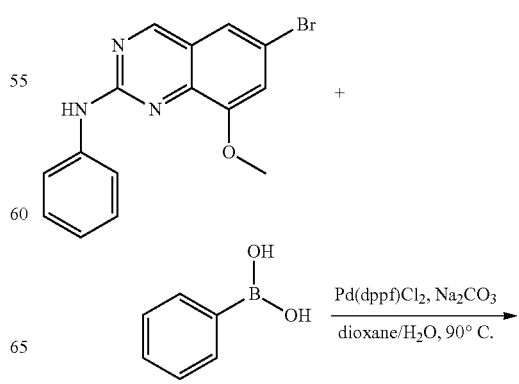

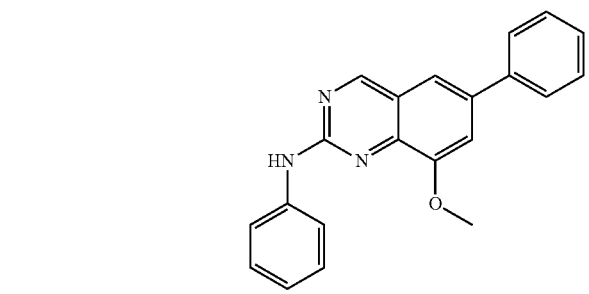

To a solution of 6-bromo-8-methoxy-N-phenylquinazolin-2-amine (150.0 mg, 0.5 mmol, 1.0 eq) and phenylboronic acid (83.2 mg, 0.7 mmol, 1.5 eq) in dioxane (10 mL) and H$_2$O (1.0 mL) was added Na$_2$CO$_3$ (95.0 mg, 0.9 mmol, 2.0 eq), followed by Pd(dppf)Cl$_2$·DCM (18.6 mg, 0.025 mmol, 0.05 eq) under N$_2$. The mixture was stirred at 90° C. for 12 h, then cooled to rt, diluted with EA (40 mL) and filtered. The filtrate was concentrated and the resulting residue was purified by column chromatography (PE/EA=4/1, v/v) to afford 8-methoxy-N,6-diphenylquinazolin-2-amine as a yellow solid (112.0 mg, 75.4%).

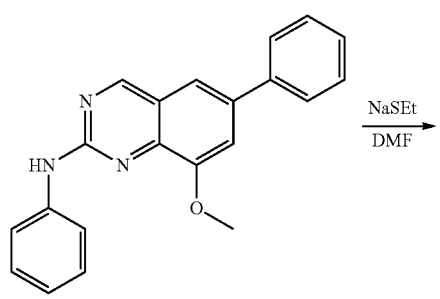

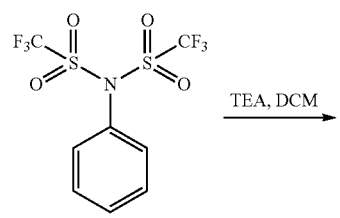

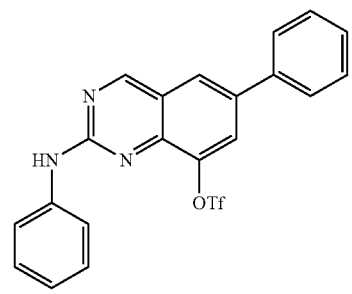

To a solution of 6-phenyl-2-(phenylamino)quinazolin-8-ol (100.0 mg, 0.32 mmol, 1.0 eq) and TEA (0.22 mL, 1.6 mmol, 5.0 eq) in DCM (10.0 mL) was added PhN(OTf)$_2$ (341 mg, 0.96 mmol, 3.0 eq). The mixture was stirred at rt overnight, then concentrated. The residue was purified by column chromatography (PE/EA=4/1) to provide 6-phenyl-2-(phenylamino)quinazolin-8-yl trifluoromethanesulfonate as a yellow solid (165.0 mg, 80.1%).

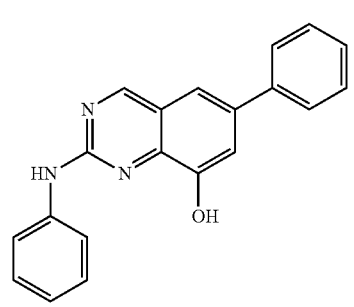

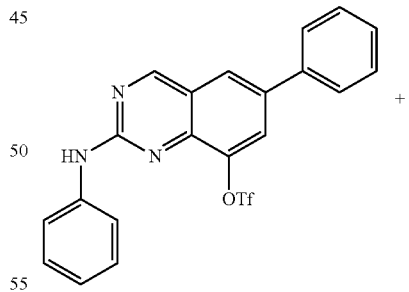

To a solution of 8-methoxy-N,6-diphenylquinazolin-2-amine (112.0 mg, 0.34 mmol, 1.0 eq) in DMF (8.0 mL) was added sodium ethanethiolate (86.0 mg, 1.02 mmol, 3.0 eq). The mixture was heated at 110° C. overnight under N$_2$, then concentrated and diluted with H$_2$O (100.0 mL), the precipitate was collected by filtration to afford 6-phenyl-2-(phenylamino)quinazolin-8-ol as a yellow solid (100.0 mg, 93.5%).

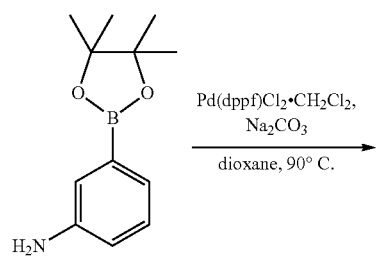

-continued

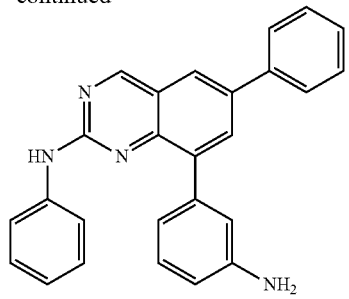

To a solution of 6-phenyl-2-(phenylamino)quinazolin-8-yl trifluoromethanesulfonate (165.0 mg, 0.36 mmol, 1.0 eq) and 3-(4,4,5,5-tetramethyl-1,3,2-dioxaborolan-2-yl)aniline (117.0 mg, 0.54 mmol, 1.5 eq) in dioxane (15 mL) and $H_2O$ (1.5 mL) was added $Na_2CO_3$ (76.0 mg, 0.72 mmol, 2.0 eq), followed by $Pd(dppf)Cl_2 \cdot DCM$ (14.6 mg, 0.018 mmol, 0.05 eq) under $N_2$. The mixture was stirred at 90° C. for 12 h, then cooled to rt, diluted with EA (40.0 mL) and filtered. The filtrate was concentrated and the resulting residue was purified by column chromatography (PE/EA=10/1, v/v) to afford 8-(3-aminophenyl)-N,6-diphenylquinazolin-2-amine as a yellow solid (113.0 mg, 82%).

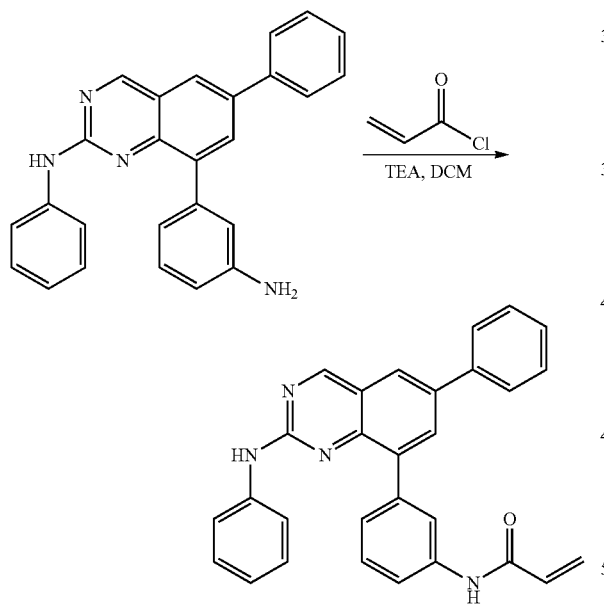

To a solution of 8-(3-aminophenyl)-N,6-diphenylquinazolin-2-amine (113.0 mg, 0.29 mmol, 1.0 eq) in DCM (10.0 mL) was added TEA (0.08 ml, 0.58 mmol, 2.0 eq), followed by acryloyl chloride (23.94 mg, 0.26 mmol, 0.9 eq). The resulting mixture was stirred at rt for 1.5 h, then washed with water, dried over anhydrous $Na_2SO_4$, concentrated and purified by column chromatography (PE/EA=4:1, v/v) to afford N-(3-(6-phenyl-2-(phenylamino)quinazolin-8-yl)phenyl)acrylamide as a yellow solid (68.0 mg, 46.6%). LRMS (M+H⁺) m/z calculated 443.2, found 443.3. ¹H NMR (DMSO-d6, 400 MHz) δ 10.28 (s, 1H), 9.94 (s, 1H), 8.26 (s, 1H), 8.11 (d, 2H), 7.85-8.03 (m, 5H), 7.61-7.66 (m, 4H), 7.42 (t, 1H), 7.11-7.17 (m, 2H), 6.88 (t, 1H), 6.46 (dd, 1H), 6.26 (d, 1H), 5.75 (d, 1H).

Example 4: Preparation of N-(3-(2-(phenylamino)-6-(pyridin-3-yl)quinazolin-8-yl)phenyl)arcylamide

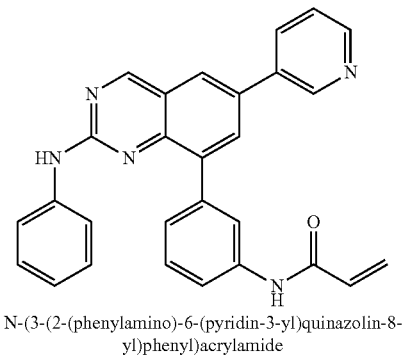 [SMILES: C=CC(=O)Nc1cccc(-c2cc(-c3cccnc3)cc3cnc(Nc4ccccc4)nc23)c1]

N-(3-(2-(phenylamino)-6-(pyridin-3-yl)quinazolin-8-yl)phenyl)acrylamide

N-(3-(2-(phenylamino)-6-(pyridin-3-yl)quinazolin-8-yl)phenyl)acrylamide (78.3 mg) was prepared as described for N-(3-(6-phenyl-2-(phenylamino)quinazolin-8-yl)phenyl)acrylamide. LRMS (M+H⁺) m/z calculated 444.2, found 444.3. ¹H NMR (DMSO-d6, 400 MHz) δ 10.27 (s, 1H), 9.99 (s, 1H), 9.43 (s, 1H), 9.08 (d, 1H), 8.612 (d, 1H), 8.34 (s, 2H), 8.27 (d, 1H), 8.18 (d, 1H), 8.10 (s, 1H), 7.87-7.95 (m, 3H), 7.50-7.56 (m, 3H), 7.13 (t, 2H), 6.88 (t, 1H), 6.48 (dd, 1H), 6.26 (d, 1H), 5.75 (s, 1H).

Example 5: Preparation of N-(3-(6-phenylquinazolin-8-yl)phenyl)acrylamide

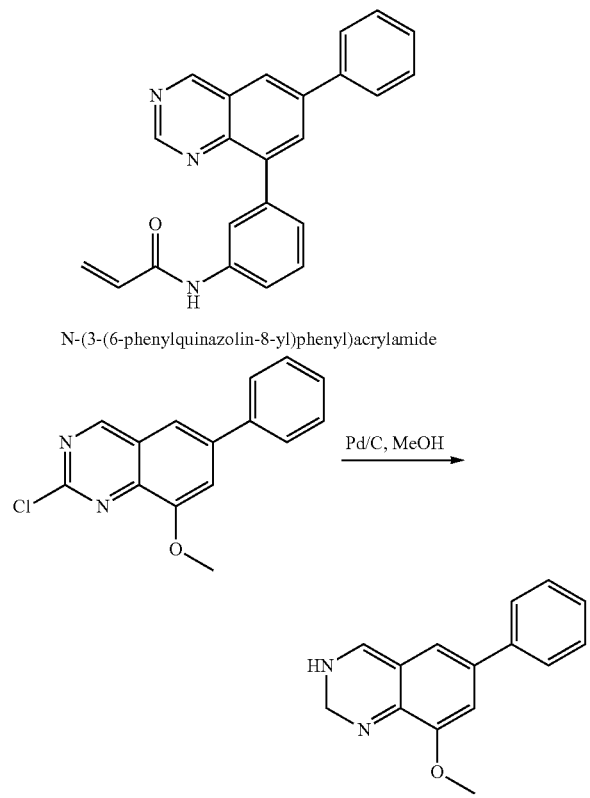

N-(3-(6-phenylquinazolin-8-yl)phenyl)acrylamide

To a solution of 2-chloro-8-methoxy-6-phenylquinazoline (150.0 mg, 0.6 mmol, 1.0 eq) in MeOH (15.0 mL) was added Pd/C (15.0 mg). The mixture was stirred at rt under $H_2$ atmosphere overnight, then filtered and concentrated to afford 8-methoxy-6-phenyl-2,3-dihydroquinazoline as a white solid (140.0 mg, quant.).

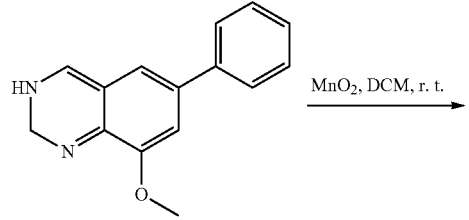

A mixture of 8-methoxy-6-phenyl-2,3-dihydroquinazoline (140.0 mg, 0.6 mmol, 1.0 eq) and $MnO_2$ (256.0 mg, 2.9 mmol, 5.0 eq) in DCM (15.0 mL) was stirred at rt overnight, then filtered and concentrated to afford 8-methoxy-6-phenylquinazoline as a yellow solid (148.0 mg, quant.).

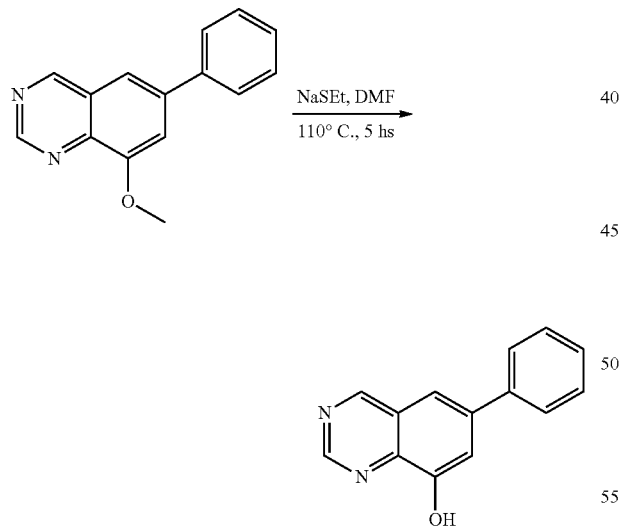

To a solution of 8-methoxy-6-phenylquinazoline (200.0 mg, 0.9 mmol, 1.0 eq) in DMF (20.0 mL) was added sodium ethanethiolate (214.0 mg, 2.5 mmol, 3.0 eq). The mixture was heated at 110° C. overnight under $N_2$, then cooled and diluted with $H_2O$ (200.0 mL)/EA (100.0 mL). The mixture was then extracted with EA (100 mL×2). The combined EA layer was dried over anhydrous $Na_2SO_4$ and concentrated to provide 6-phenylquinazolin-8-ol as a yellow solid (120.0 mg, 63.8%).

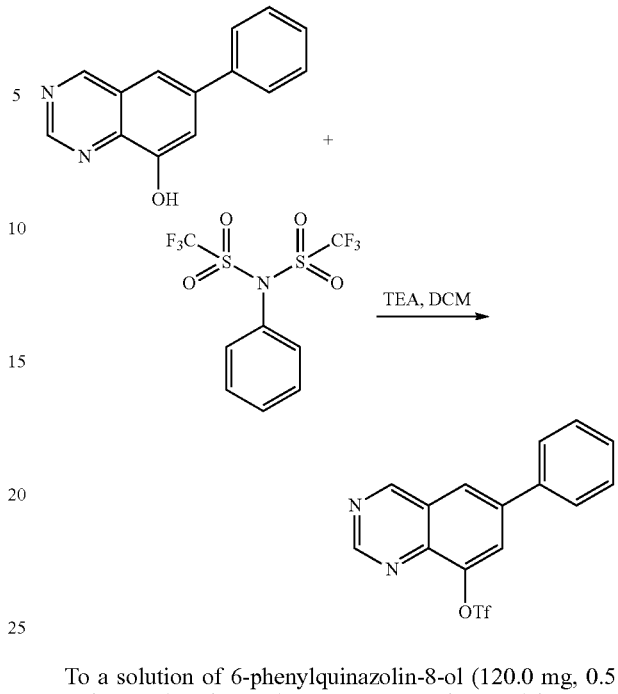

To a solution of 6-phenylquinazolin-8-ol (120.0 mg, 0.5 mmol, 1.0 eq) and TEA (0.4 mL, 2.7 mmol, 5.0 eq) in DCM (15.0 mL) was added $PhN(OTf)_2$ (579.0 mg, 1.6 mmol, 3.0 eq). The mixture was stirred at rt overnight, then concentrated. The residue was purified by column chromatography (PE/EA=4/1) to provide 6-phenylquinazolin-8-yl trifluoromethanesulfonate as a yellow solid (160.0 mg, 83.6%).

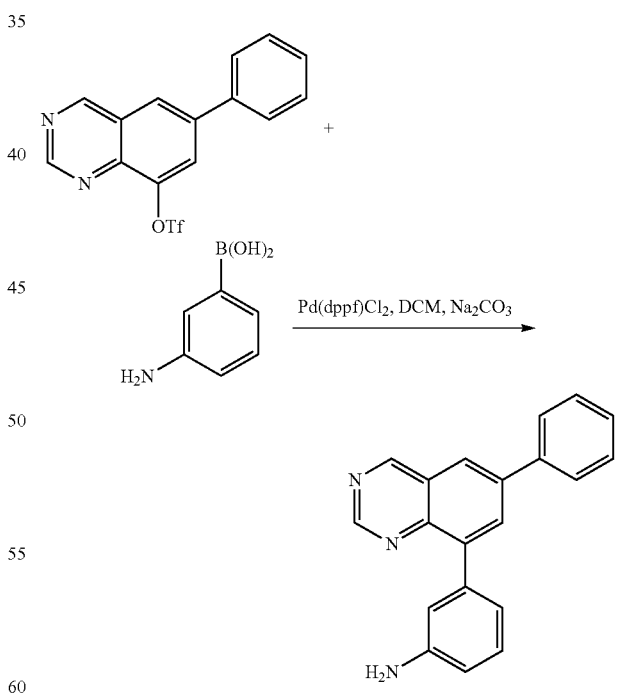

To a solution of 6-phenylquinazolin-8-yl trifluoromethanesulfonate (160.0 mg, 0.5 mmol, 1.0 eq) and (3-aminophenyl)boronic acid (119.0 mg, 0.5 mmol, 1.2 eq) in dioxane (15.0 mL) and $H_2O$ (1.5 mL) was added $Na_2CO_3$ (96.0 mg, 0.9 mmol, 2.0 eq), followed by $Pd(dppf)Cl_2$ (18.0 mg, 0.02 mmol, 0.05 eq) under $N_2$. The mixture was stirred at 90° C.

for 12 h, then cooled to rt, diluted with EA (40.0 mL) and filtered. The filtrate was concentrated and the resulting residue was purified by column chromatography (PE/EA=1/1, v/v) to afford 3-(6-phenylquinazolin-8-yl)aniline as a yellow solid (110.0 mg, 82.1%).

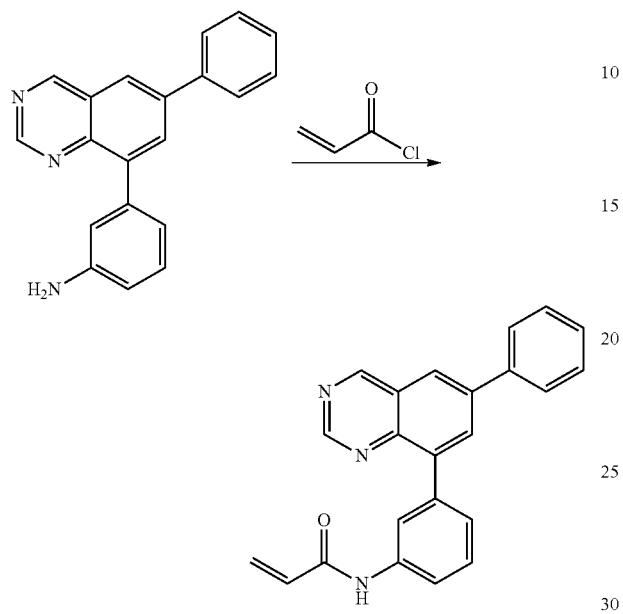

To a solution of 3-(6-phenylquinazolin-8-yl)aniline (110.0 mg, 0.4 mmol, 1.0 eq) in DCM (8.0 mL) was added TEA (0.2 mL, 1.1 mmol, 3.0 eq), followed by acryloyl chloride (0.04 mL, 0.6 mmol, 1.5 eq). The resulting mixture was stirred at rt for 1 h, then washed with brine, dried over anhydrous $Na_2SO_4$, concentrated and purified by column chromatography (PE/EA=1:1, v/v) to afford N-(3-(6-phenylquinazolin-8-yl)phenyl)acrylamide as a yellow solid (12.0 mg, 9.2%). LRMS (M+H$^+$) m/z calculated 352.4, found 352.4. $^1$H NMR. (CDCl$_3$, 400 MHz) δ 9.53 (s, 1H), 9.36 (s, 1H), 8.26 (s, 1H), 8.13 (s, 1H), 8.00 (s, 1H), 7.74 (d, 3H), 7.42-7.66 (m, 5H), 6.44 (d, 1H), 6.23 (dd, 1H), 5.76 (dd, 1H).

Example 6: Preparation of N-(3-(6-(2-chlorophenyl)quinazolin-8-yl)phenyl)acrylamide

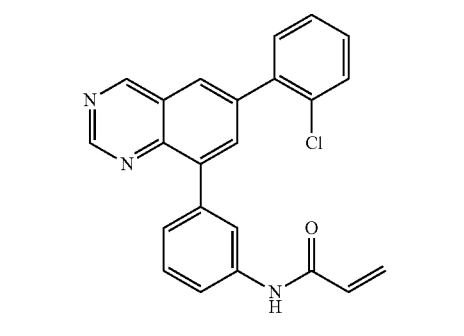

N-(3-(6-(2-chlorophenyl)quinazolin-8-yl)phenyl)acrylamide

N-(3-(6-(2-chlorophenyl)quinazolin-8-yl)phenyl)acrylamide (40.5 mg) was prepared as described for N-(3-(6-phenylquinazolin-8-yl)phenyl)acrylamide. LRMS (M+H$^+$) m/z calculated 386.1, found 386.5. $^1$H NMR (CDCl$_3$, 400 MHz) δ 9.58 (s, 1H), 9.40 (s, 1H), 8.21 (s, 1H), 8.00-8.08 (m, 2H), 7.30-7.72 (m, 7H), 6.42-6.46 (m, 1H), 6.26-6.33 (m, 1H), 5.78 (d, 1H).

Example 7: Preparation of N-(3-(6-(3-fluorophenyl)quinazolin-8-yl)phenyl)acrylamide

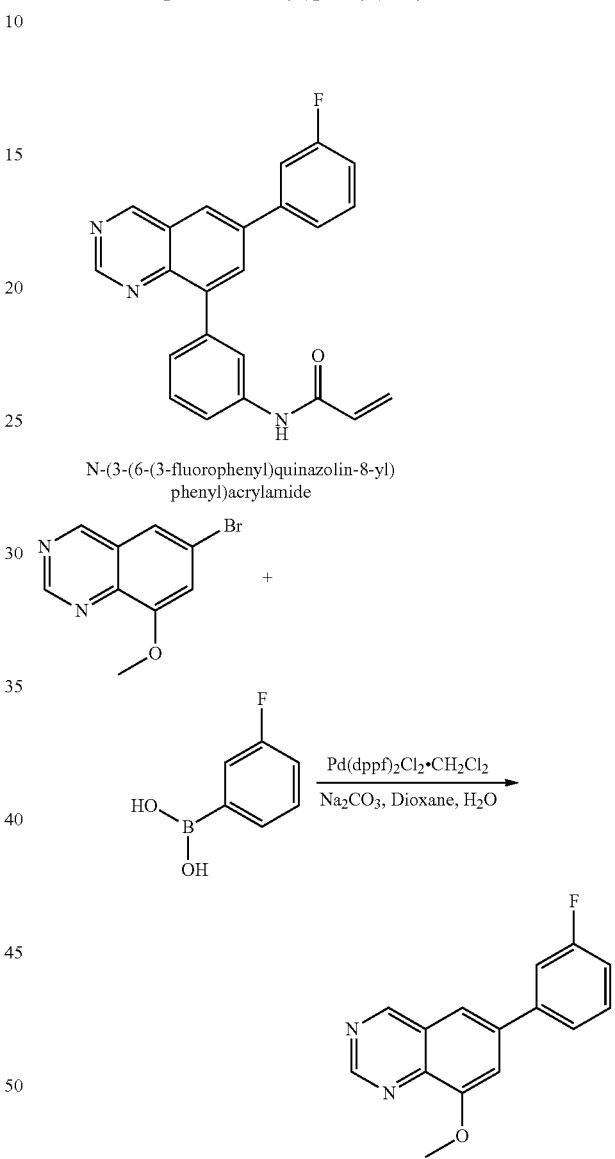

To a solution of 6-bromo-8-methoxyquinazoline (200.0 mg, 0.84 mmol, 1.0 eq) and (3-fluorophenyl)boronic acid (135 mg, 1.0 mmol, 1.2 eq) in dioxane (10.0 mL) and H$_2$O (1.0 mL) was added Na$_2$CO$_3$ (178.0 mg, 1.68 mmol, 2.0 eq), followed by Pd(dppf)Cl$_2$·CH$_2$Cl$_2$ (34 mg, 0.042 mmol, 0.05 eq) under N$_2$. The mixture was stirred at 90° C. for 18 hrs, then cooled to rt, diluted with EA (50.0 mL) and filtered. The filtrate was concentrated and the resulting residue was purified by column chromatography (PE/EA=3/1, v/v) to afford 6-(3-fluorophenyl)-8-methoxyquinazoline as a yellow solid (195 mg, 91.0%).

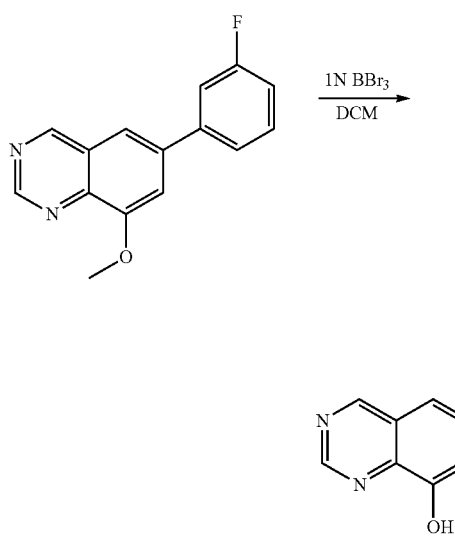

A mixture of 6-(3-fluorophenyl)-8-methoxyquinazoline (195.0 mg, 0.77 mmol, 1.0 eq) and 1M BBr$_3$ in DCM (6.0 mL, 6 mmol, 7.8 eq) was stirred at reflux overnight under N$_2$, then cooled and poured into Sat. NaHCO$_3$ (20.0 mL) and extracted it with DCM (30.0 mL×3). The DCM layers were dried over anhydrous MgSO$_4$ and concentrated to provide 6-(3-fluorophenyl)quinazolin-8-ol as a yellow solid (175 mg, 95.0%).

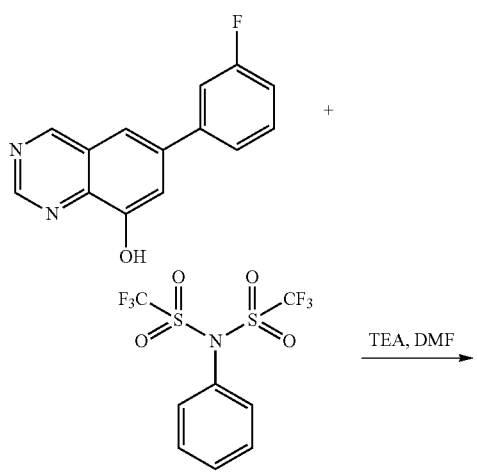

To a solution of 6-(3-fluorophenyl)quinazolin-8-ol (175 mg, 0.73 mmol, 1.0 eq) and TEA (369 mg, 3.65 mmol, 5.0 eq) in DMF (15.0 mL) was added PhN(OTf)$_2$ (1.17 g, 2.19 mmol, 3.0 eq). The mixture was stirred at rt overnight, then concentrated. The residue was purified by column chromatography (PE/EA=10/1, v/v) to provide 6-(3-fluorophenyl)quinazolin-8-yl trifluoromethanesulfonate as a yellow solid (271 mg, 99%).

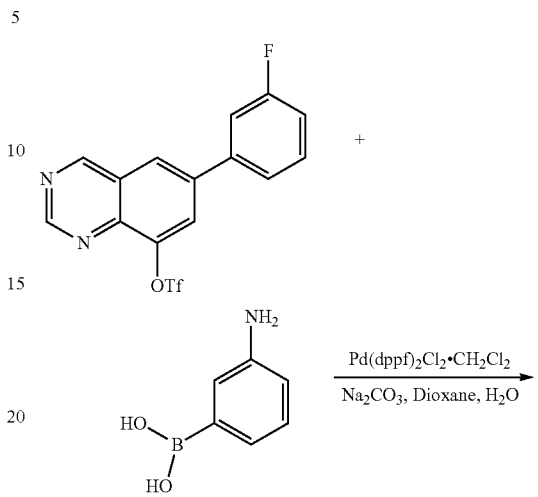

To a solution of 6-(pyridin-4-yl)quinazolin-8-yl trifluoromethanesulfonate (271 mg, 0.73 mmol, 1.0 eq) and (3-aminophenyl)boronic acid (150 mg, 1.09 mmol, 1.2 eq) in dioxane (10 mL) and H$_2$O (1 mL) was added Na$_2$CO$_3$ (155.0 mg, 1.46 mmol, 2.0 eq), followed by Pd(dppf)Cl$_2$·CH$_2$Cl$_2$ (30 mg, 0.036 mmol, 0.05 eq) under N$_2$. The mixture was stirred at 90° C. for 18 hrs, then cooled to rt, diluted with EA (40.0 mL) and filtered. The filtrate was concentrated and the resulting residue was purified by column chromatography (DCM/MeOH=50/1, v/v) to afford 3-(6-(pyridin-4-yl)quinazolin-8-yl)aniline as a yellow solid (231 mg, 99.9%).

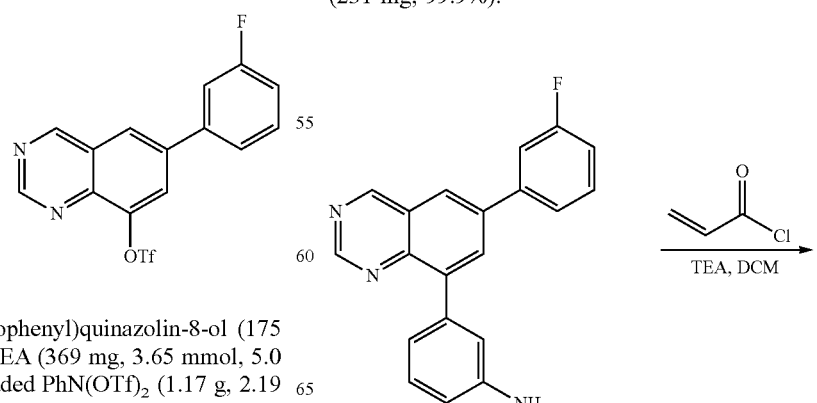

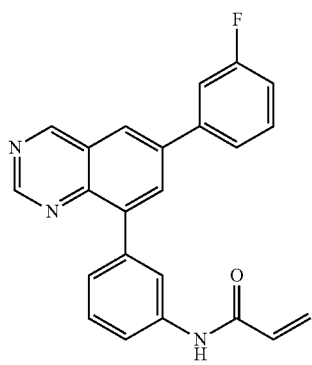

To a solution of 3-(6-(pyridin-4-yl)quinazolin-8-yl)aniline (231 mg, 0.73 mmol, 1.0 eq) in DCM (10.0 mL) was added TEA (147 mg, 1.46 mmol, 2.0 eq), followed by acryloyl chloride (53 mg, 0.59 mmol, 0.8 eq). The resulting mixture was stirred at rt for 1 h, then washed with brine, dried over anhydrous MgSO₄, concentrated. The residue was retreated with DCM and filtered to afford N-(3-(6-(pyridin-4-yl)quinazolin-8-yl)phenyl)acrylamide as a yellow solid (67 mg, 21.9%). LRMS (M+H⁺) m/z calculated 370.1, found 370.2. ¹H NMR (DMSO-d6, 400 MHz) δ 10.27 (s, 1H), 9.73 (s, 1H), 9.34 (s, 1H), 8.56 (d, 1H), 8.36 (d, 1H), 8.03 (s, 1H), 7.79-7.85 (m, 3H), 7.58-7.64 (m, 1H), 7.46-7.52 (m, 2H), 7.29-7.34 (m, 1H), 6.48 (dd, 1H), 6.27 (dd, 1H), 5.77 (d, 1H).

Example 8: Preparation of 1-(3-(6-phenylquinazolin-8-yl)pyrrolidin-1-yl)prop-2-en-1-one

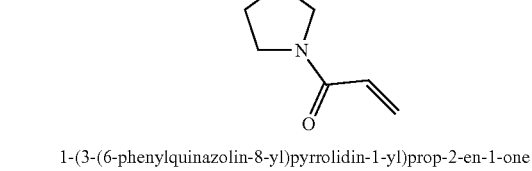

1-(3-(6-phenylquinazolin-8-yl)pyrrolidin-1-yl)prop-2-en-1-one

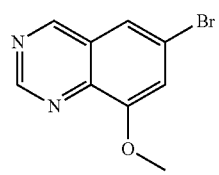 + 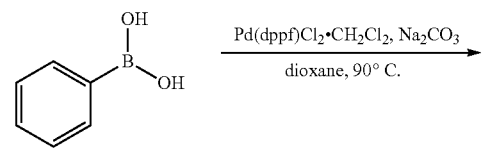 Pd(dppf)Cl₂·CH₂Cl₂, Na₂CO₃, dioxane, 90° C.

To a solution of 6-bromo-8-methoxyquinazoline (500.0 mg, 2.1 mmol, 1.0 eq) and phenylboronic acid (384.0 mg, 3.2 mmol, 1.5 eq) in dioxane (20 mL) was added Na₂CO₃ (445.0 mg, 4.2 mmol, 2.0 eq), followed by Pd(dppf)Cl₂·CH₂Cl₂ (85 mg, 0.105 mmol, 0.05 eq) under N₂. The mixture was stirred at 90° C. for 12 h, then cooled to rt, diluted with EA (40 mL) and filtered. The filtrate was concentrated and the resulting residue was purified by column chromatography (PE/EA=4/1, v/v) to afford 8-methoxy-6-phenylquinazoline as a yellow solid (500.0 mg, 99.9%).

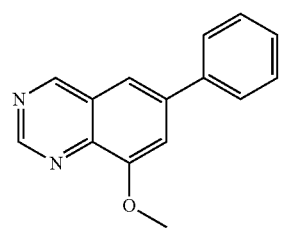

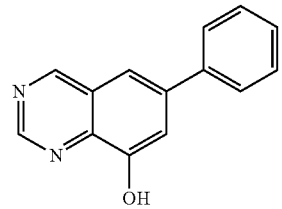 NaSEt / DMF

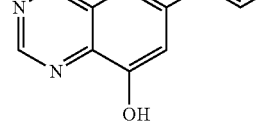

To a solution of 8-methoxy-6-phenylquinazoline (500.0 mg, 2.1 mmol, 1.0 eq) in DMF (20.0 mL) was added sodium ethanethiolate (531.0 mg, 6.3 mmol, 3.0 eq). The mixture was heated at 110° C. overnight under N₂, then cooled and concentrated. The residue was diluted with MeOH (4.0 mL) and EA (60.0 mL). Then washed with 1N HCl (5.0 mL*2). The organic layer was dried over anhydrous Na₂SO₄ and concentrated. The residue was purified by column chromatography to provide 6-phenylquinazolin-8-ol as a yellow solid (420.0 mg, crude).

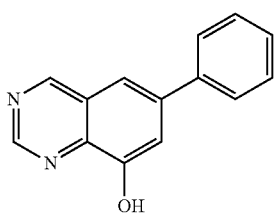 +

-continued

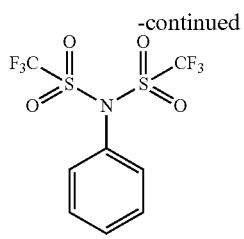

TEA, DCM

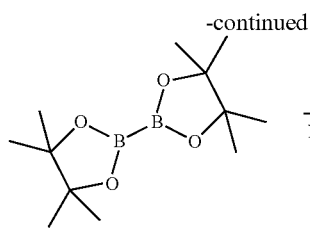

To a solution of 6-phenylquinazolin-8-ol (420.0 mg, 1.9 mmol, 1.0 eq) and TEA (1.3 mL, 9.5 mmol, 5.0 eq) in DCM (15.0 mL) was added PhN(OTf)$_2$ (2.0 g, 5.7 mmol, 3.0 eq). The mixture was stirred at rt overnight, then concentrated. The residue was purified by column chromatography (PE/EA=4/1) to provide 6-phenylquinazolin-8-yl trifluoromethanesulfonate as a yellow solid (640.0 mg, 95.0%).

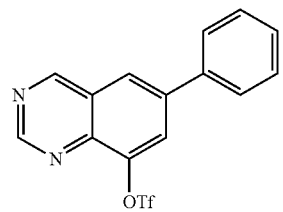 LiHMDS / THF

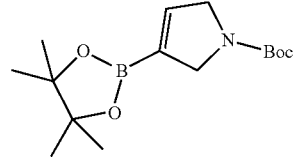

To an oven dried flask under N$_2$ was added tert-butyl 3-oxopyrrolidine-1-carboxylate (20.0 g, 0.11 mol, 1.0 eq) and THF (200 mL). The solution was cooled in acetone ice bath (−78° C.). To that was added LiHMDs (125 mL, 0.12 mol, 1.15 eq) (1 M solution in THF). The reaction mixture was stirred at −78° C. for 30 min then added dropwise a solution of 1,1,1-trifluoro-N-phenyl-N-((trifluoromethyl)sulfonyl)methanesulfonamide (46.3 g, 0.13 mol, 1.2 eq) in THF (200 mL). The reaction mixture was stirred for 30 min then warmed to 0° C. and stirred for 1.5 h. The reaction mixture was quenched with sat. sodium bicarbonate solution and then extracted with ethyl acetate. The combined extracts were washed with brine, dried over sodium sulfate, filtered and evaporated. The crude product was purified by column chromatography (PE/EA=30/1, v/v) to provide tert-butyl 3-(((trifluoromethyl)sulfonyl)oxy)-2,5-dihydro-1H-pyrrole-1-carboxylate (20.5 g, 59.8%).

-continued

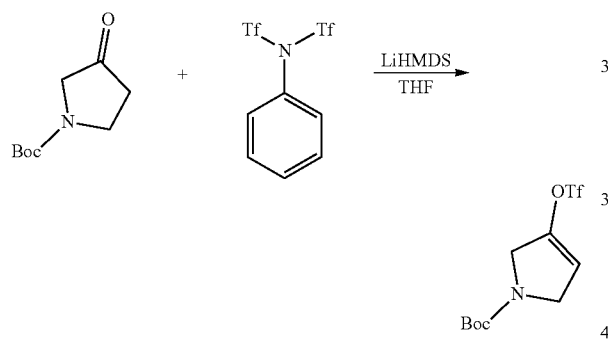

3-Trifluoromethanesulfonyloxy-2,5-dihydro-pyrrole-1-carboxylic acid tert-butyl ester (21.0 g, 66.2 mmol, 1.0 eq) was dissolved in 1,4-dioxane (300 mL) and added under N$_2$ to a degassed mixture of potassium acetate (19.5 g, 200.0 mmol, 3.0 eq), Pd(dppf)Cl$_2$·CH$_2$Cl$_2$ (2.7 g, 3.3 mmol, 0.05 eq), DPPF (1.84 g, 3.3 mmol, 0.05 eq), bis-pinacolato diborane (20.0 g, 79.5 mmol, 1.2 eq) and the reaction mixture heated at 90° C. overnight. Concentration of the crude reaction mixture, and purified on flash column chromatography (PE/EA=10/1, v/v) to afford 5-(4,4,5,5-tetramethyl-[1,3,2]dioxaborolan-2-yl)-2,5-dihydro-pyrrole-1-carboxylic acid tert-butyl ester (11.4 g, 58.3%).

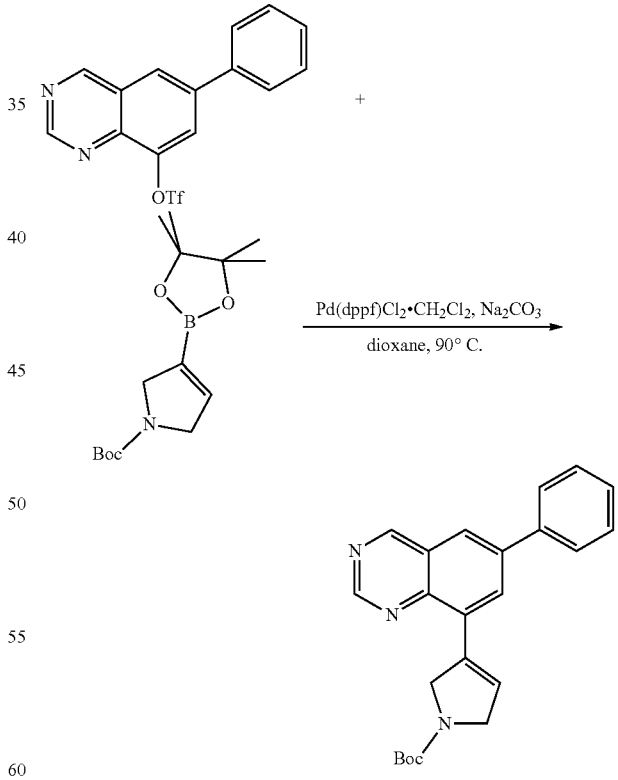

To a solution of 6-phenylquinazolin-8-yl trifluoromethanesulfonate (300.0 mg, 0.85 mmol, 1.0 eq) and tert-butyl 3-(4,4,5,5-tetramethyl-1,3,2-dioxaborolan-2-yl)-2,5-dihydro-1H-pyrrole-1-carboxylate (300.0 mg, 1.02 mmol, 1.2 eq) in dioxane (15 mL) and H$_2$O (1.5 mL) was added Na$_2$CO$_3$ (180.0 mg, 1.7 mmol, 2.0 eq), followed by Pd(dppf)

Cl$_2$·CH$_2$Cl$_2$ (35.0 mg, 0.04 mmol, 0.05 eq) under N$_2$. The mixture was stirred at 90° C. for 12 h, then cooled to rt, diluted with EA (40.0 mL) and filtered. The filtrate was concentrated and the resulting residue was purified by column chromatography (PE/EA=10/1, v/v) to afford tert-butyl 3-(6-phenylquinazolin-8-yl)-2,5-dihydro-1H-pyrrole-1-carboxylate as a yellow solid (309.0 mg, 88.0%).

A mixture of tert-butyl 3-(6-phenyl-2,3-dihydroquinazolin-8-yl)pyrrolidine-1-carboxylate (272.0 mg, 0.72 mmol, 1.0 eq) and MnO$_2$ (313.0 mg, 3.6 mmol, 5.0 eq) in DCM (10.0 mL) was stirred at rt overnight, then filtered and concentrated to afford tert-butyl 3-(6-phenylquinazolin-8-yl)pyrrolidine-1-carboxylate as a yellow solid (123.0 mg, 45.4%).

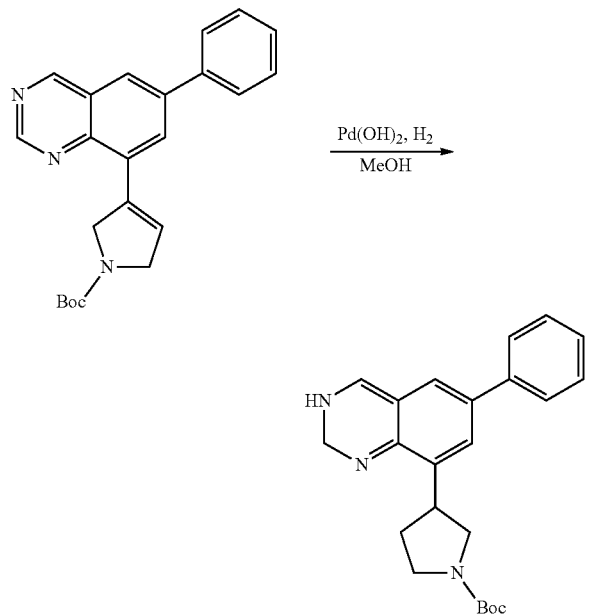

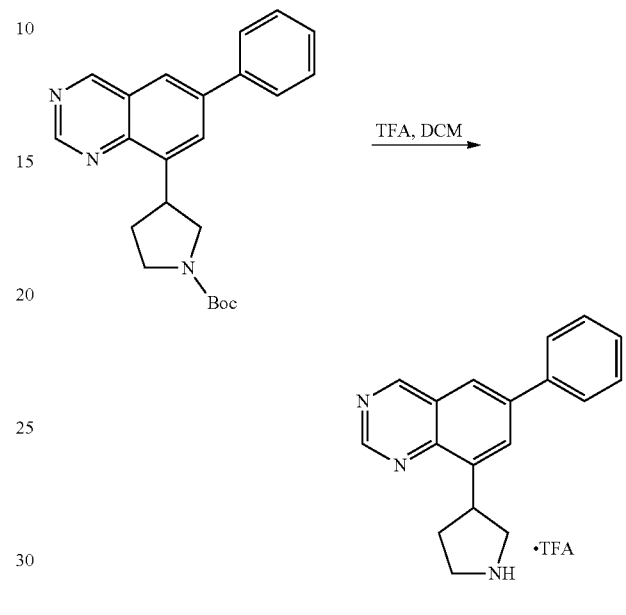

To a solution of tert-butyl 3-(6-phenylquinazolin-8-yl)-2,5-dihydro-1H-pyrrole-1-carboxylate (309.0 mg, 0.83 mmol, 1.0 eq) in MeOH (15.0 mL) was added Pd(OH)$_2$ (116.0 mg). The mixture was stirred at rt under H$_2$ atmosphere overnight, then filtered and concentrated to afford tert-butyl 3-(6-phenyl-2,3-dihydroquinazolin-8-yl)pyrrolidine-1-carboxylate as a yellow oil (272.0 mg, 87.3%).

To a solution of tert-butyl 3-(6-phenylquinazolin-8-yl)pyrrolidine-1-carboxylate (123.0 mg, 0.328 mmol, 1.0 eq) in DCM (5.0 mL) was added TFA (1.5 mL). The mixture was stirred at rt for 2 h, then concentrated to provide 6-phenyl-8-(pyrrolidin-3-yl)quinazoline as a yellow oil (221.0 mg, crude).

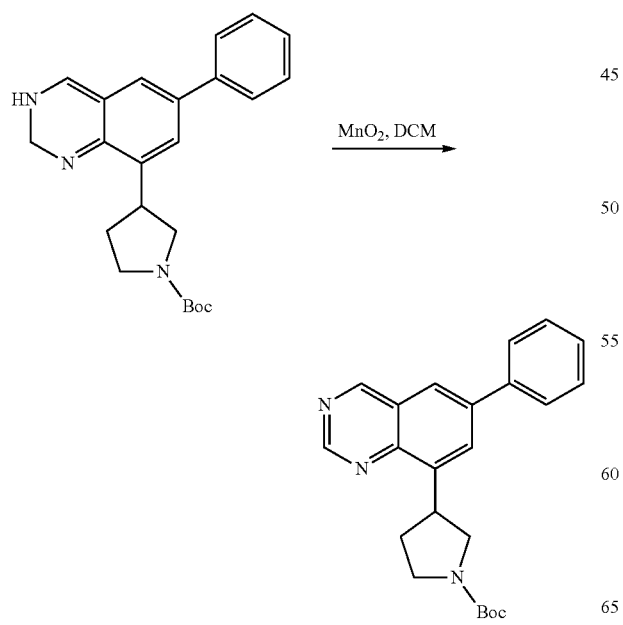

To a solution of 6-phenyl-8-(pyrrolidin-3-yl)quinazoline (221.0 mg, 0.33 mmol, 1.0 eq) in DCM (10.0 mL) was added TEA (1 mL, 7.2 mmol, 21.0 eq), followed by acryloyl chloride (27.0 mg, 0.3 mmol, 0.9 eq). The resulting mixture was stirred at rt for 1.5 h, then washed with sat. Na$_2$CO$_3$, dried over anhydrous Na$_2$SO$_4$, concentrated and purified by column chromatography (PE/EA=4:1, v/v) to afford 1-(3-(6-phenylquinazolin-8-yl)pyrrolidin-1-yl)prop-2-en-1-one as a yellow solid (34.0 mg, 46.6%). LRMS (M+H$^+$) m/z calculated 330.2, found 330.2. $^1$H NMR (DMSO-d6, 400 MHz) δ 9.63 (s, 1H), 9.36 (s, 1H), 8.37 (s, 1H), 8.27 (d, 1H), 7.88 (t, 2H), 7.54-7.57 (m, 2H), 7.45-7.48 (m, 1H), 6.65 (dd, 1H), 6.14-6.21 (m, 1H), 5.64-5.72 (m, 1H), 4.50 (d, 1H), 4.09-4.22 (m, 1H), 3.74-3.91 (m, 2H), 3.41-3.61 (m, 1H), 2.28-2.50 (m, 2H).

Example 9: Preparation of 1-(3-(6-(pyridin-3-yl)quinazolin-8-yl)pyrrolidin-1-yl)prop-2-en-1-one

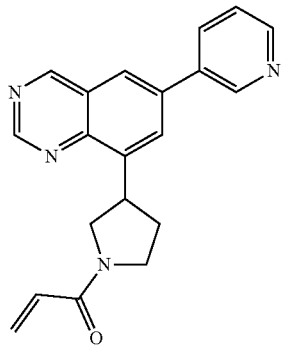

1-(3-(6-(pyridin-3-yl)quinazolin-8-yl)pyrrolidin-1-yl)prop-2-en-1-one 1-(3-(6-(Pyridin-3-yl)quinazolin-8-yl)pyrrolidin-1-yl)prop-2-en-1-one (30.9 mg) was prepared as described for 1-(3-(6-phenylquinazolin-8-yl)pyrrolidin-1-yl)prop-2-en-1-one. LRMS (M+H$^+$) m/z calculated 331.2, found 331.6. $^1$H NMR (CD$_3$OD, 400 MHz) δ 9.61 (s, 1H), 9.32 (d, 1H), 9.02 (s, 1H), 8.56 (d, 1H), 8.24-8.33 (m, 3H), 7.61-7.63 (m, 1H), 6.62-6.74 (m, 1H), 6.27-6.35 (m, 1H), 5.73-5.80 (m, 1H), 4.39-4.67 (m, 1H), 4.24-4.39 (m, 1H), 3.31-3.99 (m, 3H), 2.44-2.57 (m, 2H).

Example 10: Preparation of 1-(3-(6-phenylquinazolin-8-yl)piperidin-1-yl)prop-2-en-1-one

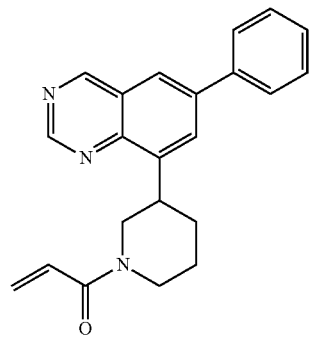

1-(3-(6-phenylquinazolin-8-yl)piperidin-1-yl)prop-2-en-1-one 1-(3-(6-Phenylquinazolin-8-yl)piperidin-1-yl)prop-2-en-1-one (22.4 mg) was prepared as described for 1-(3-(6-phenylquinazolin-8-yl)pyrrolidin-1-yl)prop-2-en-1-one. LRMS (M+H$^+$) m/z calculated 344.2, found 344.5. $^1$H NMR (CD$_3$OD, 400 MHz) δ 9.47 (s, 1H), 9.37 (s, 1H), 8.00-8.04 (m, 2H), 7.69-7.71 (m, 2H), 7.46-7.53 (m, 3H), 6.67-6.81 (m, 1H), 6.31-6.35 (m, 1H), 5.68-5.70 (m, 1H), 4.81-4.92 (m, 1H), 4.04-4.43 (m, 2H), 2.74-3.23 (m, 2H), 1.82-2.24 (m, 4H).

Example 11: Preparation of 1-(3-(6-(pyridin-3-yl)quinazolin-8-yl)piperidin-1-yl)prop-2-en-1-one

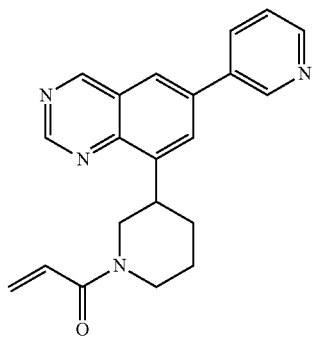

1-(3-(6-(pyridin-3-yl)quinazolin-8-yl)piperidin-1-yl)prop-2-en-1-one 1-(3-(6-(Pyridin-3-yl)quinazolin-8-yl)piperidin-1-yl)prop-2-en-1-one (16.0 mg) was prepared as described for 1-(3-(6-phenylquinazolin-8-yl)pyrrolidin-1-yl)prop-2-en-1-one. LRMS (M+H$^+$) m/z calculated 345.2, found 345.2. $^1$H NMR (DMSO-d6, 400 MHz) δ 9.69 (s, 1H), 9.41 (s, 1H), 9.14 (s, 1H), 8.70 (s, 1H), 8.34-8.46 (m, 3H), 7.62 (s, 1H), 6.17-6.97 (m, 2H), 5.71 (d, 1H), 4.18-4.58 (m, 4H), 2.65-2.86 (m, 1H), 1.61-2.07 (m, 4H).

Example 12: Preparation of N-(3-(6-(pyridin-4-yl)quinazolin-8-yl)phenyl)acrylamide

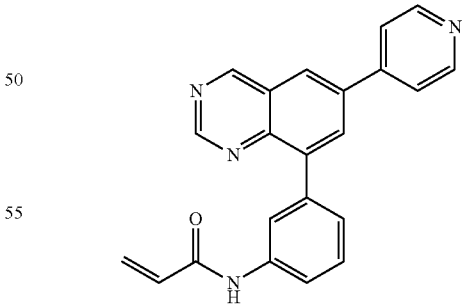

N-(3-(6-pyridin-4-yl)quinazolin-8-yl)phenyl)acrylamide

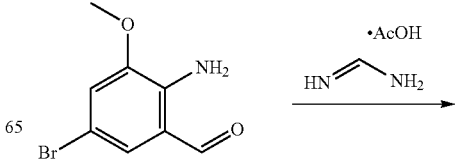

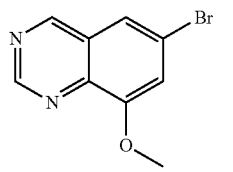

To a refluxing solution of 2-amino-5-bromo-3-methoxy-benzaldehyde (2.6 g, 11.4 mmol, 1.0 eq) in ethanol (40.0 mL) was added formamidine acetate (2.4 g, 22.8 mmol, 2.0 eq). The mixture was stirred under reflux overnight, then cooled and concentrated. The residue was purified on gel chromatography to provide 6-bromo-8-methoxyquinazoline as a white solid (1.6 g, 60%).

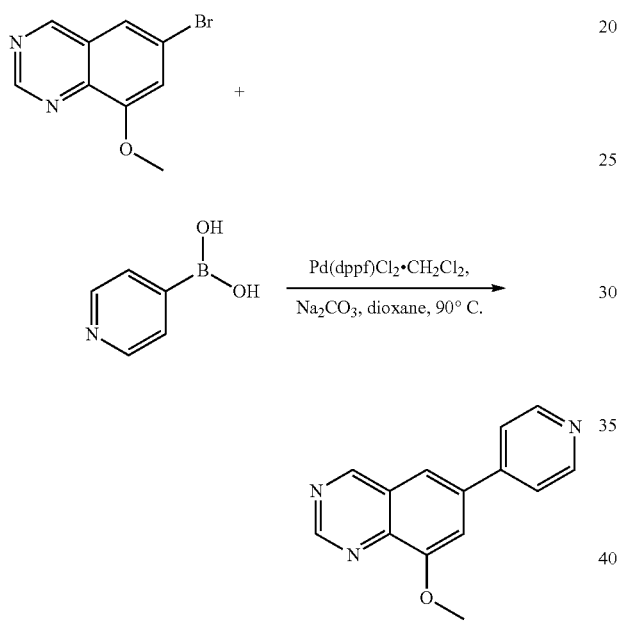

To a solution of 6-bromo-8-methoxyquinazoline (600.0 mg, 2.5 mmol, 1.0 eq) and pyridin-4-ylboronic acid (463.0 mg, 3.8 mmol, 1.5 eq) in dioxane (40.0 mL) and H$_2$O (4.0 mL) was added Na$_2$CO$_3$ (532.0 mg, 5.0 mmol, 2.0 eq), followed by Pd(dppf)Cl$_2$ (102.0 mg, 0.1 mmol, 0.05 eq) under N$_2$. The mixture was stirred at 90° C. for 12 h, then cooled to rt, diluted with EA (50.0 mL) and filtered. The filtrate was concentrated and the resulting residue was purified by column chromatography (PE/EA=1/1, v/v) to afford 8-methoxy-6-(pyridin-4-yl)quinazoline as a yellow solid (497.0 mg, 83.2%).

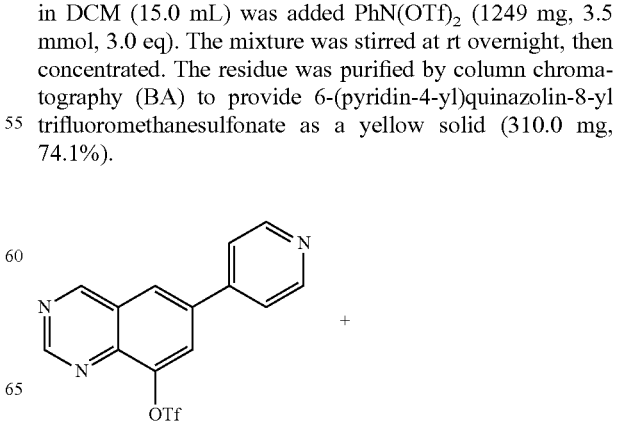

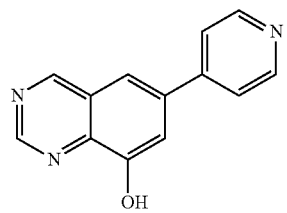

To a solution of 8-methoxy-6-(pyridin-4-yl)quinazoline (495.0 mg, 2.1 mmol, 1.0 eq) in DMF (20.0 mL) was added sodium ethanethiolate (873.5 mg, 10.4 mmol, 5.0 eq). The mixture was heated at 110° C. overnight under N$_2$, then cooled and diluted with H$_2$O (200.0 mL) and EA (100.0 mL) which was extracted with EA (100.0 mL×2). The EA layers were separated, dried over anhydrous Na$_2$SO$_4$ and concentrated to provide 6-(pyridin-4-yl)quinazolin-8-ol as a yellow solid (264.0 mg, 56.7%).

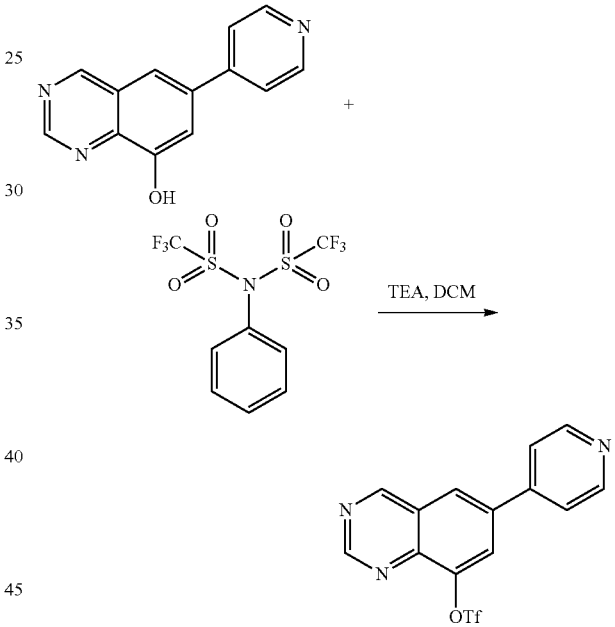

To a solution of 6-(pyridin-4-yl)quinazolin-8-ol (264.0 mg, 1.2 mmol, 1.0 eq) and TEA (0.8 mL, 5.9 mmol, 5.0 eq) in DCM (15.0 mL) was added PhN(OTf)$_2$ (1249 mg, 3.5 mmol, 3.0 eq). The mixture was stirred at rt overnight, then concentrated. The residue was purified by column chromatography (BA) to provide 6-(pyridin-4-yl)quinazolin-8-yl trifluoromethanesulfonate as a yellow solid (310.0 mg, 74.1%).

-continued

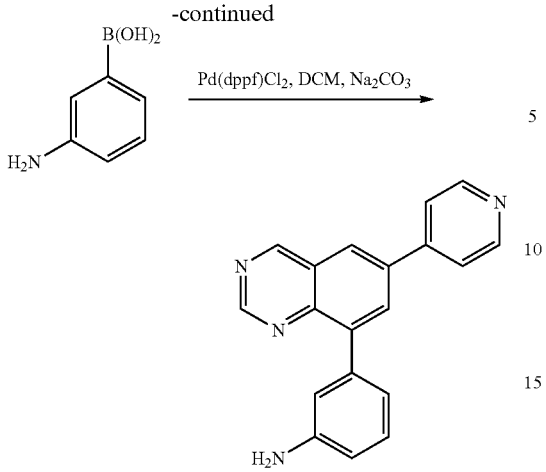

To a solution of 6-(pyridin-4-yl)quinazolin-8-yl trifluoromethanesulfonate (310.0 mg, 0.9 mmol, 1.0 eq) and (3-aminophenyl)boronic acid (230.0 mg, 1.1 mmol, 1.2 eq) in dioxane (15.0 mL) and H₂O (1.5 mL) was added Na₂CO₃ (185.0 mg, 1.74 mmol, 2.0 eq), followed by Pd(dppf)Cl₂ (36.0 mg, 0.04 mmol, 0.05 eq) under N₂. The mixture was stirred at 90° C. for 12 h, then cooled to rt, diluted with EA (40.0 mL) and filtered. The filtrate was concentrated and the resulting residue was purified via silica gel chromatography (DCM/MeOH=50/1, v/v) to afford 3-(6-(pyridin-4-yl)quinazolin-8-yl)aniline as a yellow solid (260.0 mg, 99.9%).

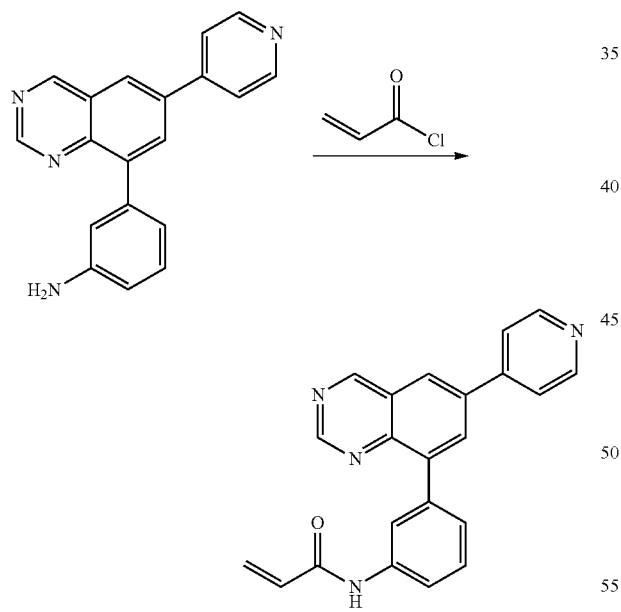

To a solution of 3-(6-(pyridin-4-yl)quinazolin-8-yl)aniline (260.0 mg, 0.9 mmol, 1.0 eq) in DCM (10.0 mL) was added TEA (0.2 mL, 1.7 mmol, 2.0 eq), followed by acryloyl chloride (0.1 mL, 0.9 mmol, 1.0 eq). The resulting mixture was stirred at rt for 1 h, then washed with brine, dried over anhydrous Na₂SO₄, concentrated. The residue was purified by column chromatography (DCM/MeOH=50:1, v/v) to afford N-(3-(6-(pyridin-4-yl)quinazolin-8-yl)phenyl)acrylamide as a yellow solid (39.0 mg, 12.7%). LRMS (M+H⁺) m/z calculated 353.1, found 353.6. ¹H NMR. (DMSO-d6, 400 MHz) δ 10.30 (s, 1H), 9.77 (s, 1H), 9.37 (s, 1H), 8.75 (d, 2H), 8.69 (s, 1H), 8.43 (s, 1H), 8.04 (s, 1H), 7.99 (d, 2H), 7.83 (s, 1H), 7.50 (d, 2H). 6.46 (dd, 1H), 6.29 (d, 1H), 5.77 (d, 1H).

Example 13: Preparation of N-(3-(6-(6-methylpyridin-3-yl)quinazolin-1-yl)phenyl)acrylamide

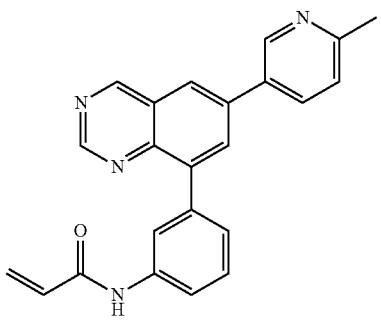

N-(3-(6-(6-methylpyridin-3-yl)quinazolin-8-yl)phenyl)acrylamide

N-(3-(6-(6-methylpyridin-3-yl)quinazolin-8-yl)phenyl)acrylamide (244.2 mg) was prepared as described for N-(3-(6-(pyridin-4-yl)quinazolin-8-yl)phenyl)acrylamide LRMS (M+H⁺) m/z calculated 367.1, found 367.5. ¹H NMR (DMSO-d6, 400 MHz) δ 10.30 (s, 1H), 9.72 (s, 1H), 9.33 (s, 1H), 9.02 (s, 1H), 8.55 (s, 1H), 8.37 (s, 1H), 8.25 (d, 1H), 8.03 (s, 1H), 7.84 (d, 1H), 7.43-7.50 (m, 3H), 6.48 (dd, 1H), 6.27 (d, 1H), 5.77 (d, 1H), 2.56 (s, 3H).

Example 14: Preparation of N-(3-(6-(2-(trifluoromethyl)pyridin-4-yl)quinazolin-8-yl)phenyl)acrylamide

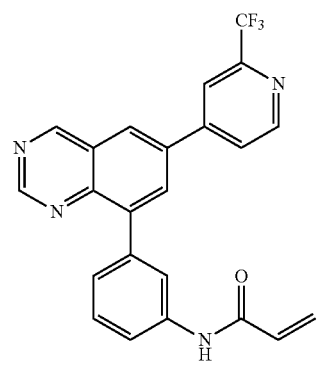

N-(3-(6-(2-(trifluoromethyl)pyridin-4-yl)quinazolin-8-yl)phenyl)acrylamide

N-(3-(6-(2-(trifluoromethyl)pyridin-4-yl)quinazolin-8-yl)phenyl)acrylamide (42.1 mg) was prepared as described for N-(3-(6-(pyridin-4-yl)quinazolin-8-yl)phenyl)acrylamide. LRMS (M+H⁺) m/z calculated 421.1, found 421.5. ¹H NMR (DMSO-d6, 400 MHz) δ 10.35 (s, 1H), 9.78 (s, 1H), 9.39 (s, 1H), 8.93 (d, 1H), 8.84 (s, 1H), 8.53 (d, 2H), 8.33 (d, 1H), 8.04 (s, 1H), 7.85 (s, 1H), 7.51 (s, 2H), 6.25-6.53 (m, 2H), 5.77 (d, 1H).

Example 15: Preparation of N-(3-(6-(pyridin-3-yl)quinazolin-8-yl)phenyl)acrylamide

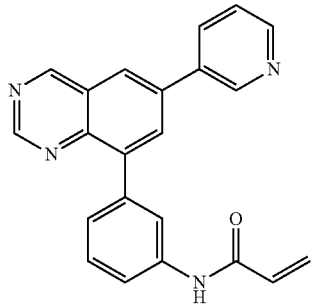

N-(3-(6-(pyridin-3-yl)quinazolin-8-yl)phenyl)acrylamide

N-(3-(6-(pyridin-3-yl)quinazolin-8-yl)phenyl)acrylamide (36.0 mg) was prepared as described for N-(3-(6-(pyridin-4-yl)quinazolin-8-yl)phenyl)acrylamide. LRMS (M+H$^+$) m/z calculated 353.4, found 353.2. $^1$H NMR. (DMSO-d6, 400 MHz) δ 10.29 (s, 1H), 9.74 (s, 1H), 9.35 (s, 1H), 9.17 (s, 1H), 8.69 (d, 1H), 8.60 (s, 1H), 8.38 (d, 2H), 8.04 (s, 1H), 7.83 (d, 1H), 7.59-7.62 (m, 1H). 7.47-7.52 (m, 2H), 6.49 (dd, 1H), 6.27 (d, 1H), 5.77 (d, 1H).

Example 16: Preparation of N-(3-(6-(5-(trifluoromethyl)pyridin-3-yl)quinazolin-8-yl)phenyl)acrylamide

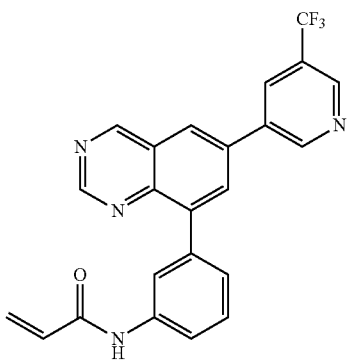

N-(3-(6-(5-(trifluoromethyl)pyridin-3-yl)quinazolin-8-yl)phenyl)acrylamide

N-(3-(6-(5-(trifluoromethyl)pyridin-3-yl)quinazolin-8-yl)phenyl)acrylamide (24 mg) was prepared as described for N-(3-(6-(pyridin-4-yl)quinazolin-8-yl)phenyl)acrylamide. LRMS (M+H$^+$) m/z calculated 421.1, found 421.2. $^1$H NMR (DMSO-d6, 400 MHz) δ 10.28 (s, 1H), 9.74 (s, 1H), 9.47 (s, 1 H), 9.37 (s, 1H), 9.07 (s, 1H), 8.76 (d, 2H), 8.54 (s, 1H), 8.03 (s, 1H), 7.84 (d, 1H), 7.49-7.51 (m, 2H), 6.45-6.52 (m, 1H), 6.27 (d, 1H), 5.76 (d, 1H).

Example 17: Preparation of N-(3-(6-(2-cyanophenyl)quinazolin-8-yl)phenyl)acrylamide

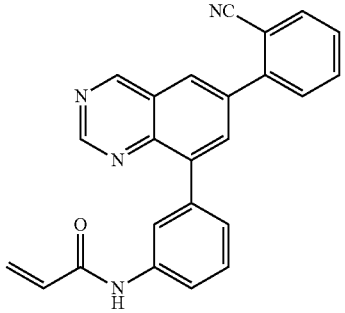

N-(3-(6-(2-cyanophenyl)quinazolin-8-yl)phenyl)acrylamide

N-(3-(6-(2-cyanophenyl)quinazolin-8-yl)phenyl)acrylamide (2 mg) was prepared as described for N-(3-(6-(pyridin-4-yl)quinazolin-8-yl)phenyl)acrylamide. LRMS (M+H$^+$) m/z calculated 377.1, found 377.2. $^1$H NMR (DMSO-d6, 400 MHz) δ 10.28 (s, 1H), 9.79 (s, 1H), 9.40 (s, 1H), 8.45 (s, 1H), 8.24 (s, 1H), 8.06 (s, 2H), 7.89 (s, 2H), 7.83 (s, 1H), 7.70 (s, 1H), 7.48 (s, 2H), 6.24-6.47 (m, 2H), 5.76-5.78 (m, 1H).

Example 18: Preparation of 1-(3-(6-(5-(trifluoromethyl)pyridin-3-yl)quinazolin-8-yl)pyrrolidin-1-yl)prop-2-en-1-one

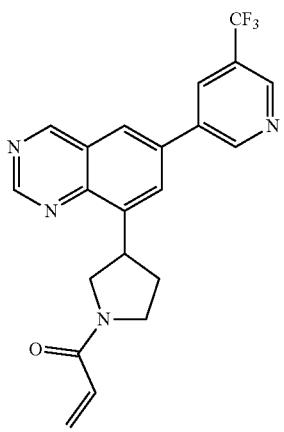

1-(3-(6-(5-(trifluoromethyl)pyridin-3-yl)quinazolin-8-yl)pyrrolidin-1-yl) prop-2-en-1-one 1-(3-(6-(5-(Trifluoromethyl)pyridin-3-yl)quinazolin-8-yl)pyrrolidin-1-yl)prop-2-en-1-one (48.1 mg) was prepared as described for 1-(3-(6-phenylquinazolin-8-yl)pyrrolidin-1-yl)prop-2-en-1-one. LRMS (M+H$^+$) m/z calculated 399.1, found 399.2. $^1$H NMR (DMSO-d6, 400 MHz) δ 9.69 (s, 1H), 9.41-9.43 (m, 2H), 9.06 (s, 1H), 8.73 (s, 1H), 8.61 (d, 1H), 8.46 (d, 1H), 6.60-6.72 (m, 1H), 6.15-6.21 (m, 1H), 5.65-5.73 (m, 1H), 4.47-4.65 (m, 1H), 4.09-4.21 (m, 1H), 3.72-3.94 (m, 2H), 3.49-3.66 (m, 1H), 2.33-2.46 (m, 2H).

Example 19: Preparation of N-(3-(6-(3-((3-(trifluoromethyl)phenyl)amino)phenyl)quinazolin-8-yl)phenyl)acrylamide

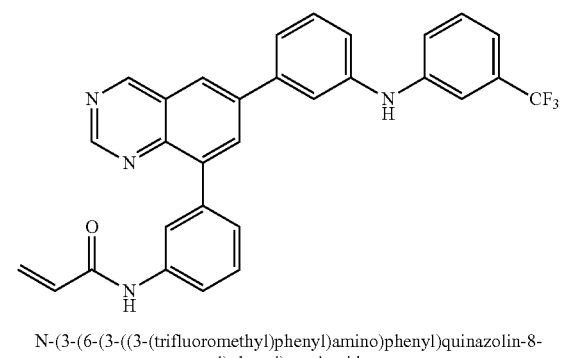

N-(3-(6-(3-((3-(trifluoromethyl)phenyl)amino)phenyl)quinazolin-8-yl)phenyl)acrylamide

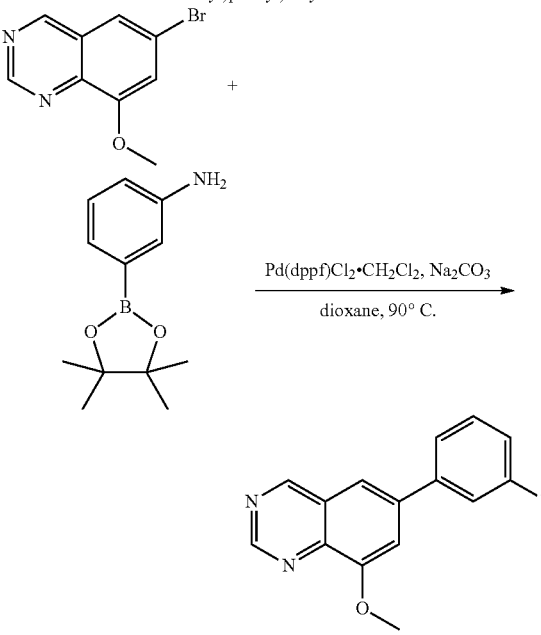

To a solution of 6-bromo-8-methoxyquinazoline (2.5 g, 10.5 mmol, 1.0 eq) and 3-(4,4,5,5-tetramethyl-1,3,2-dioxaborolan-2-yl)aniline (2.2 g, 10.0 mmol, 0.9 eq) in dioxane (30 mL) and H$_2$O (3 mL) was added Na$_2$CO$_3$ (2.3 g, 21 mmol, 2.0 eq), followed by Pd(dppf)Cl$_2$·CH$_2$Cl$_2$ (1.5 g, 2.1 mmol, 0.2 eq) under N$_2$. The mixture was stirred at 90° C. for 12 h, then cooled to rt. The resulting mixture was purified by column chromatography (EA+0.5% TEA, v/v) to afford 3-(8-methoxyquinazolin-6-yl)aniline as a yellow solid (1.8 g, 85.3%).

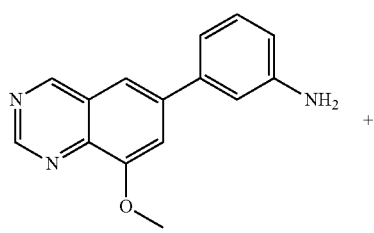

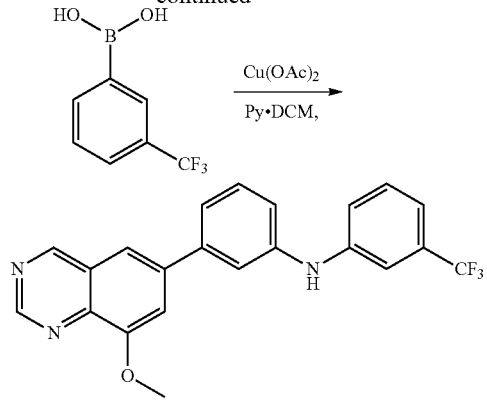

To a solution of 3-(8-methoxyquinazolin-6-yl)aniline (400 mg, 1.6 mmol, 1.0 eq), pyridine (380 mg, 4.8 mmol, 3.0 eq) and (3-(trifluoromethyl)phenyl)boronic acid (608 mg, 3.2 mmol, 2.0 eq) in DCM (10 mL) was added Cu(OAc)$_2$ (720 mg, 4.8 mmol, 3.0 eq). The mixture was stirred at 50° C. for 6 h, then cooled to rt. Cu(OAc)$_2$ was filtered. The mixture was purified by column chromatography (EA/PE=1/1+0.5% TEA, v/v) to afford 3-(8-methoxyquinazolin-6-yl)-N-(3-(trifluoromethyl)phenyl) aniline as a yellow solid (330 mg, 52.4%).

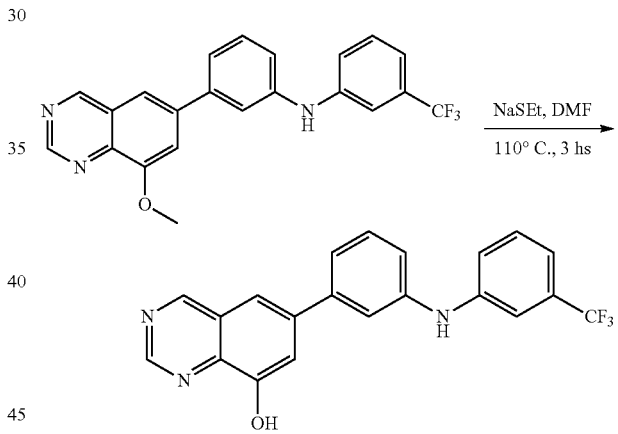

To a solution of 3-(8-methoxyquinazolin-6-yl)-N-(3-(trifluoromethyl)phenyl)aniline (330 mg, 0.83 mmol, 1.0 eq) in DMF (5.0 mL) was added sodium ethanethiolate (209 mg, 2.49 mmol, 3.0 eq). The mixture was heated at 110° C. overnight under N$_2$, then cooled to rt, concentrated and diluted with H$_2$O (200.0 mL), the precipitate was collected by filtration to afford crude 6-(3-((3-(trifluoromethyl)phenyl)amino)phenyl)quinazolin-8-ol as a yellow solid (400 mg, crude).

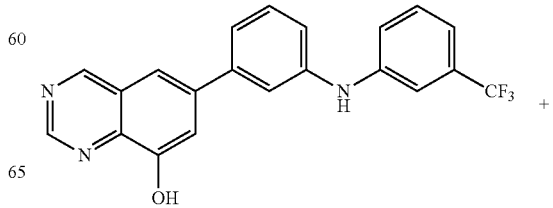

-continued

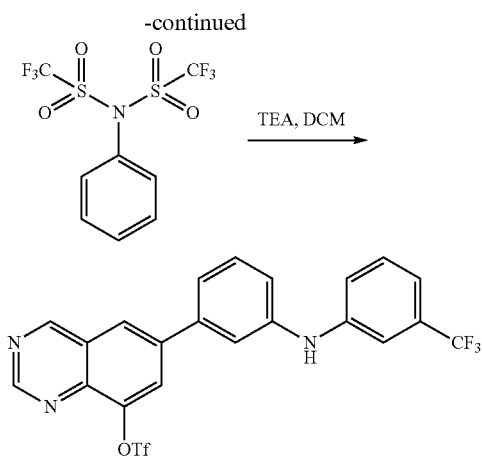

TEA, DCM

To a solution of 6-(3-((3-(trifluoromethyl)phenyl)amino)phenyl)quinazolin-8-ol (316 mg, 0.83 mmol, 1.0 eq) and TEA (1.2 mL, 8.3 mmol, 10.0 eq) in DCM (10.0 mL) was added PhN(OTf)$_2$ (890 mg, 2.5 mmol, 3.0 eq). The mixture was stirred at rt overnight, then concentrated. The residue was purified by column chromatography (DCM/MeOH=50/1, v/v) to provide 6-(3-((3-(trifluoromethyl)phenyl)amino)phenyl)quinazolin-8-yl trifluoromethanesulfonate as a yellow solid (400 mg, c.a. 100%).

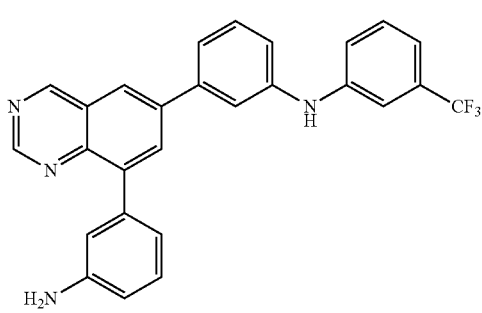

To a solution of 6-(3-((3-(trifluoromethyl)phenyl)amino)phenyl)quinazolin-8-yl trifluoromethanesulfonate (200 mg, 0.39 mmol, 1.0 eq) and 3-(4,4,5,5-tetramethyl-1,3,2-dioxaborolan-2-yl)aniline (60 mg, 0.43 mmol, 1.1 eq) in dioxane (10 mL) and H$_2$O (1 mL) was added Na$_2$CO$_3$ (85 mg, 0.78 mmol, 2.0 eq), followed by Pd(dppf)Cl$_2$·CH$_2$Cl$_2$ (65 mg, 0.078 mmol, 0.2 eq) under N$_2$. The mixture was stirred at 90° C. for 12 h, then cooled to rt. The resulting mixture was purified by column chromatography (DCM/MeOH=50/1, v/v) to afford 3-(8-(3-aminophenyl)quinazolin-6-yl)-N-(3-(trifluoromethyl)phenyl)aniline as a yellow solid (90 mg, 45.0%).

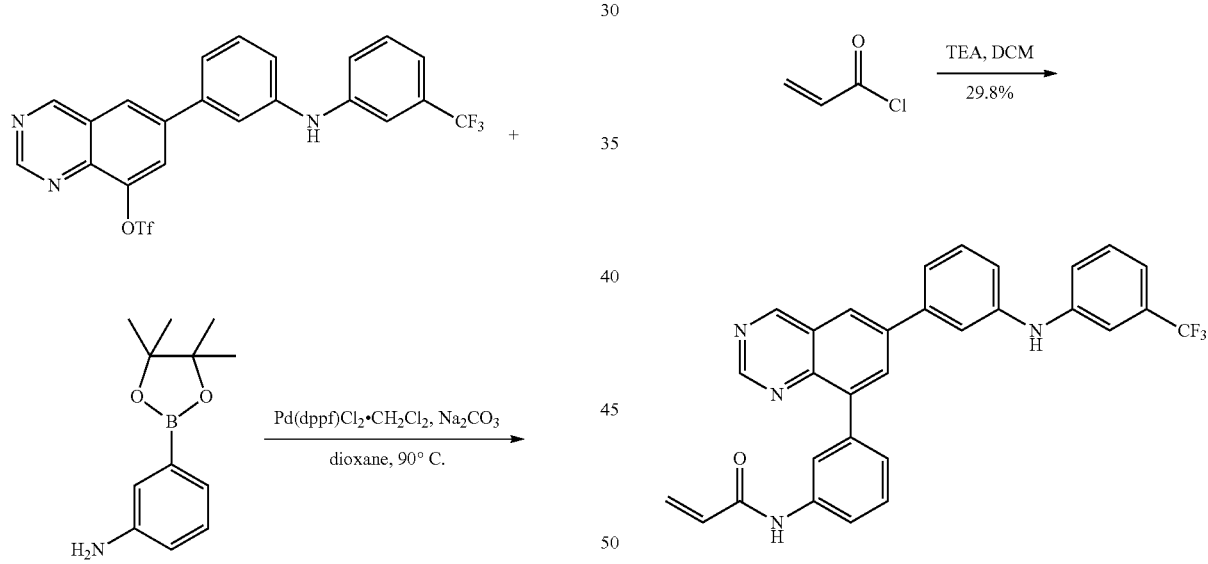

To a solution of 3-(8-(3-aminophenyl)quinazolin-6-yl)-N-(3-(trifluoromethyl)phenyl)aniline (90 mg, 0.19 mmol, 1.0 eq) in DCM (10.0 mL) was added TEA (0.06 mL, 0.38 mmol, 2.0 eq.), followed by acryloyl chloride (12.4 mg, 0.14 mmol, 0.7 eq.). The resulting mixture was stirred at rt for 1 h, then washed with brine, dried over anhydrous Na$_2$SO$_4$, concentrated. The residue was purified by column chromatography (DCM/MeOH=20/1, v/v) to afford N-(3-(6-(3-((3-(trifluoromethyl)phenyl)amino)phenyl)quinazolin-8-yl)phenyl)acrylamide as a yellow solid (25.5 mg, 42.1%). LRMS (M+H$^+$) m/z calculated 510.2, found 511.2. $^1$H NMR (DMSO-d6, 400 MHz) δ 10.29 (s, 1H), 9.74 (s, 1H), 9.33 (s, 1H), 8.76 (s, 1H), 8.47 (s, 1H), 8.28 (s, 1H), 8.06 (s, 1H), 7.81 (s, 1H), 7.12-7.61 (m, 10H), 6.45-6.47 (m, 1H), 6.25-6.30 (m, 1H), 5.77 (d, 1H).

Example 20: Preparation of N-(3-(6-(3-(phenylamino)phenyl)quinazolin-8-yl)phenyl)acrylamide

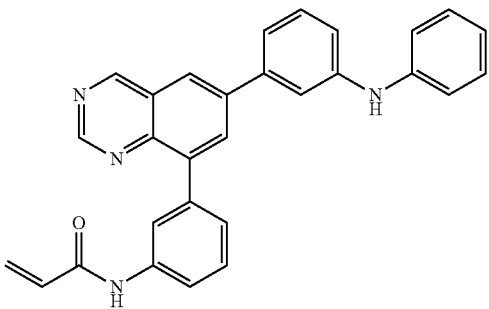

N-(3-(6-(3-(phenylamino)phenyl)quinazolin-8-yl)phenyl)acrylamide

N-(3-(6-(3-(phenylamino)phenyl)quinazolin-8-yl)phenyl)acrylamide (21.7 mg) was prepared as described for N-(3-(6-(3-((3-(trifluoromethyl)phenyl)amino)phenyl)quinazolin-8-yl)phenyl)acrylamide. LRMS (M+H⁺) m/z calculated 443.2, found 443.3. $^1$H NMR (DMSO-d6, 400 MHz) δ 10.29 (s, 1H), 9.74 (s, 1H), 9.32 (s, 1H), 8.44 (s, 1H), 8.38 (s, 1H), 8.26 (s, 1H), 8.05 (s, 1H), 7.81 (s, 1H), 7.15-7.54 (m, 10H), 6.84-6.88 (m, 1H), 6.45-6.52 (m, 1H), 6.25-6.30 (m, 1H), 5.77 (d, 1H).

Example 21: Preparation of N-(3-(6-(4-((3-(trifluoromethyl)phenyl)amino)phenyl)quinazolin-8-yl)phenyl)acrylamide

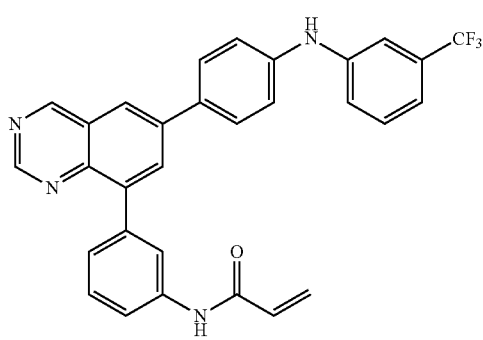

N-(3-(6-(4-((3-(trifluoromethyl)phenyl)amino)phenyl)quinazolin-8-yl)phenyl)acrylamide N-(3-(6-(4-((3-(trifluoromethyl)phenyl)amino)phenyl)quinazolin-8-yl)phenyl)acrylamide (11.6 mg) was prepared as described for N-(3-(6-(3-((3-(trifluoromethyl)phenyl)amino)phenyl)quinazolin-8-yl)phenyl)acrylamide. LRMS (M+H⁺) m/z calculated 511.2, found 511.6. $^1$H NMR (DMSO-d6, 400 MHz) δ 10.29 (s, 1H), 9.70 (s, 1H), 9.29 (s, 1H), 8.84 (s, 1H), 8.45 (s, 1H), 8.33 (s, 1H), 8.04 (s, 1H), 7.82-7.91 (m, 3H), 7.30-7.50 (m, 5H), 7.27 (d, 2H), 7.17 (d, 1H), 6.25-6.52 (m, 2H), 5.77 (d, 1H).

Example 22: Preparation of N-(3-(6-(4-(phenylamino)phenyl)quinazolin-8-yl)phenyl)acrylamide

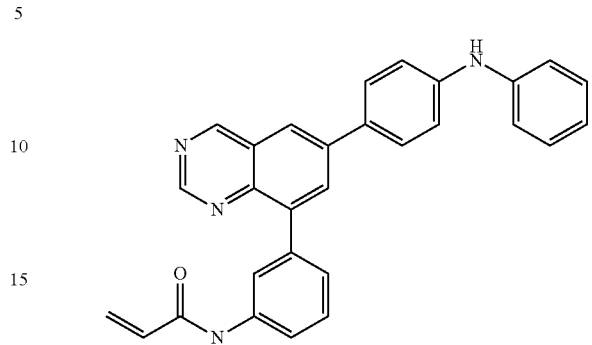

N-(3-(6-(4-(phenylamino)phenyl)quinazolin-8-yl)phenyl)acrylamide

N-(3-(6-(4-(phenylamino)phenyl)quinazolin-8-yl)phenyl)acrylamide (6.7 mg) was prepared as described for N-(3-(6-(3-((3-(trifluoromethyl)phenyl)amino)phenyl)quinazolin-8-yl)phenyl)acrylamide. LRMS (M+H⁺) m/z calculated 443.2, found 443.6. $^1$H NMR (DMSO-d6, 400 MHz) δ 10.28 (s, 1H), 9.68 (s, 1H), 9.28 (s, 1H), 8.47 (s, 1H), 8.40 (s, 1H), 8.30 (s, 1H), 8.03 (s, 1H), 7.82-7.84 (m, 3H), 7.49 (s, 2H), 7.16-7.31 (m, 6H), 6.90-6.92 (m, 1H), 6.32 (d, 2H), 5.77 (d, 1H).

Example 23: Preparation of 1-(3-(6-(3-((3-(trifluoromethyl)phenyl)amino)phenyl)quinazolin-8-yl)piperidin-1-yl)prop-2-en-1-one

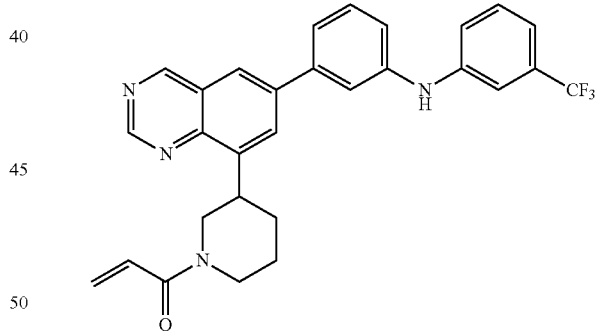

1-(3-(6-(3-((3-(trifluoromethyl)phenyl)amino)phenyl)quinazolin-8-yl)piperidin-1-yl)prop-2-en-1-one 1-(3-(6-(3-((3-(Trifluoromethyl)phenyl)amino)phenyl)quinazolin-8-yl)piperidin-1-yl)prop-2-en-1-one (19.3 mg) was prepared as described for 1-(3-(6-phenylquinazolin-8-yl)pyrrolidin-1-yl)prop-2-en-1-one. LRMS (M+H⁺) m/z calculated 503.2, found 503.3. $^1$H NMR (CD$_3$OD, 400 MHz) δ 9.55 (s, 1H), 9.28 (d, 1H), 8.20 (s, 1H), 7.35-7.52 (m, 6H), 7.21-7.23 (m, 1H), 7.10-7.12 (m, 1H), 6.87-6.90 (m, 1H), 6.21-6.25 (m, 1H), 5.73-5.78 (m, 1H), 4.68-4.78 (m, 1H), 4.43-4.47 (m, 1H), 4.07 (s, 1H), 2.89-3.25 (m, 2H), 1.75-2.20 (m, 4H).

Example 24: Preparation of N-(3-(6-(6-phenoxy-pyridin-3-yl)quinazolin-8-yl)phenyl)acrylamide

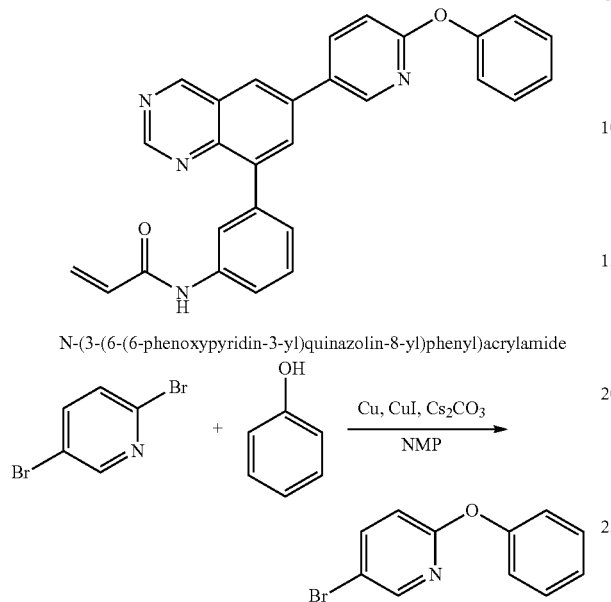

N-(3-(6-(6-phenoxypyridin-3-yl)quinazolin-8-yl)phenyl)acrylamide

A mixture of 2,5-dibromopyridine (237 mg, 1 mmol, 1.0 eq), phenol (140 mg, 1.5 mmol, 1.5 eq), Cu (32.5 mg, 0.5 mmol, 0.5 eq), CuI (95 mg, 0.5 mmol, 0.5 eq) and Cs$_2$CO$_3$ (978 mg, 3.0 mmol, 3.0 eq) in NMP (10 mL) was heated to 135° C. for 5 h under N$_2$. The solid was filtered off and the filtrate was concentrated and purified by column chromatography (EA/PE=10/1, v/v) to provide 5-bromo-2-phenoxypyridine as a brown solid (200 mg, 84.4%).

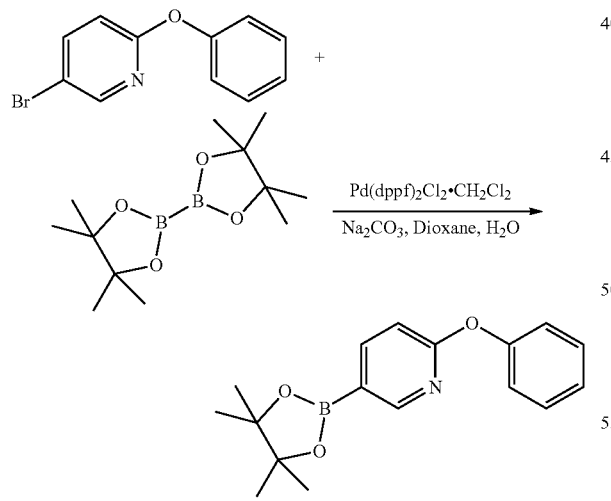

To a solution of 5-bromo-2-phenoxypyridine (200 mg, 0.8 mmol, 1.0 eq) and bis(pinacolato)diboron (264 mg, 1.04 mmol, 1.3 eq) in dioxane (10 mL) was added AcOK (102 mg, 1.04 mmol, 1.3 eq) and Pd(dppf)Cl$_2$·CH$_2$Cl$_2$ (35 mg, 0.04 mmol, 0.05 eq), the mixture was stirred at 100° C. overnight under N$_2$. The residue was diluted with aqueous Na$_2$CO$_3$ (20 mL) and extracted with EA (20 mL×3). The organic layers were separated, combined, washed with brine (20 mL*3) dried over Na$_2$SO$_4$, filtered and concentrated. The resulting residue was purified by column chromatography (PE/EA=50/1, v/v) to afford 2-phenoxy-5-(4,4,5,5-tetramethyl-1,3,2-dioxaborolan-2-yl)pyridine (300 mg, crude).

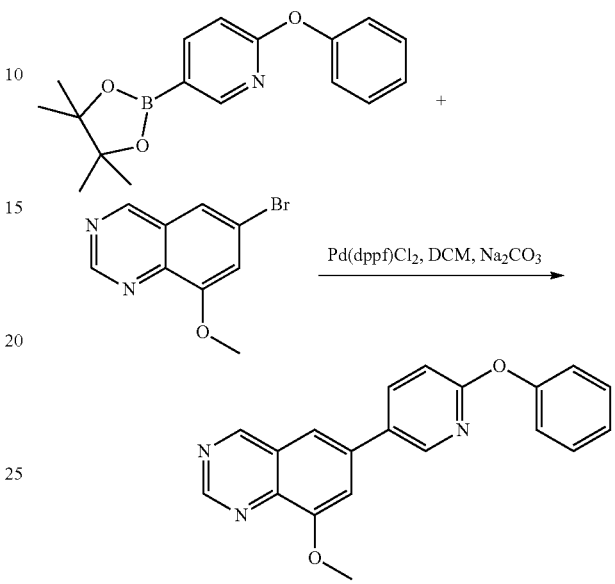

To a solution of 5-bromo-8-methoxyquinazoline (238 mg, 1.0 mmol, 1.0 eq) and 2-phenoxy-5-(4,4,5,5-tetramethyl-1,3,2-dioxaborolan-2-yl)pyridine (300 mg, 3.0 mmol, 1.0 eq) in dioxane (5.0 mL) and H$_2$O (0.5 mL) was added Na$_2$CO$_3$ (212 mg, 2.0 mmol, 2.0 eq), followed by Pd(dppf)Cl$_2$·CH$_2$Cl$_2$ (80.0 mg, 0.1 mmol, 0.1 eq) under N$_2$. The mixture was stirred at 90° C. for 12 h, then cooled to rt, diluted with EA (50.0 mL) and filtered. The filtrate was concentrated and the resulting residue was purified on flash chromatography (PE/EA=1/1, v/v) to afford 8-methoxy-6-(6-phenoxypyridin-3-yl)quinazoline as a yellow solid (210 mg, 79.5%).

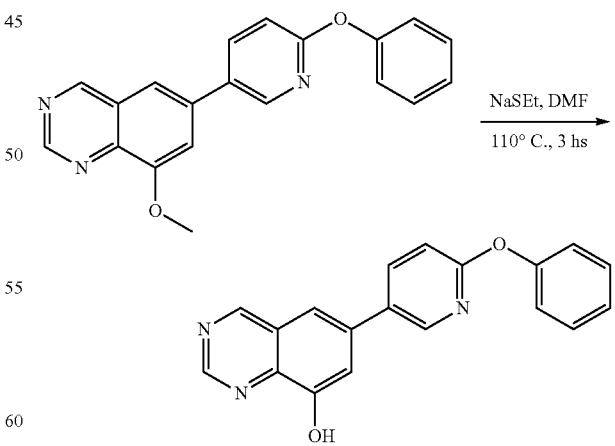

To a solution of 8-methoxy-6-(6-phenoxypyridin-3-yl)quinazoline (210 mg, 0.64 mmol, 1.0 eq) in DMF (10.0 mL) was added sodium ethanethiolate (161 mg, 1.92 mmol, 3.0 eq). The mixture was heated at 110° C. overnight under N$_2$, then cooled and diluted with H$_2$O (100.0 mL) and EA (50.0 mL) which was extracted with EA (50.0 mL*2). The EA layers were separated, dried over anhydrous Na₂SO₄ and concentrated to provide 6-(6-phenoxypyridin-3-yl)quinazolin-8-ol as a yellow solid (100.0 mg, 54.7%).

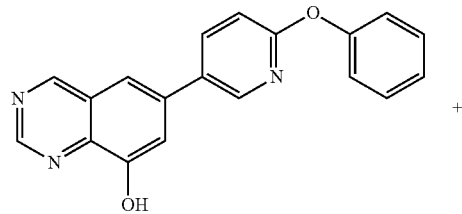

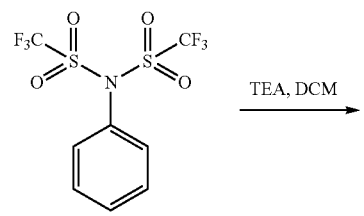

TEA, DCM

To a solution of 6-(6-phenoxypyridin-3-yl)quinazolin-8-ol (100 mg, 0.32 mmol, 1.0 eq) and TEA (0.2 mL, 1.6 mmol, 5.0 eq) in DMF (15.0 mL) was added PhN(OTf)₂ (350 mg, 0.96 mmol, 3.0 eq). The mixture was stirred at rt overnight, then concentrated. The residue was purified by column chromatography (PE/EA=1:1, v/v) to provide 6-(6-phenoxypyridin-3-yl)quinazolin-8-yl trifluoromethanesulfonate as a yellow solid (65 mg, 45.8%).

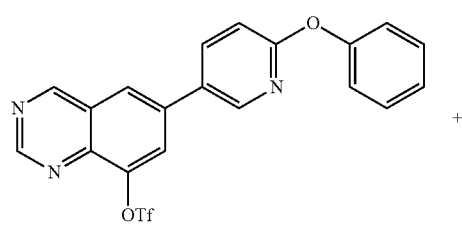

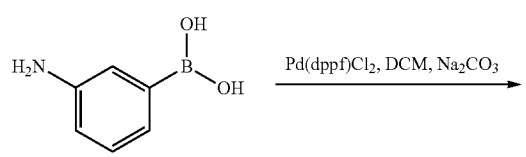

Pd(dppf)Cl₂, DCM, Na₂CO₃

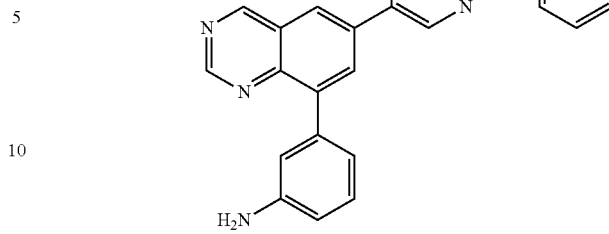

To a solution of 6-(6-phenoxypyridin-3-yl)quinazolin-8-yl trifluoromethanesulfonate (65 mg, 0.15 mmol, 1.0 eq) and (3-aminophenyl)boronic acid (22 mg, 0.17 mmol, 1.1 eq) in dioxane (5.0 mL) and H₂O (0.5 mL) was added Na₂CO₃ (31 mg, 0.3 mmol, 2.0 eq), followed by Pd(dppf)Cl₂·CH₂Cl₂ (16.0 mg, 0.02 mmol, 0.1 eq) under N₂. The mixture was stirred at 90° C. for 12 h, then cooled to rt, diluted with EA (40.0 mL) and filtered. The filtrate was concentrated and the resulting residue was purified by column chromatography (DCM/MeOH=50/1, v/v) to afford 3-(6-(6-phenoxypyridin-3-yl)quinazolin-8-yl)aniline as a yellow solid (60 mg, 98%).

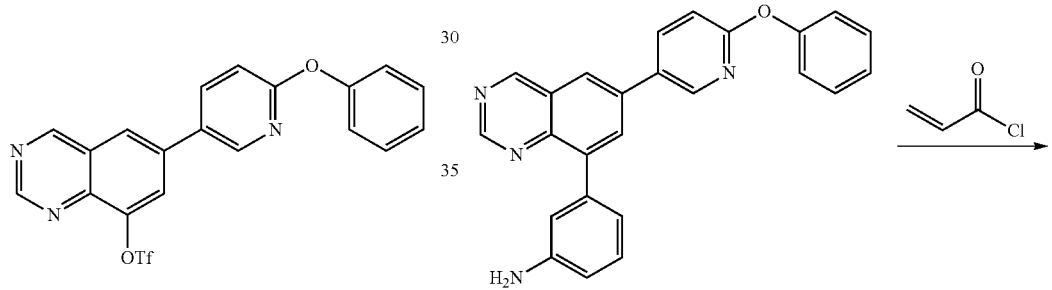

To a solution of 3-(6-(6-phenoxypyridin-3-yl)quinazolin-8-yl)aniline (60 mg, 0.15 mmol, 1.0 eq) in DCM (10.0 mL) was added TEA (0.1 mL, 0.75 mmol, 5.0 eq), followed by acryloyl chloride (12 mg, 0.13 mmol, 0.9 eq). The resulting mixture was stirred at rt for 1 h, then washed with brine, dried over anhydrous Na2SO4, concentrated. The residue was purified by column chromatography (DCM/MeOH=50:1, v/v) to afford N-(3-(6-(6-phenoxypyridin-3-yl)quinazolin-8-yl)phenyl)acrylamide as a yellow solid (14.6 mg, 21.4%) LRMS (M+H⁺) m/z calculated 445.2, found 445.7. ¹H NMR (CD₃OD, 400 MHz) δ 9.55 (s, 1H), 9.18 (d, 1H), 8.56 (s, 1H), 8.24-8.29 (m, 3H), 8.02 (s, 1H), 7.69 (s, 4H), 7.03-7.23 (m, 4H), 6.37-6.42 (m, 4H), 5.76 (s, 1H).

Example 25: Preparation of 1-(3-(6-(4-phenoxyphenyl)quinazolin-8-yl)pyrrolidin-1-yl)prop-2-en-1-one

1-(3-(6-(4-phenoxyphenyl)quinazolin-8-yl)pyrrolidin-1-yl)prop-2-en-1-one 1-(3-(6-(4-Phenoxyphenyl)quinazolin-8-yl)pyrrolidin-1-yl)prop-2-en-1-one (28.4 mg) was prepared as described for 1-(3-(6-phenylquinazolin-8-yl)pyrrolidin-1-yl)prop-2-en-1-one. LRMS (M+H$^+$) m/z calculated 422.2, found 422.2. $^1$H NMR (CD$_3$OD, 400 MHz) δ 9.57 (s, 1H), 9.25 (d, 1H), 8.12-8.15 (m, 2H), 7.72-7.75 (m, 2H), 7.35-7.39 (m, 2H), 7.02-7.09 (m, 2H), 6.58-6.69 (m, 1H), 6.27-6.34 (m, 1H), 5.72-5.80 (m, 1H), 4.29-4.33 (m, 1H), 4.19-4.24 (m, 1H), 3.62-3.92 (m, 3H), 2.36-2.52 (m, 2H).

Example 26: Preparation of N-(3-(6-(6-(4-chlorophenoxy)pyridin-3-yl)quinazolin-8-yl)phenyl)acrylamide

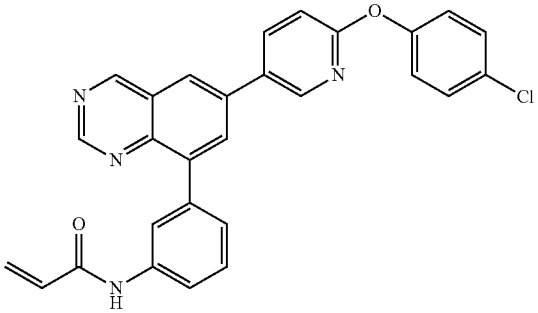

N-(3-(6-(6-(4-chlorophenoxy)pyridin-3-yl)quinazolin-8-yl)phenyl)acrylamide

N-(3-(6-(6-(4-chlorophenoxy)pyridin-3-yl)quinazolin-8-yl)phenyl)acrylamide (28.4 mg) was prepared as described for N-(3-(6-(6-phenoxypyridin-3-yl)quinazolin-8-yl)phenyl)acrylamide. LRMS (M+H$^+$) m/z calculated 479.2, found 479.2. $^1$H NMR (DMSO-d6, 400 MHz) δ 10.27 (s, 1H), 9.70 (s, 1H), 9.33 (s, 1H), 8.73 (d, 1H), 8.35-8.51 (m, 3H), 8.05 (s, 1H), 7.82 (d, 1H), 7.48-7.52 (m, 3H), 7.25-7.27 (m, 3H), 6.45-6.47 (m, 1H), 6.25-6.29 (m, 1H), 5.76-5.78 (m, 1H).

Example 27: Preparation of N-(3-(6-(4-phenoxyphenyl)quinazolin-8-yl)phenyl)acrylamide

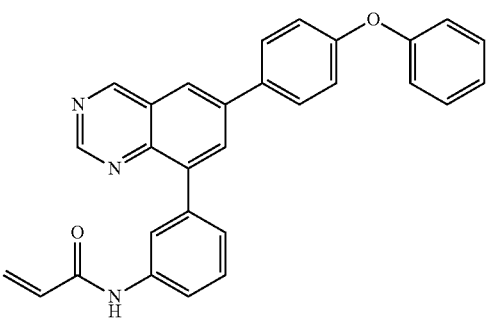

N-(3-(6-(4-phenoxyphenyl)quinazolin-8-yl)phenyl)acrylamide

N-(3-(6-(4-phenoxyphenyl)quinazolin-8-yl)phenyl)acrylamide (15.2 mg) was prepared as described for N-(3-(6-(6-phenoxypyridin-3-yl)quinazolin-8-yl)phenyl)acrylamide. LRMS (M+H$^+$) m/z calculated 444.2, found 444.3. $^1$H NMR (CDCl$_3$, 400 MHz) δ 9.57 (s, 1H), 9.35 (s, 1H), 8.29 (s, 1H), 8.14 (s, 1H), 7.08-7.15 (m, 14H), 6.30-6.46 (m, 2H), 5.30-5.79 (m, 1H).

Example 28: Preparation of 1-(3-(6-(6-phenoxypyridin-3-yl)quinazolin-8-yl)pyrrolidin-1-yl)prop-2-en-1-one

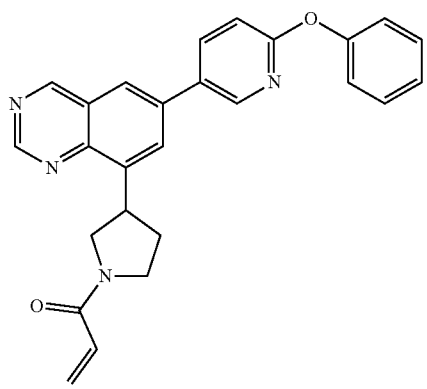

1-(3-(6-(6-phenoxypyridin-3-yl)quinazolin-8-yl)pyrrolidin-1-yl)prop-2-en-1-one 1-(3-(6-(6-Phenoxypyridin-3-yl)quinazolin-8-yl)pyrrolidin-1-yl)prop-2-en-1-one (36.1 mg) was prepared as described for 1-(3-(6-phenylquinazolin-8-yl)pyrrolidin-1-yl)prop-2-en-1-one. LRMS (M+H$^+$) m/z calculated 423.2, found 423.2. $^1$H NMR (CD$_3$OD, 400 MHz) δ 9.57 (s, 1H), 9.30 (d, 1H), 8.58 (s, 1H), 8.20-8.27 (m, 3H), 7.43-7.47 (m, 2H), 7.08-7.27 (m, 4H), 6.66-6.69 (m, 1H), 6.28-6.34 (m, 1H), 5.72-5.80 (m, 1H), 4.55-4.62 (m, 1H), 4.35-4.42 (m, 1H), 3.68-3.98 (m, 3H), 2.46-2.55 (m, 2H).

Example 29: Preparation of N-(3-(6-(6-(3-(trifluoromethyl)phenoxy)pyridin-3-yl)quinazolin-8-yl)phenyl)acrylamide

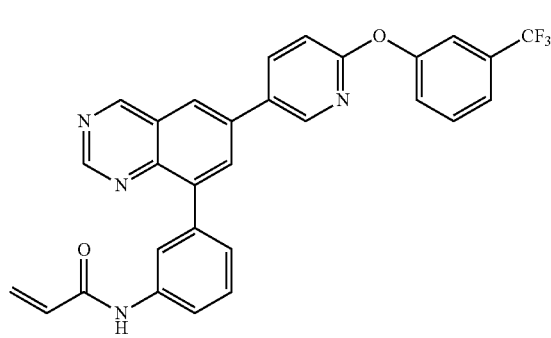

N-(3-(6-(6-(3-(trifluoromethyl)phenoxy)pyridin-3-yl)quinazolin-8-yl)phenyl)acrylamide N-(3-(6-(6-(3-(trifluoromethyl)phenoxy)pyridin-3-yl)quinazolin-8-yl)phenyl)acrylamide (23 mg) was prepared as described for 1-(3-(6-phenylquinazolin-8-yl)pyrrolidin-1-yl)prop-2-en-1-one. LRMS (M+H$^+$) m/z calculated 513.1, found 513.2. $^1$H NMR (DMSO-d6, 400 MHz) δ 10.28 (s, 1H), 9.70 (s, 1H), 9.33 (s, 1H), 8.74 (s, 1H), 8.46-8.52 (m, 2H), 8.36 (s, 1H), 8.06 (s, 1H), 7.82 (s, 1H), 7.50-7.70 (m, 6H), 7.31 (d, 1H), 6.47 (t, 1H), 6.28 (d, 1H), 5.77 (d, 1H).

Example 30: Preparation of 1-(3-(6-(6-(3-(trifluoromethyl)phenoxy)pyridin-3-yl)quinazolin-8-yl)pyrrolidin-1-yl)prop-2-en-1-one

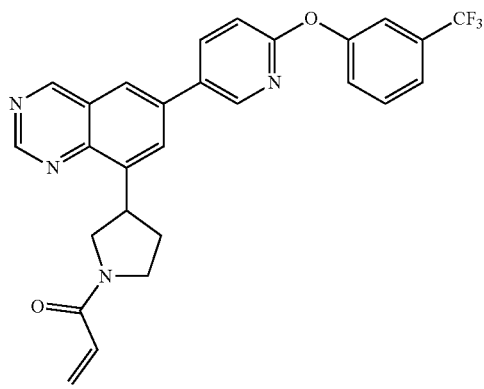

1-(3-(6-(6-(3-(trifluoromethyl)phenoxy)pyridin-3-yl)quinazolin-8-yl)pyrrolidin-1-yl)prop-2-en-1-one 1-(3-(6-(6-(3-(Trifluoromethyl)phenoxy)pyridin-3-yl)quinazolin-8-yl)pyrrolidin-1-yl)prop-2-en-1-one (24.1 mg) was prepared as described for 1-(3-(6-phenylquinazolin-8-yl)pyrrolidin-1-yl)prop-2-en-1-one. LRMS (M+H$^+$) m/z calculated 491.2, found 491.3. $^1$H NMR (CD$_3$OD, 400 MHz) δ 9.53 (d, 1H), 9.28 (d, 1H), 8.55 (t, 1H), 8.17-8.30 (m, 3H), 7.44-7.65 (m, 4H), 7.19 (d, 1H), 6.65-6.68 (m, 1H), 6.27-6.34 (m, 1H), 5.71-5.79 (m, 1H), 4.57-4.60 (m, 1H), 4.22-4.34 (m, 1H), 3.66-3.84 (m, 3H), 2.46-2.48 (m, 1H).

Example 31: Preparation of 4-(8-(3-acrylamidophenyl)quinazolin-6-yl)-N-(pyridin-2-yl)benzamide

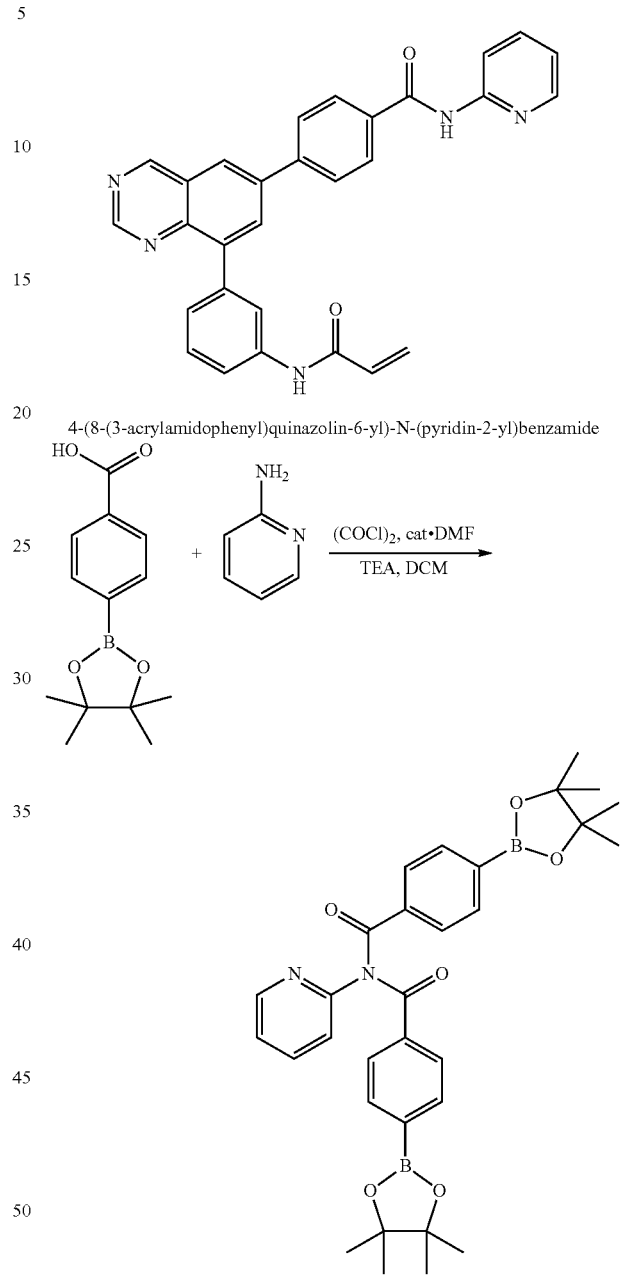

4-(8-(3-acrylamidophenyl)quinazolin-6-yl)-N-(pyridin-2-yl)benzamide

To a solution of 4-(4,4,5,5-tetramethyl-1,3,2-dioxaborolan-2-yl)benzoic acid (5.0 g, 20.2 mmol, 1.0 eq) in DCM (100 mL) was added oxalyl chloride (5 mL, 50.4 mmol, 2.5 eq) and the mixture was stirred at rt for 4 h. The mixture was concentrated to provide 4-(4,4,5,5-tetramethyl-1,3,2-dioxaborolan-2-yl)benzoyl chloride as a grey solid. The solution of 4-(4,4,5,5-tetramethyl-1,3,2-dioxaborolan-2-yl)benzoyl chloride (crude) in CH$_3$CN (200 mL) was added pyridin-2-amine (4.47 g, 50.4 mmol, 2.5 eq) and the reaction mixture was stirred at rt for 2 h. The mixture was diluted with aqueous Na$_2$CO$_3$ (200 mL) and extracted with EA (100 mL*3). The organic layers were separated, combined, dried over Na$_2$SO$_4$, filtered and concentrated. The resulting residue was purified by column chromatography (PE/EA=50/1, v/v) to afford N-(pyridin-2-yl)-4-(4,4,5,5-tetramethyl-1,3,2-dioxaborolan-2-yl)-N-(4-(4,4,5,5-tetramethyl-1,3,2-dioxaborolan-2-yl)benzoyl)benzamide (3.3 g, 29.6%).

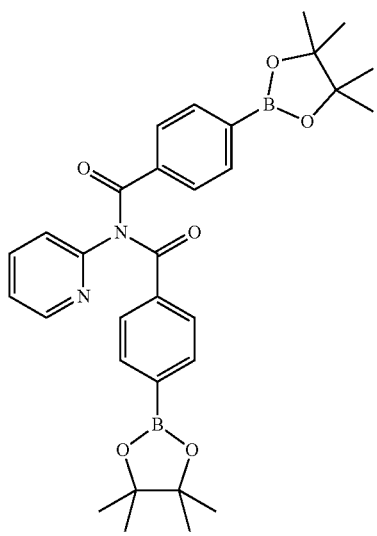

2N NaOH, MeOH →

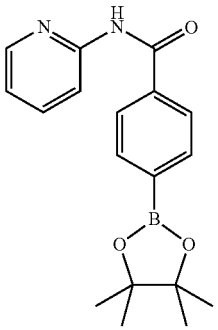

To a solution of N-(pyridin-2-yl)-4-(4,4,5,5-tetramethyl-1,3,2-dioxaborolan-2-yl)-N-(4-(4,4,5,5-tetramethyl-1,3,2-dioxaborolan-2-yl)benzoyl)benzamide (8.0 g, 14.5 mmol, 1.0 eq) in MeOH (100 mL) was added 2N NaOH (72.5 mL, 145 mmol, 10.0 eq) and the mixture was stirred at rt for overnight. The mixture was diluted with aqueous Na$_2$CO$_3$ (200 mL) and extracted with EA (100 mL*3). The organic layers were separated, combined, dried over Na$_2$SO$_4$, filtered and concentrated. The resulting residue was purified by column chromatography (PE/EA=50/1, v/v) to afford N-(pyridin-2-yl)-4-(4,4,5,5-tetramethyl-1,3,2-dioxaborolan-2-yl)-N-(4-(4,4,5,5-tetramethyl-1,3,2-dioxaborolan-2-yl)benzoyl)benzamide (3.3 g, 29.6%). The mixture was diluted with aqueous Na$_2$CO$_3$ (200 mL) and extracted with EA (100 mL×3). The organic layers were separated, combined, dried over Na$_2$SO$_4$, filtered and concentrated. The resulting residue was purified by column chromatography (PE/EA=20/1, v/v) to afford N-(pyridin-2-yl)-4-(4,4,5,5-tetramethyl-1,3,2-dioxaborolan-2-yl)benzamide (4.5 g, 96.0%).

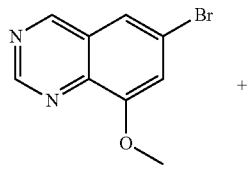

+

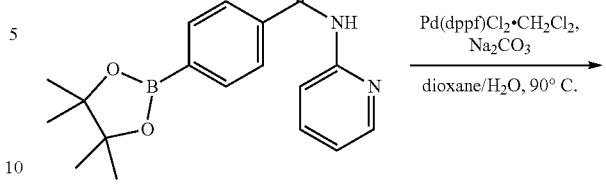

Pd(dppf)Cl$_2$•CH$_2$Cl$_2$, Na$_2$CO$_3$
dioxane/H$_2$O, 90° C.
→

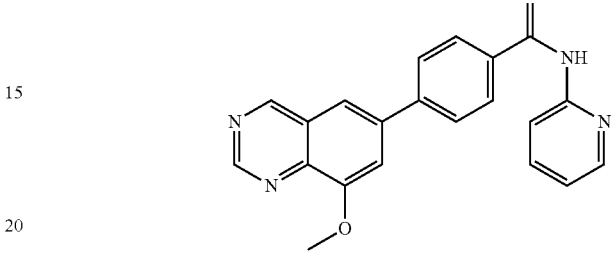

To a solution of 6-bromo-8-methoxyquinazoline (272 mg, 1.14 mmol, 1.0 eq) and N-(pyridin-2-yl)-4-(4,4,5,5-tetramethyl-1,3,2-dioxaborolan-2-yl)benzamide (444 mg, 1.4 mmol, 1.2 eq) in dioxane (20 mL) and H$_2$O (2 mL) was added Na$_2$CO$_3$ (242 mg, 2.0 mmol, 2.0 eq), followed by Pd(dppf)Cl$_2$·CH$_2$Cl$_2$ (46 mg, 0.057 mmol, 0.05 eq) under N$_2$. The mixture was stirred at 90° C. for 12 h, then cooled to rt. The resulting mixture was purified by column chromatography (DCM/MeOH=50/1, v/v) to afford 4-(8-methoxyquinazolin-6-yl)-N-(pyridin-2-yl)benzamide as a yellow solid (398 mg, 79.4%).

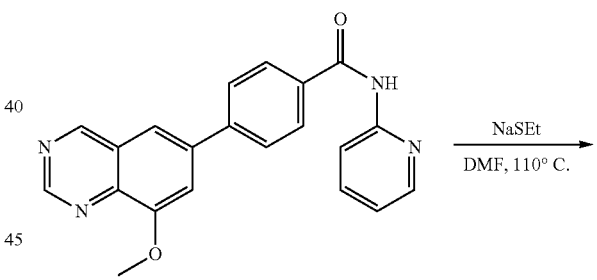

NaSEt
DMF, 110° C.
→

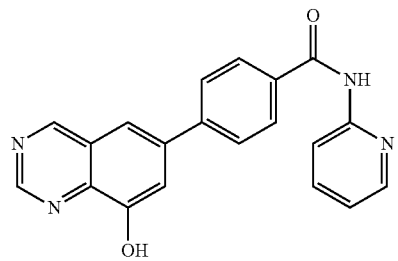

To a solution of 4-(8-methoxyquinazolin-6-yl)-N-(pyridin-2-yl)benzamide (398 mg, 1.12 mmol, 1.0 eq) in DMF (20.0 mL) was added sodium ethanethiolate (469 mg, 5.6 mmol, 5.0 eq). The mixture was heated at 110° C. overnight under N$_2$, then cooled to rt, concentrated and diluted with H$_2$O (200.0 mL), the precipitate was collected by filtration to afford crude 4-(8-hydroxyquinazolin-6-yl)-N-(pyridin-2-yl)benzamide as a yellow solid (334 mg, 87.2%).

357

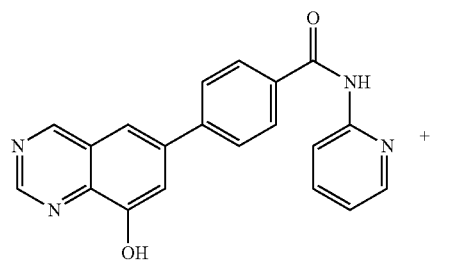

+

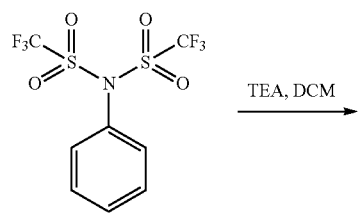

TEA, DCM →

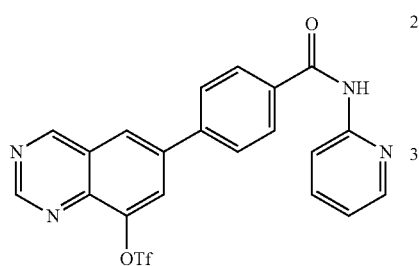

To a solution of 4-(8-hydroxyquinazolin-6-yl)-N-(pyridin-2-yl)benzamide (334 mg, 1.0 mmol, 1.0 eq) and TEA (0.55 mL, 4 mmol, 4.0 eq) in DMF (10.0 mL) was added PhN(OTf)$_2$ (714 mg, 2 mmol, 2.0 eq). The mixture was stirred at rt overnight, then concentrated. The residue was purified by column chromatography (DCM/MeOH=50/1, v/v) to provide 6-(4-(pyridin-2-ylcarbamoyl)phenyl)quinazolin-8-yl trifluoromethanesulfonate as a yellow solid (120 mg, 22.5%).

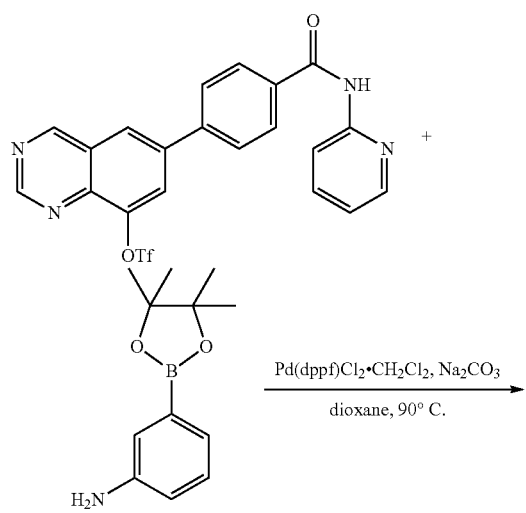

Pd(dppf)Cl$_2$·CH$_2$Cl$_2$, Na$_2$CO$_3$
dioxane, 90° C. →

358
-continued

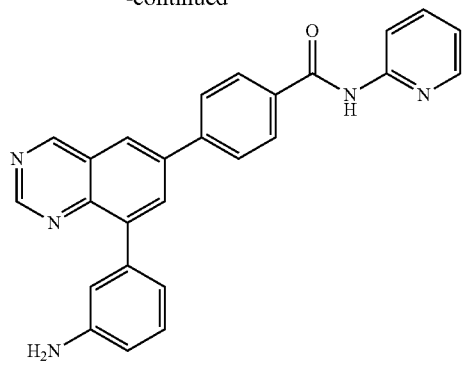

To a solution of 6-(4-(pyridin-2-ylcarbamoyl)phenyl)quinazolin-8-yl trifluoromethanesulfonate (120 mg, 0.32 mmol, 1.0 eq) and 3-(4,4,5,5-tetramethyl-1,3,2-dioxaborolan-2-yl)aniline (527 mg, 0.39 mmol, 1.2 eq) in dioxane (15.0 mL) and H$_2$O (1.5 mL) was added Na$_2$CO$_3$ (68 mg, 0.64 mmol, 2.0 eq), followed by Pd(dppf)Cl$_2$·CH$_2$Cl$_2$ (13.0 mg, 0.016 mmol, 0.05 eq) under N$_2$. The mixture was stirred at 90° C. for 12 h, then cooled to rt. The resulting mixture was purified by column chromatography (DCM/MeOH=20/1, v/v) to afford 4-(8-(3-aminophenyl)quinazolin-6-yl)-N-(pyridin-2-yl)benzamide as a yellow solid (113 mg, 84.9%).

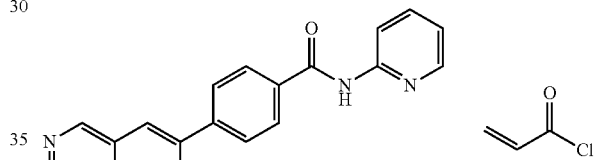

TEA, THF →

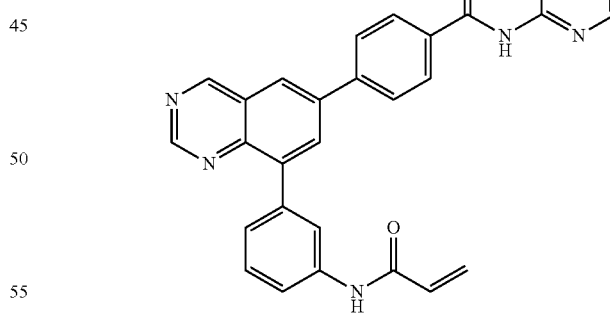

To a solution of 4-(8-(3-aminophenyl)quinazolin-6-yl)-N-(pyridin-2-yl)benzamide (113.0 mg, 0.27 mmol, 1.0 eq) in THF (10.0 mL) was added TEA (54.5 mg, 0.54 mmol, 2.0 eq), followed by acryloyl chloride (21.9 mg, 0.24 mmol, 0.9 eq). The resulting mixture was stirred at rt for 1 h, then washed with brine, dried over anhydrous Na$_2$SO$_4$, concentrated. The residue was purified by column chromatography (DCM/MeOH=20/1, v/v) to afford 4-(8-(3-acrylamidophenyl)quinazolin-6-yl)-N-(pyridin-2-yl)benzamide as a yellow solid (47.6 mg, 42.1%). LRMS (M+H$^+$) m/z calculated 472.2, found 472.2. ¹H NMR (DMSO-d6, 400 MHz) δ 10.91 (s, 1H), 10.30 (s, 1H), 9.76 (s, 1H), 9.35 (s, 1H), 8.64 (s, 1H), 8.42 (s, 2H), 8.23-8.25 (m, 2H), 8.05-8.12 (m, 3H), 7.86-7.89 (m, 2H), 7.50-7.52 (m, 2H), 7.20 (t, 1H), 6.48 (q, 1H), 6.25-6.30 (m, 1H), 5.78 (d, 1H).

Example 32: Preparation of 4-(8-(1-acryloyl-1,2,5,6-tetrahydropyridin-3-yl)quinazolin-6-yl)-N-(pyridin-2-yl)benzamide

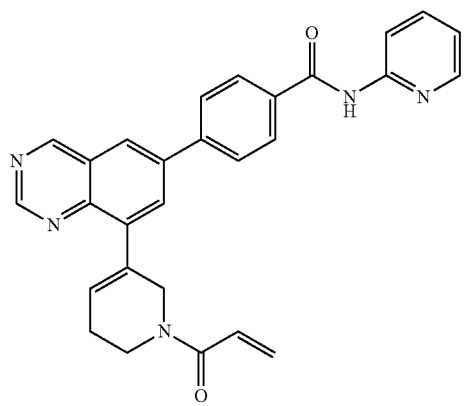

4-(8-(1-acryloyl-1,2,5,6-tetrahydropyridin-3-yl)quinazolin-6-yl)-N-(pyridin-2-yl)benzamide 4-(8-(1-Acryloyl-1,2,5,6-tetrahydropyridin-3-yl)quinazolin-6-yl)-N-(pyridin-2-yl)benzamide (26.5 mg) was prepared as described for 1-(3-(6-phenylquinazolin-8-yl)pyrrolidin-1-yl)prop-2-en-1-one. LRMS (M+H⁺) m/z calculated 462.2, found 462.2. ¹H NMR (CD₃OD, 400 MHz) δ 9.54 (s, 1H), 9.22 (d, 1H), 8.31-8.34 (m, 2H), 8.19-8.21 (m, 2H), 8.05-8.07 (m, 2H), 7.92-7.93 (m, 2H), 7.78-7.82 (m, 1H), 7.12-7.16 (m, 1H), 6.85-6.89 (m, 1H), 6.20-6.29 (m, 1H), 5.76-5.81 (m, 1H), 4.77-4.88 (m, 2H), 3.91- 3.92 (m, 2H), 2.46-2.50 (m, 2H).

Example 33: Preparation of 4-(8-(3-acrylamidophenyl)quinazolin-6-yl)-N-(4-methylpyridin-2-yl)benzamide

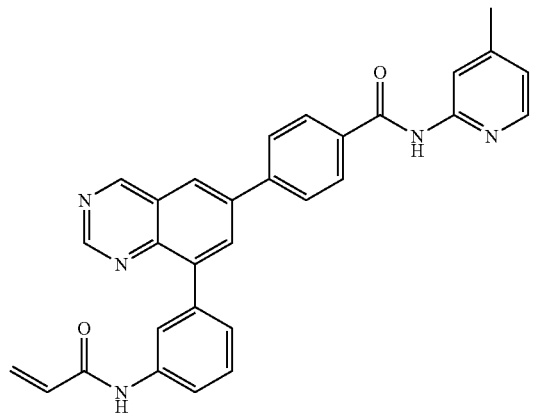

4-(8-(3-acrylamidophenyl)quinazolin-6-yl)-N-(4-methylpyridin-2-yl)benzamide 4-(8-(3-Acrylamidophenyl)quinazolin-6-yl)-N-(4-methylpyridin-2-yl)benzamide (5.7 mg) was prepared as described for 4-(8-(3-acrylamidophenyl)quinazolin-6-yl)-N-(pyridin-2-yl)benzamide. LRMS (M+H⁺) m/z calculated 486.2, found 486.2. ¹H NMR (DMSO-d6, 400 MHz) δ 10.94 (s, 1H), 10.32 (s, 1H), 9.77 (s, 1H), 9.35 (s, 1H), 8.63 (s, 1H), 8.41 (s, 1H), 8.22-8.29 (m, 3H), 8.05-8.12 (m, 4H), 7.84-7.86 (d, 1H), 7.49-7.53 (t, 2H), 7.01-7.14 (dd, 1H). 6.46-6.53 (m, 1H). 6.25-6.29 (d, 1H), 5.76-5.78 (d, 1H), 2.44 (s, 3H).

Example 34: Preparation of 5-(8-(3-acrylamidophenyl)quinazolin-6-yl)-N-phenylpicolinamide

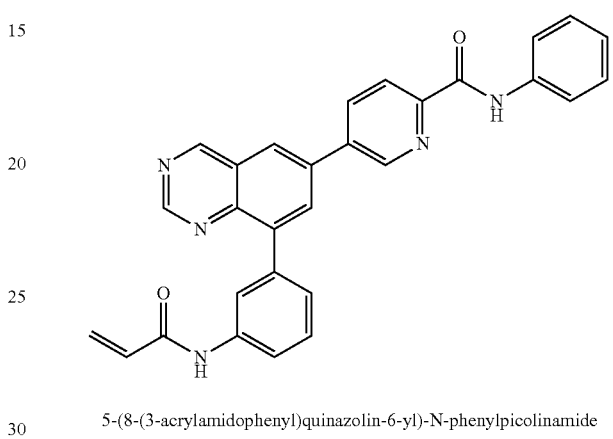

5-(8-(3-acrylamidophenyl)quinazolin-6-yl)-N-phenylpicolinamide 5-(8-(3-Acrylamidophenyl)quinazolin-6-yl)-N-phenylpicolinamide (11.2 mg) was prepared as described for 4-(8-(3-acrylamidophenyl)quinazolin-6-yl)-N-(pyridin-2-yl)benzamide. LRMS (M+H⁺) m/z calculated 472.2, found 472.2. ¹H NMR (DMSO-d6, 400 MHz) δ 10.72 (s, 1H), 10.30 (s, 1H), 9.79 (s, 1H), 9.38 (s, 1H), 9.28 (s, 1H), 8.71 (s, 1H), 8.63 (d, 1H), 8.48 (s, 1H), 8.32 (d, 1H), 8.08 (s, 1H), 7.82-7.96 (m, 3H), 7.13-7.54 (m, 5H), 6.25-6.52 (m, 2H), 5.76 (d, 1H).

Example 35: Preparation of 4-(8-(3-acrylamidophenyl)quinazolin-6-yl)-N-(3-(trifluoromethyl)phenyl)benzamide

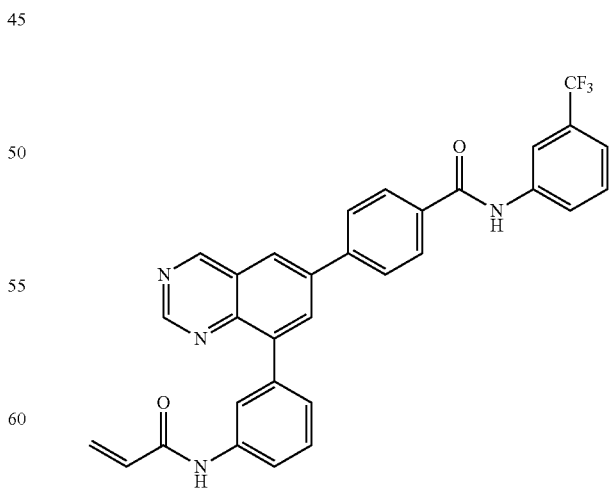

4-(8-(3-acrylamidophenyl)quinazolin-6-yl)-N-(3-(trifluoromethyl)phenyl)benzamide 4-(8-(3-Acrylamidophenyl)quinazolin-6-yl)-N-(3-(trifluoromethyl)phenyl)benzamide (5.1 mg) was prepared as described for 4-(8-(3-acrylamidophenyl)quinazolin-6-yl)-N-(pyridin-2-yl)benzamide. LRMS (M+H⁺) m/z calculated 539.2, found 539.2. ¹H NMR (DMSO-d6, 400 MHz) δ 10.66 (s, 1H), 10.28 (s, 1H), 9.77 (s, 1H), 9.35 (s, 1H), 8.63 (s, 1H), 8.42 (s, 1H), 8.29 (s, 1H), 8.14 (m, 4H), 8.09 (d, 1H), 8.05 (s, 1H), 7.82 (d, 1H), 7.63 (t, 1H), 7.49 (m, 3H), 6.49 (m, 1H), 6.29 (d, 1H), 5.75 (d, 1H).

Example 36: Preparation of 4-(8-(3-acrylamidophenyl)quinazolin-6-yl)-N-phenylbenzamide

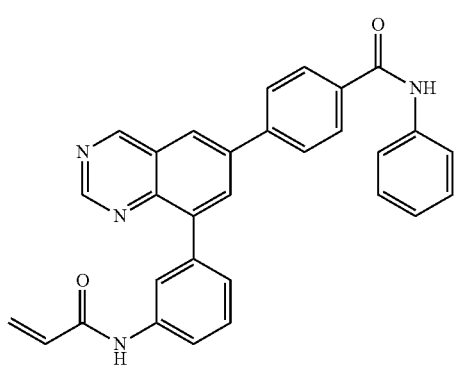

4-(8-(3-acrylamidophenyl)quinazolin-6-yl)-N-phenylbenzamide 4-(8-(3-Acrylamidophenyl)quinazolin-6-yl)-N-phenylbenzamide (5.9 mg) was prepared as described for 4-(8-(3-acrylamidophenyl)quinazolin-6-yl)-N-(pyridin-2-yl)benzamide. LRMS (M+H⁺) m/z calculated 471.2, found 471.2. ¹H NMR (DMSO-d6, 400 MHz) δ 10.36 (s, 1H), 10.29 (s, 1H), 9.77 (s, 1H), 9.35 (s, 1H), 8.63 (s, 1H), 8.42 (s, 1H), 8.12-8.17 (m, 4H), 8.05 (s, 1H), 7.81-7.83 (m, 3H), 7.50-7.52 (m, 2H), 7.38 (t, 2H), 7.13 (t, 1H), 6.45-6.52 (m, 2H), 6.27 (d, 1H), 5.77 (d, 1H).

Example 37: Preparation of 4-(8-(3-acrylamidophenyl)quinazolin-6-yl)-3-chloro-N-(pyridin-2-yl)benzamide

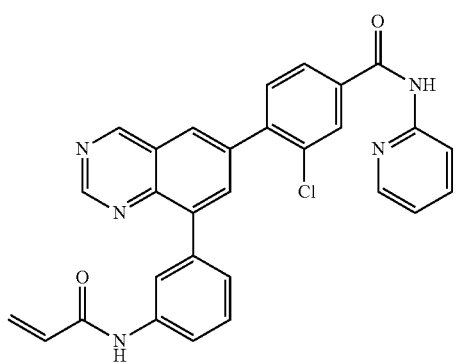

4-(8-(3-acrylamidophenyl)quinazolin-6-yl)-3-chloro-N-(pyridin-2-yl)benzamide 4-(8-(3-Acrylamidophenyl)quinazolin-6-yl)-3-chloro-N-(pyridin-2-yl)benzamide (26.8 mg) was prepared as described for 4-(8-(3-acrylamidophenyl)quinazolin-6-yl)-N-(pyridin-2-yl)benzamide. LRMS (M+H⁺) m/z calculated 506.1, found 506.1. ¹H NMR (DMSO-d6, 400 MHz) δ 11.07 (s, 1H), 10.28 (s, 1H), 9.77 (s, 1H), 9.39 (s, 1H), 8.35 (d, 1H), 8.32 (d, 2H), 8.17 (d, 1H), 8.14 (m, 2H), 8.05 (s, 1H), 7.88 (m, 1H), 7.78 (d, 2H), 7.48 (s, 2H), 7.21 (m, 1H), 6.48 (m, 1H), 6.25 (m, 1H), 5.75 (d, 1H).

Example 38: Preparation of 5-(8-(3-acrylamidophenyl)quinazolin-6-yl)-N-(3-(trifluoromethyl)phenyl)picolinamide

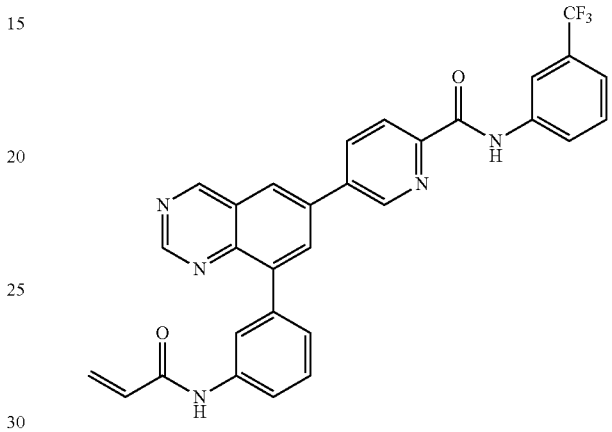

5-(8-(3-acrylamidophenyl)quinazolin-6-yl)-N-(3-(trifluoromethyl)phenyl)picolinamide 5-(8-(3-Acrylamidophenyl)quinazolin-6-yl)-N-(3-(trifluoromethyl)phenyl)picolinamide (9.8 mg) was prepared as described for 4-(8-(3-acrylamidophenyl)quinazolin-6-yl)-N-(pyridin-2-yl)benzamide. LRMS (M+H⁺) m/z calculated 540.2, found 540.2. ¹H NMR (DMSO-d6, 400 MHz) δ 11.12 (s, 1H), 10.30 (s, 1H), 9.79 (s, 1H), 9.38 (s, 1H), 9.30 (s, 1H), 8.72 (s, 1H), 8.65 (d, 1H), 8.48 (s, 2H), 8.08-8.35 (m, 3H), 7.49-7.85 (m, 5H), 6.25-6.48 (m, 2H), 5.76-5.79 (m, 1H).

Example 39: Preparation of 5-(8-(3-acrylamidophenyl)quinazolin-6-yl)-N-(pyridin-2-yl)picolinamide

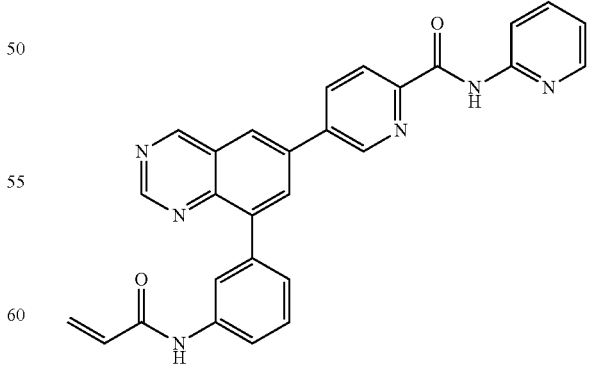

5-(8-(3-acrylamidophenyl)quinazolin-6-yl)-N-(pyridin-2-yl)picolinamide 5-(8-(3-Acrylamidophenyl)quinazolin-6-yl)-N-(pyridin-2-yl)picolinamide (3.5 mg) was prepared as described for 4-(8-(3-acrylamidophenyl)quinazolin-6-yl)-N-(pyridin-2-yl)benzamide. LRMS (M+H⁺) m/z calculated 473.2, found 473.2. ¹H NMR (DMSO-d6, 400 MHz) δ 10.47 (s, 1H), 10.29 (s, 1H), 9.78 (s, 1H), 9.36 (s, 1H), 9.38 (s, 1H), 8.31-8.74 (m, 6H), 8.06 (s, 1H), 7.22-7.96 (m, 5H), 6.25-6.51 (m, 2H), 5.76-5.78 (m, 1H).

Example 40: Preparation of 5-(8-(3-acrylamidophenyl)quinazolin-6-yl)-N-(m-tolyl)picolinamide

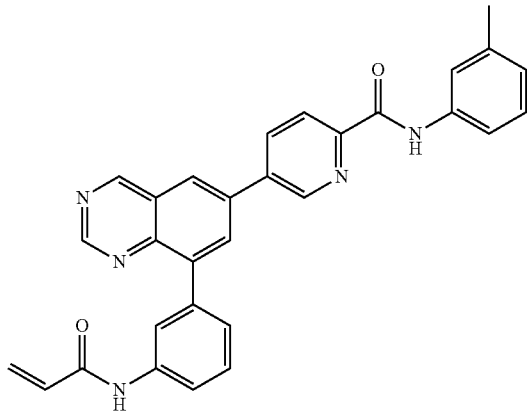

5-(8-(3-acrylamidophenyl)quinazolin-6-yl)-N-(m-tolyl)picolinamide 5-(8-(3-Acrylamidophenyl)quinazolin-6-yl)-N-(m-tolyl)picolinamide (14.7 mg) was prepared as described for 4-(8-(3-acrylamidophenyl)quinazolin-6-yl)-N-(pyridin-2-yl)benzamide. LRMS (M+H⁺) m/z calculated 486.2, found 486.2. ¹H NMR (DMSO-d6, 400 MHz) δ 10.60 (s, 1H), 10.30 (d, 1H), 9.79 (s, 1H), 9.38 (s, 1H), 9.28 (s, 1H), 8.71 (s, 1H), 8.63 (d, 1H), 8.48 (s, 1H), 8.31 (d, 1H), 8.08 (s, 1H), 7.72-7.84 (m, 3H), 7.50-7.52 (m, 2H), 7.27-7.29 (m, 1H), 6.97 (d, 1H), 6.25-6.48 (m, 2H), 5.76-5.79 (m, 1H), 2.34 (s, 3H).

Example 41: Preparation of 5-(8-(1-acryloylpyrrolidin-3-yl)quinazolin-6-yl)-N-phenylpicolinamide

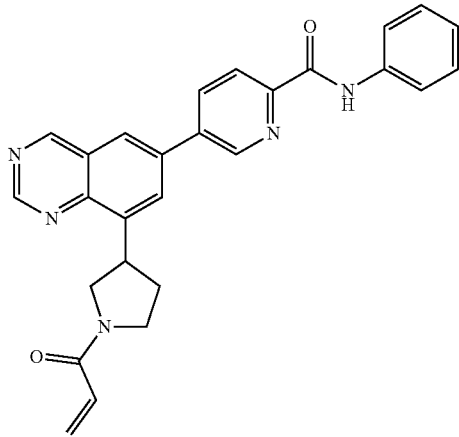

5-(8-(1-acryloylpyrrolidin-3-yl)quinazolin-6-yl)-N-phenylpicolinamide 5-(8-(1-Acryloylpyrrolidin-3-yl)quinazolin-6-yl)-N-phenylpicolinamide (41.3 mg) was prepared as described for 1-(3-(6-phenylquinazolin-8-yl)pyrrolidin-1-yl)prop-2-en-1-one. LRMS (M+H⁺) m/z calculated 450.2, found 450.3. ¹H NMR (DMSO-d6, 400 MHz) δ 10.69 (s, 1H), 9.73 (s, 1H), 9.42 (s, 1H), 9.23 (s, 1H), 8.31-8.59 (m, 4H), 7.94 (d, 2H), 7.38-7.41 (m, 2H), 7.13-7.17 (m, 1H), 6.16-6.69 (m, 2H), 5.66-5.75 (m, 1H), 4.49-4.63 (m, 1H), 4.11-4.24 (m, 1H), 3.54-3.94 (m, 3H), 2.31-2.50 (m, 2H).

Example 42: Preparation of 4-(8-(1-acryloylpyrrolidin-3-yl)quinazolin-6-yl)-N-phenylbenzamide

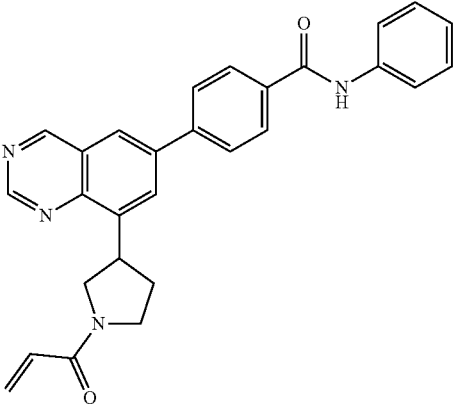

4-(8-(1-acryloylpyrrolidin-3-yl)quinazolin-6-yl)-N-phenylbenzamide 4-(8-(1-Acryloylpyrrolidin-3-yl)quinazolin-6-yl)-N-phenylbenzamide (69.6 mg) was prepared as described for 1-(3-(6-phenylquinazolin-8-yl)pyrrolidin-1-yl)prop-2-en-1-one. LRMS (M+H⁺) m/z calculated 449.2, found 449.3. ¹H NMR (DMSO-d6, 400 MHz) δ 10.35 (s, 1H), 9.71 (s, 1H), 9.39 (s, 1H), 8.48 (d, 1H), 8.35 (d, 1H), 8.13-8.16 (m, 2H), 8.05-8.08 (m, 2H), 7.80-7.83 (m, 2H), 7.38 (t, 2H), 7.14 (t, 1H), 6.61-6.72 (m, 1H), 6.16-6.22 (m, 1H), 5.66-5.73 (m, 1H), 4.54 (dt, 1H), 4.16 (t, 1H), 3.62-3.90 (m, 2H), 3.50-3.60 (m, 1H), 2.31-2.50 (m, 2H).

Example 43: Preparation of 4-(8-(1-acryloylpyrrolidin-3-yl)quinazolin-6-yl)-3-chloro-N-(pyridin-2-yl)benzamide

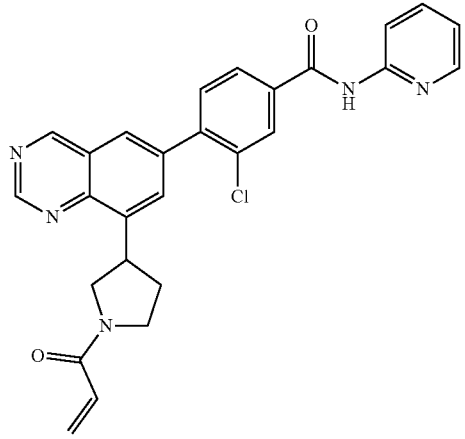

4-(8-(1-acryloylpyrrolidin-3-yl)quinazolin-6-yl)-3-chloro-N-(pyridin-2-yl)benzamide 4-(8-(1-acryloylpyrrolidin-3-yl)quinazolin-6-yl)-3-chloro-N-(pyridin-2-yl)benzamide (8.4 mg) was prepared as described for 1-(3-(6-phenylquinazolin-8-yl)pyrrolidin-1-yl)prop-2-en-1-one. LRMS (M+H$^+$) m/z calculated 484.1, found 484.1. $^1$H NMR (DMSO-d6, 400 MHz) δ 8.43 (s, 1H), 9.71 (s, 1H), 9.43 (s, 1H), 8.42 (s, 1H), 8.30 (s, 1H), 8.22 (m, 2H), 8.16 (m, 2H), 7.89 (t, 1H), 7.74 (d, 1H), 7.21 (t, 1H), 6.62 (m, 1H), 6.14 (m, 1H), 5.65 (m, 1H), 4.49 (m, 1H), 4.17 (m, 1H), 3.76 (m, 2H), 3.55 (m, 1H), 2.31 (m, 1H), 2.18 (m, 1H).

Example 44: Preparation of 4-(8-(1-acryloylpyrrolidin-3-yl)quinazolin-6-yl)-N-(3-(trifluoromethyl)phenyl)benzamide

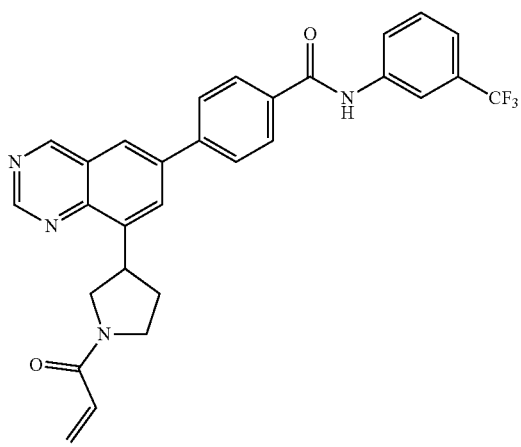

4-(8-(1-acryloylpyrrolidin-3-yl)quinazolin-6-yl)-N-(3-(trifluoromethyl)phenyl)benzamide 4-(8-(1-Acryloylpyrrolidin-3-yl)quinazolin-6-yl)-N-(3-(trifluoromethyl)phenyl)benzamide (6.4 mg) was prepared as described for 1-(3-(6-phenylquinazolin-8-yl)pyrrolidin-1-yl)prop-2-en-1-one. LRMS (M+H$^+$) m/z calculated 517.2, found 517.2. $^1$H NMR (DMSO-d6, 400 MHz) δ 10.65 (s, 1H), 9.71 (s, 1H), 9.43 (s, 1H), 8.50 (s, 1H), 8.33 (m, 2H), 8.16 (d, 2H), 8.09 (m, 3H), 7.63 (t, 1H), 7.47 (d, 1H), 6.65 (m, 1H), 6.17 (m, 1H), 5.68 (m, 1H), 4.56 (m, 1H), 4.19 (m, 1H), 3.90 (m, 2H), 3.59 (m, 1H), 2.44 (m, 1H), 2.35 (m, 1H).

Example 45: Preparation of 4-(8-(1-acryloylpyrrolidin-3-yl)quinazolin-6-yl)-N-(pyridin-2-yl)benzamide

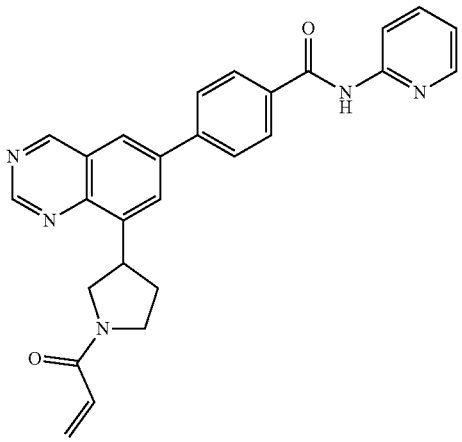

4-(8-(1-acryloylpyrrolidin-3-yl)quinazolin-6-yl)-N-(pyridin-2-yl)benzamide 4-(8-(1-Acryloylpyrrolidin-3-yl)quinazolin-6-yl)-N-(pyridin-2-yl)benzamide (33.6 mg) was prepared as described for 1-(3-(6-phenylquinazolin-8-yl)pyrrolidin-1-yl)prop-2-en-1-one. LRMS (M+H$^+$) m/z calculated 450.2, found 450.3. $^1$H NMR (DMSO-d6, 400 MHz) δ 10.90 (s, 1H), 9.70 (s, 1H), 9.39 (s, 1H), 8.50 (d, 1H), 8.41 (t, 1H), 8.33 (s, 1H), 8.23 (d, 3H), 8.04-8.07 (m, 2H), 7.87 (dd, 1H), 7.18-7.21 (m, 1H), 6.64-6.70 (m, 1H), 6.16-6.22 (m, 1H), 5.66-5.76 (m, 1H), 4.46-4.65 (m, 1H), 4.09-4.20 (m, 1H), 3.77-3.91 (m, 2H), 3.46-3.64 (m, 1H), 2.33-2.50 (m, 2H).

Example 46: Preparation of 5-(8-(1-acryloylpyrrolidin-3-yl)quinazolin-6-yl)-N-(m-tolyl)picolinamide

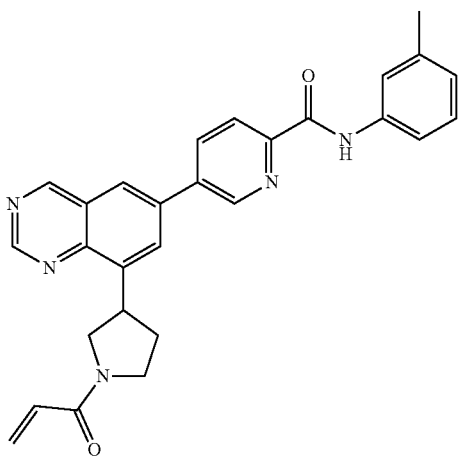

5-(8-(1-acryloylpyrrolidin-3-yl)quinazolin-6-yl)-N-(m-tolyl)picolinamide 5-(8-(1-Acryloylpyrrolidin-3-yl)quinazolin-6-yl)-N-(m-tolyl)picolinamide (5 mg) was prepared as described for 1-(3-(6-phenylquinazolin-8-yl)pyrrolidin-1-yl)prop-2-en-1-one. LRMS (M+H$^+$) m/z calculated 464.2, found 464.0. $^1$H NMR (DMSO-d6, 400 MHz) δ 9.61 (d, 1H), 9.33 (d, 1H), 9.13 (s, 1H), 8.29-8.45 (m, 4H), 7.57-7.61 (m, 2H), 7.26 (t, 1H), 6.99 (d, 1H), 6.58-6.74 (m, 1H), 6.34-6.36 (m, 1H), 5.77-5.79 (m, 1H), 4.25-4.45 (m, 2H), 3.62-4.02 (m, 3H), 2.49-2.53 (m, 2H), 2.37 (s, 3H).

Example 47: Preparation of N-(3-(2-amino-6-(2-chlorophenyl)quinazolin-8-yl)phenyl)acrylamide

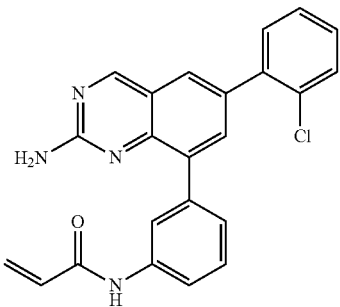

N-(3-(2-amino-6-(2-chlorophenyl)quinazolin-8-yl)phenyl)acrylamide

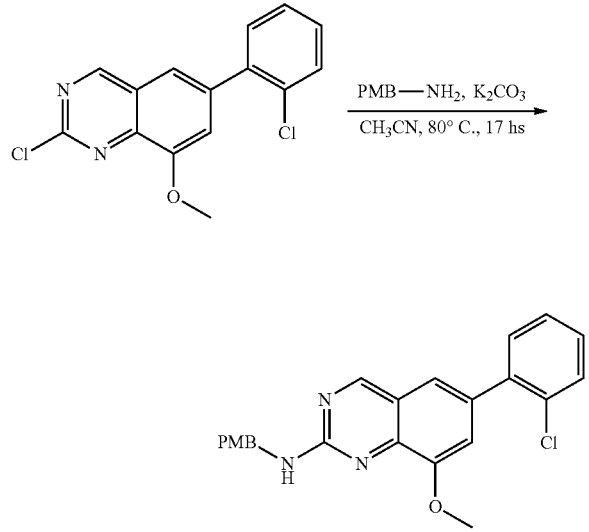

To a solution of 2-chloro-6-(2-chlorophenyl)-8-methoxyquinazoline (200.0 mg, 0.7 mmol, 1.0 eq) and PMB-NH₂ (270.0 mg, 2.0 mmol, 3.0 eq) in CH₃CN (15.0 mL) was added K₂CO₃ (455.0 mg, 3.3 mmol, 5.0 eq). The mixture was stirred at 80° C. overnight, then diluted with EA (20.0 mL), washed with brine, dried over anhydrous Na₂SO₄ and concentrated. The resulting residue was purified by column chromatography (PE/EA=4:1, v/v) to afford 6-(2-chlorophenyl)-8-methoxy-N-(4-methoxybenzyl)quinazolin-2-amine as a yellow solid (175.0 mg, 65.8%).

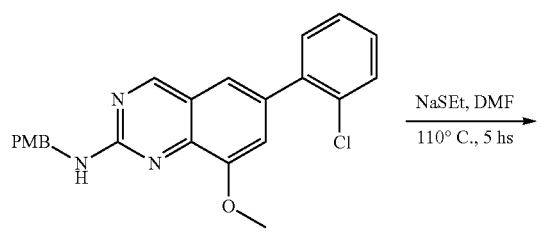

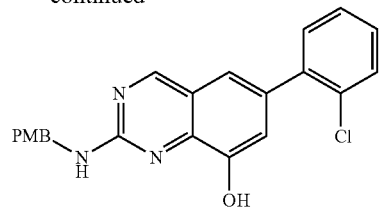

To a solution of 6-(2-chlorophenyl)-8-methoxy-N-(4-methoxybenzyl)quinazolin-2-amine (175.0 mg, 0.4 mmol, 1.0 eq) in DMF (8.0 mL) was added sodium ethanethiolate (114.2 mg, 1.3 mmol, 3.0 eq). The mixture was heated at 110° C. for 5 h under N₂. The mixture was concentrated and the residue was diluted with MeOH (4.0 mL) and EA (60.0 mL), then washed with 1N HCl (5.0 mL×2). The EA layer was concentrated and the residue was purified by column chromatography to provide 6-(2-chlorophenyl)-2-phenylquinazolin-8-ol as a brown solid (169.0 mg, quant.).

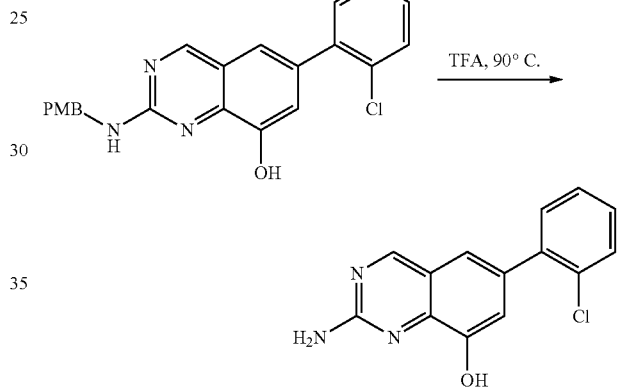

A mixture of 6-(2-chlorophenyl)-2-((4-methoxybenzyl)amino)quinazolin-8-ol (169.0 mg, 0.4 mmol, 1.0 eq) in TFA (5.0 mL) was stirred at 90° C. for 2 h, then concentrated and the residue was diluted with a mixture of EA (15.0 mL) and sat. Na₂CO₃ (5.0 mL). The organic phase was separated and dried with anhydrous Na₂SO₄, concentrated to provide 2-amino-6-(2-chlorophenyl)quinazolin-8-ol as a brown solid (111.0 mg, 95%).

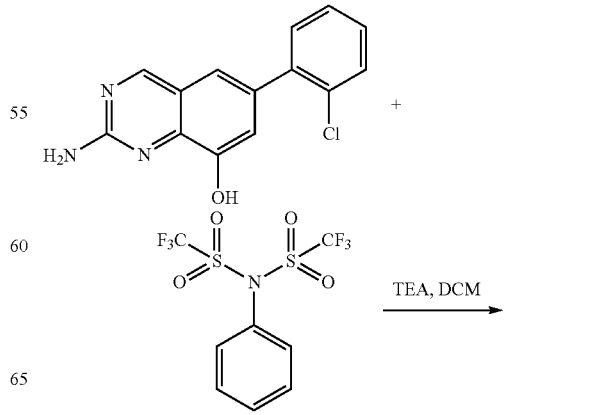

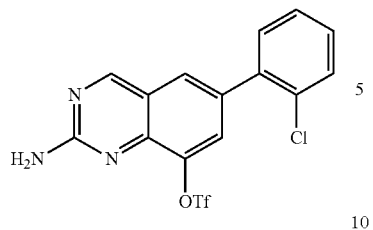

To a solution of 2-amino-6-(2-chlorophenyl)quinazolin-8-ol (111.0 mg, 0.4 mmol, 1.0 eq) and TEA (0.3 mL, 2.1 mmol, 5.0 eq) in DCM (10.0 mL) was added PhN(OTf)$_2$ (439.0 mg, 1.2 mmol, 3.0 eq). The mixture was stirred at rt overnight, then concentrated. The residue was purified by column chromatography (PE/EA=10/1) to provide 2-amino-6-(2-chlorophenyl)quinazolin-8-yl trifluoromethanesulfonate as a yellow solid (100.0 mg, 60.6%).

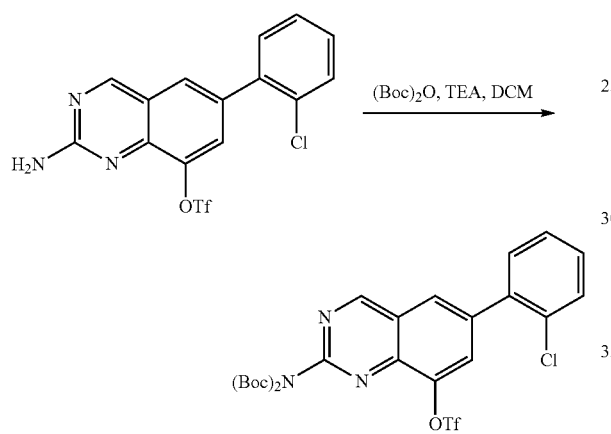

To a solution of 2-amino-6-(2-chlorophenyl)quinazolin-8-yl trifluoromethanesulfonate (100.0 mg, 0.3 mmol, 1.0 eq), cat. DMAP and TEA (37.6 mg, 0.4 mmol, 1.5 eq) in DCM (5.0 mL) was added (Boc)$_2$O (109.0 mg, 0.5 mmol, 2.0 eq). The mixture was stirred at rt overnight, concentrated and the residue was purified by column chromatography (PE/EA=10:1) to provide 2-((tert-butoxycarbonyl)amino)-6-(2-chlorophenyl)quinazolin-8-yl trifluoromethanesulfonate as a brown oil (115.0 mg, 76.8%).

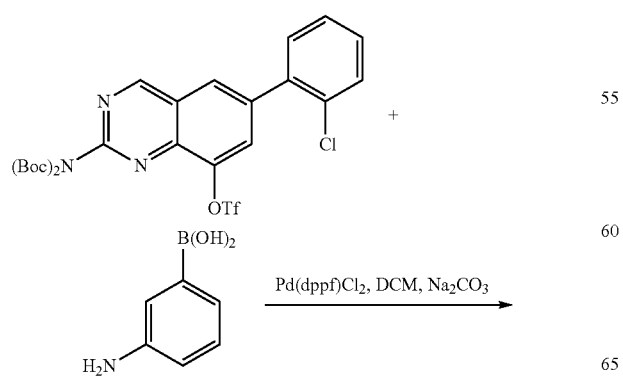

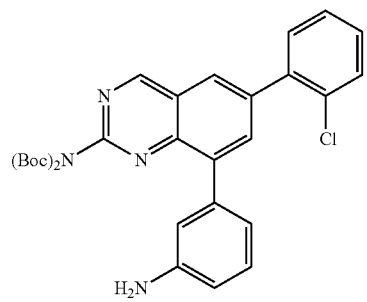

To a solution of 2-((tert-butoxycarbonyl)amino)-6-(2-chlorophenyl)quinazolin-8-yl trifluoromethanesulfonate (115.0 mg, 0.2 mmol, 1.0 eq) and (3-aminophenyl)boronic acid (50.0 mg, 0.2 mmol, 1.2 eq) in dioxane (10.0 mL) and H$_2$O (1.0 mL) was added Na$_2$CO$_3$ (40.0 mg, 0.4 mmol, 2.0 eq), followed by Pd(dppf)Cl$_2$ (8.0 mg, 0.01 mmol, 0.05 eq) under N$_2$. The mixture was stirred at 90° C. for 12 h, then cooled to rt, diluted with EA (30.0 mL) and filtered. The filtrate was concentrated. The resulting residue was purified by column chromatography (PE/EA=4/1, v/v) to afford 3-(6-(2-chlorophenyl)-2-phenylquinazolin-8-yl)aniline as a yellow solid (30.0 mg, 28.8%).

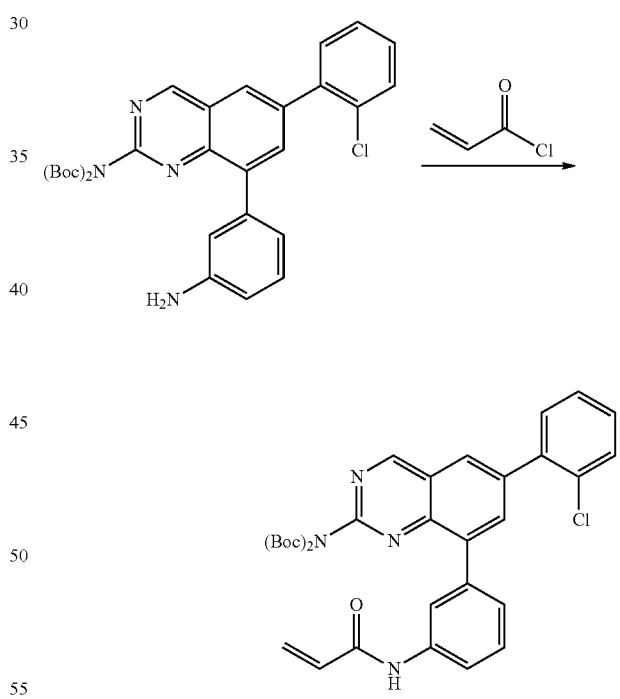

To a solution of tert-butyl (8-(3-aminophenyl)-6-(2-chlorophenyl)quinazolin-2-yl)carbamate (0.0 mg, 0.05 mmol, 1.0 eq) in DCM (8.0 mL) was added TEA (16.6 mg, 0.2 mmol, 3.0 eq), followed by acryloyl chloride (7.3 mg, 0.1 mmol, 1.5 eq). The resulting mixture was stirred at rt for 1 h, then washed with brine, dried over anhydrous Na$_2$SO$_4$, concentrated and purified by column chromatography (PE/EA=4:1, v/v) to afford tert-butyl (8-(3-acrylamidophenyl)-6-(2-chlorophenyl)quinazolin-2-yl)carbamate as a white solid (50.0 mg, ca. 100%).

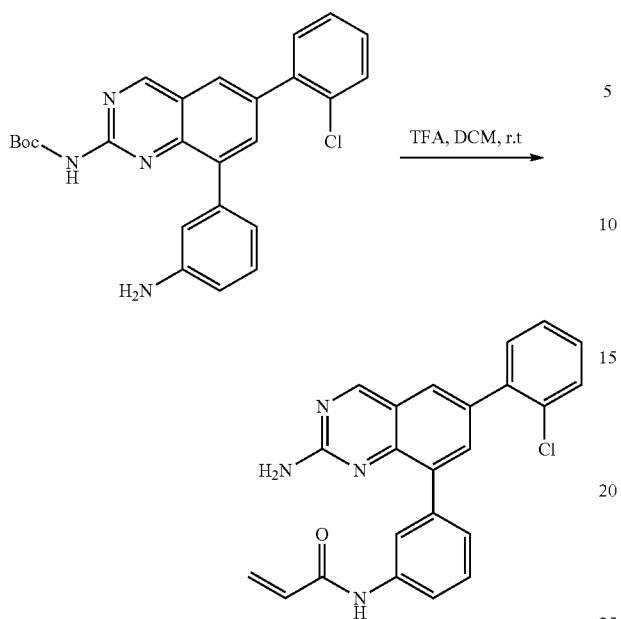

To a solution of tert-butyl (8-(3-acrylamidophenyl)-6-(2-chlorophenyl)quinazolin-2-yl)carbamate (50.0 mg, 0.1 mmol, 1.0 eq) in DCM (5.0 mL) was added TFA (2.0 mL). The mixture was stirred at rt for 1 h, then concentrated. The residue was purified on prep-TLC to provide N-(3-(2-amino-6-(2-chlorophenyl)-quinazolin-8-yl)phenyl)acrylamide as a white solid (20.0 mg, 91%). LRMS (M+H$^+$) m/z calculated 401.1, found 401.2. $^1$H NMR (CD$_3$OD, 400 MHz) δ 9.16 (s, 1H), 7.95 (s, 1H), 7.84 (d, 2H), 7.74 (t, 1H), 7.53 (t, 2H), 7.38-7.45 (m, 4H), 6.34-6.50 (m, 2H), 5.77 (d, 1H).
75

Example 48: Preparation of N-(3-(2-amino-6-phenylquinazolin-8-yl)phenyl)acrylamide

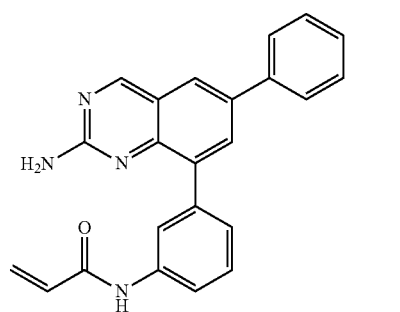

N-(3-(2-amino-6-phenylquinazolin-8-yl)phenyl)acrylamide

N-(3-(2-amino-6-phenylquinazolin-8-yl)phenyl)acrylamide (5.0 mg) was prepared as described for N-(3-(2-amino-6-(2-chlorophenyl)-quinazolin-8-yl)phenyl)acrylamide.
LRMS (M+H$^+$) m/z calculated 367.1, found 367.4. $^1$H NMR. (CD$_3$CD, 400 MHz) δ 9.19 (s, 1H), 8.05 (d, 2H), 7.96 (s, 1H), 7.76 (d, 3H), 7.45-7.50 (m, 4H), 7.38 (t, 1H), 6.39-6.46 (m, 2H), 5.78 (d, 1H).

Example 49: Preparation of N-(3-(2-amino-6-(pyridin-3-yl)quinazolin-8-yl)phenyl)acrylamide

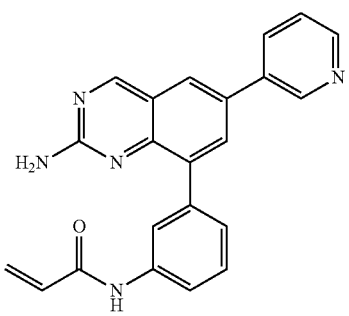

N-(3-(2-amino-6-(pyridin-3-yl)quinazolin-8-yl)phenyl)acrylamide

N-(3-(2-amino-6-(pyridin-3-yl)quinazolin-8-yl)phenyl)acrylamide (25.4 mg) was prepared as described for N-(3-(6-(pyridin-4-yl)quinazolin-8-yl)phenyl)acrylamide. LRMS (M+H$^+$) m/z calculated 368.2, found 368.2. $^1$H NMR (DMSO-d6, 400 MHz) δ 10.21 (s, 1H), 9.24 (s, 1H), 9.03 (s, 1H), 8.58 (s, 1H), 8.22 (s, 2H), 8.00 (s, 1H), 7.87 (s, 1H), 7.82 (s, 1H), 7.53 (s, 1H), 7.43 (s, 2H), 6.94 (s, 2H), 6.46 (m, 1H), 6.28 (d, 1H), 5.75 (d, 1H).

Example 50: Preparation of N-(3-(2-amino-6-(6-methylpyridin-3-yl)quinazolin-8-yl)phenyl)acrylamide

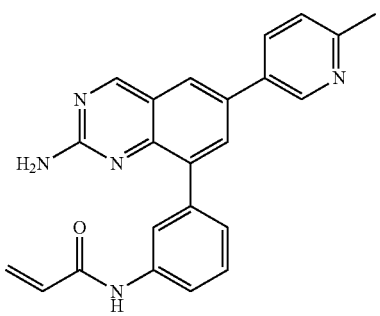

N-(3-(2-amino-6-(6-methylpyridin-3-yl)quinazolin-8-yl)phenyl)acrylamide

N-(3-(2-amino-6-(6-methylpyridin-3-yl)quinazolin-8-yl)phenyl)acrylamide (3.5 mg) was prepared as described for N-(3-(6-(pyridin-4-yl)quinazolin-8-yl)phenyl)acrylamide.
LRMS (M+H$^+$) m/z calculated 381.2, found 382.6. $^1$H NMR (DMSO-d6, 400 MHz) δ 10.21 (s, 1H), 9.23 (s, 1H), 8.89 (s, 1H), 8.18 (s, 1H), 8.13 (d, 1H), 8.09 (s, 1H), 7.83-7.98 (m, 2H), 7.36-7.45 (m, 3H), 6.91 (s, 2H), 6.25-6.52 (m, 2H), 5.76 (d, 1H). 2.78 (s, 3H).

Example 51: Preparation of 1-(3-(2-amino-6-(6-methylpyridin-3-yl)quinazolin-8-yl)piperidin-1-yl)prop-2-en-1-one

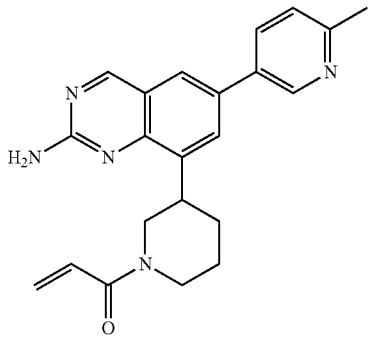

1-(3-(2-amino-6-(6-methylpyridin-3-yl)quinazolin-8-yl)piperidin-1-yl)prop-2-en-1-one 1-(3-(2-Amino-6-(6-methylpyridin-3-yl)quinazolin-8-yl)piperidin-1-yl)prop-2-en-1-one (16.8 mg) was prepared as described for 1-(3-(6-phenylquinazolin-8-yl)pyrrolidin-1-yl)prop-2-en-1-one. LRMS (M+H$^+$) m/z calculated 374.2, found 374.3. $^1$H NMR (DMSO-d6, 400 MHz) δ 9.16 (s, 1H), 8.87 (d, 1H), 7.96-8.08 (m, 3H), 7.37 (d, 1H), 6.80-6.93 (m, 3H), 6.12 (d, 1H), 5.63-5.71 (m, 1H), 4.45-4.57 (m, 1H), 4.15 (d, 1H), 3.75-3.82 (m, 1H), 3.31-3.39 (m, 0.5H), 3.09-3.24 (m, 2H), 2.65-2.79 (m, 0.5H), 2.53 (s, 3H), 1.82-1.99 (m, 3H).

Example 52: Preparation of 1-(3-(2-amino-6-(pyridin-3-yl)quinazolin-8-yl)piperidin-1-yl)prop-2-en-1-one

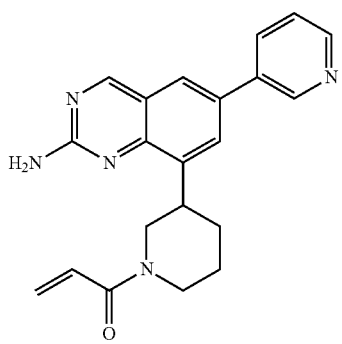

1-(3-(2-amino-6-(pyridin-3-yl)quinazolin-8-yl)piperidin-1-yl)prop-2-en-1-one 1-(3-(2-Amino-6-(pyridin-3-yl)quinazolin-8-yl)piperidin-1-yl)prop-2-en-1-one (10.9 mg) was prepared as described for 1-(3-(6-phenylquinazolin-8-yl)pyrrolidin-1-yl)prop-2-en-1-one. LRMS (M+H$^+$) m/z calculated 360.2, found 360.2. $^1$H NMR (DMSO-d6, 400 MHz) δ 9.18 (s, 1H), 9.04 (s, 1H), 8.61 (d, 1H), 8.26 (d, 1H), 8.10 (s, 1H), 8.02 (d, 1H), 7.56 (t, 1H), 6.97 (s, 2H), 6.82 (m, 1H), 6.10 (d, 1H), 5.87 (m, 1H), 4.55 (m, 1H), 4.17 (d, 1H), 3.77 (m, 1H), 2.79 (m, 2H), 2.00 (m, 2H), 1.83 (m, 1H), 1.55 (m, 1H).

Example 53: Preparation of 1-(3-(2-amino-6-(4-phenoxyphenyl)quinazolin-8-yl)piperidin-1-yl)prop-2-en-1-one

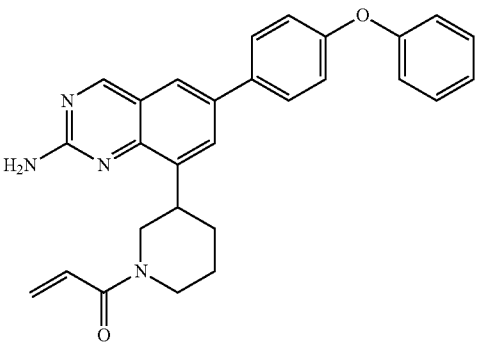

1-(3-(2-amino-6-(4-phenoxyphenyl)quinazolin-8-yl)piperidin-1-yl)prop-2-en-1-one 1-(3-(2-Amino-6-(4-phenoxyphenyl)quinazolin-8-yl)piperidin-1-yl)prop-2-en-1-one (7.3 mg) was prepared as described for 1-(3-(6-phenylquinazolin-8-yl)pyrrolidin-1-yl)prop-2-en-1-one. LRMS (M+H$^+$) m/z calculated 451.2, found 451.5. $^1$H NMR (CD$_3$OD, 400 MHz) δ 9.07 (d, 1H), 7.85-7.89 (m, 2H), 7.68-7.70 (m, 2H), 7.36-7.39 (m, 2H), 7.03-7.15 (m, 5H), 6.82-6.91 (m, 1H), 6.19-6.25 (m, 1H), 5.71-5.78 (m, 1H), 4.59-4.67 (m, 1H), 4.19-4.35 (m, 1H), 3.82 (s, 1H), 2.82-2.96 (m, 2H), 1.48-1.73 (m, 3H), 1.55-1.62 (m, 1H).

Example 54: Preparation of 1-(3-(2-amino-6-(4-phenoxyphenyl)quinazolin-8-yl)pyrrolidin-1-yl)prop-2-en-1-one

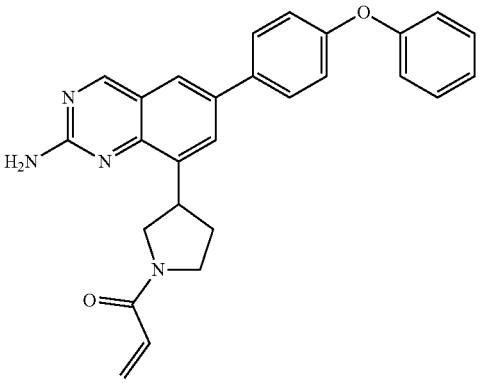

1-(3-(2-amino-6-(4-phenoxyphenyl)quinazolin-8-yl)pyrrolidin-1-yl)prop-2-en-1-one 1-(3-(2-Amino-6-(4-phenoxyphenyl)quinazolin-8-yl)pyrrolidin-1-yl)prop-2-en-1-one (9.3 mg) was prepared as described for 1-(3-(6-phenylquinazolin-8-yl)pyrrolidin-1-yl)prop-2-en-1-one. LRMS (M+H$^+$) m/z calculated 437.2, found 437.3. $^1$H NMR (DMSO-d6, 400 MHz) δ 9.16 (s, 1H), 7.97 (d, 2H), 7.77-7.80 (m, 2H), 7.42 (t, 2H), 7.06-7.19 (m, 5H), 6.94 (s, 1H), 6.60-6.70 (m, 1H), 6.14-6.19 (m, 1H), 5.64-5.71 (m, 1H), 4.30-4.35 (m, 0.5H), 4.17-4.23 (m, 1H), 4.06-4.11 (m, 0.5H), 3.84-3.89 (m, 0.5H), 3.61-3.78 (m, 2H), 3.42-3.49 (m, 0.5H), 2.24-2.39 (m, 2H).

Example 55: Preparation of 4-(8-(3-acrylamidophenyl)-2-aminoquinazolin-6-yl)-N-(4-methylpyridin-2-yl)benzamide

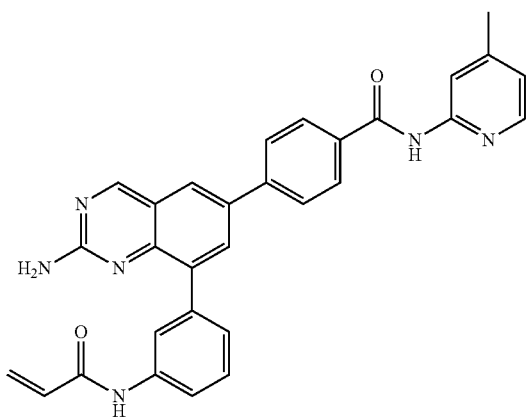

4-(8-(3-acrylamidophenyl)-2-aminoquinazolin-6-yl)-N-(4-methylpyridin-2-yl)benzamide 4-(8-(3-Acrylamidophenyl)-2-aminoquinazolin-6-yl)-N-(4-methylpyridin-2-yl)benzamide (7.7 mg) was prepared as described for 4-(8-(3-acrylamidophenyl)quinazolin-6-yl)-N-(pyridin-2-yl)benzamide. LRMS (M+H$^+$) m/z calculated 501.2, found 501.3. $^1$H NMR (DMSO-d6, 400 MHz) δ 10.76 (s, 1H), 10.23 (s, 1H), 9.26 (s, 1H), 7.83-8.27 (m, 11H), 7.44 (s, 2H), 6.95-7.03 (m, 2H), 6.25-6.47 (m, 2H), 5.76-5.78 (m, 1H), 2.37 (s, 3H).

Example 56: Preparation of 4-(8-(3-acrylamidophenyl)-2-aminoquinazolin-6-yl)-N-(pyridin-2-yl)benzamide

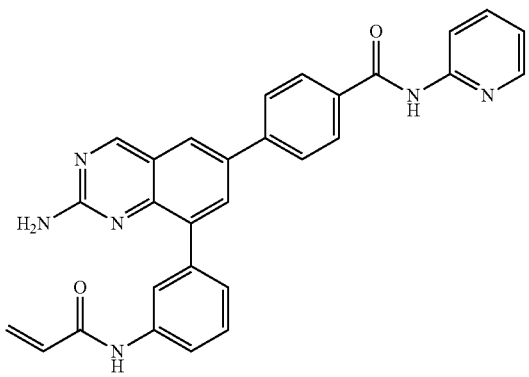

4-(8-(3-acrylamidophenyl)-2-aminoquinazolin-6-yl)-N-(pyridin-2-yl)benzamide 4-(8-(3-Acrylamidophenyl)-2-aminoquinazolin-6-yl)-N-(pyridin-2-yl)benzamide (4.0 mg) was prepared as described for 4-(8-(3-acrylamidophenyl)quinazolin-6-yl)-N-(pyridin-2-yl)benzamide. LRMS (M+H$^+$) m/z calculated 487.2, found 487.7. $^1$H NMR (DMSO-d6, 400 MHz) δ 10.84 (s, 1H), 10.23 (s, 1H), 9.26 (s, 1H), 8.42 (s, 1H), 8.19-8.40 (m, 4H), 8.05 (s, 1H), 7.97 (d, 2H), 7.84-7.87 (m, 3H), 7.43-7.45 (m, 2H), 7.17-7.20 (m, 1H), 6.95 (s, 2H), 6.25-6.52 (m, 2H), 5.76 (d, 1H).

Example 57: Preparation of 5-(8-(3-acrylamidophenyl)-2-aminoquinazolin-6-yl)-N-phenylpicolinamide

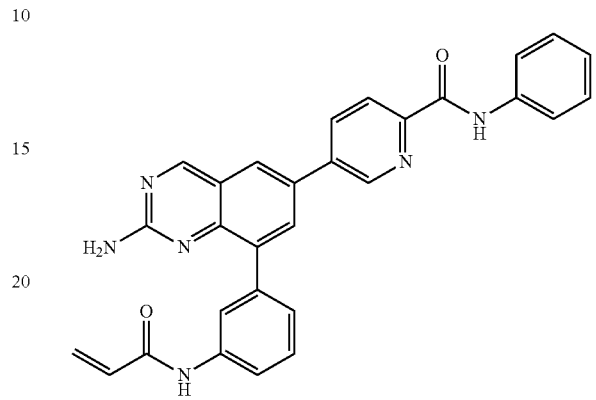

5-(8-(3-acrylamidophenyl)-2-aminoquinazolin-6-yl)-N-phenylpicolinamide 5-(8-(3-Acrylamidophenyl)-2-aminoquinazolin-6-yl)-N-phenylpicolinamide (1.2 mg) was prepared as described for 4-(8-(3-acrylamidophenyl)quinazolin-6-yl)-N-(pyridin-2-yl)benzamide. LRMS (M+H$^+$) m/z calculated 487.2, found 487.2. $^1$H NMR (DMSO-d6, 400 MHz) δ 10.65 (s, 1H), 10.22 (s, 1H), 9.28 (s, 1H), 9.17 (s, 1H), 8.50 (m, 1H), 8.34 (s, 1H), 8.25 (d, 1H), 8.10 (s, 1H), 7.90-7.95 (m, 3H), 7.82 (d, 1H), 7.36-7.46 (m, 4H), 7.14 (d, 1H), 7.00 (d, 1H), 6.44-6.51 (m, 2H), 6.24-6.29 (m, 1H), 5.75-5.78 (m, 1H).

Example 58: Preparation of N-(3-(4-amino-6-phenylquinazolin-8-yl)phenyl)acrylamide

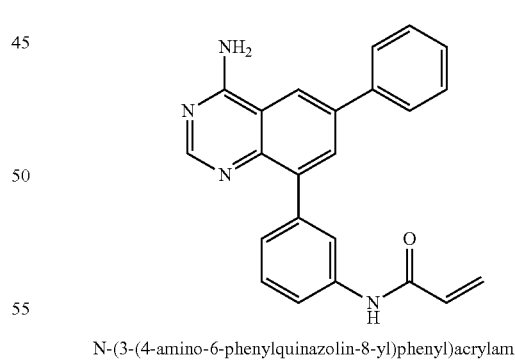

N-(3-(4-amino-6-phenylquinazolin-8-yl)phenyl)acrylamide

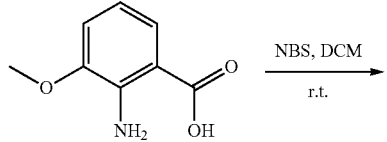

-continued

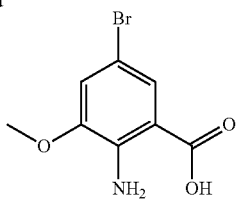

To a solution of 2-amino-3-methoxybenzoic acid (10.0 g, 59.8 mmol, 1.0 eq) in DCM (150 mL) was added NBS (10.6 g, 59.8 mmol, 1.0 eq) and the mixture was stirred at rt for 2 h. The solid was filtered and washed with DCM (100 mL*2) to provide 2-amino-5-bromo-3-methoxybenzoic acid as a grey solid (12.1 g, 82.2%).

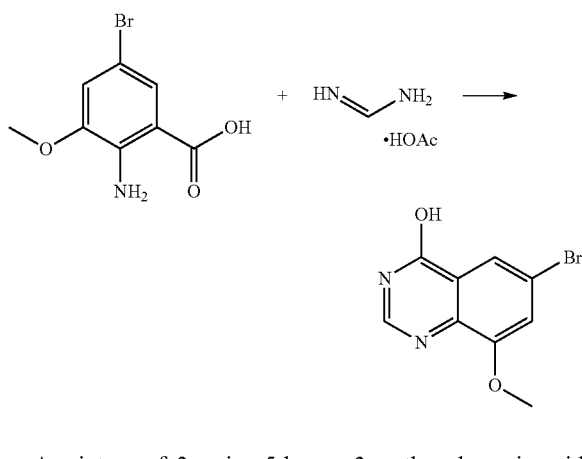

A mixture of 2-amino-5-bromo-3-methoxybenzoic acid (5.13 g, 20.9 mmol, 1.0 eq) and formimidamide acetate (21.7 g, 209 mmol, 10.0 eq) was stirred at 150° C. for 2 h, then cooled and poured into ice-water. The solid was collected by filtration, washed with H₂O for three times, and dried in vacuo to afford 6-bromo-8-methoxyquinazolin-4-ol as a grey solid (4.7 g, 88.7%).

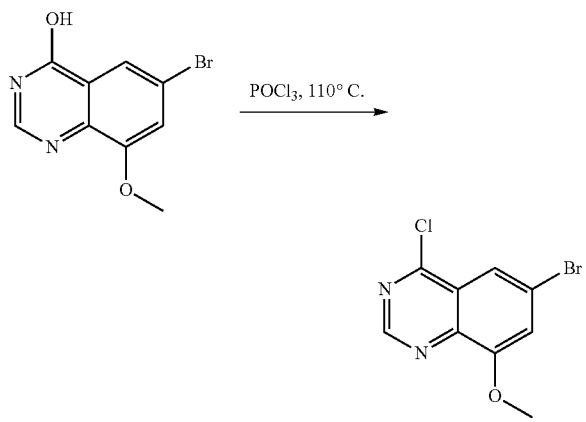

A solution of 6-bromo-8-methoxyquinazolin-4-ol (4.7 g, 18.5 mmol, 1.0 eq) in POCl₃ (50 mL) was refluxed for 12 h, then cooled to rt and concentrated. The resulting residue was dissolved in EA (100 mL) and poured into ice-water with vigorous stirring. The organic phase was separated and washed with brine, dried over anhydrous Na₂SO₄ and concentrated. The resulting residue was purified by column chromatography (PE/EA=4/1, v/v) to afford 6-bromo-4-chloro-8-methoxyquinazoline as a yellow solid (2.8 g, 56.0%).

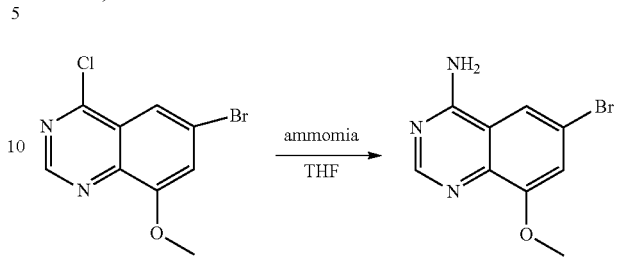

To a solution of ammonia hydroxide (9 mL) in THF (17 mL) cooled to 0° C. was added a solution of 6-bromo-4-chloro-8-methoxyquinazoline (2.98 g, 1.09 mmol, 1 eq) in THF (17 mL). Then MeCN (51 mL) was added, The mixture was stirred at rt for overnight. The reaction mixture was concentrated. The residue was washed with H₂O (20 mL) to afford 6-bromo-8-methoxyquinazolin-4-amine as a yellow solid (2.35 g, 85%).

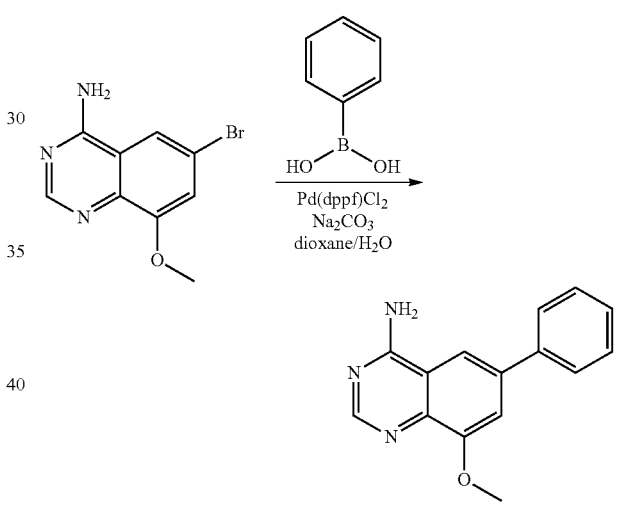

To a solution of 6-bromo-8-methoxyquinazolin-4-amine (253 mg, 1 mmol, 1 eq) and phenylboronic acid (134 mg, 1.1 mmol, 1.1 eq) in dioxane (10 mL) and H₂O (1 mL) was added Na₂CO₃ (212 mg, 2 mmol, 2 eq), followed by Pd(dppf)Cl₂·CH₂Cl₂ (163 mg, 0.2 mmol, 0.2 eq) under N₂. The mixture was stirred at 90° C. under N₂ for 12 h, then cooled to rt. The reaction mixture was concentrated and the resulting residue was purified by column chromatography (DCM/MeOH=20/1, v/v) to afford 8-methoxy-6-phenylquinazolin-4-amine (204 mg, 81.2%).

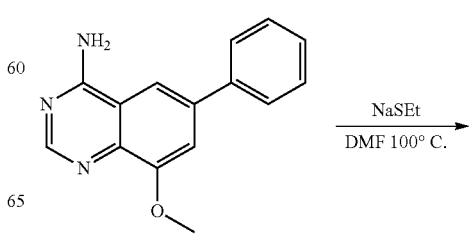

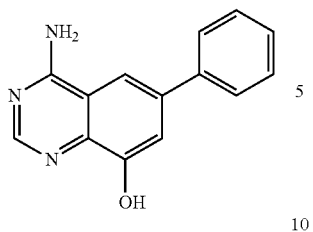

To a solution of 8-methoxy-6-phenylquinazolin-4-amine (276 mg, 1.1 mmol, 1 eq) in DMF (8 mL) was added sodium ethanethiolate (277 mg, 3.3 mmol, 3 eq). The mixture was heated to 100° C. for 3 h. The mixture was concentrated, the residue was diluted with H$_2$O (150 mL) and EA (30 mL) and brine (30 mL). The organic layer was concentrated to provide 4-amino-6-phenylquinazolin-8-ol as a yellow solid (284 mg, crude).

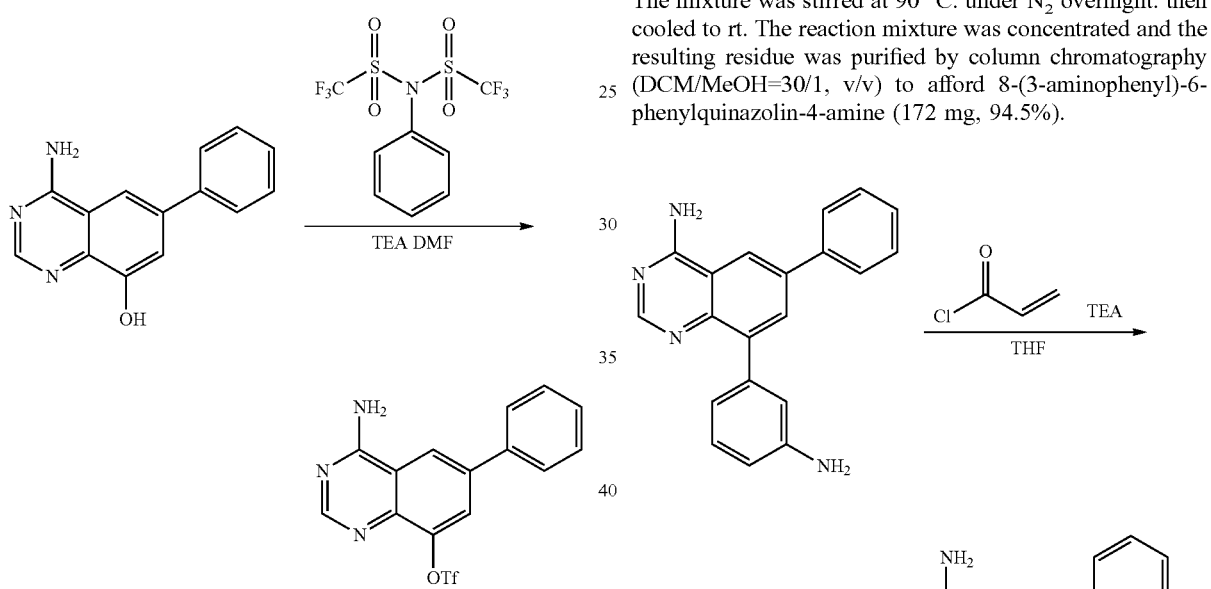

To a solution of 4-amino-6-phenylquinazolin-8-ol (284 mg, 1.1 mmol 1 eq) and TEA (0.76 mL, 5.5 mmol, 5 eq) in DMF (15 mL) was added PhN(OTf)$_2$ (1.77 g, 3.3 mmol, 3 eq). The mixture was stirred at rt overnight, then concentrated. The residue was purified by column chromatography (DCM/MeOH=40/1) to provide 4-amino-6-phenylquinazolin-8-yl trifluoromethanesulfonate as a yellow solid (216 mg, 53.6%).

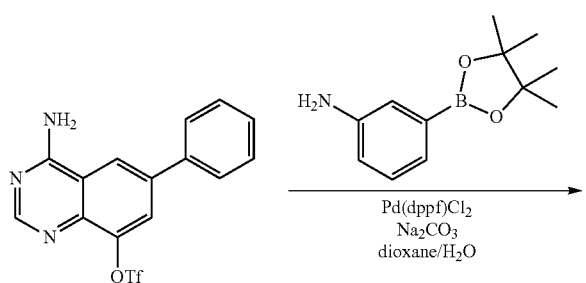

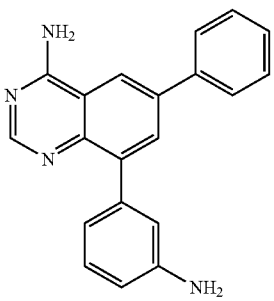

To a solution of 4-amino-6-phenylquinazolin-8-yl trifluoromethanesulfonate (216 mg, 0.59 mmol, 1 eq) and 3-(4,4,5,5-tetramethyl-1,3,2-dioxaborolan-2-yl)aniline (142 mg, 0.65 mmol, 1.1 eq) in dioxane (20 mL) and H$_2$O (2 mL) was added Na$_2$CO$_3$ (125 mg, 1.18 mmol, 2 eq), followed by Pd(dppf)Cl$_2$·CH$_2$Cl$_2$ (96 mg, 0.118 mmol, 0.2 eq) under N$_2$. The mixture was stirred at 90° C. under N$_2$ overnight. then cooled to rt. The reaction mixture was concentrated and the resulting residue was purified by column chromatography (DCM/MeOH=30/1, v/v) to afford 8-(3-aminophenyl)-6-phenylquinazolin-4-amine (172 mg, 94.5%).

To a solution of 8-(3-aminophenyl)-6-phenylquinazolin-4-amine (172 mg, 0.615 mmol, 1 eq.) in THF (10 mL) was added TEA (0.43 mL, 3.1 mmol, 5 eq.), followed by acryloyl chloride (28 mg, 0.31 mmol, 0.5 eq.). The resulting mixture was stirred at −78° C. for 1 h, then concentrated and purified by column chromatography (DCM/MeOH=40/1, v/v) to afford N-(3-(4-amino-6-phenylquinazolin-8-yl)phenyl)acrylamide as a yellow solid (76.3 mg, 40.7%). LRMS (M+H$^+$) m/z calculated 367.1, found 367.1. $^1$H NMR (DMSO-d6, 400 MHz) δ 10.23 (s, 1H), 8.59 (s, 1H), 8.39 (s, 1H), 7.79-8.05 (m, 7H), 7.53 (s, 2H), 7.42 (s, 3H), 6.48 (m, 1H), 6.28 (m, 1H), 5.77 (m, 1H).

Example 59: Preparation of N-(3-(4-amino-6-(3-(phenylamino)phenyl)quinazolin-8-yl)phenyl)acrylamide

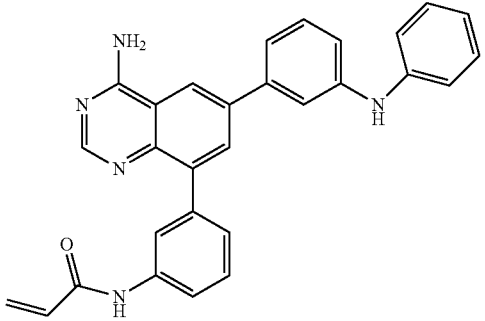

N-(3-(4-amino-6-(3-(phenylamino)phenyl)quinazolin-8-yl)phenyl)acrylamide

N-(3-(4-amino-6-(3-(phenylamino)phenyl)quinazolin-8-yl)phenyl)acrylamide (13.5 mg). was prepared as described for N-(3-(4-amino-6-phenylquinazolin-8-yl)phenyl)acrylamide. LRMS (M+H⁺) m/z calculated 457.2, found 457.2. $^1$H NMR (DMSO-d6, 400 MHz) δ 10.23 (s, 1H), 8.53 (s, 1H), 8.37 (s, 1H), 8.32 (s, 1H), 7.93 (d, 2H), 7.77 (d, 1H), 7.14-7.50 (m, 12H), 6.85 (d, 1H), 6.48 (m, 1H), 6.28 (d, 1H), 5.75 (m, 1H).

Example 60: Preparation of 1-(3-(4-amino-6-(4-phenoxyphenyl)quinazolin-8-yl)piperidin-1-yl)prop-2-en-1-one

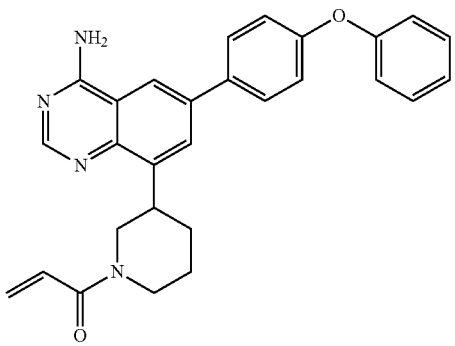

1-(3-(4-amino-6-(4-phenoxyphenyl)quinazolin-8-yl)piperidin-1-yl)prop-2-en-1-one 1-(3-(4-Amino-6-(4-phenoxyphenyl)quinazolin-8-yl)piperidin-1-yl)prop-2-en-1-one (23.9 mg) was prepared as described for 1-(3-(6-phenylquinazolin-8-yl)pyrrolidin-1-yl)prop-2-en-1-one. LRMS (M+H⁺) m/z calculated 451.2, found 451.2. $^1$H NMR (DMSO-d6, 400 MHz) δ 8.43 (s, 2H), 7.98 (d, 2H), 7.87 (d, 3H), 7.43 (t, 2H), 7.17 (d, 3H), 7.06 (d, 2H), 6.85 (m, 1H), 6.10 (d, 1H), 5.68 (t, 1H), 4.53 (m, 1H), 4.23 (m, 0.5H), 4.15 (m, 0.5H), 3.80 (m, 1H), 3.18 (m, 1H), 3.10 (m, 0.5H), 2.72 (m, 0.5H), 2.02 (m, 2H), 1.86 (m, 1H), 1.56 (m, 1H).

Example 61: Preparation of 1-(3-(4-amino-6-phenylquinazolin-8-yl)piperidin-1-yl)prop-2-en-1-one

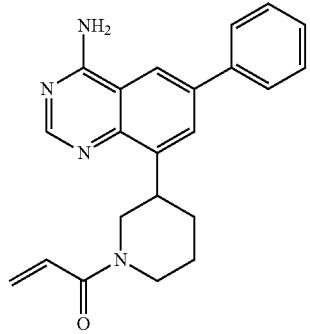

1-(3-(4-amino-6-phenylquinazolin-8-yl)piperidin-1-yl)prop-2-en-1-one 1-(3-(4-Amino-6-phenylquinazolin-8-yl)piperidin-1-yl)prop-2-en-1-one (19.2 mg) was prepared as described for 1-(3-(6-phenylquinazolin-8-yl)pyrrolidin-1-yl)prop-2-en-1-one. LRMS (M+H⁺) m/z calculated 359.2, found 359.2. $^1$H NMR (DMSO-d6, 400 MHz) δ 8.42 (s, 2H), 7.99 (d, 2H), 7.85 (d, 3H), 7.56 (t, 2H), 7.43 (s, 1H), 6.89 (m, 1H), 6.14 (d, 2H), 5.64 (t, 1H), 4.53 (t, 1H), 4.21 (d, 0.5H), 4.10 (d, 0.5H), 3.81 (m, 1H), 3.24 (m, 1H), 3.04 (m, 0.5H), 2.74 (m, 0.5H), 2.02 (m, 2H), 1.86 (m, 1H), 1.58 (m, 1H).

Example 62: Preparation of 4-(8-(1-acryloylpiperidin-3-yl)quinazolin-5-yl)-N-(pyridin-2-yl)benzamide

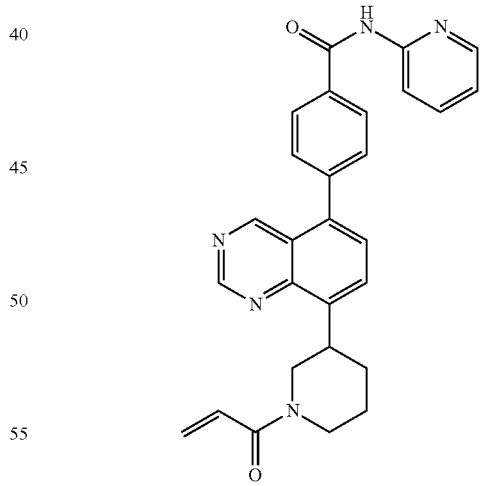

4-(8-(1-acryloylpiperidin-3-yl)quinazolin-5-yl)-N-(pyridin-2-yl)benzamide

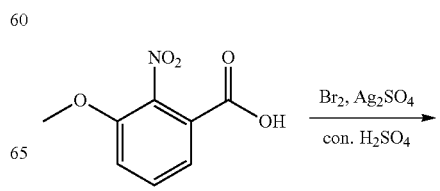

-continued

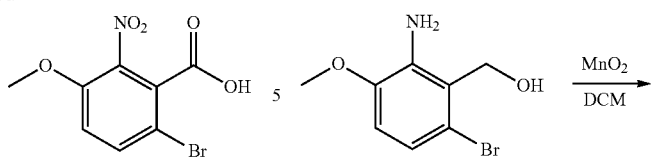

To a suspended solution of 3-methoxy-2-nitrobenzoic acid (22.96 g, 116.5 mmol, 1.0 eq) in con. H₂SO₄ (450 mL) was added Br₂ (18.65 g, 116.5 mmol, 1.0 eq) at 0° C., after the mixture stirred in dark at that temperature for 2 h, poured into ice (1350 mL), then warmed to rt and filtered and washed with water (100 mL×2) to provide 6-bromo-3-methoxy-2-nitrobenzoic acid as a yellow solid (23.1 g, 71.8%).

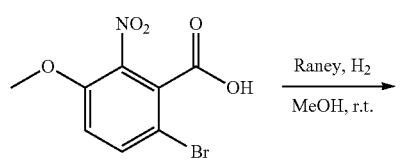

To a solution of 6-bromo-3-methoxy-2-nitrobenzoic acid (23.1 g, 83.0 mmol, 1.0 eq) in methanol (300 mL) was added Raney Ni and degassed with hydrogen, the reaction mixture was stirred at rt overnight. Then filtrated and concentrated to provide 2-amino-6-bromo-3-methoxybenzoic acid as a white solid (20.5 g, 100%).

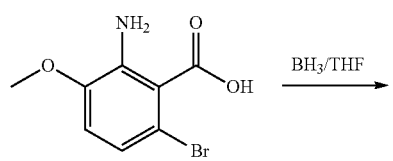

To a solution of 2-amino-6-bromo-3-methoxybenzoic acid (2.0 g, 8.1 mmol, 1.0 eq) in THF (24 mL) was added borohydride in THF (24.3 mL, 1N, 3.0 eq) under ice/water bath and the reaction mixture was stirred at 50° C. overnight. Then the mixture was cooled to 0° C., quenched with MeOH (10 mL) and concentrated to 2 mL. The residue was diluted with aqueous Na₂CO₃ (30 mL) and extracted with EA (50 mL*3). The organic layers were separated, combined, dried over Na₂SO₄, filtered and concentrated to afford (2-amino-6-bromo-3-methoxyphenyl)methanol (705 mg, 33.3%).

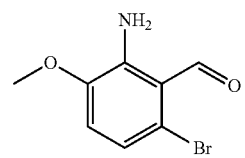

A mixture of (2-amino-6-bromo-3-methoxyphenyl)methanol (705 mg, 3.05 mmol, 1.0 eq) and MnO₂ (1.33 g, 15.3 mmol, 5.0 eq) in DCM (25 mL) was stirred at rt overnight. The solid was filtered off and the filtrate was concentrated to provide 2-amino-6-bromo-3-methoxybenzaldehyde as a brown solid (695 g, 99.4%).

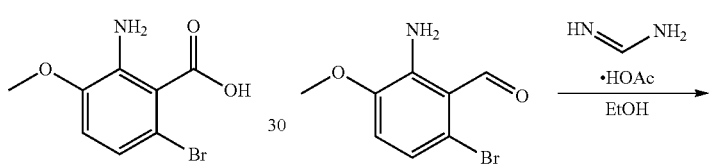

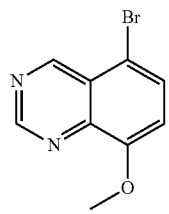

To a refluxing solution of 2-amino-6-bromo-3-methoxybenzaldehyde (695 mg, 3.02 mmol, 1.0 eq) in ethanol (30.0 mL) was added formamidine acetate (628 mg, 6.04 mmol, 2.0 eq). The mixture was stirred under reflux overnight, then cooled and concentrated. The residue was purified on gel chromatography to provide 5-bromo-8-methoxyquinazoline as a white solid (595 mg, 82.3%).

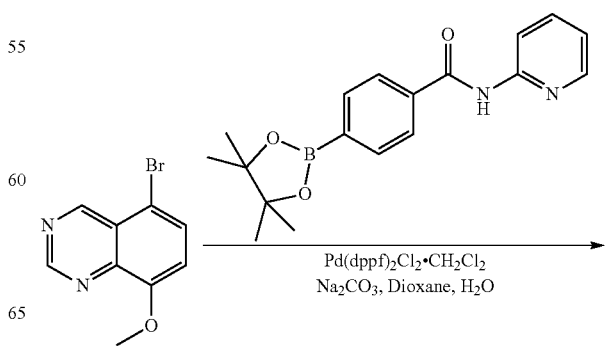

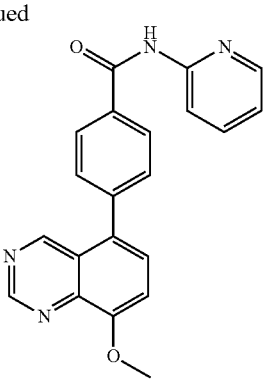

To a solution of 5-bromo-8-methoxyquinazoline (595 mg, 2.5 mmol, 1.0 eq) and N-(pyridin-2-yl)-4-(4,4,5,5-tetramethyl-1,3,2-dioxaborolan-2-yl)benzamide (967 mg, 3.0 mmol, 1.2 eq) in dioxane (40.0 mL) and H₂O (4.0 mL) was added Na₂CO₃ (528 mg, 5.0 mmol, 2.0 eq), followed by Pd(dppf)Cl₂·CH₂Cl₂ (101.0 mg, 0.12 mmol, 0.05 eq) under N₂. The mixture was stirred at 90° C. for 12 h, then cooled to rt, diluted with EA (50.0 mL) and filtered. The filtrate was concentrated and the resulting residue was purified on flash chromatography (PE/EA=1/1, v/v) to afford 4-(8-methoxyquinazolin-5-yl)-N-(pyridin-2-yl)benzamide as a yellow solid (655 mg, 73.3%).

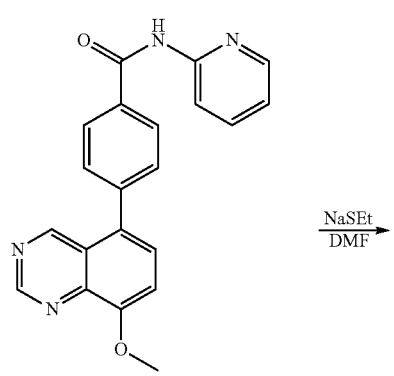

To a solution of 4-(8-methoxyquinazolin-5-yl)-N-(pyridin-2-yl)benzamide (835 mg, 2.3 mmol, 1.0 eq) in DMF (20.0 mL) was added sodium ethanethiolate (589 mg, 7.02 mmol, 3.0 eq). The mixture was heated at 110° C. overnight under N₂, then cooled and diluted with H₂O (200.0 mL) and EA (100.0 mL) which was extracted with EA (100.0 mL*2). The EA layers were separated, dried over anhydrous Na₂SO₄ and concentrated to provide 4-(8-hydroxyquinazolin-5-yl)-N-(pyridin-2-yl)benzamide as a yellow solid (691.0 mg, 87.8%).

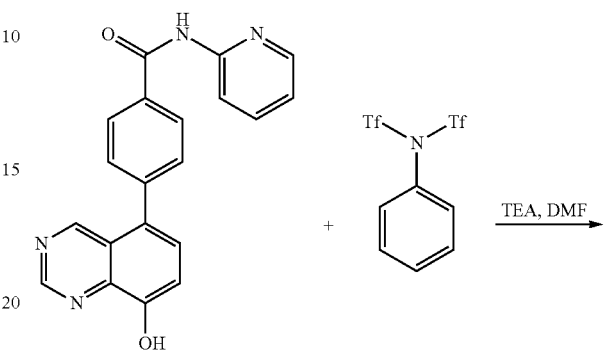

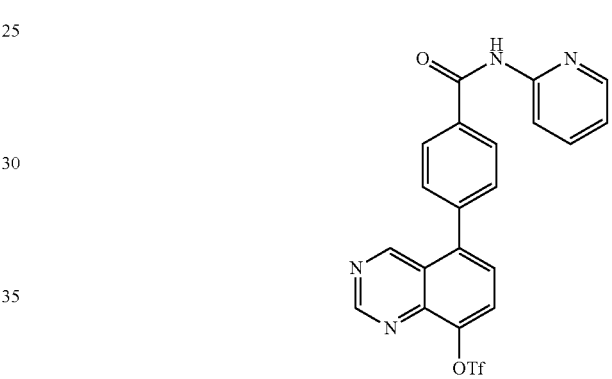

To a solution of 4-(8-hydroxyquinazolin-5-yl)-N-(pyridin-2-yl)benzamide (691 mg, 2.02 mmol, 1.0 eq) and TEA (1.4 mL, 10.1 mmol, 5.0 eq) in DMF (15.0 mL) was added PhN(OTf)₂ (3.25 g, 6.06 mmol, 3.0 eq). The mixture was stirred at rt overnight, then concentrated. The residue was purified by column chromatography (PE/EA=1/1, v/v) to provide 5-(4-(pyridin-2-ylcarbamoyl)phenyl)quinazolin-8-yl trifluoromethanesulfonate as a yellow solid (734 mg, 76.6%).

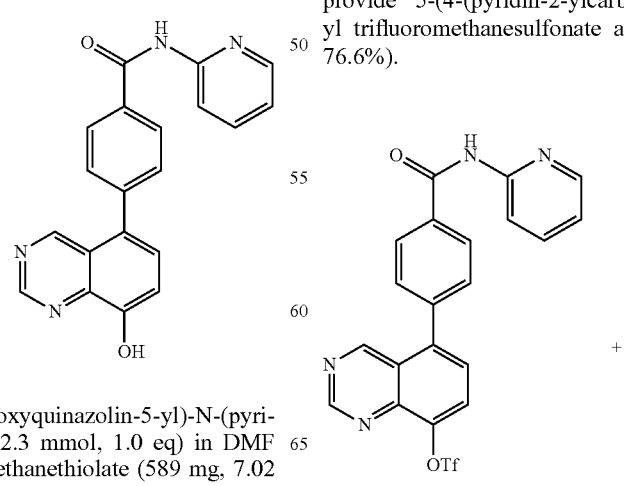

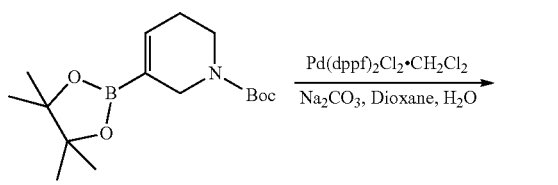

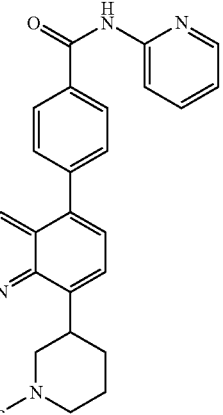

To a solution of tert-butyl 3-(5-(4-(pyridin-2-ylcarbamoyl)phenyl)quinazolin-8-yl)-5,6-dihydropyridine-1(2H)-carboxylate (232 mg, 0.46 mmol, 1.0 eq) in methanol (25 mL) was added Pd(OH)₂ (64 mg, 0.46 mmol, 1.0 eq), and the mixture was degassed with hydrogen. After stirred at rt for 18 h, the mixture was filtrated and concentrated to afford the crude tert-butyl 3-(5-(4-(pyridin-2-ylcarbamoyl)phenyl)-2,3-dihydroquinazolin-8-yl)piperidine-1-carboxylate (232 mg, crude).

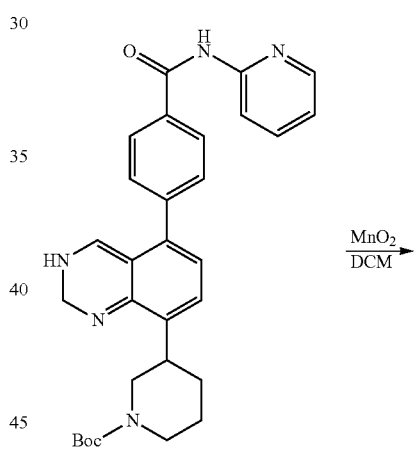

To a solution of 5-(4-(pyridin-2-ylcarbamoyl)phenyl)quinazolin-8-yl trifluoromethanesulfonate (294 mg, 0.62 mmol, 1.0 eq) and tert-butyl 3-(4,4,5,5-tetramethyl-1,3,2-dioxaborolan-2-yl)-5,6-dihydropyridine-1(2H)-carboxylate (230.0 mg, 0.74 mmol, 1.2 eq) in dioxane (25.0 mL) and H₂O (2.5 mL) was added Na₂CO₃ (131 mg, 1.24 mmol, 2.0 eq), followed by Pd(dppf)Cl₂·CH₂Cl₂ (51.0 mg, 0.062 mmol, 0.1 eq) under N₂. The mixture was stirred at 90° C. for 12 h, then cooled to rt, diluted with EA (40.0 mL) and filtered. The filtrate was concentrated and the resulting residue was purified via silica gel chromatography (DCM/MeOH=50/1, v/v) to afford tert-butyl 3-(5-(4-(pyridin-2-ylcarbamoyl)phenyl)quinazolin-8-yl)-5,6-dihydropyridine-1(2H)-carboxylate as a yellow solid (232 mg, 73.8%).

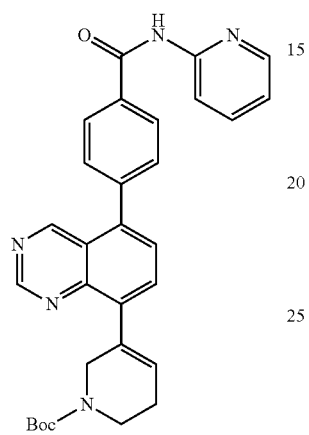

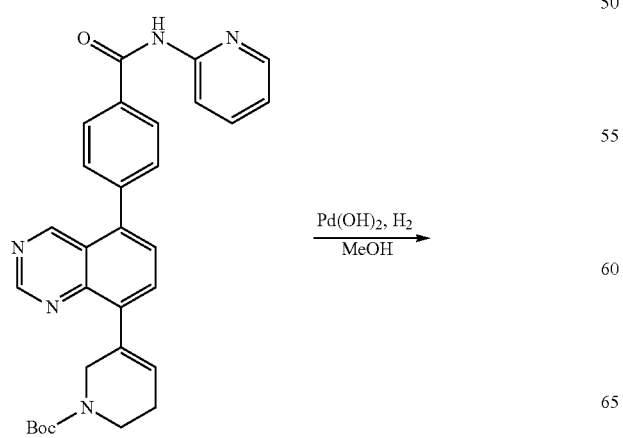

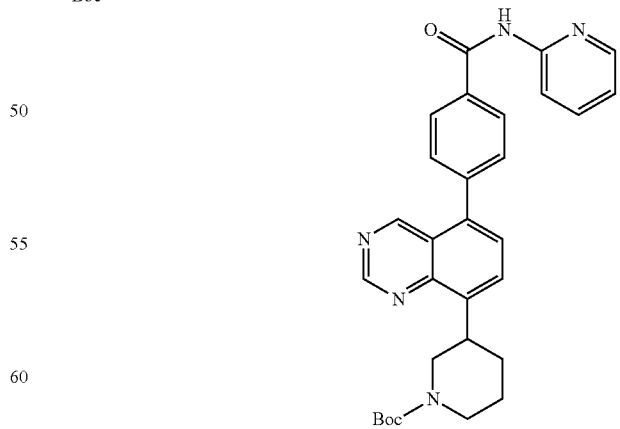

A mixture of the crude tert-butyl 3-(5-(4-(pyridin-2-ylcarbamoyl)phenyl)-2,3-dihydroquinazolin-8-yl)piperidine-1-carboxylate (232 mg, 0.46 mmol, 1.0 eq) and MnO₂ (409 mg, 4.6 mmol, 10.0 eq) in DCM (30 mL) was stirred at reflux overnight. The solid was filtered off and the filtrate was concentrated and purified on flash chromatography (PE/EA=1/1, v/v) to afford tert-butyl 3-(5-(4-(pyridin-2-ylcarbamoyl)phenyl)quinazolin-8-yl)piperidine-1-carboxylate (75 mg, 31.4% for two steps).

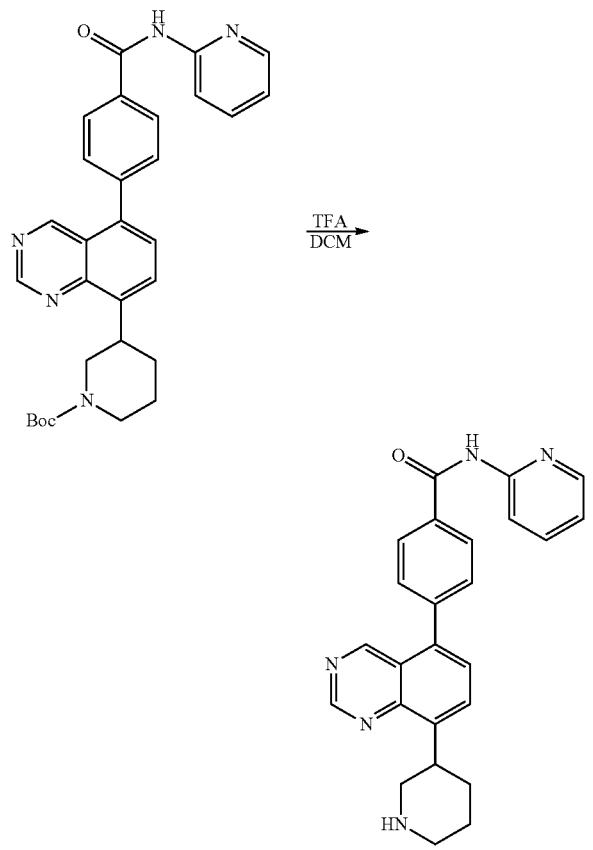

To a solution of tert-butyl 3-(5-(4-(pyridin-2-ylcarbamoyl)phenyl)quinazolin-8-yl)piperidine-1-carboxylate (75 mg, 0.15 mmol, 1.0 eq) in DCM (3 mL) was added TFA (1.5 mL), and the mixture was stirred at rt for 2 h, then concentrated to provide the crude 4-(8-(piperidin-3-yl)quinazolin-5-yl)-N-(pyridin-2-yl)benzamide as a TFA salt (79 mg, crude) which was used to the next step without further purification.

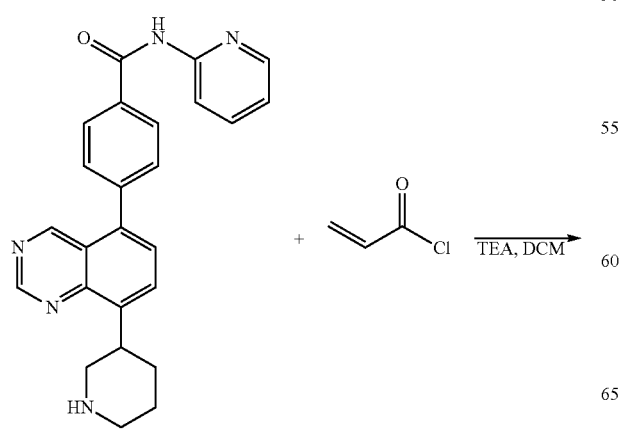

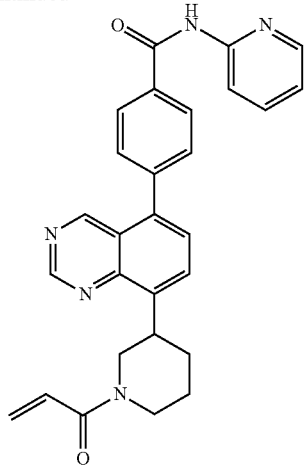

To a solution of 4-(8-(piperidin-3-yl)quinazolin-5-yl)-N-(pyridin-2-yl)benzamide TFA salt (79 mg, 0.15 mmol, 1.0 eq) in DCM (10.0 mL) was added TEA (0.1 mL, 0.75 mmol, 5.0 eq), followed by acryloyl chloride (12 mg, 0.13 mmol, 0.9 eq). The resulting mixture was stirred at rt for 1 h, then washed with brine, dried over anhydrous Na$_2$SO$_4$, concentrated. The residue was purified by column chromatography (DCM/MeOH=50/1, v/v) to afford N-(3-(6-(pyridin-4-yl)quinazolin-8-yl)phenyl)acrylamide as a yellow solid (15.3 mg, 22.5%). LRMS (M+H$^+$) m/z calculated 464.2, found 464.2. $^1$H NMR (DMSO-d6, 400 MHz) δ 10.93 (s, 1H), 9.42 (s, 2H), 8.43 (d, 1H), 8.24 (d, 3H), 8.08 (s, 1H), 7.88 (t, 1H), 7.78 (d, 3H), 7.20 (t, 1H), 6.84-6.94 (m, 1H), 6.15 (d, 1H), 5.71 (t, 1H), 4.62 (t, 1H), 3.97-4.32 (m, 2H), 2.74-3.26 (m, 2H), 1.88-2.06 (m, 3H), 1.58-1.64 (m, 1H).

Example 63: Preparation of 4-(8-(3-acrylamidophenyl)quinazolin-5-yl)-N-(pyridin-2-yl)benzamide

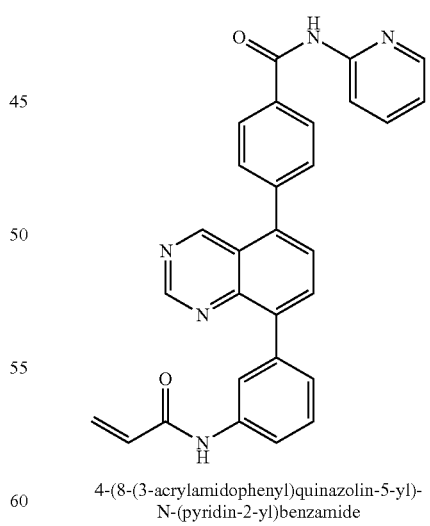

4-(8-(3-acrylamidophenyl)quinazolin-5-yl)-
N-(pyridin-2-yl)benzamide 4-(8-(3-Acrylamidophenyl)quinazolin-5-yl)-N-(pyridin-2-yl)benzamide (43.5 mg) was prepared as described for N-(3-(6-(pyridin-4-yl)quinazolin-8-yl)phenyl)acrylamide. LRMS (M+H$^+$) m/z calculated 472.2, found 472.2. $^1$H NMR (DMSO-d6, 400 MHz) δ 10.94 (s, 1H), 10.34 (s, 1H), 9.46

(s, 1H), 9.36 (s, 1H), 8.25 (d, 3H), 8.12 (d, 1H), 8.06 (s, 1H), 7.79-7.87 (m, 5H), 7.44-7.51 (m, 2H), 7.20 (s, 1H), 6.47-6.49 (m, 1H), 6.29 (d, 1H), 5.78 (d, 1H).

Example 64: Preparation of 4-(8-(1-acryloylpyrrolidin-3-yl)quinazolin-5-yl)-N-(pyridin-2-yl)benzamide

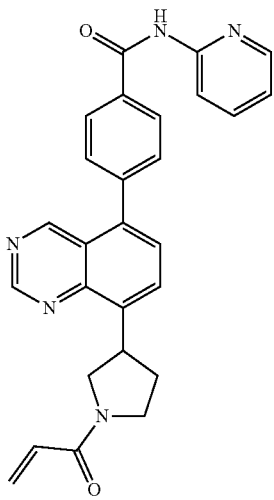

4-(8-(1-acryloylpyrrolidin-3-yl)quinazolin-5-yl)-N-(pyridin-2-yl)benzamide 4-(8-(1-acryloylpyrrolidin-3-yl)quinazolin-5-yl)-N-(pyridin-2-yl)benzamide (9.2 mg) was prepared as described for N-(3-(6-(pyridin-4-yl)quinazolin-8-yl)phenyl)acrylamide. LRMS (M+H⁺) m/z calculated 450.2, found 450.2. ¹H NMR (DMSO-d6, 400 MHz) δ 10.93 (s, 1H), 9.43 (t, 2H), 8.22-8.26 (m, 3H), 8.43 (d, 1H), 8.07 (dd, 1H), 7.88 (t, 1H), 7.74-7.77 (m, 3H), 7.20 (d, 1H), 6.60-6.71 (m, 1H), 6.16-6.22 (m, 1H), 5.66-5.74 (m, 1H), 4.50-4.61 (m, 1H), 4.10-4.25 (m, 1H), 3.85-3.90 (m, 0.5H), 3.71-3.79 (m, 1.5H), 3.51-3.59 (m, 1H), 2.20-2.37 (m, 1.5H), 1.95-2.03 (m, 0.5H).

Example 65: Preparation of 4-(8-(1-acryloylpyrrolidin-3-yl)-4-aminoquinazolin-5-yl)-N-(pyridin-2-yl)benzamide

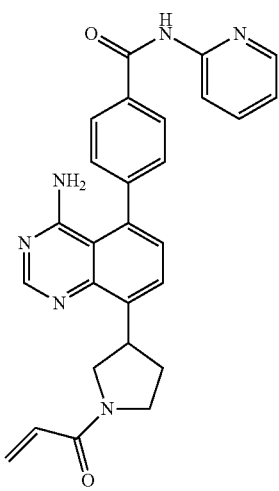

4-(8-(1-acryloylpyrrolidin-3-yl)-4-aminoquinazolin-5-yl)-N-(pyridin-2-yl)benzamide

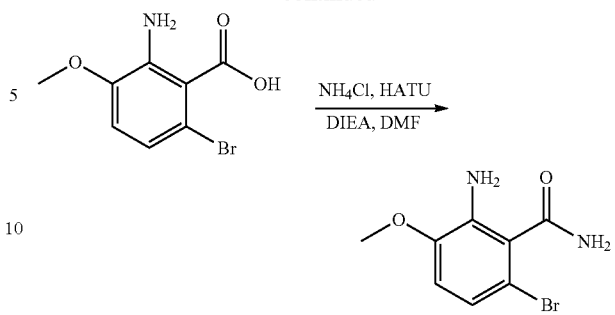

A mixture of 2-amino-6-bromo-3-methoxybenzoic acid (4.7 g, 19.1 mmol, 1.0 eq), NH₄Cl (3.07 g, 57.3 mmol, 3.0 eq), HATU (8.74 g, 23.0 mmol, 1.2 eq) and DIEA (7.39 g, 57.3 mmol, 3.0 eq) in DMF (100 mL) was stirred at rt for overnight, then the solvent was evaporated and the residue was purified by column chromatography (PE/EA=1/1, v/v) to afford 2-amino-6-bromo-3-methoxybenzamide (3.8 g, 81%).

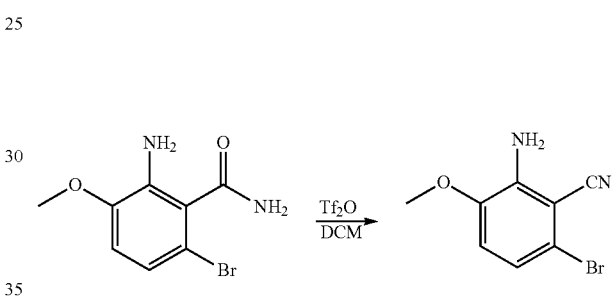

To a solution of (972 mg, 3.97 mmol, 1.0 eq) in DCM (30 mL) was added TFA (15 mL). The resulting mixture was heated to 100° C. for overnight. Then the mixture was concentrated and the residue was purified by column chromatography (PE/EA=1/1, v/v) to afford 2-amino-6-bromo-3-methoxybenzonitrile (207 mg, 23%).

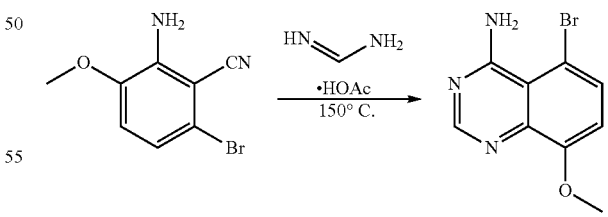

A mixture of 2-amino-6-bromo-3-methoxybenzonitrile (528 mg, 2.33 mmol, 1.0 eq) and formamidine acetate (3.63 g, 35.0 mmol, 15.0 eq). The mixture was stirred 150° C. for 3 h, then the mixture was poured into 2N NaOH (30 mL), and extracted it with DCM (50*4), the combined organic phase was washed with water (50 mL*4) and dried over MgSO₄, filtered and concentrated to afford 5-bromo-8-methoxyquinazolin-4-amine (327 mg, 56%).

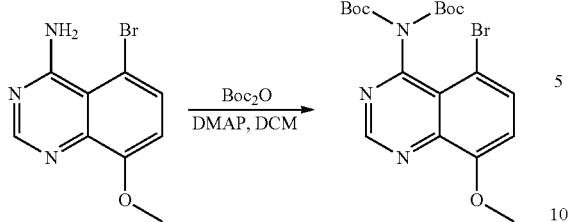

To a solution of 5-bromo-8-methoxyquinazolin-4-amine (277 mg, 1.1 mmol, 1.0 eq) and DMAP (14 mg, 0.11 mmol, 0.1 eq) in DCM (20 mL) was added Boc$_2$O (594 mg, 2.75 mmol, 2.5 eq), the resulting mixture was stirred at rt for overnight. Then concentrated and purified by column chromatography (DCM/MeOH=60/1, v/v) to afford 4-(N, N-di(tert-butyloxy carbonyl)-amino)-5-bromo-8-methoxyquinazoline (348 mg, 70.1%).

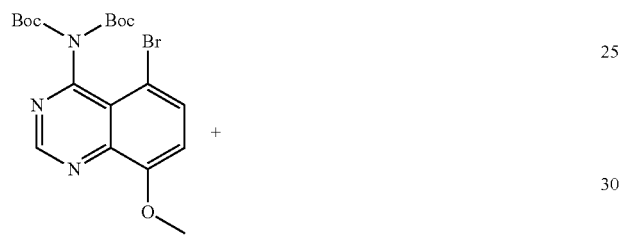

To a solution of 4-(N, N-di(tert-butyloxy carbonyl)-amino)-5-bromo-8-methoxyquinazoline (348 mg, 0.77 mmol, 1.0 eq) and N-(pyridin-2-yl)-4-(4,4,5,5-tetramethyl-1,3,2-dioxaborolan-2-yl)benzamide (373 mg, 1.15 mmol, 1.5 eq) in dioxane (22 mL) and H$_2$O (2.2 mL) was added Na$_2$CO$_3$ (163 mg, 1.54 mmol, 2.0 eq), followed by Pd(dppf)Cl$_2$·CH$_2$Cl$_2$ (125 mg, 0.15 mmol, 0.2 eq) under N$_2$. The mixture was stirred at 90° C. for 12 h, then cooled to rt, diluted with EA (50.0 mL) and filtered. The filtrate was concentrated and the resulting residue was purified on flash chromatography (DCM/MeOH=20/1, v/v) to afford 4-(4-amino-8-methoxyquinazolin-5-yl)-N-(pyridin-2-yl)benzamide as a yellow solid (312 mg, 100%).

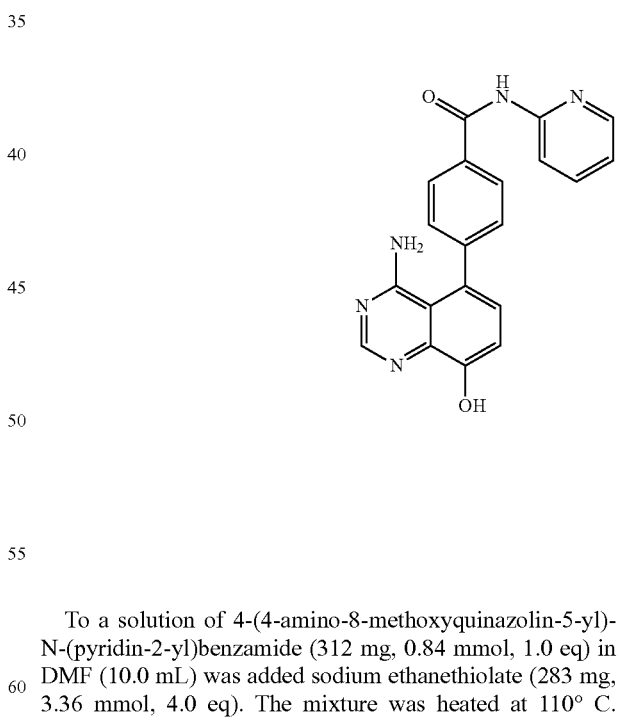

To a solution of 4-(4-amino-8-methoxyquinazolin-5-yl)-N-(pyridin-2-yl)benzamide (312 mg, 0.84 mmol, 1.0 eq) in DMF (10.0 mL) was added sodium ethanethiolate (283 mg, 3.36 mmol, 4.0 eq). The mixture was heated at 110° C. overnight under N$_2$, then cooled and diluted with H$_2$O (100.0 mL) and EA (100.0 mL) which was extracted with EA (100.0 mL*2). The EA layers were separated, dried over anhydrous Na$_2$SO$_4$ and concentrated to provide 4-(4-amino-8-hydroxyquinazolin-5-yl)-N-(pyridin-2-yl)benzamide as a yellow solid (309 mg, 100%).

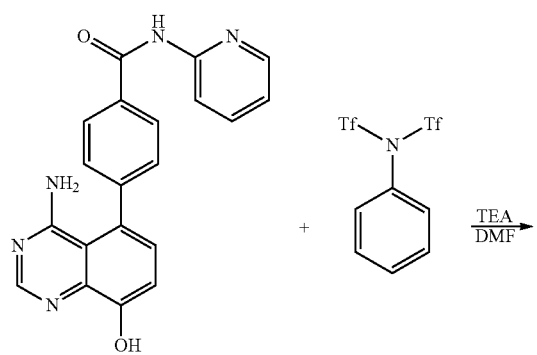

To a solution of 4-amino-5-(4-(pyridin-2-ylcarbamoyl) phenyl)quinazolin-8-yl trifluoromethanesulfonate (121 mg, 0.25 mmol, 1.0 eq) and tert-butyl 3-(4,4,5,5-tetramethyl-1,3,2-dioxaborolan-2-yl)-2,5-dihydro-1H-pyrrole-1-carboxylate (109 mg, 0.37 mmol, 1.5 eq) in dioxane/water (20 mL/2 mL) was added $Na_2CO_3$ (535 m, 5 mol, 2.0 eq), followed by $Pd(dppf)Cl_2 \cdot CH_2Cl_2$ (40 mg, 0.05 mmol, 0.2 eq) under $N_2$. The mixture was stirred at 90° C. for 12 h, then cooled to rt, diluted with EA (40 mL) and filtered. The filtrate was concentrated and the resulting residue was purified on flash chromatography (DCM/MeOH=30/1, v/v) to afford tert-butyl 3-(4-amino-5-(4-(pyridin-2-ylcarbamoyl)phenyl)quinazolin-8-yl)-2,5-dihydro-H-pyrrole-1-carboxylate as a yellow solid (94 mg, 75.2%).

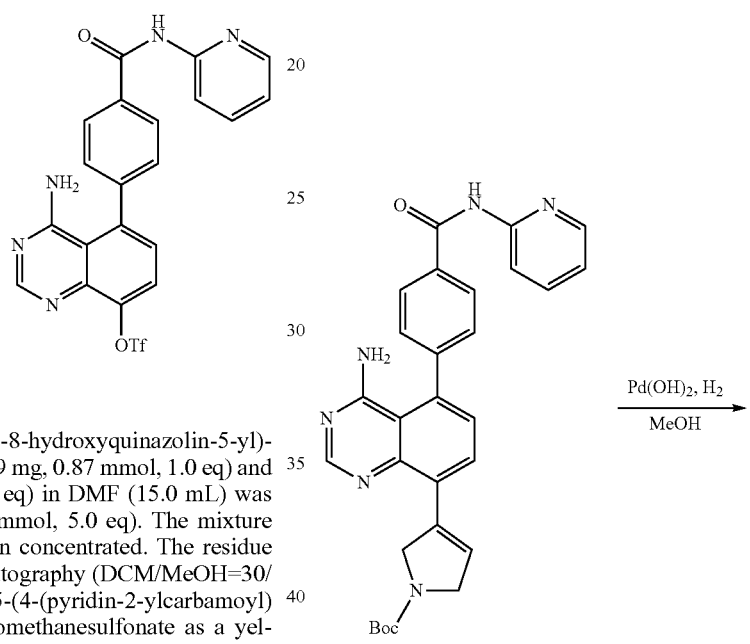

To a solution of 4-(4-amino-8-hydroxyquinazolin-5-yl)-N-(pyridin-2-yl)benzamide (309 mg, 0.87 mmol, 1.0 eq) and TEA (440 mg, 4.35 mmol, 5.0 eq) in DMF (15.0 mL) was added $PhN(OT)_2$ (2.33 g, 4.3 mmol, 5.0 eq). The mixture was stirred at rt overnight, then concentrated. The residue was purified by column chromatography (DCM/MeOH=30/1, v/v) to provide 4-amino-5-(4-(pyridin-2-ylcarbamoyl) phenyl)quinazolin-8-yl trifluoromethanesulfonate as a yellow solid (121 mg, 29%).

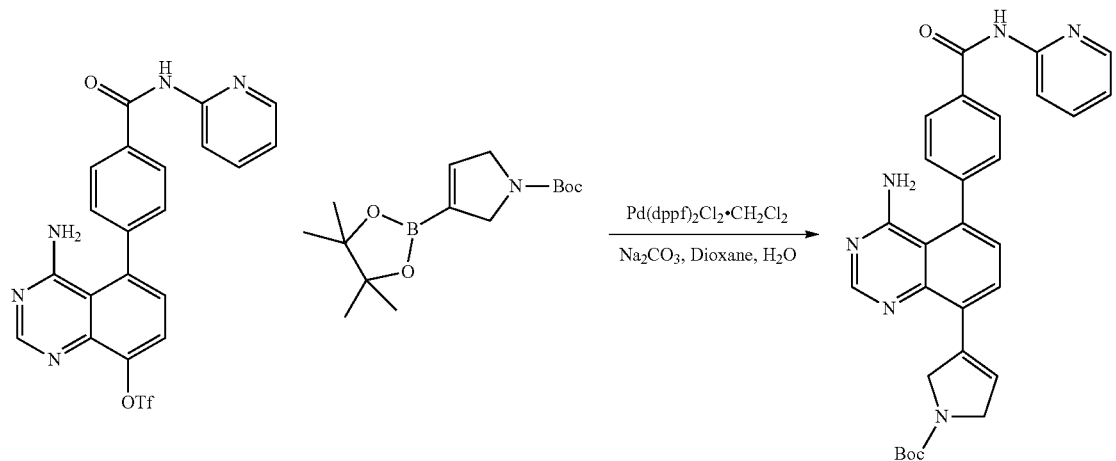 [SMILES: Nc1ncnc2c(OS(=O)(=O)C(F)(F)F)ccc(-c3ccc(C(=O)Nc4ccccn4)cc3)c12 ; CC(C)(C)OC(=O)N1CC=C(B2OC(C)(C)C(C)(C)O2)C1 ; CC(C)(C)OC(=O)N1CC=C(c2ccc(-c3ccc(C(=O)Nc4ccccn4)cc3)c3c(N)ncnc23)C1]

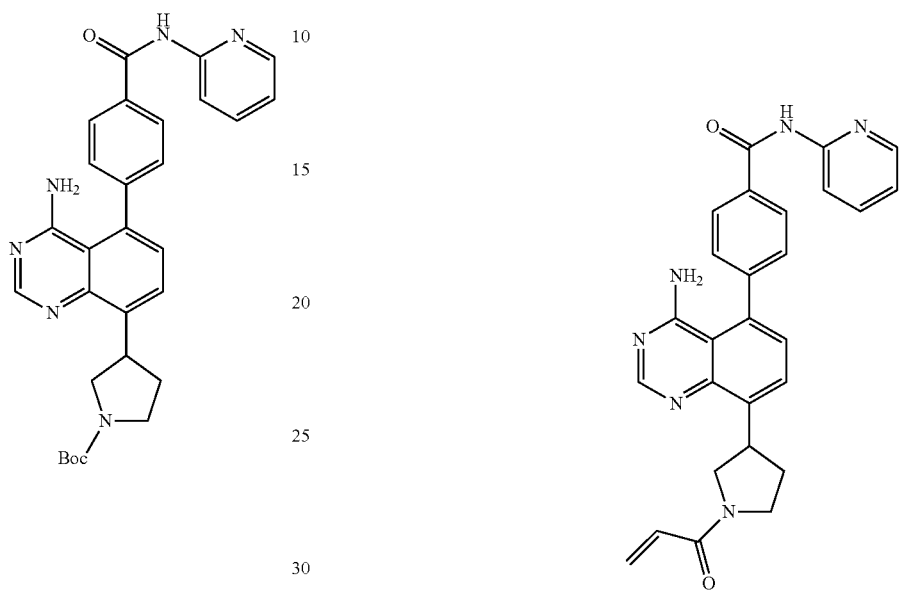

To a solution of tert-butyl 3-(4-amino-5-(4-(pyridin-2-ylcarbamoyl)phenyl)quinazolin-8-yl)-2,5-dihydro-1H-pyrrole-1-carboxylate (94 mg, 0.19 mmol, 1.0 eq) in methanol (20 mL) was added Pd(OH)$_2$ (86 mg, 0.61 mmol, 3.3 eq, 20%), and the mixture was degassed with hydrogen. After stirred at rt for 48 h, the mixture was filtrated and concentrated, purified on flash chromatography (DCM/MeOH=20/1, v/v) to afford tert-butyl 3-(4-amino-5-(4-(pyridin-2-ylcarbamoyl)phenyl)quinazolin-8-yl)pyrrolidine-1-carboxylate a yellow solid (30 mg, 32%).

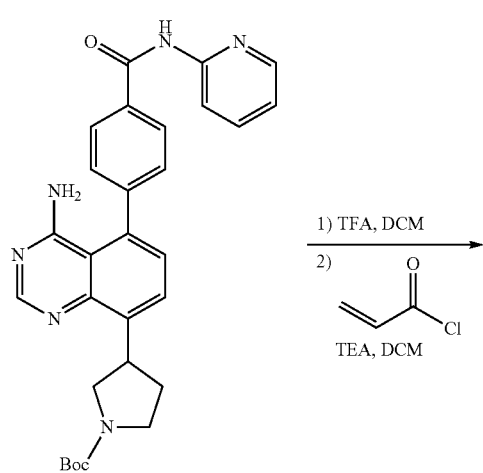

To a solution of tert-butyl 3-(4-amino-5-(4-(pyridin-2-ylcarbamoyl)phenyl)quinazolin-8-yl)pyrrolidine-1-carboxylate (30 mg, 0.059 mmol, 1.0 eq) in DCM (2 mL) was added TFA (2 mL), and the mixture was stirred at rt for 2 h, and concentrated. The residue was dissolved in DCM (10.0 mL) and TEA (48 mg, 0.47 mmol, 8.0 eq) was added, followed by acryloyl chloride (4.2 mg, 0.047 mmol, 0.8 eq). The resulting mixture was stirred at rt for 1 h, then washed with brine, dried over anhydrous Na$_2$SO$_4$, concentrated. The residue was purified by column chromatography (DCM/MeOH=50/1, v/v) to afford 4-(8-(1-acryloylpyrrolidin-3-yl)-4-aminoquinazolin-5-yl)-N-(pyridin-2-yl)benzamide as a yellow solid (6.9 mg, 25%). LRMS (M+H$^+$) m/z calculated 465.2, found 465.2. $^1$H NMR (DMSO-d6, 400 MHz) δ 10.91 (s, 1H), 8.52 (s, 1H), 8.41 (d, 1H), 8.18 (m, 4H), 7.59-7.91 (m, 3H), 7.58 (d, 2H), 7.28 (m, 1H), 7.19 (m, 1H), 6.64 (m, 1H), 6.19 (m, 1H), 5.67 (m, 1H), 4.40 (m, 1H), 4.17 (m, 0.5H), 4.07 (m, 0.5H), 3.72 (m, 3H), 2.30 (m, 1H), 2.17 (m, 1H).

399

Example 66: Preparation of 4-(5-(1-acryloylpyrroli-din-3-yl)pyrrolo[1,2-c]pyrimidin-7-yl)-N-phenylbenzamide

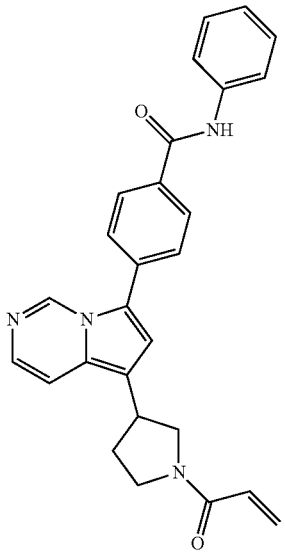

4-(5-(1-acryloylpyrrolidin-3-yl)pyrrolo[1,2-c]pyrimidin-7-yl)-N-phenylbenzamide

To a solution of 1H-pyrrole-2-carbaldehyde (9.51 g, 100.0 mmol, 1.0 eq) in DCM (150.0 mL) was added DBU (15.2 g, 100.0 mmol, 1.0 eq), followed by ethyl 2-isocyanoacetate (11.3 g, 100.0 mmol, 1.0 eq). The resulting mixture was heated to refluxed for 3 h, then 10% AcOH (250 mL), and separated, the organic phase was washed with water (100 mL×2), dried over anhydrous MgSO₄, filtrated and concentrated. The residue was purified by column chromatography (PE/EA=4/1, v/v) to afford ethyl pyrrolo[1,2-c]pyrimidine-3-carboxylate as a yellow solid (18.5 g, 97.3%).

400

-continued

To a solution of ethyl pyrrolo[1,2-c]pyrimidine-3-carboxylate (18.5 g, 97.0 mmol, 1.0 eq) in methanol (100 mL) was added aq. 2N NaOH (100 mL, 200.0 mmol, 2.06 eq), the resulting mixture was stirred at rt for overnight. Then the organic solvent was evaporated and the water phase was acidified by 4N HCl until PH=4, then a lot of solid was produced, and filtrated, washed with water, dried to provide pyrrolo[1,2-c]pyrimidine-3-carboxylic acid as brown solid (15.6 g, yield: 98.9%).

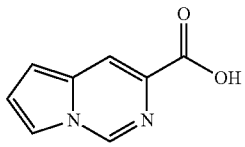

A mixture of pyrrolo[1,2-c]pyrimidine-3-carboxylic acid (5.0 g, 30.8 mmol, 1.0 eq) and oxydibenzene (50 mL) was heated to 260° C. for 8 h, then petrol was added, and filtrated, the filtrate was purified by column chromatography (PE/EA=4/1, v/v) to provide pyrrolo[1,2-c]pyrimidine (610 mg, yield: 16.7%).

To a solution of pyrrolo[1,2-c]pyrimidine (300 mg, 2.54 mmol, 1.0 eq) in DCM (15 mL) was added NBS (950 mg, 5.33 mmol, 2.1 eq), and after stirred at rt for 2 h, the resulting mixture was concentrated and purified by column chromatography (PE/EA=10/1, v/v) to provide 5,7-dibromopyrrolo[1,2-c]pyrimidine (452 mg, yield: 64.4%).

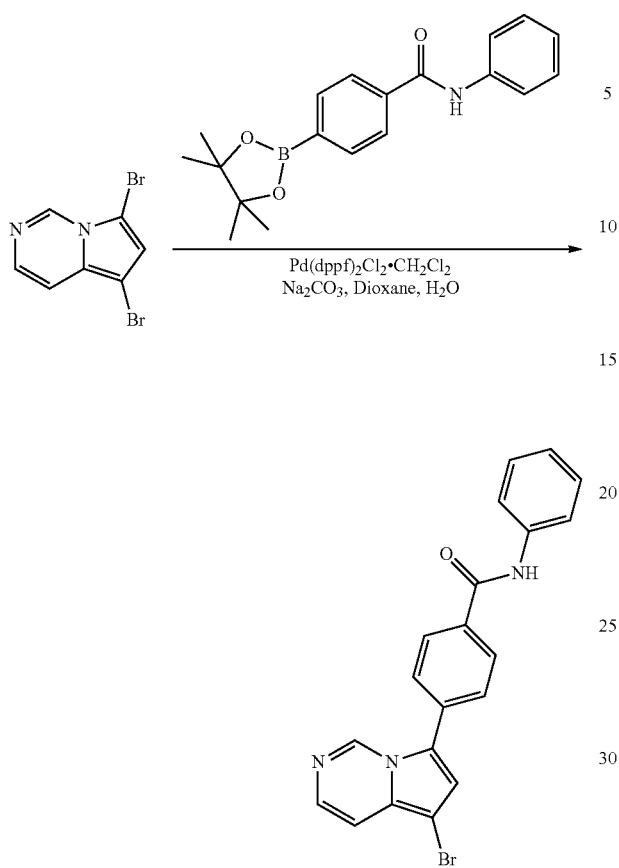

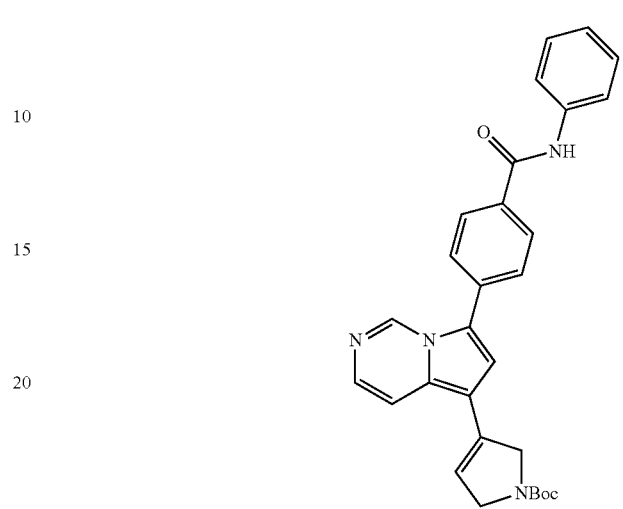

To a solution of 5,7-dibromopyrrolo[1,2-c]pyrimidine (617 mg, 2.23 mmol, 1.0 eq) and N-phenyl-4-(4,4,5,5-tetramethyl-1,3,2-dioxaborolan-2-yl)benzamide (650.0 mg, 2.01 mmol, 0.9 eq) in dioxane/water (30 mL/3 mL) was added Na$_2$CO$_3$ (473 mg, 4.46 mmol, 2.0 eq), followed by Pd(dppf)Cl$_2$·CH$_2$Cl$_2$ (91 mg, 0.11 mmol, 0.05 eq) under N$_2$. The mixture was stirred at 90° C. for 12 h, then cooled to rt, diluted with EA (40 mL) and filtered. The filtrate was concentrated and the resulting residue was purified by column chromatography (DCM/MeOH=25/1, v/v) to afford 4-(5-bromopyrrolo[1,2-c]pyrimidin-7-yl)-N-phenylbenzamide as a yellow solid (201 mg, 23.1%).

To a solution of 4-(5-bromopyrrolo[1,2-c]pyrimidin-7-yl)-N-phenylbenzamide (170 mg, 0.44 mmol, 1.0 eq) and tert-butyl 3-(4,4,5,5-tetramethyl-1,3,2-dioxaborolan-2-yl)-2,5-dihydro-1H-pyrrole-1-carboxylate (154 mg, 0.52 mmol, 1.2 eq) in dioxane/water (20 mL/2 mL) was added Na$_2$CO$_3$ (93 mg, 0.88 mmol, 2.0 eq), followed by Pd(dppf)Cl$_2$·CH$_2$Cl$_2$ (18 mg, 0.022 mmol, 0.05 eq) under N$_2$. The mixture was stirred at 90° C. for 12 h, then cooled to rt, diluted with EA (20 mL) and filtered. The filtrate was concentrated and the resulting residue was purified on flash chromatography (PE/EA=1/1, v/v) to afford tert-butyl 3-(7-(4-(phenylcarbamoyl)phenyl)pyrrolo[1,2-c]pyrimidin-5-yl)-2,5-dihydro-1H-pyrrole-1-carboxylate as a yellow solid (120 mg, 49%).

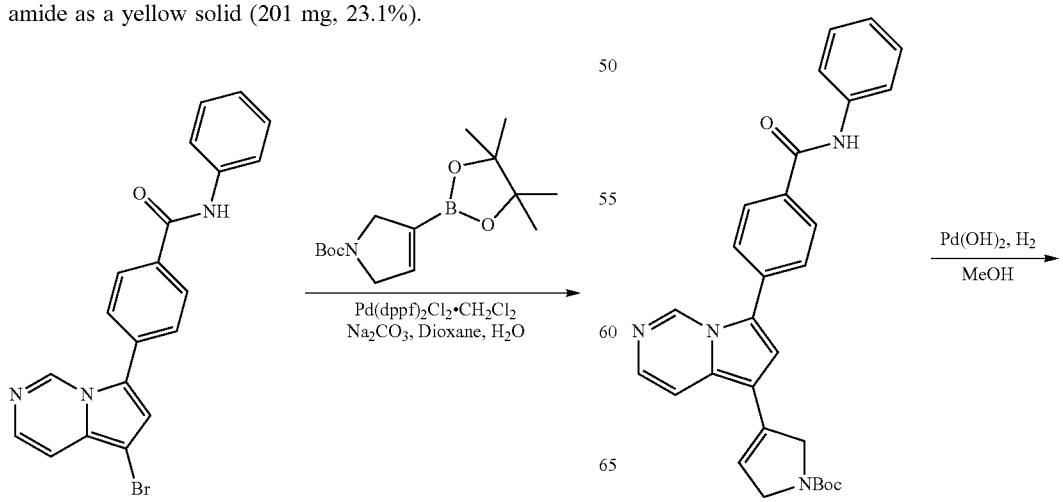

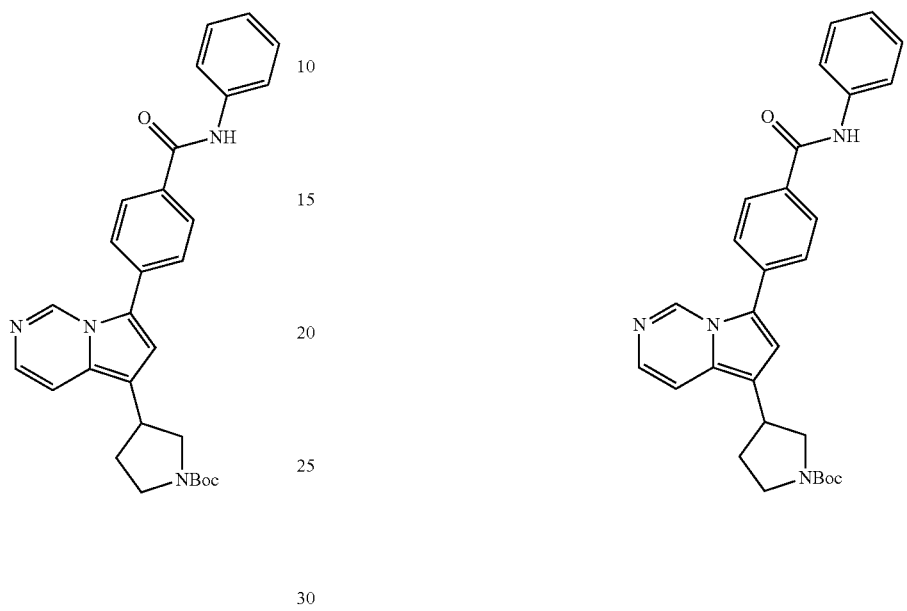

To a solution of tert-butyl 3-(7-(4-(phenylcarbamoyl)phenyl)pyrrolo[1,2-c]pyrimidin-5-yl)-2,5-dihydro-1H-pyrrole-1-carboxylate (120 mg, 0.25 mmol, 1.0 eq) in methanol (20 mL) was added Pd(OH)$_2$ (175 mg, 0.25 mmol, 1.0 eq, 20%), and the mixture was degassed with hydrogen. After stirred at rt for 3 h, the mixture was filtrated and concentrated, purified on prepare-TLC (PE/EA=1/2, v/v) to afford tert-butyl 3-(7-(4-(phenylcarbamoyl)phenyl)pyrrolo[1,2-c]pyrimidin-5-yl)pyrrolidine-1-carboxylate as a yellow solid (16.5 mg, 14%).

To a solution of tert-butyl 3-(7-(4-(phenylcarbamoyl)phenyl)pyrrolo[1,2-c]pyrimidin-5-yl)-2,5-dihydro-1H-pyrrole-1-carboxylate (120 mg, 0.25 mmol, 1.0 eq) in methanol (20 mL) was added Pd(OH)$_2$ (175 mg, 0.25 mmol, 1.0 eq, 20%), and the mixture was degassed with hydrogen. After stirred at rt for 3 h, the mixture was filtrated and concentrated, purified on prepare-TLC (PE/EA=1/2, v/v) to afford tert-butyl 3-(7-(4-(phenylcarbamoyl)phenyl)pyrrolo[1,2-c]pyrimidin-5-yl)pyrrolidine-1-carboxylate as a yellow solid (16.5 mg, 14%).

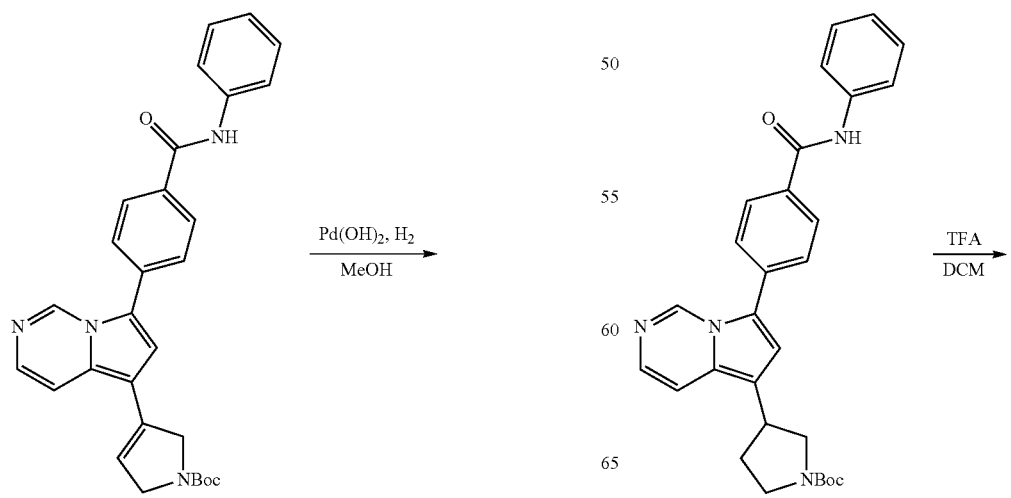

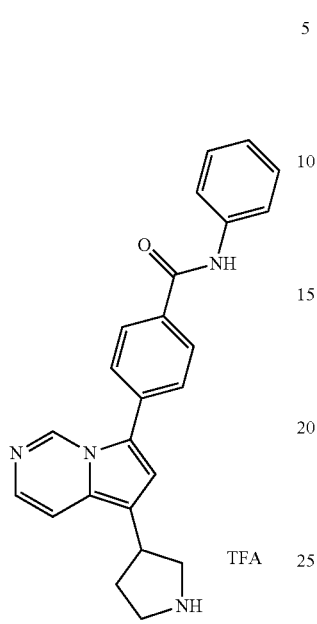

To a solution of tert-butyl 3-(7-(4-(phenylcarbamoyl)phenyl)pyrrolo[1,2-c]pyrimidin-5-yl)pyrrolidine-1-carboxylate (16.5 mg, 0.035 mmol, 1.0 eq) in DCM (1 mL) was added TFA (0.5 mL), and the mixture was stirred at rt for 2 h, then concentrated to provide the crude N-phenyl-4-(5-(pyrrolidin-3-yl)pyrrolo[1,2-c]pyrimidin-7-yl)benzamide as a TFA salt which was used to the next step without further purification.

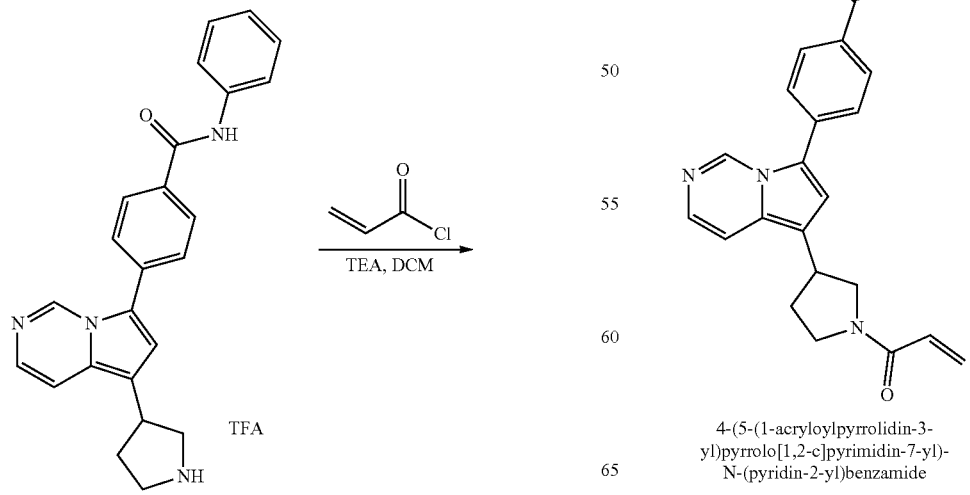

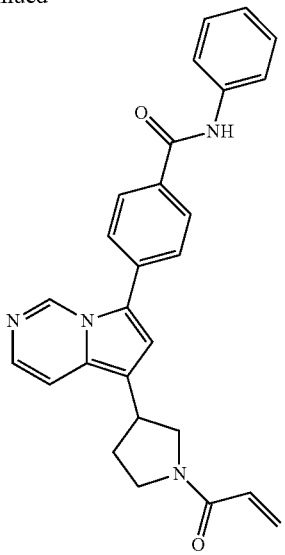

To a solution of the crude N-phenyl-4-(5-(pyrrolidin-3-yl)pyrrolo[1,2-c]pyrimidin-7-yl)benzamide TFA salt (17.3 mg, 0.035 mmol, 1.0 eq) in DCM (10 mL) was added TEA (11 mg, 0.11 mmol, 3.0 eq), followed by acryloyl chloride (2.8 mg, 0.032 mmol, 0.9 eq). The resulting mixture was stirred at rt for 1 h, then washed with brine, dried over anhydrous Na$_2$SO$_4$, concentrated and purified on flash chromatography (PE/EA=4/1, v/v) to afford 4-(5-(1-acryloylpyrrolidin-3-yl)pyrrolo[1,2-c]pyrimidin-7-yl)-N-phenylbenzamide as a yellow solid (8.1 mg, 53.1%). LRMS (M+H$^+$) m/z calculated 437.2, found 437.3. $^1$H NMR (DMSO-d6, 400 MHz) δ 9.32 (s, 1H), 8.18 (d, 1H), 8.12 (d, 2H), 7.71-7.75 (m, 2H), 7.52-7.63 (m, 2H), 7.33-7.41 (m, 4H), 7.16-7.22 (m, 1H), 7.06 (s, 1H), 6.43-6.50 (m, 2H), 5.73-5.76 (m, 1H), 4.05-4.14 (m, 1H), 3.83-3.94 (m, 1H), 3.62-3.79 (m, 2H), 2.37-2.50 (m, 1H), 2.08-2.22 (m, 2H).

Example 67: Preparation of 4-(5-(1-acryloylpyrrolidin-3-yl)pyrrolo[1,2-c]pyrimidin-7-yl)-N-(pyridin-2-yl)benzamide 4-(5-(1-acryloylpyrrolidin-3-yl)pyrrolo[1,2-c]pyrimidin-7-yl)-N-(pyridin-2-yl)benzamide 4-(5-(1-Acryloylpyrrolidin-3-yl)pyrrolo[1,2-c]pyrimidin-7-yl)-N-(pyridin-2-yl)benzamide (8.1 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 438.2, found 438.3. $^1$H NMR (DMSO-d6, 400 MHz) δ 10.85 (s, 1H), 9.23 (s, 1H), 8.41 (d, 1H), 8.16-8.23 (m, 3H), 7.81-7.88 (m, 3H), 7.59-7.64 (m, 1H), 7.45 (d, 1H), 7.26 (d, 1H), 7.16-7.20 (m, 1H), 6.60-6.66 (m, 1H), 6.14-6.20 (m, 1H), 5.65-5.72 (m, 1H), 3.86-4.09 (m, 1H), 3.64-3.80 (m, 2H), 3.37-3.58 (m, 2H), 2.07-2.43 (m, 2H).

Example 68: Preparation of 4-(5-(1-acryloylpyrrolidin-3-yl)pyrrolo[1,2-c]pyrimidin-7-yl)-N-(3-(trifluoromethyl)phenyl)benzamide

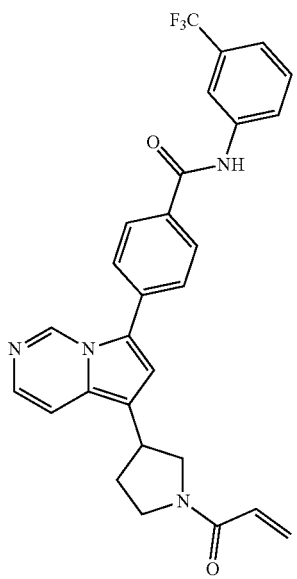

4-(5-(1-acryloylpyrrolidin-3-yl)pyrrolo[1,2-c]pyrimidin-7-yl)-
N-(3-(trifluoromethyl)phenyl)benzamide 4-(5-(1-Acryloylpyrrolidin-3-yl)pyrrolo[1,2-c]pyrimidin-7-yl)-N-(3-(trifluoromethyl)phenyl)benzamide (11.4 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 505.2, found 505.3. $^1$H NMR (DMSO-d6, 400 MHz) δ 10.61 (s, 1H), 9.24 (s, 1H), 8.29 (s, 1H), 8.09-8.14 (m, 3H), 7.86-7.89 (m, 2H), 7.60-7.64 (m, 2H), 7.44-7.48 (m, 2H), 7.26 (d, 1H), 7.26 (d, 1H), 6.60-6.69 (m, 1H), 6.15-6.19 (m, 1H), 5.65-5.71 (m, 1H), 3.93-4.11 (m, 1H), 3.71-3.89 (m, 3H), 3.62-3.69 (m, 1H), 2.27-2.44 (m, 1H), 2.01-2.18 (m, 1H).

Example 69: Preparation of 4-(5-(1-acryloylpyrrolidin-3-yl)pyrrolo[1,2-c]pyrimidin-7-yl)-N-(4-fluoropyridin-2-yl)benzamide

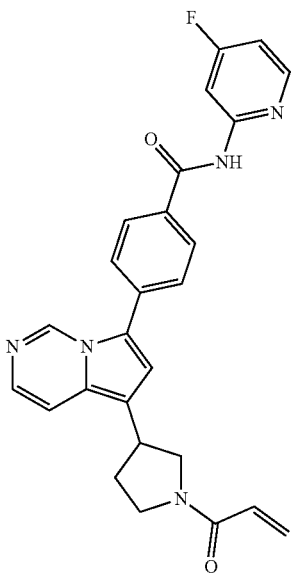

4-(5-(1-acryloylpyrrolidin-3-yl)pyrrolo[1,2-c]pyrimidin-7-yl)-
N-(4-fluoropyridin-2-yl)benzamide 4-(5-(1-Acryloylpyrrolidin-3-yl)pyrrolo[1,2-c]pyrimidin-7-yl)-N-(4-fluoropyridin-2-yl)benzamide (9.4 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 456.2, found 456.3. $^1$H NMR (DMSO-d6, 400 MHz) δ 11.18 (s, 1H), 9.24 (s, 1H), 8.43-8.47 (m, 1H), 8.17 (d, 2H), 8.08 (dd, 1H), 7.83-7.86 (m, 2H), 7.59-7.64 (m, 1H), 7.45 (d, 1H), 7.26 (d, 1H), 7.12-7.16 (m, 1H), 6.62-6.66 (m, 1H), 6.14-6.20 (m, 1H), 5.65-5.71 (m, 1H), 3.95-4.08 (m, 1H), 3.41-3.86 (m, 4H), 1.96-2.38 (m, 2H).

Example 70: Preparation of 4-(5-(1-acryloylpyrrolidin-3-yl)pyrrolo[1,2-c]pyrimidin-7-yl)-N-(4-chloropyridin-2-yl)benzamide

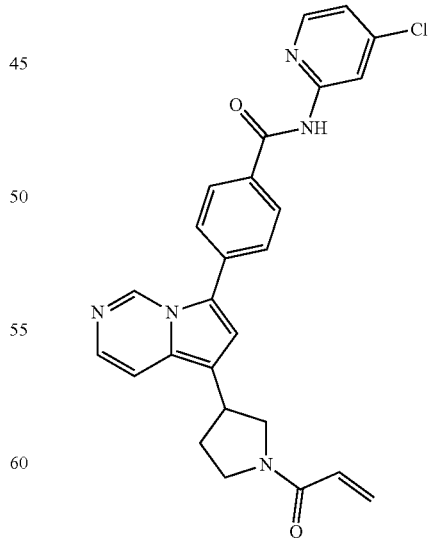

4-(5-(1-acryloylpyrrolidin-3-yl)pyrrolo[1,2-c]pyrimidin-7-yl)-
N-(4-chloropyridin-2-yl)benzamide 4-(5-(1-Acryloylpyrrolidin-3-yl)pyrrolo[1,2-c]pyrimidin-7-yl)-N-(4-chloropyridin-2-yl)benzamide (13 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 471.2, found 472.2. $^1$H NMR (DMSO-d6, 400 MHz) δ 11.14 (s, 1H), 9.23 (s, 1H), 8.40 (d, 1H), 8.34 (s, 1H), 8.17 (d, 2H), 7.82-7.85 (m, 2H), 7.58-7.64 (m, 1H), 7.45 (d, 1H), 7.32-7.34 (m, 1H), 7.25-7.27 (m, 1H), 6.62-6.66 (m, 1H), 6.14-6.19 (m, 1H), 6.64-6.71 (m, 1H), 4.08 (t, 1H), 3.94 (t, 1H), 3.68-3.88 (m, 3H), 2.03-2.33 (m, 2H).

Example 71: Preparation of 4-(5-(3-acrylamidophenyl)pyrrolo[1,2-c]pyrimidin-7-yl)-N-(pyridin-2-yl)benzamide

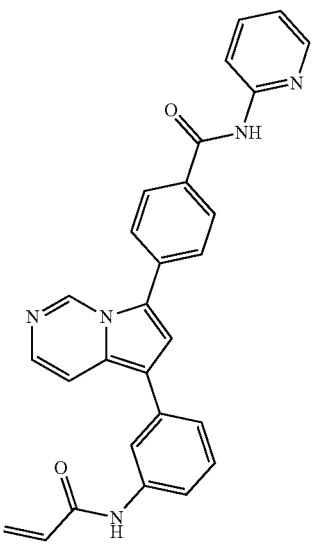

4-(5-(3-acrylamidophenyl)pyrrolo[1,2-c]pyrimidin-7-yl)-N-(pyridin-2-yl)benzamide 4-(5-(3-Acrylamidophenyl)pyrrolo[1,2-c]pyrimidin-7-yl)-N-(pyridin-2-yl)benzamide (7.0 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 460.2, found 460.2. $^1$H NMR (DMSO-d6, 400 MHz) δ 9.17 (s, 1H), 8.82 (s, 1H), 8.43 (d, 1H), 8.33 (d, 1H), 8.08-8.10 (m, 3H), 7.68-7.82 (m, 4H), 7.56 (d, 1H), 7.31-7.48 (m, 4H), 7.23 (s, 1H), 7.11 (t, 1H), 6.49 (d, 1H), 6.27-6.34 (m, 1H), 5.81 (d, 1H).

Example 72: Preparation of 1-(3-(7-(4-phenoxyphenyl)pyrrolo[1,2-c]pyrimidin-5-yl)pyrrolidin-1-yl)prop-2-en-1-one

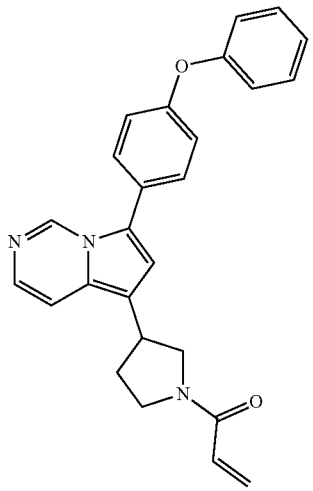

1-(3-(7-(4-phenoxyphenyl)pyrrolo[1,2-c]pyrimidin-5-yl)pyrrolidin-1-yl)prop-2-en-1-one 1-(3-(7-(4-Phenoxyphenyl)pyrrolo[1,2-c]pyrimidin-5-yl)pyrrolidin-1-yl)prop-2-en-1-one (95 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 410.2, found 410.3. $^1$H NMR (DMSO-d6, 400 MHz) δ 9.05 (s, 1H), 7.65-7.67 (m, 2H), 7.52-7.58 (m, 1H), 7.42-7.46 (m, 2H), 7.36-7.38 (m, 1H), 7.10-7.21 (m, 5H), 7.03 (d, 1H), 6.59-6.68 (m, 1H), 6.13-6.19 (m, 1H), 5.64-5.71 (m, 1H), 4.06 (t, 1H), 3.93 (t, 1H), 3.63-3.84 (m, 2H), 3.41-3.55 (m, 1H), 2.04-2.34 (m, 2H).

Example 73: Preparation of N-(3-(7-(4-phenoxyphenyl)pyrrolo[1,2-c]pyrimidin-5-yl)phenyl)acrylamide

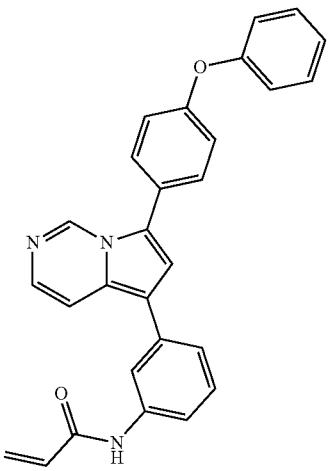

N-(3-(7-(4-phenoxyphenyl)pyrrolo[1,2-c]pyrimidin-5-yl)phenyl)acrylamide

N-(3-(7-(4-phenoxyphenyl)pyrrolo[1,2-c]pyrimidin-5-yl)phenyl)acrylamide (87 mg) was prepared as described for 4-(5-(1-acryloylpyrrolidin-3-yl)pyrrolo[1,2-c]pyrimidin-7-yl)-N-phenylbenzamide. LRMS (M+H⁺) m/z calculated 432.2, found 432.7. ¹H NMR (CD₃OD, 400 MHz) δ 9.06 (s, 1H), 8.06 (s, 1H), 7.71 (d, 1H), 7.62-7.64 (m, 2H), 7.38-7.46 (m, 6H), 7.13-7.20 (m, 4H), 7.08 (d, 1H), 6.40-6.46 (m, 2H), 5.58 (d, 1H).

Example 74: Preparation of N-(3-(2-amino-8-phenyl-9H-purin-9-yl)phenyl)acrylamide

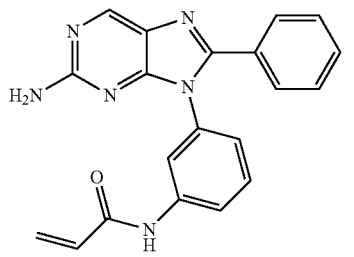

N-(3-(2-amino-8-phenyl-9H-purin-9-yl)phenyl)acrylamide

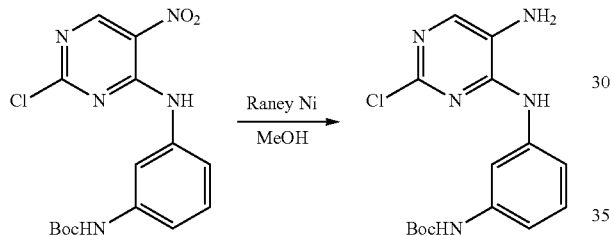

To a mixture of tert-butyl (3-((2-chloro-5-nitropyrimidin-4-yl)amino)phenyl)carbamate (500 mg, 1.37 mmol, 1.0 eq) in methanol (10.0 mL) was added Raney Ni (50 mg) and degassed with hydrogen for 3 times. The mixture was stirred at rt for overnight, then filtered and concentrated. The resulting residue was purified on flash chromatography (DCM/MeOH=30/1, v/v) to afford tert-butyl (3-((5-amino-2-chloropyrimidin-4-yl)amino)phenyl)carbamate (315 mg, 69%).

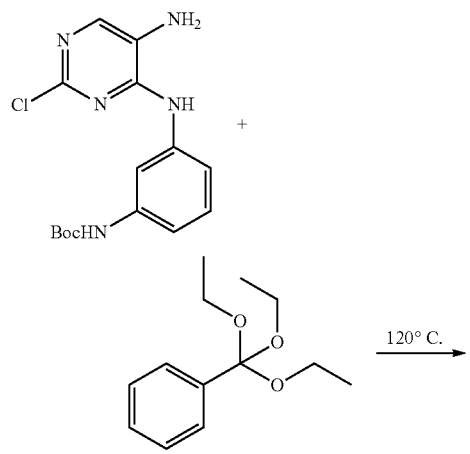

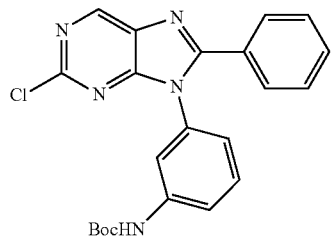

A mixture of tert-butyl (3-((5-amino-2-chloropyrimidin-4-yl)amino)phenyl)carbamate (2.0 g, 6.0 mmol, 1.0 eq) and (triethoxymethyl)benzene (15 mL) was stirred at 120° C. overnight, then cooled to rt and purified on flash chromatography (PE/EA=1/1, v/v) to afford tert-butyl (3-(2-chloro-8-phenyl-9H-purin-9-yl)phenyl)carbamate as a brown solid (1.59 g, 63%).

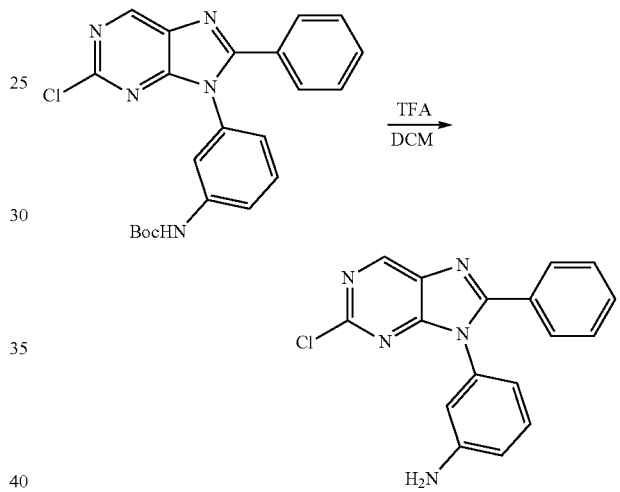

To a solution of tert-butyl (3-(2-chloro-8-phenyl-9H-purin-9-yl)phenyl)carbamate (400 mg, 0.95 mmol, 1.0 eq) in DCM (6 mL) was added TFA (3 mL) and stirred at rt for 1 h, then concentrated. The residue was basified with Sat. NaHCO₃, extracted it with EA (30 mL×2), and the organic phase was washed with brine (60 mL×2), dried with Na₂SO₄, filtered and concentrated to afford 3-(2-chloro-8-phenyl-9H-purin-9-yl)aniline as a brown solid (305 mg, 100%).

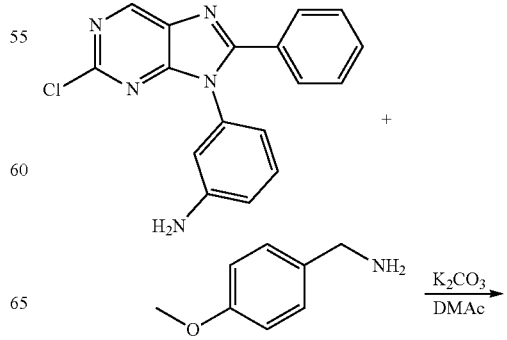

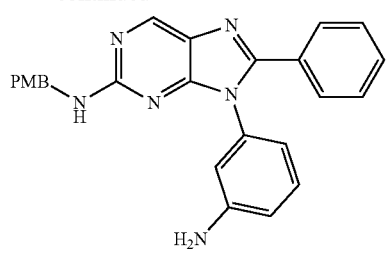

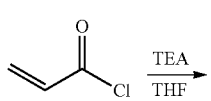

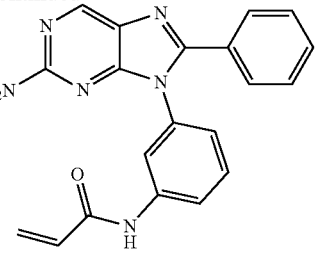

To a solution of 3-(2-chloro-8-phenyl-9H-purin-9-yl)aniline (305 mg, 0.95 mmol, 1.0 eq) and (4-methoxyphenyl)methanamine (389 mg, 2.84 mmol, 3.0 eq) in DMAc (8.0 mL) was added K₂CO₃ (654 mg, 4.74 mmol, 5.0 eq). The mixture was stirred at 120° C. overnight, then diluted with EA (80.0 mL), washed with brine, dried over anhydrous Na₂SO₄ and concentrated. The resulting residue was purified on flash chromatography (PE/EA=1/2, v/v) to afford 9-(3-aminophenyl)-N-(4-methoxybenzyl)-8-phenyl-9H-purin-2-amine as a yellow solid (400 mg, 100%).

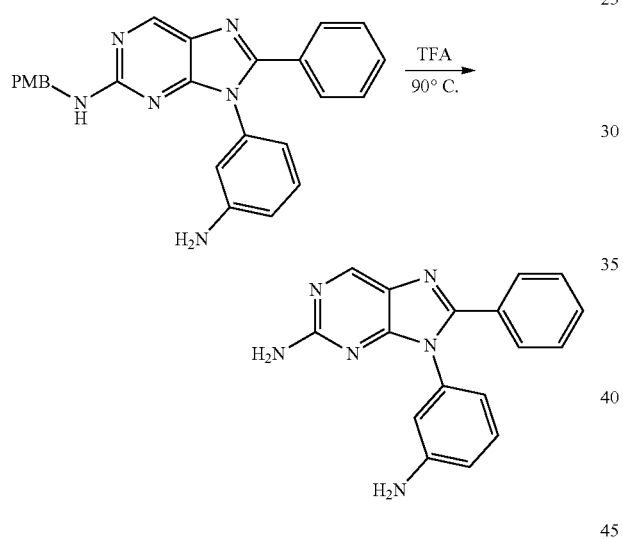

A mixture of 9-(3-aminophenyl)-N-(4-methoxybenzyl)-8-phenyl-9H-purin-2-amine (400 mg, 0.95 mmol, 1.0 eq) in TFA (5.0 mL) was stirred at 90° C. overnight, then concentrated and the residue was diluted with a mixture of EA (15.0 mL) and sat. Na₂CO₃ (5.0 mL). The organic phase was separated and dried with anhydrous Na₂SO₄, concentrated to provide 9-(3-aminophenyl)-8-phenyl-9H-purin-2-amine as a brown solid (280 mg, 95%).

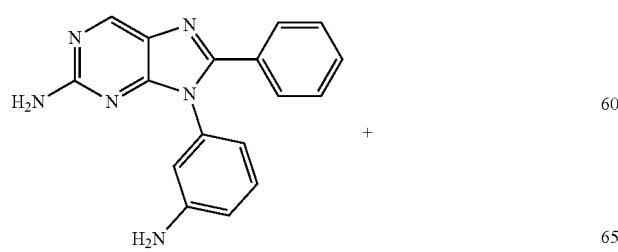

+

To a solution of the crude 9-(3-aminophenyl)-8-phenyl-9H-purin-2-amine (143 mg, 0.47 mmol, 1.0 eq) in THF (8 mL) was added TEA (0.3 mL, 2.37 mmol, 5.0 eq), followed by acryloyl chloride (21 mg, 0.24 mmol, 0.5 eq) at −78° C. The resulting mixture was stirred at that temperature for 4 h, then diluted with EA (50 mL) and washed with brine (25 mL×2), dried over anhydrous Na₂SO₄, concentrated and purified on flash chromatography (DCM/MeOH=40/1, v/v) to afford N-(3-(2-amino-8-phenyl-9H-purin-9-yl)phenyl)acrylamide as a white solid (23 mg, 13.6%). LRMS (M+H⁺) m/z calculated 357.1, found 357.5. ¹H NMR (DMSO-d6, 400 MHz) δ 10.38 (s, 1H), 8.72 (s, 1H), 7.79 (d, 1H), 7.73 (s, 1H), 7.44-7.51 (m, 3H), 7.35-7.38 (m, 3H), 7.06 (d, 1H), 6.64 (s, 2H), 6.38-6.45 (m, 1H), 6.25 (d, 1H), 5.78 (d, 1H).

Example 75: Preparation of 1-(3-(2-amino-8-(2-chlorophenyl)-9H-purin-9-yl)pyrrolidin-1-yl)prop-2-en-1-one

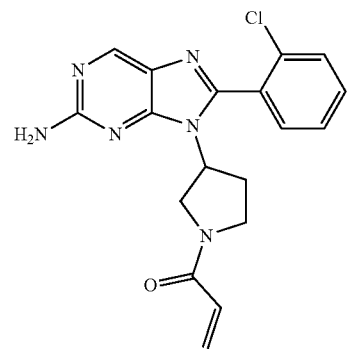

1-(3-(2-amino-8-(2-chlorophenyl)-9H-purin-9-yl)pyrrolidin-1-yl)prop-2-en-1-one

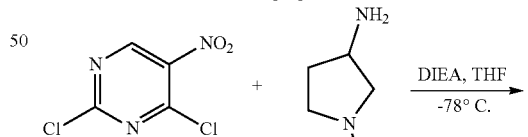

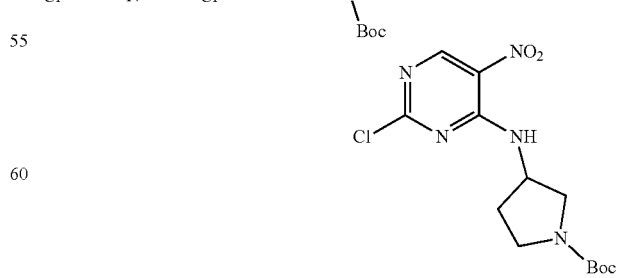

To a solution of 2,4-dichloro-5-nitropyrimidine (4.7 g, 24.0 mmol, 1.0 eq) and DIEA (8.0 mL, 48.0 mmol, 2.0 eq)

in THF (100.0 mL) at −78° C. was added tert-butyl 3-aminopyrrolidine-1-carboxylate (4.5 g, 24.0 mmol, 1.0 eq) dropwise. The mixture was stirred at −78° C. for 5 h, then concentrated. The resulting residue was purified by column chromatography (EA/PE=1/3, v/v) to afford tert-butyl 3-((2-chloro-5-nitropyrimidin-4-yl)amino)pyrrolidine-1-carboxylate as a yellow solid (7.2 g, 79%).

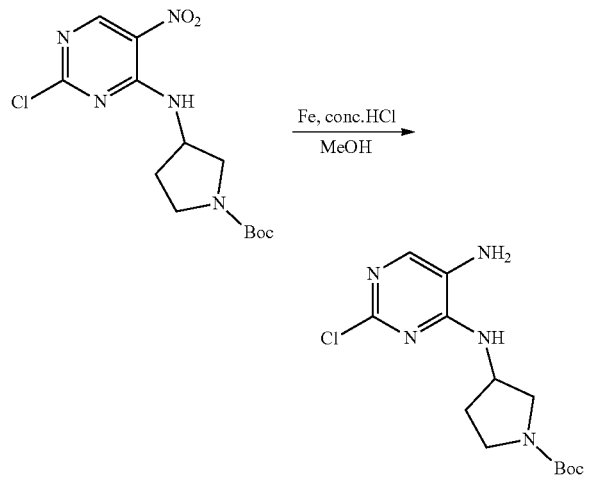

To a mixture of tert-butyl 3-((2-chloro-5-nitropyrimidin-4-yl)amino)pyrrolidine-1-carboxylate (860.0 mg, 2.5 mmol, 1.0 eq) in methanol (30.0 mL) was added HCl (0.2 mL, 1.1 eq) and Fe (840.0 mg, 15.0 mmol, 6.0 eq). The mixture was stirred at reflux for 12 h, then cooled to rt and concentrated. The resulting residue was purified by column chromatography (DCM/MeOH=30/1, v/v) to afford tert-butyl 3-((5-amino-2-chloropyrimidin-4-yl)amino)pyrrolidine-1-carboxylate (500 mg, 63.7%).

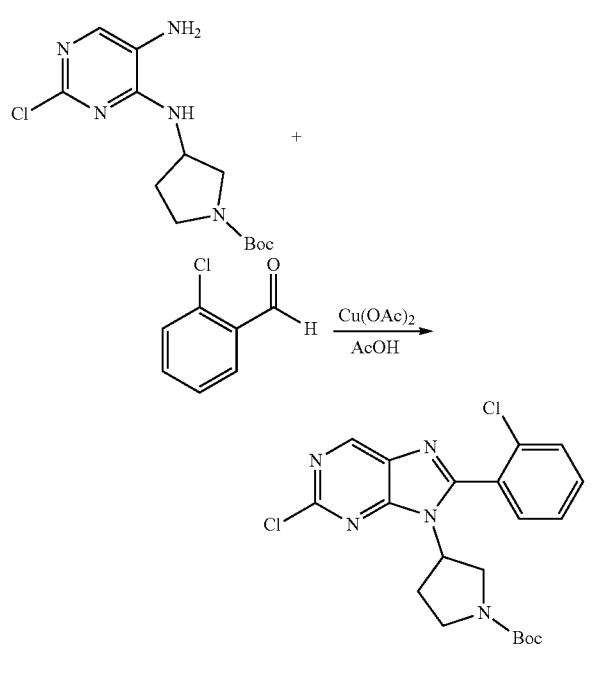

To a solution of tert-butyl 3-((5-amino-2-chloropyrimidin-4-yl)amino)pyrrolidine-1-carboxylate (500 mg, 1.6 mmol, 1.0 eq) in acetic acid (10 mL) was added 2-chlorobenzaldehyde (291 mg, 2.1 mmol, 1.3 eq) and Cu(OAc)$_2$ (146 mg, 0.8 mmol, 0.5 eq). The resulting reaction mixture was stirred at 100° C. overnight. Then the solvent was removed under reduced pressure. The resulting residues was dissolved in EA (50 mL), and washed with sat. NaHCO$_3$ (30 mL), followed by brine (30 mL), dried over Na$_2$SO$_4$, filtered and concentrated, purified by column chromatography (DCM/MeOH=40/1, v/v) to afford tert-butyl 3-(2-chloro-8-(2-chlorophenyl)-9H-purin-9-yl)pyrrolidine-1-carboxylate (150 mg, 22.7%).

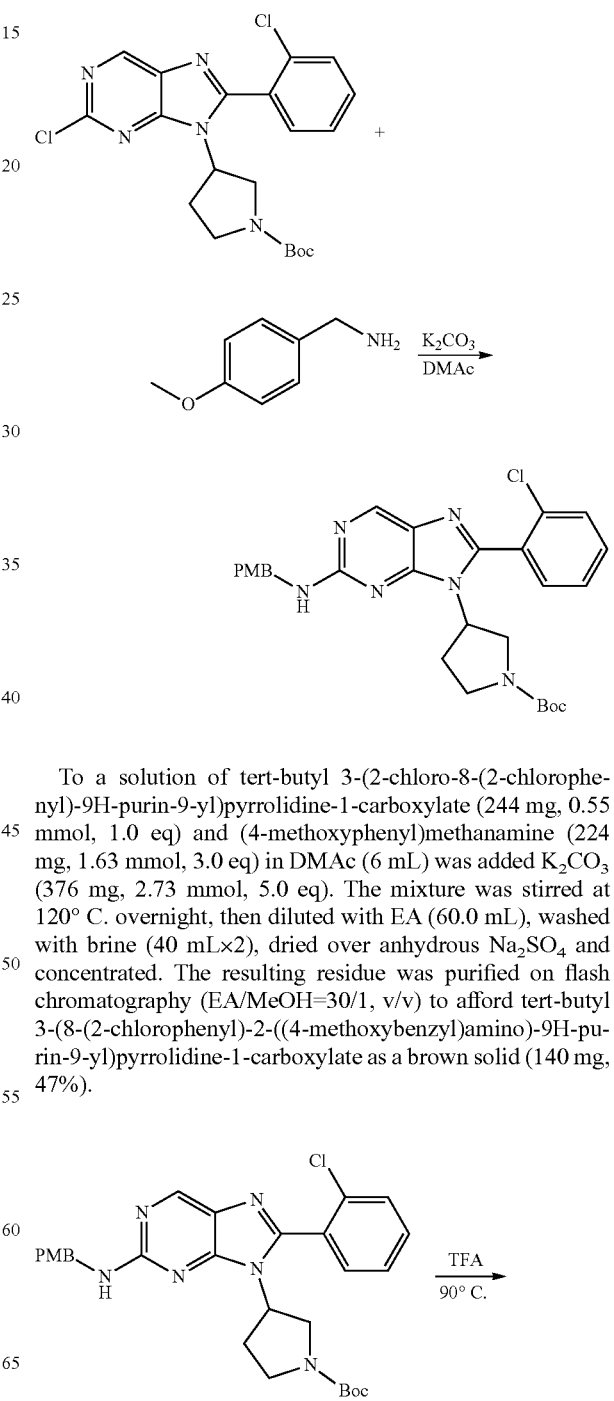

To a solution of tert-butyl 3-(2-chloro-8-(2-chlorophenyl)-9H-purin-9-yl)pyrrolidine-1-carboxylate (244 mg, 0.55 mmol, 1.0 eq) and (4-methoxyphenyl)methanamine (224 mg, 1.63 mmol, 3.0 eq) in DMAc (6 mL) was added K$_2$CO$_3$ (376 mg, 2.73 mmol, 5.0 eq). The mixture was stirred at 120° C. overnight, then diluted with EA (60.0 mL), washed with brine (40 mL×2), dried over anhydrous Na$_2$SO$_4$ and concentrated. The resulting residue was purified on flash chromatography (EA/MeOH=30/1, v/v) to afford tert-butyl 3-(8-(2-chlorophenyl)-2-((4-methoxybenzyl)amino)-9H-purin-9-yl)pyrrolidine-1-carboxylate as a brown solid (140 mg, 47%).

-continued

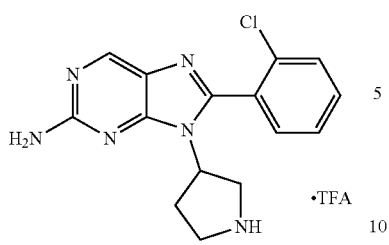

A mixture of tert-butyl 3-(8-(2-chlorophenyl)-2-((4-methoxybenzyl)amino)-9H-purin-9-yl)pyrrolidine-1-carboxylate (320 mg, 0.56 mmol, 1.0 eq) in TFA (8.0 mL) was stirred at 90° C. overnight, then concentrated to provide the crude 8-(2-chlorophenyl)-9-(pyrrolidin-3-yl)-9H-purin-2-amine as a brown TFA salt (178 mg, 99%).

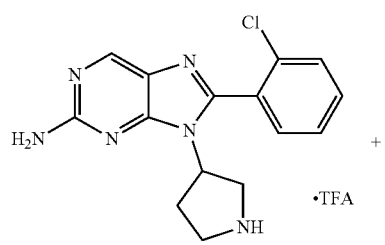

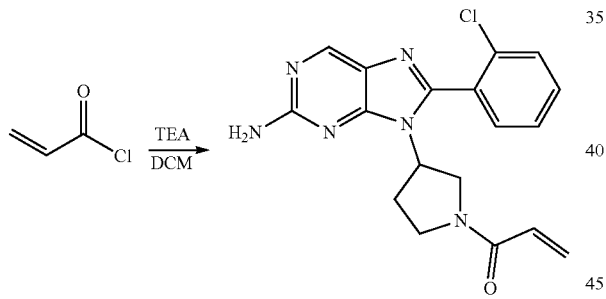

To a solution of the crude 8-(2-chlorophenyl)-9-(pyrrolidin-3-yl)-9H-purin-2-amine TFA salt (178 mg, 0.56 mmol, 1.0 eq) in DCM (13 mL) was added TEA (0.4 mL, 2.82 mmol, 5.0 eq), followed by acryloyl chloride (51 mg, 0.56 mmol, 1.0 eq) at −78° C. The resulting mixture was stirred at that temperature for 30 mins, then warmed to room temperature and diluted with DCM (10 mL) and washed with brine (20 mL×2), dried over anhydrous $Na_2SO_4$, concentrated and purified on flash chromatography (EA/MeOH=30/1, v/v), and crystallized from PE/EA (10/1, v/v) to afford 1-(3-(2-amino-8-(2-chlorophenyl)-9H-purin-9-yl)pyrrolidin-1-yl)prop-2-en-1-one as a white solid (35 mg, 17%). LRMS (M+H$^+$) m/z calculated 369.1, found 369.5. $^1$H NMR (DMSO-d6, 400 MHz) δ 8.66 (s, 1H), 7.62-7.70 (m, 3H), 7.52-7.56 (m, 1H), 6.64 (d, 2H), 6.54-6.58 (m, 1H), 6.14 (d, 1H), 5.64-5.70 (m, 1H), 4.51-4.61 (m, 1H), 3.88-4.01 (m, 3H), 3.61-3.75 (m, 1H), 2.85-3.04 (m, 1H), 2.16-2.33 (m, 1H).

Example 76: Preparation of 1-(3-(2-amino-8-phenyl-9H-purin-9-yl)pyrrolidin-1-yl)prop-2-en-1-one

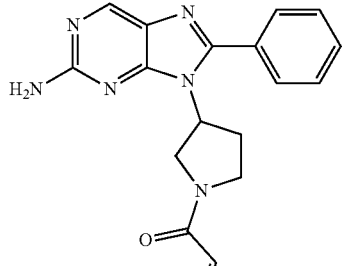

1-(3-(2-amino-8-phenyl-9H-purin-9-yl)pyrrolidin-1-yl)prop-2-en-1-one 1-(3-(2-Amino-8-phenyl-9H-purin-9-yl)pyrrolidin-1-yl)prop-2-en-1-one (75.5 mg) was prepared as described for 1-(3-(2-amino-8-(2-chlorophenyl)-9H-purin-9-yl)pyrrolidin-1-yl)prop-2-en-1-one. LRMS (M+H$^+$) m/z calculated 335.2, found 335.2. $^1$H NMR (DMSO-d6, 400 MHz) δ 8.62 (s, 1H), 7.71 (s, 2H), 7.54 (s, 2H), 6.55 (d, 3H), 6.15 (d, 3H), 5.69 (t, 1H), 4.93 (m, 1H), 4.28 (m, 1H), 4.10 (m, 1H), 3.94 (m, 1H), 3.78 (m, 1H), 3.02 (m, 1H), 2.24 (m, 1H).

Example 77: Preparation of 1-(3-(2-amino-8-phenyl-9H-purin-9-yl)pyrrolidin-1-yl)prop-2-en-1-one

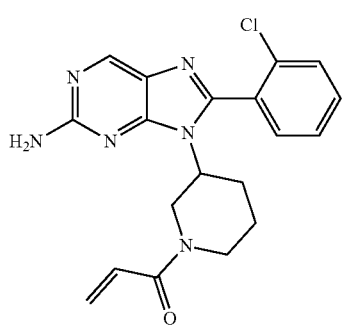

1-(3-(2-amino-8-(2-chlorophenyl)-9H-purin-9-yl)piperidin-1-yl)prop-2-en-1-one 1-(3-(2-Amino-8-(2-chlorophenyl)-9H-purin-9-yl)piperidin-1-yl)prop-2-en-1-one (35 mg) was prepared as described for 1-(3-(2-amino-8-(2-chlorophenyl)-9H-purin-9-yl)pyrrolidin-1-yl)prop-2-en-1-one. LRMS (M+H$^+$) m/z calculated 382.1, found 383.5. $^1$H NMR (DMSO-d6, 400 MHz) δ 8.66 (s, 1H), 7.60-7.67 (m, 3H), 7.53-7.55 (m, 1H), 6.61-6.81 (m, 3H), 5.98-6.08 (m, 1H), 5.64-5.67 (m, 1H), 4.40-4.45 (m, 1H), 4.22-4.25 (m, 1H), 4.04-4.06 (m, 1H), 3.56-3.69 (m, 2H), 2.89-2.93 (m, 1H), 1.96-2.00 (m, 1H), 1.81-1.84 (m, 1H), 1.23-1.32 (m, 1H).

Example 78: Preparation of 1-(3-(8-(2-fluorophenyl)-9H-purin-9-yl)pyrrolidin-1-yl)prop-2-en-1-one

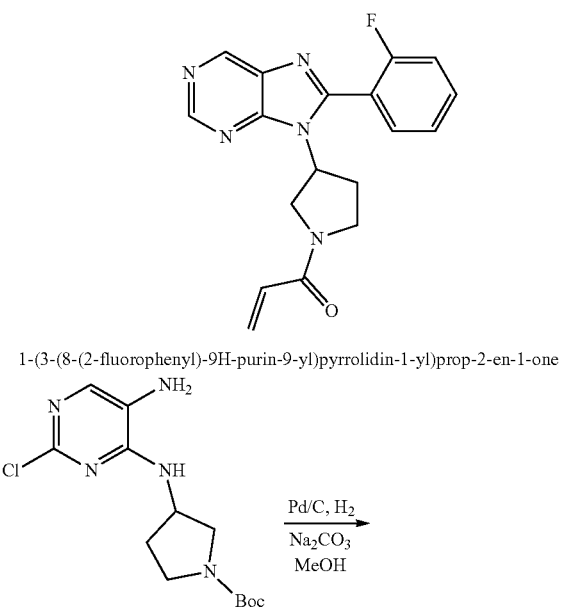

1-(3-(8-(2-fluorophenyl)-9H-purin-9-yl)pyrrolidin-1-yl)prop-2-en-1-one

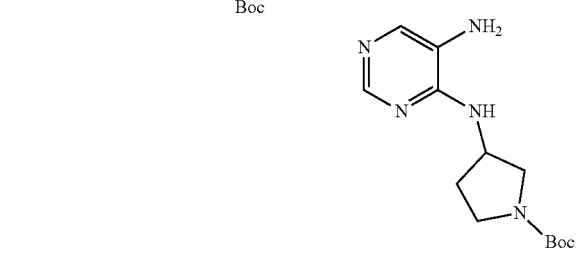

To a solution of tert-butyl 3-((5-amino-2-chloropyrimidin-4-yl)amino)pyrrolidine-1-carboxylate (2.4 g, 7.64 mmol, 1.0 eq) in methanol (60 mL) was added Na$_2$CO$_3$ (1.2 g, 11.5 mmol, 1.5 eq), followed by Pd/C (1.2 g), and the resulting mixture was degassed with hydrogen for 3 times. After stirred at 50° C. overnight, the reaction mixture was filtered and concentrated. The resulting residue was dissolved in EA (100 mL), and washed with water (100 mL×2), dried over anhydrous Na$_2$SO$_4$, filtered and concentrated to provide tert-butyl 3-((5-aminopyrimidin-4-yl)amino)pyrrolidine-1-carboxylate as a yellow solid (2.14 g, 100%).

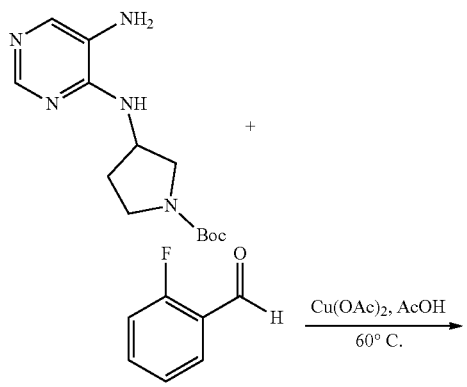

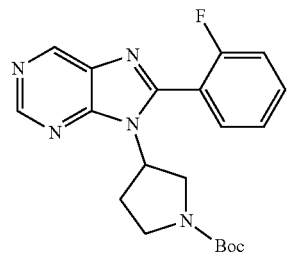

To a solution of tert-butyl 3-((5-aminopyrimidin-4-yl)amino)pyrrolidine-1-carboxylate (400 mg, 1.43 mmol, 1.0 eq) in acetic acid (20 mL) was added 2-chlorobenzaldehyde (230 mg, 1.86 mmol, 1.3 eq) and Cu(OAc)$_2$ (130 mg, 0.72 mmol, 0.5 eq). The resulting reaction mixture was stirred at 100° C. overnight. Then the solvent was removed under reduced pressure. The resulting residues was dissolved in EA (50 mL), and washed with sat. NaHCO$_3$ (30 mL), followed by brine (30 mL), dried over Na$_2$SO$_4$, filtered and concentrated, purified by column chromatography (EA, 100%) to afford tert-butyl 3-(8-(2-fluorophenyl)-9H-purin-9-yl)pyrrolidine-1-carboxylate (392 mg, 72%).

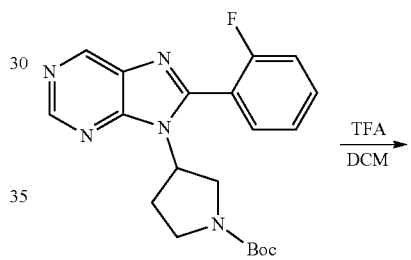

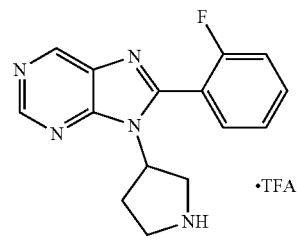

To a solution of tert-butyl 3-(8-(2-fluorophenyl)-9H-purin-9-yl)pyrrolidine-1-carboxylate (392 mg, 1.02 mmol, 1.0 eq) in DCM (2.5 L) was added TFA (2.5 mL). The resulting mixture was stirred at rt overnight. Then concentrated to provide the crude 8-(2-fluorophenyl)-9-(pyrrolidin-3-yl)-9H-purine as a brown TFA salt (279 mg, 100%).

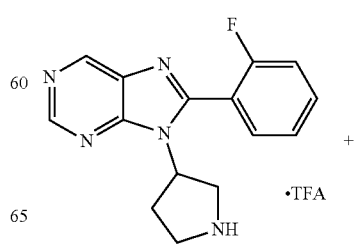

-continued

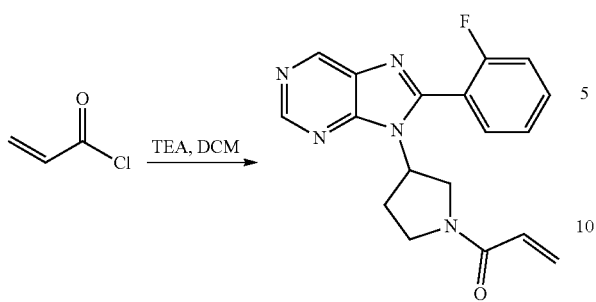

To a solution of the crude 8-(2-chlorophenyl)-9-(pyrrolidin-3-yl)-9H-purin-2-amine TFA salt (290 mg, 1.02 mmol, 1.0 eq) in DCM (20 mL) was added TEA (0.7 mL, 5.12 mmol, 5.0 eq), followed by acryloyl chloride (185 mg, 2.05 mmol, 2.0 eq) at −78° C. The resulting mixture was stirred at that temperature for 30 mins, then warmed to room temperature and diluted with DCM (30 mL) and washed with brine (30 mL×2), dried over anhydrous $Na_2SO_4$, concentrated and purified on flash chromatography (EA/MeOH=30/1, v/v) to afford 1-(3-(8-(2-fluorophenyl)-9H-purin-9-yl)pyrrolidin-1-yl)prop-2-en-1-one as a white solid (257 mg, 74%). LRMS (M+H$^+$) m/z calculated 338.1, found 338.4. $^1$H NMR (DMSO-d6, 400 MHz) δ 9.26 (s, 1H), 9.00 (d, 1H), 7.68-7.74 (m, 3H), 7.60-7.63 (m, 1H), 6.53-6.63 (m, 1H), 6.15 (d, 1H), 5.64-5.74 (m, 1H), 4.75-4.85 (m, 1H), 3.98-4.12 (m, 1H), 3.62-3.82 (m, 1H), 2.88-2.95 (m, 1H), 2.22-2.32 (m, 1H).

Example 79: Preparation of 1-(3-(8-(2-chlorophenyl)-9H-purin-9-yl)pyrrolidin-1-yl)prop-2-en-1-one

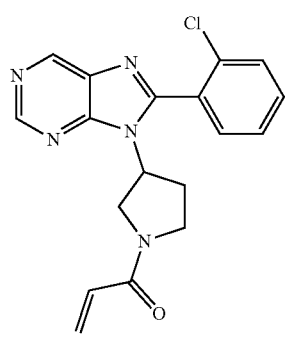

1-(3-(8-(2-chlorophenyl)-9H-purin-9-yl)pyrrolidin-1-yl)prop-2-en-1-one 1-(3-(2-Amino-8-(2-chlorophenyl)-9H-purin-9-yl)piperidin-1-yl)prop-2-en-1-one (81.7 mg) was prepared as described for 1-(3-(8-(2-fluorophenyl)-9H-purin-9-yl)pyrrolidin-1-yl)prop-2-en-1-one. LRMS (M+H$^+$) m/z calculated 354.1, found 354.4. $^1$H NMR (DMSO-d6, 400 MHz) δ 9.25 (d, 1H), 8.99 (d, 1H), 7.75-7.77 (m, 2H), 7.47-7.54 (m, 2H), 6.50-6.64 (m, 1H), 6.14-6.48 (m, 1H), 5.65-5.73 (m, 1H), 4.94-5.04 (m, 1H), 3.81-4.21 (m, 3H), 3.43-6.66 (m, 1H), 2.93-3.03 (m, 1H), 2.33-2.35 (m, 1H).

Example 80: Preparation of 1-(3-(8-phenyl-9H-purin-9-yl)pyrrolidin-1-yl)prop-2-en-1-one

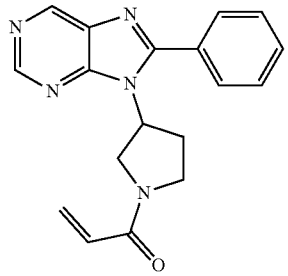

1-(3-(8-phenyl-9H-purin-9-yl)pyrrolidin-1-yl)prop-2-en-1-one 1-(3-(8-Phenyl-9H-purin-9-yl)pyrrolidin-1-yl)prop-2-en-1-one (97.9 mg) was prepared as described for 1-(3-(8-(2-fluorophenyl)-9H-purin-9-yl)pyrrolidin-1-yl)prop-2-en-1-one. LRMS (M+H$^+$) m/z calculated 320.1, found 320.5. $^1$H NMR (DMSO-d6, 400 MHz) δ 9.21 (d, 1H), 8.95 (d, 1H), 7.81 (s, 2H), 7.65 (s, 3H), 6.50-6.68 (m, 1H), 6.17 (d, 1H), 5.66-5.76 (m, 1H), 5.13-5.25 (m, 1H), 4.32-4.37 (m, 0.5H), 4.12-4.22 (m, 1H), 3.97-4.04 (m, 1H), 3.82-3.88 (m, 0.5H), 3.62-3.68 (m, 0.5H), 3.39-3.46 (m, 0.5H), 2.94-3.10 (m, 1H), 2.33-2.41 (m, 1H).

Example 81: Preparation of 1-(3-(8-phenyl-9H-purin-9-yl)piperidin-1-yl)prop-2-en-1-one

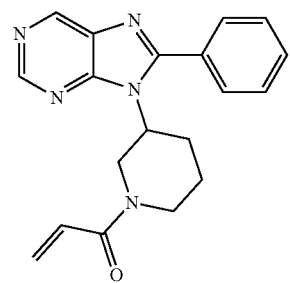

1-(3-(8-phenyl-9H-purin-9-yl)piperidin-1-yl)prop-2-en-1-one 1-(3-(8-Phenyl-9H-purin-9-yl)piperidin-1-yl)prop-2-en-1-one (98.6 mg) was prepared as described for 1-(3-(8-(2-fluorophenyl)-9H-purin-9-yl)pyrrolidin-1-yl)prop-2-en-1-one. LRMS (M+H$^+$) m/z calculated 334.2, found 334.5. $^1$H NMR (DMSO-d6, 400 MHz) δ 9.22 (s, 1H), 8.96 (s, 1H), 7.63-7.79 (m, 5H), 6.79-6.83 (m, 1H), 6.12 (t, 1H), 5.69 (d, 1H), 4.69-4.71 (m, 0.5H), 4.47-4.53 (m, 1H), 4.14-4.29 (m, 2H), 3.73-3.75 (m, 0.5H), 3.13-3.14 (m, 1H), 2.86-2.93 (m, 1H), 2.66-2.69 (m, 0.5H), 2.05-2.15 (m, 1H), 1.81-1.90 (m, 1H).

Example 82: Preparation of N-(3-(8-phenyl-9H-purin-9-yl)phenyl)acrylamide

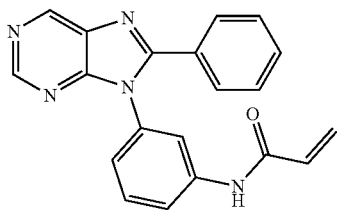

N-(3-(8-phenyl-9H-purin-9-yl)acrylamide

N-(3-(8-phenyl-9H-purin-9-yl)phenyl)acrylamide (43.6 mg) was prepared as described for 1-(3-(8-(2-fluorophenyl)-9H-purin-9-yl)pyrrolidin-1-yl)prop-2-en-1-one. LRMS (M+H⁺) m/z calculated 342.1, found 342.2.1H NMR (DMSO-d6, 400 MHz) δ 10.44 (s, 1H), 9.30 (s, 1H), 8.92 (s, 1H), 7.88 (s, 1H), 7.81 (d, 1H), 7.62 (d, 2H), 7.42-7.52 (m, 4H), 7.12 (d, 1H), 6.42-6.46 (m, 1H), 6.23-6.27 (m, 1H), 5.78 (d, 1H).

Example 83: Preparation of 1-(3-(2-amino-6-phenylquinazolin-8-yl)pyrrolidin-1-yl)prop-2-en-1-one

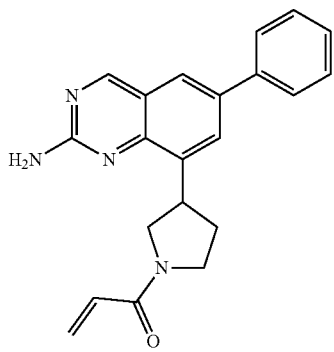

1-(3-(2-amino-6-phenylquinazolin-8-yl)pyrrolidin-1-yl)prop-2-en-1-one 1-(3-(2-amino-6-phenylquinazolin-8-yl)pyrrolidin-1-yl)prop-2-en-1-one (9.7 mg) was prepared as described for 1-(3-(6-phenylquinazolin-8-yl)pyrrolidin-1-yl)prop-2-en-1-one. LRMS (M+H⁺) m/z calculated 345.2, found 345.2. ¹H NMR (DMSO-d₆, 400 MHz) δ 9.18 (s, 1H), 8.01 (s, 1H), 7.94 (d, 1 H), 7.77 (t, 2H), 7.49 (t, 2H), 7.38 (t, 1H), 6.95 (d, 2H), 6.61-6.71 (m, 1H), 6.17 (d, 1H), 5.65-5.72 (m, 1H), 4.06-4.36 (m, 2H), 3.40-3.87 (m, 3H), 2.25-2.44 (m, 2H).

Example 84: Preparation of 1-(3-(6-(2-fluorophenyl)quinazolin-8-yl)pyrrolidin-1-yl)prop-2-en-1-one

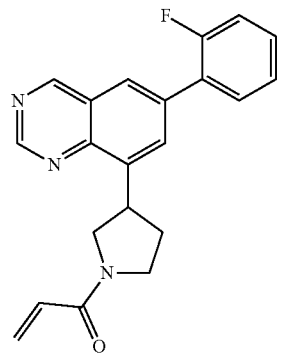

1-(3-(6-(2-fluorophenyl)quinazolin-8-yl)pyrrolidin-1-yl)prop-2-en-1-one 1-(3-(6-(2-fluorophenyl)quinazolin-8-yl)pyrrolidin-1-yl)prop-2-en-1-one (38.5 mg) was prepared as described for N-(3-(6-(pyridin-4-yl)quinazolin-8-yl)phenyl)acrylamide. LRMS (M+H⁺) m/z calculated 348.1, found 348.2. ¹H NMR (CDCl₃, 400 MHz) δ 9.46 (s, 1H), 9.37 (s, 1H), 8.01 (s, 2H), 7.51-7.46 (m, 1H), 7.40-7.46 (m, 1H), 7.29-7.32 (m, 1H), 7.20-7.24 (m, 1H), 6.38-6.57 (m, 2H), 5.66-5.74 (m, 1H), 4.60-4.70 (m, 1H), 4.25-4.37 (m, 1H), 3.62-4.00 (m, 3H), 2.25-2.64 (m, 2H).

Example 85: Preparation of 1-(3-(2-amino-6-(2-fluorophenyl)quinazolin-8-yl)pyrrolidin-1-yl)prop-2-en-1-one

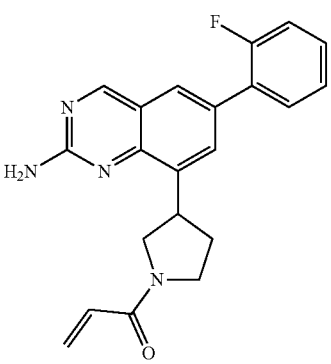

1-(3-(2-amino-6-(2-fluorophenyl)quinazolin-8-yl)pyrrolidin-1-yl)prop-2-en-1-one 1-(3-(2-amino-6-(2-fluorophenyl)quinazolin-8-yl)pyrrolidin-1-yl)prop-2-en-1-one (11.2 mg) was prepared as described for 1-(3-(6-phenylquinazolin-8-yl)pyrrolidin-1-yl)prop-2-en-1-one. LRMS (M+H⁺) m/z calculated 363.2, found 363.2. ¹H NMR (CDCl₃, 400 MHz) δ 9.08 (s, 1H), 7.79 (s, 2H), 7.46-7.50 (m, 1H), 7.32-7.40 (m, 1H), 7.16-7.26 (m, 2H), 6.41-6.57 (m, 2H), 5.65-5.72 (m, 1H), 5.21 (s, 2H), 4.24-4.44 (m, 2H), 3.58-3.99 (m, 3H), 2.26-2.56 (m, 2H).

Example 86: Preparation of 1-(3-(6-(2-fluoro-4-((4-(trifluoromethyl)pyridin-2-yl)oxy)phenyl)quinazolin-8-yl)pyrrolidin-1-yl)prop-2-en-1-one

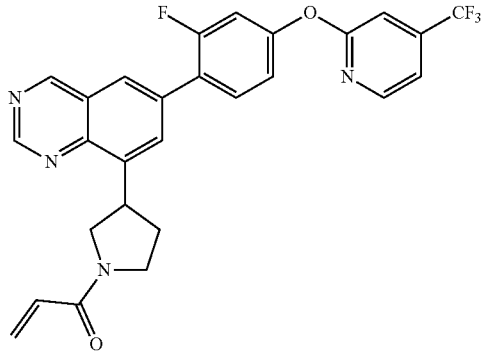

1-(3-(6-(2-fluoro-4-((4-(trifluoromethyl)pyridin-2-yl)oxy)phenyl)quinazolin-8-yl)pyrrolidin-1-yl)prop-2-en-1-one 1-(3-(6-(2-fluoro-4-((4-(trifluoromethyl)pyridin-2-yl)oxy)phenyl)quinazolin-8-yl)pyrrolidin-1-yl)prop-2-en-1-one (31.8 mg) was prepared as described for 1-(3-(6-phenylquinazolin-8-yl)pyrrolidin-1-yl)prop-2-en-1-one. LRMS (M+H$^+$) m/z calculated 509.2, found 509.3. $^1$H NMR (CDCl$_3$, 400 MHz) δ 9.51 (s, 1H), 9.37 (s, 1H), 8.38 (d, 1H), 8.06 (s, 2H), 7.58 (s, 1H), 7.28-7.34 (m, 2H), 7.10-7.23 (m, 2H), 6.41-6.53 (m, 2H), 5.66-5.74 (m, 1H), 4.63-4.70 (m, 1H), 4.27-4.38 (m, 1H), 3.66-4.00 (m, 3H), 2.15-2.63 (m, 2H).

Example 87: N-(3-(6-(2-chloro-4-((4-(trifluoromethyl)pyridin-2-yl)oxy)phenyl)quinazolin-8-yl)phenyl)acrylamide

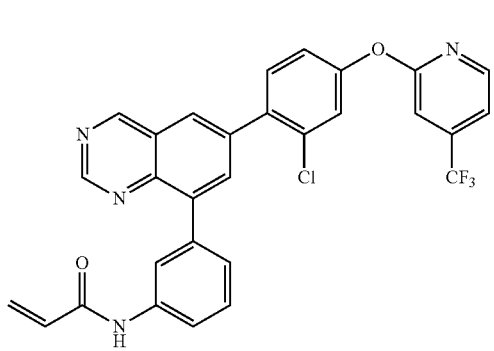

N-(3-(6-(2-chloro-4-((4-(trifluoromethyl)pyridin-2-yl)oxy)phenyl)quinazolin-8-yl)phenyl)acrylamide N-(3-(6-(2-chloro-4-((4-(trifluoromethyl)pyridin-2-yl)oxy)phenyl)quinazolin-8-yl)phenyl)acrylamide (21.2 mg) was prepared as described for 1-(3-(6-phenylquinazolin-8-yl)pyrrolidin-1-yl)prop-2-en-1-one. LRMS (M+H$^+$) m/z calculated 546.1, found 546.1. $^1$H NMR (DMSO-d$_6$, 400 MHz) δ 10.26 (s, 1H), 9.47 (s, 1H), 9.37 (s, 1H), 8.47 (d, 1H), 8.32 (s, 1H), 8.14 (s, 1H), 8.06 (s, 1H), 7.80 (d, 1H), 7.70 (d, 1H), 7.62 (d, 2H), 7.57 (d, 1H), 7.47 (m, 2H), 7.39 (dd, 1H), 6.48 (m, 1H), 6.25 (d, 1H), 5.75 (d, 1H).

Example 88: 4-(8-(3-acrylamidophenyl)quinazolin-6-yl)-3-fluoro-N-(pyridin-2-yl)benzamide

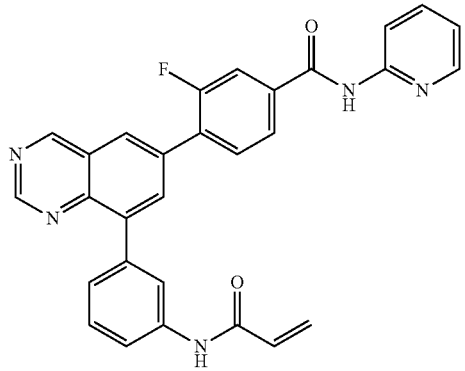

4-(8-(3-acrylamidophenyl)quinazolin-6-yl)-3-fluoro-N-(pyridin-2-yl)benzamide 4-(8-(3-acrylamidophenyl)quinazolin-6-yl)-3-fluoro-N-(pyridin-2-yl)benzamide (5.5 mg) was prepared as described for 4-(8-(3-acrylamidophenyl)quinazolin-6-yl)-N-(pyridin-2-yl)benzamide. LRMS (M+H$^+$) m/z calculated 490.2, found 490.2. $^1$H NMR (DMSO-d$_6$, 400 MHz) δ 11.02 (s, 1H), 10.38 (s, 1H), 9.79 (s, 1H), 9.38 (s, 1H), 8.50 (s, 1H), 8.44 (s, 1H), 7.84-8.26 (m, 8H), 7.50 (s, 2H), 7.21-7.23 (m, 1H), 5.78-6.51 (m, 3H).

Example 89: 4-(8-(3-acrylamidophenyl)quinazolin-6-yl)-3-fluoro-N-(pyridin-2-yl)benzamide

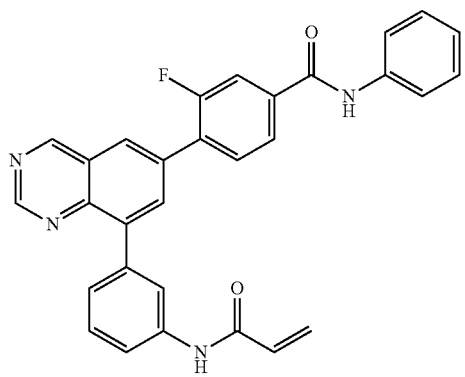

4-(8-(3-acrylamidophenyl)quinazolin-6-yl)-3-fluoro-N-phenylbenzamide 4-(8-(3-acrylamidophenyl)quinazolin-6-yl)-3-fluoro-N-(pyridin-2-yl)benzamide (22.8 mg) was prepared as described for 4-(8-(3-acrylamidophenyl)quinazolin-6-yl)-N-(pyridin-2-yl)benzamide. LRMS (M+H$^+$) m/z calculated 489.2, found 489.2. $^1$H NMR (DMSO-d$_6$, 400 MHz) δ 10.43 (s, 1H), 10.34 (s, 1H), 9.79 (s, 1H), 9.38 (s, 1H), 8.50 (s, 1H), 8.26 (s, 1H), 7.14-8.02 (m, 12H), 5.75-6.51 (m, 3H).

Example 90: N-(3-(2-amino-6-(2-cyanophenyl)quinazolin-8-yl)phenyl)acrylamide

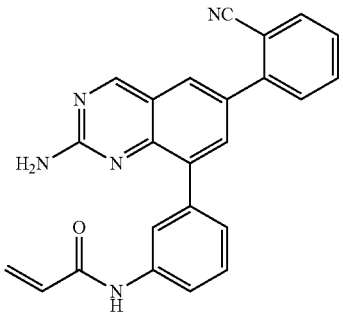

N-(3-(2-amino-6-(2-cyanophenyl)quinazolin-8-yl)phenyl)acrylamide

N-(3-(2-amino-6-(2-cyanophenyl)quinazolin-8-yl)phenyl)acrylamide (5.6 mg) was prepared as described for 1-(3-(6-phenylquinazolin-8-yl)pyrrolidin-1-yl)prop-2-en-1-one. LRMS (M+H$^+$) m/z calculated 392.1, found 392.2. $^1$H NMR (DMSO-d$_6$, 400 MHz) δ 10.2 (s, 1H), 9.27 (s, 1H), 8.06 (s, 1H), 8.00 (d, 1H), 7.80-7.88 (m, 5H), 7.61 (t, 1H), 7.41-7.43 (m, 2H), 7.00-7.01 (m, 2H), 6.51-6.53 (m, 1H), 6.28-6.29 (m, 1H), 5.75 (d, 1H).

Example 91: Preparation of N-(3-(6-(6-(3-fluorophenoxy)pyridin-3-yl)quinazolin-8-yl)phenyl)acrylamide

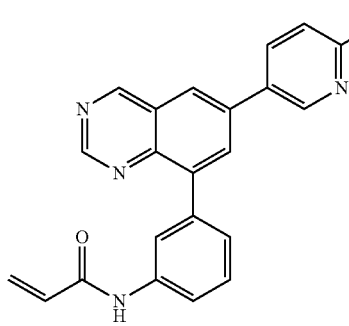

N-(3-(6-(6-(3-fluorophenoxy)pyridin-3-yl)quinazolin-8-yl)phenyl)acrylamide

N-(3-(6-(6-(3-fluorophenoxy)pyridin-3-yl)quinazolin-8-yl)phenyl)acrylamide (20.4 mg) was prepared as described for 1-(3-(6-phenylquinazolin-8-yl)pyrrolidin-1-yl)prop-2-en-1-one. LRMS (M+H$^+$) m/z calculated 491.2, found 491.3. $^1$H NMR (CD$_3$OD, 400 MHz) δ 9.53 (d, 1H), 9.28 (d, 1H), 8.55 (t, 1H), 8.17-8.30 (m, 3H), 7.44-7.65 (m, 4H), 7.19 (d, 1H), 6.65-6.68 (m, 1H), 6.27-6.34 (m, 1H), 5.71-5.79 (m, 1H), 4.57-4.60 (m, 1H), 4.22-4.34 (m, 1H), 3.66-3.84 (m, 3H), 2.46-2.48 (m, 1H).

Example 92: Preparation of 5-(8-(3-acrylamidophenyl)quinazolin-6-yl)-N-(3-fluorophenyl)picolinamide

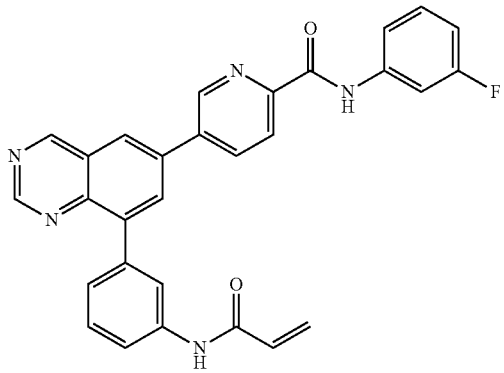

5-(8-(3-acrylamidophenyl)quinazolin-6-yl)-N-(3-fluorophenyl)picolinamide 5-(8-(3-Acrylamidophenyl)quinazolin-6-yl)-N-(3-fluorophenyl)picolinamide (28 mg) was prepared as described for 4-(8-(3-acrylamidophenyl)quinazolin-6-yl)-N-(pyridin-2-yl)benzamide. LRMS (M+H$^+$) m/z calculated 490.2, found 490.2. $^1$H NMR (DMSO-d6, 400 MHz) δ 10.95 (s, 1H), 10.29 (s, 1H), 9.79 (s, 1H), 9.38 (s, 1H), 9.29 (s, 1H), 8.71 (s, 1H), 8.65 (d, 1H), 8.48 (s, 1H), 8.33 (d, 1H), 8.08 (s, 1H), 7.93 (d, 1H), 7.81 (t, 2H), 7.51 (d, 2H), 7.42 (t, 1H), 6.98 (t, 1H), 6.48 (d, 1H), 6.27 (d, 1H), 5.77 (d, 1H).

Example 93: Preparation of 5-(8-(1-acryloylpyrrolidin-3-yl)quinazolin-6-yl)-N-(3-(trifluoromethyl)phenyl)picolinamide

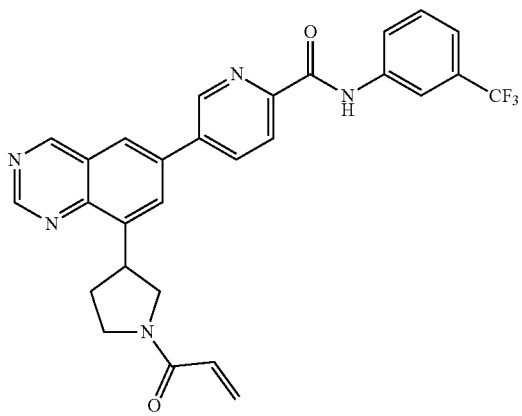

5-(8-(1-acryloylpyrrolidin-3-yl)quinazolin-6-yl)-N-(3-(trifluoromethyl)phenyl)picolinamide 5-(8-(1-Acryloylpyrrolidin-3-yl)quinazolin-6-yl)-N-(3-(trifluoromethyl)phenyl)picolinamide (36.7 mg) was prepared as described for 4-(8-(3-acrylamidophenyl)quinazolin-6-yl)-N-(pyridin-2-yl)benzamide. LRMS (M+H$^+$) m/z calculated 518.2, found 518.3. $^1$H NMR (DMSO-d6, 400 MHz) δ 11.08 (s, 1H), 9.73 (s, 1H), 9.43 (s, 1H), 9.23 (s, 3H), 8.60 (d, 2H), 8.32-8.47 (m, 3H), 8.23 (d, 1H), 7.63 (t, 1H), 7.49 (d, 1H), 6.61-6.69 (m, 1H), 6.16-6.21 (m, 1H), 5.66-5.73 (m, 1H), 4.49-4.63 (m, 1H), 4.13- 4.24 (m, 1H), 3.75-3.92 (m, 2H), 3.53-3.66 (m, 1H), 2.33-2.43 (m, 2H)

Example 94: Preparation of 4-(8-(1-acryloylpyrrolidin-3-yl)quinazolin-6-yl)-3-fluoro-N-(pyridin-2-yl)benzamide

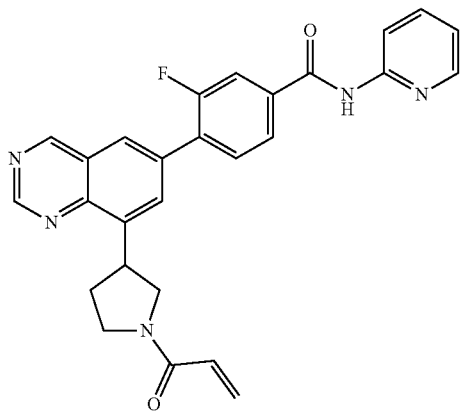

4-(8-(1-acryloylpyrrolidin-3-yl)quinazolin-6-yl)-3-fluoro-N-(pyridin-2-yl)benzamide 4-(8-(1-Acryloylpyrrolidin-3-yl)quinazolin-6-yl)-3-fluoro-N-(pyridin-2-yl)benzamide (10.7 mg) was prepared as described for 4-(8-(3-acrylamidophenyl)quinazolin-6-yl)-N-(pyridin-2-yl)benzamide. LRMS (M+H$^+$) m/z calculated 468.2, found 468.3. $^1$H NMR (DMSO-d6, 400 MHz) δ 11.02 (s, 1H), 9.73 (s, 1H), 9.43 (s, 1H), 7.88-8.43 (m, 8H), 7.21-7.22 (m, 1H), 5.67-6.66 (m, 3H), 4.01-4.60 (m, 2H), 5.55-3.87 (m, 3H), 2.33-2.39 (m, 2H).

Example 95: Preparation of 1-(3-(6-(6-(3-fluorophenoxy)pyridin-3-yl)quinazolin-8-yl)pyrrolidin-1-yl)prop-2-en-1-one

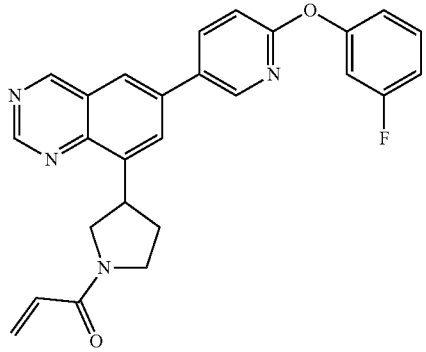

1-(3-(6-(6-(3-fluorophenoxy)pyridin-3-yl)quinazolin-8-yl)pyrrolidin-1-yl)prop-2-en-1-one 1-(3-(6-(6-(3-Fluorophenoxy)pyridin-3-yl)quinazolin-8-yl)pyrrolidin-1-yl)prop-2-en-1-one (7.5 mg) was prepared as described for 1-(3-(6-phenylquinazolin-8-yl)pyrrolidin-1-yl)prop-2-en-1-one. LRMS (M+H$^+$) m/z calculated 440.2, found 440.2. $^1$H NMR (CD$_3$OD, 400 MHz) δ 9.56 (s, 1H), 9.29 (d, 1H), 8.58 (m, 1H), 8.19-8.31 (m, 3H), 7.15-7.45 (m, 4H), 6.96-6.99 (m, 1H), 6.32-6.34 (m, 1H), 5.72-5.80 (m, 1H), 4.55-4.62 (m, 1H), 4.25-4.35 (m, 1H), 3.59-3.83 (m, 3H), 2.46-2.50 (m, 2H).

Example 96: Preparation of N-(3-(6-(6-(3-fluorophenoxy)pyridin-3-yl)quinazolin-8-yl)phenyl)acrylamide

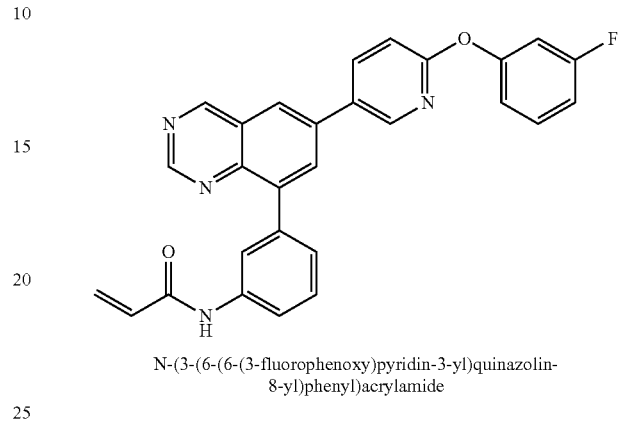

N-(3-(6-(6-(3-fluorophenoxy)pyridin-3-yl)quinazolin-8-yl)phenyl)acrylamide

N-(3-(6-(6-(3-fluorophenoxy)pyridin-3-yl)quinazolin-8-yl)phenyl)acrylamide (24.8 mg) was prepared as described for 1-(3-(6-phenylquinazolin-8-yl)pyrrolidin-1-yl)prop-2-en-1-one. LRMS (M+H$^+$) m/z calculated 491.2, found 491.3. $^1$H NMR (CD$_3$OD, 400 MHz) δ 9.53 (d, 1H), 9.28 (d, 1H), 8.55 (t, 1H), 8.17-8.30 (m, 3H), 7.44-7.65 (m, 4H), 7.19 (d, 1H), 6.65-6.68 (m, 1H), 6.27-6.34 (m, 1H), 5.71-5.79 (m, 1H), 4.57-4.60 (m, 1H), 4.22-4.34 (m, 1H), 3.66-3.84 (m, 3H), 2.46-2.48 (m, 1H).

Example 97: Preparation of 5-(8-(1-acryloylpyrrolidin-3-yl)quinazolin-6-yl)-N-(3-fluorophenyl)picolinamide

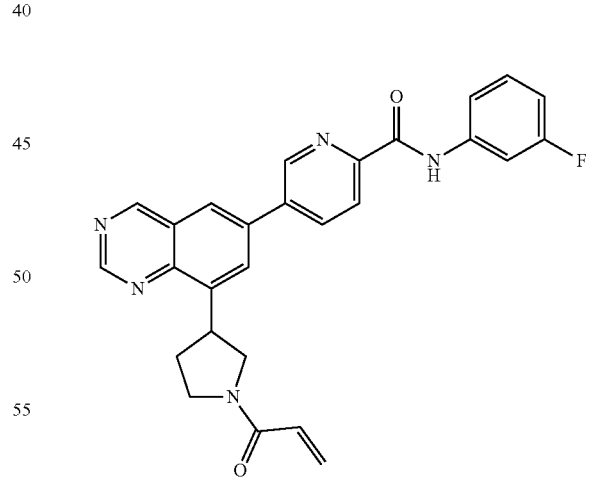

5-(8-(1-acryloylpyrrolidin-3-yl)quinazolin-6-yl)-N-(3-flurophenyl)picolinamide 5-(8-(1-Acryloylpyrrolidin-3-yl)quinazolin-6-yl)-N-(3-fluorophenyl)picolinamide (28 mg) was prepared as described for 4-(8-(3-acrylamidophenyl)quinazolin-6-yl)-N-(pyridin-2-yl)benzamide. LRMS (M+H$^+$) m/z calculated 468.2, found 468.3. $^1$H NMR (DMSO-d6, 400 MHz) δ 10.92 (s, 1H), 9.73 (s, 1H), 9.43 (s, 1H), 9.23 (s, 1H), 8.59 (s, 2H), 8.31-8.43 (m, 2H), 7.93 (d, 1H), 7.79 (d, 1H), 7.43 (t, 1H), 6.98 (t, 1H), 6.65 (dd, 1H), 6.19 (d, 1H), 5.66-5.73 (m, 1H), 4.49-4.62 (m, 1H), 4.11-4.24 (m, 1H), 3.75-3.92 (m, 2H), 3.36-3.66 (m, 1H), 2.33-2.43 (m, 2H).

Example 98: Preparation of N-(3-(2-amino-6-(4-((4-(trifluoromethyl)pyridin-2-yl)oxy)phenyl)quinazolin-8-yl)phenyl)acrylamide

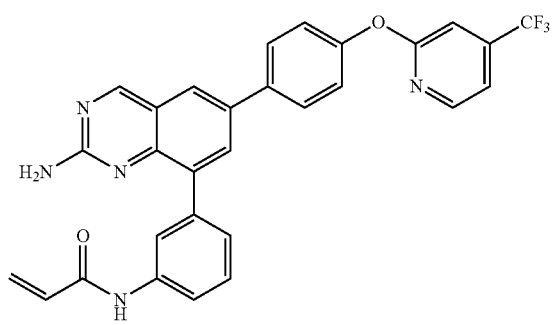

N-(3-(2-amino-6-(4-((4-(trifluoromethyl)pyridin-2-yl)oxy)phenyl)quinazolin-8-yl)phenyl)acrylamide N-(3-(2-amino-6-(4-((4-(trifluoromethyl)pyridin-2-yl)oxy)phenyl)quinazolin-8-yl)phenyl)acrylamide (9.2 mg) was prepared as described for 1-(3-(6-phenylquinazolin-8-yl)pyrrolidin-1-yl)prop-2-en-1-one. LRMS (M+H$^+$) m/z calculated 528.2, found 528.2. $^1$H NMR (DMSO-d6, 400 MHz) δ 10.22 (s, 1H), 9.25 (s, 1H), 8.44 (d, 1H), 8.16 (s, 1H), 7.99 (s, 1H), 7.86-7.89 (m, 3H), 7.83 (d, 1H), 7.51 (s, 2H), 7.41-7.47 (m, 2H), 7.33 (d, 2H), 6.87 (s, 1H), 6.45-6.52 (m, 1H), 6.28 (d, 1H), 5.77 (s, 1H).

Example 99: Preparation of N-(3-(6-(4-(pyridin-2-yloxy)phenyl)quinazolin-8-yl)phenyl)acrylamide

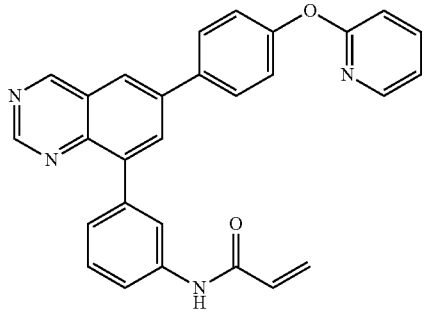

N-(3-(6-(4-(pyridin-2-yloxy)phenyl)quinazolin-8-yl)phenyl)acrylamide

N-(3-(6-(4-(pyridin-2-yloxy)phenyl)quinazolin-8-yl)phenyl)acrylamide (42.1 mg) was prepared as described for 1-(3-(6-phenylquinazolin-8-yl)pyrrolidin-1-yl)prop-2-en-1-one. LRMS (M+H$^+$) m/z calculated 445.2, found 445.2. $^1$H NMR (DMSO-d6, 400 MHz) δ 10.27 (s, 1H), 9.73 (s, 1H), 9.32 (s, 1H), 8.51 (s, 1H), 8.35 (s, 1H), 8.20 (d, 1H), 8.04 (s, 1H), 7.98 (d, 2H), 7.91 (t, 1H), 7.83 (d, 1H), 7.46-7.53 (m, 2H), 7.32 (d, 2H), 7.17 (t, 1H), 7.12 (d, 1H), 6.44-6.52 (m, 1H), 6.28 (d, 1H), 5.77 (d, 1H).

Example 100: Preparation of 1-(3-(6-(6-(2-fluorophenoxy)pyridin-3-yl)quinazolin-8-yl)pyrrolidin-1-yl)prop-2-en-1-one

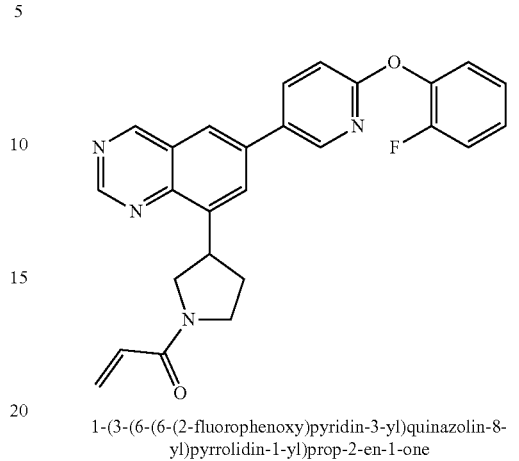

1-(3-(6-(6-(2-fluorophenoxy)pyridin-3-yl)quinazolin-8-yl)pyrrolidin-1-yl)prop-2-en-1-one 1-(3-(6-(6-(2-Fluorophenoxy)pyridin-3-yl)quinazolin-8-yl)pyrrolidin-1-yl)prop-2-en-1-one (23.3 mg) was prepared as described for 1-(3-(6-phenylquinazolin-8-yl)pyrrolidin-1-yl)prop-2-en-1-one. LRMS (M+H$^+$) m/z calculated 440.2, found 440.2. $^1$H NMR (CD$_3$OD, 400 MHz) δ 9.56 (s, 1H), 9.37 (d, 1H), 8.64 (m, 1H), 8.26-8.42 (m, 3H), 7.28-7.41 (m, 5H), 6.58-6.73 (m, 1H), 6.14-6.20 (m, 1H), 5.62-5.70 (m, 1H), 4.45-4.55 (m, 1H), 4.15-4.25 (m, 1H), 3.53-3.82 (m, 3H), 2.42-2.48 (m, 2H).

Example 101: Preparation of N-(3-(6-(6-(morpholine-4-carbonyl)pyridin-3-yl)quinazolin-8-yl)phenyl)acrylamide

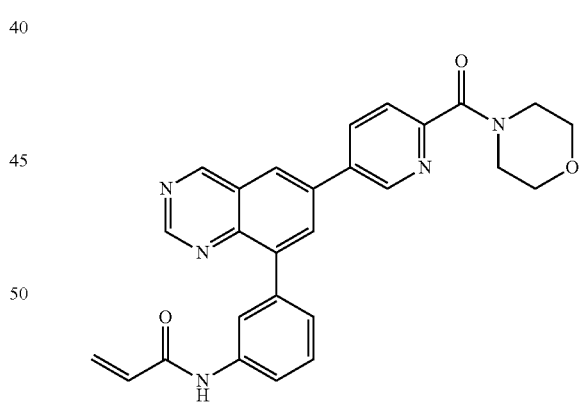

N-(3-(6-(6-(morpholine-4-carbonyl)pyridin-3-yl)quinazolin-8-yl)phenyl)acrylamide N-(3-(6-(6-(morpholine-4-carbonyl)pyridin-3-yl)quinazolin-8-yl)phenyl)acrylamide (19.4 mg) was prepared as described for 4-(8-(3-acrylamidophenyl)quinazolin-6-yl)-N-(pyridin-2-yl)benzamide. LRMS (M+H$^+$) m/z calculated 465.2, found 465.2. $^1$H NMR (DMSO-d6, 400 MHz) δ 10.27 (s, 1H), 9.74 (s, 1H), 9.34 (d, 1H), 8.55 (s, 1H), 8.36 (s, 1H), 8.01-8.05 (m, 3H), 7.82 (d, 1H), 7.49-7.61 (m, 4H), 6.45-6.47 (m, 1H), 6.27-6.29 (m, 1H), 5.75-5.78 (m, 1H), 3.56-3.64 (m, 8H).

Example 102: Preparation of N-(3-(6-(6-(pyrrolidine-1-carbonyl)pyridin-3-yl)quinazolin-8-yl)phenyl)acrylamide

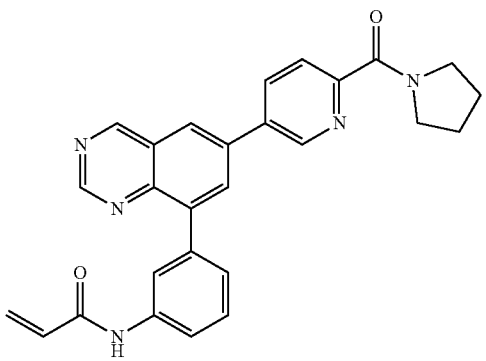

N-(3-(6-(6-(pyrrolidine-1-carbonyl)pyridin-3-yl)quinazolin-8-yl)phenyl)acrylamide N-(3-(6-(6-(pyrrolidine-1-carbonyl)pyridin-3-yl)quinazolin-8-yl)phenyl)acrylamide (26.7 mg) was prepared as described for 4-(8-(3-acrylamidophenyl)quinazolin-6-yl)-N-(pyridin-2-yl)benzamide. LRMS (M+H$^+$) m/z calculated 449.2, found 449.2. $^1$H NMR (DMSO-d6, 400 MHz) δ 10.27 (s, 1H), 9.74 (s, 1H), 9.34 (d, 1H), 8.56 (s, 1H), 8.36 (s, 1H), 8.00-8.05 (m, 3H), 7.82 (d, 1H), 7.70-7.71 (m, 2H), 7.51 (s, 1H), 6.45-6.50 (m, 1H), 6.25-6.29 (m, 1H), 5.76-5.78 (m, 1H), 3.43-3.51 (m, 4H), 1.87 (s, 1H).

Example 103: Preparation of N-(3-(2-amino-6-(5-chloropyridin-3-yl)quinazolin-8-yl)phenyl)acrylamide

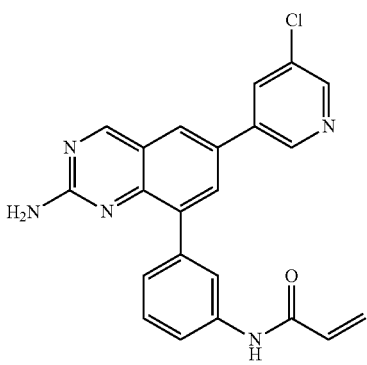

N-(3-(2-amino-6-(5-chloropyridin-3-yl)quinazolin-8-yl)phenyl)acrylamide

N-(3-(2-amino-6-(5-chloropyridin-3-yl)quinazolin-8-yl)phenyl)acrylamide (44.4 mg) was prepared as described for 1-(3-(6-phenylquinazolin-8-yl)pyrrolidin-1-yl)prop-2-en-1-one. LRMS (M+H$^+$) m/z calculated 402.1, found 402.2. $^1$H NMR (DMSO-d6, 400 MHz) δ 10.22 (s, 1H), 9.23 (s, 1H), 9.01 (s, 1H), 8.62 (s, 1H), 7.83-8.42 (m, 5H), 7.42-7.44 (m, 2H), 7.00 (s, 2H), 5.75-6.49 (m, 3H).

Example 104: Preparation of 1-(3-(2-amino-6-(4-((4-(trifluoromethyl)pyridin-2-yl)oxy)phenyl)quinazolin-8-yl)pyrrolidin-1-yl)prop-2-en-1-one

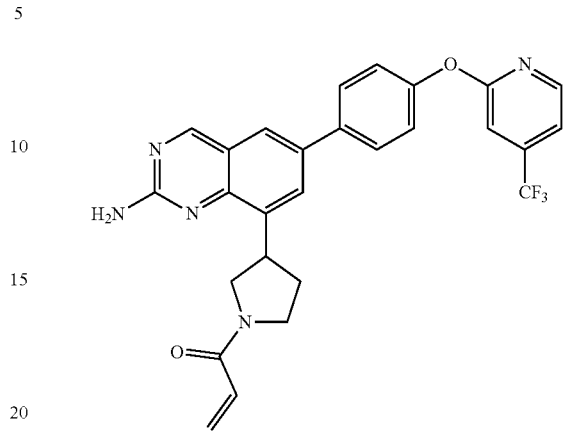

1-(3-(2-amino-6-(4-((4-(trifluoromethyl)pyridin-2-yl)oxy)phenyl)quinazolin-8-yl)pyrrolidin-1-yl)prop-2-en-1-one 1-(3-(2-Amino-6-(4-((4-(trifluoromethyl)pyridin-2-yl)oxy)phenyl)quinazolin-8-yl)pyrrolidin-1-yl)prop-2-en-1-one (19.2 mg) was prepared as described for 1-(3-(6-phenylquinazolin-8-yl)pyrrolidin-1-yl)prop-2-en-1-one. LRMS (M+H$^+$) m/z calculated 506.2, found 506.2. $^1$H NMR (DMSO-d6, 400 MHz) δ 9.17 (s, 1H), 8.43 (d, 1H), 8.01 (m, 2H), 7.82 (m, 2H), 7.50 (s, 2H), 7.30 (d, 2H), 6.93 (d, 2H), 6.63 (m, 1H), 6.15 (dd, 1H), 5.64 (m, 1H), 4.22 (m, 1H), 4.05 (m, 1H), 3.77 (m, 2H), 3.45 (m, 1H), 2.37 (m, 1H), 2.29 (m, 1H).

Example 105: Preparation of N-(3-(6-(2-fluoro-4-((3-fluoropyridin-2-yl)oxy)phenyl)quinazolin-8-yl)phenyl)acrylamide

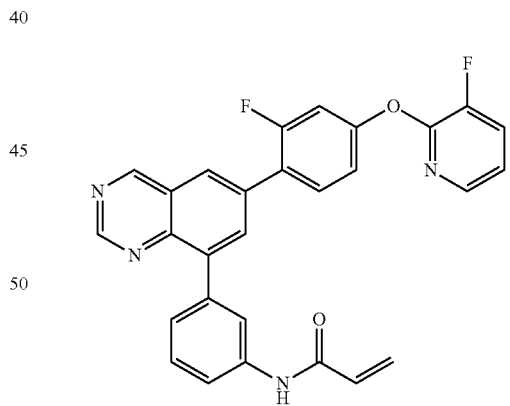

N-(3-(6-(2-fluoro-4-((3-fluoropyridin-2-yl)oxy)phenyl)quinazolin-8-yl)phenyl)acrylamide N-(3-(6-(2-fluoro-4-((3-fluoropyridin-2-yl)oxy)phenyl)quinazolin-8-yl)phenyl)acrylamide (14.7 mg) was prepared as described for 1-(3-(6-phenylquinazolin-8-yl)pyrrolidin-1-yl)prop-2-en-1-one. LRMS (M+H$^+$) m/z calculated 481.1, found 481.2. $^1$H NMR (DMSO-d6, 400 MHz) δ 10.27 (s, 1H), 9.76 (s, 1H), 9.36 (s, 1H), 8.43 (s, 1H), 8.22 (s, 1H), 8.04 (s, 2H), 7.81-7.96 (m, 3H), 7.47-7.50 (m, 2H), 7.41 (d, 1H), 7.23-7.30 (m, 2H), 6.44-6.49 (m, 1H), 6.27 (d, 1H), 5.77 (d, 1H).

Example 106: Preparation of N-(3-(6-(4-((3-chloropyridin-2-yl)oxy)-2-fluorophenyl)quinazolin-8-yl)phenyl)acrylamide

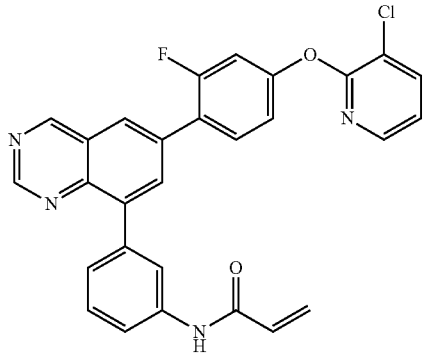

N-(3-(6-(4-((3-chloropyridin-2-yl)oxy)-2-fluorophenyl)quinazolin-8-yl)phenyl)acrylamide N-(3-(6-(4-((3-chloropyridin-2-yl)oxy)-2-fluorophenyl)quinazolin-8-yl)phenyl)acrylamide (20.4 mg) was prepared as described for 1-(3-(6-phenylquinazolin-8-yl)pyrrolidin-1-yl)prop-2-en-1-one. LRMS (M+H$^+$) m/z calculated 497.1, found 497.2. $^1$H NMR (DMSO-d6, 400 MHz) δ 10.27 (s, 1H), 9.76 (s, 1H), 9.36 (s, 1H), 8.43 (s, 1H), 8.22 (s, 1H), 8.11-8.17 (m, 2H), 8.04 (s, 1H), 7.81-7.88 (m, 2H), 7.47-7.50 (m, 2H), 7.39 (d, 1H), 7.21-7.28 (m, 2H), 6.44-6.51 (m, 1H), 6.27 (d, 1H), 5.77 (d, 1H).

Example 107: Preparation of 1-(3-(6-(4-(pyridin-2-yloxy)phenyl)quinazolin-8-yl)pyrrolidin-1-yl)prop-2-en-1-one

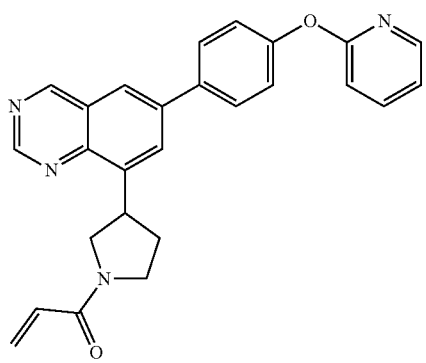

1-(3-(6-(4-(pyridin-2-yloxy)phenyl)quinazolin-8-yl)pyrrolidin-1-yl)prop-2-en-1-one 1-(3-(6-(4-(Pyridin-2-yloxy)phenyl)quinazolin-8-yl)pyrrolidin-1-yl)prop-2-en-1-one (9.4 mg) was prepared as described for 1-(3-(6-phenylquinazolin-8-yl)pyrrolidin-1-yl)prop-2-en-1-one. LRMS (M+H$^+$) m/z calculated 423.2, found 423.3. $^1$H NMR (DMSO-d6, 400 MHz) δ 9.66 (s, 1H), 9.36 (s, 1H), 8.26 (m, 4H), 7.92 (m, 3H), 7.29 (dd, 2H), 7.17 (m, 2H), 6.63 (m, 1H), 6.15 (m, 1H), 5.76 (m, 1H), 4.46 (m, 1H), 4.15 (m, 1H), 3.83 (m, 2H), 3.54 (m, 2H), 2.37 (m, 1H), 2.32 (m, 1H).

Example 108: Preparation of 1-(3-(6-(2-fluoro-4-((3-fluoropyridin-2-yl)oxy)phenyl)quinazolin-8-yl)pyrrolidin-1-yl)prop-2-en-1-one

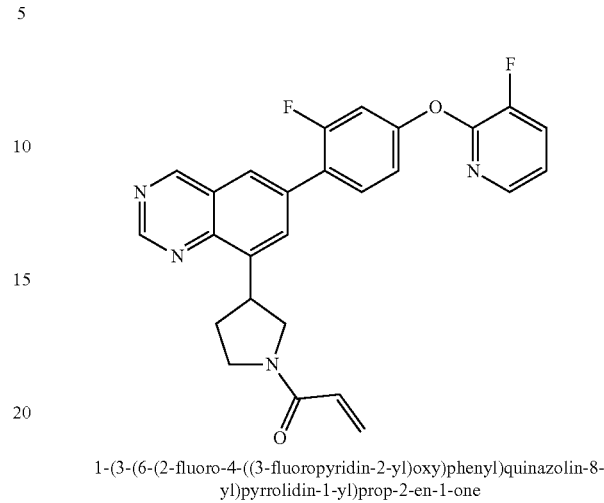

1-(3-(6-(2-fluoro-4-((3-fluoropyridin-2-yl)oxy)phenyl)quinazolin-8-yl)pyrrolidin-1-yl)prop-2-en-1-one 1-(3-(6-(2-Fluoro-4-((3-fluoropyridin-2-yl)oxy)phenyl)quinazolin-8-yl)pyrrolidin-1-yl)prop-2-en-1-one (10.0 mg) was prepared as described for 1-(3-(6-phenylquinazolin-8-yl)pyrrolidin-1-yl)prop-2-en-1-one. LRMS (M+H$^+$) m/z calculated 459.2, found 459.2. $^1$H NMR (DMSO-d6, 400 MHz) δ 9.70 (s, 1H), 9.40 (s, 1H), 8.29 (s, 1H), 8.15 (d, 1H), 8.03 (d, 1H), 7.93 (t, 1H), 7.79 (t, 1H), 7.38 (d, 1H), 7.23-7.31 (m, 2H), 6.59-6.70 (m, 1H), 6.14-6.19 (m, 1H), 5.64-5.72 (m, 1H), 4.45-4.61 (m, 1H), 4.09-4.23 (m, 1H), 3.74-3.88 (m, 2H), 3.52-3.59 (m, 1H), 2.31-2.41 (m, 2H).

Example 109: Preparation of 4-(8-(3-acrylamidophenyl)quinazolin-6-yl)-N-(4-cyanopyridin-2-yl)benzamide

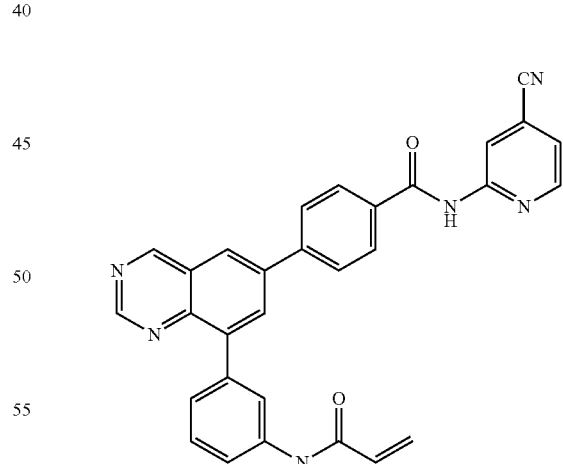

4-(8-(3-acrylamidophenyl)quinazolin-6-yl)-N-(4-cyanopyridin-2-yl)benzamide 4-(8-(3-Acrylamidophenyl)quinazolin-6-yl)-N-(4-cyanopyridin-2-yl)benzamide (6.8 mg) was prepared as described for 4-(8-(3-acrylamidophenyl)quinazolin-6-yl)-N-(pyridin-2-yl)benzamide. LRMS (M+H$^+$) m/z calculated 497.2, found 497.3. $^1$H NMR (DMSO-d6, 400 MHz) δ 11.39 (s, 1H), 10.28 (s, 1H), 9.77 (s, 1H), 9.35 (s, 1H), 8.64-8.69 (m, 2H), 8.56 (s, 1H), 8.42 (s, 1H), 8.25 (d, 2H), 8.05-8.14 (m, 2H), 7.65 (d, 1H), 7.50-7.52 (m, 2H), 6.47-6.51 (m, 1H), 6.28 (d, 1H), 5.77 (d, 1H).

Example 110: Preparation of N-(3-(2-amino-6-(5-methoxypyridin-3-yl)quinazolin-8-yl)phenyl)acrylamide

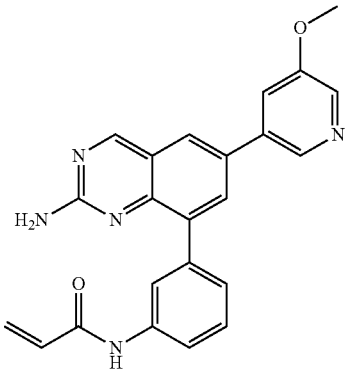

N-(3-(2-amino-6-(5-methoxypyridin-3-yl)quinazolin-8-yl)phenyl)acrylamide

N-(3-(2-amino-6-(5-methoxypyridin-3-yl)quinazolin-8-yl)phenyl)acrylamide (29 mg) was prepared as described for 1-(3-(6-phenylquinazolin-8-yl)pyrrolidin-1-yl)prop-2-en-1-one. LRMS (M+H$^+$) m/z calculated 398.2, found 398.3. $^1$H NMR (DMSO-d6, 400 MHz) δ 10.21 (s, 1H), 9.23 (s, 1H), 8.62 (s, 1H), 8.27 (d, 2H), 8.03 (s, 1H), 7.83-7.86 (m, 2H), 7.77 (s, 1H), 7.43 (s, 2H), 6.93 (s, 2H), 6.44-6.48 (m, 1H), 6.27 (d, 1H), 5.76 (d, 1H), 3.93 (s, 3H).

Example 111: Preparation of N-(3-(2-amino-6-(5-fluoropyridin-3-yl)quinazolin-8-yl)phenyl)acrylamide

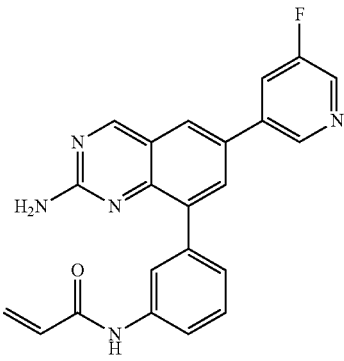

N-(3-(2-amino-6-(5-fluoropyridin-3-yl)quinazolin-8-yl)phenyl)acrylamide

N-(3-(2-amino-6-(5-fluoropyridin-3-yl)quinazolin-8-yl)phenyl)acrylamide (40.2 mg) was prepared as described for 1-(3-(6-phenylquinazolin-8-yl)pyrrolidin-1-yl)prop-2-en-1-one. LRMS (M+H$^+$) m/z calculated 386.1, found 386.2. $^1$H NMR (DMSO-d6, 400 MHz) δ 10.22 (s, 1H), 9.23 (s, 1H), 8.94 (s, 1H), 8.58 (s, 1H), 7.83-8.30 (m, 5H), 7.42-7.44 (m, 2H), 6.98 (s, 2H), 5.75-6.47 (m, 3H).

Example 112: Preparation of N-(3-(6-(2-fluoro-4-(pyridin-2-yloxy)phenyl)quinazolin-8-yl)phenyl)acrylamide

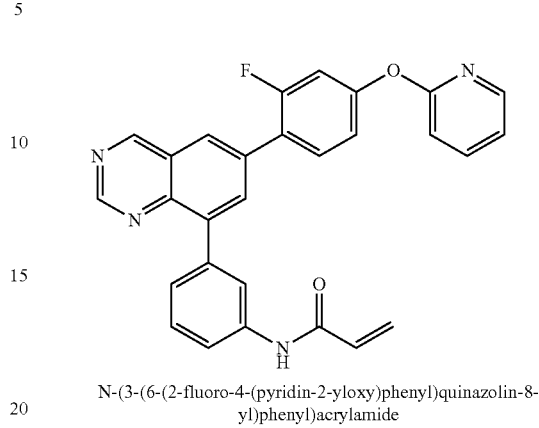

N-(3-(6-(2-fluoro-4-(pyridin-2-yloxy)phenyl)quinazolin-8-yl)phenyl)acrylamide

N-(3-(6-(2-fluoro-4-(pyridin-2-yloxy)phenyl)quinazolin-8-yl)phenyl)acrylamide (71.2 mg) was prepared as described for 1-(3-(6-phenylquinazolin-8-yl)pyrrolidin-1-yl)prop-2-en-1-one. LRMS (M+H$^+$) m/z calculated 463.1, found 463.1. $^1$H NMR (DMSO-d6, 400 MHz) 10.28 (s, 1H), 9.75 (s, 1H), 9.35 (s, 1H), 8.41 (s, 1H), 8.21-8.23 (m, 2H), 8.04 (s, 1H), 7.91 (t, 1H), 7.83-7.85 (m, 2H), 7.48-7.50 (m, 2H), 7.32 (dd, 1H), 7.17-7.19 (m, 3H), 6.47-6.50 (m, 1H), 6.25-6.27 (m, 1H), 5.75-5.77 (m, 1H).

Example 113: Preparation of 4-(8-(3-acrylamidophenyl)quinazolin-6-yl)-N-(pyridin-3-yl)benzamide

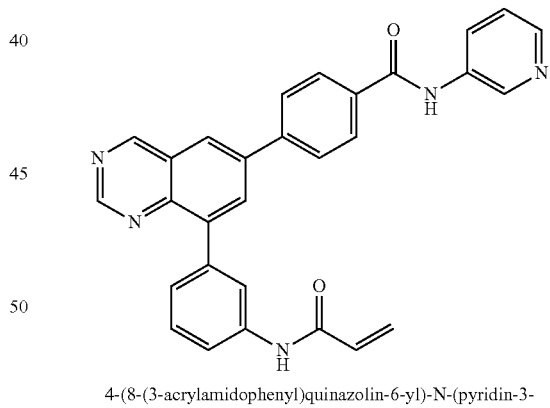

4-(8-(3-acrylamidophenyl)quinazolin-6-yl)-N-(pyridin-3-yl)benzamide 4-(8-(3-Acrylamidophenyl)quinazolin-6-yl)-N-(pyridin-3-yl)benzamide (3.8 mg) was prepared as described for 4-(8-(3-acrylamidophenyl)quinazolin-6-yl)-N-(pyridin-2-yl)benzamide. LRMS (M+H$^+$) m/z calculated 472.2, found 472.2. $^1$H NMR (DMSO-d6, 400 MHz) δ 10.75 (s, 1H), 10.37 (s, 1H), 9.77 (s, 1H), 9.35 (s, 1H), 9.08 (s, 1H), 8.64 (d, 1H), 8.35-8.43 (m, 3H), 8.20 (dd, 4H), 8.06 (s, 1H), 7.87 (d, 1H), 7.50-7.55 (m, 3H), 6.49-6.53 (m, 1H), 6.29 (d, 1H), 5.76-5.79 (m, 1H).

Example 114: Preparation of 1-(3-(6-(2-fluoro-4-(pyridin-2-yloxy)phenyl)quinazolin-8-yl)pyrrolidin-1-yl)prop-2-en-1-one

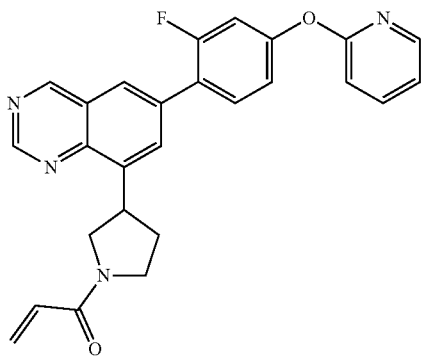

1-(3-(6-(2-fluoro-4-(pyridin-2-yloxy)phenyl)quinazolin-8-yl)pyrrolidin-1-yl)prop-2-en-1-one 1-(3-(6-(2-Fluoro-4-(pyridin-2-yloxy)phenyl)quinazolin-8-yl)pyrrolidin-1-yl)prop-2-en-1-one (22.2 mg) was prepared as described for 1-(3-(6-phenylquinazolin-8-yl)pyrrolidin-1-yl)prop-2-en-1-one. LRMS (M+H$^+$) m/z calculated 441.2, found 441.2. $^1$H NMR (DMSO-d6, 400 MHz) δ 9.69 (s, 1H), 9.40 (s, 1H), 8.28 (s, 1H), 8.21 (d, 1H), 8.17 (d, 1H), 7.94 (t, 1H), 7.77 (t, 1H), 7.27-7.29 (m, 1H), 7.16-7.18 (m, 3H), 6.63-6.65 (m, 1H), 6.17-6.19 (m, 1H), 5.71-5.73 (m, 1H), 4.49-4.51 (m, 1H), 4.13- 4.15 (m, 1H), 3.80-3.82 (m, 2H), 3.58-3.60 (m, 1H), 2.40-2.42 (m, 1H), 2.23-2.25 (m, 1H).

Example 115: Preparation of 4-(8-(1-acryloylpyrrolidin-3-yl)quinazolin-6-yl)-N-(pyridin-3-yl)benzamide

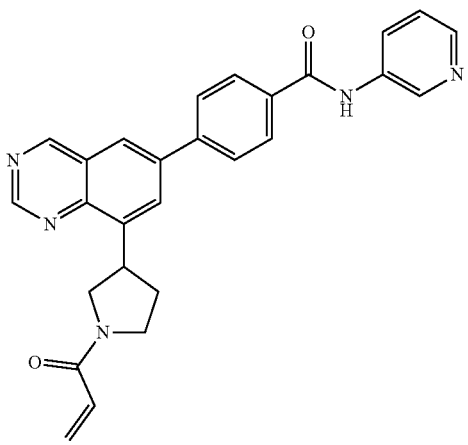

4-(8-(1-acryloylpyrrolidin-3-yl)quinazolin-6-yl)-N-(pyridin-3-yl)benzamide 4-(8-(1-Acryloylpyrrolidin-3-yl)quinazolin-6-yl)-N-(pyridin-3-yl)benzamide (17.2 mg) was prepared as described for 4-(8-(3-acrylamidophenyl)quinazolin-6-yl)-N-(pyridin-2-yl)benzamide. LRMS (M+H$^+$) m/z calculated 450.2, found 450.3. $^1$H NMR (DMSO-d6, 400 MHz) δ 10.61 (s, 1H), 9.73 (s, 1H), 9.44 (s, 1H), 9.03 (s, 1H), 8.55 (d, 1H), 8.30-8.48 (m, 7H), 7.46-7.49 (m, 1H), 6.66-6.77 (m, 1H), 6.21-6.27 (m, 1H), 5.71-5.78 (m, 1H), 4.49-4.68 (m, 1H), 4.17-4.26 (m, 1H), 3.80-3.96 (m, 3H), 2.38- 2.49 (m, 2H).

Example 116: Preparation of 4-(8-(3-acrylamidophenyl)quinazolin-6-yl)-3-chloro-N-(4-(trifluoromethyl)pyridin-2-yl)benzamide

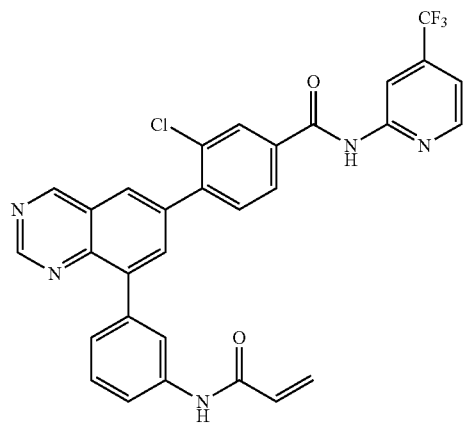

4-(8-(1-acrylamidophenyl)quinazolin-6-yl)-3-chloro-N-(4-(trifluoromethyl)pyridin-2-yl)benzamide 4-(8-(3-Acrylamidophenyl)quinazolin-6-yl)-3-chloro-N-(4-(trifluoromethyl)pyridin-2-yl)benzamide (17.9 mg) was prepared as described for 4-(8-(3-acrylamidophenyl)quinazolin-6-yl)-N-(pyridin-2-yl)benzamide. LRMS (M+H$^+$) m/z calculated 574.1, found 574.2. $^1$H NMR (DMSO-d6, 400 MHz) δ 11.56 (s, 1H), 10.33 (s, 1H), 9.78 (s, 1H), 9.40 (s, 1H), 8.59 (d, 1H), 8.36 (s, 1H), 8.35 (s, 2H), 7.48-8.19 (m, 8H), 5.76-6.48 (m, 3H).

Example 117: Preparation of N-(3-(6-(4-(pyridin-3-yloxy)phenyl)quinazolin-8-yl)phenyl)acrylamide

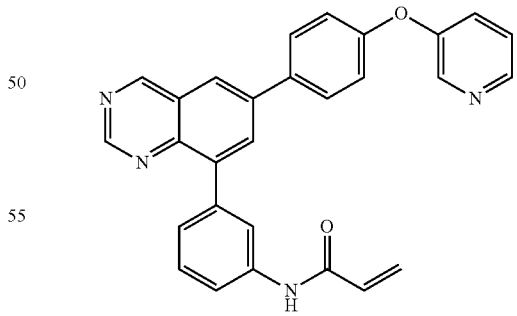

N-(3-(6-(4-pyridin-3-yloxy)phenyl)quinazolin-8-yl)phenyl)acrylamide

N-(3-(6-(4-(pyridin-3-yloxy)phenyl)quinazolin-8-yl)phenyl)acrylamide (14.1 mg) was prepared as described for 1-(3-(6-phenylquinazolin-8-yl)pyrrolidin-1-yl)prop-2-en-1-one. LRMS (M+H$^+$) m/z calculated 445.2, found 445.2. $^1$H NMR (DMSO-d6, 400 MHz) δ 10.29 (s, 1H), 9.72 (s, 1H), 9.31 (s, 1H), 8.48 (s, 1H), 8.42-8.55 (m, 3H), 8.32 (s, 1H), 8.05 (s, 1H), 7.99 (d, 2H), 7.82 (d, 1H), 7.46-7.55 (m, 4H), 7.25 (d, 2H), 6.45-6.52 (m, 1H), 6.28 (dd, 1H), 5.77 (dd, 1H).

Example 118: Preparation of N-(3-(6-(pyridin-2-yl)quinazolin-8-yl)phenyl)acrylamide

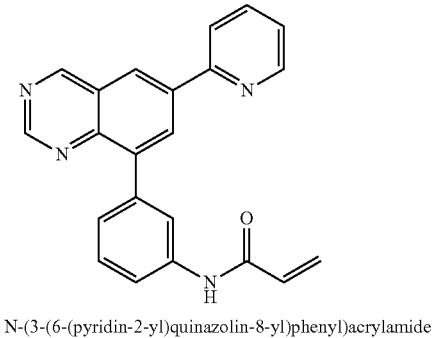 [SMILES: C=CC(=O)Nc1cccc(-c2cc(-c3ccccn3)cc3cncnc23)c1]

N-(3-(6-(pyridin-2-yl)quinazolin-8-yl)phenyl)acrylamide

N-(3-(6-(pyridin-2-yl)quinazolin-8-yl)phenyl)acrylamide (28.7 mg) was prepared as described for 1-(3-(6-phenylquinazolin-8-yl)pyrrolidin-1-yl)prop-2-en-1-one. LRMS (M+H$^+$) m/z calculated 353.1, found 353.3. $^1$H NMR (DMSO-d6, 400 MHz) δ 10.38 (s, 1H), 9.78 (s, 1H), 9.34 (s, 1H), 8.92 (s, 1H), 8.78 (s, 2H), 8.29 (d, 1H), 7.99-8.05 (m, 2H), 7.85 (s, 1H), 7.47-7.50 (m, 3H), 6.49-6.55 (m, 1H), 6.28 (d, 1H), 5.77 (d, 1H).

Example 119: Preparation of N-(3-(6-(3-methoxy-4-(pyridin-2-yloxy)phenyl)quinazolin-8-yl)phenyl)acrylamide

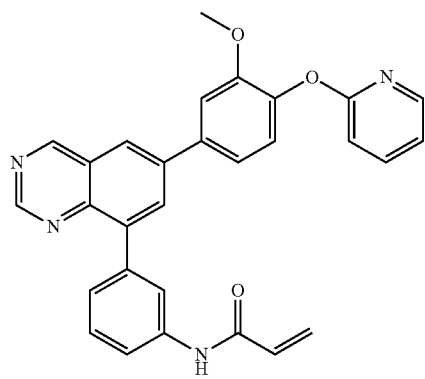

N-(3-(6-(3-methoxy-4-(pyridin-2-yloxy)phenyl)quinazolin-8-yl)phenyl)acrylamide

N-(3-(6-(3-methoxy-4-(pyridin-2-yloxy)phenyl)quinazolin-8-yl)phenyl)acrylamide (34.9 mg) was prepared as described for 1-(3-(6-phenylquinazolin-8-yl)pyrrolidin-1-yl)prop-2-en-1-one. LRMS (M+H$^+$) m/z calculated 475.2, found 475.2. $^1$H NMR (DMSO-d6, 400 MHz) δ 10.27 (s, 1H), 9.73 (s, 1H), 9.32 (s, 1H), 8.54 (d, 1H), 8.40 (d, 1H), 8.10-8.11 (m, 1H), 8.03 (s, 1H), 7.82-7.86 (m, 2H), 7.64 (d, 1H), 7.49-7.53 (m, 3H), 7.30 (d, 1H), 7.08-7.11 (m, 1H), 7.04 (d, 1H), 6.45-6.01 (m, 1H), 6.25-6.29 (m, 1H), 6.75-6.78 (m, 1H).

Example 120: Preparation of 4-(8-(3-acrylamidophenyl)quinazolin-6-yl)-3-chloro-N-(4-cyclopropylpyridin-2-yl)benzamide

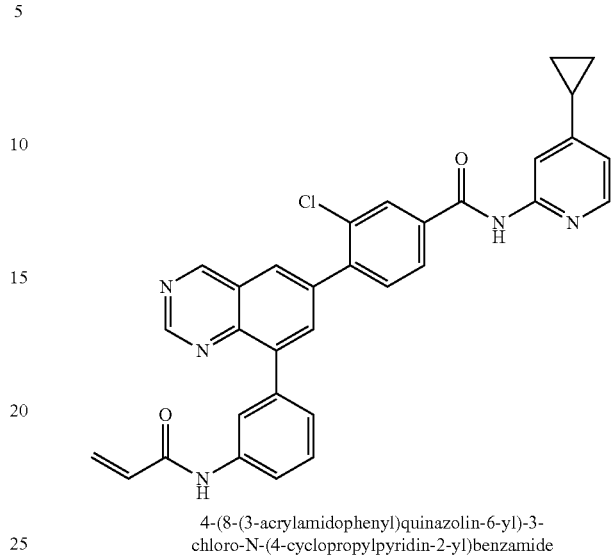

4-(8-(3-acrylamidophenyl)quinazolin-6-yl)-3-chloro-N-(4-cyclopropylpyridin-2-yl)benzamide 4-(8-(3-Acrylamidophenyl)quinazolin-6-yl)-3-chloro-N-(4-cyclopropylpyridin-2-yl)benzamide (32.1 mg) was prepared as described for 4-(8-(3-acrylamidophenyl)quinazolin-6-yl)-N-(pyridin-2-yl)benzamide. LRMS (M+H$^+$) m/z calculated 546.2, found 546.2. $^1$H NMR (DMSO-d6, 400 MHz) δ 10.97 (s, 1H), 10.28 (s, 1H), 9.77 (s, 1H), 9.39 (s, 1H), 8.36 (s, 1H), 8.35 (s, 1H), 8.32 (d, 1H), 8.14-8.16 (m, 2H), 8.06 (s, 1H), 7.97 (s, 1H), 7.82 (d, 2H), 7.48-7.50 (m, 2H), 6.89-6.91 (m, 1H), 6.44-6.49 (m, 1H), 6.25-6.29 (m, 1H), 5.76-5.78 (m, 1H), 2.00 (t, 1H), 1.09-1.13 (m, 2H), 0.81-0.84 (m, 2H).

Example 121: Preparation of 4-(8-(3-acrylamidophenyl)quinazolin-6-yl)-3-chloro-N-(4-cyanopyridin-2-yl)benzamide

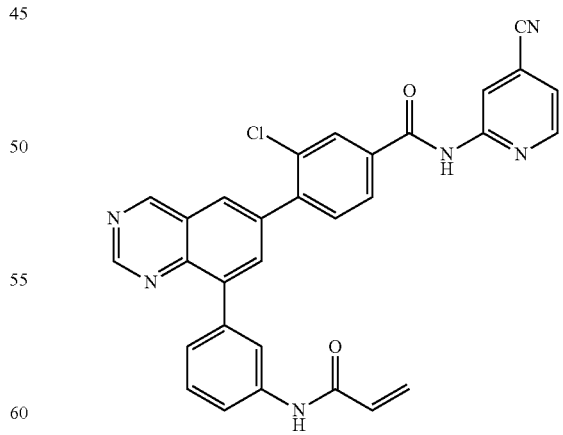

4-(8-(3-acrylamidophenyl)quinazolin-6-yl)-3-chloro-N-(4-cyanopyridin-2-yl)benzamide 4-(8-(3-Acrylamidophenyl)quinazolin-6-yl)-3-chloro-N-(4-cyanopyridin-2-yl)benzamide (7 mg) was prepared as described for 4-(8-(3-acrylamidophenyl)quinazolin-6-yl)-N-

(pyridin-2-yl)benzamide. LRMS (M+H⁺) m/z calculated 531.1, found 531.2. ¹H NMR (DMSO-d6, 400 MHz) δ 11.54 (s, 1H), 10.35 (s, 1H), 9.78 (s, 1H), 9.39 (s, 1H), 8.69 (s, 1H), 8.54 (s, 1H), 8.35 (s, 2H), 7.49- 8.17 (m, 8H), 5.75-6.51 (m, 3H).

Example 122: Preparation of N-(3-(6-(2-methoxy-4-(pyridin-2-yloxy)phenyl)quinazolin-8-yl)phenyl)acrylamide

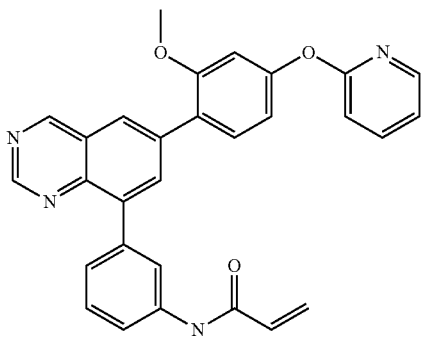

N-(3-(6-(2-methoxy-4-(pyridin-2-yloxy)phenyl)quinazolin-8-yl)phenyl)acrylamide

N-(3-(6-(2-methoxy-4-(pyridin-2-yloxy)phenyl)quinazolin-8-yl)phenyl)acrylamide (14.9 mg) was prepared as described for 1-(3-(6-phenylquinazolin-8-yl)pyrrolidin-1-yl)prop-2-en-1-one. LRMS (M+H⁺) m/z calculated 475.2, found 475.2. ¹H NMR (DMSO-d6, 400 MHz) δ 10.25 (s, 1H), 9.70 (s, 1H), 9.31 (s, 1H), 8.28 (s, 1H), 8.21 (d, 1H), 8.17 (s, 1H), 8.06 (s, 1H), 7.89 (t, 1H), 7.78 (d, 1H), 7.56-7.58 (m, 1H), 7.47-7.50 (m, 2H), 7.17 (t, 1H), 7.09 (d, 1H), 7.02 (s, 1H), 6.88 (d, 1H), 6.46-6.48 (m, 1H), 6.29 (d, 1H), 5.78 (d, 1H), 3.81 (s, 3H).

Example 123: Preparation of 4-(8-(1-acryloylpyrrolidin-3-yl)quinazolin-6-yl)-N-(4-cyclopropylpyridin-2-yl)benzamide

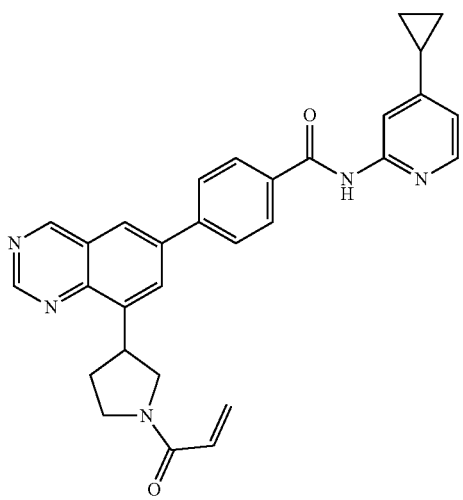

4-(8-(1-acryloylpyrrolidin-3-yl)quinazolin-6-yl)-N-(4-cyclopropylpyridin-2-yl)benzamide 4-(8-(1-Acryloylpyrrolidin-3-yl)quinazolin-6-yl)-N-(4-cyclopropylpyridin-2-yl)benzamide (31.8 mg) was prepared as described for 4-(8-(3-acrylamidophenyl)quinazolin-6-yl)-N-(pyridin-2-yl)benzamide. LRMS (M+H⁺) m/z calculated 490.2, found 490.3. ¹H NMR (DMSO-d6, 400 MHz) δ 10.78 (s, 1H), 9.69 (s, 1H), 9.39 (s, 1H), 9.69 (s, 1H), 8.49-8.50 (m, 1H), 8.36 (d, 1H), 8.20-8.22 (m, 3H), 7.99-8.06 (m, 3H), 6.89 (d, 1H), 6.67 (q, 1H), 6.20-6.22 (m, 1H), 5.67-5.69 (m, 1H), 4.46-4.62 (m, 1H), 4.11-4.21 (m, 1H), 3.71-3.88 (m, 3H), 2.44-2.50 (m, 2H), 2.00 (t, 1H), 1.08-1.13 (m, 2H), 0.80- 0.84 (m, 2H).

Example 124: Preparation of 4-(8-(1-acryloylpyrrolidin-3-yl)quinazolin-6-yl)-N-(4-cyanopyridin-2-yl)benzamide

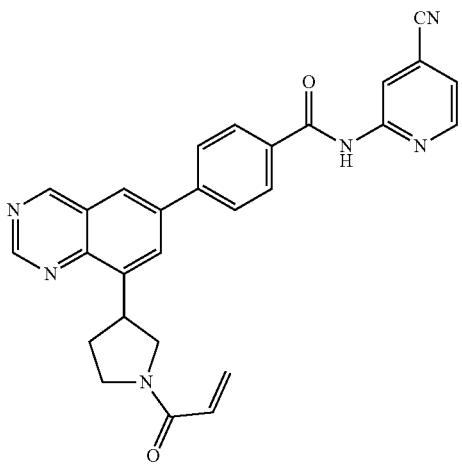

4-(8-(1-acryloylpyrrolidin-3-yl)quinazolin-6-yl)-N-(4-cyanopyridin-2-yl)benzamide 4-(8-(1-Acryloylpyrrolidin-3-yl)quinazolin-6-yl)-N-(4-cyanopyridin-2-yl)benzamide (46.2 mg) was prepared as described for 4-(8-(3-acrylamidophenyl)quinazolin-6-yl)-N-(pyridin-2-yl)benzamide. LRMS (M+H⁺) ¹H NMR (DMSO-d6, 400 MHz) δ 11.38 (s, 1H), 9.70 (s, 1H), 9.39 (s, 1H), 8.68 (d, 1H), 8.55 (s, 1H), 8.49-8.51 (m, 1H), 8.37 (d, 1H), 8.23 (d, 2H), 8.05-8.09 (m, 2H), 7.65 (d, 1H), 6.61-6.70 (m, 1H), 6.16-6.22 (m, 1H), 5.65-5.75 (m, 1H), 4.46-4.65 (m, 1H), 4.12-4.22 (m, 1H), 3.77-3.91 (m, 2H), 3.51-3.62 (m, 1H), 2.33-2.44 (m, 2H).

Example 125: Preparation of 4-(8-(1-acryloylpyrrolidin-3-yl)quinazolin-6-yl)-N-(4-(trifluoromethyl)pyridin-2-yl)benzamide

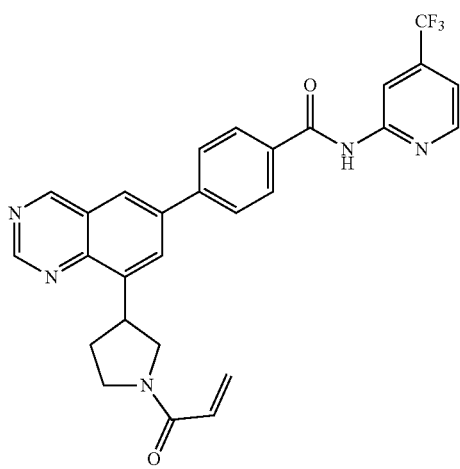

4-(8-(1-acryloylpyrrolidin-3-yl)quinazolin-6-yl)-N-(4-(trifluoromethyl)pyridin-2-yl)benzamide 4-(8-(1-Acryloylpyrrolidin-3-yl)quinazolin-6-yl)-N-(4-(trifluoromethyl)pyridin-2-yl)benzamide (91.0 mg) was prepared as described for 4-(8-(3-acrylamidophenyl)quinazolin-6-yl)-N-(pyridin-2-yl)benzamide. LRMS (M+H$^+$) m/z calculated 518.2, found 518.3. $^1$H NMR (DMSO-d6, 400 MHz) δ 11.40 (s, 1H), 9.70 (s, 1H), 9.39 (s, 1H), 8.71 (d, 1H), 8.59 (s, 1H), 8.50 (d, 1H), 8.33-8.40 (m, 1H), 8.23-8.25 (m, 2H), 8.05-8.08 (m, 2H), 7.56 (d, 1H), 6.62-6.70 (m, 1H), 6.16-6.22 (m, 1H), 5.66- 5.73 (m, 1H), 4.41-4.63 (m, 1H), 4.16-4.22 (m, 1H), 3.69-3.89 (m, 2H), 3.49-3.58 (m, 1H), 2.36-2.50 (m, 2H).

Example 126: Preparation of 4-(5-(1-acryloylpyrrolidin-3-yl)pyrrolo[1,2-c]pyrimidin-7-yl)-3-fluoro-N-(pyridin-2-yl)benzamide

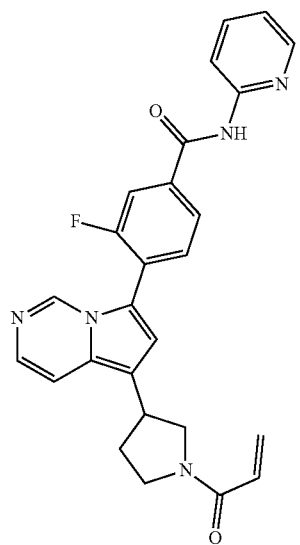

4-(5-(1-acryloylpyrrolidin-3-yl)pyrrolo[1,2-c]pyrimidin-7-yl)-3-fluoro-N-(pyridin-2-yl)benzamide 4-(5-(1-Acryloylpyrrolidin-3-yl)pyrrolo[1,2-c]pyrimidin-7-yl)-3-fluoro-N-(pyridin-2-yl)benzamide (18.0 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 456.2, found 456.3. $^1$H NMR (DMSO-d6, 400 MHz) δ 10.97 (s, 1H), 8.83 (s, 1H), 8.42 (s, 1H), 8.21 (d, 1H), 8.09-8.03 (m, 2H), 7.89-7.80 (m, 2H), 7.67-7.61 (m, 1H), 7.48 (d, 1H), 7.22-7.18 (m, 2H), 6.64 (dd, 1H), 6.19-6.14 (m, 1H), 5.71-5.67 (m, 1H), 4.09-3.93 (m, 1H), 3.84-3.54 (m, 4H), 2.32-1.98 (m, 2H).

Example 127: Preparation of 4-(8-(3-acrylamidophenyl)quinazolin-6-yl)-2-fluoro-N-(4-(trifluoromethyl)pyridin-2-yl)benzamide

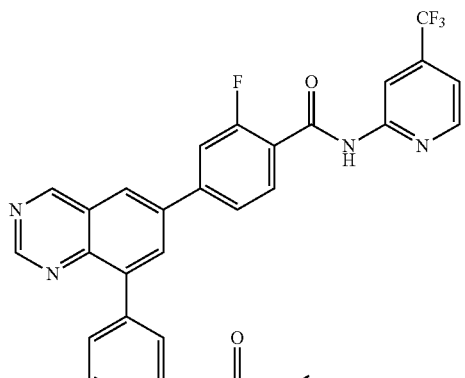

4-(8-(3-acrylamidophenyl)quinazolin-6-yl)-2-fluoro-N-(4-(trifluoromethyl)pyridin-2-yl)benzamide 4-(8-(3-Acrylamidophenyl)quinazolin-6-yl)-2-fluoro-N-(4-(trifluoromethyl)pyridin-2-yl)benzamide (13.6 mg) was prepared as described for 4-(8-(3-acrylamidophenyl)quinazolin-6-yl)-N-(pyridin-2-yl)benzamide. LRMS (M+H$^+$) m/z calculated 558.1, found 558.2. $^1$H NMR (DMSO-d6, 400 MHz) δ 11.40 (s, 1H), 10.48 (s, 1H), 9.76 (s, 1H), 9.36 (s, 1H), 8.44-8.69 (m, 4H), 7.49-8.09 (m, 8H), 5.75-6.56 (m, 3H).

Example 128: Preparation of 2-(4-(8-(1-acryloylpyrrolidin-3-yl)quinazolin-6-yl)benzamido)isonicotinamide

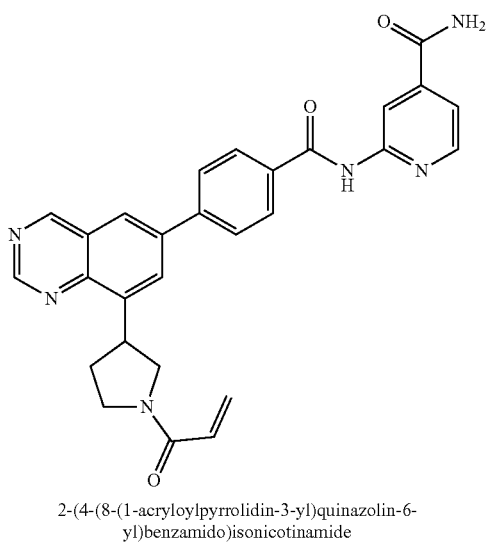 [SMILES: C=CC(=O)N1CCC(c2cc(-c3ccc(C(=O)Nc4cc(C(N)=O)ccn4)cc3)cc3cncnc23)C1]

2-(4-(8-(1-acryloylpyrrolidin-3-yl)quinazolin-6-yl)benzamido)isonicotinamide 2-(4-(8-(1-Acryloylpyrrolidin-3-yl)quinazolin-6-yl)benzamido)isonicotinamide (7.8 mg) was prepared as described for 4-(8-(3-acrylamidophenyl)quinazolin-6-yl)-N-(pyridin-2-yl)benzamide. LRMS (M+H$^+$) m/z calculated 493.2, found 493.2. $^1$H NMR (DMSO-d6, 400 MHz) δ 11.06 (s, 1H), 9.70 (s, 1H), 9.40 (s, 1H), 8.60 (s, 1H), 8.49-8.54 (m, 2H), 8.36 (d, 1H), 8.23-8.25 (m, 3H), 8.05-8.08 (m, 2H), 7.71 (s, 1H), 7.56-7.57 (m, 1H), 6.62-6.70 (m, 1H), 6.16-6.22 (m, 1H), 5.66-5.73 (m, 1H), 4.40-4.63 (m, 1H), 4.16-4.22 (m, 1H), 3.62-3.89 (m, 3H), 2.34-2.50 (m, 2H).

Example 129: Preparation of 4-(8-(3-acrylamidophenyl)quinazolin-6-yl)-3-fluoro-N-(4-(trifluoromethyl)pyridin-2-yl)benzamide

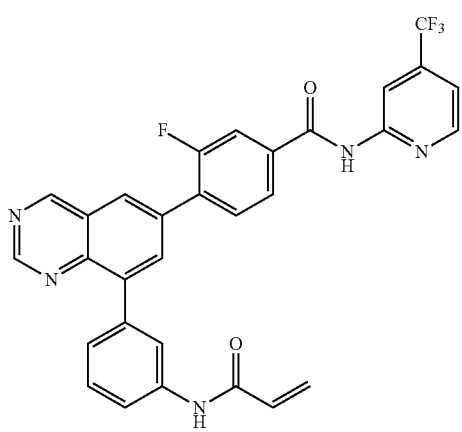

4-(8-(3-acrylamidophenyl)quinazolin-6-yl)-3-fluoro-N-(4-(trifluoromethyl)pyridin-2-yl)benzamide 4-(8-(3-Acrylamidophenyl)quinazolin-6-yl)-3-fluoro-N-(4-(trifluoromethyl)pyridin-2-yl)benzamide (17.3 mg) was prepared as described for 4-(8-(3-acrylamidophenyl)quinazolin-6-yl)-N-(pyridin-2-yl)benzamide. LRMS (M+H$^+$) m/z calculated 558.1, found 558.2. $^1$H NMR (DMSO-d6, 400 MHz) δ 11.50 (s, 1H), 10.29 (s, 1H), 9.79 (s, 1H), 9.38 (s, 1H), 8.72 (d, 1H), 8.54 (d, 1H), 8.26 (s, 1H), 7.99-8.14 (m, 4H), 7.82 (s, 1H), 7.58 (d, 1H), 7.49 (d, 1H), 6.45-6.52 (m, 1H), 6.25-6.30 (m, 1H), 5.76-5.79 (m, 1H).

Example 130: Preparation of 4-(5-(1-acryloylpyrrolidin-3-yl)pyrrolo[1,2-c]pyrimidin-7-yl)-3-fluoro-N-(4-(trifluoromethyl)pyridin-2-yl)benzamide

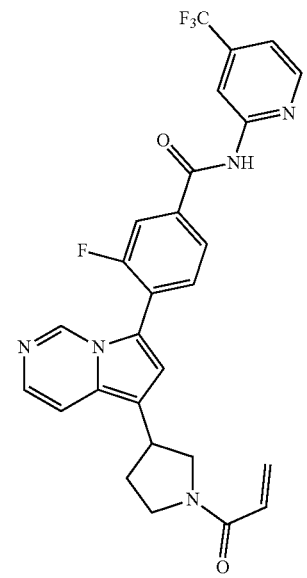

4-(5-(1-acryloylpyrrolidin-3-yl)pyrrolo[1,2-c]pyrimidin-7-yl)-3-fluoro-N-(4-(trifluoromethyl)pyridin-2-yl)benzamide 4-(5-(1-Acryloylpyrrolidin-3-yl)pyrrolo[1,2-c]pyrimidin-7-yl)-3-fluoro-N-(4-(trifluoromethyl)pyridin-2-yl)benzamide (17.0 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 524.2, found 524.2. $^1$H NMR (DMSO-d6, 400 MHz) δ 11.46 (s, 1H), 8.85 (d, 1H), 8.71 (d, 1H), 8.56 (s, 1H), 8.11-8.05 (m, 2H), 7.85-7.83 (m, 1H), 7.67-7.57 (m, 2H), 7.48 (d, 1H), 7.22 (d, 1H), 6.68-6.59 (m, 1H), 6.19-6.14 (m, 1H), 5.68-5.67 (m, 1H), 4.12-3.93 (m, 1H), 3.84-3.40 (m, 4H), 2.36-2.25 (m, 1H), 2.17-1.96 (m, 1H).

Example 131: Preparation of 4-(8-(3-acrylamidophenyl)quinazolin-6-yl)-N-(4-cyclopropylpyridin-2-yl)benzamide

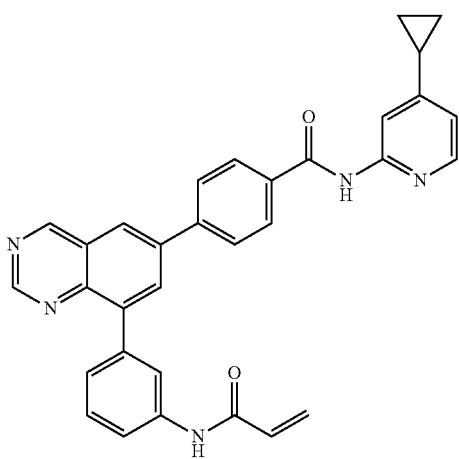

4-(8-(3-acrylamidophenyl)quinazolin-6-yl)-N-(4-cyclopropylpyridin-2-yl)benzamide 4-(8-(3-Acrylamidophenyl)quinazolin-6-yl)-N-(4-cyclopropylpyridin-2-yl)benzamide (22.5 mg) was prepared as described for 4-(8-(3-acrylamidophenyl)quinazolin-6-yl)-N-(pyridin-2-yl)benzamide. LRMS (M+H$^+$) m/z calculated 512.2, found 512.3. $^1$H NMR (DMSO-d6, 400 MHz) δ 10.78 (s, 1H), 10.28 (s, 1H), 9.76 (s, 1H), 9.35 (s, 1H), 8.63 (d, 1H), 8.42 (d, 1H), 8.21-8.24 (m, 3H), 7.99-8.11 (m, 4H), 7.85 (d, 1H), 7.48-7.52 (m, 2H), 6.89 (d, 1H), 6.45-6.52 (m, 1H), 6.25-6.30 (m, 1H), 5.77 (d, 1H), 1.99-2.01 (m, 1H), 1.09-1.12 (m, 2H), 0.81-0.84 (m, 2H).

Example 132: Preparation of 4-(8-(3-acrylamidophenyl)quinazolin-6-yl)-2-fluoro-N-(pyridin-2-yl)benzamide

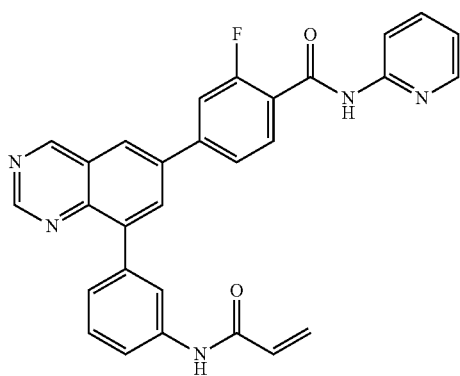

4-(8-(3-acrylamidophenyl)quinazolin-6-yl)-2-fluoro-N-(pyridin-2-yl)benzamide 4-(8-(3-Acrylamidophenyl)quinazolin-6-yl)-2-fluoro-N-(pyridin-2-yl)benzamide (10.8 mg) was prepared as described for 4-(8-(3-acrylamidophenyl)quinazolin-6-yl)-N-(pyridin-2-yl)benzamide. LRMS (M+H$^+$) m/z calculated 490.2, found 490.1. $^1$H NMR (CD$_3$OD, 400 MHz) δ 9.55 (s, 1H), 9.37 (s, 1H), 9.76 (s, 1H), 8.20-8.44 (m, 5H), 8.06 (s, 1H), 7.29-7.83 (m, 6H), 7.13-7.16 (m, 3H), 6.30-6.47 (m, 2H), 5.78 (d, 1H).

Example 133: Preparation of 2-(4-(8-(3-acrylamidophenyl)quinazolin-6-yl)-3-chlorobenzamido)isonicotinamide

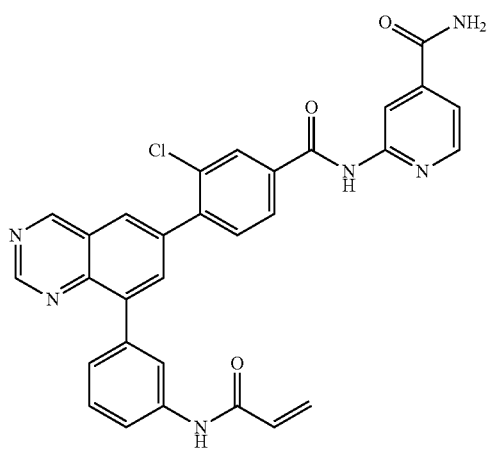

2-(4-(8-(3-acrylamidophenyl)quinazolin-6-yl)-3-chlorobenzamido)isonicotinamide 2-(4-(8-(3-Acrylamidophenyl)quinazolin-6-yl)-3-chlorobenzamido)isonicotinamide (44.2 mg) was prepared as described for 4-(8-(3-acrylamidophenyl)quinazolin-6-yl)-N-(pyridin-2-yl)benzamide. LRMS (M+H$^+$) m/z calculated 549.1, found 549.2. $^1$H NMR (DMSO-d6, 400 MHz) δ 11.22 (s, 1H), 10.30 (s, 1H), 9.78 (s, 1H), 9.39 (s, 1H), 8.06-8.58 (m, 8H), 7.50-7.85 (m, 6H), 5.76-6.30 (m, 3H).

Example 134: Preparation of 1-(3-(6-(2-methoxy-4-(pyridin-2-yloxy)phenyl)quinazolin-8-yl)pyrrolidin-1-yl)prop-2-en-1-one

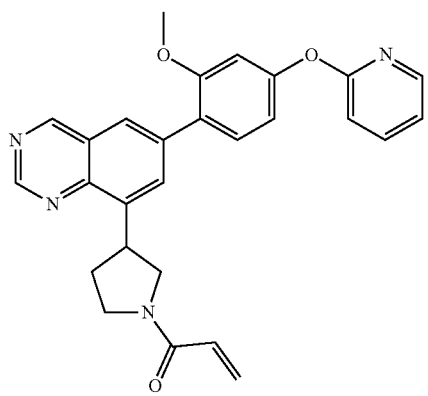

1-(3-(6-(2-methoxy-4-(pyridin-2-yloxy)phenyl)quinazolin-8-yl)pyrrolidin-1-yl)prop-2-en-1-one 1-(3-(6-(2-Methoxy-4-(pyridin-2-yloxy)phenyl)quinazolin-8-yl)pyrrolidin-1-yl)prop-2-en-1-one (33.9 mg) was prepared as described for 1-(3-(6-phenylquinazolin-8-yl)pyrrolidin-1-yl)prop-2-en-1-one. LRMS (M+H⁺) m/z calculated 453.2, found 453.2. $^1$H NMR (DMSO-d6, 400 MHz) δ 9.63 (s, 1H), 9.35 (s, 1H), 8.21 (s, 1H), 8.15 (s, 1H), 8.04 (d, 1H), 7.89 (t, 1H), 7.50 (d, 1H), 7.17 (t, 1H), 7.08 (d, 1H), 6.99 (s, 1H), 6.83 (d, 1H), 6.64-6.68 (m, 1H), 6.15-6.17 (m, 1H), 5.66-5.68 (m, 1H), 4.48-4.50 (m, 1H), 4.09-4.11 (m, 1H), 3.78 (s, 3H), 3.70-3.75 (m, 2H), 3.55-3.60 (m, 1H), 2.35-2.37 (m, 1H), 2.29-2.31 (m, 1H).

Example 135: Preparation of N-(3-(6-(3-fluoro-4-(pyridin-2-yloxy)phenyl)quinazolin-8-yl)phenyl)acrylamide

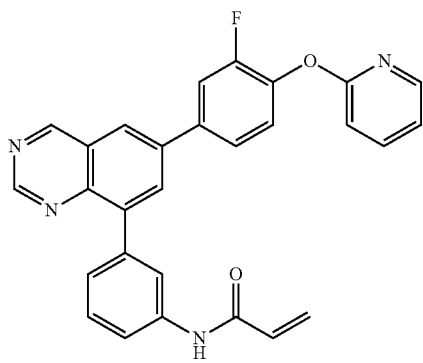

N-(3-(6-(3-fluoro-4-(pyridin-2-yloxy)phenyl)quinazolin-8-yl)phenyl)acrylamide

N-(3-(6-(3-fluoro-4-(pyridin-2-yloxy)phenyl)quinazolin-8-yl)phenyl)acrylamide (20.0 mg) was prepared as described for 1-(3-(6-phenylquinazolin-8-yl)pyrrolidin-1-yl)prop-2-en-1-one. LRMS (M+H⁺) m/z calculated 463.1, found 463.2. $^1$H NMR (DMSO-d6, 400 MHz) δ 10.02 (s, 1H), 9.72 (s, 1H), 9.34 (s, 1H), 8.57 (d, 1H), 8.40 (d, 1H), 8.14-8.16 (m, 1H), 7.83-8.04 (m, 6H), 7.49-7.54 (m, 3H), 7.16-7.21 (m, 2H), 6.45-6.48 (m, 1H), 6.25-6.30 (m, 1H), 5.75-5.79 (m, 1H).

Example 136: Preparation of 4-(5-(1-acryloylpyrrolidin-3-yl)pyrrolo[1,2-c]pyrimidin-7-yl)-N-(4-(trifluoromethyl)pyridin-2-yl)benzamide

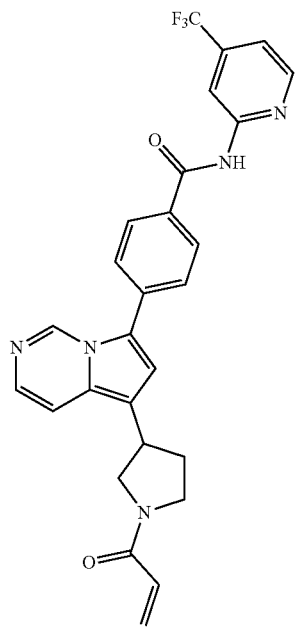

4-(5-(1-acryloylpyrrolidin-3-yl)pyrrolo[1,2-c]pyrimidin-7-yl)-N-(4-(trifluoromethyl)pyridin-2-yl)benzamide 4-(5-(1-Acryloylpyrrolidin-3-yl)pyrrolo[1,2-c]pyrimidin-7-yl)-N-(4-(trifluoromethyl)pyridin-2-yl)benzamide (41.8 mg) was prepared as described for 4-(5-(1-acryloylpyrrolidin-3-yl)pyrrolo[1,2-c]pyrimidin-7-yl)-N-phenylbenzamide. LRMS (M+H⁺) m/z calculated 506.2, found 506.3. $^1$H NMR (DMSO-d6, 400 MHz) δ 11.34 (s, 1H), 9.24 (s, 1H), 8.69 (d, 1H), 8.57 (s, 1H), 8.19 (d, 1H), 7.84-7.87 (m, 1H), 7.55-7.64 (m, 2H), 7.45 (d, 1H), 7.26 (d, 1H), 6.60-6.69 (m, 1H), 6.14-6.20 (m, 1H), 5.65-5.71 (m, 1H), 4.06-4.11 (m, 1H), 3.84-3.98 (m, 2H), 3.40-3.55 (m, 2H), 2.07-2.20 (m, 2H).

Example 137: Preparation of 4-(8-(3-acrylamidophenyl)quinazolin-6-yl)-N-(4-(trifluoromethyl)pyridin-2-yl)benzamide

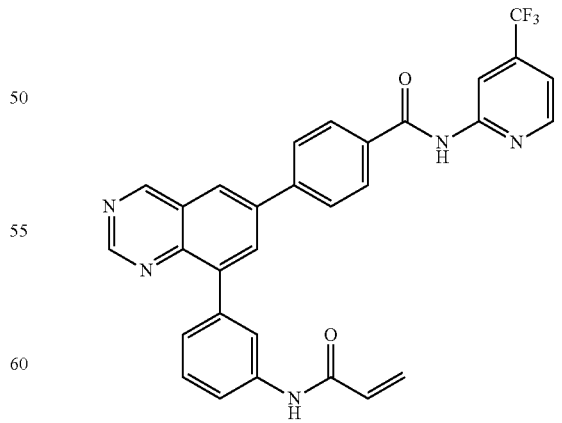

4-(8-(3-acrylamidophenyl)quinazolin-6-yl)-N-(4-(trifluoromethyl)pyridin-2-yl)benzamide 4-(8-(3-Acrylamidophenyl)quinazolin-6-yl)-N-(4-(trifluoromethyl)pyridin-2-yl)benzamide (10.7 mg) was prepared as described for 4-(8-(3-acrylamidophenyl)quinazolin-6-yl)-N-(pyridin-2-yl)benzamide. LRMS (M+H⁺) m/z calculated 540.2, found 540.2. ¹H NMR (DMSO-d6, 400 MHz) δ 11.40 (s, 1H), 10.30 (s, 1H), 9.76 (s, 1H), 9.35 (s, 1H), 8.71 (d, 1H), 8.59-8.63 (m, 1H), 8.42 (d, 1H), 8.25 (d, 2H), 8.12 (d, 2H), 8.05 (s, 1H), 7.84 (d, 1H), 7.50-7.57 (m, 3H), 6.46-6.50 (m, 1H), 6.28-6.30 (m, 1H), 5.76-5.79 (m, 1H).

Example 138: Preparation of 2-(4-(8-(3-acrylamidophenyl)quinazolin-6-yl)benzamido)isonicotinamide

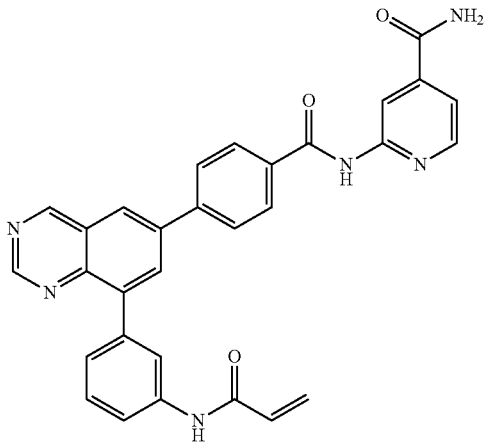

2-(4-(8-(3-acrylamidophenyl)quinazolin-6-yl)benzamido)isonicotinamide 2-(4-(8-(3-Acrylamidophenyl)quinazolin-6-yl)benzamido)isonicotinamide (7.5 mg) was prepared as described for 4-(8-(3-acrylamidophenyl)quinazolin-6-yl)-N-(pyridin-2-yl)benzamide. LRMS (M+H⁺) m/z calculated 515.2, found 515.3. ¹H NMR (DMSO-d6, 400 MHz) δ 11.07 (s, 1H), 10.28 (s, 1H), 9.77 (s, 1H), 9.35 (s, 1H), 8.65 (d, 2H), 8.53 (d, 1H), 8.43 (d, 1H), 8.24-8.27 (m, 3H), 8.05-8.13 (m, 3H), 7.84 (d, 1H), 7.50-7.57 (m, 3H), 6.45-6.48 (m, 1H), 6.28-6.30 (m, 1H), 5.76-5.79 (m, 1H).

Example 139: Preparation of 4-(8-(3-acrylamidophenyl)quinazolin-6-yl)-N-(4-cyclopropylpyridin-2-yl)-2-fluorobenzamide

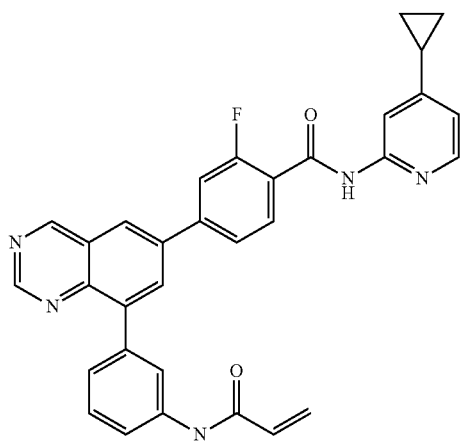

4-(8-(3-acrylamidophenyl)quinazolin-6-yl)-N-(4-cyclopropylpyridin-2-yl)-2-fluorobenzamide 4-(8-(3-Acrylamidophenyl)quinazolin-6-yl)-N-(4-cyclopropylpyridin-2-yl)-2-fluorobenzamide (31.1 mg) was prepared as described for 4-(8-(3-acrylamidophenyl)quinazolin-6-yl)-N-(pyridin-2-yl)benzamide. LRMS (M+H⁺) m/z calculated 530.2, found 530.3. ¹H NMR (DMSO-d6, 400 MHz) δ 10.72 (s, 1H), 10.28 (s, 1H), 9.75 (s, 1H), 9.36 (s, 1H), 8.66 (d, 1H), 8.43 (d, 1H), 8.19 (d, 1H), 7.83-8.05 (m, 6H), 7.49-7.53 (m, 2H), 6.88-6.90 (m, 1H), 6.48-6.52 (m, 1H), 6.28-6.30 (m, 1H), 5.79 (d, 1H), 1.98-2.01 (m, 1H), 1.09-1.12 (m, 2H), 0.81-0.82 (m, 2H).

Example 140: Preparation of 4-(8-(3-acrylamidophenyl)quinazolin-6-yl)-N-(4-cyclopropylpyridin-2-yl)-2-methoxybenzamide

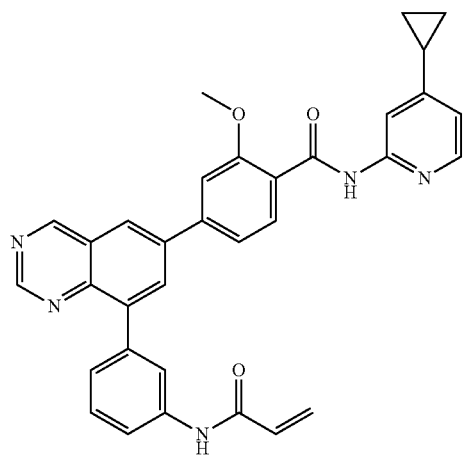

4-(8-(3-acrylamidophenyl)quinazolin-6-yl)-N-(4-cyclopropylpyridin-2-yl)-2-methoxybenzamide 4-(8-(3-Acrylamidophenyl)quinazolin-6-yl)-N-(4-cyclopropylpyridin-2-yl)-2-methoxybenzamide (6 mg) was prepared as described for 4-(8-(3-acrylamidophenyl)quinazolin-6-yl)-N-(pyridin-2-yl)benzamide. LRMS (M+H⁺) m/z calculated 542.2, found 542.3. ¹H NMR (DMSO-d6, 400 MHz) δ 10.44 (s, 1H), 10.28 (s, 1H), 9.76 (s, 1H), 9.35 (s, 1H), 8.64 (d, 1H), 8.45 (d, 1H), 8.17 (d, 1H), 8.04-8.10 (m, 3H), 7.83-7.84 (m, 1H), 7.68-7.74 (m, 2H), 7.49-7.51 (m, 2H), 6.87-6.89 (m, 1H), 6.45-6.50 (m, 1H), 6.25-6.30 (m, 1H), 5.75-5.79 (m, 1H), 4.16 (s, 3H), 1.98-2.01 (m, 1H), 1.09-1.12 (m, 2H), 0.81-0.83 (m, 2H).

Example 141: Preparation of 4-(8-(3-acrylamidophenyl)quinazolin-6-yl)-2-methoxy-N-(pyridin-2-yl)benzamide

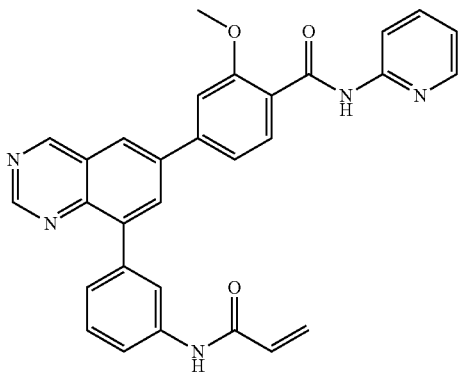

4-(8-(3-acrylamidophenyl)quinazolin-6-yl)-2-methoxy-N-(4-pyridin-2-yl)benzamide 4-(8-(3-Acrylamidophenyl)quinazolin-6-yl)-2-methoxy-N-(pyridin-2-yl)benzamide (9.7 mg) was prepared as described for 4-(8-(3-acrylamidophenyl)quinazolin-6-yl)-N-(pyridin-2-yl)benzamide. LRMS (M+H$^+$) m/z calculated 502.2, found 502.2. $^1$H NMR (DMSO-d6, 400 MHz) δ 10.53 (s, 1H), 10.29 (s, 1H), 9.76 (s, 1H), 9.35 (s, 1H), 8.65 (d, 1H), 8.29-8.45 (m, 3H), 8.04-8.10 (m, 2H), 7.84-7.89 (m, 2H), 7.68-7.75 (m, 2H), 7.49-7.51 (m, 2H), 7.18-7.20 (m, 1H), 6.45-6.52 (m, 1H), 6.25-6.30 (m, 1H), 5.76-5.79 (m, 1H), 4.16 (s, 3H).

Example 142: Preparation of 4-(8-(1-acryloylpyrrolidin-3-yl)quinazolin-6-yl)-N-(5-(trifluoromethyl)pyridin-2-yl)benzamide

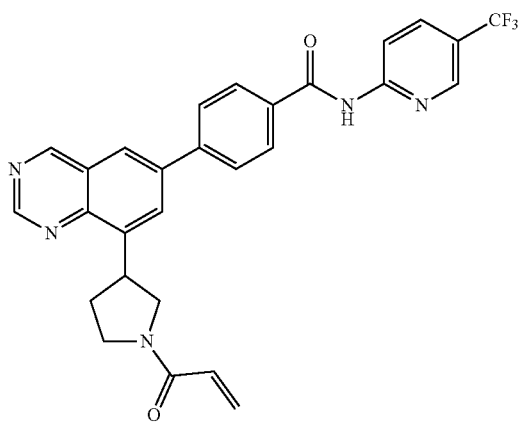

4-(8-(1-acryloylpyrrolidin-3-yl)quinazolin-6-yl)-N-(5-(trifluoromethyl)pyridin-2-yl)benzamide 4-(8-(3-Acrylamidophenyl)quinazolin-6-yl)-2-methoxy-N-(pyridin-2-yl)benzamide (32 mg) was prepared as described for 4-(8-(3-acrylamidophenyl)quinazolin-6-yl)-N-(pyridin-2-yl)benzamide. LRMS (M+H$^+$) m/z calculated 518.2, found 518.3. $^1$H NMR (DMSO-d6, 400 MHz) δ 11.38 (s, 1H), 9.70 (s, 1H), 9.40 (s, 1H), 8.81 (s, 1H), 8.23-8.51 (m, 6H), 8.05-8.09 (m, 2H), 6.64-6.69 (m, 1H), 6.16-6.22 (m, 1H), 5.66-5.73 (m, 1H), 4.47-4.62 (m, 1H), 4.11-4.21 (m, 1H), 3.77-3.89 (m, 3H), 2.36-2.47 (m, 2H).

Example 143: Preparation of 1-(3-(7-(4-((4-(trifluoromethyl)pyridin-2-yl)oxy)phenyl)pyrrolo[1,2-c]pyrimidin-5-yl)pyrrolidin-1-yl)prop-2-en-1-one

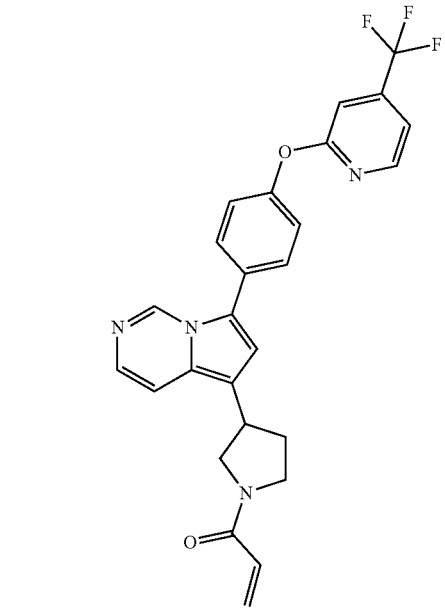

1-(3-(7-(4-((4-(trifluoromethyl)pyridin-2-yl)oxy)phenyl)pyrrolo[1,2-c]pyrimidin-5-yl)pyrrolidin-1-yl)prop-2-en-1-one 1-(3-(7-(4-((4-(Trifluoromethyl)pyridin-2-yl)oxy)phenyl)pyrrolo[1,2-c]pyrimidin-5-yl)pyrrolidin-1-yl)prop-2-en-1-one (28 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 479.2, found 479.3. $^1$H NMR (DMSO-d6, 400 MHz) δ 9.11 (s, 1H), 8.44 (d, 1H), 7.75-7.72 (m, 2H), 7.60-7.52 (m, 3H), 7.40-7.32 (m, 3H), 7.10 (d, 1H), 6.63 (dd, 1H), 6.18 (dd, 1H), 5.67 (dd, 1H), 4.09-3.91 (m, 1H), 3.82-3.42 (m, 4H), 2.34-2.22 (m, 1H), 2.18-2.05 (m, 1H).

Example 144: Preparation of 4-(8-(3-acrylamidophenyl)quinazolin-6-yl)-2-methoxy-N-(4-(trifluoromethyl)pyridin-2-yl)benzamide

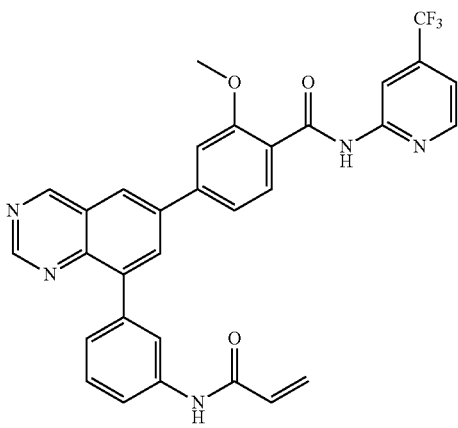

4-(8-(3-acrylamidophenyl)quinazolin-6-yl)-2-methoxy-N-(4-(trifluoromethyl)pyridin-2-yl)benzamide 4-(8-(3-Acrylamidophenyl)quinazolin-6-yl)-2-methoxy-N-(4-(trifluoromethyl)pyridin-2-yl)benzamide (6 mg) was prepared as described for 4-(8-(3-acrylamidophenyl)quinazolin-6-yl)-N-(pyridin-2-yl)benzamide. LRMS (M+H$^+$) m/z calculated 570.2, found 570.2. $^1$H NMR (DMSO-d6, 400 MHz) δ 10.92-10.93 (m, 1H), 10.29 (s, 1H), 9.76 (s, 1H), 9.36 (s, 1H), 8.61-8.68 (m, 3H), 8.44 (d, 1H), 8.05 (d, 1H), 7.69-7.85 (m, 3H), 7.51-7.57 (m, 3H), 6.45-6.52 (m, 1H), 6.27 (d, 1H), 5.77 (d, 1H), 4.17 (s, 3H).

Example 145: Preparation of 1-(3-(2-amino-6-(2-fluoro-4-(pyridin-2-yloxy)phenyl)quinazolin-8-yl)pyrrolidin-1-yl)prop-2-en-1-one

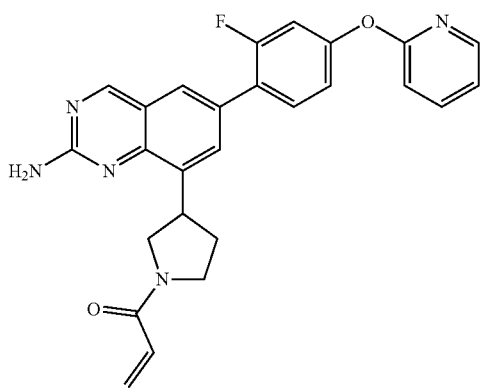

1-(3-(2-amino-6-(2-fluoro-4-(pyridin-2-yloxy)phenyl)quinazolin-8-yl)pyrrolidin-1-yl)prop-2-en-1-one 1-(3-(2-Amino-6-(2-fluoro-4-(pyridin-2-yloxy)phenyl)quinazolin-8-yl)pyrrolidin-1-yl)prop-2-en-1-one (9.7 mg) was prepared as described for 1-(3-(6-phenylquinazolin-8-yl)pyrrolidin-1-yl)prop-2-en-1-one. LRMS (M+H$^+$) m/z calculated 456.2, found 456.2. $^1$H NMR (DMSO-d6, 400 MHz) δ 9.18 (s, 1H), 8.20 (d, 1H), 7.90 (s, 2H), 7.83 (d, 1H), 7.66 (t, 1H), 7.19-7.21 (m, 2H), 7.12 (t, 2H), 6.99 (d, 2H), 6.64-6.70 (m, 1H), 6.13-6.15 (m, 1H), 5.66-5.68 (m, 1H), 4.32-4.34 (m, 0.5H), 4.20-4.25 (m, 1H), 4.07-4.09 (m, 0.5H), 3.72-3.78 (m, 2H), 3.45-3.47 (m, 1H), 2.36-2.38 (m, 2H).

Example 146: Preparation of 1-(3-(6-(3-methoxy-4-(pyridin-2-yloxy)phenyl)quinazolin-8-yl)pyrrolidin-1-yl)prop-2-en-1-one

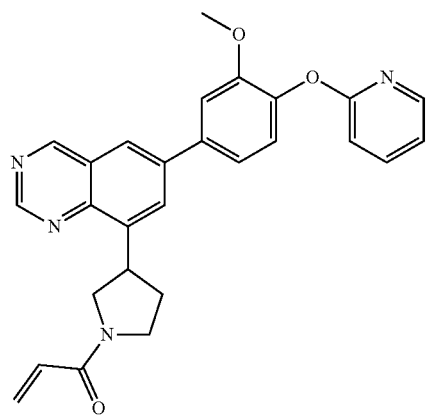

1-(3-(6-(3-methoxy-4-(pyridin-2-yloxy)phenyl)quinazolin-8-yl)pyrrolidin-1-yl)prop-2-en-1-one 1-(3-(6-(3-Methoxy-4-(pyridin-2-yloxy)phenyl)quinazolin-8-yl)pyrrolidin-1-yl)prop-2-en-1-one (14.4 mg) was prepared as described for 1-(3-(6-phenylquinazolin-8-yl)pyrrolidin-1-yl)prop-2-en-1-one. LRMS (M+H$^+$) m/z calculated 453.2, found 453.3. $^1$H NMR (DMSO-d6, 400 MHz) δ 9.67 (s, 1H), 9.37 (d, 1H), 8.42 (s, 1H), 8.30 (d, 1H), 8.09 (d, 1H), 7.82-7.85 (m, 1H), 7.56 (s, 1H), 7.45-7.49 (m, 1H), 7.28-7.30 (m, 1H), 7.03-7.10 (m, 1H), 6.62-6.72 (m, 1H), 6.15-6.21 (m, 1H), 5.65-5.72 (m, 1H), 4.45-4.63 (m, 1H), 4.09-4.22 (m, 1H), 3.75-3.91 (m, 5H), 3.49-3.65 (m, 1H), 2.35-2.40 (m, 2H).

Example 147: Preparation of 4-(8-(1-acryloylpyrrolidin-3-yl)quinazolin-6-yl)-N-(pyridazin-4-yl)benzamide

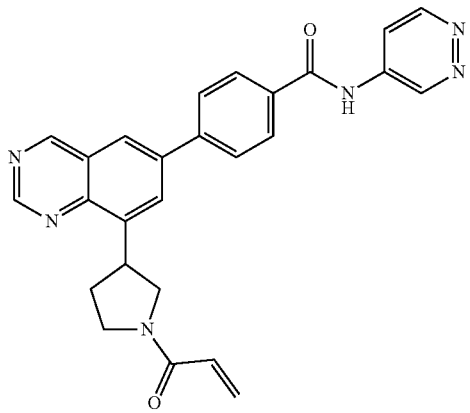

4-(8-(1-acryloylpyrrolidin-3-yl)quinazolin-6-yl)-N-(pyridazin-4-yl)benzamide 4-(8-(1-Acryloylpyrrolidin-3-yl)quinazolin-6-yl)-N-(pyridazin-4-yl)benzamide (9.5 mg) was prepared as described for 4-(8-(3-acrylamidophenyl)quinazolin-6-yl)-N-(pyridin-2-yl)benzamide. LRMS (M+H$^+$) m/z calculated 451.2, found 451.2. $^1$H NMR (DMSO-d6, 400 MHz) δ 10.92 (m, 1H), 9.72 (s, 1H), 9.58 (d, 1H), 9.40 (d, 1H), 9.12 (d, 1H), 8.50-8.52 (m, 1H), 8.36 (d, 1H), 8.11-8.20 (m, 4H), 6.62-6.70 (m, 1H), 6.16-6.22 (m, 1H), 5.66-5.74 (m, 1H), 4.46-4.62 (m, 1H), 4.21-4.49 (m, 1H), 3.64-3.88 (m, 3H), 2.41-2.49 (m, 2H).

Example 148: Preparation of 4-(5-(1-acryloylpyrrolidin-3-yl)pyrrolo[1,2-c]pyrimidin-7-yl)-2-fluoro-N-(4-methoxypyridin-2-yl)benzamide

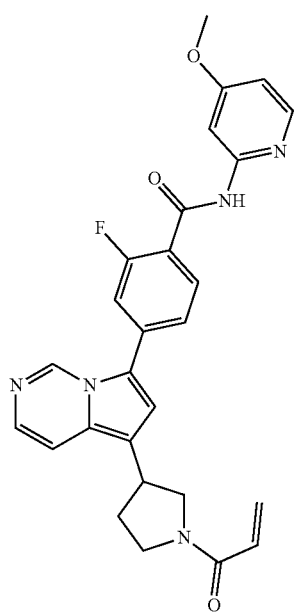

4-(5-(1-acryloylpyrrolidin-3-yl)pyrrolo[1,2-c]pyrimidin-7-yl)-2-fluoro-N-(4-methoxypyridin-2-yl)benzamide 4-(5-(1-Acryloylpyrrolidin-3-yl)pyrrolo[1,2-c]pyrimidin-7-yl)-2-fluoro-N-(4-methoxypyridin-2-yl)benzamide (39 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 486.2, found 486.3. $^1$H NMR (DMSO-d6, 400 MHz) δ 10.66 (s, 1H), 9.24 (s, 1H), 8.19 (d, 1H), 7.80-7.85 (m, 2H), 7.60-7.72 (m, 3H), 7.46-7.48 (m, 1H), 7.30 (d, 1H), 6.79-6.81 (m, 1H), 6.59-6.69 (m, 1H), 6.14-6.19 (m, 1H), 5.65-5.71 (m, 1H), 4.06-4.10 (m, 0.5H), 3.62-3.97 (m, 7.5H), 2.03-2.33 (m, 2H).

Example 149: Preparation of 4-(5-(1-acryloylpyrrolidin-3-yl)pyrrolo[1,2-c]pyrimidin-7-yl)-N-(4-cyclopropylpyridin-2-yl)-3-fluorobenzamide

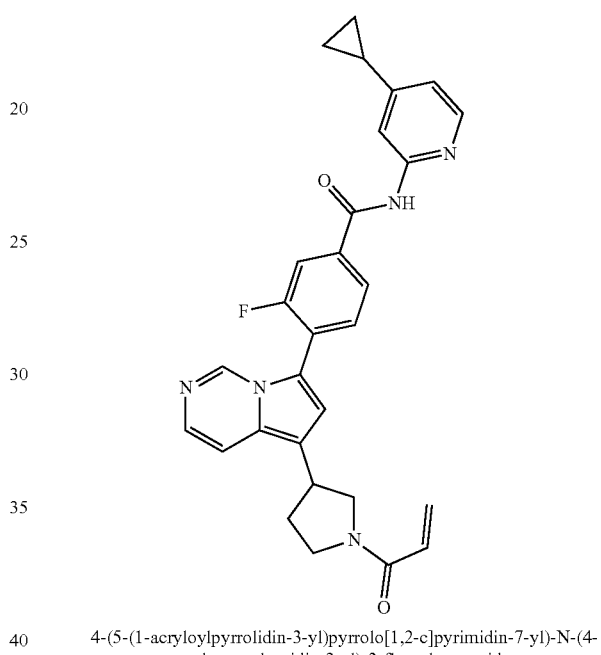

4-(5-(1-acryloylpyrrolidin-3-yl)pyrrolo[1,2-c]pyrimidin-7-yl)-N-(4-cyclopropylpyridin-2-yl)-3-fluorobenzamide 4-(5-(1-Acryloylpyrrolidin-3-yl)pyrrolo[1,2-c]pyrimidin-7-yl)-N-(4-cyclopropylpyridin-2-yl)-3-fluorobenzamide (30 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 496.2, found 496.3. $^1$H NMR (DMSO-d6, 400 MHz) δ 10.86 (s, 1H), 8.83 (d, 1H), 8.22 (d, 1H), 8.08-7.96 (m, 3H), 7.83-7.61 (m, 2H), 7.48 (d, 1H), 7.21 (d, 1H), 6.89 (d, 1H), 6.68-6.59 (m, 1H), 6.19-6.13 (m, 1H), 5.70-5.64 (m, 1H), 4.11-3.92 (m, 1H), 3.83-3.45 (m, 4H), 2.32-2.26 (m, 1H), 2.17-2.00 (m, 2H), 1.12-1.08 (m, 2H), 0.85- 0.80 (m, 2H).

Example 150: Preparation of 4-(5-(1-acryloylpyrrolidin-3-yl)pyrrolo[1,2-c]pyrimidin-7-yl)-3-fluoro-N-(4-methoxypyridin-2-yl)benzamide

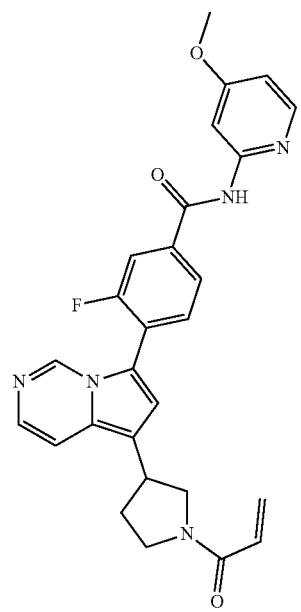

4-(5-(1-acryloylpyrrolidin-3-yl)pyrrolo[1,2-c]pyrimidin-7-yl)-3-fluoro-N-(4-methoxypyridin-2-yl)benzamide 4-(5-(1-Acryloylpyrrolidin-3-yl)pyrrolo[1,2-c]pyrimidin-7-yl)-3-fluoro-N-(4-methoxypyridin-2-yl)benzamide (24.5 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 486.2, found 486.3. $^1$H NMR (DMSO-d6, 400 MHz) δ 10.93 (s, 1H), 8.83 (d, 1H), 8.23 (d, 1H), 8.08-8.02 (m, 2H), 7.85-7.79 (m, 2H), 7.67-7.61 (m, 1H), 7.48 (d, 1H), 7.21 (d, 1H), 6.82-6.80 (m, 1H) 6.65-6.61 (m, 1H), 6.19-6.13 (m, 1H), 5.70-5.67 (m, 1H), 4.09-3.91 (m, 1H), 3.87 (s, 3H), 3.72-3.40 (m, 4H), 2.37-2.24 (m, 1H), 2.17-2.00 (m, 1H).

Example 151: Preparation of 4-(5-(1-acryloylpyrrolidin-3-yl)pyrrolo[1,2-c]pyrimidin-7-yl)-N-(4-cyanopyridin-2-yl)-3-fluorobenzamide

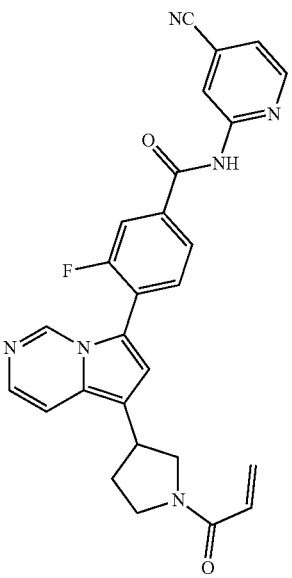

4-(5-(1-acryloylpyrrolidin-3-yl)pyrrolo[1,2-c]pyrimidin-7-yl)-N-(4-cyanopyridin-2-yl)-3-fluorobenzamide 4-(5-(1-Acryloylpyrrolidin-3-yl)pyrrolo[1,2-c]pyrimidin-7-yl)-N-(4-cyanopyridin-2-yl)-3-fluorobenzamide (14.5 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 481.2, found 481.2. $^1$H NMR (DMSO-d6, 400 MHz) δ 11.43 (s, 1H), 8.84 (d, 1H), 8.68 (d, 1H), 8.53 (s, 1H), 8.10-8.04 (m, 2H), 7.86-7.81 (m, 1H), 7.67-7.62 (m, 2H), 7.48 (d, 1H), 7.22 (d, 1H) 6.68-6.59 (m, 1H), 6.18-6.14 (m, 1H), 5.71-5.65 (m, 1H), 4.11-3.96 (m, 1H), 3.87-3.58 (m, 4H), 2.36-2.27 (m, 1H), 2.14-2.00 (m, 1H).

Example 152: Preparation of 4-(5-(1-acryloylpyrrolidin-3-yl)pyrrolo[1,2-c]pyrimidin-7-yl)-2-fluoro-N-(4-(trifluoromethyl)pyridin-2-yl)benzamide

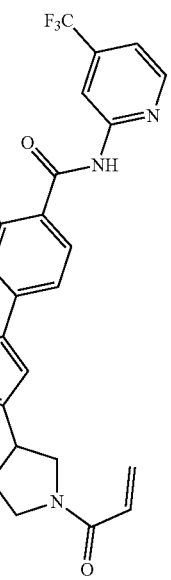

4-(5-(1-acryloylpyrrolidin-3-yl)pyrrolo[1,2-c]pyrimidin-7-yl)-2-fluoro-N-(4-(trifluoromethyl)pyridin-2-yl)benzamide 4-(5-(1-Acryloylpyrrolidin-3-yl)pyrrolo[1,2-c]pyrimidin-7-yl)-2-fluoro-N-(4-(trifluoromethyl)pyridin-2-yl)benzamide (25.5 mg) was prepared as described for 4-(5-(1-acryloylpyrrolidin-3-yl)pyrrolo[1,2-c]pyrimidin-7-yl)-N-phenylbenzamide. LRMS (M+H⁺) m/z calculated 524.2, found 524.2. ¹H NMR (DMSO-d6, 400 MHz) δ 11.29 (s, 1H), 9.25 (s, 1H), 6.68 (d, 1 H), 8.54 (s, 1H), 7.47-7.86 (m, 6H), 7.32 (d, 1H), 6.59-6.69 (m, 1H), 6.12-6.20 (m, 1H), 5.68 (t, 1H), 3.52-4.11 (m, 5H), 2.01-2.32 (m, 2H).

Example 153: Preparation of 4-(8-(3-acrylamidophenyl)quinazolin-6-yl)-N-(4-cyclopropylpyridin-2-yl)-3-fluorobenzamide

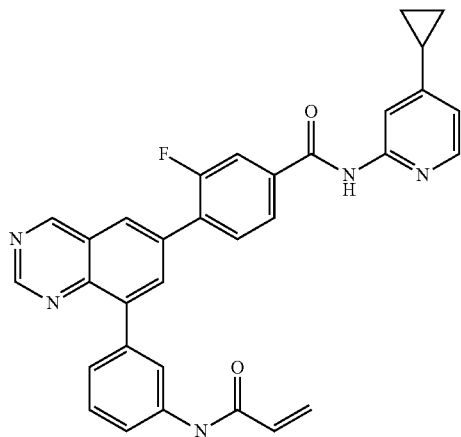

4-(8-(3-acrylamidophenyl)quinazolin-6-yl)-N-(4-cyclopropylpyridin-2-yl)-3-fluorobenzamide 4-(8-(3-Acrylamidophenyl)quinazolin-6-yl)-N-(4-cyclopropylpyridin-2-yl)-3-fluorobenzamide (2.5 mg) was prepared as described for 4-(8-(3-acrylamidophenyl)quinazolin-6-yl)-N-(pyridin-2-yl)benzamide. LRMS (M+H⁺) m/z calculated 530.2, found 530.3. ¹H NMR (DMSO-d6, 400 MHz) δ 10.91 (s, 1H), 10.30 (s, 1H), 9.79 (s, 1H), 9.39 (s, 1H), 8.51 (s, 1H), 8.23-8.26 (m, 2H), 7.98-8.11 (m, 7H), 7.83 (s, 1H), 6.91 (d, 1H), 6.45-6.49 (m, 1H), 6.30 (d, 1H), 5.78 (d, 1H), 1.98-2.02 (m, 1H), 1.09-1.12 (m, 2H), 0.82-0.83 (m, 2H).

Example 154: Preparation of 4-(8-(3-acrylamidophenyl)quinazolin-6-yl)-N-(4-cyanopyridin-2-yl)-3-fluorobenzamide

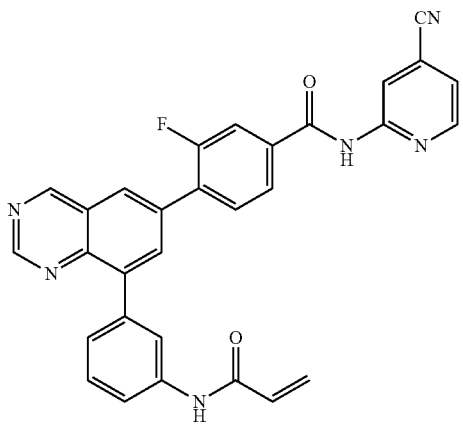

4-(8-(3-acrylamidophenyl)quinazolin-6-yl)-N-(4-cyanopyridin-2-yl)-3-fluorobenzamide 4-(8-(3-Acrylamidophenyl)quinazolin-6-yl)-N-(4-cyanopyridin-2-yl)-3-fluorobenzamide (2.8 mg) was prepared as described for 4-(8-(3-acrylamidophenyl)quinazolin-6-yl)-N-(pyridin-2-yl)benzamide. LRMS (M+H⁺) m/z calculated 515.2, found 515.2. ¹H NMR (DMSO-d6, 400 MHz) δ 11.49 (br, 1H), 10.30 (s, 1H), 9.79 (s, 1H), 9.38 (s, 1H), 8.69 (d, 1H), 8.53 (d, 2H), 8.26 (s, 1H), 7.97- 8.13 (m, 4H), 7.83 (s, 1H), 7.67 (d, 1H), 7.49 (d, 1H), 6.45-6.52 (m, 1H), 6.25-6.30 (m, 1H), 5.76-5.79 (m, 1H).

Example 155: Preparation of 4-(8-(1-acryloylpyrrolidin-3-yl)quinazolin-6-yl)-N-(pyridin-4-yl)benzamide

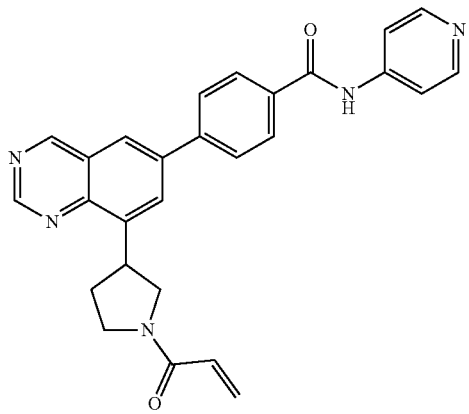

4-(8-(1-acryloylpyrrolidin-3-yl)quinazolin-6-yl)-N-(pyridin-4-yl)benzamide 4-(8-(1-Acryloylpyrrolidin-3-yl)quinazolin-6-yl)-N-(pyridin-4-yl)benzamide (7.8 mg) was prepared as described for 4-(8-(3-acrylamidophenyl)quinazolin-6-yl)-N-(pyridin-2-yl)benzamide. LRMS (M+H$^+$) m/z calculated 450.2, found 450.2. $^1$H NMR (DMSO-d6, 400 MHz) δ 10.75 (s, 1H), 9.76 (s, 1H), 9.44 (d, 1H), 8.55 (d, 1H), 8.36-8.43 (m, 1H), 8.12-8.21 (m, 4H), 7.88 (d, 1H), 6.65-6.73 (m, 1H), 6.19-6.26 (m, 1H), 5.70-5.78 (m, 1H), 4.50-4.68 (m, 1H), 4.15-4.29 (m, 1H), 3.81-3.93 (m, 3H), 2.35- 2.49 (m, 2H).

Example 156: Preparation of 4-(8-(3-acrylamidophenyl)quinazolin-6-yl)-N-(4-cyanopyridin-2-yl)-2-methoxybenzamide

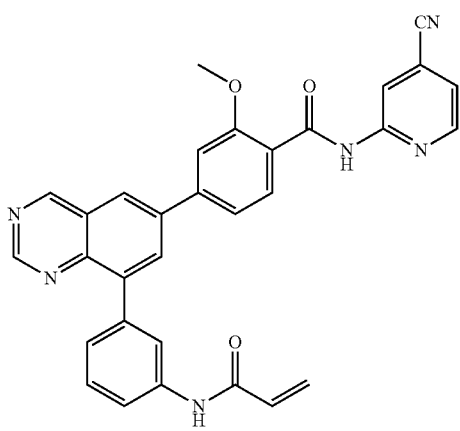

4-(8-(3-acrylamidophenyl)quinazolin-6-yl)-N-(4-cyanopyridin-2-yl)2-methoxybenzamide 4-(8-(3-Acrylamidophenyl)quinazolin-6-yl)-N-(4-cyanopyridin-2-yl)-2-methoxybenzamide (8.7 mg) was prepared as described for 4-(8-(3-acrylamidophenyl)quinazolin-6-yl)-N-(pyridin-2-yl)benzamide. LRMS (M+H$^+$) m/z calculated 527.2, found 527.2. $^1$H NMR (DMSO-d6, 400 MHz) δ 10.88 (s, 1H), 10.29 (s, 1H), 9.77 (s, 1H), 9.35 (s, 1H), 8.58-8.65 (m, 3H), 8.45 (s, 4H), 8.03 (d, 2H), 7.64-7.75 (m, 4H), 7.50-7.51 (m, 2H), 6.29-6.31 (m, 1H), 6.23 (d, 1H), 5.75-5.78 (m, 1H), 4.15 (s, 3H).

Example 157: Preparation of N-(3-(2-amino-6-(2-fluoro-4-(pyridin-2-yloxy)phenyl)quinazolin-8-yl)phenyl)acrylamide

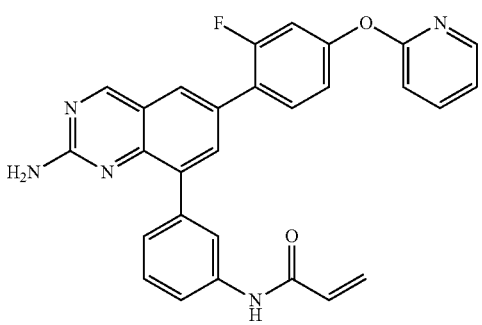

N-(3-(2-amino-6-(2-fluoro-4-(pyridin-2-yloxy)phenyl)quinazolin-8-yl)phenyl)acrylamide N-(3-(2-amino-6-(2-fluoro-4-(pyridin-2-yloxy)phenyl)quinazolin-8-yl)phenyl)acrylamide (16.4 mg) was prepared as described for 1-(3-(6-phenylquinazolin-8-yl)pyrrolidin-1-yl)prop-2-en-1-one. LRMS (M+H$^+$) m/z calculated 478.2, found 478.2. $^1$H NMR (DMSO-d6, 400 MHz) δ 10.22 (s, 1H), 9.23 (s, 1H), 8.21 (m, 1H), 8.04 (s, 1H), 7.89 (m, 3H), 7.71 (m, 2H), 7.42 (s, 2H), 7.23 (m, 2H), 7.11 (m, 2H), 6.91 (s, 2H), 6.47 (m, 1H), 6.24 (m, 1H), 5.75 (m, 1H).

Example 158: Preparation of N-(3-(2-amino-6-(3-fluoro-4-(pyridin-2-yloxy)phenyl)quinazolin-8-yl)phenyl)acrylamide

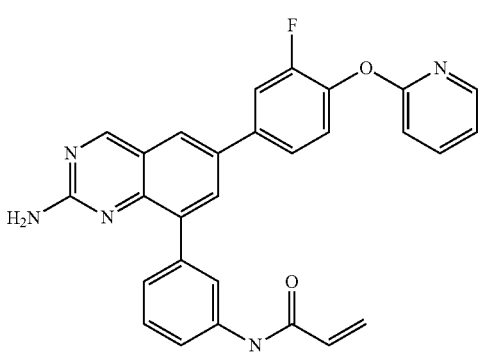

N-(3-(2-amino-6-(3-fluoro-4-(pyridin-2-yloxy)phenyl)quinazolin-8-yl)phenyl)acrylamide N-(3-(2-amino-6-(3-fluoro-4-(pyridin-2-yloxy)phenyl)quinazolin-8-yl)phenyl)acrylamide (20.4 mg) was prepared as described for 1-(3-(6-phenylquinazolin-8-yl)pyrrolidin-1-yl)prop-2-en-1-one. LRMS (M+H$^+$) m/z calculated 478.2, found 478.2. $^1$H NMR (DMSO-d6, 400 MHz) δ 10.21 (s, 1H), 9.22 (s, 1H), 8.20 (d, 1H), 8.14 (d, 1H), 8.00 (d, 1H), 7.87-7.90 (m, 4H), 7.67 (dd, 1H), 7.44-7.46 (m, 3H), 7.18-7.24 (m, 2H), 6.91 (s, 2H), 6.46-6.48 (m, 1H), 6.27-6.29 (m, 1H), 5.75-5.77 (m, 1H).

Example 159: Preparation of 1-(3-(7-(2-fluoro-4-(pyridin-2-yloxy)phenyl)pyrrolo[1,2-c]pyrimidin-5-yl)pyrrolidin-1-yl)prop-2-en-1-one

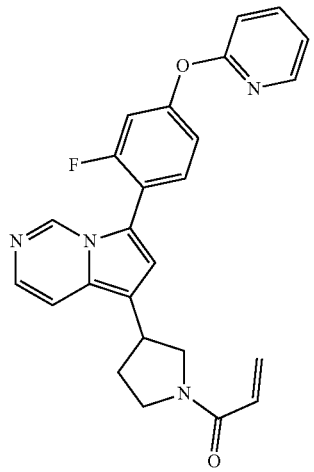

1-(3-(7-(2-fluoro-4-(pyridin-2-yloxy)phenyl)pyrrolo[1,2-c]pyrimidin-5-yl)pyrrolidin-1-yl)prop-2-en-1-one 1-(3-(7-(2-Fluoro-4-(pyridin-2-yloxy)phenyl)pyrrolo[1,2-c]pyrimidin-5-yl)pyrrolidin-1-yl)prop-2-en-1-one (7.2 mg) was prepared as described for 4-(5-(1-acryloylpyrrolidin-3-yl)pyrrolo[1,2-c]pyrimidin-7-yl)-N-phenylbenzamide. LRMS (M+H⁺) m/z calculated 429.2, found 429.3. ¹H NMR (DMSO-d6, 400 MHz) δ 8.75 (s, 1H), 8.24 (s, 1H), 7.93 (t, 1H), 7.58-7.66 (m, 2H), 7.42 (d, 1H), 7.08-7.31 (m, 5H), 6.62-6.66 (m, 1H), 6.14-6.18 (m, 1H), 5.67-5.72 (m, 1H), 3.45-4.09 (m, 5H), 2.25-2.36 (m, 2H).

Example 160: Preparation of 1-(3-(6-(3-fluoro-4-(pyridin-2-yloxy)phenyl)quinazolin-8-yl)pyrrolidin-1-yl)prop-2-en-1-one

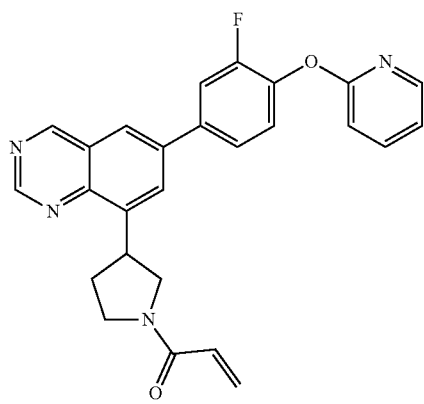

1-(3-(6-(3-fluoro-4-(pyridin-2-yloxy)phenyl)quinazolin-8-yl)pyrrolidin-1-yl)prop-2-en-1-one 1-(3-(6-(3-Fluoro-4-(pyridin-2-yloxy)phenyl)quinazolin-8-yl)pyrrolidin-1-yl)prop-2-en-1-one (23 mg) was prepared as described for 1-(3-(6-phenylquinazolin-8-yl)pyrrolidin-1-yl)prop-2-en-1-one. LRMS (M+H⁺) m/z calculated 441.2, found 441.2. ¹H NMR (DMSO-d6, 400 MHz) δ 9.66 (s, 1H), 9.38 (d, 1H), 8.44-8.46 (m, 1H), 8.38 (d, 1H), 8.13-8.15 (m, 1H), 7.93-7.99 (m, 2H), 7.80-7.82 (m, 1H), 7.50-7.52 (m, 1H), 7.20-7.30 (m, 2H), 6.65-6.67 (m, 1H), 6.19-6.21 (m, 1H), 5.69-5.71 (m, 1H), 4.61- 4.63 (m, 1H), 4.17-4.19 (m, 1H), 3.87-3.89 (m, 2H), 3.59-3.61 (m, 1H), 2.69-2.71 (m, 1H), 2.37-2.39 (m, 1H).

Example 161: Preparation of 4-(5-(1-acryloylpyrrolidin-3-yl)pyrrolo[1,2-c]pyrimidin-7-yl)-N-(4-cyanopyridin-2-yl)benzamide

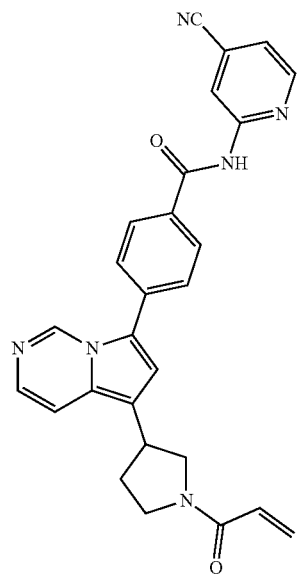

4-(5-(1-acryloylpyrrolidin-3-yl)pyrrolo[1,2-c]pyrimidin-7-yl)-N-(4-cyanopyridin-2-yl)benzamide 4-(5-(1-Acryloylpyrrolidin-3-yl)pyrrolo[1,2-c]pyrimidin-7-yl)-N-(4-cyanopyridin-2-yl)benzamide (31 mg) was prepared as described for 4-(5-(1-acryloylpyrrolidin-3-yl)pyrrolo[1,2-c]pyrimidin-7-yl)-N-phenylbenzamide. LRMS (M+H⁺) m/z calculated 463.2, found 463.2. ¹H NMR (DMSO-d6, 400 MHz) δ 11.33 (s, 1H), 9.24 (s, 1H), 8.67-8.54 (m, 2H), 8.18 (d, 2H), 7.86-7.83 (m, 2 H), 7.64-7.59 (m, 2H), 7.46-7.25 (m, 2H), 6.66-6.62 (m, 1H), 6.18-6.14 (m, 1H), 5.75-5.65 (m, 1H), 4.08-3.92 (m, 1H), 3.84-3.52 (m, 4H), 2.36-2.28 (m, 1H), 2.21-2.05 (m, 1H).

Example 162: Preparation of 4-(5-(1-acryloylpyrrolidin-3-yl)pyrrolo[1,2-c]pyrimidin-7-yl)-N-(4-methoxypyridin-2-yl)benzamide

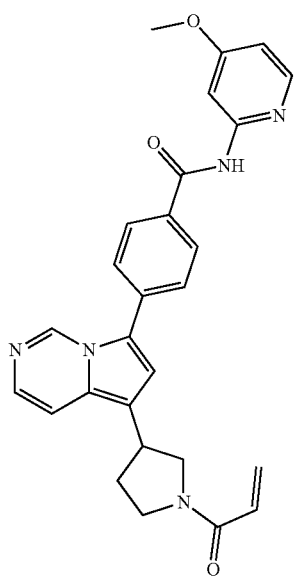

4-(5-(1-acryloylpyrrolidin-3-yl)pyrrolo[1,2-c]pyrimidin-7-yl)-N-(4-methoxypyridin-2-yl)benzamine 4-(5-(1-Acryloylpyrrolidin-3-yl)pyrrolo[1,2-c]pyrimidin-7-yl)-N-(4-methoxypyridin-2-yl)benzamide (22 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 468.2, found 468.3. $^1$H NMR (DMSO-d6, 400 MHz) δ 10.79 (s, 1H), 9.22 (s, 1H), 8.22-8.15 (m, 3H), 7.87-7.81 (m, 3H), 7.63-7.58 (m, 1H), 7.44 (d, 1H), 7.25 (d, 1H), 6.81-6.78 (m, 1H), 6.66-6.62 (m, 1H), 6.19-6.14 (m, 1H), 5.71-5.64 (m, 1H), 4.08-3.94 (m, 1H), 3.87 (s, 3H), 3.75-3.57 (m, 4H), 2.35-2.24 (m, 1H), 2.15-2.00 (m, 1H).

Example 163: Preparation of 4-(8-(3-acrylamidophenyl)quinazolin-6-yl)-2-chloro-N-(pyridin-2-yl)benzamide

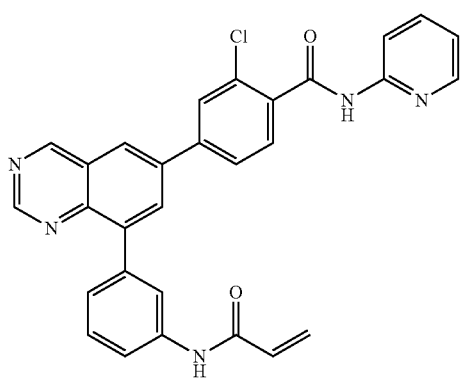

4-(8-(3-acrylamidophenyl)quinazolin-6-yl)-2-chloro-N-(pyridin-2-yl)benzamide 4-(8-(3-Acrylamidophenyl)quinazolin-6-yl)-2-chloro-N-(pyridin-2-yl)benzamide (37.2 mg) was prepared as described for 4-(8-(3-acrylamidophenyl)quinazolin-6-yl)-N-(pyridin-2-yl)benzamide. LRMS (M+H$^+$) m/z calculated 506.1, found 506.2. $^1$H NMR (DMSO-d6, 400 MHz) δ 11.10 (s, 1H), 10.29 (s, 1H), 9.76 (s, 1H), 9.36 (s, 1H), 8.65 (d, 1H), 8.37-8.42 (m, 2H), 8.17-8.22 (m, 2H), 8.03 (s, 2H), 7.75-7.87 (m, 3H), 7.48-7.53 (m, 2H), 7.19-7.20 (m, 1H), 6.45-6.49 (m, 1H), 6.30 (d, 1H), 5.76-5.79 (m, 1H).

Example 164: Preparation of 4-(5-(1-acryloylpyrrolidin-3-yl)pyrrolo[1,2-c]pyrimidin-7-yl)-N-(4-cyclopropylpyridin-2-yl)benzamide

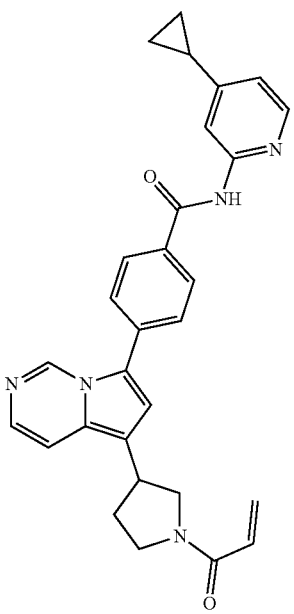

4-(5-(1-acryloylpyrrolidin-3-yl)pyrrolo[1,2-c]pyrimidin-7-yl)-N-(4-cyclopropylpyridin-2-yl)benzamide 4-(5-(1-Acryloylpyrrolidin-3-yl)pyrrolo[1,2-c]pyrimidin-7-yl)-N-(4-cyclopropylpyridin-2-yl)benzamide (33 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 478.2, found 478.3. $^1$H NMR (DMSO-d6, 400 MHz) δ 10.72 (s, 1H), 9.22 (s, 1H), 8.21-8.15 (m, 3H), 7.97 (s, 1H), 7.83-7.81 (m, 2H), 7.63-7.58 (m, 1H), 7.44 (d, 1H), 7.25 (d, 1H), 6.87 (d, 1H), 6.66-6.59 (m, 1H), 6.18-6.14 (m, 1H), 5.71-5.64 (m, 1H), 4.10-3.93 (m, 1H), 3.84-3.52 (m, 4H), 2.37-2.25 (m, 1H), 2.16-2.00 (m, 2H), 1.11-1.09 (m, 2H), 0.85-0.81 (m, 2H).

Example 165: Preparation of 4-(5-(1-acryloylpyrrolidin-3-yl)pyrrolo[1,2-c]pyrimidin-7-yl)-N-(4-cyclopropylpyridin-2-yl)-2-fluorobenzamide

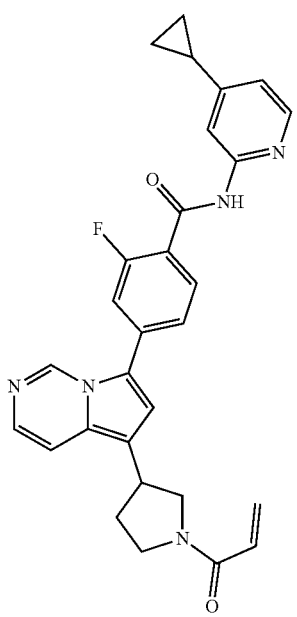

4-(5-(1-acryloylpyrrolidin-3-yl)pyrrolo[1,2-c]pyrimidin-7-yl)-N-(4-cyclopropylpyridin-2-yl)-2-fluorobenzamide 4-(5-(1-Acryloylpyrrolidin-3-yl)pyrrolo[1,2-c]pyrimidin-7-yl)-N-(4-cyclopropylpyridin-2-yl)-2-fluorobenzamide (19.4 mg) was prepared as described for 4-(5-(1-acryloylpyrrolidin-3-yl)pyrrolo[1,2-c]pyrimidin-7-yl)-N-phenylbenzamide. LRMS (M+H$^+$) m/z calculated 496.2, found 496.3. $^1$H NMR (DMSO-d6, 400 MHz) δ 10.60 (s, 1H), 9.24 (s, 1H), 8.18 (d, 1H), 7.97 (s, 1H), 7.80-7.84 (m, 1H), 7.60-7.72 (m, 3H), 7.47 (d, 1H), 7.30 (d, 1H), 6.88-6.89 (m, 1H), 6.59-6.69 (m, 1H), 6.14-6.20 (m, 1H), 5.65-5.72 (m, 1H), 4.06-4.11 (m, 0.5H), 3.92-3.97 (m, 0.5H), 3.52-3.89 (m, 4H), 2.06-2.30 (m, 2H), 1.97-2.03 (m, 1H), 1.09-1.11 (m, 2H), 0.80-0.82 (m, 2H).

Example 166: Preparation of N-(3-(2-amino-6-(2-methoxy-4-(pyridin-2-yloxy)phenyl)quinazolin-8-yl)phenyl)acrylamide

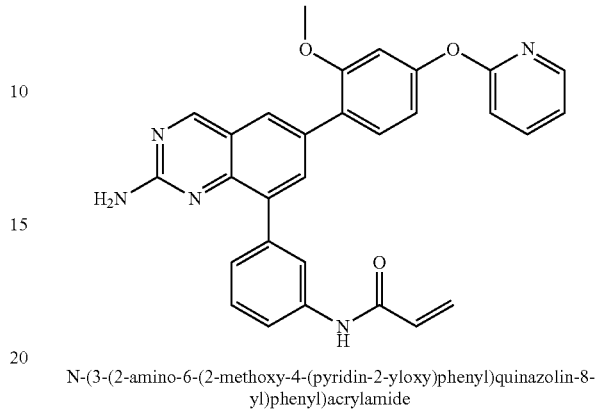

N-(3-(2-amino-6-(2-methoxy-4-(pyridin-2-yloxy)phenyl)quinazolin-8-yl)phenyl)acrylamide N-(3-(2-amino-6-(2-methoxy-4-(pyridin-2-yloxy)phenyl)quinazolin-8-yl)phenyl)acrylamide (33.3 mg) was prepared as described for 1-(3-(6-phenylquinazolin-8-yl)pyrrolidin-1-yl)prop-2-en-1-one. LRMS (M+H$^+$) m/z calculated 490.2, found 490.2. $^1$H NMR (DMSO-d6, 400 MHz) δ 10.19 (s, 1H), 9.20 (s, 1H), 8.20-8.22 (m, 1H), 7.89-7.91 (m, 3H), 7.81-7.83 (m, 1H), 7.77 (d, 1H), 7.42-7.50 (m, 3H), 7.16-7.18 (m, 1H), 7.09 (d, 1H), 6.96 (d, 1H), 6.81-6.90 (m, 3H), 6.46-6.48 (m, 1H), 6.29-6.31 (m, 1H), 5.77-5.80 (m, 1H), 3.79 (s, 3H).

Example 167: Preparation of 1-(3-(7-(3-methoxy-4-(pyridin-2-yloxy)phenyl)pyrrolo[1,2-c]pyrimidin-5-yl)pyrrolidin-1-yl)prop-2-en-1-one

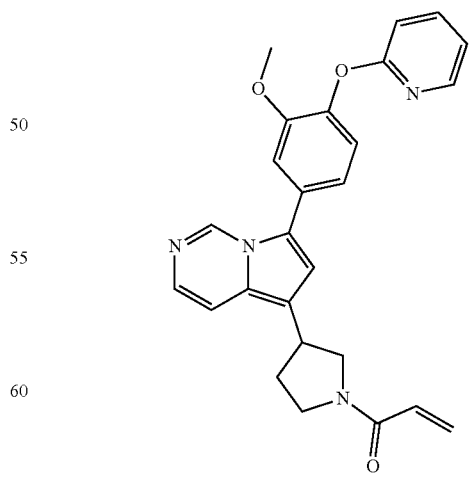

1-(3-(7-(3-methoxy-4-(pyridin-2-yloxy)phenyl)pyrrolo[1,2-c]pyrimidin-5-yl)pyrrolidin-1-yl)prop-2-en-1-one 1-(3-(7-(3-Methoxy-4-(pyridin-2-yloxy)phenyl)pyrrolo[1,2-c]pyrimidin-5-yl)pyrrolidin-1-yl)prop-2-en-1-one (8.5 mg) was prepared as described for 4-(5-(1-acryloylpyrrolidin-3-yl)pyrrolo[1,2-c]pyrimidin-7-yl)-N-phenylbenzamide. LRMS (M+H⁺) m/z calculated 441.2, found 441.3. ¹H NMR (DMSO-d6, 400 MHz) δ 9.17 (s, 1H), 8.10 (d, 1H), 7.85-7.81 (m, 1H), 7.60-7.55 (m, 1H), 7.40-7.25 (m, 4H), 7.15-7.02 (m, 3H), 6.68-6.59 (m, 1H), 6.19-6.15 (m, 1H), 5.71-5.63 (m, 1H), 4.10-3.93 (m, 1H), 3.84-3.54 (m, 7H), 2.38-2.24 (m, 1H), 2.16-1.99 (m, 1H).

Example 168: Preparation of 1-(3-(2-amino-6-(2-methoxy-4-(pyridin-2-yloxy)phenyl)quinazolin-8-yl)pyrrolidin-1-yl)prop-2-en-1-one

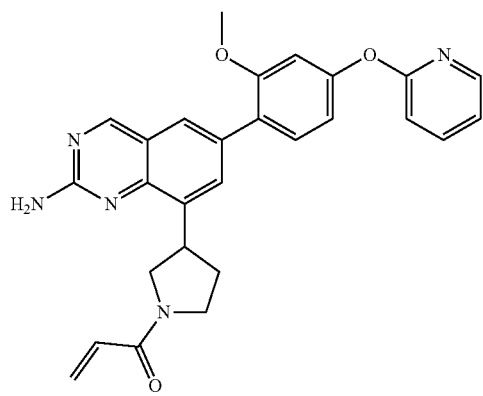

1-(3-(2-amino-6-(2-methoxy-4-(pyridin-2-yloxy)phenyl)quinazolin-8-yl)pyrrolidin-1-yl)prop-2-en-1-one 1-(3-(2-Amino-6-(2-methoxy-4-(pyridin-2-yloxy)phenyl)quinazolin-8-yl)pyrrolidin-1-yl)prop-2-en-1-one (26.7 mg) was prepared as described for 1-(3-(6-phenylquinazolin-8-yl)pyrrolidin-1-yl)prop-2-en-1-one. LRMS (M+H⁺) m/z calculated 468.2, found 468.3. ¹H NMR (DMSO-d6, 400 MHz) δ 9.13 (s, 1H), 8.21 (d, 1H), 7.88 (t, 1H), 7.73-7.78 (m, 2H), 7.42 (d, 1H), 7.16 (t, 1H), 7.07 (d, 1H), 6.88-6.94 (m, 3H), 6.79 (d, 1H), 6.59-6.66 (m, 1H), 6.16 (d, 1H), 5.63-5.70 (m, 1H), 4.04-4.34 (m, 2H), 3.65-3.71 (m, 1H), 3.57-3.61 (m, 1H), 3.39-3.46 (m, 1H), 2.14-2.44 (m, 2H).

Example 169: Preparation of 1-(3-(7-(2-methoxy-4-(pyridin-2-yloxy)phenyl)pyrrolo[1,2-c]pyrimidin-5-yl)pyrrolidin-1-yl)prop-2-en-1-one

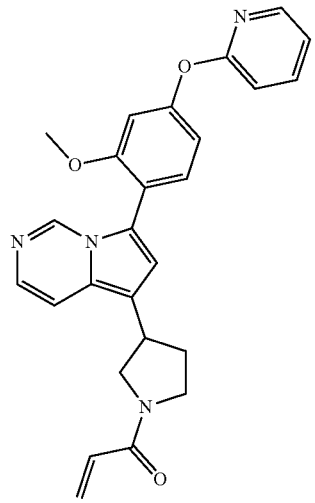

1-(3-(7-(2-methoxy-4-(pyridin-2-yloxy)phenyl)pyrrolo[1,2-c]pyrimidin-5-yl)pyrrolidin-1-yl)prop-2-en-1-one 1-(3-(7-(2-Methoxy-4-(pyridin-2-yloxy)phenyl)pyrrolo[1,2-c]pyrimidin-5-yl)pyrrolidin-1-yl)prop-2-en-1-one (54.1 mg) was prepared as described for 4-(5-(1-acryloylpyrrolidin-3-yl)pyrrolo[1,2-c]pyrimidin-7-yl)-N-phenylbenzamide. LRMS (M+H⁺) m/z calculated 441.2, found 441.3. ¹H NMR (DMSO-d6, 400 MHz) δ 8.45 (s, 1H), 8.22 (d, 1H), 7.90 (t, 1H), 7.53-7.59 (m, 1H), 7.37-7.41 (m, 2H), 7.18 (t, 1H), 7.11 (d, 1H), 7.01 (s, 1H), 6.93 (d, 1H), 6.60-6.69 (m, 1H), 6.16 (d, 1H), 5.68 (t, 1H), 4.08 (t, 1H), 3.94 (t, 1H), 3.84 (s, 3H), 3.39-3.69 (m, 2H), 1.99-2.35 (m, 2H).

Example 170: Preparation of 4-(8-(3-acrylamidophenyl)-5-aminoquinazolin-6-yl)-N-(pyridin-2-yl)benzamide

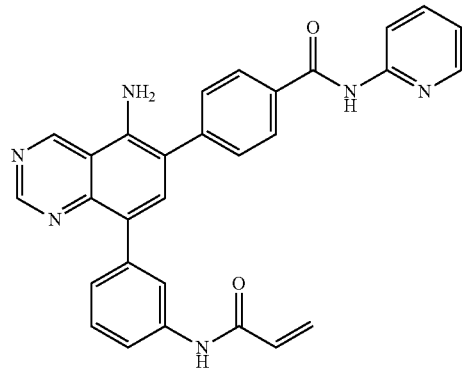

4-(8-(3-acrylamidophenyl)-5-aminoquinazolin-6-yl)-N-(pyridin-2-yl)benzamide 4-(8-(3-Acrylamidophenyl)-5-aminoquinazolin-6-yl)-N-(pyridin-2-yl)benzamide (2.1 mg) was prepared as described for 1-(3-(6-phenylquinazolin-8-yl)pyrrolidin-1-yl)prop-2-en-1-one. LRMS (M+H⁺) m/z calculated 487.2, found 487.3. ¹H NMR (DMSO-d6, 400 MHz) δ 10.85 (s, 1H), 10.19 (s, 1H), 9.95 (s, 1H), 9.21 (s, 1H), 8.42 (d, 1H), 8.22-8.25 (m, 3H), 7.74-7.91 (m, 2H), 7.69-7.74 (m, 4H), 7.39-7.44 (m, 2H), 7.18-7.22 (m, 1H), 6.44-6.50 (m, 3H), 6.24-6.28 (m, 1H), 5.74-5.77 (m, 1H).

Example 171: Preparation of 4-(8-(3-acrylamidophenyl)-5-aminoquinazolin-6-yl)-N-(4-cyclopropylpyridin-2-yl)benzamide

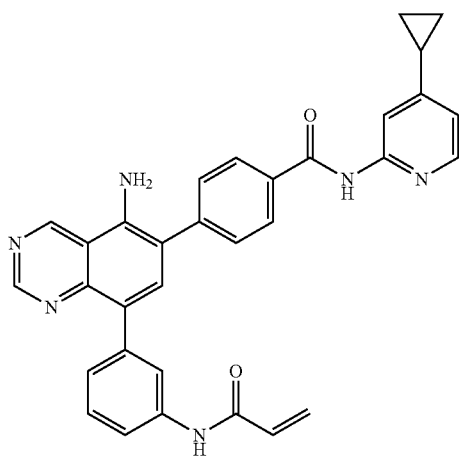

4-(8-(3-acrylamidophenyl)-5-aminoquinazolin-6-yl)-N-(4-cyclopropylpyridin-2-yl)benzamide 4-(8-(3-Acrylamidophenyl)-5-aminoquinazolin-6-yl)-N-(4-cyclopropylpyridin-2-yl)benzamide (9.2 mg) was prepared as described for 1-(3-(6-phenylquinazolin-8-yl)pyrrolidin-1-yl)prop-2-en-1-one. LRMS (M+H⁺) m/z calculated 527.2, found 527.3. ¹H NMR (DMSO-d6, 400 MHz) δ 10.72 (s, 1H), 10.17 (s, 1H), 9.95 (s, 1H), 9.20 (s, 1H), 8.20-8.22 (m, 3H), 8.00 (s, 1H), 7.89 (s, 1H), 7.68-7.23 (m, 4H), 7.38-7.43 (m, 2H), 6.88 (d, 1H), 6.43-6.49 (m, 3H), 6.24-6.27 (m, 1H), 5.73-5.76 (m, 1H), 1.98-2.02 (m, 1H), 1.09-1.12 (m, 2H), 0.81-0.84 (m, 2H).

Example 172: Preparation of 4-(5-(1-acryloylpyrrolidin-3-yl)pyrrolo[1,2-c]pyrimidin-7-yl)-N-(4-cyanopyridin-2-yl)-2-fluorobenzamide

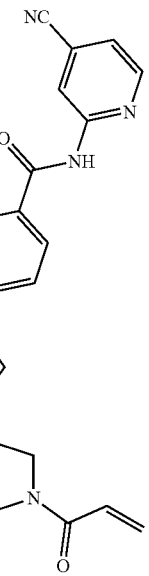

4-(5-(1-acryloylpyrrolidin-3-yl)pyrrolo[1,2-c]pyrimidin-7-yl)-N-(4-cyanopyridin-2-yl)-2-fluorobenzamide 4-(5-(1-Acryloylpyrrolidin-3-yl)pyrrolo[1,2-c]pyrimidin-7-yl)-N-(4-cyanopyridin-2-yl)-2-fluorobenzamide (12.8 mg) was prepared as described for 4-(5-(1-acryloylpyrrolidin-3-yl)pyrrolo[1,2-c]pyrimidin-7-yl)-N-phenylbenzamide. LRMS (M+H⁺) m/z calculated 481.2, found 481.2. ¹H NMR (DMSO-d6, 400 MHz) δ 11.28 (s, 1H), 9.25 (s, 1H), 8.65 (d, 1H), 8.52 (s, 1H), 7.81-7.85 (m, 1H), 7.61-7.75 (m, 4H), 7.47 (d, 1H), 7.32 (d, 1H), 6.59-6.69 (m, 1H), 6.15-6.19 (m, 1H), 5.65-5.76 (m, 1H), 4.06-4.11 (m, 0.5H), 3.92-3.97 (m, 0.5H), 3.52-3.89 (m, 4H), 1.97-2.17 (m, 2H).

Example 173: Preparation of N-(3-(5-amino-6-(2-fluoro-4-(pyridin-2-yloxy)phenyl)quinazolin-8-yl)phenyl)acrylamide

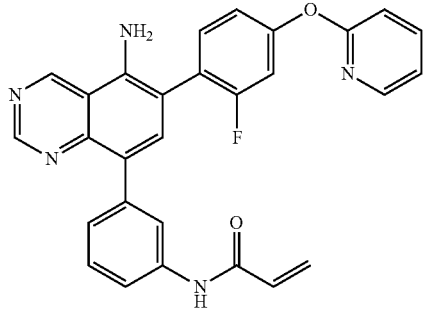

N-(3-(5-amino-6-(2-fluoro-4-(pyridin-2-yloxy)phenyl)quinazolin-8-yl)phenyl)acrylamide N-(3-(5-amino-6-(2-fluoro-4-(pyridin-2-yloxy)phenyl)quinazolin-8-yl)phenyl)acrylamide (13 mg) was prepared as described for 1-(3-(6-phenylquinazolin-8-yl)pyrrolidin-1- yl)prop-2-en-1-one. LRMS (M+H⁺) m/z calculated 478.2, found 478.2. ¹H NMR (DMSO-d6, 400 MHz) δ 10.17 (s, 1H), 9.93 (s, 1H), 9.20 (s, 1H), 8.25 (d, 1H), 7.87-7.93 (m, 2H), 7.72 (d, 1H), 7.62 (s, 1H), 7.55 (t, 1H), 7.36-7.41 (m, 2H), 7.11-7.23 (m, 4H), 6.39-6.51 (m, 2H), 6.25 (d, 1H), 5.74 (d, 1H).

Example 174: Preparation of 1-(3-(5-amino-6-(2-fluoro-4-(pyridin-2-yloxy)phenyl)quinazolin-8-yl)pyrrolidin-1-yl)prop-2-en-1-one

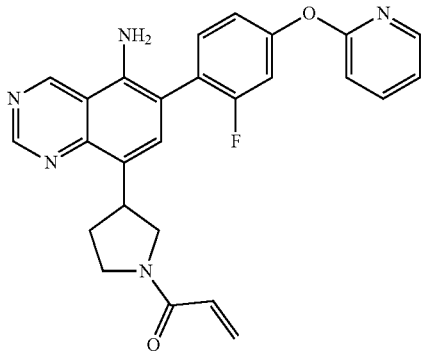

1-(3-(5-amino-6-(2-fluoro-4-(pyridin-2-yloxy)phenyl)quinazolin-8-yl)pyrrolidin-1-yl)prop-2-en-1-one 1-(3-(5-Amino-6-(2-fluoro-4-(pyridin-2-yloxy)phenyl)quinazolin-8-yl)pyrrolidin-1-yl)prop-2-en-1-one (127.2 mg) was prepared as described for 1-(3-(6-phenylquinazolin-8-yl)pyrrolidin-1-yl)prop-2-en-1-one. LRMS (M+H⁺) m/z calculated 456.2, found 456.2. ¹H NMR (DMSO-d6, 400 MHz) δ 9.87 (s, 1H), 9.24 (s, 1H), 8.24 (d, 1H), 7.92 (t, 1H), 7.45-7.58 (m, 2H), 7.20-7.23 (m, 2H), 7.10-7.15 (m, 2H), 6.56-6.67 (m, 1H), 6.13-6.17 (m, 3H), 5.61-5.69 (m, 1H), 4.21-4.35 (m, 1H), 4.01-4.12 (m, 1H), 3.46-3.80 (m, 3H), 2.12-2.25 (m, 2H).

Example 175: Preparation of N-(3-(6-(4-((4-(trifluoromethyl)pyridin-2-yl)oxy)phenyl)quinazolin-8-yl)phenyl)acrylamide

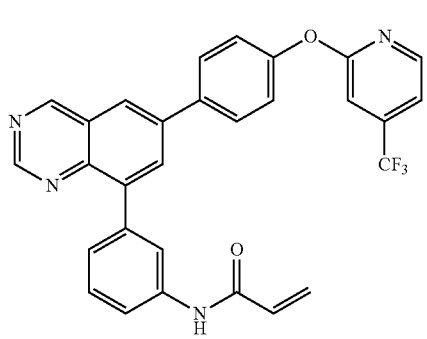

N-(3-(6-(4-((4-(trifluoromethyl)pyridin-2-yl)oxy)phenyl)quinazolin-8-yl)phenyl)acrylamide N-(3-(6-(4-((4-(trifluoromethyl)pyridin-2-yl)oxy)phenyl)quinazolin-8-yl)phenyl)acrylamide (31 mg) was prepared as described for 1-(3-(6-phenylquinazolin-8-yl)pyrrolidin-1-yl)prop-2-en-1-one. LRMS (M+H⁺) m/z calculated 513.2, found 513.2. ¹H NMR (DMSO-d6, 400 MHz) δ 10.29 (s, 1H), 9.73 (s, 1H), 9.32 (s, 1H), 8.36-8.52 (m, 3H), 7.78-8.05 (m, 4H), 7.32-7.62 (m, 6H), 6.48-6.51 (m, 1H), 6.25-6.29 (m, 1H), 5.77 (br, 1H).

Example 176: Preparation of 4-(8-(3-acrylamidophenyl)-5-aminoquinazolin-6-yl)-N-(4-cyanopyridin-2-yl)benzamide

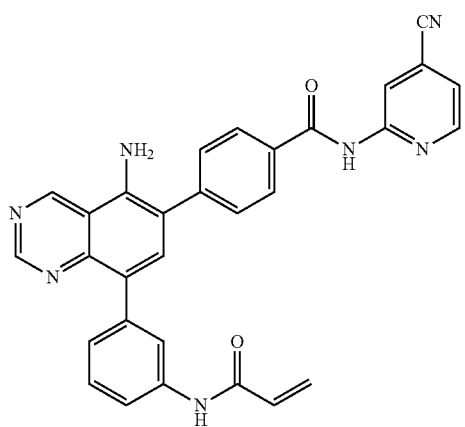

4-(8-(3-acrylamidophenyl)-5-aminoquinazolin-6-yl)-N-(4-cyanopyridin-2-yl)benzamide 4-(8-(3-Acrylamidophenyl)-5-aminoquinazolin-6-yl)-N-(4-cyanopyridin-2-yl)benzamide (4.7 mg) was prepared as described for 1-(3-(6-phenylquinazolin-8-yl)pyrrolidin-1-yl)prop-2-en-1-one. LRMS (M+H⁺) m/z calculated 512.2, found 512.3. ¹H NMR (CD₃OD, 400 MHz) δ 9.58 (br, 1H), 9.18 (s, 1H), 8.72 (s, 1H), 8.46 (s, 1H), 8.02-8.07 (m, 2H), 7.90 (s, 1H), 7.56-7.73 (m, 4H), 7.25-7.37 (m, 3H), 6.28-6.39 (m, 2H), 5.70 (d, 1H).

Example 177: Preparation of 4-(8-(3-acrylamidophenyl)-5-aminoquinazolin-6-yl)-3-fluoro-N-(pyridin-2-yl)benzamide

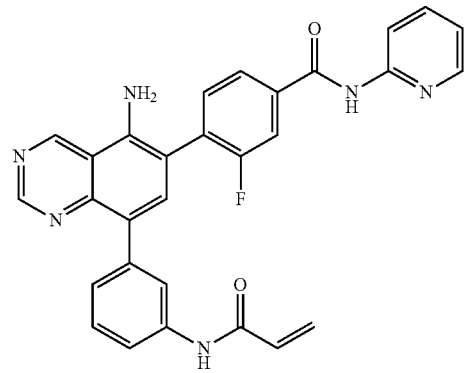

4-(8-(3-acrylamidophenyl)-5-aminoquinazolin-6-yl)-3-fluoro-N-(pyridin-2-yl)benzamide 4-(8-(3-Acrylamidophenyl)-5-aminoquinazolin-6-yl)-3-fluoro-N-(pyridin-2-yl)benzamide (15 mg) was prepared as described for 1-(3-(6-phenylquinazolin-8-yl)pyrrolidin-1-yl)prop-2-en-1-one. LRMS (M+H⁺) m/z calculated 505.2, found 505.2. ¹H NMR (DMSO-d6, 400 MHz) δ 10.96 (s, 1H), 10.18 (s, 1H), 9.94 (s, 1H), 9.21 (s, 1H), 8.43 (d, 1H), 8.22 (d, 1H), 8.06-8.09 (m, 2H), 7.86-7.90 (m, 2H), 7.62-7.73 (m, 3H), 7.35-7.41 (m, 2H), 7.15-7.35 (m, 1H), 6.42-6.53 (m, 3H), 6.25 (d, 1H), 5.74 (d, 1H).

Example 178: Preparation of 4-(8-(3-acrylamidophenyl)-5-aminoquinazolin-6-yl)-3-fluoro-N-(pyridin-2-yl)benzamide

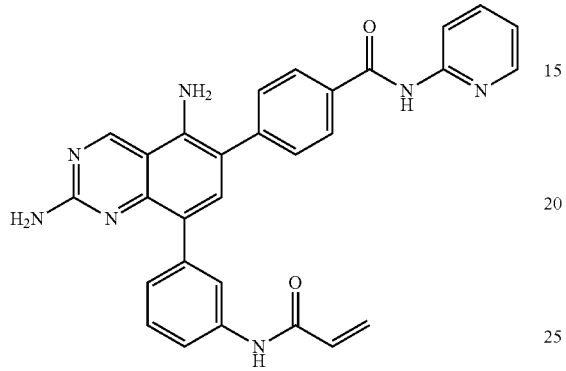

4-(8-(3-acrylamidophenyl)-2,5-diaminoquinazolin-6-yl)-N-(pyridin-2-yl)benzamide 4-(8-(3-Acrylamidophenyl)-2,5-diaminoquinazolin-6-yl)-N-(pyridin-2-yl)benzamide (2.3 mg) was prepared as described for 1-(3-(6-phenylquinazolin-8-yl)pyrrolidin-1-yl)prop-2-en-1-one. LRMS (M+H⁺) m/z calculated 502.2, found 502.2. ¹H NMR (DMSO-d6, 400 MHz) δ 10.80 (s, 1H), 10.13 (s, 1H), 9.50 (s, 1H), 9.41 (s, 1H), 8.16-8.24 (m, 3H), 7.86 (t, 1H), 7.73 (t, 2H), 7.65 (t, 2H), 7.32-7.40 (m, 3H), 7.18 (t, 1H), 6.66 (s, 2H), 6.42-6.46 (m, 1H), 6.24 (d, 1H), 6.04 (s, 2H), 5.73 (s, 1H).

Example 179: Preparation of N-(3-(5-amino-6-(4-(pyridin-2-yloxy)phenyl)quinazolin-8-yl)phenyl)acrylamide

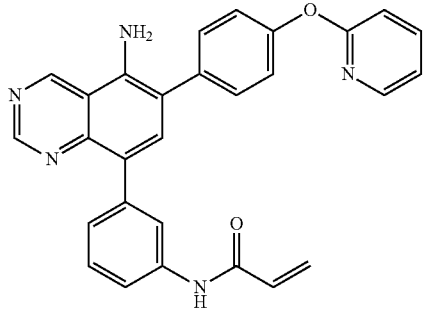

N-(3-(5-amino-6-(4-(pyridin-2-yloxy)phenyl)quinazolin-8-yl)phenyl)acrylamide

N-(3-(5-amino-6-(4-(pyridin-2-yloxy)phenyl)quinazolin-8-yl)phenyl)acrylamide (6.0 mg) was prepared as described for 1-(3-(6-phenylquinazolin-8-yl)pyrrolidin-1-yl)prop-2-en-1-one. LRMS (M+H⁺) m/z calculated 460.2, found 460.1. ¹H NMR (DMSO-d6, 400 MHz) δ 10.16 (s, 1H), 9.94 (s, 1H), 9.19 (s, 1H), 8.22 (s, 1H), 7.89 (s, 2H), 7.74 (d, 1H), 7.69 (s, 1H), 7.62 (d, 2H), 7.40-7.45 (m, 2H), 7.29 (d, 2H), 7.19 (s, 1H), 7.10 (d, 1H), 6.24-6.51 (m, 4H), 5.75 (d, 1H).

Example 180: Preparation of N-(3-(6-(2-fluoro-4-((4-(trifluoromethyl)pyridin-2-yl)oxy)phenyl)quinazolin-8-yl)phenyl)acrylamide

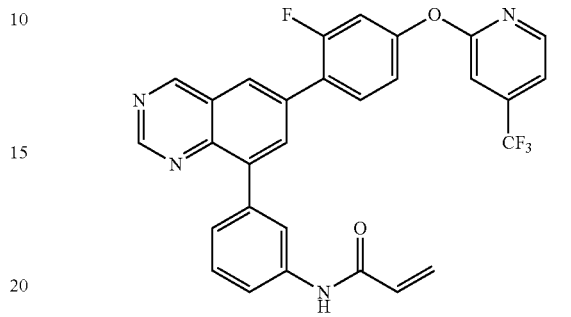

N-(3-(6-(2-fluoro-4-((4-(trifluoromethyl)pyridin-2-yl)oxy)phenyl)quinazolin-8-yl)phenyl)acrylamide N-(3-(6-(2-fluoro-4-((4-(trifluoromethyl)pyridin-2-yl)oxy)phenyl)quinazolin-8-yl)phenyl)acrylamide (5.5 mg) was prepared as described for 1-(3-(6-phenylquinazolin-8-yl)pyrrolidin-1-yl)prop-2-en-1-one. LRMS (M+H⁺) m/z calculated 531.1, found 531.1. ¹H NMR (CDCl₃, 400 MHz) δ 9.51 (s, 1H), 9.38 (s, 1H), 8.38 (d, 1H), 8.18 (s, 1H), 8.12 (s, 1H), 7.99 (s, 1H), 7.51-7.73 (m, 6H), 7.29 (d, 1H), 7.10-7.17 (m, 2H), 7.44 (d, 1H), 6.27-6.30 (m, 1H), 5.77 (d, 1H).

Example 181: Preparation of 1-(3-(5-amino-6-(4-(pyridin-2-yloxy)phenyl)quinazolin-8-yl)pyrrolidin-1-yl)prop-2-en-1-one

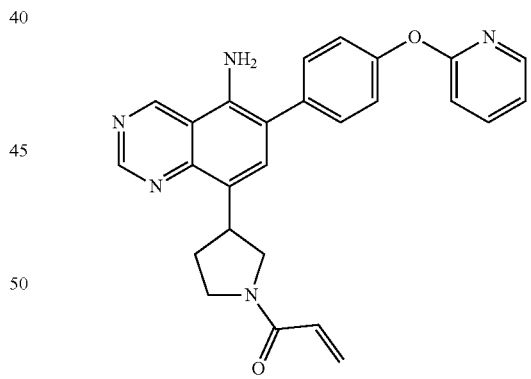

1-(3-(5-amino-6-(4-(pyridin-2-yloxy)phenyl)quinazolin-8-yl)pyrrolidin-1-yl)prop-2-en-1-one 1-(3-(5-Amino-6-(4-(pyridin-2-yloxy)phenyl)quinazolin-8-yl)pyrrolidin-1-yl)prop-2-en-1-one (20.6 mg) was prepared as described for 1-(3-(6-phenylquinazolin-8-yl)pyrrolidin-1-yl)prop-2-en-1-one. LRMS (M+H⁺) m/z calculated 438.2, found 438.2. ¹H NMR (DMSO-d6, 400 MHz) δ 9.87 (s, 1H), 9.22 (s, 1H), 8.20 (d, 1H), 7.89 (t, 1H), 7.63 (s, 1H), 7.55 (d, 2H), 7.26 (d, 2H), 7.17 (t, 1H), 7.10 (d, 1H), 6.58-6.63 (m, 1H), 6.10-6.16 (m, 3H), 5.61-5.71 (m, 1H), 4.36 (d, 1H), 4.19-4.25 (m, 1H), 3.61-3.71 (m, 2H), 3.32-3.46 (m, 1H), 2.18-2.26 (m, 2H).

Example 182: Preparation of N-(3-(5-amino-6-(4-phenoxyphenyl)quinazolin-8-yl)phenyl)acrylamide

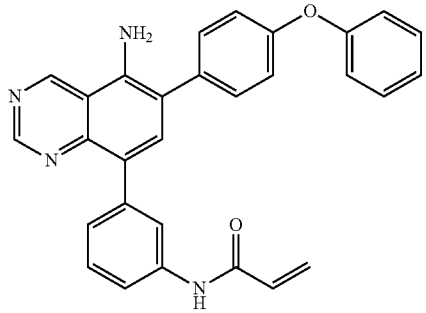

N-(3-(5-amino-6-(4-phenoxyphenyl)quinazolin-8-yl)phenyl)acrylamide

N-(3-(5-amino-6-(4-phenoxyphenyl)quinazolin-8-yl)phenyl)acrylamide (8.3 mg) was prepared as described for 1-(3-(6-phenylquinazolin-8-yl)pyrrolidin-1-yl)prop-2-en-1-one. LRMS (M+H⁺) m/z calculated 459.2, found 459.2. ¹H NMR (DMSO-d6, 400 MHz) δ 10.17 (s, 1H), 9.92 (s, 1H), 9.17 (s, 1H), 7.89 (s, 1H), 7.71 (d, 1H), 7.65 (s, 1H), 7.56 (d, 2H), 7.37-7.44 (m, 4H), 7.12-7.20 (m, 5H), 6.23-6.47 (m, 4H), 5.74 (d, 1H).

Example 183: Preparation of 4-(1-(1-acryloylpyrrolidin-3-yl)-5-aminoimidazo[1,5-c]pyrimidin-3-yl)-N-(pyridin-2-yl)benzamide

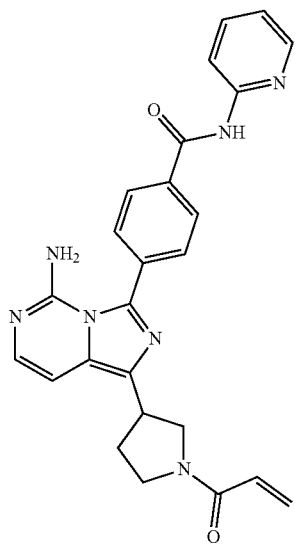

4-(1-(1-acryloylpyrrolidin-3-yl)-5-aminoimizado[1,5-c]pyrimidin-3-yl)-N-(pyridin-2-yl)benzamide

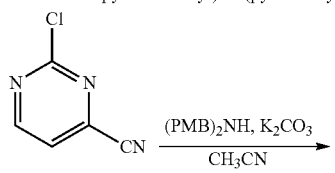

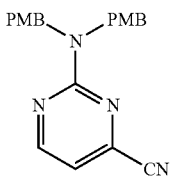

A mixture of 2-chloropyrimidine-4-carbonitrile (100.0 g, 0.71 mol, 1.0 eq) and bis(4-methoxybenzyl)amine (184.0 g, 0.71 mol, 1.0 eq) in CH₃CN (1.0 L) was stirred under reflux for 2 h, then cooled and filtered. The mixture was concentrated, diluted with 0.5 N HCl (1.0 L), extracted with EA (1.0 L×2). The combined EA layers were dried over anhydrous Na₂SO₄ and concentrated. The resulting residue was triturated with (PE/EA=10/1, v/v, 1 L) to provide 2-(bis(4-methoxybenzyl)amino)pyrimidine-4-carbonitrile as a as orange solid (220.0 g, 85.9%).

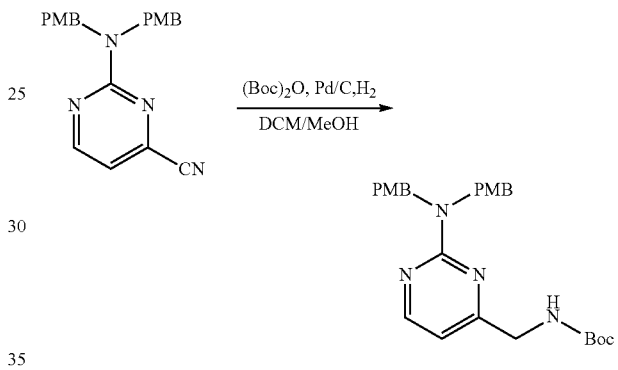

To a solution of 2-(bis(4-methoxybenzyl)amino)pyrimidine-4-carbonitrile (55.0 g, 0.15 mol, 1.0 eq) in DCM/MeOH (200 mL/800 mL) was added (Boc)₂O (64.0 g, 0.29 mol, 1.9 eq), Pd/C (5.5 g, 10% w/w). and HOAc (55.0 mL) successively. The mixture was stirred at rt under H₂ atmosphere overnight, filtered, concentrated and purified by column chromatography (PE/EA=5/1-2/1, v/v) to afford tert-butyl ((2-(bis(4-methoxybenzyl)amino)pyrimidin-4-yl)methyl)carbamate (37.5 g, 53%).

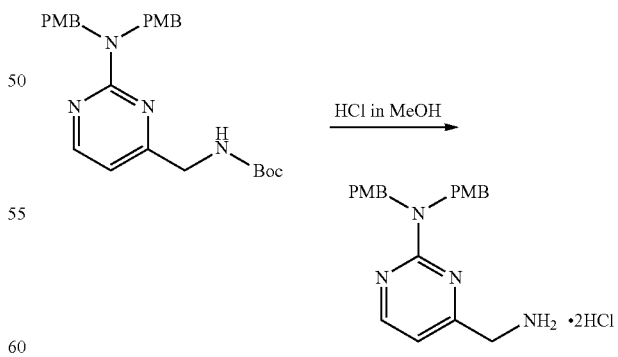

A solution of tert-butyl ((2-(bis(4-methoxybenzyl)amino)pyrimidin-4-yl)methyl)carbamate (150.0 g, 0.32 mmol, 1.0 eq) in 4 N HCl in MeOH (1.0 L) was stirred at rt overnight, then concentrated to provide crude 4-(aminomethyl)-N,N-bis(4-methoxybenzyl)pyrimidin-2-amine hydrochloride as a yellow oil (crude).

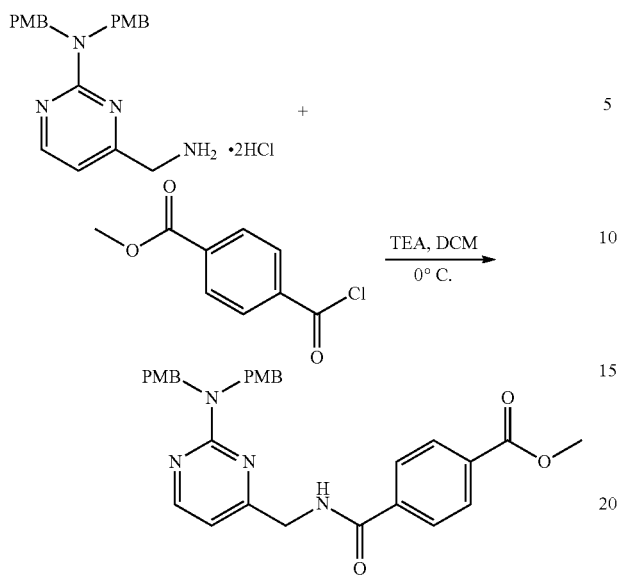

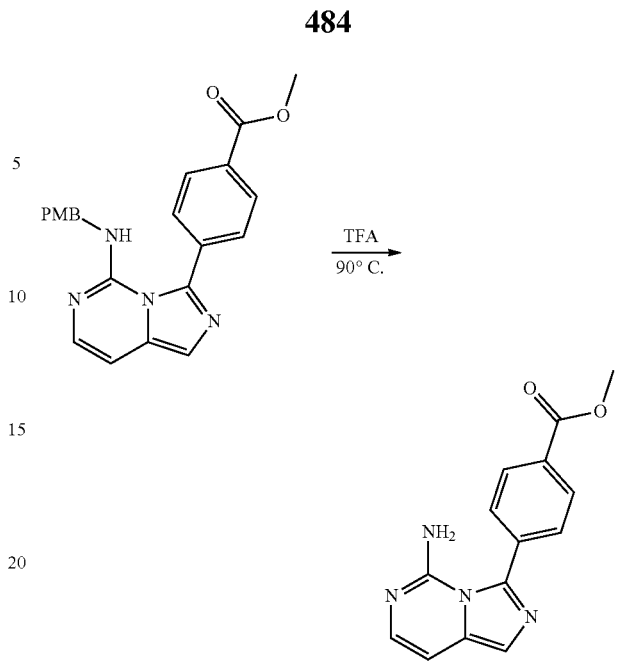

To a solution of crude 4-(aminomethyl)-N,N-bis(4-methoxybenzyl)pyrimidin-2-amine hydrochloride (145.0 g, 0.31 mol, 1.0 eq) in DCM (1.0 L) at 0° C. was added TEA (175.0 mL, 1.25 mol, 4.0 eq), followed by the addition of methyl 4-(chlorocarbonyl)benzoate (62.0 g, 0.31 mol, 1.0 eq) in DCM (1.0 L) dropwise. The resulting mixture was stirred at 0° C. for 2 h, then washed with saturated Na₂CO₃, dried over anhydrous Na₂SO₄, concentrated and triturated with (PE/EA=3/1, v/v, 800.0 mL) to afford methyl 4-(((2-(bis(4-methoxybenzyl)amino)pyrimidin-4-yl)methyl)carbamoyl)benzoate (140.0 g, 70.0%).

A solution of methyl 4-(5-((4-methoxybenzyl)amino)imidazo[1,5-c]pyrimidin-3-yl)benzoate (7.0 g, 18.0 mmol, 1.0 eq) in TFA (50.0 mL) was heated under reflux for 7 h. Then the mixture was cooled to rt and concentrated. The reside was diluted with aqueous Na₂CO₃ (100.0 mL) and extracted with DCM (100.0 mL×3). The combined organic layers were separated and washed with brine, dried over anhydrous Na₂SO₄ and concentrated. The resulting residue was purified by column chromatography (DCM/MeOH=50/1, v/v) to afford methyl 4-(5-aminoimidazo[1,5-c]pyrimidin-3-yl)benzoate as a yellow solid (3.8 g, 79.0%).

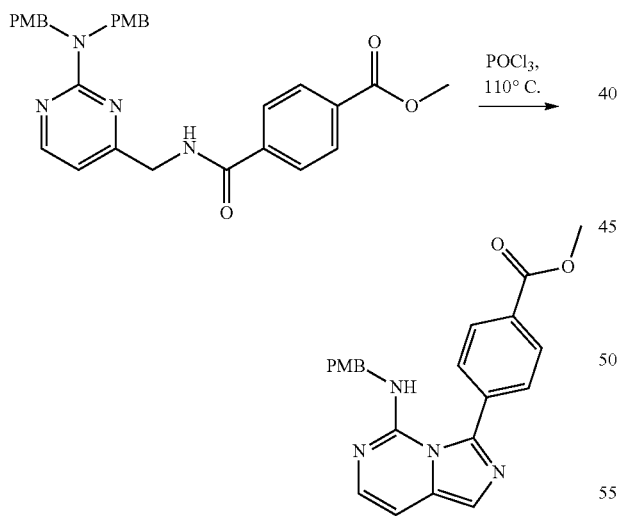

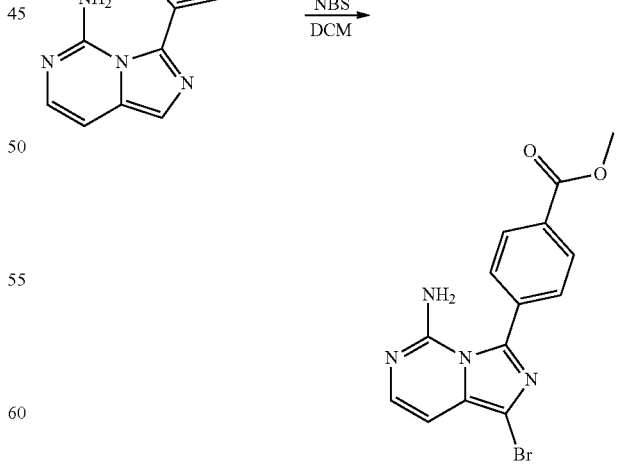

A mixture of methyl 4-(((2-(bis(4-methoxybenzyl)amino)pyrimidin-4-yl)methyl)carbamoyl)benzoate (15.0 g, 28.5 mmol, 1.0 eq) in POCl₃ (100.0 mL) was stirred at 110° C. for 5 h, then cooled and concentrated. The residue was diluted with DCM (200.0 mL), washed with satd. Na₂CO₃, dried over anhydrous Na₂SO₄ and concentrated. The resulting residue was purified by column chromatography (DCM/MeOH=100/1-50/1, v/v) to afford methyl 4-(5-((4-methoxybenzyl)amino)imidazo[1,5-c]pyrimidin-3-yl)benzoate (7.0 g, 64%).

To a solution of methyl 4-(5-aminoimidazo[1,5-c]pyrimidin-3-yl)benzoate (3.8 g, 14.2 mmol, 1.0 eq) in DCM (100.0 mL) was added NBS (2.3 g, 12.8 mmol, 0.9 eq) at 0° C. in portions and the mixture was stirred at 0° C. for 30 min.

Then the mixture was poured into water and extracted with DCM (150.0 mL×3). The combined organic layers were separated and washed with brine, dried over anhydrous Na₂SO₄ and concentrated. The resulting residue was purified by column chromatography (DCM/MeOH=50:1, v/v) to afford methyl 4-(5-amino-1-bromoimidazo[1,5-c]pyrimidin-3-yl)benzoate as a yellow solid (3.5 g, 71%).

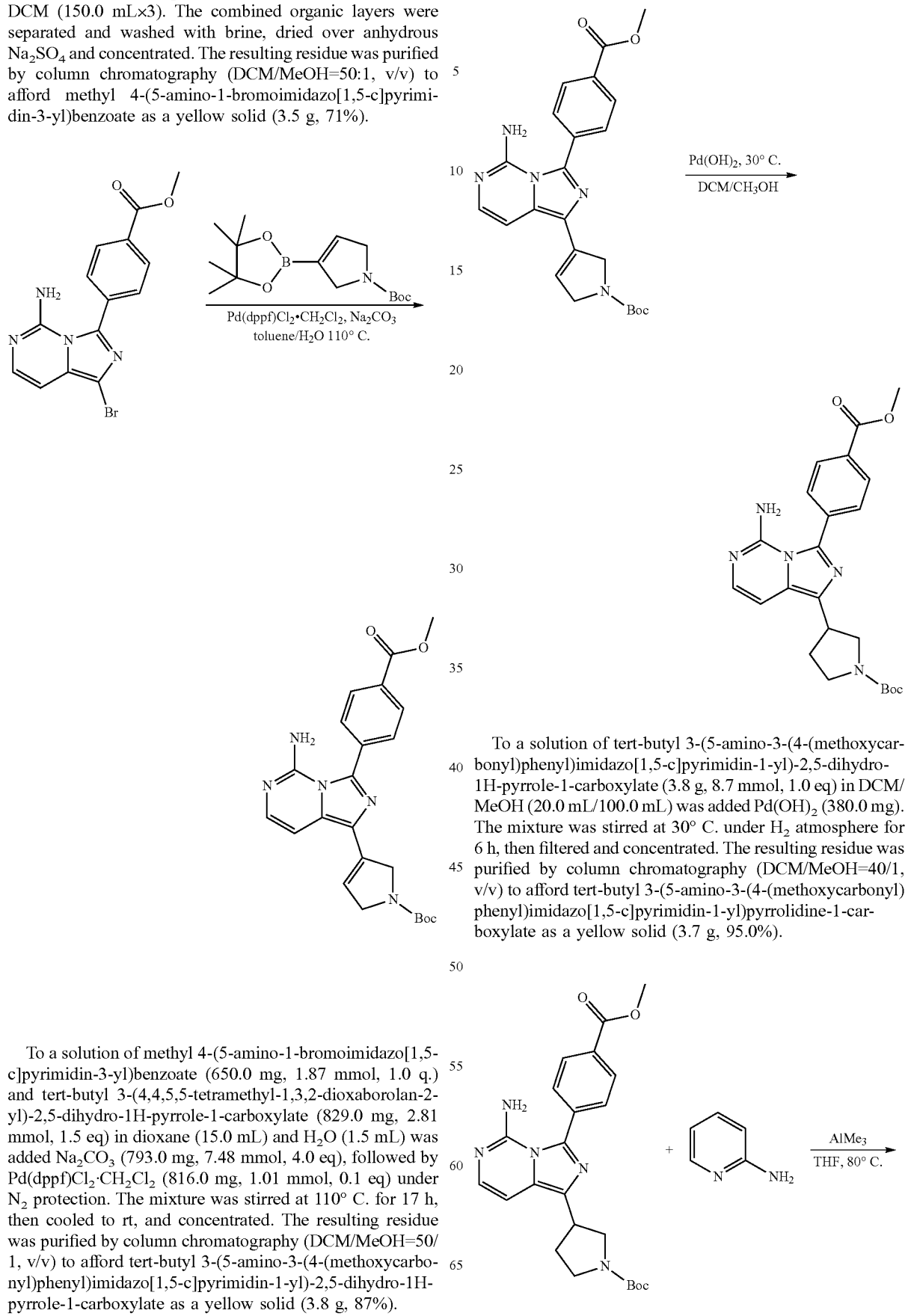

To a solution of methyl 4-(5-amino-1-bromoimidazo[1,5-c]pyrimidin-3-yl)benzoate (650.0 mg, 1.87 mmol, 1.0 q.) and tert-butyl 3-(4,4,5,5-tetramethyl-1,3,2-dioxaborolan-2-yl)-2,5-dihydro-1H-pyrrole-1-carboxylate (829.0 mg, 2.81 mmol, 1.5 eq) in dioxane (15.0 mL) and H₂O (1.5 mL) was added Na₂CO₃ (793.0 mg, 7.48 mmol, 4.0 eq), followed by Pd(dppf)Cl₂·CH₂Cl₂ (816.0 mg, 1.01 mmol, 0.1 eq) under N₂ protection. The mixture was stirred at 110° C. for 17 h, then cooled to rt, and concentrated. The resulting residue was purified by column chromatography (DCM/MeOH=50/1, v/v) to afford tert-butyl 3-(5-amino-3-(4-(methoxycarbonyl)phenyl)imidazo[1,5-c]pyrimidin-1-yl)-2,5-dihydro-1H-pyrrole-1-carboxylate as a yellow solid (3.8 g, 87%).

To a solution of tert-butyl 3-(5-amino-3-(4-(methoxycarbonyl)phenyl)imidazo[1,5-c]pyrimidin-1-yl)-2,5-dihydro-1H-pyrrole-1-carboxylate (3.8 g, 8.7 mmol, 1.0 eq) in DCM/MeOH (20.0 mL/100.0 mL) was added Pd(OH)₂ (380.0 mg). The mixture was stirred at 30° C. under H₂ atmosphere for 6 h, then filtered and concentrated. The resulting residue was purified by column chromatography (DCM/MeOH=40/1, v/v) to afford tert-butyl 3-(5-amino-3-(4-(methoxycarbonyl)phenyl)imidazo[1,5-c]pyrimidin-1-yl)pyrrolidine-1-carboxylate as a yellow solid (3.7 g, 95.0%).

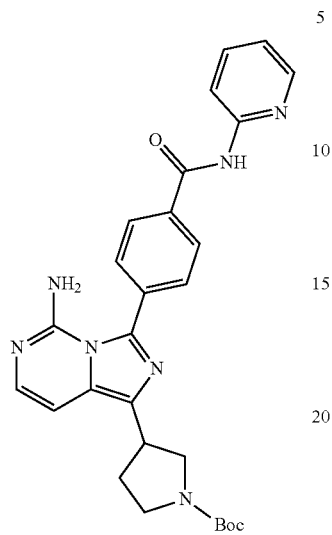

To a solution of tert-butyl 3-(5-amino-3-(4-(methoxycarbonyl) phenyl)imidazo[1,5-c]pyrimidin-1-yl)pyrrolidine-1-carboxylate (1.9 g, 4.34 mmol, 1.0 eq) and pyridin-2-amine (1.22 g, 13.0 mmol, 3.0 eq) in THF (150.0 mL) was added AlMe$_3$ (21.7 mL, 21.7 mmol, 5.0 eq) at 0° C. The mixture was stirred at 80° C. for 17 h. Then the mixture was poured into satd. NH$_4$Cl and extracted with DCM (150.0 mL×3). The combined organic layers were separated and washed with brine, dried over anhydrous Na$_2$SO$_4$ and concentrated. The resulting residue was purified by column chromatography (DCM/MeOH=20/1, v/v) to afford tert-butyl 3-(5-amino-3-(4-(pyridin-2-ylcarbamoyl)phenyl)imidazo[1,5-c]pyrimidin-1-yl)pyrrolidine-1-carboxylate (420.0 mg, 35.0%).

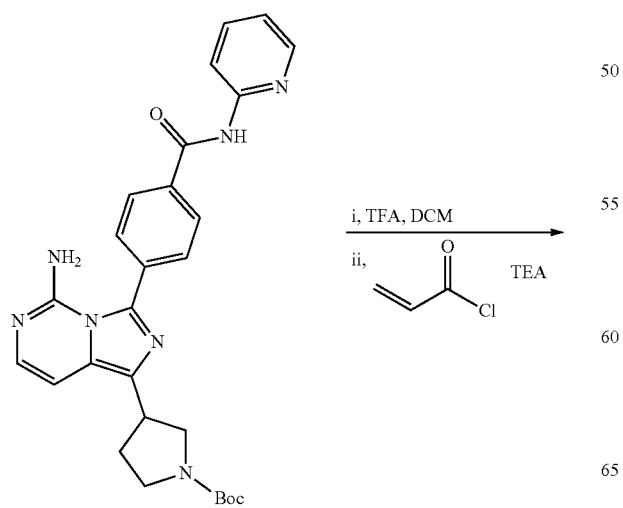

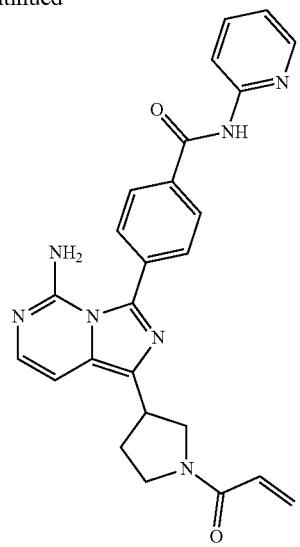

To a solution of tert-butyl 3-(5-amino-3-(4-(pyridin-2-ylcarbamoyl) phenyl)imidazo [1,5-c]pyrimidin-1-yl)pyrrolidine-1-carboxylate (250.0 mg, 0.5 mmol, 1.0 eq) in DCM (10.0 mL) was added TFA (2.0 mL), and the mixture was stirred at rt for 30 min, then concentrated. The residue was dissolved in DCM (10.0 mL), and TEA (404 mg, 4.00 mmol, 8.0 eq) was added, followed by acryloyl chloride (42.0 mg, 0.4 mmol, 0.8 eq). The resulting mixture was stirred at rt for 1 h, then washed with brine, dried over anhydrous Na$_2$SO$_4$ and concentrated. The resulting residue was purified by column chromatography (DCM/MeOH=20/1, v/v) to afford 4-(1-(1-acryloylpyrrolidin-3-yl)-5-aminoimidazo[1,5-c]pyrimidin-3-yl)-N-(pyridin-2-yl)benzamide (112.0 mg, 49%) as yellow solid. LCMS (M+H$^+$) m/z calculated 454.2, found 454.2. $^1$H NMR (DMSO-d6, 400 MHz) δ 10.91 (s, 1H), 8.40 (d, 1H), 8.14-8.23 (m, 3H), 7.86-7.88 (m, 1H), 7.72-7.84 (m, 2H), 7.18-7.20 (m, 2H), 7.02-7.69 (m, 1H), 6.58-6.65 (m, 1H), 6.37 (s, 2H), 6.18-6.42 (m, 1H), 5.62-5.69 (m, 1H), 3.89-4.03 (m, 0.5H), 3.72-3.88 (m, 3.5H), 3.33-3.45 (m, 1H), 2.28-2.32 (m, 2H).

Example 184: Preparation of 1-(3-(5-amino-3-(4-(pyridin-2-yloxy)phenyl)imidazo[1,5-c]pyrimidin-1-yl)pyrrolidin-1-yl)prop-2-en-1-one 1-(3-(5-amino-3-(4-(pyridin-2-yloxy)phenyl)imidazo[1,5-c]pyrimidin-1-yl)pyrrolidin-1-yl)prop-2-en-1-one 1-(3-(5-Amino-3-(4-(pyridin-2-yloxy)phenyl)imidazo[1,5-c]pyrimidin-1-yl)pyrrolidin-1-yl)prop-2-en-1-one (6.3 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 427.2, found 427.2. ¹H NMR (DMSO-d6, 400 MHz) δ 8.17-8.19 (m, 1H), 7.77 (t, 1H), 7.61-7.63 (m, 2H), 7.28-7.30 (m, 1H), 7.22 (t, 2H), 7.08-7.19 (m, 2H), 6.88 (t, 1H), 6.78-6.83 (m, 2H), 6.40-6.49 (m, 2H), 5.68-5.70 (m, 1H), 3.63-4.15 (m, 5H), 2.30-2.34 (m, 2H).

Example 185: Preparation of (R/S))-1-(3-(5-amino-3-(4-(pyridin-2-yloxy)phenyl)imidazo[1,5-c]pyrimidin-1-yl)pyrrolidin-1-yl)prop-2-en-1-one

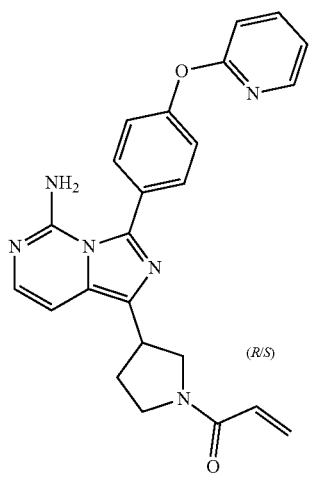

(R/S))-1-(3-(5-amino-3-(4-(pyridin-2-yloxy)phenyl)imidazo[1,5-c]pyrimidin-1-yl)pyrrolidin-1-yl)prop-2-en-1-one (R/S))-1-(3-(5-amino-3-(4-(pyridin-2-yloxy)phenyl)imidazo[1,5-c]pyrimidin-1-yl)pyrrolidin-1-yl)prop-2-en-1-one (10 mg, >99% chemical purity; >99.0% e.e) was prepared via chiral preparation of 1-(3-(5-amino-3-(4-(pyridin-2-yloxy)phenyl)imidazo[1,5-c]pyrimidin-1-yl)pyrrolidin-1-yl)prop-2-en-1-one LRMS (M+H) m/z calculated 427.2, found 427.2. ¹H NMR (CD₃Cl, 400 MHz) δ 8.20 (d, 1H), 7.75 (t, 1H), 7.61-7.65 (m, 2H), 7.27-7.30 (m, 2H), 6.99-7.15 (m, 3H), 6.77 (t, 1H), 6.35-6.54 (m, 2H), 5.70 (t, 2H), 3.58-4.15 (m, 5H), 2.32-2.52 (m, 2H).

Example 186: Preparation of (S/R))-1-(3-(5-amino-3-(4-(pyridin-2-yloxy)phenyl)imidazo[1,5-c]pyrimidin-1-yl)pyrrolidin-1-yl)prop-2-en-1-one

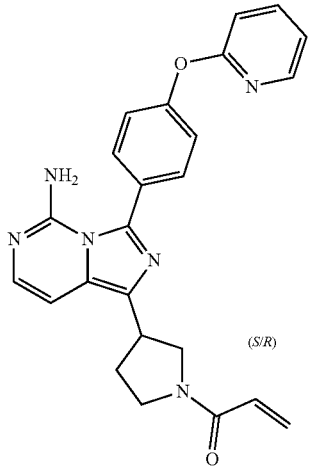

(S/R)-1-(3-(5-amino-3-(4-(pyridin-2-yloxy)phenyl)imidazo[1,5-c]pyrimidin-1-yl)prop-2-en-1-one (S/R))-1-(3-(5-amino-3-(4-(pyridin-2-yloxy)phenyl)imidazo[1,5-c]pyrimidin-1-yl)pyrrolidin-1-yl)prop-2-en-1-one (7 mg, >91% chemical purity; >92.7% e.e) was prepared via chiral preparation of 1-(3-(5-amino-3-(4-(pyridin-2-yloxy)phenyl)imidazo[1,5-c]pyrimidin-1-yl)pyrrolidin-1-yl)prop-2-en-1-one LRMS (M+H⁺) m/z calculated 427.2, found 427.2. ¹H NMR (CD₃Cl, 400 MHz) δ 8.20 (d, 1H), 7.75 (t, 1H), 7.61-7.65 (m, 2H), 7.27-7.30 (m, 2H), 6.99-7.15 (m, 3H), 6.77 (t, 1H), 6.35-6.54 (m, 2H), 5.70 (t, 2H), 3.58-4.15 (m, 5H), 2.32-2.52 (m, 2H).

Example 187: Preparation of N-(3-(6-(4-((4-cyclopropylpyridin-2-yl)oxy)phenyl)quinazolin-8-yl)phenyl)acrylamide

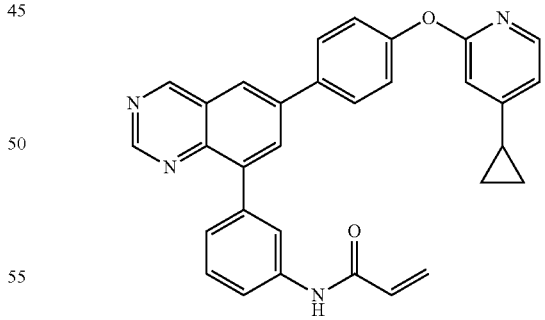

N-(3-(6-(4-((4-cyclopropylpyridin-2-yl)oxy)phenyl)quinazolin-8-yl)phenyl)acrylamide N-(3-(6-(4-((4-cyclopropylpyridin-2-yl)oxy)phenyl)quinazolin-8-yl)phenyl)acrylamide (37.0 mg) was prepared as described for 1-(3-(6-phenylquinazolin-8-yl)pyrrolidin-1-yl)prop-2-en-1-one. LRMS (M+H⁺) m/z calculated 485.2, found 485.2. ¹H NMR (DMSO-d6, 400 MHz) δ 10.28 (s, 1H), 9.72 (s, 1H), 9.32 (s, 1H), 8.49 (s, 1H), 8.34 (s, 1H), 7.95-8.04 (m, 4H), 7.83 (s, 1H), 7.50 (s, 2H), 7.28 (s, 2H), 6.85 (m, 2H), 6.45-6.51 (m, 1H), 6.25-6.29 (m, 1H), 5.76-5.78 (m, 1H), 1.99 (s, 1H), 1.24 (s, 2H), 1.09 (s, 2H).

Example 188: Preparation of N-(3-(6-(4-((4-cyanopyridin-2-yl)oxy)phenyl)quinazolin-8-yl)phenyl)acrylamide

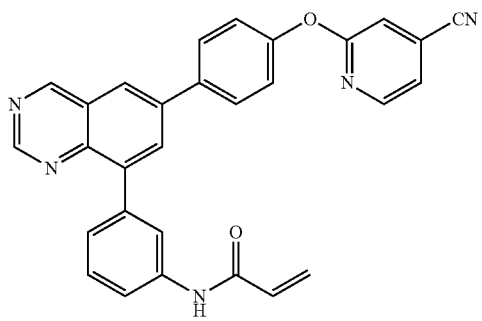

N-(3-(6-(4-((4-cyanopyridin-2-yl)oxy)phenyl)quinazolin-8-yl)phenyl)acrylamide

N-(3-(6-(4-((4-cyanopyridin-2-yl)oxy)phenyl)quinazolin-8-yl)phenyl)acrylamide (20.9 mg) was prepared as described for 1-(3-(6-phenylquinazolin-8-yl)pyrrolidin-1-yl)prop-2-en-1-one. LRMS (M+H⁺) m/z calculated 470.2, found 470.1. ¹H NMR (DMSO-d6, 400 MHz) δ 9.73 (s, 1H), 9.33 (s, 1H), 8.52 (d, 1H), 8.42 (d, 1H), 8.36 (s, 1H), 8.00-8.05 (m, 3H), 7.83 (d, 1H), 7.74 (s, 1H), 7.62 (d, 1H), 7.47-7.53 (m, 2H), 7.37-7.39 (m, 2H), 6.45-6.52 (m, 1H), 6.25-6.29 (m, 1H), 5.78 (d, 1H).

Example 189: Preparation of N-(3-(5-amino-6-(2-fluoro-4-((4-(trifluoromethyl)pyridin-2-yl)oxy)phenyl)quinazolin-8-yl)phenyl)acrylamide

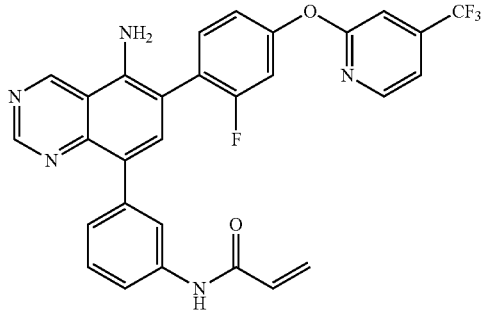

N-(3-(5-amino-6-(2-fluoro-4-((4-(trifluoromethyl)pyridin-2-yl)oxy)phenyl)quinazolin-8-yl)phenyl)acrylamide N-(3-(5-amino-6-(2-fluoro-4-((4-(trifluoromethyl)pyridin-2-yl)oxy)phenyl)quinazolin-8-yl)phenyl)acrylamide (10.4 mg) was prepared as described for 1-(3-(6-phenylquinazolin-8-yl)pyrrolidin-1-yl)prop-2-en-1-one. LRMS (M+H⁺) m/z calculated 546.1, found 546.2. ¹H NMR (DMSO-d6, 400 MHz) δ 10.17 (s, 1H), 9.93 (s, 1H), 9.20 (s, 1H), 8.49 (d, 1H), 7.88 (s, 1H), 7.71-7.73 (m, 2H), 7.55-7.62 (m, 3H), 7.35-7.41 (m, 2H), 7.21-7.23 (m, 1H), 6.41-6.45 (m, 2H), 7.23-7.27 (m, 1H), 5.75 (d, 1H).

Example 190: Preparation of N-(3-(5-amino-6-(4-((4-(trifluoromethyl)pyridin-2-yl)oxy)phenyl)quinazolin-8-yl)phenyl)acrylamide

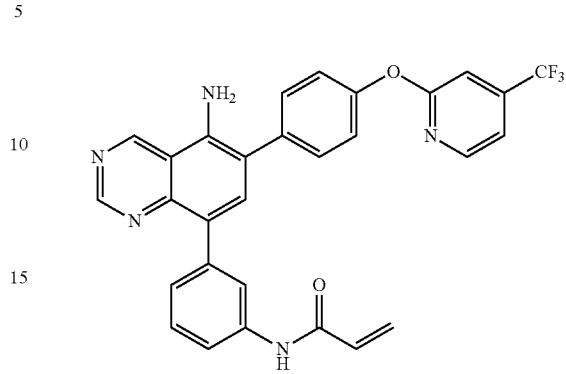

N-(3-(5-amino-6-(4-((4-(trifluoromethyl)pyridin-2-yl)oxy)phenyl)quinazolin-8-yl)phenyl)acrylamide N-(3-(5-amino-6-(4-((4-(trifluoromethyl)pyridin-2-yl)oxy)phenyl)quinazolin-8-yl)phenyl)acrylamide (1.3 mg) was prepared as described for 1-(3-(6-phenylquinazolin-8-yl)pyrrolidin-1-yl)prop-2-en-1-one. LRMS (M+H⁺) m/z calculated 528.2, found 528.2. ¹H NMR (DMSO-d6, 400 MHz) δ 10.18 (s, 1H), 9.94 (s, 1H), 9.19 (s, 1H), 8.46 (d, 1H), 7.90 (s, 1H), 7.63-7.74 (m, 4H), 7.53 (m, 2H), 7.35-7.44 (m, 4H), 6.36-6.49 (m, 1H), 6.25 (d, 2H), 5.73-5.76 (m, 1H).

Example 191: Preparation of 4-(8-(3-acrylamidophenyl)-5-aminoquinazolin-6-yl)-3-chloro-N-(pyridin-2-yl)benzamide

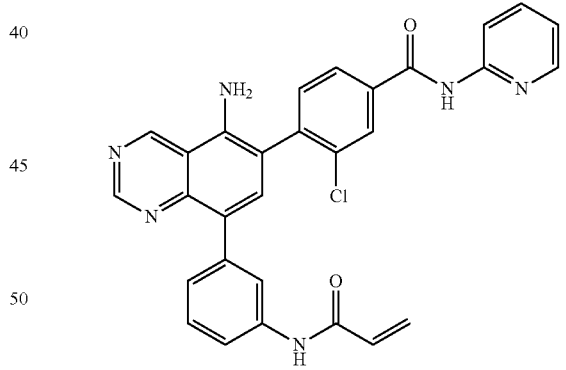

4-(8-(3-acrylamidophenyl)-5-aminoquinazolin-6-yl)-3-chloro-N-(pyridin-2-yl)benzamide 4-(8-(3-Acrylamidophenyl)-5-aminoquinazolin-6-yl)-3-chloro-N-(pyridin-2-yl)benzamide (9.8 mg) was prepared as described for 1-(3-(6-phenylquinazolin-8-yl)pyrrolidin-1-yl)prop-2-en-1-one. LRMS (M+H⁺) m/z calculated 521.1, found 521.2. ¹H NMR (DMSO-d6, 400 MHz) δ 11.01 (s, 1H), 10.18 (s, 1H), 9.93 (s, 1H), 9.22 (s, 1H), 8.23-8.43 (m, 2H), 8.15-8.21 (m, 2H), 7.88-7.90 (m, 2H), 7.66-7.72 (m, 2H), 7.55 (s, 1H), 7.37-7.40 (m, 2H), 7.20-7.23 (m, 1H), 6.36-6.45 (m, 1H), 5.76-6.36 (m, 2H), 5.73 (d, 1H).

Example 192: Preparation of 2-(4-(8-(3-acrylamidophenyl)quinazolin-6-yl)phenoxy)isonicotinamide

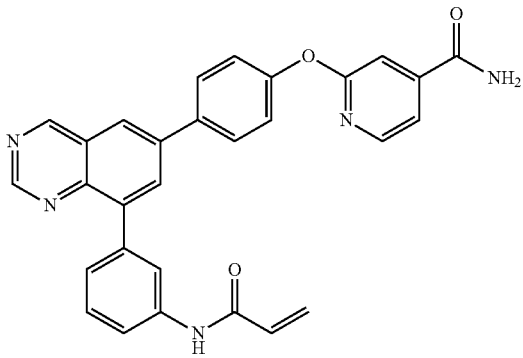

2-(4-(8-(3-acrylamidophenyl)quinazolin-6-yl)phenoxy)isonicotinamide 2-(4-(8-(3-Acrylamidophenyl)quinazolin-6-yl)phenoxy)isonicotinamide (129.9 mg) was prepared as described for 1-(3-(6-phenylquinazolin-8-yl)pyrrolidin-1-yl)prop-2-en-1-one. LRMS (M+H$^+$) m/z calculated 488.2, found 488.2. $^1$H NMR (DMSO-d6, 400 MHz) δ 10.29 (s, 1H), 9.74 (s, 1H), 9.33 (s, 1H), 8.52 (d, 1H), 8.29-8.37 (m, 3H), 8.00-8.05 (m, 3H), 7.80-7.85 (m, 2H), 7.47-7.56 (m, 4H), 7.35 (d, 2H), 6.46-6.52 (m, 1H), 6.25-6.30 (m, 1H), 5.77 (d, 1H).

Example 193: Preparation of 1-(3-(5-amino-6-(4-phenoxyphenyl)quinazolin-8-yl)pyrrolidin-1-yl)prop-2-en-1-one

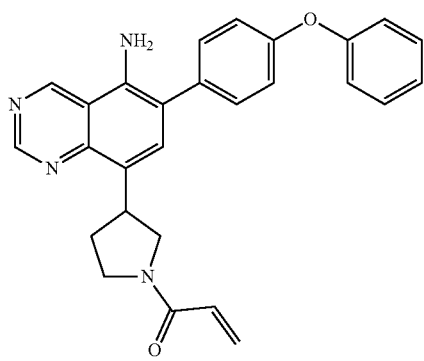

1-(3-(5-amino-6-(4-phenoxyphenyl)quinazolin-8-yl)pyrrolidin-1-yl)prop-2-en-1-one 1-(3-(5-Amino-6-(4-phenoxyphenyl)quinazolin-8-yl)pyrrolidin-1-yl)prop-2-en-1-one (5.3 mg) was prepared as described for 1-(3-(6-phenylquinazolin-8-yl)pyrrolidin-1-yl)prop-2-en-1-one. LRMS (M+H$^+$) m/z calculated 437.2, found 437.2. $^1$H NMR (DMSO-d6, 400 MHz) δ 9.86 (s, 1H), 9.21 (s, 1H), 7.61 (s, 1H), 7.50-7.53 (m, 2H), 7.42-7.46 (m, 2H), 7.19 (s, 1H), 7.11-7.14 (m, 3H), 6.73-6.77 (m, 1H), 6.57-6.67 (m, 1H), 6.14-6.15 (m, 1H), 6.09-6.11 (m, 2H), 5.62-5.69 (m, 1H), 4.33-4.39 (m, 1H), 4.18-4.23 (m, 1H), 3.61-3.81 (m, 2H), 3.38-3.48 (m, 1H), 2.14-2.32 (m, 2H).

Example 194: Preparation of N-(3-(6-(4-((4-cyanopyridin-2-yl)oxy)-2-fluorophenyl)quinazolin-8-yl)phenyl)acrylamide

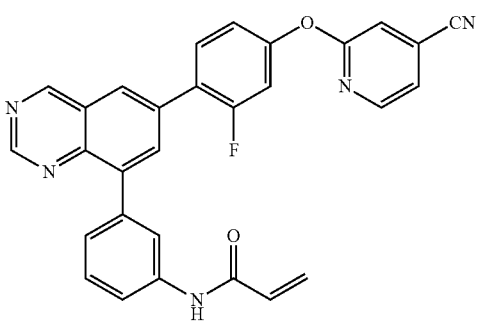

N-(3-(6-(4-((4-cyanopyridin-2-yl)oxy)-2-fluorophenyl)quinazolin-8-yl)phenyl)acrylamide N-(3-(6-(4-((4-cyanopyridin-2-yl)oxy)-2-fluorophenyl)quinazolin-8-yl)phenyl)acrylamide (17 mg) was prepared as described for 1-(3-(6-phenylquinazolin-8-yl)pyrrolidin-1-yl)prop-2-en-1-one. LRMS (M+H$^+$) m/z calculated 487.1, found 487.1. $^1$H NMR (DMSO-d6, 400 MHz) δ 10.29 (s, 1H), 9.76 (s, 1H), 9.36 (s, 1H), 8.42-8.45 (m, 2H), 8.21 (s, 1H), 8.05 (s, 1H), 7.81-7.87 (m, 3H), 7.65-7.67 (m, 1H), 7.48-7.49 (m, 2H), 7.26-7.43 (m, 1H), 7.23 (d, 1H), 6.44-6.47 (m, 1H), 6.29 (d, 1H), 5.77 (d, 1H).

Example 195: Preparation of 1-(3-(5-amino-6-(4-((4-(trifluoromethyl)pyridin-2-yl)oxy)phenyl)quinazolin-8-yl)pyrrolidin-1-yl)prop-2-en-1-one

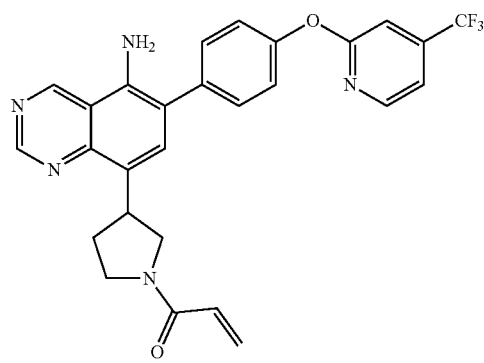

1-(3-(5-amino-6-(4-((4-(trifluoromethyl)pyridin-2-yl)oxy)phenyl)quinazolin-8-yl)pyrrolidin-1-yl)prop-2-en-1-one 1-(3-(5-Amino-6-(4-((4-(trifluoromethyl)pyridin-2-yl)oxy)phenyl)quinazolin-8-yl)pyrrolidin-1-yl)prop-2-en-1-one (1.6 mg) was prepared as described for 1-(3-(6-phenylquinazolin-8-yl)pyrrolidin-1-yl)prop-2-en-1-one. LRMS (M+H$^+$) m/z calculated 506.2, found 506.2. $^1$H NMR (DMSO-d6, 400 MHz) δ 9.88 (s, 1H), 9.23 (s, 1H), 8.46 (d, 1H), 7.53-7.64 (m, 5H), 7.35 (dd, 2H), 6.57-6.68 (m, 1H), 6.12-6.18 (m, 3H), 5.62-5.70 (m, 1H), 3.61-4.39 (m, 5H), 1.99-2.33 (m, 1H).

Example 196: Preparation of 2-(4-(8-(3-acrylamidophenyl)quinazolin-6-yl)-3-fluorophenoxy)isonicotinamide

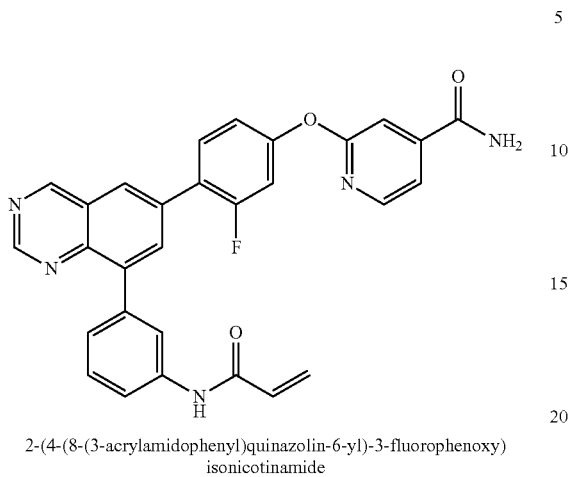

2-(4-(8-(3-acrylamidophenyl)quinazolin-6-yl)-3-fluorophenoxy)isonicotinamide 2-(4-(8-(3-Acrylamidophenyl)quinazolin-6-yl)-3-fluorophenoxy)isonicotinamide (14 mg) was prepared as described for 1-(3-(6-phenylquinazolin-8-yl)pyrrolidin-1-yl)prop-2-en-1-one. LRMS (M+H$^+$) m/z calculated 506.2, found 506.2. $^1$H NMR (DMSO-d6, 400 MHz) δ 10.29 (s, 1H), 9.77 (s, 1H), 9.37 (s, 1H), 8.23-8.43 (m, 4H), 8.05 (s, 1H), 7.82-7.88 (m, 2H), 7.16-7.60 (m, 6H), 6.74-6.76 (m, 1H), 6.45-6.51 (m, 1H), 6.26-6.30 (m, 1H), 5.76 (d, 1H).

Example 197: Preparation of 1-(3-(5-amino-6-(2-fluoro-4-((4-(trifluoromethyl)pyridin-2-yl)oxy)phenyl)quinazolin-8-yl)pyrrolidin-1-yl)prop-2-en-1-one

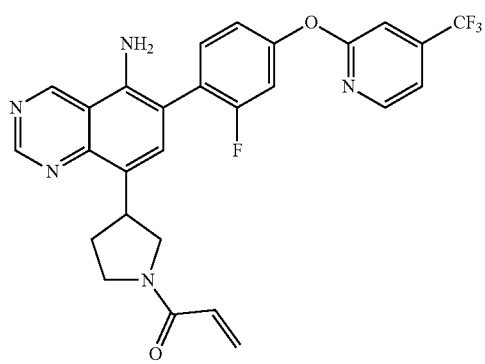

1-(3-(5-amino-6-(2-fluoro-4-((4-(trifluoromethyl)pyridin-2-yl)oxy)phenyl)quinazolin-8-yl)pyrrolidin-1-yl)prop-2-en-1-one 1-(3-(5-Amino-6-(2-fluoro-4-((4-(trifluoromethyl)pyridin-2-yl)oxy)phenyl)quinazolin-8-yl)pyrrolidin-1-yl)prop-2-en-1-one (5.9 mg) was prepared as described for 1-(3-(6-phenylquinazolin-8-yl)pyrrolidin-1-yl)prop-2-en-1-one. LRMS (M+H$^+$) m/z calculated 524.2, found 524.2. $^1$H NMR (DMSO-d6, 400 MHz) δ 10.15 (d, 1H), 9.22 (d, 1H), 8.38 (d, 1H), 7.70 (s, 1H), 7.46 (m, 1H), 7.26-7.31 (m, 2H), 7.13-7.16 (m, 2H), 6.40-6.55 (m, 2H), 5.64-5.72 (m, 1H), 3.50-4.48 (m, 5H), 2.15-2.51 (m, 2H).

Example 198: Preparation of 1-(3-(5-amino-3-(4-((4-(trifluoromethyl)pyridin-2-yl)oxy)phenyl)imidazo[1,5-c]pyrimidin-1-yl)pyrrolidin-1-yl)prop-2-en-1-one

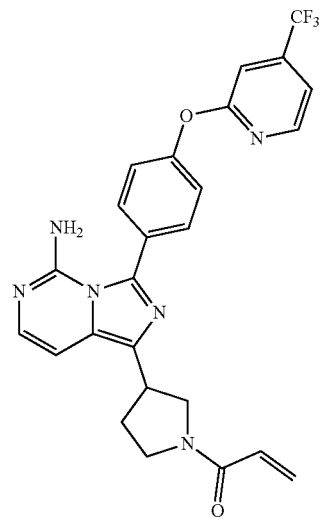

1-(3-(5-amino-3-(4-((4-(trifluoromethyl)pyridin-2-yl)oxy)phenyl)imidazo[1,5-c]pyrimidin-1-yl)pyrrolidin-1-yl)prop-2-en-1-one 1-(3-(5-Amino-3-(4-((4-(trifluoromethyl)pyridin-2-yl)oxy)phenyl)imidazo[1,5-c]pyrimidin-1-yl)pyrrolidin-1-yl)prop-2-en-1-one (23 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H$^+$) m/z calculated 495.2, found 495.2. $^1$H NMR (DMSO-d6, 400 MHz) δ 8.45 (s, 1H), 7.65 (d, 2H), 7.55 (d, 2H), 7.34 (d, 2H), 7.13 (d, 1H), 6.94-9.99 (m, 1H), 6.61-6.65 (m, 1H), 6.31 (s, 2H), 6.15 (dd, 1H), 5.63-5.70 (m, 1H), 3.84-4.02 (m, 2H), 3.66-3.75 (m, 3H), 2.24-2.31 (m, 1H).

Example 199: Preparation of 4-(8-(1-acryloylpyrrolidin-3-yl)-4-aminoimidazo[1,5-a][1,3,5]triazin-6-yl)-N-(pyridin-2-yl)benzamide

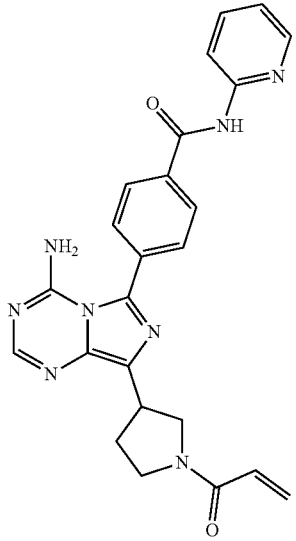

4-(8-(1-acryloylpyrrolidin-3-yl)-4-aminoimidazo[1,5-a][1,3,5]triazin-6-yl)-N-(pyridin-2-yl)benzamide

497

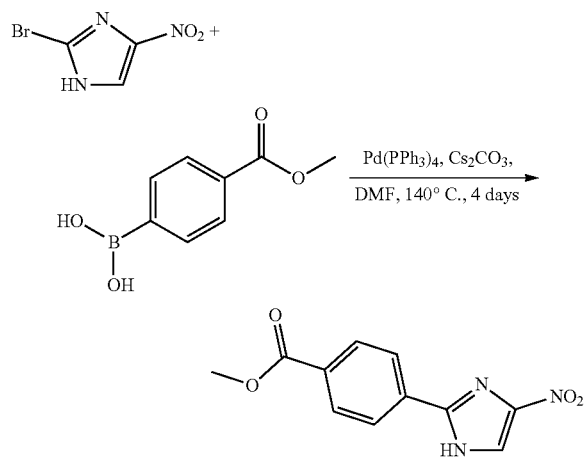

To a solution of 2-bromo-4-nitro-1H-imidazole (20.0 g, 104.0 mmol, 1.0 eq) and (4-(methoxycarbonyl)phenyl)boronic acid (37.0 g, 208.0 mmol, 2.0 eq) in DMF (500.0 mL) was added $Cs_2CO_3$ (102.0 g, 312 mmol, 3.0 eq), followed by $Pd(PPh_3)_4$ (3.6 g, 3.12 mmol, 0.03 eq) under $N_2$ protection. The mixture was stirred at 140° C. for 3 day, then cooled to rt and concentrated. The resulting residue was triturated with (PE/EA=1/1, v/v, 3.0 L) to afford crude methyl 4-(4-nitro-1H-imidazol-2-yl)benzoate as a brown solid (20.6 g, 80%).

To a mixture of methyl 4-(4-nitro-1H-imidazol-2-yl)benzoate (18.6 g, 75.3 mmol, 1.0 eq) and $K_2CO_3$ (16 g, 113.0 mmol, 1.5 eq) in DMF (100.0 mL) was added $Br_2$ (12.0 g, 75.3 mmol, 1.0 eq) dropwise at rt. The mixture was stirred at 60° C. for 3 h, then poured into ice-water and the basified by aq. $NH_3H_2O$ until pH=10. The solid was filtered and the filtrate was acidated to pH 6 with 1 N HCl, filtered, and dried in vacuum to afford methyl 4-(5-bromo-4-nitro-1H-imidazol-2-yl)benzoate (9.7 g, 46%).

498

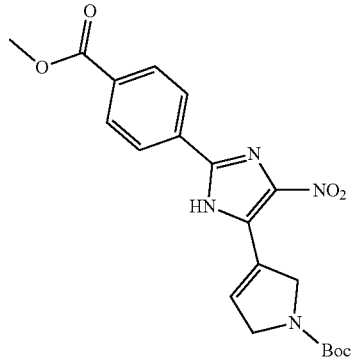

To a solution of methyl 4-(5-bromo-4-nitro-1H-imidazol-2-yl)benzoate (9.9 g, 30.4 mmol, 1.0 eq) and tert-butyl 3-(4,4,5,5-tetramethyl-1,3,2-dioxaborolan-2-yl)-2,5-dihydro-1H-pyrrole-1-carboxylate (10.8 g, 36.4 mmol, 1.2 eq) in dioxane (250.0 mL) and $H_2O$ (25.0 mL) was added $Na_2CO_3$ (9.7 g, 91.2 mmol, 3.0 eq), followed by Pd(dppf)$Cl_2 \cdot CH_2Cl_2$ (744 mg, 0.9 mmol, 0.03 eq) under $N_2$ protection. The mixture was stirred at 80° C. for 17 h, then cooled to rt and concentrated. The resulting residue was purified by column chromatography (DCM/MeOH=30/1, v/v) to afford tert-butyl 3-(2-(4-(methoxycarbonyl)phenyl)-4-nitro-1H-imidazol-5-yl)-2,5-dihydro-1H-pyrrole-1-carboxylate as a brown solid (8.7 g, 69%).

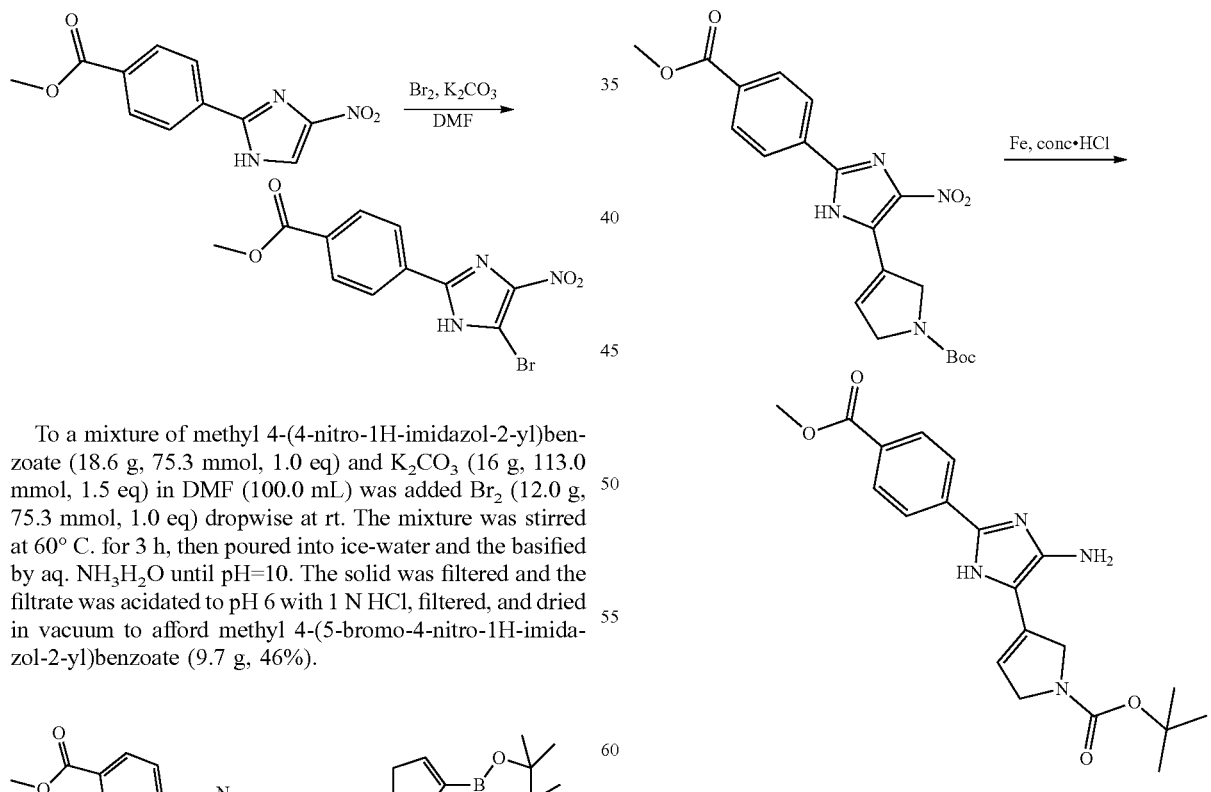

To a mixture of tert-butyl 3-(2-(4-(methoxycarbonyl)phenyl)-4-nitro-1H-imidazol-5-yl)-2,5-dihydro-1H-pyrrole-1-carboxylate (8.7 g, 21.0 mmol, 1.0 eq) in MeOH/DCM (200.0 mL/20.0 mL) was added HCl (5.3 mL, 63.0 mmol, 3.0 eq) and Fe (11.8 g, 210.0 mmol, 10.0 eq). The mixture was stirred at 60° C. for 2 h, then cooled to rt and concentrated. The resulting residue was purified by column chromatography (DCM/MeOH=30/1, v/v) to afford tert-butyl 3-(4-amino-2-(4-(methoxycarbonyl)phenyl)-1H-imidazol-5-yl)-2,5-dihydro-1H-pyrrole-1-carboxylate (6.7 g, 63.7%).

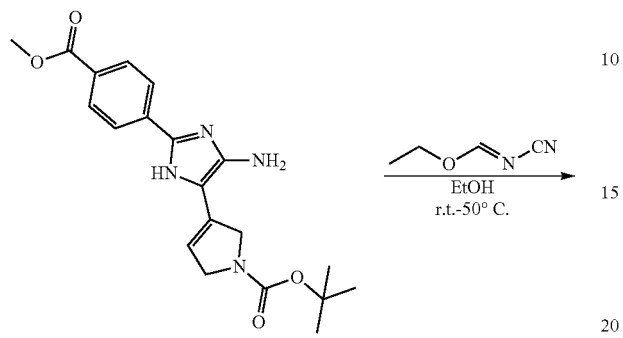

A mixture of tert-butyl 3-(4-amino-2-(4-(methoxycarbonyl)phenyl)-1H-imidazol-5-yl)-2,5-dihydro-1H-pyrrole-1-carboxylate (6.0 g, 15.6 mmol, 1.0 eq), (E)-ethyl N-cyanoformimidate (1.6 g, 18.8 mmol, 1.2 eq) and TEA (4.4 mL, 31.2 mmol, 2.0 eq) in dioxane (60.0 mL) was stirred at rt for 17 h, then heated at 60° C. for 1.5 h and concentrated. The resulting residue purified by column chromatography (EA/PE=2/1, v/v) to afford tert-butyl 3-(4-amino-6-(4-(methoxycarbonyl)phenyl)imidazo[1,5-a][1,3,5]triazin-8-yl)-2,5-dihydro-1H-pyrrole-1-carboxylate (1.8 g, 26%).

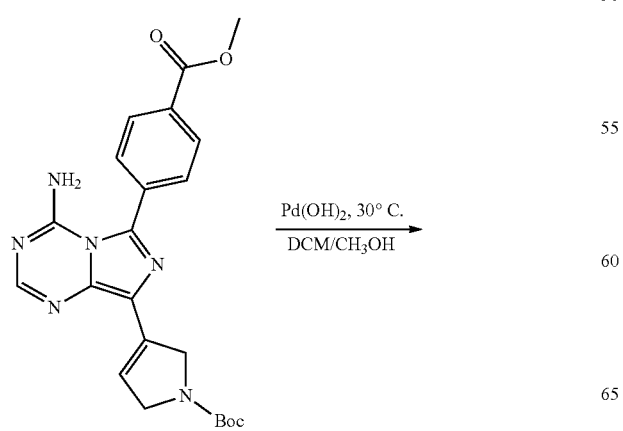

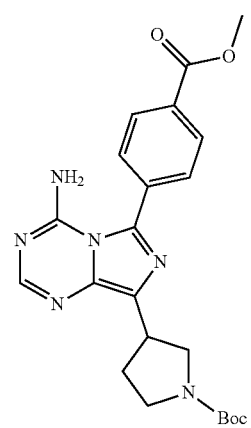

To a solution of tert-butyl 3-(4-amino-6-(4-(methoxycarbonyl)phenyl)imidazo[1,5-a][1,3,5]triazin-8-yl)-2,5-dihydro-1H-pyrrole-1-carboxylate (1.8 g, 4.1 mmol, 1.0 eq) in MeOH/DCM (100.0 mL/40.0 mL) was added Pd(OH)₂ (540.0 mg) at rt. The mixture was stirred at 30° C. for 8 h, then cooled to rt, diluted with DCM (40.0 mL) and filtered. The filtrate was concentrated and the resulting residue was purified by column chromatography (EA/PE=2/1, v/v) to afford tert-butyl 3-(4-amino-6-(4-(methoxycarbonyl)phenyl)imidazo[1,5-a][1,3,5]triazin-8-yl)pyrrolidine-1-carboxylate as a yellow solid (1.14 g, 64.0%).

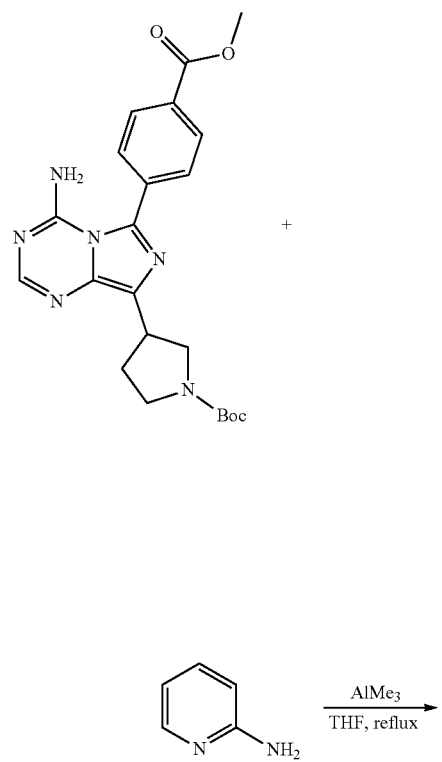

-continued

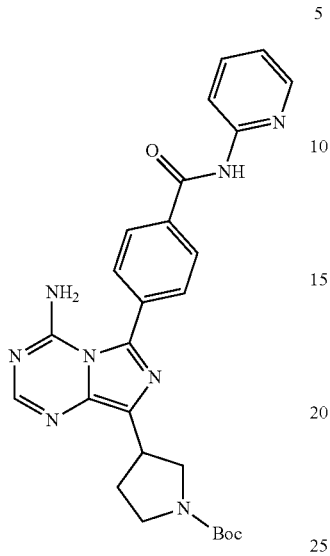

To a solution of tert-butyl 3-(4-amino-6-(4-(methoxycarbonyl)phenyl)imidazo[1,5-a][1,3,5]triazin-8-yl)pyrrolidine-1-carboxylate (400.0 mg, 0.9 mmol, 1.0 eq) and pyridin-2-amine (258.0 mg, 2.7 mmol, 3.0 eq) in THF (40.0 mL) was added AlMe₃ (4.5 mL, 4.5 mmol, 5.0 eq) at 0° C. The mixture was stirred at 80° C. for 17 h. The mixture was poured into satd. NH₄Cl and extracted with DCM (150.0 mL×3). The combined organic layers were separated and washed with brine, dried over anhydrous Na₂SO₄ and concentrated. The resulting residue was purified by column chromatography (DCM/MeOH=20/1, v/v) to afford tert-butyl 3-(4-amino-6-(4-(pyridin-2-ylcarbamoyl)phenyl)imidazo[1,5-a][1,3,5]triazin-8-yl)pyrrolidine-1-carboxylate (85.0 mg, 17.0%).

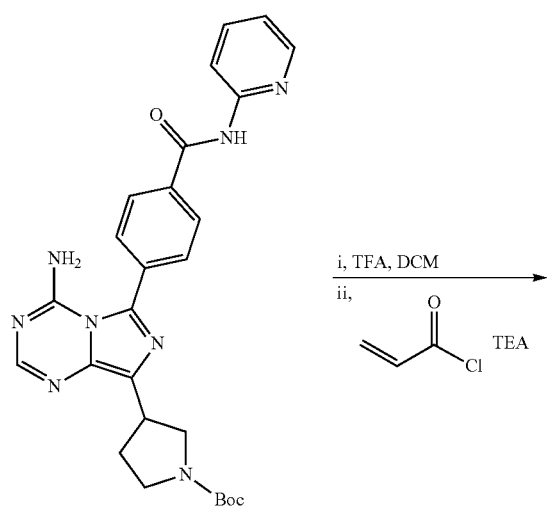

-continued

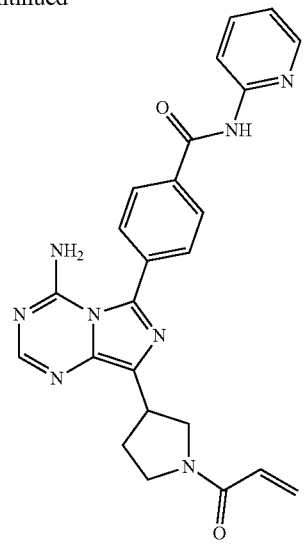

To a solution of tert-butyl 3-(4-amino-6-(4-(pyridin-2-ylcarbamoyl)phenyl)imidazo[1,5-a][1,3,5]triazin-8-yl)pyrrolidine-1-carboxylate (85.0 mg, 0.17 mmol, 1.0 eq) in DCM (4.0 mL) was added TFA (1.0 mL) and the mixture was stirred at rt for 30 min, then concentrated. The residue was dissolved in DCM (3.0 mL), and TEA (35.0 mg, 0.34 mmol, 2.0 eq) was added, followed by acryloyl chloride (11.0 mg, 0.12 mmol, 0.7 eq). The resulting mixture was stirred at rt for 1 h, then washed with brine, dried over anhydrous Na₂SO₄ and concentrated. The resulting residue was purified by column chromatography (DCM/MeOH=20/1, v/v) and prep-HPLC to afford 4-(8-(1-acryloylpyrrolidin-3-yl)-4-aminoimidazo[1,5-a][1,3,5]triazin-6-yl)-N-(pyridin-2-yl)benzamide (19.5 mg, 24%) as a off-white solid. LRMS (M+H⁺) m/z calculated 455.2, found 455.2. ¹H NMR (CD₃OD, 400 MHz) δ 8.35 (d, 1H), 8.22 (d, 1H), 8.12 (d, 2H), 7.77-7.85 (m, 4H), 7.16 (t, 1H), 6.58-6.65 (m, 1H), 6.25-6.30 (m, 1H), 5.73 (t, 1H), 3.55-4.06 (m, 5H), 2.34-2.41 (m, 2H).

Example 200: Preparation of N-(3-(6-(4-((4-cyclopropylpyridin-2-yl)oxy)-2-fluorophenyl)quinazolin-8-yl)phenyl)acrylamide

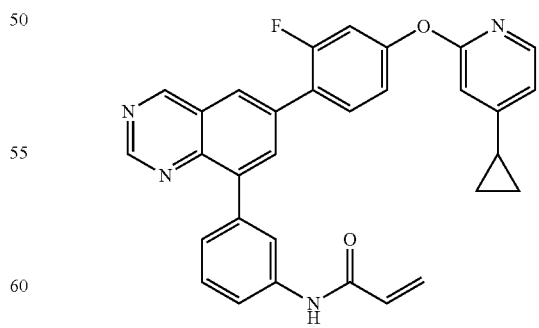

N-(3-(6-(4-((4-cyclopropylpyridin-2-yl)oxy)-2-fluorophenyl)quinazolin-8-yl)phenyl)acrylamide N-(3-(6-(4-((4-cyclopropylpyridin-2-yl)oxy)-2-fluorophenyl)quinazolin-8-yl)phenyl)acrylamide (51 mg) was prepared as described for 1-(3-(6-phenylquinazolin-8-yl)pyrrolidin-1-yl)prop-2-en-1-one. LRMS (M+H⁺) m/z calculated 503.2, found 503.3. ¹H NMR (DMSO-d6, 400 MHz) δ 10.30 (s, 1H), 9.76 (s, 1H), 9.36 (s, 1H), 8.42 (s, 1H), 8.21 (s, 1H), 8.02-8.04 (m, 2H), 7.80-7.84 (m, 2H), 7.48-7.50 (m, 2H), 7.27 (dd, 1H), 7.15 (dd, 1H), 6.90-6.93 (m, 2H), 6.45-6.52 (m, 1H), 6.25-6.30 (m, 1H), 5.77 (dd, 1H), 2.00-2.02 (m, 1H), 1.10 (dd, 2H), 0.88 (dd, 2H).

Example 201: Preparation of 4-(8-(1-acryloylpyrrolidin-3-yl)-4-aminoimidazo[1,5-a][1,3,5]triazin-6-yl)-N-(4-cyclopropylpyridin-2-yl)benzamide

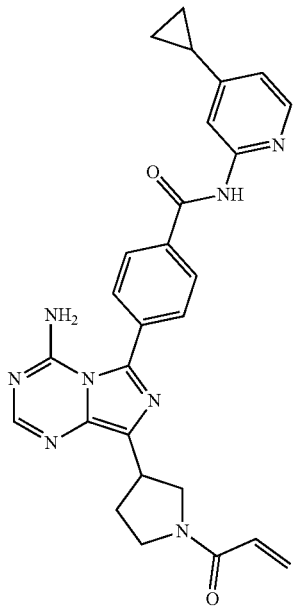

4-(8-(1-acryloylpyrrolidin-3-yl)-4-aminoimidazo[1,5-a][1,3,5]triazin-6-yl)-N-(4-cyclopropylpyridin-2-yl)benzamide 4-(8-(1-Acryloylpyrrolidin-3-yl)-4-aminoimidazo[1,5-a][1,3,5]triazin-6-yl)-N-(4-cyclopropylpyridin-2-yl)benzamide (1.1 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H⁺) m/z calculated 495.2, found 495.2. ¹H NMR (DMSO-d6, 400 MHz) δ 10.78 (s, 1H), 8.15-8.22 (m, 3H), 7.98 (s, 1H), 7.88 (s, 1H), 7.72 (d, 2H), 6.88 (d, 1H), 6.58-6.66 (m, 1H), 6.11 (dd, 1H), 5.66 (t, 1H), 3.65-4.02 (m, 5H), 2.24-2.36 (m, 2H), 1.99 (t, 1H), 1.10 (dd, 2H), 0.81 (dd, 2H).

Example 202: Preparation of 4-(8-(3-acrylamidophenyl)-5-aminoquinazolin-6-yl)-3-chloro-N-(4-cyclopropylpyridin-2-yl)benzamide

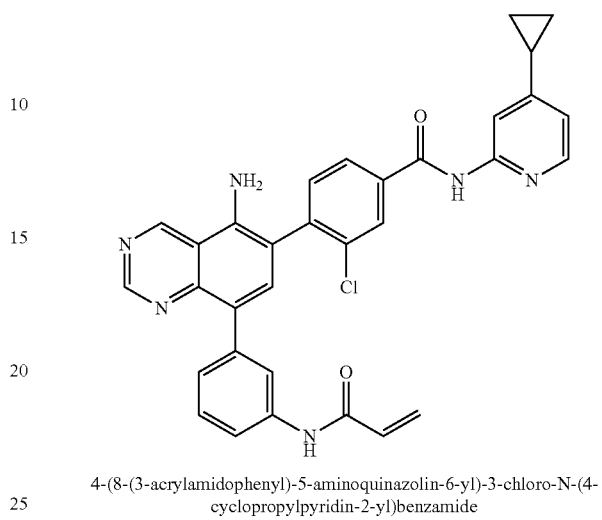

4-(8-(3-acrylamidophenyl)-5-aminoquinazolin-6-yl)-3-chloro-N-(4-cyclopropylpyridin-2-yl)benzamide 4-(8-(3-Acrylamidophenyl)-5-aminoquinazolin-6-yl)-3-chloro-N-(4-cyclopropylpyridin-2-yl)benzamide (12.5 mg) was prepared as described for 1-(3-(6-phenylquinazolin-8-yl)pyrrolidin-1-yl)prop-2-en-1-one. LRMS (M+H⁺) m/z calculated 561.2, found 561.2. ¹H NMR (DMSO-d6, 400 MHz) δ 10.91 (s, 1H), 10.17 (s, 1H), 9.93 (s, 1H), 9.21 (s, 1H), 8.37-8.43 (m, 10H), 6.90 (dd, 1H), 6.26-6.36 (m, 4H), 5.77 (dd, 1H), 2.00-2.05 (m, 1H), 1.09-1.12 (m, 2H), 0.81-0.82 (m, 2H).

Example 203: Preparation of 4-(8-(3-acrylamidophenyl)quinazolin-6-yl)-3-cyano-N-(pyridin-2-yl)benzamide

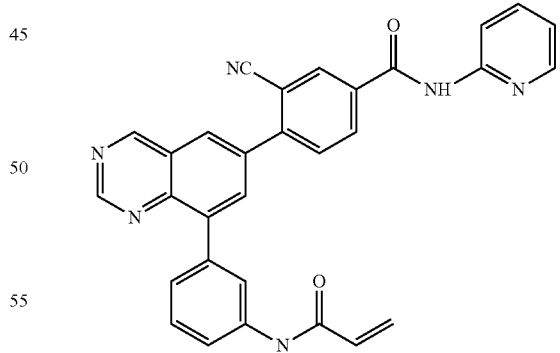

4-(8-(3-acrylamidophenyl)quinazolin-6-yl)-3-cyano-N-(pyridin-2-yl)benzamide 4-(8-(3-Acrylamidophenyl)quinazolin-6-yl)-3-cyano-N-(pyridin-2-yl)benzamide (35.5 mg) was prepared as described for 4-(8-(3-acrylamidophenyl)quinazolin-6-yl)-N-(pyridin-2-yl)benzamide. LRMS (M+H⁺) m/z calculated 497.2, found 497.2. ¹H NMR (DMSO-d6, 400 MHz) δ 11.20 (s, 1H), 10.31 (s, 1H), 9.83 (s, 1H), 9.43 (s, 1H), 8.72 (s, 1H), 8.54 (s, 1H), 8.44-8.51 (m, 2H), 8.32 (s, 1H), 8.23 (d, 1H), 8.04-8.08 (m, 2H), 7.83-7.91 (m, 2H), 7.51 (s, 1H), 7.22 (t, 1H), 6.45-6.52 (m, 1H), 6.25-6.29 (m, 1H), 5.76 (d, 1H).

Example 204: Preparation of 4-(8-(3-acrylamidophenyl)-5-aminoquinazolin-6-yl)-N-(4-cyclopropylpyridin-2-yl)-3-fluorobenzamide

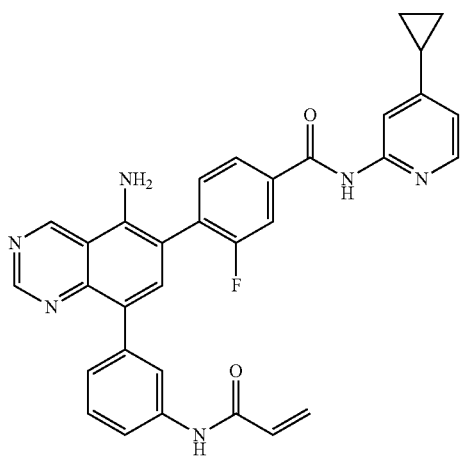

4-(8-(3-acrylamidophenyl)-5-aminoquinazolin-6-yl)-N-(4-cyclopropylpyridin-2-yl)-3-fluorobenzamide 4-(8-(3-Acrylamidophenyl)-5-aminoquinazolin-6-yl)-N-(4-cyclopropylpyridin-2-yl)-3-fluorobenzamide (9.5 mg) was prepared as described for 1-(3-(6-phenylquinazolin-8-yl)pyrrolidin-1-yl)prop-2-en-1-one. LRMS (M+H⁺) m/z calculated 545.2, found 545.2. ¹H NMR (DMSO-d6, 400 MHz) δ 10.86 (s, 1H), 10.18 (s, 1H), 9.94 (s, 1H), 9.21 (s, 1H), 8.23 (d, 1H), 8.05-8.22 (m, 3H), 7.99 (s, 1H), 7.62-7.87 (m, 3H), 7.40-7.42 (m, 2H), 6.87-6.90 (m, 2H), 6.75 (m, 1H), 6.48-6.65 (m, 2H), 6.27 (d, 1H), 5.76 (d, 1H), 1.98-2.00 (m, 1H), 1.09-1.11 (m, 2H), 0.82-0.85 (m, 2H).

Example 205: Preparation of N-(3-(5-amino-6-(2-chloro-4-(pyridin-2-yloxy)phenyl)quinazolin-8-yl)phenyl)acrylamide

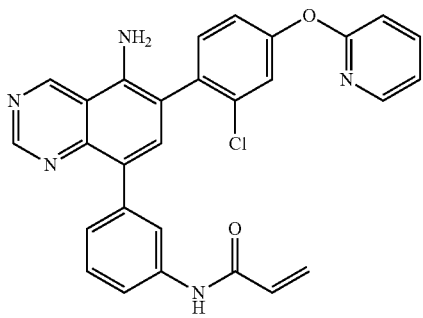

N-(3-(5-amino-6-(2-chloro-4-(pyridin-2-yloxy)phenyl)quinazolin-8-yl)phenyl)acrylamide 4-(8-(3-Acrylamidophenyl)-5-aminoquinazolin-6-yl)-N-(4-cyclopropylpyridin-2-yl)-3-fluorobenzamide (3.0 mg) was prepared as described for 1-(3-(6-phenylquinazolin-8-yl)pyrrolidin-1-yl)prop-2-en-1-one. LRMS (M+H⁺) m/z calculated 494.1, found 494.1. ¹H NMR (DMSO-d6, 400 MHz) δ 10.15 (s, 1H), 9.92 (s, 1H), 9.20 (s, 1H), 8.25 (d, 1H), 7.92-7.95 (m, 2H), 7.70-7.75 (m, 1H), 7.15-7.56 (m, 8H), 6.41-6.47 (m, 1H), 6.28 (m, 3H), 5.74 (d, 1H).

Example 206: Preparation of 4-(5-amino-1-(1-(but-2-ynoyl)pyrrolidin-3-yl)imidazo[1,5-c]pyrimidin-3-yl)-N-(pyridin-2-yl)benzamide

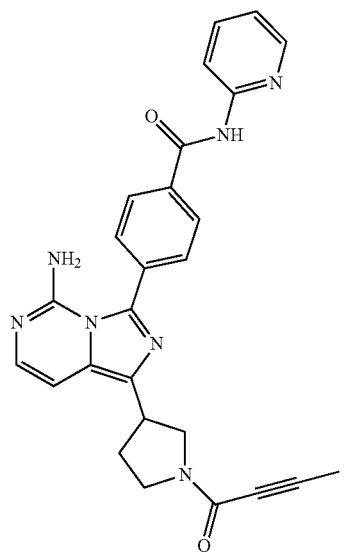

4-(5-amino-1-(1-(but-2-ynoyl)pyrrolidin-3-yl)imidazo[1,5-c]pyrimidin-3-yl)-N-(pyridin-2-yl)benzamide

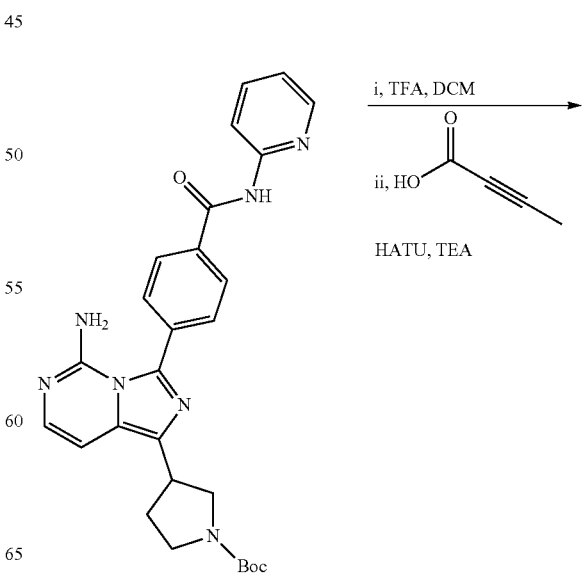

507
-continued

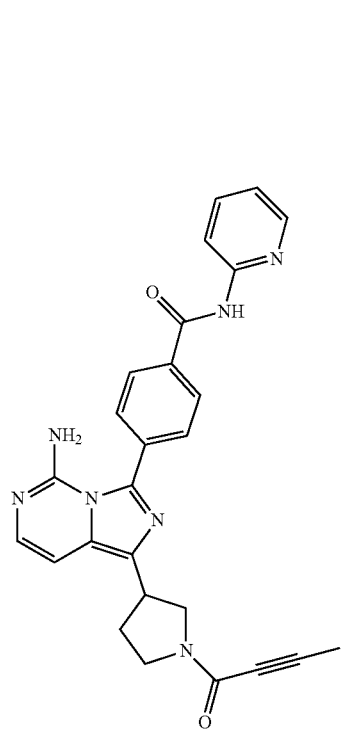

To a solution of tert-butyl 3-(5-amino-3-(4-(pyridin-2-ylcarbamoyl)phenyl)imidazo[1,5-c]pyrimidin-1-yl)pyrrolidine-1-carboxylate (510.0 mg, 1.02 mmol, 1.0 eq) in DCM (20.0 mL) was added TFA (5.0 mL) at rt, and the mixture was stirred at rt for 30 min, then concentrated. The resulting residue was dissolved in DCM (20.0 mL), and TEA (824.0 mg, 8.16 mmol, 8.0 eq) was added, followed by but-2-ynoic acid (69.0 mg, 0.82 mmol, 0.8 eq) and HATU (388. mg, 1.02 mmol, 1.0 eq). The resulting mixture was stirred at rt for 1 h, then washed with brine, dried over anhydrous $Na_2SO_4$ and concentrated. The resulting residue was purified on silica gel chromatography (DCM/MeOH=20/1, v/v) to afford 4-(5-amino-1-(1-(but-2-ynoyl)pyrrolidin-3-yl)imidazo[1,5-c]pyrimidin-3-yl)-N-(pyridin-2-yl)benzamide (211.0 mg, 44%) as a yellow solid. LCMS (M+H$^+$) m/z calculated 466.2, found 466.2. $^1$H NMR (DMSO-d6, 400 MHz) δ 10.91 (s, 1H), 8.42-8.41 (d, 1H), 8.24-8.15 (m, 3H), 7.89-7.87 (m, 1H), 7.73-7.71 (m, 2H), 7.20-7.18 (m, 2H), 7.02-7.97 (m, 1H), 6.37 (s, 2H), 3.81-3.32 (m, 5H), 2.28-2.24 (m, 2H), 2.03-1.98 (d, 3H).

Example 207: Preparation of 4-(4-amino-8-(1-(but-2-ynoyl)pyrrolidin-3-yl)imidazo[1,5-a][1,3,5]triazin-6-yl)-N-(pyridin-2-yl)benzamide

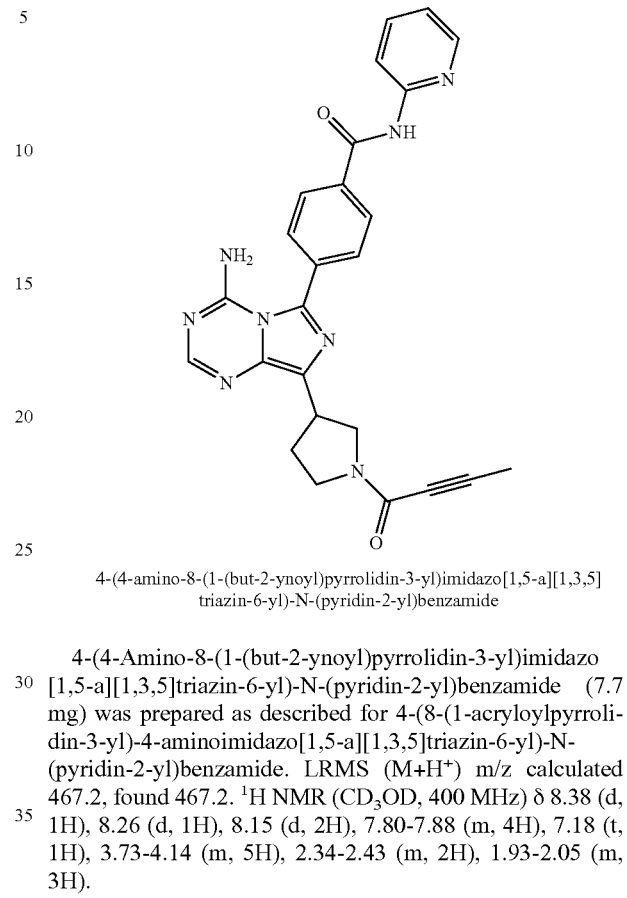

4-(4-amino-8-(1-(but-2-ynoyl)pyrrolidin-3-yl)imidazo[1,5-a][1,3,5]triazin-6-yl)-N-(pyridin-2-yl)benzamide 4-(4-Amino-8-(1-(but-2-ynoyl)pyrrolidin-3-yl)imidazo[1,5-a][1,3,5]triazin-6-yl)-N-(pyridin-2-yl)benzamide (7.7 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H$^+$) m/z calculated 467.2, found 467.2. $^1$H NMR (CD$_3$OD, 400 MHz) δ 8.38 (d, 1H), 8.26 (d, 1H), 8.15 (d, 2H), 7.80-7.88 (m, 4H), 7.18 (t, 1H), 3.73-4.14 (m, 5H), 2.34-2.43 (m, 2H), 1.93-2.05 (m, 3H).

Example 208: Preparation of 1-(3-(5-amino-3-(3-fluoro-4-((4-(trifluoromethyl)pyridin-2-yl)oxy)phenyl)imidazo[1,5-c]pyrimidin-1-yl)pyrrolidin-1-yl)prop-2-en-1-one

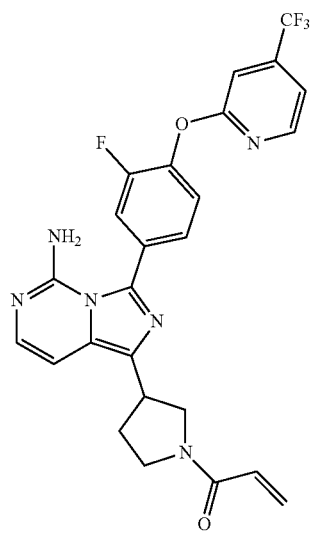

1-(3-(5-amino-3-(3-fluoro-4-((4-(trifluoromethyl)pyridin-2-yl)oxy)phenyl)imidazo[1,5-c]pyrimidin-1-yl)pyrrolidin-1-yl)prop-2-en-1-one 1-(3-(5-Amino-3-(3-fluoro-4-((4-(trifluoromethyl)pyridin-2-yl)oxy)phenyl)imidazo[1,5-c]pyrimidin-1-yl)pyrrolidin-1-yl)prop-2-en-1-one (19 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 513.2, found 513.2. ¹H NMR (CD₃OD, 400 MHz) δ 8.31 (d, 1H), 7.59 (d, 1H), 7.43-7.52 (m, 4H), 7.14 (d, 1H), 6.95 (t, 1H), 6.59-6.67 (m, 1H), 6.26-6.31 (m, 1H), 5.74 (t, 1H), 3.67-4.08 (m, 5H), 1.82-1.87 (m, 2H).

Example 209: Preparation of 1-(3-(5-amino-3-(3-fluoro-4-((4-(trifluoromethyl)pyridin-2-yl)oxy)phenyl)imidazo[1,5-c]pyrimidin-1-yl)pyrrolidin-1-yl)but-2-yn-1-one

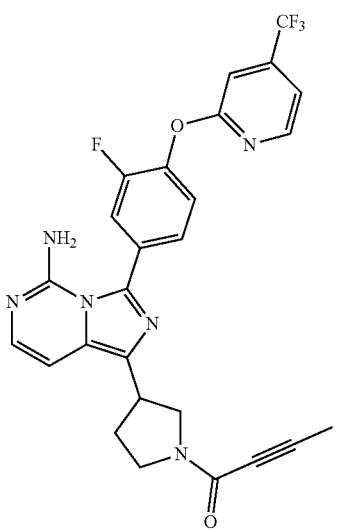

1-(3-(5-amino-3-(3-fluoro-4-((4-(trifluoromethyl)pyridin-2-yl)oxy)phenyl)imidazo[1,5-c]pyrimidin-1-yl)pyrrolidin-1-yl)but-2-yn-1-one 1-(3-(5-Amino-3-(3-fluoro-4-((4-(trifluoromethyl)pyridin-2-yl)oxy)phenyl)imidazo[1,5-c]pyrimidin-1-yl)pyrrolidin-1-yl)but-2-yn-1-one (12.3 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one LRMS (M+H⁺) m/z calculated 525.2, found 525.2. ¹H NMR (CD₃OD, 400 MHz) δ 8.31 (d, 1H), 7.43-7.61 (m, 3H), 7.13-7.16 (m, 2H), 6.92-6.97 (m, 1H), 6.74-6.78 (m, 1H), 3.30-4.20 (m, 5H), 2.34 (t, 2H), 2.00-2.05 (m, 3H).

Example 210: Preparation of 1-(3-(5-amino-3-(3-fluoro-4-(pyridin-2-yloxy)phenyl)imidazo[1,5-c]pyrimidin-1-yl)pyrrolidin-1-yl)prop-2-en-1-one

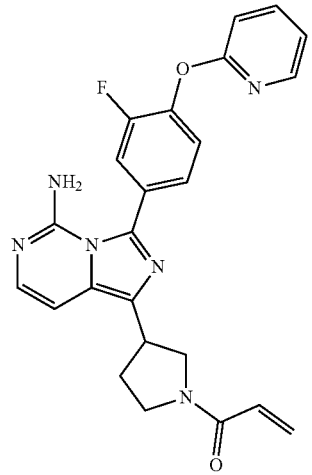

1-(3-(5-amino-3-(3-fluoro-4-(pyridin-2-yloxy)phenyl)imidazo[1,5-c]pyrimidin-1-yl)pyrrolidin-1-yl)prop-2-en-1-one 1-(3-(5-Amino-3-(3-fluoro-4-(pyridin-2-yloxy)phenyl)imidazo[1,5-c]pyrimidin-1-yl)pyrrolidin-1-yl)prop-2-en-1-one (23.5 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one LRMS (M+H⁺) m/z calculated 445.2, found 445.2. ¹H NMR (CD₃OD, 400 MHz) δ 8.15 (d, 1H), 7.86 (t, 1H), 7.39-7.58 (m, 3H), 7.14-7.18 (m, 3H), 6.95 (t, 1H), 6.59-6.77 (m, 1H), 6.25-6.31 (m, 1H), 5.76 (t, 1H), 3.66-4.08 (m, 5H), 2.30-2.42 (m, 2H).

Example 211: Preparation of 1-(3-(5-amino-3-(3-fluoro-4-(pyridin-2-yloxy)phenyl)imidazo[1,5-c]pyrimidin-1-yl)pyrrolidin-1-yl)but-2-yn-1-one

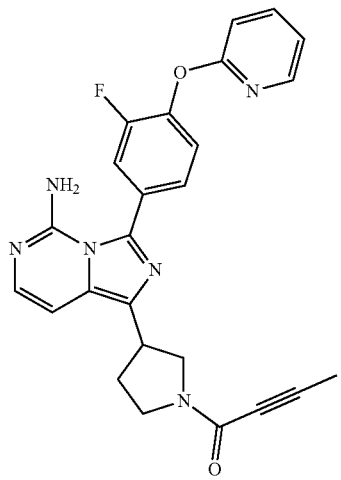

1-(3-(5-amino-3-(3-fluoro-4-(pyridin-2-yloxy)phenyl)imidazo[1,5-c]pyrimidin-1-yl)pyrrolidin-1-yl)but-2-yn-1-one 1-(3-(5-Amino-3-(3-fluoro-4-(pyridin-2-yloxy)phenyl)imidazo[1,5-c]pyrimidin-1-yl)pyrrolidin-1-yl)but-2-yn-1-one (18.7 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one LRMS (M+H⁺) m/z calculated 525.2, found 525.2. ¹H NMR (CD₃OD, 400 MHz) δ 8.31 (d, 1H), 7.43-7.61 (m, 3H), 7.13-7.16 (m, 2H), 6.92-6.97 (m, 1H), 6.74-6.78 (m, 1H), 3.80-4.20 (m, 5H), 2.34 (t, 2H), 2.00-2.05 (m, 3H).

Example 212: Preparation of 1-(3-(5-amino-3-(4-((4-methoxypyridin-2-yl)oxy)phenyl)imidazo[1,5-c]pyrimidin-1-yl)pyrrolidin-1-yl)prop-2-en-1-one

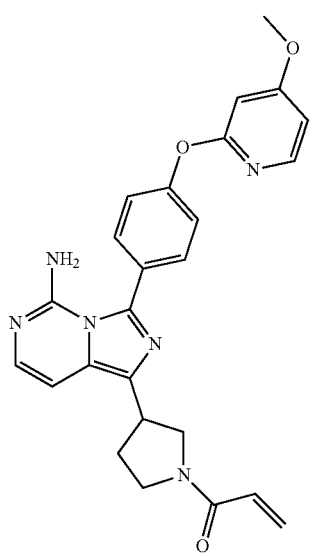

1-(3-(5-amino-3-(4-((4-methoxypyridin-2-yl)oxy)phenyl)imidazo[1,5-c]pyrimidin-1-yl)pyrrolidin-1-yl)prop-2-en-1-one

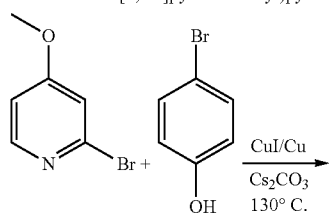

A mixture of 2-bromo-4-methoxypyridine (2.0 g, 10.64 mmol, 1.0 eq), 4-bromophenol (2.8 g, 15.96 mmol, 1.5 eq), Cu (72.0 mg, 1.1 mmol, 0.1 eq), CuI (216 mg, 1.1 mmol, 0.1 eq) and Cs₂CO₃ (6.9 g, 21.28 mmol, 2.0 eq) in NMP (40.0 mL) was heated at 130° C. for 17 h under N₂. The solid was filtered off, and the filtrate was concentrated. The resulting residue was purified by column chromatography (EA/PE=10/1, v/v) to provide 2-(4-bromophenoxy)-4-methoxypyridine as a brown solid (2.5 g, 83%).

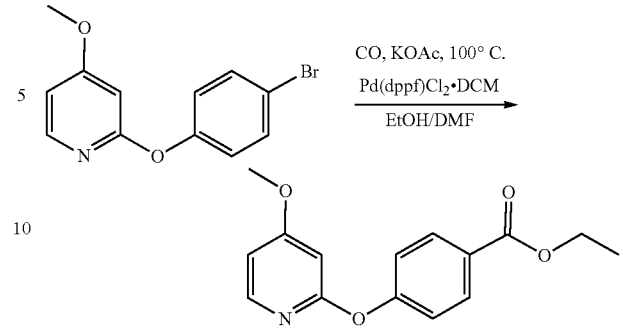

A mixture of 2-(4-bromophenoxy)-4-methoxypyridine (2.5 g, 8.93 mmol, 1.0 eq), Pd(dppf)Cl₂·DCM (726.0 mg, 0.89 mmol, 0.1 eq) and KOAc (2.6 g, 26.79 mmol, 3.0 eq) in EtOH/DMF (20.0 ml/20.0 mL) was heated at 100° C. for 17 h under CO. The solid was filtered off, and the filtrate was concentrated. The resulting residue was purified by column chromatography (EA/PE=10/1, v/v) to provide ethyl 4-((4-methoxypyridin-2-yl)oxy)benzoate as a brown solid (2.1 g, 88%).

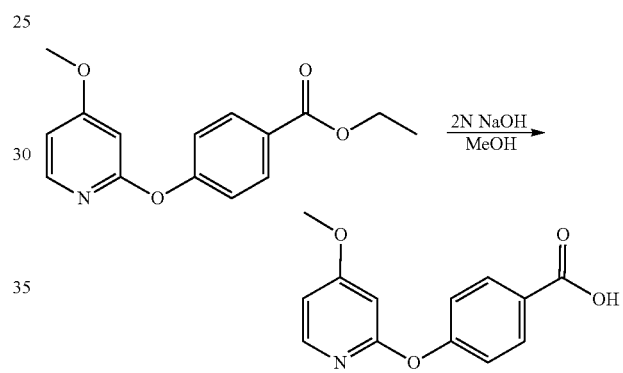

To a solution of ethyl 4-((4-methoxypyridin-2-yl)oxy)benzoate (2.1 g, 7.69 mmol, 1.0 eq) in methanol (40.0 mL) was added aq. 2N NaOH (7.7 mL, 15.38 mmol, 2.0 eq), the resulting mixture was stirred at rt overnight. The mixture was concentrated and the water phase was acidified by 4N HCl to pH 4. The precipitate was filtrated, washed with water, and dried in vacuum to provide 4-(pyridin-2-yloxy)benzoic acid as brown solid (1.8 g, 96%).

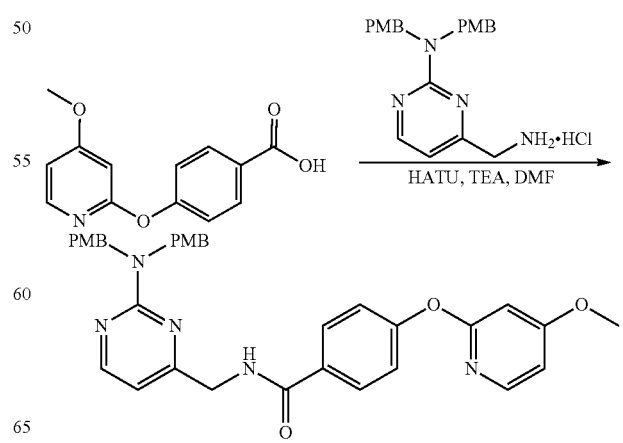

513

A mixture of 4-((4-methoxypyridin-2-yl)oxy)benzoic acid (1.8 g, 7.35 mmol, 1.0 eq), 4-(aminomethyl)-N,N-bis(4-methoxybenzyl)pyrimidin-2-amine (3.9 g, 8.82 mmol, 1.2 eq), HATU (3.35 g, 8.82 mmol, 1.2 eq) and TEA (3.7 g, 36.75 mmol, 5.0 eq) in DMF (50.0 mL) was stirred at rt overnight, then the solvent was evaporated. The resulting residue was purified by column chromatography (PE/EA=1/1, v/v) to afford N-((2-(bis(4-methoxybenzyl)amino)pyrimidin-4-yl)methyl)-4-((4-methoxypyridin-2-yl)oxy)benzamide (3.8 g, 88%).

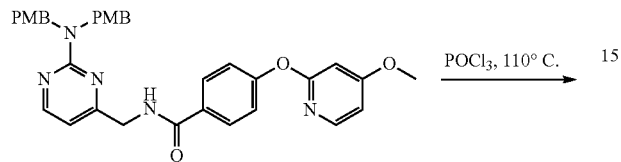

A mixture of N-((2-(bis(4-methoxybenzyl)amino)pyrimidin-4-yl)methyl)-4-((4-methoxypyridin-2-yl)oxy)benzamide (3.8 g, 6.43 mmol, 1.0 eq) in POCl₃ (50.0 mL) was stirred at 110° C. for 4 h. The solvent was evaporated, and the resulting residue was purified by column chromatography (PE/EA=1/1, v/v) to afford N-(4-methoxybenzyl)-3-(4-((4-methoxypyridin-2-yl)oxy)phenyl) imidazo [1,5-c]pyrimidin-5-amine (1.5 g, 52%).

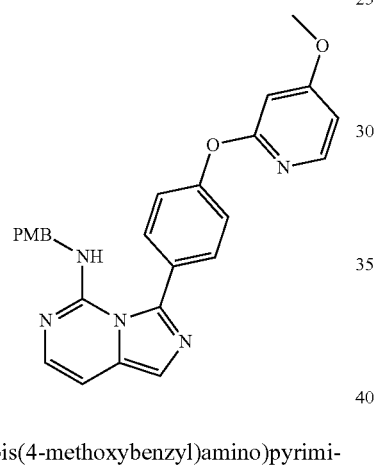

514

-continued

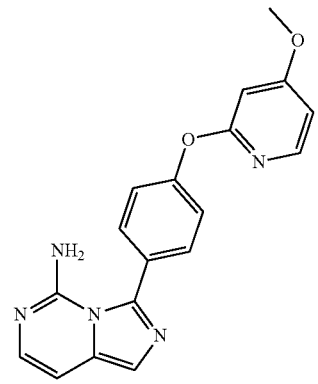

A mixture of N-(4-methoxybenzyl)-3-(4-((4-methoxypyridin-2-yl)oxy)phenyl)imidazo[1,5-c]pyrimidin-5-amine (1.5 g, 6.43 mmol, 1.0 eq) in TFA (20.0 mL) was stirred at 90° C. for 4 h. The solvent was evaporated, and the resulting residue was purified by column chromatography (DCM/MeOH=50/1, v/v) to afford 3-(4-((4-methoxypyridin-2-yl)oxy)phenyl)imidazo[1,5-c]pyrimidin-5-amine (700.0 mg, 64%).

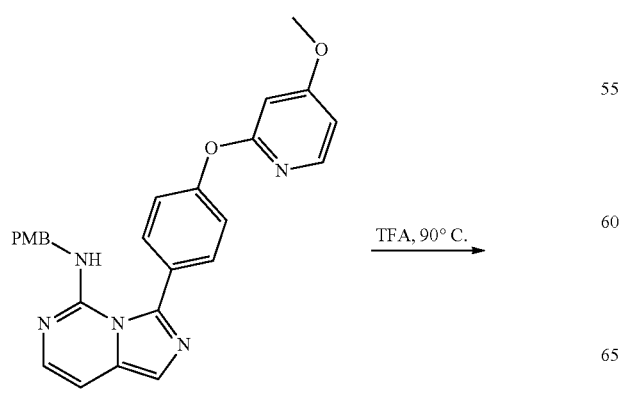

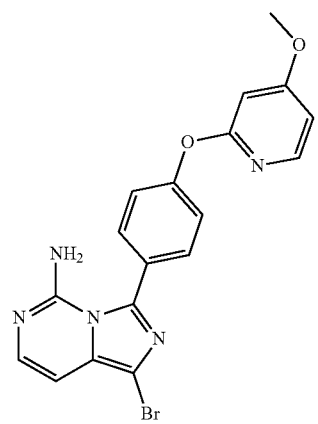

To a solution of 3-(4-((4-methoxypyridin-2-yl)oxy)phenyl)imidazo[1,5-c]pyrimidin-5-amine (700.0 mg, 2.1 mmol, 1.0 eq) in DCM (30.0 mL) was added NBS (299.0 mg, 1.68 mmol, 0.8 eq) at 0° C. and the mixture was stirred at 0° C. for 30 min. The mixture was poured into water and extracted with DCM (35.0 mL×3). The combined organic layers were separated and washed with brine, dried over anhydrous Na$_2$SO$_4$ and concentrated. The resulting residue was purified by column chromatography (DCM/MeOH=50/1, v/v) to afford 1-bromo-3-(4-((4-methoxypyridin-2-yl)oxy)phenyl)imidazo[1,5-c]pyrimidin-5-amine (650.0 mg, 75%).

(DCM/MeOH=50/1, v/v) to afford tert-butyl 3-(5-amino-3-(4-((4-methoxypyridin-2-yl)oxy)phenyl)imidazo[1,5-c]pyrimidin-1-yl)-2,5-dihydro-1H-pyrrole-1-carboxylate as a yellow solid (410.0 mg, 52%).

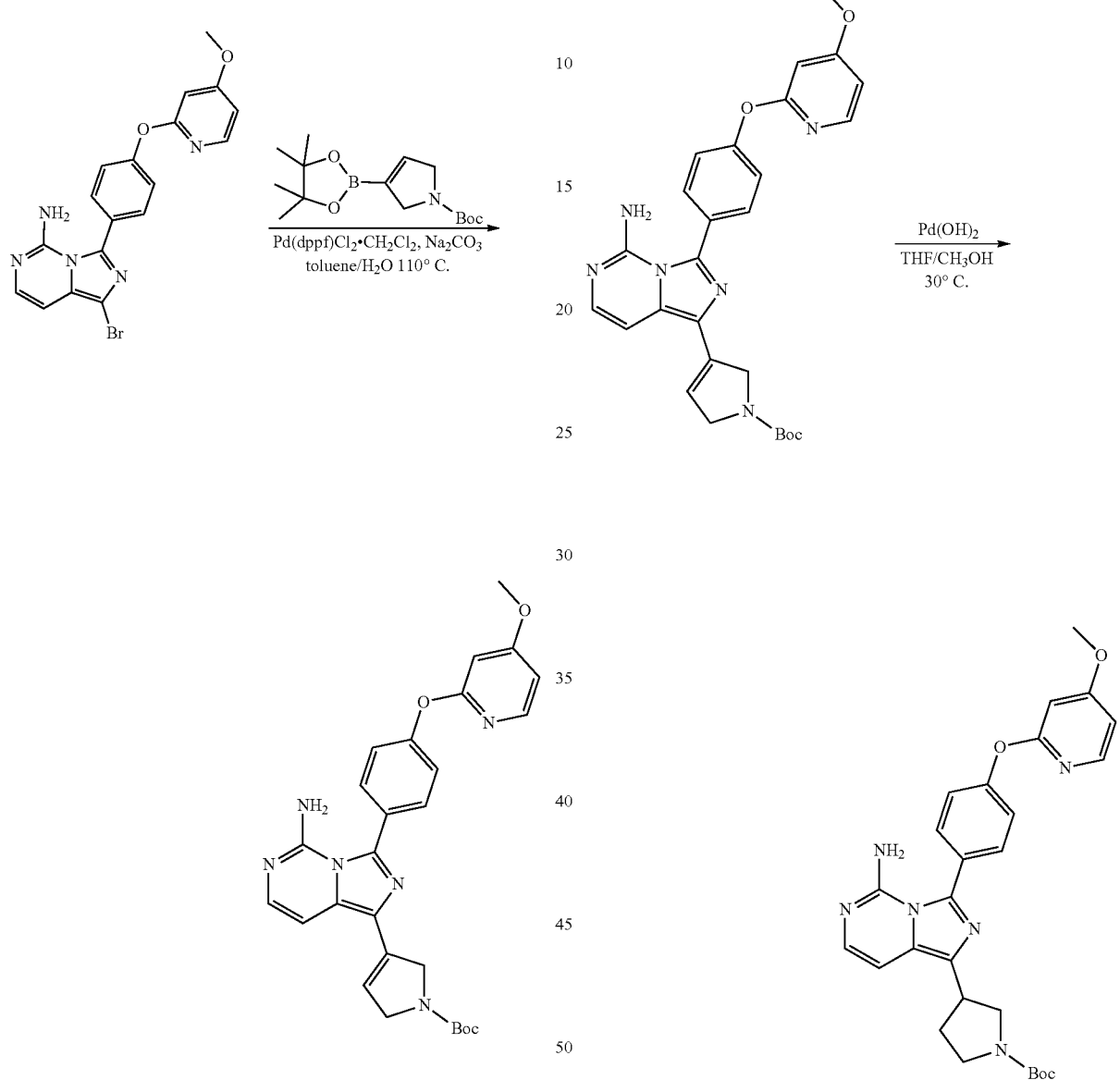

To a solution of 1-bromo-3-(4-((4-methoxypyridin-2-yl)oxy)phenyl)imidazo[1,5-c]pyrimidin-5-amine (650.0 mg, 1.58 mmol, 1.0 q) and tert-butyl 3-(4,4,5,5-tetramethyl-1,3,2-dioxaborolan-2-yl)-2,5-dihydro-1H-pyrrole-1-carboxylate (698.0 mg, 2.37 mmol, 1.5 eq) in dioxane (30.0 mL) and H$_2$O (3.0 mL) was added Na$_2$CO$_3$ (670.0 mg, 6.32 mmol, 4.0 eq), followed by Pd(dppf)Cl$_2$·CH$_2$Cl$_2$ (131.0 mg, 0.16 mmol, 0.1 eq) under N$_2$ protection. The mixture was stirred at 110° C. for 17 h, then cooled to rt, diluted with EA (40.0 mL) and filtered. The filtrate was concentrated and the resulting residue was purified by column chromatography To a solution of tert-butyl 3-(5-amino-3-(4-((4-methoxypyridin-2-yl)oxy)phenyl)imidazo [1,5-c]pyrimidin-1-yl)-2,5-dihydro-1H-pyrrole-1-carboxylate (410.0 mg, 0.82 mmol, 1.0 eq) in DCM (5.0 mL) and MeOH (15.0 mL) was added Pd(OH)$_2$ (150.0 mg) at rt. The mixture was stirred at 30° C. for 6 h, then cooled to rt, diluted with DCM (40.0 mL) and filtered. The filtrate was concentrated and the resulting residue was purified by column chromatography (DCM/MeOH=20/1, v/v) to afford tert-butyl 3-(5-amino-3-(4-((4-methoxypyridin-2-yl)oxy)phenyl)imidazo[1,5-c]pyrimidin-1-yl)pyrrolidine-1-carboxylate as a yellow solid (350.0 mg, 85.4%).

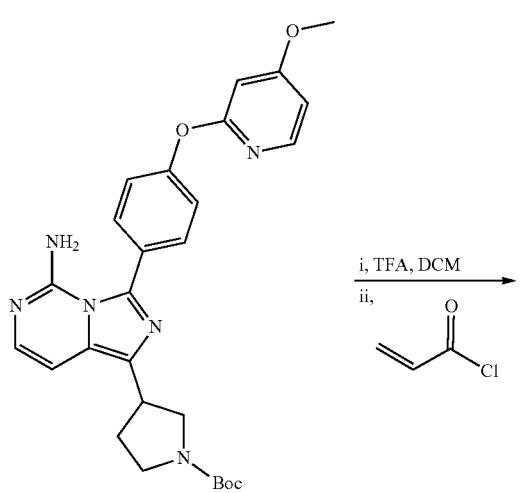

i, TFA, DCM
ii,

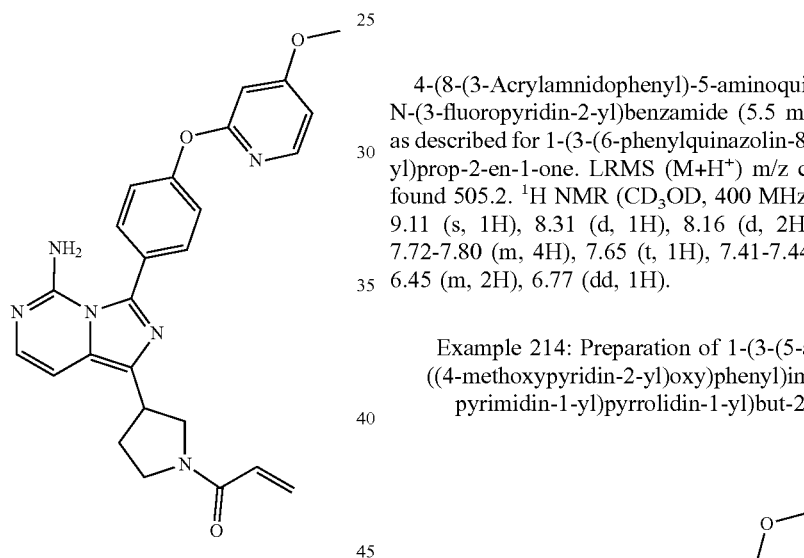

Example 213: Preparation of 4-(8-(3-acrylamidophenyl)-5-aminoquinazolin-6-yl)-N-(3-fluoropyridin-2-yl)benzamide 4-(8-(3-acrylamidophenyl)-5-aminoquinazolin-6-yl)-N-(3-fluoropyridin-2-yl)benzamide 4-(8-(3-Acrylamnidophenyl)-5-aminoquinazolin-6-yl)-N-(3-fluoropyridin-2-yl)benzamide (5.5 mg) was prepared as described for 1-(3-(6-phenylquinazolin-8-yl)pyrrolidin-1-yl)prop-2-en-1-one. LRMS (M+H$^+$) m/z calculated 505.2, found 505.2. $^1$H NMR (CD$_3$OD, 400 MHz) δ 9.80 (s, 1H), 9.11 (s, 1H), 8.31 (d, 1H), 8.16 (d, 2H), 7.95 (s, 1H), 7.72-7.80 (m, 4H), 7.65 (t, 1H), 7.41-7.44 (m, 3H), 6.33-6.45 (m, 2H), 6.77 (dd, 1H).

Example 214: Preparation of 1-(3-(5-amino-3-(4-((4-methoxypyridin-2-yl)oxy)phenyl)imidazo[1,5-c]pyrimidin-1-yl)pyrrolidin-1-yl)but-2-yn-1-one To a solution of tert-butyl 3-(5-amino-3-(4-((4-methoxypyridin-2-yl)oxy)phenyl)imidazo [1,5-c]pyrimidin-1-yl)pyrrolidine-1-carboxylate (175.0 mg, 0.35 mmol, 1.0 eq) in DCM (20.0 mL) was added TFA (2.0 mL). The mixture was stirred at rt for 30 min, then concentrated. The resulting residue was dissolved in DCM (20.0 mL), and TEA (282.0 mg, 2.79 mmol, 8.0 eq) was added, followed by acryloyl chloride (25.0 mg, 0.28 mmol, 0.8 eq). The resulting mixture was stirred at rt for 1 h, then washed with brine, dried over anhydrous Na$_2$SO$_4$, and concentrated. The residue was purified by column chromatography (DCM/MeOH=20/1, v/v) to afford 1-(3-(5-amino-3-(4-((4-methoxypyridin-2-yl)oxy)phenyl)imidazo[1,5-c]pyrimidin-1-yl)pyrrolidin-1-yl)prop-2-en-1-one (27.0 mg, 17%) as a yellow solid. LRMS (M+H$^+$) m/z calculated 457.2, found 457.2. $^1$H NMR (DMSO-d6, 400 MHz) δ 7.99 (d, 1H), 7.62 (d, 2H), 7.25 (d, 2H), 7.10-7.12 (m, 1H), 6.93-6.98 (m, 1H), 6.78-6.79 (m, 1H), 6.58-6.69 (m, 2H), 6.28 (s, 2H), 6.12-6.16 (m, 1H), 5.63-5.69 (m, 1H), 4.00-4.02 (m, 1H), 3.83-3.87 (m, 4H), 3.65-3.74 (m, 2H), 3.49-3.51 (m, 1H), 2.23-2.30 (m, 2H).

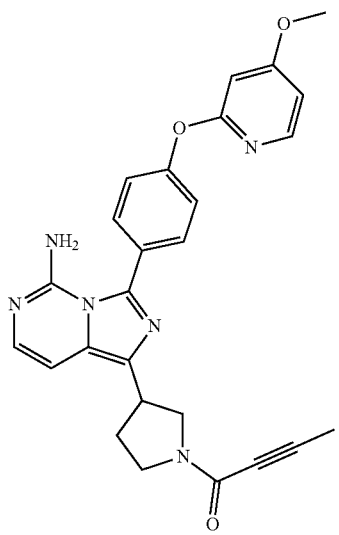

1-(3-(5-amino-3-(4-((4-methoxypyridin-2-yl)oxy)phenyl)imidazo[1,5-c]pyrimidin-1-yl)pyrrolidin-1-yl)but-2-yn-1-one -continued

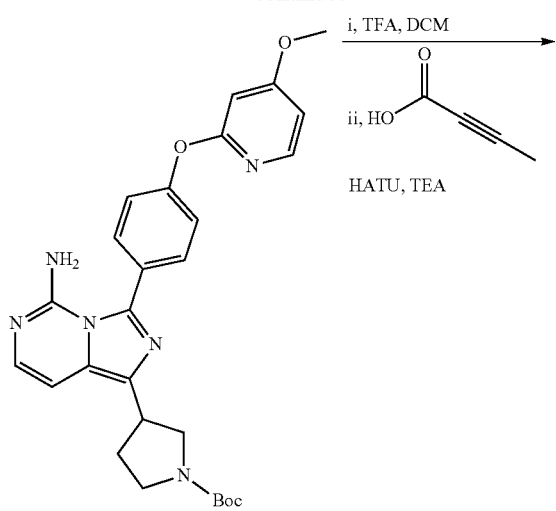

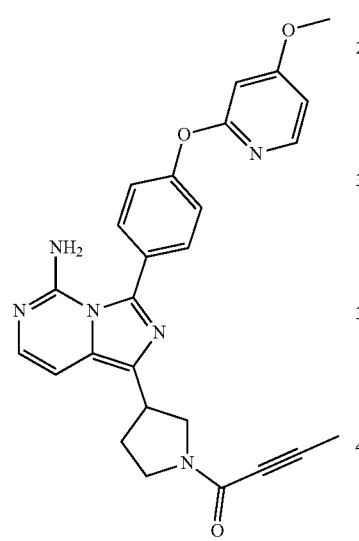

To a solution of tert-butyl 3-(5-amino-3-(4-((4-methoxy-pyridin-2-yl)oxy)phenyl) imidazo[1,5-c]pyrimidin-1-yl) pyrrolidine-1-carboxylate (175.0 mg, 0.35 mmol, 1.0 eq) in DCM (20.0 mL) was added TFA (2.0 mL) at rt and the mixture was stirred at rt for 30 min, then concentrated. The resulting residue was dissolved in DCM (20.0 mL) and TEA (282.0 mg, 2.79 mmol, 8.0 eq) was added, followed by but-2-ynoic acid (24.0 mg, 0.28 mmol, 0.8 eq) and HATU (133.0 mg, 0.35 mmol, 1.0 eq). The resulting mixture was stirred at rt for 1 h, then washed with brine, dried over anhydrous Na$_2$SO$_4$ and concentrated. The resulting residue was purified by column chromatography (DCM/MeOH=20/1, v/v) to afford 1-(3-(5-amino-3-(4-((4-methoxypyridin-2-yl)oxy)phenyl)imidazo[1,5-c]pyrimidin-1-yl)pyrrolidin-1-yl)but-2-yn-1-one (34.0 mg, 21%) as a yellow solid. LCMS (M+H$^+$) m/z calculated 469.2, found 469.2. $^1$H NMR (DMSO-d6, 400 MHz) δ 8.00 (d, 1H), 7.63 (d, 2H), 7.26 (d, 2H), 7.12-7.14 (m, 1H), 6.94-6.97 (m, 1H), 6.79-6.80 (m, 1H), 6.70 (s, 1H), 6.23 (s, 2H), 4.00-4.02 (m, 0.5H), 3.78-3.87 (m, 6.5H), 3.64-3.66 (m, 1H), 2.22-2.26 (m, 2H), 1.98-2.03 (m, 3H).

Example 215: Preparation of 1-(3-(5-amino-3-(3-methoxy-4-(pyridin-2-yloxy)phenyl)imidazo[1,5-c]pyrimidin-1-yl)pyrrolidin-1-yl)prop-2-en-1-one

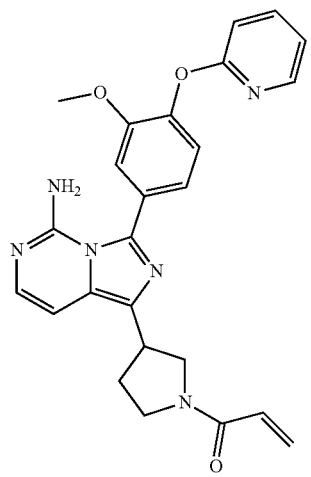

1-(3-(5-amino-3-(3-methoxy-4-(pyridin-2-yloxy)phenyl)imidazo[1,5-c]pyrimidin-1-yl)pyrrolidin-1-yl)prop-2-en-1-one 1-(3-(5-Amino-3-(3-fluoro-4-(pyridin-2-yloxy)phenyl) imidazo[1,5-c]pyrimidin-1-yl)pyrrolidin-1-yl)prop-2-en-1-one (26.5 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one. LRMS (M+H$^+$) m/z calculated 457.2, found 457.2. $^1$H NMR (DMSO-d6, 400 MHz) δ 8.22 (d, 1H), 7.83 (t, 1 H), 7.35 (s, 1H), 7.25 (d, 1H), 7.04-7.18 (m, 4H), 6.93-6.98 (m, 1H), 6.59-6.66 (m, 1H), 6.35 (s, 2H), 6.12-6.18 (m, 1H), 3.65-3.88 (m, 8H), 2.22-2.33 (m, 2H).

Example 216: Preparation of 1-(3-(5-amino-3-(3-methoxy-4-(pyridin-2-yloxy)phenyl)imidazo[1,5-c]pyrimidin-1-yl)pyrrolidin-1-yl)but-2-yn-1-one

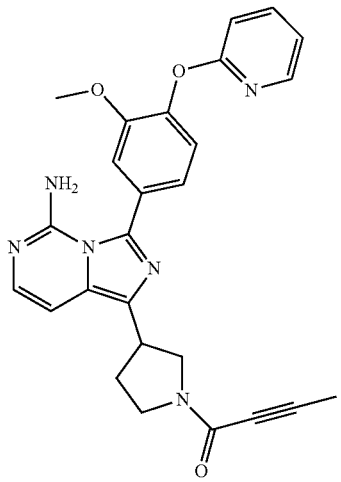

1-(3-(5-amino-3-(3-methoxy-4-(pyridin-2-yloxy)phenyl)imidazo[1,5-c]pyrimidin-1-yl)pyrrolidin-1-yl)but-2-yn-1-one 1-(3-(5-Amino-3-(3-methoxy-4-(pyridin-2-yloxy)phenyl)imidazo[1,5-c]pyrimidin-1-yl)pyrrolidin-1-yl)but-2-yn-1-one (21 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one. LRMS (M+H⁺) m/z calculated 469.2, found 469.2. ¹H NMR (DMSO-d6, 400 MHz) δ 8.16 (s, 1H), 7.86 (t, 1H), 7.35 (s, 1H), 7.26 (d, 1H), 7.05-7.19 (m, 3H), 6.94-6.98 (m, 1H), 6.75 (d, 1H), 6.35 (s, 1H), 3.71-3.80 (m, 8H), 2.22-2.38 (m, 2H), 2.00 (d, 3H).

Example 217: Preparation of 4-(8-(1-acryloylpyrrolidin-3-yl)-5-aminoquinazolin-6-yl)-N-(3-fluoropyridin-2-yl)benzamide

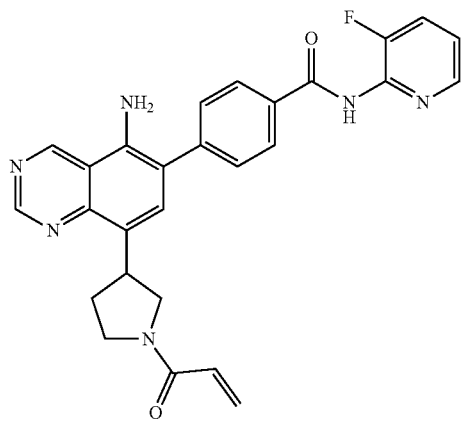

4-(8-(1-acryloylpyrrolidin-3-yl)-5-aminoquinazolin-6-yl)-N-(3-fluoropyridin-2-yl)benzamide 4-(8-(1-Acryloylpyrrolidin-3-yl)-5-aminoquinazolin-6-yl)-N-(3-fluoropyridin-2-yl)benzamide (12.9 mg) was prepared as described for 1-(3-(6-phenylquinazolin-8-yl)pyrrolidin-1-yl)prop-2-en-1-one. LRMS (M+H⁺) m/z calculated 483.2, found 483.3. ¹H NMR (CD₃OD, 400 MHz) δ 9.88 (s, 1H), 9.33 (d, 1H), 8.32 (d, 1H), 8.14 (dd, 2H), 7.65-7.77 (m, 4H), 7.39-7.44 (m, 1H), 6.58-6.70 (m, 1H), 6.25-6.31 (m, 1H), 5.70-5.78 (m, 1H), 4.11-4.44 (m, 2H), 3.55-3.70 (m, 3H), 2.34-2.39 (m, 2H).

Example 218: Preparation of 1-(3-(5-amino-3-(3-fluoro-4-((4-methoxypyridin-2-yl)oxy)phenyl)imidazo[1,5-c]pyrimidin-1-yl)pyrrolidin-1-yl)prop-2-en-1-one

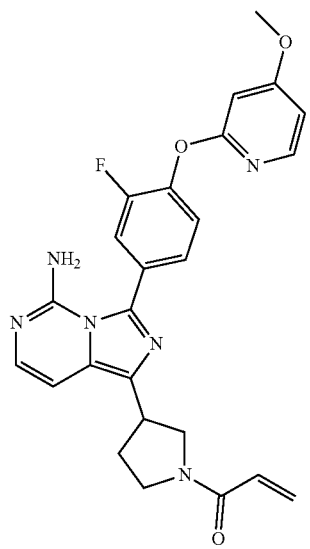

1-(3-(5-amino-3-(3-fluoro-4-((4-methoxypyridin-2-yl)oxy)phenyl)imidazo[1,5-c]pyrimidin-1-yl)pyrrolidin-1-yl)prop-2-en-1-one 1-(3-(5-Amino-3-(3-fluoro-4-((4-methoxypyridin-2-yl)oxy)phenyl)imidazo[1,5-c]pyrimidin-1-yl)pyrrolidin-1-yl)prop-2-en-1-one (22 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 475.2, found 475.2. ¹H NMR (DMSO-d6, 400 MHz) δ 7.95 (d, 1H), 7.60 (d, 1H), 7.43 (s, 2H), 7.16-7.17 (m, 1H), 6.99-7.01 (m, 1H), 6.76-6.79 (m, 2H), 6.52-6.63 (m, 3H), 6.13-6.18 (m, 1H), 5.66-5.68 (m, 1H), 4.01-4.03 (m, 1H), 3.88-3.89 (m, 4H), 3.66-3.72 (m, 2H), 3.48-3.49 (m, 1H), 2.26-2.31 (m, 2H).

Example 219: Preparation of 4-(8-(3-acrylamidophenyl)-5-aminoquinazolin-6-yl)-3-chloro-N-(3-fluoropyridin-2-yl)benzamide

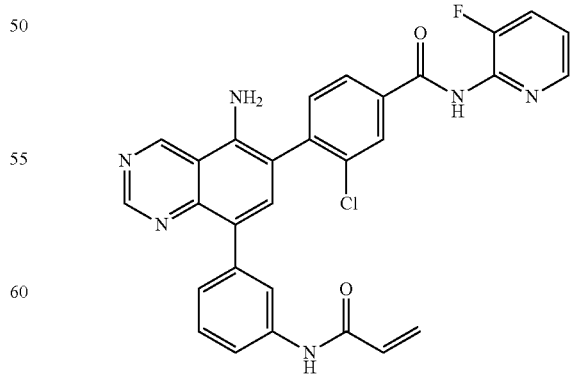

4-(8-(3-acrylamidophenyl)-5-aminoquinazolin-6-yl)-3-chloro-N-(3-fluoropyridin-2-yl)benzamide 4-(8-(3-Acrylamidophenyl)-5-aminoquinazolin-6-yl)-3-chloro-N-(3-fluoropyridin-2-yl)benzamide (3.5 mg) was prepared as described for 1-(3-(6-phenylquinazolin-8-yl)pyrrolidin-1-yl)prop-2-en-1-one. LRMS (M+H⁺) m/z calculated 539.1, found 539.2. ¹H NMR (DMSO-d6, 400 MHz) δ 11.00 (s, 1H), 10.17 (s, 1H), 9.93 (s, 1H), 9.21 (s, 1H), 8.35 (s, 1H), 8.30 (s, 1H), 8.13 (d, 1H), 7.86 (s, 2H), 7.66-7.68 (m, 2H), 7.57 (s, 1H) 7.39-7.47 (m, 3H), 6.29-6.42 (m, 4H), 5.76 (t, 1H).

Example 220: Preparation of 1-(3-(5-amino-3-(4-((3-(trifluoromethyl)pyridin-2-yl)oxy)phenyl)imidazo[1,5-c]pyrimidin-1-yl)pyrrolidin-1-yl)prop-2-en-1-one

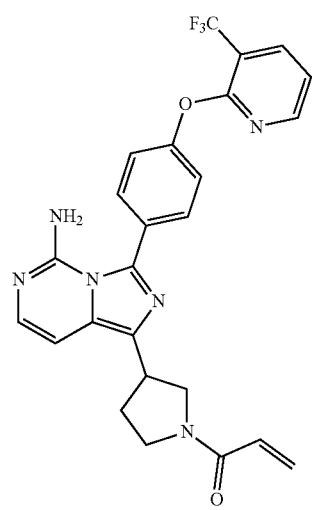

1-(3-(5-amino-3-(4-((3-(trifluoromethyl)pyridin-2-yl)oxy) imidazo[1,5-c]pyrimidin-1-yl)pyrrolidin-1-yl)prop-2-en-1-one 1-(3-(5-Amino-3-(4-((3-(trifluoromethyl)pyridin-2-yl)oxy)phenyl)imidazo[1,5-c]pyrimidin-1-yl)pyrrolidin-1-yl)prop-2-en-1-one (17 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 495.2, found 495.2. ¹H NMR (DMSO-d6, 400 MHz) δ 8.44 (d, 1H), 8.33 (d, 1H), 7.67 (d, 2H), 7.37-7.41 (m, 3H), 7.63-7.71 (m, 1H), 7.13-7.15 (m, 1H), 6.61-6.67 (m, 1H), 6.31 (s, 2H), 6.17-6.18 (m, 1H), 5.64-5.69 (m, 1H), 4.03-4.05 (m, 0.5H), 3.81-3.86 (m, 1.5H), 3.69-3.71 (m, 2H), 3.44-3.52 (m, 1H), 2.19-2.29 (m, 2H).

Example 221: Preparation of 1-(3-(5-amino-3-(4-((3-(trifluoromethyl)pyridin-2-yl)oxy)phenyl)imidazo[1,5-c]pyrimidin-1-yl)pyrrolidin-1-yl)but-2-yn-1-one

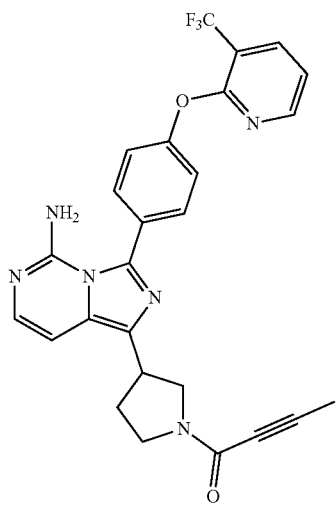

1-(3-(5-amino-3-(4-((3-(trifluoromethyl)pyridin-2-yl)oxy)phenyl) imidazo[1,5-c]pyrimidin-1-yl)pyrrolidin-1-yl)but-2-yn-1-one 1-(3-(5-Amino-3-(4-((3-(trifluoromethyl)pyridin-2-yl)oxy)phenyl)imidazo[1,5-c]pyrimidin-1-yl)pyrrolidin-1-yl)but-2-yn-1-one (31 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one. LRMS (M+H⁺) m/z calculated 507.2, found 507.2. ¹H NMR (DMSO-d6, 400 MHz) δ 8.44 (d, 1H), 8.30 (d, 1H), 7.64-7.67 (m, 2H), 6.93-7.40 (m, 5H), 6.31 (s, 2H), 3.62-4.03 (m, 5H), 2.19-2.26 (m, 2H), 1.98-2.03 (m, 3H).

Example 222: Preparation of N-(3-(5-amino-3-(4-((3-(trifluoromethyl)pyridin-2-yl)oxy)phenyl)imidazo[1,5-c]pyrimidin-1-yl)phenyl)acrylamide

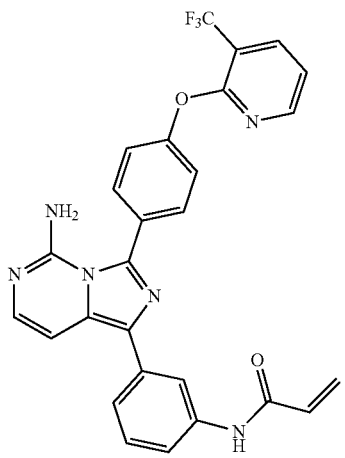

N-(3-(5-amino-3-(4-((3-(trifluoromethyl)pyridin-2-yl)oxy)phenyl) imidazo[1,5-c]pyrimidin-1-yl)phenyl)acrylamide N-(3-(5-Amino-3-(4-((3-(trifluoromethyl)pyridin-2-yl)oxy)phenyl)imidazo[1,5-c]pyrimidin-1-yl)phenyl)acrylamide (17 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 517.2, found 517.2. ¹H NMR (DMSO-d6, 400 MHz) δ 10.23 (s, 1H), 8.46 (s, 1H), 8.29-8.34 (m, 2H), 7.76 (d, 2H), 7.64 (s, 2H), 7.26-7.41 (m, 6H), 6.46-6.50 (m, 3H), 6.30 (d, 1H), 5.78 (d, 1H).

Example 223: Preparation of 1-(3-(5-amino-3-(3-methoxy-4-((4-(trifluoromethyl)pyridin-2-yl)oxy)phenyl)imidazo[1,5-c]pyrimidin-1-yl)pyrrolidin-1-yl)prop-2-en-1-one

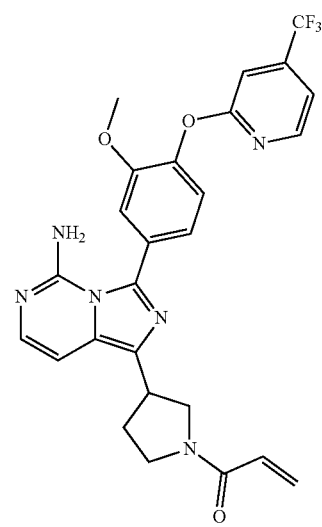

1-(3-(5-amino-3-(3-methoxy-4-((4-(trifluoromethyl)pyridin-2-yl)oxy)phenyl)imidazo[1,5-c]pyrimidin-1-yl)pyrrolidin-1-yl)prop-2-en-1-one 1-(3-(5-Amino-3-(3-methoxy-4-((4-(trifluoromethyl)pyridin-2-yl)oxy)phenyl)imidazo[1,5-c]pyrimidin-1-yl)pyrrolidin-1-yl)prop-2-en-1-one (10 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 525.2, found 525.2. ¹H NMR (CD₃OD, 400 MHz) δ 8.56 (s, 1H), 7.33-7.41 (m, 4H), 7.25 (d, 1H), 7.12 (d, 1H), 6.94 (t, 1H), 6.59-6.69 (m, 1H), 6.28 (d, 1H), 5.75 (t, 1H), 3.56-4.10 (m, 5H), 3.76 (s, 3H), 2.31-2.42 (m, 2H).

Example 224: Preparation of 1-(3-(5-amino-3-(3-methoxy-4-((4-(trifluoromethyl)pyridin-2-yl)oxy)phenyl)imidazo[1,5-c]pyrimidin-1-yl)pyrrolidin-1-yl)but-2-yn-1-one

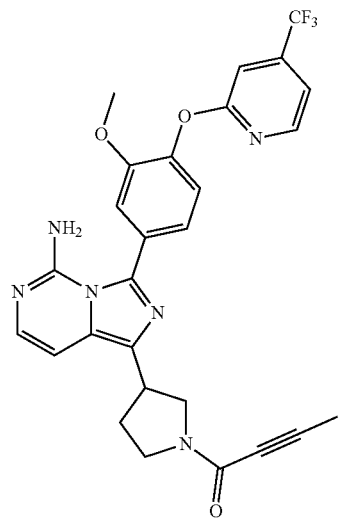

1-(3-(5-amino-3-(3-methoxy-4-((4-(trifluoromethyl)pyridin-2-yl)oxy)phenyl)imidazo[1,5-c]pyrimidin-1-yl)pyrrolidin-1-yl)but-2-yn-1-one 1-(3-(5-Amino-3-(3-methoxy-4-((4-(trifluoromethyl)pyridin-2-yl)oxy)phenyl)imidazo[1,5-c]pyrimidin-1-yl)pyrrolidin-1-yl)but-2-yn-1-one (4.5 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one. LRMS (M+H⁺) m/z calculated 537.2, found 537.2. ¹H NMR (CDCl₃, 400 MHz) δ 8.25 (s, 1H), 7.29-7.42 (m, 3H), 7.18-7.24 (m, 2H), 6.81-6.95 (m, 2H), 3.58-4.18 (m, 10H), 2.34-2.46 (m, 2H), 2.02 (d, 3H).

Example 225: Preparation of 1-(3-(5-amino-3-(3-fluoro-4-((3-(trifluoromethyl)pyridin-2-yl)oxy)phenyl)imidazo[1,5-c]pyrimidin-1-yl)pyrrolidin-1-yl)prop-2-en-1-one

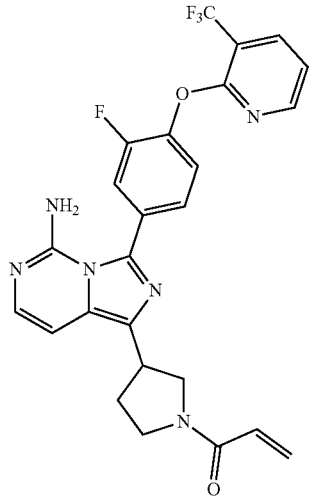

1-(3-(5-amino-3-(3-fluoro-4-((3-(trifluoromethyl)pyridin-2-yl)oxy)phenyl)imizado[1,5-c]pyrimdin-1-yl)pyrrolidin-1-yl)prop-2-en-1-one 1-(3-(5-Amino-3-(3-fluoro-4-((3-(trifluoromethyl)pyridin-2-yl)oxy)phenyl)imidazo[1,5-c]pyrimidin-1-yl)pyrrolidin-1-yl)prop-2-en-1-one (28.9 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 513.2, found 513.2. ¹H NMR (CDCl₃, 400 MHz) δ 8.25 (d, 1H), 8.04 (d, 1H), 7.38-7.51 (m, 4H), 7.16-7.21 (m, 2H), 6.83 (t, 1H), 6.4-6.45 (in, 2H), 5.65-5.72 (in, 1H), 3.63-4.12 (m, 5H), 2.03-2.58 (m, 2H).

Example 226: Preparation of 1-(3-(5-amino-3-(4-((3-fluoropyridin-2-yl)oxy)phenyl)imidazo[1,5-c]pyrimidin-1-yl)pyrrolidin-1-yl)prop-2-en-1-one

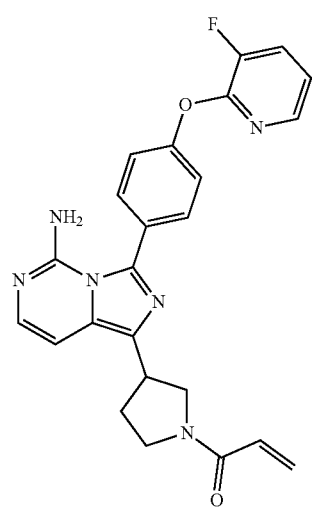

1-(3-(5-amino-3-(4-((3-fluoropyridin-2-yl)oxy)phenyl)imizado[1,5-c]pyrimidin-1-yl)pyrrolidin-1-yl)prop-2-en-1-one 1-(3-(5-Amino-3-(4-((3-fluoropyridin-2-yl)oxy)phenyl)imidazo[1,5-c]pyrimidin-1-yl)pyrrolidin-1-yl)prop-2-en-1-one (22 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 445.2, found 445.2. ¹H NMR (DMSO-d6, 400 MHz) δ 8.05 (d, 1H), 7.93 (t, 1H), 7.65 (dd, 2H), 7.32 (d, 2H), 7.25-7.29 (m, 1H), 7.13 (dd, 1H), 6.94-6.99 (m, 1H), 6.59-6.68 (m, 1H), 6.29 (s, 2H), 6.12-6.18 (m, 1H), 5.63-5.76 (m, 1H), 3.84-4.03 (m, 2H), 3.66-3.75 (m, 2H), 3.52-3.54 (m, 1H), 2.25-2.31 (m, 2H).

Example 227: Preparation of 2-(4-(1-(1-acryloylpyrrolidin-3-yl)-5-aminoimidazo[1,5-c]pyrimidin-3-yl)phenoxy)nicotinonitrile

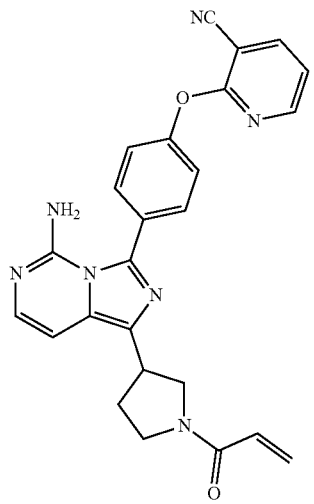

2-(4-(1-(1-acryloylpyrrolidin-3-yl)-5-aminoimidazo[1,5-c]pyrimidin-3-yl)phenoxy)nicotinonitrile 2-(4-(1-(1-Acryloylpyrrolidin-3-yl)-5-aminoimidazo[1,5-c]pyrimidin-3-yl)phenoxy)nicotinonitrile (11.4 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 452.2, found 452.2. ¹H NMR (DMSO-d6, 400 MHz) δ 8.42-8.47 (m, 2H), 7.67 (dd, 2H), 7.35-7.41 (m, 3H), 7.14 (dd, 2H), 6.95-7.00 (m, 1H), 6.59-6.67 (m, 1H), 6.31 (s, 2H), 6.12-6.18 (m, 1H), 5.63-5.70 (m, 1H), 3.85-4.03 (m, 3H), 3.63-3.75 (m, 3H), 2.13-2.31 (m, 2H).

Example 228: Preparation of 1-(3-(5-amino-3-(4-((3-fluoropyridin-2-yl)oxy)phenyl)imidazo[1,5-c]pyrimidin-1-yl)pyrrolidin-1-yl)but-2-yn-1-one

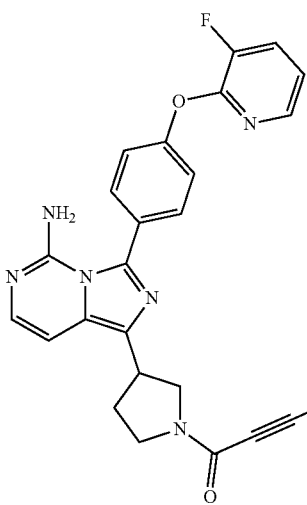

1-(3-(5-amino-3-(4-((3-fluoropyridin-2-yl)oxy)phenyl)imizado[1,5-c]pyrimidin-1-yl)pyrrolidin-1-yl)but-2-yn-1-one 1-(3-(5-Amino-3-(4-((3-fluoropyridin-2-yl)oxy)phenyl) imidazo[1,5-c]pyrimidin-1-yl)pyrrolidin-1-yl)but-2-yn-1-one (7 mg) was prepared as described for 1-(3-(5-amino-3-(4-((4-methoxypyridin-2-yl)oxy)phenyl)imidazo[1,5-c] pyrimidin-1-yl)pyrrolidin-1-yl)but-2-yn-1-one. LRMS (M+H$^+$) m/z calculated 457.2, found 457.2. $^1$H NMR (DMSO-d6, 400 MHz) δ 8.03 (d, 1H), 7.92-7.94 (m, 1H), 7.65 (d, 2H), 7.25-7.33 (m, 3H), 7.12-7.17 (m, 1H), 6.93-6.98 (m, 1H), 6.29 (s, 2H), 4.03 (t, 1H), 3.76-3.90 (m, 2H), 3.61-3.73 (m, 2H), 2.22-2.33 (m, 2H), 2.00 (d, 3H).

Example 229: Preparation of 2-(4-(5-amino-1-(1-(but-2-ynoyl)pyrrolidin-3-yl)imidazo[1,5-c]pyrimidin-3-yl)phenoxy)nicotinonitrile

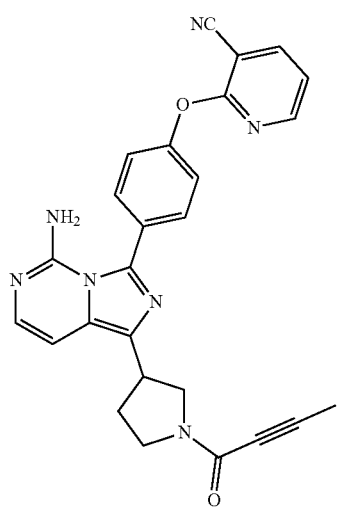

2-(4-(5-amino-1-(1-(but-2-ynoyl)pyrrolidin-3-yl)imizado[1,5-c] pyrimidin-3-yl)phenoxy)nicotinonitrile 2-(4-(5-Amino-1-(1-(but-2-ynoyl)pyrrolidin-3-yl)imidazo[1,5-c]pyrimidin-3-yl)phenoxy)nicotinonitrile (21 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one. LRMS (M+H$^+$) m/z calculated 464.2, found 464.2. $^1$H NMR (DMSO-d6, 400 MHz) δ 8.43-8.46 (m, 2H), 7.68 (d, 2H), 7.36-7.42 (m, 3H), 7.13-7.15 (m, 1H), 6.93-6.99 (m, 1H), 6.31 (s, 1H), 4.03 (t, 1H), 3.77-3.88 (m, 2H), 3.65-3.73 (m, 2H), 2.17-2.14 (m, 2H), 2.00 (d, 2H).

Example 230: Preparation of 4-(1-(1-acryloylpyrrolidin-3-yl)-5-aminoimidazo[1,5-c]pyrimidin-3-yl)-2-fluoro-N-(pyridin-2-yl)benzamide

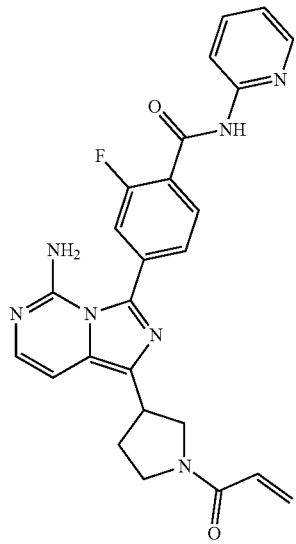

4-(1-(1-acryloylpyrrolidin-3-yl)-5-aminoimizado[1,5-c]pyrimidin-3-yl)-2-fluoro-N-(pyridin-2-yl)benzamide 4-(1-(1-Acryloylpyrrolidin-3-yl)-5-aminoimidazo[1,5-c]pyrimidin-3-yl)-2-fluoro-N-(pyridin-2-yl)benzamide (24 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H$^+$) m/z calculated 472.2, found 472.2. $^1$H NMR (DMSO-d6, 400 MHz) δ 10.81 (s, 1H), 8.39 (d, 1H), 8.21 (d, 1H), 7.78-7.90 (m, 2H), 7.53 (t, 2H), 7.18-7.22 (m, 2H), 6.99-7.04 (m, 1H), 6.61-6.65 (m, 1H), 6.46 (s, 2H), 6.12-6.18 (m, 1H), 5.63-5.67 (m, 1H), 3.41-3.89 (m, 5H), 2.11-2.19 (m, 2H).

Example 231: Preparation of 4-(5-amino-1-(1-(but-2-ynoyl)pyrrolidin-3-yl)imidazo[1,5-c]pyrimidin-3-yl)-2-fluoro-N-(pyridin-2-yl)benzamide

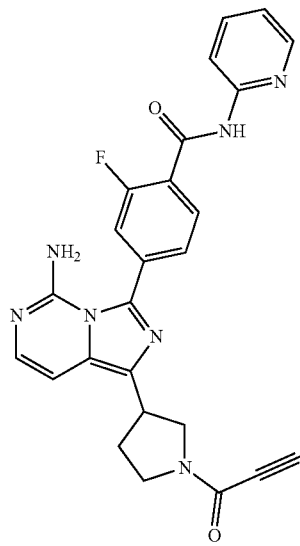

4-(5-amino-1-(1-(but-2-ynoyl)pyrrolidin-3-yl)imizado[1,5-c] pyrimidin-3-yl)-2-fluoro-N-(pyridin-2-yl)benzamide 4-(5-Amino-1-(1-(but-2-ynoyl)pyrrolidin-3-yl)imidazo[1,5-c]pyrimidin-3-yl)-2-fluoro-N-(pyridin-2-yl)benzamide (10 mg) was prepared as described for 4-(5-amino-1-(1-(but-2-ynoyl)pyrrolidin-3-yl)imidazo[1,5-c]pyrimidin-3-yl)-N-(pyridin-2-yl)benzamide. LRMS (M+H⁺) m/z calculated 484.2, found 484.1. ¹H NMR (DMSO-d6, 400 MHz) δ 10.81 (s, 1H), 8.39 (d, 1H), 8.21 (d, 1H), 7.79-7.89 (m, 2H), 7.53 (t, 2H), 7.18-7.23 (m, 2H), 6.98-7.03 (m, 1H), 6.46 (s, 2H), 3.62-4.04 (m, 4H), 3.31-3.48 (m, 1H), 2.21-2.27 (m, 2H), 2.00 (d, 3H).

Example 232: Preparation of 1-(3-(5-amino-3-(4-((3-fluoropyridin-2-yl)oxy)-3-methoxyphenyl)imidazo[1,5-c]pyrimidin-1-yl)piperidin-1-yl)prop-2-en-1-one

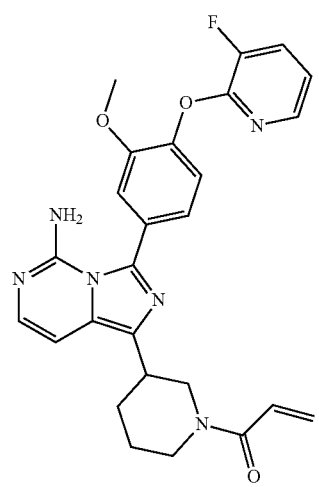

1-(3-(5-amino-3-(4-((3-fluoropyridin-2-yl)oxy)-3-methoxyphenyl)imizado[1,5-c]pyrimidin-1-yl)piperidin-1-yl)prop-2-en-1-one 1-(3-(5-Amino-3-(4-((3-fluoropyridin-2-yl)oxy)-3-methoxyphenyl)imidazo[1,5-c]pyrimidin-1-yl)piperidin-1-yl)prop-2-en-1-one (18.3 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 489.2, found 489.3. ¹H NMR (CD₃OD, 400 MHz) δ 7.80 (d, 1H), 7.69 (t, 1H), 7.40 (d, 1H), 7.33 (d, 1H), 7.25 (t, 1H), 7.10-7.14 (m, 2H), 6.93 (d, 1H), 6.82-6.92 (m, 1H), 6.22 (t, 1H), 5.74-5.77 (m, 1H), 4.68 (dd, 1H), 4.18 (t, 1H), 3.79 (s, 3H), 3.74-3.77 (t, 0.5H), 3.00-3.22 (m, 2H), 2.95 (t, 0.5H), 2.08 (s, 2H), 1.82 (s, 1H).

Example 233: Preparation of 1-(3-(5-amino-3-(4-((3-fluoropyridin-2-yl)oxy)-3-methoxyphenyl)imidazo[1,5-c]pyrimidin-1-yl)pyrrolidin-1-yl)prop-2-en-1-one

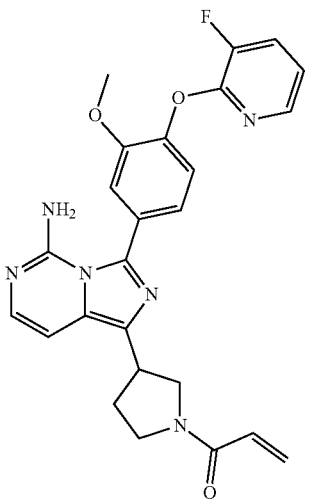

1-(3-(5-amino-3-(4-((3-fluoropyridin-2-yl)oxy)-3-methoxyphenyl)imizado[1,5-c]pyrimidin-1-yl)pyrrolidin-1-yl)prop-2-en-1-one 1-(3-(5-Amino-3-(4-((3-fluoropyridin-2-yl)oxy)-3-methoxyphenyl)imidazo[1,5-c]pyrimidin-1-yl)pyrrolidin-1-yl)prop-2-en-1-one (10.1 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 475.2, found 475.2. 1H NMR (CD₃OD, 400 MHz) δ 7.80 (dd, 1H), 7.69 (t, 1H), 7.39 (t, 1H), 7.33 (d, 1H), 7.23-7.26 (m, 1H), 6.91-6.95 (m, 1H), 6.64-6.77 (m, 1H), 3.65-3.85 (m, 8H), 2.43-2.49 (m, 2H).

Example 234: Preparation of 2-(4-(1-(1-acryloylpiperidin-3-yl)-5-aminoimidazo[1,5-c]pyrimidin-3-yl)-2-fluorophenoxy)nicotinonitrile

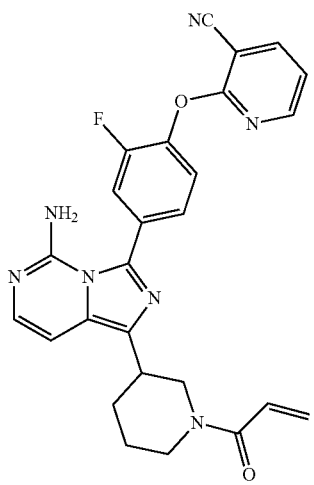

2-(4-(1-(1-acryloylpiperidin-3-yl)-5-aminoimizado[1,5-c]pyrimidin-3-yl)-2-fluorophenoxy)nicotinonitrile 2-(4-(1-(1-Acryloylpiperidin-3-yl)-5-aminoimidazo[1,5-c]pyrimidin-3-yl)-2-fluorophenoxy)nicotinonitrile (10.1 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H⁺) m/z calculated 484.2, found 484.2. ¹H NMR (CD₃OD, 400 MHz) δ 8.29-8.33 (m, 2H), 7.77 (dd, 1H), 7.63 (d, 2H), 7.32-7.34 (m, 1H), 7.31 (d, 1H), 6.96-6.98 (m, 1H), 6.74-6.87 (m, 1H), 6.20 (t, 1H), 6.69-6.78 (m, 1H), 4.58-4.69 (m, 2H), 4.18 (t, 1H), 3.04-3.25 (m, 2H), 2.08 (s, 2H), 1.94 (s, 1H), 1.65 (s, 1H).

Example 235: Preparation of 4-(1-(1-acryloylpiperidin-3-yl)-5-aminoimidazo[1,5-c]pyrimidin-3-yl)-N-(pyridin-2-yl)benzamide

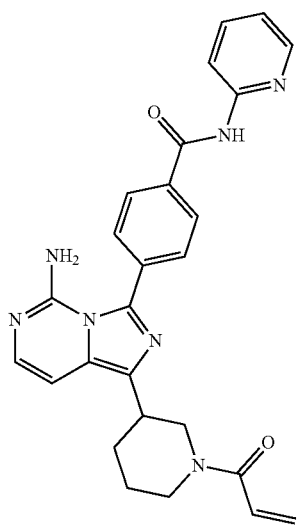

4-(1-(1-acryloylpiperidin-3-yl)-5-aminoimidazo[1,5-c]pyrimidin-3-yl)-N-(pyridin-2-yl)benzamide 4-(1-(1-Acryloylpiperidin-3-yl)-5-aminoimidazo[1,5-c]pyrimidin-3-yl)-N-(pyridin-2-yl)benzamide (4.9 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H⁺) m/z calculated 468.2, found 468.3. ¹H NMR (CD₃OD, 400 MHz) δ 8.38 (d, 1H), 8.25 (d, 1H), 8.14 (d, 2H), 7.78-7.88 (m, 3H), 7.15-7.20 (m, 2H), 6.98 (dd, 1H), 6.77-6.87 (m, 1H), 6.20 (t, 1H), 6.69-6.78 (m, 1H), 4.65 (dd, 1H), 4.19 (s, 1H), 3.53 (t, 0.5H), 1.73-1.76 (m, 1H), 3.05-3.22 (m, 2H), 2.88 (t, 0.5H), 2.19 (s, 1H), 1.65 (s, 1H), 1.30 (s, 1H).

Example 236: Preparation of 4-(5-amino-1-(1-(but-2-ynoyl)piperidin-3-yl)imidazo[1,5-c]pyrimidin-3-yl)-N-(pyridin-2-yl)benzamide

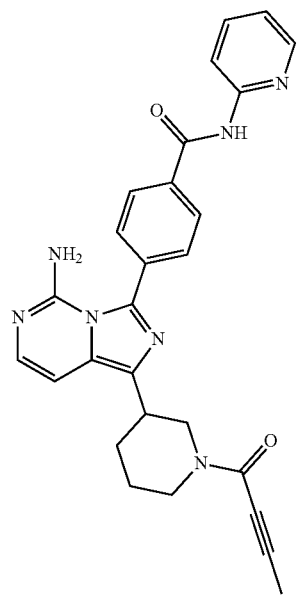

4-(5-amino-1-(1-(but-2-ynoyl)piperidin-3-yl)imidazo[1,5-c]pyrimidin-3-yl)-N-(pyridin-2-yl)benzamide 4-(5-Amino-1-(1-(but-2-ynoyl)piperidin-3-yl)imidazo[1,5-c]pyrimidin-3-yl)-N-(pyridin-2-yl)benzamide (7.3 mg) was prepared as described for 4-(5-amino-1-(1-(but-2-ynoyl)pyrrolidin-3-yl)imidazo[1,5-c]pyrimidin-3-yl)-N-(pyridin-2-yl)benzamide. LRMS (M+H⁺) m/z calculated 480.2, found 480.3. ¹H NMR (CD₃OD, 400 MHz) δ 8.37 (d, 1H), 8.25 (d, 1H), 8.14 (dd, 2H), 7.78-7.85 (m, 3H), 7.14-7.20 (m, 2H), 6.96-7.00 (m, 1H), 4.47 (dd, 1.5H), 3.30 (t, 0.5H), 3.05-3.07 (m, 3H), 2.06 (s, 2H), 1.95 (s, 1H), 1.82-1.89 (m, 3H), 1.73-1.76 (m, 1H).

Example 237: Preparation of 4-(4-amino-8-(1-(but-2-ynoyl)pyrrolidin-3-yl)imidazo[1,5-a][1,3,5]triazin-6-yl)-N-(4-cyclopropylpyridin-2-yl)benzamide (237)

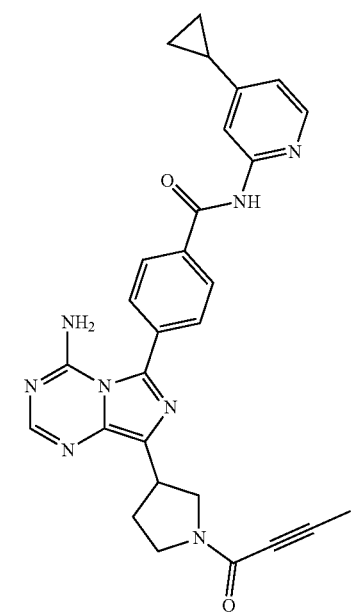

4-(4-amino-8-(1-(but-2-ynoyl)pyrrolidin-3-yl)imidazo[1,5-a][1,3,5]triazin-6-yl)-N-(4-cyclopropylpyridin-2-yl)benzamide 4-(4-Amino-8-(1-(but-2-ynoyl)pyrrolidin-3-yl)imidazo[1,5-a][1,3,5]triazin-6-yl)-N-(4-cyclopropylpyridin-2-yl)benzamide (5.9 mg) was prepared as described for 4-(5-amino-1-(1-(but-2-ynoyl)pyrrolidin-3-yl)imidazo[1,5-c]pyrimidin-3-yl)-N-(pyridin-2-yl)benzamide. LRMS (M+H$^+$) m/z calculated 507.2, found 507.2. $^1$H NMR (CD$_3$OD, 400 MHz) δ 7.97-8.17 (m, 5H), 7.74-7.88 (m, 2H), 6.89 (d, 1H), 3.73-4.02 (m, 3H), 3.54-3.68 (m, 2H), 2.36-2.44 (m, 2H), 1.97-2.05 (m, 4H), 1.12-1.17 (m, 2H), 0.85-0.89 (m, 2H).

Example 238: Preparation of 4-(1-(1-acryloylpyrrolidin-3-yl)-5-aminoimidazo[1,5-c]pyrimidin-3-yl)-N-(4-cyclopropylpyridin-2-yl)benzamide

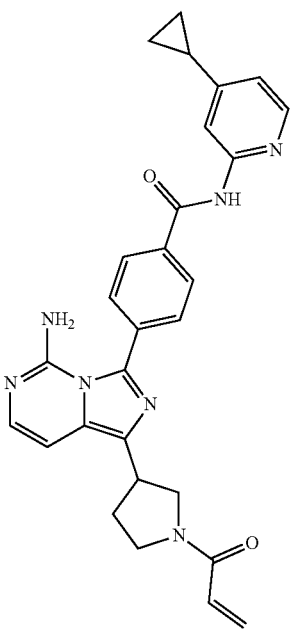

4-(1-(1-acryloylpyrrolidin-3-yl)-5-aminoimidazo[1,5-c]pyrimidin-3-yl)-N-(4-cyclopropylpyridin-2-yl)benzamide 4-(1-(1-Acryloylpyrrolidin-3-yl)-5-aminoimidazo[1,5-c]pyrimidin-3-yl)-N-(4-cyclopropylpyridin-2-yl)benzamide (8.9 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H$^+$) m/z calculated 494.2, found 494.3. $^1$H NMR (CD$_3$OD, 400 MHz) δ 8.14 (dd, 3H), 7.97 (s, 1H), 7.78 (d, 2H), 7.16 (dd, 1H), 6.88-6.99 (m, 2H), 6.59-6.67 (m, 1H), 6.28 (d, 1H), 3.5-4.09 (m, 6H), 2.31-2.42 (m, 2H), 1.96-2.00 (m, 1H), 1.12-1.16 (m, 2H), 0.87-0.89 (m, 2H).

Example 239: Preparation of 4-(5-amino-1-(1-(but-2-ynoyl)pyrrolidin-3-yl)imidazo[1,5-c]pyrimidin-3-yl)-N-(4-cyclopropylpyridin-2-yl)benzamide

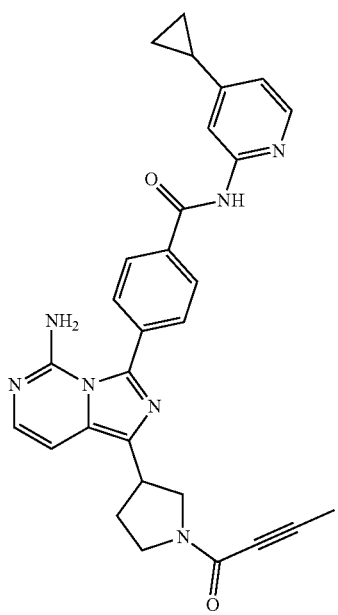

4-(5-amino-1-(1-(but-2-ynoyl)pyrrolidin-3-yl)imidazo[1,5-c]pyrimidin-3-yl)-N-(4-cyclopropylpyridin-2-yl)benzamide 4-(5-Amino-1-(1-(but-2-ynoyl)pyrrolidin-3-yl)imidazo[1,5-c]pyrimidin-3-yl)-N-(4-cyclopropylpyridin-2-yl)benzamide (14.5 mg) was prepared as described for 4-(5-amino-1-(1-(but-2-ynoyl)pyrrolidin-3-yl)imidazo[1,5-c]pyrimidin-3-yl)-N-(pyridin-2-yl)benzamide. LRMS (M+H$^+$) m/z calculated 506.2, found 506.3. $^1$H NMR (CD$_3$OD, 400 MHz) δ 8.10-8.17 (m, 3H), 7.96 (s, 1H), 7.78 (dd, 2H), 7.14-7.17 (m, 1H), 6.88-6.99 (m, 2H), 3.49-4.14 (m, 8H), 2.32-2.41 (m, 2H), 1.11-1.16 (m, 2H), 0.82-0.89 (m, 2H).

Example 240: Preparation of 4-(1-(1-acryloylpyrrolidin-3-yl)-5-aminoimidazo[1,5-c]pyrimidin-3-yl)-N-(4-methoxypyridin-2-yl)benzamide

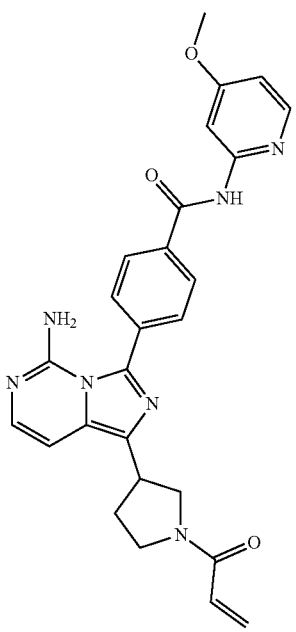

4-(1-(1-acryloylpyrrolidin-3-yl)-5-aminoimidazo[1,5-c]pyrimidin-3-yl)-N-(4-methoxypyridin-2-yl)benzamide 4-(1-(1-Acryloylpyrrolidin-3-yl)-5-aminoimidazo[1,5-c]pyrimidin-3-yl)-N-(4-methoxypyridin-2-yl)benzamide (10.4 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H$^+$) m/z calculated 484.2, found 484.3. $^1$H NMR (CD$_3$OD, 400 MHz) δ 8.16 (dd, 3H), 7.90 (s, 1H), 7.81 (d, 2H), 7.18 (dd, 1H), 6.69-7.01 (m, 1H), 6.79 (dd, 1H), 6.61-6.69 (m, 1H), 6.30 (d, 1H), 5.77 (t, 1H), 3.32-4.11 (m, 8H), 2.35-2.44 (m, 2H).

Example 241: Preparation of 4-(5-Amino-1-(1-(but-2-ynoyl)pyrrolidin-3-yl)imidazo[1,5-c]pyrimidin-3-yl)-N-(4-methoxypyridin-2-yl)benzamide

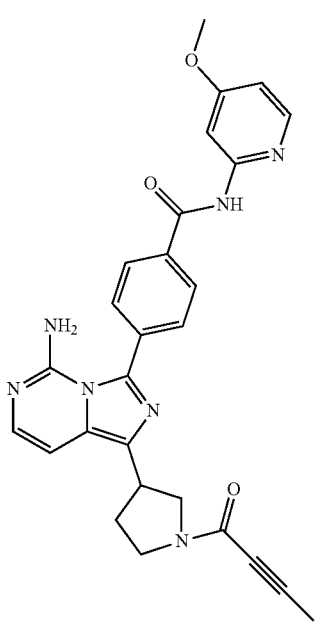

4-(5-amino-1-(1-(but-2-ynoyl)pyrrolidin-3-yl)imidazo[1,5-c]pyrimidin-3-yl)-N-(4-methoxypyridin-2-yl)benzamide 4-(5-Amino-1-(1-(but-2-ynoyl)pyrrolidin-3-yl)imidazo[1,5-c]pyrimidin-3-yl)-N-(4-methoxypyridin-2-yl)benzamide (10.6 mg) was prepared as described for 4-(5-amino-1-(1-(but-2-ynoyl)pyrrolidin-3-yl)imidazo[1,5-c]pyrimidin-3-yl)-N-(pyridin-2-yl)benzamide. LRMS (M+H$^+$) m/z calculated 496.2, found 496.3. $^1$H NMR (CD$_3$OD, 400 MHz) δ 8.12-8.19 (m, 3H), 7.80-7.90 (m, 3H), 7.17-7.20 (m, 1H), 6.97-7.01 (m, 1H), 3.51-4.17 (m, 8H), 2.46 (t, 2H), 2.04 (d, 3H).

Example 242: Preparation of 4-(1-(1-acryloylpyrrolidin-3-yl)-5-aminoimidazo[1,5-c]pyrimidin-3-yl)-N-(4-(trifluoromethyl)pyridin-2-yl)benzamide

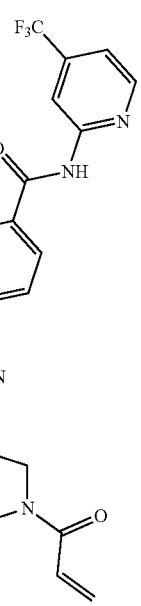

4-(1-(1-acryloylpyrrolidin-3-yl)-5-aminoimidazo[1,5-c]pyrimidin-3-yl)-N-(4-(trifluoromethyl)pyridin-2-yl)benzamide 4-(1-(1-Acryloylpyrrolidin-3-yl)-5-aminoimidazo[1,5-c]pyrimidin-3-yl)-N-(4-(trifluoromethyl)pyridin-2-yl)benzamide (10.0 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H$^+$) m/z calculated 522.2, found 522.2. $^1$H NMR (CD$_3$OD, 400 MHz) δ 8.61 (t, 3H), 8.15 (d, 2H), 7.79 (d, 2H), 7.43 (d, 1H), 7.16 (dd, 1H), 6.98 (t, 1H), 6.59-6.69 (m, 1H), 6.26-6.31 (m, 1H), 5.74 (t, 1H), 3.56-4.10 (m, 6H), 2.31-2.42 (m, 2H).

Example 243: Preparation of 1-(3-(5-amino-3-(4-(pyridin-2-yloxy)phenyl)imidazo[1,5-c]pyrimidin-1-yl)piperidin-1-yl)prop-2-en-1-one Example 244: Preparation of 1-(3-(5-amino-3-(4-(pyridin-2-yloxy)phenyl)imidazo[1,5-c]pyrimidin-1-yl)piperidin-1-yl)but-2-yn-1-one

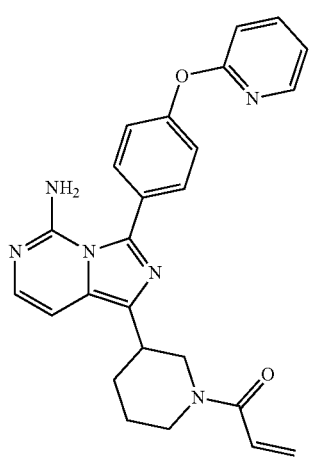

1-(3-(5-amino-3-(4-(pyridin-2-yloxy)phenyl)imidazo[1,5-c]pyrimidin-1-yl)prop-2-en-1-one

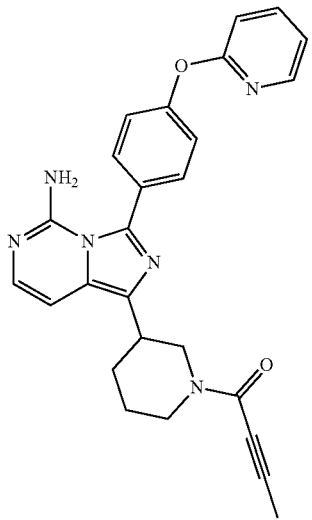

1-(3-(5-amino-3-(4-(pyridin-2-yloxy)phenyl)imidazo[1,5-c]pyrimidin-1-yl)piperidin-1-yl)but-2-yn-1-one 1-(3-(5-Amino-3-(4-(pyridin-2-yloxy)phenyl)imidazo[1,5-c]pyrimidin-1-yl)piperidin-1-yl)prop-2-en-1-one (11.4 mg) was prepared as described for 1-(3-(5-amino-3-(4-((4-methoxypyridin-2-yl)oxy)phenyl)imidazo[1,5-c]pyrimidin-1-yl)pyrrolidin-1-yl)prop-2-en-1-one. LRMS (M+H$^+$) m/z calculated 441.2, found 441.3. $^1$H NMR (CD$_3$OD, 400 MHz) δ 8.15 (d, 1H), 8.02 (t, 1H), 7.68 (t, 2H), 7.28 (d, 2H), 7.09-7.19 (m, 3H), 6.89 (d, 1H), 6.74-6.86 (m, 2H), 6.20 (t, 1H), 5.69-5.77 (m, 2H), 4.63 (dd, 1H), 4.18 (t, 1H), 3.50 (t, 0.5H), 3.02-3.21 (m, 2H), 2.85 (t, 0.5H), 2.06 (s, 2H), 1.92 (s, 1H), 1.65 (s, 1H).

1-(3-(5-Amino-3-(4-(pyridin-2-yloxy)phenyl)imidazo[1,5-c]pyrimidin-1-yl)piperidin-1-yl)but-2-yn-1-one (12.3 mg) was prepared as described for 1-(3-(5-amino-3-(4-((4-methoxypyridin-2-yl)oxy)phenyl)imidazo[1,5-c]pyrimidin-1-yl)pyrrolidin-1-yl)but-2-yn-1-one. LRMS (M+H$^+$) m/z calculated 453.2, found 453.3. $^1$H NMR (CD$_3$OD, 400 MHz) δ 8.14 (s, 1H), 7.90 (t, 1H), 7.67 (d, 2H), 7.28 (d, 2H), 7.08-7.19 (m, 3H), 6.90-7.08 (m, 1H), 4.45-4.56 (m, 2H), 3.50 (t, 0.5H), 3.15-3.23 (m, 2H), 3.10 (d, 1H), 2.83 (t, 0.5H), 1.88-2.06 (m, 6H), 1.24 (s, 1H).

Example 245: Preparation of 4-(5-Amino-1-(1-(but-2-ynoyl)pyrrolidin-3-yl)imidazo[1,5-c]pyrimidin-3-yl)-N-(4-cyclopropylpyridin-2-yl)-2-fluorobenzamide

Example 246: Preparation of 4-(1-(1-acryloylpyrrolidin-3-yl)-5-aminoimidazo[1,5-c]pyrimidin-3-yl)-N-(4-cyclopropylpyridin-2-yl)-2-fluorobenzamide

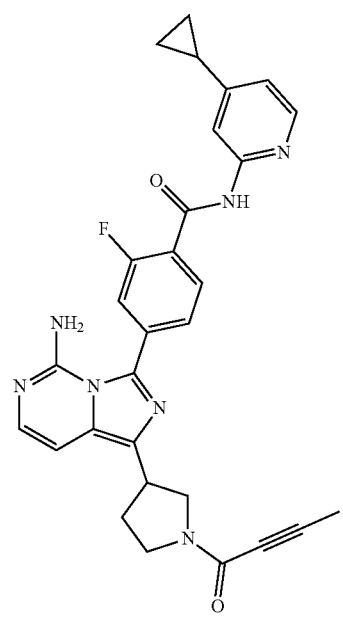

4-(5-amino-1-(1-(but-2-ynoyl)pyrrolidin-3-yl)imidazo[1,5-c]pyrimidin-3-yl)-
N-(4-cyclopropylpyridin-2-yl)-2-fluorobenzamide

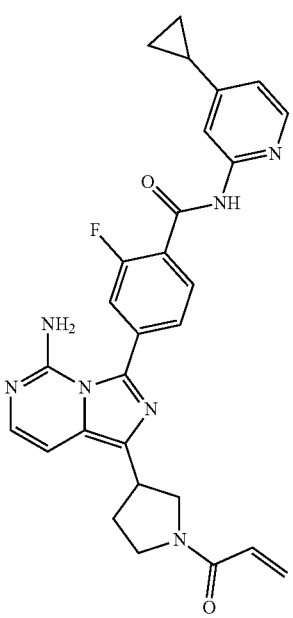

4-(1-(1-acryloylpyrrolidin-3-yl)-5-aminoimidazo[1,5-c]pyrimidin-3-yl)-
N-(4-cyclopropylpyridin-2-yl)-2-fluorobenzamide 4-(5-Amino-1-(1-(but-2-ynoyl)pyrrolidin-3-yl)imidazo[1,5-c]pyrimidin-3-yl)-N-(4-cyclopropylpyridin-2-yl)-2-fluorobenzamide (24.1 mg) was prepared as described for 4-(5-amino-1-(1-(but-2-ynoyl)pyrrolidin-3-yl)imidazo[1,5-c]pyrimidin-3-yl)-N-(pyridin-2-yl)benzamide. LRMS (M+H$^+$) m/z calculated 524.2, found 524.3. $^1$H NMR (DMSO-d6, 400 MHz) δ 10.56 (s, 1H), 8.18 (d, 1H), 7.97 (s, 1H), 7.79 (t, 1H), 7.50-7.54 (m, 2H), 7.20-7.22 (m, 1H), 6.98-7.02 (m, 1H), 6.88 (d, 1H), 6.44 (s, 1H), 3.48-4.07 (m, 6H), 2.50-2.51 (m, 2H), 2.02 (d, 4H), 1.09-1.11 (m, 2H), 0.80-0.86 (m, 2H).

4-(1-(1-Acryloylpyrrolidin-3-yl)-5-aminoimidazo[1,5-c]pyrimidin-3-yl)-N-(4-cyclopropylpyridin-2-yl)-2-fluorobenzamide (38.4 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H$^+$) m/z calculated 512.2, found 512.3. $^1$H NMR (DMSO-d6, 400 MHz) δ 10.66 (s, 1H), 8.18 (d, 1H), 7.97 (s, 1H), 7.79 (t, 1H), 7.52 (t, 1H), 7.21 (d, 1H), 6.98-7.03 (m, 1H), 6.88 (d, 1H), 6.61-6.65 (m, 1H), 6.44 (s, 2H), 6.15 (t, 1H), 5.66 (t, 1H), 3.43-4.00 (m, 5H), 2.31-2.39 (m, 2H), 2.00 (t, 1H), 1.08-1.13 (m, 2H), 0.78-0.83 (m, 2H).

Example 247: Preparation of 4-(1-(1-acryloylpyrrolidin-3-yl)-5-aminoimidazo[1,5-c]pyrimidin-3-yl)-N-(pyridin-2-yl)-3-(trifluoromethyl)benzamide

Example 248: Preparation of 4-(5-amino-1-(1-(but-2-ynoyl)pyrrolidin-3-yl)imidazo[1,5-c]pyrimidin-3-yl)-N-(pyridin-2-yl)-3-(trifluoromethyl)benzamide

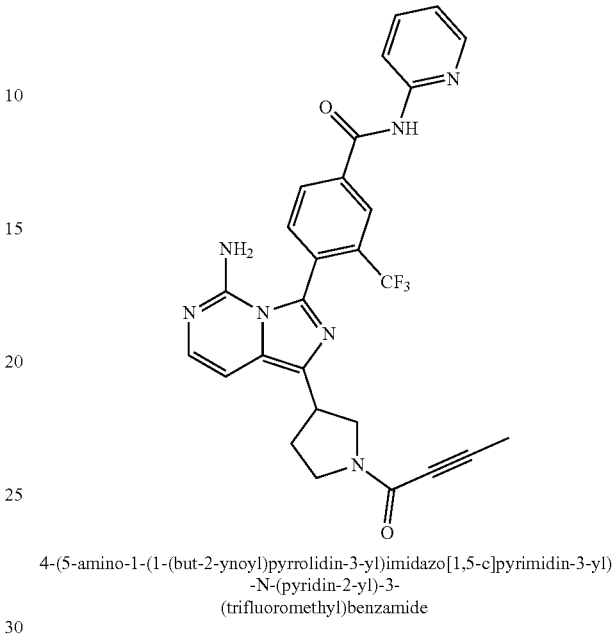

4-(5-amino-1-(1-(but-2-ynoyl)pyrrolidin-3-yl)imidazo[1,5-c]pyrimidin-3-yl)-N-(pyridin-2-yl)-3-(trifluoromethyl)benzamide 4-(5-Amino-1-(1-(but-2-ynoyl)pyrrolidin-3-yl)imidazo[1,5-c]pyrimidin-3-yl)-N-(pyridin-2-yl)-3-(trifluoromethyl)benzamide (30.7 mg) was prepared as described for 4-(5-amino-1-(1-(but-2-ynoyl)pyrrolidin-3-yl)imidazo[1,5-c]pyrimidin-3-yl)-N-(pyridin-2-yl)benzamide. LRMS (M+H$^+$) m/z calculated 534.2, found 534.3. $^1$H NMR (DMSO-d6, 400 MHz) δ 11.25 (s, 1H), 8.51 (s, 1H), 8.43 (d, 1H), 8.37 (d, 1H), 8.23 (d, 1H), 7.82-7.91 (m, 2H), 7.20-7.23 (m, 1H), 7.13-7.15 (m, 1H), 7.97-7.00 (m, 1H), 6.06 (s, 2H), 4.02 (t, 0.5H), 3.78-383 (m, 4H), 3.65-3.43 (m, 0.5H), 2.21-2.29 (m, 2H), 1.98 (t, 3H).

Example 249: Inhibitory Activity Against Selected Kinases

Inhibitory activities of compounds against BTK, EGFR T790M, EGFR L858R, and EGFR L858R/T790M were measured using Z'-LYTE® Method from Life Technologies as briefly described in the following.

Test Compounds are screened in 1% DMSO (final) in the well. For 10 point titrations, 3-fold serial dilutions are conducted from the starting concentration. All ATP Solutions are diluted to a 4× working concentration in Kinase Buffer (50 mM HEPES pH 7.5, 0.01% BRIJ-35, 10 mM MgCl$_2$, 1 mM EGTA). Peptide/Kinase Mixtures are diluted to a 2× working concentration in the appropriate Kinase Buffers as described below.

(i) Peptide/Kinase Mixtures for Measurement of EGFR (ErbB1) L858R:

The 2×EGFR (ErbB1) L858R/Tyr 04 mixture is prepared in 50 mM HEPES pH 7.5, 0.01% BRIJ-35, 10 mM MgCl$_2$, 4 mM MnCl$_2$, 1 mM EGTA, 2 mM DTT. The final 10 μL Kinase Reaction consists of 0.2-1.68 ng EGFR (ErbB1) L858R and 2 μM Tyr 04 in 50 mM HEPES pH 7.5, 0.01% BRIJ-35, 10 mM MgCl$_2$, 2 mM MnCl$_2$, 1 mM EGTA, 1 mM

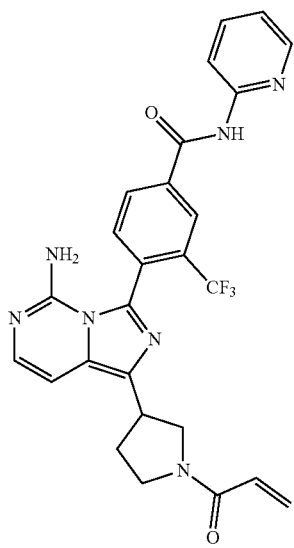

4-(1-(1-acryloylpyrrolidin-3-yl)-5-aminoimidazo[1,5-c]pyrimidin-3-yl)-N-(pyridin-2-yl)-3-(trifluoromethyl)benzamide 4-(1-(1-Acryloylpyrrolidin-3-yl)-5-aminoimidazo[1,5-c]pyrimidin-3-yl)-N-(pyridin-2-yl)-3-(trifluoromethyl)benzamide (45.1 mg) was prepared as described for 4-(8-(1-acryloylpyrrolidin-3-yl)-4-aminoimidazo[1,5-a][1,3,5]triazin-6-yl)-N-(pyridin-2-yl)benzamide. LRMS (M+H$^+$) m/z calculated 522.2, found 522.3. $^1$H NMR (DMSO-d6, 400 MHz) δ 11.25 (s, 1H), 8.51 (s, 1H), 8.44 (d, 1H), 8.37 (d, 1H), 8.22 (d, 2H), 7.82-7.91 (m, 2H), 7.22 (t, 1H), 7.14 (d, 2H), 6.99-7.02 (m, 1H), 6.58-6.65 (m, 1H), 6.10 (t, 3H), 5.66-5.68 (m, 1H), 3.58-3.87 (m, 5H), 2.20-2.23 (m, 2H).

DTT. After the 1 hour Kinase Reaction incubation, 5 µL of a 1:64 dilution of Development Reagent B is added.

(ii) Peptide/Kinase Mixtures for Measurement of EGFR (ErbB1) T790M:

The 2×EGFR (ErbB1) T790M/Tyr 04 mixture is prepared in 50 mM HEPES pH 6.5, 0.01% BRIJ-35, 10 mM MgCl$_2$, 1 mM EGTA, 0.02% NaN$_3$. The final 10 µL Kinase Reaction consists of 3.9-30.2 ng EGFR (ErbB1) T790M and 2 µM Tyr 04 in 50 mM HEPES pH 7.0, 0.01% BRIJ-35, 10 mM MgCl$_2$, 1 mM EGTA, 0.01% NaN3. After the 1 hour Kinase Reaction incubation, 5 µL of a 1:64 dilution of Development Reagent B is added.

(iii) Peptide/Kinase Mixtures for Measurement of EGFR (ErbB1) L858R/T790M:

The 2×EGFR (ErbB1) T790M L858R/Tyr 04 mixture is prepared in 50 mM HEPES pH 6.5, 0.01% BRIJ-35, 10 mM MgCl$_2$, 1 mM EGTA, 0.02% NaN$_3$. The final 10 µL Kinase Reaction consists of 0.38-4.22 ng EGFR (ErbB1) T790M L858R and 2 µM Tyr 04 in 50 mM HEPES pH 7.0, 0.01% BRIJ-35, 10 mM MgCl$_2$, 1 mM EGTA, 0.01% NaN$_3$. After the 1 hour Kinase Reaction incubation, 5 µL of a 1:64 dilution of Development Reagent B is added.

(iv) Peptide/Kinase Mixtures for Measurement of BTK:

The 2×BTK/Tyr 01 mixture is prepared in 50 mM HEPES pH 7.5, 0.01% BRIJ-35, 10 mM MgCl2, 1 mM EGTA. The final 10 µL Kinase Reaction consists of 1.04-10.4 ng BTK and 2 µM Tyr 01 in 50 mM HEPES pH 7.5, 0.01% BRIJ-35, 10 mM MgCl2, 1 mM EGTA. After the 1 hour Kinase Reaction incubation, 5 µL of a 1:256 dilution of Development Reagent B is added.

Reaction starts by 30-second shaking of mixture consisting of 2.5 µL 4× test compound, 5 µL 2× kinase reaction mixture and 2.5 µL 4×ATP Solution on Bar-coded Corning, low volume NBS, black 384-well plate (Corning Cat. #3676). Then the mixture is incubated for 60-minute at room temperature for the kinase reaction, followed by addition of 5 µL of a 1:1024 dilution of development reagent A and 30-second plate shake. The mixture is then incubated for another 60-minute at room temperature for development reaction. Finally fluorescence is read by plate reader.

SelecteScreen's Lantha® method from Life Technologies was used to measure compound's activities in inhibition of EGFR del746_750.

Test Compounds are screened in 1% DMSO (final) in the well. For 10 point titrations, 3-fold serial dilutions are conducted from the starting concentration.

Components for EGFR del745_750:
  Kinase Buffer A: 50 mM HEPES pH 7.5, 0.01% BRIJ-35, 10 mM MgCl2, 1 mM EGTA
  Kinase/Antibody Mixtures for EGFR del745_750: EGFR del745_750 10 nM, Antibody: Eu-anti-GST 2 nM, Tracer 199 10 nM, Inhibitor: SB202190 88.2 nM, All Kinase/Antibody Mixtures are diluted to a 2× working concentration in the appropriate Kinase Buffer
  Tracer: The 4× AlexaFluor® labeled Tracer is prepared in Kinase Buffer.

To start the measurement, the following components are added to individual wells of bar-coded, low volume, white 384-well plate (Greiner Cat. #784207):
  1. 160 nL—100× Test Compound in 100% DMSO.
  2. 3.84 µL—Kinase Buffer:
  3. 8.0 µL—2× Kinase/Antibody Mixture
  4. 4.0 µL—4× Tracer The mixture above is then shaken for 30-second following by 60-minute incubation at room temperature. Finally the plate is read on fluorescence plate reader.

Tables 2-6 shows % inhibition against BTK, EGFR T790M, EGFR L858R, EGFR L858R/T790M, and EGFR del746_750 of several compounds at 100 nM. The Z'-LYTE assay was carried out with ATP concentration at Km. The scale utilized in Tables 2-6 is as follows: ++ more than 50% inhibition and + less than 50% inhibition.

TABLE 2

Biological activity of illustrative compounds against BTK

| % Inhibition | Compounds |
| --- | --- |
| + | C001, C002, C009, C011, C012, C014, C015, C016, C018, C019, C020, C021, C022, C024, C025, C026, C027, C029, C030, C031, C032, C033, C034, C036, C037, C039, C040, C042, C043, C044, C045, C046, C049, C054, C056, C057, C058, C059, C060, C062, C066, C068, C070, C072, C077, C079, C080, C082, C083, C084, C085, C087, C090, C093, C094, C095, C097, C098, C1, C104, C109, C113, C115, C124, C126, C127, C128, C130, C133, C138, C140, C141, C142, C143, C144, C145, C146, C147, C148, C149, C150, C151, C152, C155, C156, C159, C162, C165, C167, C168, C169, C170, C172, C173, C174, C176, C177, C178, C179, C181, C182, C187, C188, C192, C193, C195, C211, C215, C219 |
| ++ | C003, C004, C005, C006, C007, C008, C010, C013, C017, C023, C028, C035, C038, C041, C047, C048, C050, C051, C052, C053, C055, C061, C063, C064, C065, C067, C069, C071, C073, C074, C075, C076, C078, C081, C086, C088, C089, C091, C092, C096, C099, C101, C102, C103, C105, C106, C107, C108, C110, C111, C112, C114, C116, C117, C118, C119, C120, C121, C122, C123, C125, C129, C131, C132, C134, C135, C136, C137, C139, C153, C154, C157, C158, C160, C161, C163, C164, C166, C171, C175, C180, C183, C184, C185, C186, C189, C190, C191, C194, C196, C197, C198, C199, C200, C201, C202, C203, C204, C205, C206, C207, C208, C209, C210, C212, C213, C214, C216, C217, C218, C220, C221, C222, C223, C224, C225, C226, C227 |

TABLE 3

Biological activity of illustrative compounds against EGFR L858R

| % Inhibition | Compounds |
| --- | --- |
| + | C042, C008, C052, C064 |
| +− | C003, C013, C051, C073, C074, C076 |

TABLE 4

Biological activity of illustrative compounds against EGFR T790M

| % Inhibition | Compounds |
| --- | --- |
| + | C008, C042, C052, C003, C013, C064, C073, C074, C076 |
| ++ | C051 |

TABLE 5

Biological activity of illustrative compounds against EGFR L858R/T790M

| % Inhibition | Compounds |
| --- | --- |
| + | C008, C042, C052, C003, C013, C064, C073, C074, C076 |
| ++ | C051 |

TABLE 6

Biological activity of illustrative compounds against EGFR del745_750

| % Inhibition | Compounds |
|---|---|
| + | C042, C008, C052 |
| ++ | C074, C013, C073, C003, C076, C051 |

To determine $IC_{50}$ of a compound against a kinase, a series of concentrations of the compound were tested for the inhibition. $IC_{50}$ was calculated by plotting the concentration of compound vs the percentage of inhibition in treated wells using GraphPad Prism 5. Table 7 shows $IC_{50}$ values of several compounds of the invention against BTK. The scale utilized in Table 7 is as follows: ++ less than 100 nM and + greater than 100 nM.

TABLE 7

$IC_{50}$ of several illustrative compounds against BTK

| $IC_{50}$ | Compounds |
|---|---|
| + | C187, C188, C192, C193, C195 |
| ++ | C003, C004, C005, C006, C007, C008, C013, C023, C028, C035, C038, C048, C051, C052, C053, C061, C064, C065, C067, C073, C074, C075, C076, C078, C086, C091, C099, C102, C103, C105, C106, C111, C112, C116, C117, C120, C121, C122, C129, C131, C132, C135, C137, C139, C153, C157, C158, C161, C163, C166, C171, C175, C183, C184, C185, C186, C189, C190, C191, C194, C196, C197, C198, C199, C201, C204, C206, C208, C210, C212, C216, C218, C224, C225, C228, C229, C230, C231, C232, C233, C234, C235, C236, C237, C238, C239, C240, C241, C242, C243, C244, C247, C248 |

Example 250: Inhibitory Activity Against Cancer Cell Growth

OCI-Ly10 cells were cultured in Iscove's DMEM supplemented with 20% fetal bovine serum and 1× penicillin/streptomycin/glutamine. The cells were maintained in T175 flasks under 5% CO2 in a 37° C. humidified incubator for 5 days prior to plating and assay.

Cells were pooled by centrifugation (200 rcf, 8 minutes) and resuspended in fresh medium to a concentration of 2.00E+05 cells/ml. 200 µl of the cell suspension was added to each well (40,000 cells/well) of a black-walled 96 well plate to which 1 µl of compound (n=3 per concentration) in 100% DMSO (0.5% final concentration) was added per well. Vehicle and cell free wells were also included in the assay. The dosed cells were cultured under normal conditions for 72 hours.

Cell proliferation is measured using the dye Alamar Blue (resazurin). Resazurin is reduced to resorufin by cellular enzymes and is fluorescent (544 nm excitation, 612 nm emission). Fluorescence intensity is proportional to cell number. Resazurin was prepared in PBS to a stock concentration of 440 µM. 40 µl of the 440 µM resazurin stock solution was added 3 hours prior to the 72 hour termination of the assay. The plate was returned to normal culture conditions and fluorescence measurements were collected using a Cytation3 multimode plate reader (Biotek) at 72 hours.

Data for representative compounds are shown below. Table 8 shows $IC_{50}$ values of several compounds of the invention against OCI-LY10 cells. The scale utilized in Table 8 is as follows: ++ less than 50 nM and + greater than 50 nM.

TABLE 8

$IC_{50}$ of several illustrative compounds in OCI-LY10 cells

| $IC_{50}$ | Compounds |
|---|---|
| ++ | C052, C235, C236, C238, C204, C240, C185, C099, C210, C197, C065, C184, C112, C196, C230, C199, C139, C135, C105, C183, C186, C131, C008, C120 |
| + | C102, C035, C163, C121 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A compound of Formula (II):

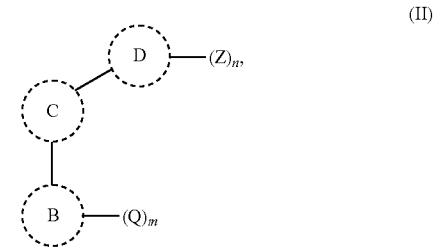

or a pharmaceutically acceptable salt thereof, wherein:

is selected from the group consisting of phenyl, piperidine, and pyrrolidine, each of which is substituted with E;

is selected from the group consisting of

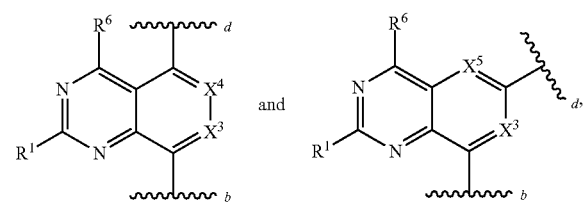

wherein ⌇b is a point of attachment for

and ⌇d is a point of attachment for

is selected from the group consisting of phenyl and pyridine;
X³ is C—R³;
X⁴ is C—R⁴;
X⁵ is C—R⁵;
R¹, R³, R⁴, R⁵, and R⁶ are each independently selected from the group consisting of hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, and optionally substituted carbamimidoyl;
Q and Z are each independently selected at each occurrence from hydrogen, cyano, halo, hydroxy, azido, nitro, carboxy, oxo, sulfinyl, sulfanyl, sulfonyl, optionally substituted alkoxy, optionally substituted cycloalkyloxy, optionally substituted aryloxy, optionally substituted heteroaryloxy, optionally substituted heterocycloalkyloxy, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbamimidoyl, and E;
E is selected from the group consisting of

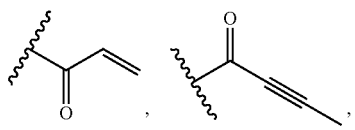

-continued

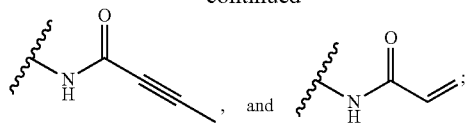

m is 0, 1, 2, 3, or 4; and
n is 0, 1, 2, 3, 4, or 5.
2. The compound or salt of claim 1, wherein

is selected from the group consisting of

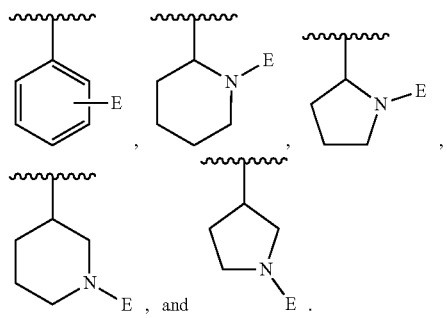

3. The compound or salt of claim 1, wherein

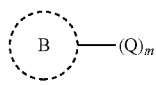

is

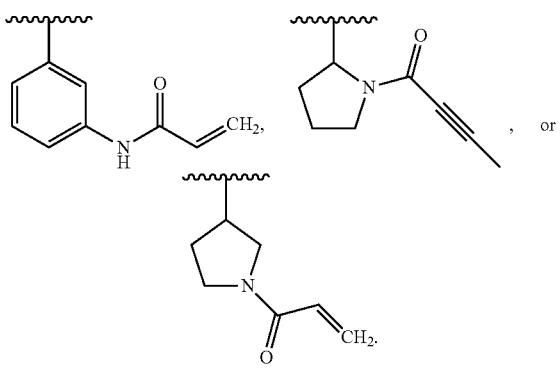

4. The compound or salt of claim 1, wherein Z is independently selected at each occurrence from cyano, halo, optionally substituted aryloxy, optionally substituted amino, and optionally substituted aminocarbonyl.
5. A compound selected from the group consisting of:
4-(8-(1-acryloylpiperidin-3-yl)quinazolin-5-yl)-N-(pyridin-2-yl)benzamide,
4-(8-(3-acrylamidophenyl)quinazolin-5-yl)-N-(pyridin-2-yl)benzamide, 4-(8-(1-acryloylpyrrolidin-3-yl)quinazolin-5-yl)-N-(pyridin-2-yl)benzamide,
4-(8-(1-acryloylpyrrolidin-3-yl)-4-aminoquinazolin-5-yl)-N-(pyridin-2-yl)benzamide,
4-(8-(3-acrylamidophenyl)-5-aminoquinazolin-6-yl)-N-(pyridin-2-yl)benzamide,
4-(8-(3-acrylamidophenyl)-5-aminoquinazolin-6-yl)-N-(4-cyclopropylpyridin-2-yl)benzamide,
N-(3-(5-amino-6-(2-fluoro-4-(pyridin-2-yloxy)phenyl)quinazolin-8-yl)phenyl)acrylamide,
1-(3-(5-amino-6-(2-fluoro-4-(pyridin-2-yloxy)phenyl)quinazolin-8-yl)pyrrolidin-1-yl)prop-2-en-1-one,
4-(8-(3-acrylamidophenyl)-5-aminoquinazolin-6-yl)-N-(4-cyanopyridin-2-yl)benzamide,
4-(8-(3-acrylamidophenyl)-5-aminoquinazolin-6-yl)-3-fluoro-N-(pyridin-2-yl)benzamide,
4-(8-(3-acrylamidophenyl)-2,5-diaminoquinazolin-6-yl)-N-(pyridin-2-yl)benzamide,
N-(3-(5-amino-6-(4-(pyridin-2-yloxy)phenyl)quinazolin-8-yl)phenyl)acrylamide,
1-(3-(5-amino-6-(4-(pyridin-2-yloxy)phenyl)quinazolin-8-yl)pyrrolidin-1-yl)prop-2-en-1-one,
N-(3-(5-amino-6-(4-phenoxyphenyl)quinazolin-8-yl)phenyl)acrylamide,
N-(3-(5-amino-6-(2-fluoro-4-((4-(trifluoromethyl)pyridin-2-yl)oxy)phenyl)quinazolin-8-yl)phenyl)acrylamide,
N-(3-(5-amino-6-(4-((4-(trifluoromethyl)pyridin-2-yl)oxy)phenyl)quinazolin-8-yl)phenyl)acrylamide,
4-(8-(3-acrylamidophenyl)-5-aminoquinazolin-6-yl)-3-chloro-N-(pyridin-2-yl)benzamide,
1-(3-(5-amino-6-(4-phenoxyphenyl)quinazolin-8-yl)pyrrolidin-1-yl)prop-2-en-1-one,
1-(3-(5-amino-6-(4-((4-(trifluoromethyl)pyridin-2-yl)oxy)phenyl)quinazolin-8-yl)pyrrolidin-1-yl)prop-2-en-1-one,
4-(8-(3-acrylamidophenyl)-5-aminoquinazolin-6-yl)-3-chloro-N-(4-cyclopropylpyridin-2-yl)benzamide,
4-(8-(3-acrylamidophenyl)-5-aminoquinazolin-6-yl)-N-(4-cyclopropylpyridin-2-yl)-3-fluorobenzamide,
N-(3-(5-amino-6-(2-chloro-4-(pyridin-2-yloxy)phenyl)quinazolin-8-yl)phenyl)acrylamide,
4-(8-(3-acrylamidophenyl)-5-aminoquinazolin-6-yl)-N-(3-fluoropyridin-2-yl)benzamide,
4-(8-(1-acryloylpyrrolidin-3-yl)-5-aminoquinazolin-6-yl)-N-(3-fluoropyridin-2-yl)benzamide, and
4-(8-(3-acrylamidophenyl)-5-aminoquinazolin-6-yl)-3-chloro-N-(3-fluoropyridin-2-yl)benzamide,
or a pharmaceutically acceptable salt thereof.

6. A pharmaceutical composition comprising a pharmaceutically acceptable carrier and the compound or salt of claim 1.

7. The compound or salt of claim 1, wherein $R^1$ and $R^6$ are each independently selected from the group consisting of hydrogen, cyano, halo, hydroxy, optionally substituted alkyl, optionally substituted aryl, optionally substituted heteroaryl, and optionally substituted amino.

8. The compound or salt of claim 1, wherein $R^1$ and $R^6$ are each independently selected from the group consisting of hydrogen and —$NH_2$.

9. The compound or salt of claim 1, wherein $R^3$ and $R^4$ are each independently selected from the group consisting of hydrogen, cyano, halo, hydroxy, optionally substituted alkyl, optionally substituted aryl, optionally substituted heteroaryl, and optionally substituted amino.

10. The compound or salt of claim 1, wherein $R^3$ and $R^4$ are each independently hydrogen.

11. The compound or salt of claim 1, wherein $R^5$ is selected from the group consisting of cyano, halo, hydroxy, optionally substituted alkyl, optionally substituted aryl, optionally substituted heteroaryl, and optionally substituted amino.

12. The compound or salt of claim 1, wherein $R^5$ is —$NH_2$.

13. The compound or salt of claim 1, wherein is

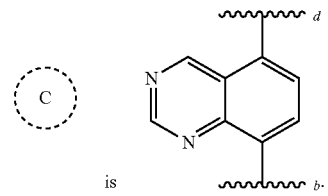

14. The compound or salt of claim 1, wherein is

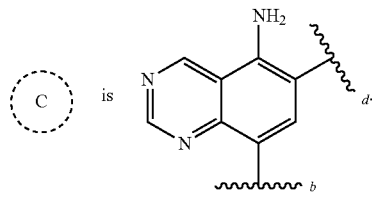

15. The compound or salt of claim 1, wherein

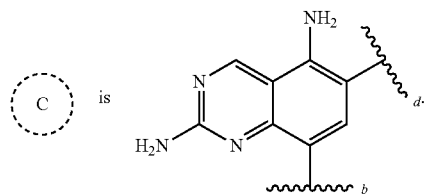

* * * * *